(12) United States Patent
Guo et al.

(10) Patent No.: US 8,906,944 B2
(45) Date of Patent: *Dec. 9, 2014

(54) COMPOUNDS AS TYROSINE KINASE MODULATORS

(71) Applicant: Allergan, Inc., Irvine, CA (US)

(72) Inventors: Xialing Guo, San Clemente, CA (US); Zhen Zhu, Foothill Ranch, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/673,437

(22) Filed: Nov. 9, 2012

(65) Prior Publication Data

US 2013/0065880 A1     Mar. 14, 2013

Related U.S. Application Data

(63) Continuation-in-part of application No. 12/875,218, filed on Sep. 3, 2010.

(60) Provisional application No. 61/239,603, filed on Sep. 3, 2009, provisional application No. 61/306,616, filed on Feb. 22, 2010, provisional application No. 61/356,699, filed on Jun. 21, 2010, provisional application No. 61/360,531, filed on Jul. 1, 2010.

(51) Int. Cl.
| | | |
|---|---|---|
| C07D 401/04 | (2006.01) |
| A61K 31/4439 | (2006.01) |
| C07D 409/14 | (2006.01) |
| C07D 405/14 | (2006.01) |
| C07D 401/14 | (2006.01) |
| C07D 409/04 | (2006.01) |

(52) U.S. Cl.
CPC ............ *C07D 401/04* (2013.01); *C07D 409/14* (2013.01); *C07D 405/14* (2013.01); *C07D 401/14* (2013.01); *C07D 409/04* (2013.01)
USPC ...... 514/343; 546/194; 546/276.4; 546/280.4

(58) Field of Classification Search
None
See application file for complete search history.

(56) References Cited

U.S. PATENT DOCUMENTS 8,614,234 B2 * 12/2013 Guo et al. .................... 514/343

* cited by examiner

*Primary Examiner* — Zinna Northington Davis
(74) *Attorney, Agent, or Firm* — Barbara C. Potts

(57) ABSTRACT

The present invention is directed to novel compounds of Formula I. The compounds of the present invention are potent tyrosine kinase modulators, and are suitable for the treatment and prevention of diseases and conditions related to abnormal activities of tyrosine kinase receptors.

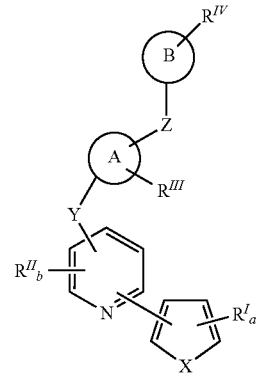

Formula I

4 Claims, 4 Drawing Sheets

COMPOUNDS AS TYROSINE KINASE MODULATORS

CROSS REFERENCE TO RELATED APPLICATIONS

This application is a continuation in part of U.S. application Ser. No. 12/875,218, filed Aug. 31, 2010, now U.S. Pat. No. 8,614,234, which claims priority under 35 U.S.C. 119(e) to U.S. Provisional Application Nos. 61/239,603, filed on Sep. 3, 2009, 61/306,616, filed on Feb. 22, 2010, 61/356,699 filed on Jun. 21, 2010 and 61/360,531 filed on Jul. 1, 2010, all of which are expressly incorporated herein by reference in their entireties.

FIELD OF THE INVENTION

The present invention is directed to novel compounds with multiple aromatic components capable of modulating, regulating and/or inhibiting tyrosine kinase signal transduction. The present invention is also directed to methods of prevention and/or treatment of disorders related to unregulated tyrosine kinase signal transduction, including but not limited to, cell growth disorders, metabolic disorders, blood vessel proliferative disorders, inflammatory disorders, neurodegenerative diseases and immune disorders.

BACKGROUND OF THE INVENTION

Protein tyrosine kinases ("PTKs") play an important role in the control of cell growth and differentiation. PTKs comprise a large and diverse class of proteins having enzymatic activity. PTKs can be of the receptor-type (having extracellular, transmembrane and intracellular domains) or the non-receptor type (being wholly intracellular). For example, signal transduction mediated by receptor tyrosine kinases ("RTKs") is initiated by extracellular interaction with a specific growth factor (i.e., a ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to RTKs, it has been shown also that tyrosine phosphorylation sites function as high-affinity binding sites for SH2 (src homology) domains of signaling molecules. Several intracellular substrate proteins that associate with RTKs have been identified and are divided into two principal groups: (1) substrates which have a catalytic domain; and (2) substrates which lack a catalytic domain but serve as adapters and associate with catalytically active molecules. The specificity of the interactions between receptors or proteins and SH2 domains of their substrates is determined by the amino acid residues immediately surrounding the phosphorylated tyrosine residue. Differences in binding affinities between SH2 domains and the amino acid sequences surrounding the phosphotyrosine residues on particular receptors are consistent with the observed differences in their substrate phosphorylation profiles. These observations suggest that the function of each RTK is determined not only by its pattern of expression and ligand availability, but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

The RTKs comprise a large family of transmembrane receptors with diverse biological activities. The intrinsic function of RTKs is activated upon ligand binding, which results in phosphorylation of the receptor and multiple cellular substrates, and subsequently in a variety of cellular responses. At present, at least nineteen distinct RTK subfamilies have been identified. One RTK subfamily, designated the HER subfamily, is believed to be comprised of EGFR, HER2, HER3 and HER4. Ligands to the HER subfamily of receptors include epithelial growth factor (EGF), TGF-α, amphiregulin, HB-EGF, betacellulin and heregulin. The second subfamily of RTKs, designated the insulin subfamily, is comprised of the INS-R, the IGF-1R and the IR-R. The third RTK subfamily, the "PDGF" family, includes the PDGF α and β receptors, CSFIR, c-kit and FLK-II. Another subfamily of RTKs, identified as the FLK family, is believed to be comprised of the kinase insert domain-receptor fetal liver kinase-1 (KDR/FLK-1), the fetal liver kinase 4 (FLK-4) and the fms-like tyrosine kinase 1 (flt-1). Each of these receptors was initially believed to be a receptor for hematopoietic growth factors. Two other subfamilies of RTKs have been designated as the FGF receptor family (FGFR1, FGFR2, FGFR3 and FGFR4) and the Met subfamily (c-met and Ron). Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs, and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025-2031, which is incorporated herein by reference.

Many of the protein tyrosine kinases (PTKs), whether an RTK or non-receptor tyrosine kinase, have been found to be involved in cellular signaling pathways leading to cellular signal cascades and pathogenic conditions such as cancer, psoriasis and hyper immune responses. In view of the importance of PTKs to the control, regulation and modulation of cell proliferation and the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (Kendall & Thomas, 1994, Proc. Nat'l Acad. Sci. 90: 10705-09; Kim, et al, 1993, Nature 362: 841-844), RNA ligands (Jellinek, et al, Biochemistry 33: 10450-56); Takano, et al, 1993, Mol. Bio. Cell 4:358A; Kinsella, et al, 1992, Exp. Cell Res. 199: 56-62; Wright, et al, 1992, J. Cellular Phys. 152: 448-57) and tyrosine kinase inhibitors (U.S. Pat. No. 5,330,992; Mariani, et al, 1994, Proc. Am. Assoc. Cancer Res. 35: 2268).

More recently, attempts have been made to identify small molecules which act as tyrosine kinase inhibitors. For example, bis monocyclic, bicyclic or heterocyclic aryl compounds (PCT Application No. WO 92/20642), vinylene-azaindole derivatives (PCT Application No. WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT Application No. WO 94/03427), tricyclic polyhydroxylic compounds (PCT Application No. WO 92/21660) and benzylphosphonic acid compounds (PCT Application No. WO 91/15495) have been described as compounds for use as tyrosine kinase inhibitors for use in the treatment of cancer.

In addition, other small molecules were studied as tyrosine kinase inhibitors, such as the compounds disclosed in U.S. Pat. Nos. 6,765,012; 6,541,504; 6,747,025; 5,792,783; 5,834,504; 5,883,113; 5,883,116 and 5,886,020, all of which are incorporated by reference in their entireties.

The identification and use of compounds which specifically inhibit signal transduction by modulating the activity of receptor and non-receptor tyrosine is one aspect of the present invention.

SUMMARY OF THE INVENTION

The present invention is directed to compounds represented by Formula I capable of modulating, regulating and/or inhibiting tyrosine kinase signal transduction, and uses of the compounds and compositions incorporating the compounds for disease treatment and prevention.

The compounds of the present invention can be found in general Formula I:

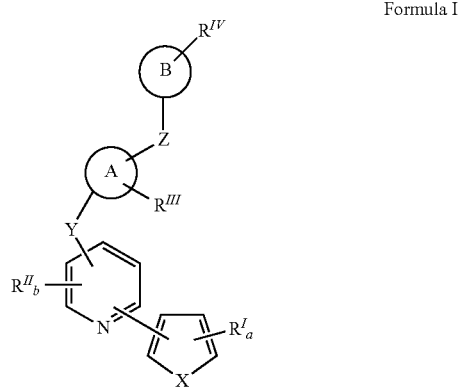

Formula I wherein
X is selected from the group consisting of $NR^1$, O, $S(O)_n$;
n is 0 or an integer of from 1 to 2;
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl($NR^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;
$R^I$ is selected from the group consisting of hydrogen, halogen, $C_1$ to $C_8$ alkyl, $S(O)_fR^4$, $(CR^5R^6)_dC(O)OR^4$, $S(O)_f(CR^5R^6)_dC(O)OR^4$, $(CR^5R^6)_dAr$, $NR^4(CR^5R^6)_dAr$, $O(CR^5R^6)_dAr$, $S(O)_f(CR^5R^6)_dAr$, $(CR^5R^6)_dS(O)_fR^4$, $NR^4(CR^5R^6)_dS(O)_fR^4$, $O(CR^5R^6)_dS(O)_fR^4$, $S(O)_f(CR^5R^6)_eS(O)_fR^4$, $(CR^5R^6)_dC(O)N(R^4)_2$, $NR^4(CR^5R^6)_dC(O)N(R^4)_2$, $O(CR^5R^6)_dC(O)N(R^4)_2$, $S(O)_f(CR^5R^6)_eC(O)N(R^4)_2$, $(CR^5, R^6)_dOR^4$, $S(O)_f(CR^5R^6)_dOR^4$, $(CR^5R^6)_dOSO_2R^4$, $S(O)_f(CR^5R^6)_eOSO_2R^4$, $(CR^5R^6)_dP(O)(OR^4)_2$, $S(O)_f(CR^5R^6)_eP(O)(OR^4)_2$, $OC(O)(CR^5R^6)_dN(R^4)_2$, $C(O)(CR^5R^6)_dN(R^4)_2$, $C(O)N=S(O)R^5R^6$, $NR^2C(O)(CR^5R^6)_dN(R^4)_2$, $(CR^5R^6)_dR^5$, $S(O)_f(CR^5R^6)_dR^5$, $HNC(O)R^4$, $HN-C(O)OR^4$, $(CR^5R^6)_dN(R^4)_2$, $S(O)_f(CR^5R^6)_dN(R^4)_2$, $OC(O)OR^4$, $(CR^5R^6)_dC(O)(CR^5R^6)_dR^4$, $(CR^5R^6)_dC(O)(CR^5R^6)_dOR^4$, and $(CR^5R^6)_dC(O)(CR^5R^6)_dN(R^4)_2$, wherein each $R^4$ is independently selected from the group consisting of hydrogen, hydroxyl, $C_1$-$C_8$ alkyl, aryl, $C_1$-$C_8$ hydroxyalkyl, $C_1$-$C_8$ alkoxyalkyl, $(CR^5R^6)_d$ and $N(R^4)_2$ may form a 3-7 membered heterocyclic ring, comprising of aziridine, azetidine, pyrrolidine, 5-fluoropyrrolidine, piperidine, 6-fluoropiperidine, N-methylpiperazine, morpholine, 2,6-dimethylmorpholine, thiomorpholine, and wherein said heterocyclic ring may be optionally substituted with up to three of $R^5$; wherein $R^5$ and $R^6$ are independently selected from the group consisting of hydrogen, halo, hydroxyl, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl, sulfonate and $CR^5R^6$ may represent a carbocyclic or heterocyclic ring of from 5 to 6 carbons or alternatively, $(CR^5R^6)_d$ and $(CR^5R^6)_e$ may form a 3-7 membered carbocyclic or heterocyclic ring, wherein the ring may be optionally substituted with up to three of hydroxyl, halo, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl and sulfonate;
a is 0 or an integer of from 1 to 3;
d is 0 or an integer of from 1 to 5;
e is an integer of from 1 to 4;
f is 0 or an integer of from 1 to 2;
$R^{II}$ is independently selected from the group consisting of hydrogen, alkoxy, alkoxyalkoxy, alkoxyalkyl, alkyl, aryloxy, aryloxyalkyl, halo, haloalkoxy, haloalkyl, hydroxy, hydroxyalkoxy, hydroxyalkyl, ($NR^2R^3$)alkoxy, ($NR^2R^3$)alkenyl, ($NR^2R^3$)alkyl, ($NR^2R^3$)carbonylalkenyl, and ($NR^2R^3$)carbonylalkyl, wherein $R^2$ and $R^3$ are independently selected from the group consisting of hydrogen, alkyl, alkylcarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;
b is 0 or an integer of from 1 to 2;
Y is selected from the group consisting of:
(1') —$(CH_2)$g-O—$(CH_2)$h-;
(2') —$(CH_2)$g-$NR^1$—$(CH_2)$h-;
(3') —$(CH_2)$g-$S(O)_n$—$(CH_2)$h-;
(4') —$(CH_2)$g-$SO_2NR^2$—$(CH_2)$h-;
(5') —$(CH_2)$g-$NR^2SO_2$—$(CH_2)$h-;
(6') —$(CH_2)$g-CO—$(CH_2)$h-;
(7') —$(CH_2)$g-$C(O)NR^2$—$(CH_2)$h-;
(8') —$(CH_2)$g-$NR^2C(O)$—$(CH_2)$h-;
(9') —$(CH_2)$g-C≡C—$(CH_2)$h-;
(10') —$(CH_2)$g-$NR^2C(O)NR^3$—$(CH_2)$h-;
(11') —$(CH_2)$g-$(CH_2)$h-;
(12') —$(CH_2)$g-$CF_2$—$(CH_2)$h-;
(13') —$(CH_2)$g-$CCl_2$—$(CH_2)$h-;
(14') —$(CH_2)$g-CHF—$(CH_2)$h-;
(15') —$(CH_2)$g-CH(OH)—$(CH_2)$h-;
(16') —$(CH_2)$g-$CR^2R^3$—$(CH_2)$h-;
(17') —$(CH_2)$g-C≡C—$(CH_2)$h-;
and (18') a single bond;

wherein g is 0 or an integer of from 1 to 3;

h is 0 or an integer of from 1 to 3;

$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl($NR^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;

$R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered cyclic ring;

Ring A is selected from the group consisting of:

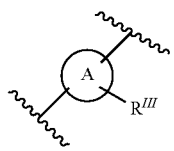

(i) Phenyl;

(ii) Naphthyl;

(iii) A 5 or 6 membered monocyclic heteroaryl group which have 1-5 heteroatoms independently selected from the group consisting of O, N and S;

and (iv) An 8 to 10 membered bicyclic heteroaryl group which have 1-6 heteroatoms independently selected from the group consisting of O, N and S;

Ring A can be illustrated but not limited to the following:

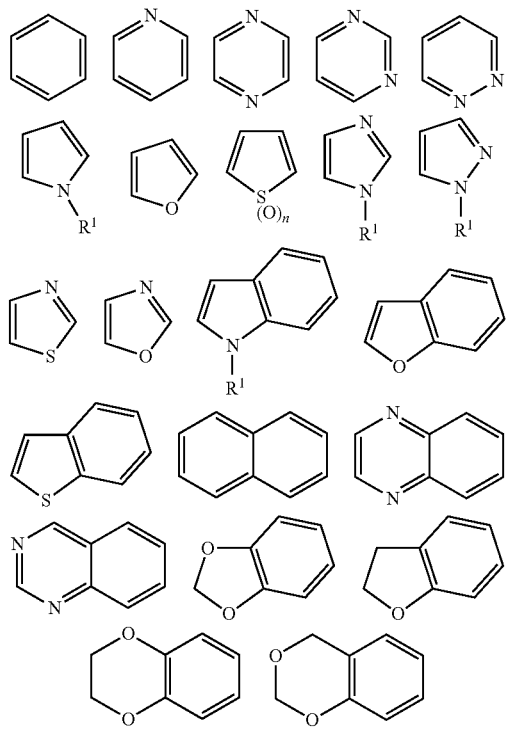

wherein $R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl($NR^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;

$R^{III}$ represents optionally 1-3 substituents independently selected from the group consisting of $C_1$-$C_5$ linear or branched alkyl, $C_1$-$C_5$ linear or branched haloalkyl, $C_1$-$C_5$ alkoxy, hydroxy, amino, $C_1$-$C_5$ alkylamino, C1-C6 dialkylamino, halogen, cyano, and nitro;

Z is selected from the group consisting of (1') $(CH_2)_iN(R^7)C(O)N(R^8)(CH_2)_j$;

(2') $(CH_2)_iN(R^7)C(S)N(R^8)(CH_2)_j$;

(3') $(CH_2)_iN(R^7)C(O)$;

(4') $C(O)N(R^8)(CH_2)_j$;

(5') $(CH_2)_iN(R^7)S(O)_2$;

and (6') $S(O)_2N(R^8)(CH_2)_j$;

wherein i is 0 or 1;

j is 0 or 1;

$R^7$ and $R^8$ are independently selected from the group consisting of hydrogen and alkyl.

Ring B is selected from the group consisting of:

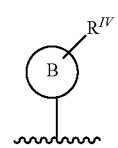

(i') Phenyl;

(ii') Naphthyl;

(iii') A 5 or 6 membered monocyclic heteroaryl group which have 1-3 heteroatoms independently selected from the group consisting of O, N and S;

and (iv') An 8 to 10 membered bicyclic heteroaryl group which have 1-3 heteroatoms independently selected from the group consisting of O, N and S;

Ring B can be illustrated but not limited to the following:

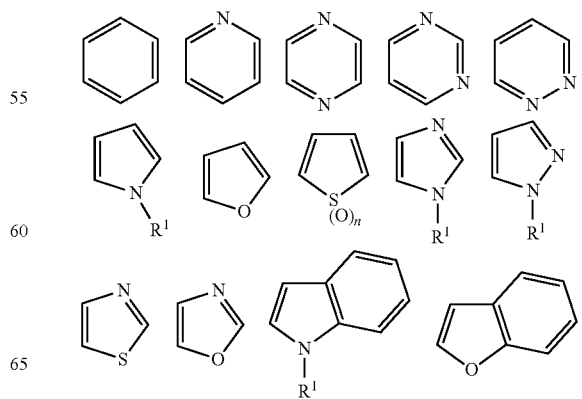

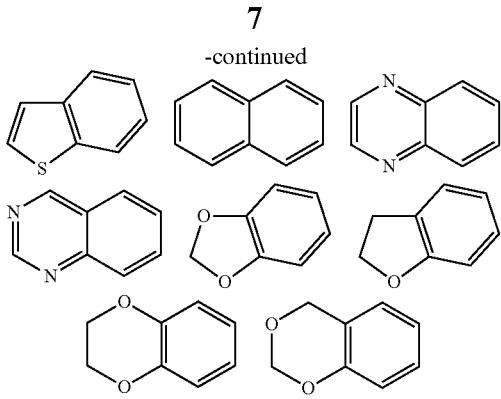

wherein

R¹ is independently selected from the group consisting of hydrogen, alkenyl, alkoxyalkyl, CF₃, alkyl, alkylcarbonyl, alkoxycarbonyl, aryl, heterocycloalkyl, hydroxyalkyl, and alkyl(NR²R³), wherein R² and R³ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively R² and R³ and may be taken together to form a 5-7 membered heterocyclic ring with N;

$R^{IV}$ represents optionally 1-3 substituents, independently selected from the group consisting of alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —NR⁹R¹⁰; wherein R⁹ and R¹⁰ are independently selected from the group consisting of hydrogen, alkyl, alkylcarbonyl, aryl, arylalkyl, cycloalkyl, cycloalkylalkyl, heterocyclyl, and heterocyclylalkyl.

Some embodiments of the present invention are included in the following paragraphs:

(1) A compound according to Formula I, including any tautomer, stereoisomer, diastereoisomeric form, polymorphic form, crystal form, a solvate, a hydrate, a metabolite, a pharmaceutically acceptable salt or prodrug, mixture of different stereoisomers, and any mixture of different crystal forms.

(2) A compound of Formula I in the form of a prodrug.

(3) The compound according to paragraph 1, wherein Z is selected from the group consisting of (CH₂)ᵢN(R⁷)C(O), C(O)N(R⁸)(CH₂)ⱼ, (CH₂)ᵢN(R⁷)S(O)₂ and S(O)₂N(R⁸)(CH₂)ⱼ.

(4) The compound according to paragraphs 1-3, wherein Y is selected from the group consisting of —(CH₂)g-O—(CH₂)h-; —(CH₂)g-NR¹—(CH₂)h-; —(CH₂)g-S(O)ₙ—(CH₂)h-; —(CH₂)g-CO—(CH₂)h-; —(CH₂)g-NR²SO₂—(CH₂)h-; —(CH₂)g-CO—(CH₂)h-; —(CH₂)g-C(O)NR²—(CH₂)h-; —(CH₂)g-NR²C(O)—(CH₂)h-; —(CH₂)g-C≡C—(CH₂)h-; —(CH₂)g-NR²C(O)NR³—(CH₂)h and a single bond.

(5) The compound according to paragraphs 1-4, wherein Ring A and Ring B are independently selected from the group consisting of

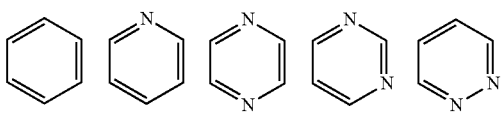

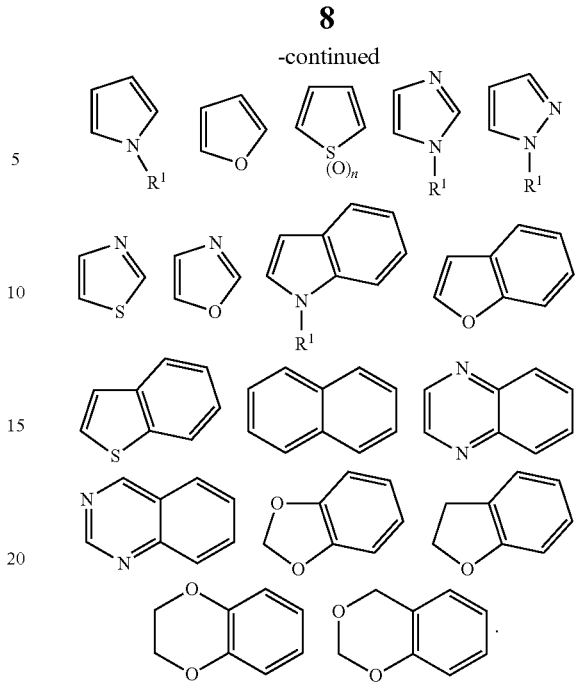

(6) The compound according to paragraphs 1-5, wherein Y is selected from the group consisting of —(CH₂)g-(CH₂)h-; —(CH₂)g-CF₂—(CH₂)h-; —(CH₂)g-CCl₂—(CH₂)h-; —(CH₂)g-CHF—(CH₂)h-; —(CH₂)g-CH(OH)—(CH₂)h-; —(CH₂)g-CR²R³—(CH₂)h-; and —(CH₂)g-C≡C—(CH₂)h-.

(7) The compound according to paragraphs 1-6, wherein X is NH.

(8) A compound selected from the group consisting of (1') [({5-[4-(2-fluoro-5-{[(2-fluoro-5-methylphenyl)amino]carbonyl}phenoxy)pyridin-2-yl]-1H-pyrrol-3-yl}carbonyl)amino]acetic acid;

(2') methyl [({5-[4-(2-fluoro-5-{[(2-fluoro-5-methylphenyl)amino]carbonyl}phenoxy)pyridin-2-yl]-1H-pyrrol-3-yl}carbonyl)amino]acetate;

(3') ({[5-(4-{3-[(3-methyl-2-furoyl)amino]phenoxy}pyridin-2-yl)-1H-pyrrol-3-yl]carbonyl}amino)acetic acid;

(4') methyl ({[5-(4-{3-[(3-methyl-2-furoyl)amino]phenoxy}pyridin-2-yl)-1H-pyrrol-3-yl]carbonyl}amino)acetate;

(5') 5-[4-({3-[(3-methyl-2-furoyl)amino]phenyl}amino)pyridin-2-yl]-1H-pyrrole-3-carboxylic acid;

(6') methyl 5-[4-({3-[(3-methyl-2-furoyl)amino]phenyl}amino)pyridin-2-yl]-1H-pyrrole-3-carboxylate;

(7') 5-[4-(2-fluoro-5-{[(2-fluoro-5-methylphenyl)amino]carbonyl}phenoxy)pyridin-2-yl]-N-hydroxy-1H-pyrrole-3-carboxamide;

(8') 4-fluoro-N-(2-fluoro-5-methylphenyl)-3-[(2-{4-[(3-hydroxypiperidin-1-yl)carbonyl]-1H-pyrrol-2-yl}pyridin-4-yl)oxy]benzamide;

(9) N-(2,3-dihydroxypropyl)-5-[4-(3-{[(2-fluoro-5-methylphenyl)amino]carbonyl}phenoxy)pyridin-2-yl]-1H-pyrrole-3-carboxamide;

(10) N-(2-fluoro-5-methylphenyl)-3-[(2-{4-[(3-hydroxypyrrolidin-1-yl)carbonyl]-1H-pyrrol-2-yl}pyridin-4-yl)oxy]benzamide;

(11') 5-[4-(3-{[(2-fluoro-5-methylphenyl)amino]carbonyl}phenoxy)pyridin-2-yl]-N-hydroxy-1H-pyrrole-3-carboxamide;

(12') methyl 5-[4-(2-fluoro-5-{[(2-fluoro-5-methylphenyl) amino]carbonyl}phenoxy)pyridin-2-yl]-1H-pyrrole-3-carboxylate;
(13') 5-[4-(2-fluoro-5-{[(2-fluoro-5-methylphenyl)amino] carbonyl}phenoxy)pyridin-2-yl]-1H-pyrrole-3-carboxylic acid;
(14') N-ethyl-5-(4-{3-[(3-methyl-2-furoyl)amino] phenoxy}pyridin-2-yl)-1H-pyrrole-3-carboxamide;
(15') N-(2,3-dihydroxypropyl)-5-(4-{3-[(3-methyl-2-furoyl) amino]phenoxy}pyridin-2-yl)-1H-pyrrole-3-carboxamide;
(16') 5-(4-{3-[(3-methyl-2-furoyl)amino]phenoxy}pyridin-2-yl)-1H-pyrrole-3-carboxamide;
(17') N-hydroxy-5-(4-{3-[(3-methyl-2-furoyl)amino] phenoxy}pyridin-2-yl)-1H-pyrrole-3-carboxamide;
(18') N-(3-{[2-(4-{[(3R)-3-hydroxypyrrolidin-1-yl]carbonyl}-1H-pyrrol-2-yl)pyridin-4-yl]oxy}phenyl)-3-methyl-2-furamide;
(19') 5-[4-(3-{[(2-fluoro-5-methylphenyl)amino] carbonyl}phenoxy)pyridin-2-yl]-1H-pyrrole-3-carboxylic acid;
(20') methyl 5-[4-(3-{[(2-fluoro-5-methylphenyl)amino] carbonyl}phenoxy)pyridin-2-yl]-1H-pyrrole-3-carboxylate;
(21') 2,3-dihydroxypropyl 5-(4-{3-[(3-methyl-2-furoyl) amino]phenoxy}pyridin-2-yl)-1H-pyrrole-3-carboxylate;
(22') 5-[4-(3-{[(3-methylphenyl)amino]carbonyl}phenoxy) pyridin-2-yl]-1H-pyrrole-3-carboxylic acid;
(23') methyl 5-[4-(3-{[(3-methylphenyl)amino] carbonyl}phenoxy)pyridin-2-yl]-1H-pyrrole-3-carboxylate;
(24') 2-hydroxyethyl 5-[4-(3-{[(3-methyl-2-thienyl)carbonyl]amino}phenoxy)pyridin-2-yl]-1H-pyrrole-3-carboxylate;
(25') 2-hydroxyethyl 5-(4-{3-[(3-methyl-2-furoyl)amino] phenoxy}pyridin-2-yl)-1H-pyrrole-3-carboxylate;
(26') 5-[4-(3-{[(3-methyl-2-thienyl)carbonyl] amino}phenoxy)pyridin-2-yl]-1H-pyrrole-3-carboxylic acid;
(27') methyl 5-[4-(3-{[(3-methyl-2-thienyl)carbonyl] amino}phenoxy)pyridin-2-yl]-1H-pyrrole-3-carboxylate;
(28') 5-(4-{4-fluoro-3-[(3-methyl-2-furoyl)amino] phenoxy}pyridin-2-yl)-1H-pyrrole-3-carboxylic acid;
(29') methyl 5-(4-{4-fluoro-3-[(3-methyl-2-furoyl)amino] phenoxy}pyridin-2-yl)-1H-pyrrole-3-carboxylate;
(30') N-[dimethyl(oxido)-lambda~4~-sulfanylidene]-5-(4-{3-[(3-methyl-2-furoyl)amino]phenoxy}pyridin-2-yl)-1H-pyrrole-3-carboxamide;
(31') N-(3-{[2-(4-{[(3S)-3-hydroxypyrrolidin-1-yl]carbonyl}-1H-pyrrol-2-yl)pyridin-4-yl]oxy}phenyl)-3-methyl-2-furamide;
(32') 5-(4-{3-[(3-methyl-2-furoyl)amino]phenoxy}pyridin-2-yl)-1H-pyrrole-3-carboxylic acid;
(33') methyl 5-(4-{3-[(3-methyl-2-furoyl)amino] phenoxy}pyridin-2-yl)-1H-pyrrole-3-carboxylate;
(34') 3-methyl-N-(3-[2-(1H-pyrrol-2-yl)pyridin-4-yl]oxy phenyl)-2-furamide;
(35') methyl 4-(4-{3-[(3-methyl-2-furoyl)amino] phenoxy}pyridin-2-yl)-1H-pyrrole-2-carboxylate;
(36') 2-fluoro-5-methyl-N-(4-[2-(1H-pyrrol-2-yl)pyridin-4-yl]oxy phenyl)benzamide; and (37') 3-methyl-N-(4-[2-(1H-pyrrol-2-yl)pyridin-4-yl]oxy phenyl)-2-furamide.

(9) The compound according to paragraph 1, wherein Z is $(CH_2)_iN(R^7)C(O)N(R^8)(CH_2)_j$ or $(CH_2)_iN(R^7)C(S)N(R^8)(CH_2)_j$, provided that when Ring B is pyrazole, $R^{IV}$ is not a phenyl or substituted phenyl.

(10) The compound according to paragraph 9, wherein Y is selected from the group consisting of —$(CH_2)$g-O—$(CH_2)$h-; —$(CH_2)$g-$NR^1$—$(CH_2)$h-; —$(CH_2)$g-$S(O)_n$—$(CH_2)$h-; —$(CH_2)$g-$SO_2NR^2$—$(CH_2)$h-; —$(CH_2)$g-$NR^2SO_2$—$(CH_2)$h-; —$(CH_2)$g-CO—$(CH_2)$h-; —$(CH_2)$g-$C(O)NR^2$—$(CH_2)$h-; —$(CH_2)$g-$NR^2C(O)$—$(CH_2)$h-; —$(CH_2)$g-C≡C—$(CH_2)$h-; —$(CH_2)$g-$NR^2C(O)NR^3$—$(CH_2)_n$, and a single bond.

(11) The compound according to paragraph 9, wherein Y is selected from the group consisting of —$(CH_2)$g-$(CH_2)$h-; —$(CH_2)$g-$CF_2$—$(CH_2)$h-; —$(CH_2)$g-$CCl_2$—$(CH_2)$h-; —$(CH_2)$g-CHF—$(CH_2)$h-; —$(CH_2)$g-CH(OH)—$(CH_2)$h-; —$(CH_2)$g-$CR^2R^3$—$(CH_2)$h-; and —$(CH_2)$g-C═C—$(CH_2)$h-.

(12) The compound according to paragraphs 9-11, wherein Ring A and Ring B are independently selected from the group consisting of

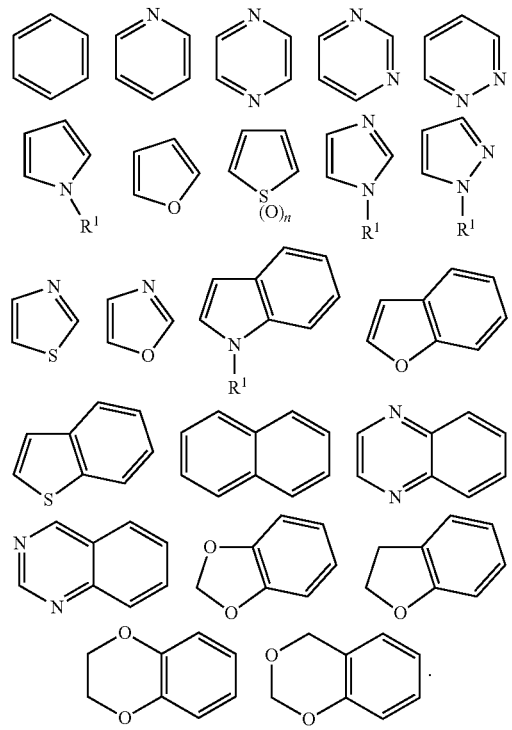

(13) The compound according to paragraphs 9-12, wherein X is NH.
(14) The compound according to paragraphs 9-12, wherein X is S.
(15) The compound according to paragraphs 9-14, wherein $R^I$ is selected from the group consisting of hydrogen, halogen, $C_1$ to $C_8$ alkyl, $(CR^5R^6)_dC(O)OR^4$, $(CR^5R^6)_dAr$, $NR^4(CR^5R^6)_dAr$, $(CR^5R^6)_dC(O)N(R^4)_2$, $NR^4(CR^5R^6)_dC(O)N(R^4)_2$, $O(CR^5R^6)_dC(O)N(R^4)_2$, $(CR^5, R^6)_dOR^4$, $OC(O)(CR^5R^6)_dN(R^4)_2$, $C(O)(CR^5R^6)_dN(R^4)_2$, $C(O)N═S(O)R^5R^6$, $NR^2C(O)(CR^5R^6)_dN(R^4)_2$, $(CR^5R^6)_dR^5$, $HNC(O)R^4$, HN—$C(O)OR^4$, $(CR^5R^6)_dN(R^4)_2$, $S(O)_f(CR^5R^6)_dN(R^4)_2$, $OC(O)OR^4$, $(CR^5R^6)_dC(O)(CR^5R^6)_dR^4$, $(CR^5R^6)_dC(O)(CR^5R^6)_dOR^4$, and $(CR^5R^6)_dC(O)(CR^5R^6)_dN(R^4)_2$, wherein each $R^4$ is independently selected from the group consisting of hydrogen, hydroxyl, $C_1$-$C_8$ alkyl, aryl, $C_1$-$C_8$ hydroxyalkyl, $C_1$-$C_8$ alkoxyalkyl, $(CR^5R^6)_d$ and $N(R^4)_2$ may form a 3-7 membered heterocyclic ring, comprising of aziridine, azetidine, pyrrolidine, 5-fluoropyrrolidine, piperidine, 6-fluoropiperidine, N-methylpiperazine, morpholine, 2,6-dimethylmorpholine, thiomorpholine, and wherein said heterocyclic ring may be optionally substituted with up to three of $R^5$; wherein $R^5$ and $R^6$ are independently selected from the group consisting of hydrogen, halo, hydroxyl, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl, sulfonate and $CR^5R^6$ may represent a carbocyclic or heterocyclic ring of from 5 to 6 carbons or alternatively, $(CR^5R^6)_d$ and $(CR^5R^6)_e$ may form a 3-7 membered carbocyclic or heterocyclic ring, wherein the ring may be optionally substituted with up to three of hydroxyl, halo, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl and sulfonate.

(16) A compound of Formula II:

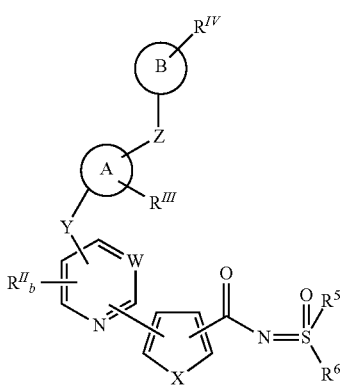

Formula II wherein

W is C or N;

X is selected from the group consisting of $NR^1$, O, and $S(O)_n$;

n is 0 or an integer of from 1 to 2;

$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl($NR^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;

$R^5$ and $R^6$ are independently selected from the group consisting of hydrogen, halo, hydroxyl, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl, sulfonate;

$R^{II}$ is independently selected from the group consisting of hydrogen, alkoxy, alkoxyalkoxy, alkoxyalkyl, alkyl, aryloxy, aryloxyalkyl, halo, haloalkoxy, haloalkyl, hydroxy, hydroxyalkoxy, hydroxyalkyl, ($NR^2R^3$)alkoxy, ($NR^2R^3$)alkenyl, ($NR^2R^3$)alkyl, ($NR^2R^3$)carbonylalkenyl, and ($NR^2R^3$)carbonylalkyl, wherein $R^2$ and $R^3$ are independently selected from the group consisting of hydrogen, alkyl, alkylcarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;

b is 0 or an integer of from 1 to 2;

Y is selected from the group consisting of:

(1') —$(CH_2)$g-O—$(CH_2)$h-;
(2') —$(CH_2)$g-$NR^1$—$(CH_2)$h-;
(3') —$(CH_2)$g-$S(O)_n$—$(CH_2)$h-;
(4') —$(CH_2)$g-$SO_2NR^2$—$(CH_2)$h-;
(5') —$(CH_2)$g-$NR^2SO_2$—$(CH_2)$h-;
(6') —$(CH_2)$g-CO—$(CH_2)$h-;
(7') —$(CH_2)$g-$C(O)NR^2$—$(CH_2)$h-;
(8') —$(CH_2)$g-$NR^2C(O)$—$(CH_2)$h-;
(9') —$(CH_2)$g-C≡C—$(CH_2)$h-;
(10') —$(CH_2)$g-$NR^2C(O)NR^3$—$(CH_2)$h-;
(11') —$(CH_2)$g-$(CH_2)$h-;
(12') —$(CH_2)$g-$CF_2$—$(CH_2)$h-;
(13') —$(CH_2)$g-$CCl_2$—$(CH_2)$h-;
(14') —$(CH_2)$g-CHF—$(CH_2)$h-;
(15') —$(CH_2)$g-CH(OH)—$(CH_2)$h-;
(16') —$(CH_2)$g-$CR^2R^3$—$(CH_2)$h-;
(17') —$(CH_2)$g-C=C—$(CH_2)$h-;
and (18') a single bond;

wherein g is 0 or an integer of from 1 to 3;

h is 0 or an integer of from 1 to 3;

$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl(N $R^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;

$R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered cyclic ring;

Ring A is selected from the group consisting of:

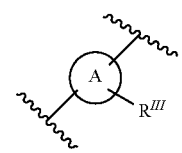

(i) Phenyl;
(ii) Naphthyl;
(iii) A 5 or 6 membered monocyclic heteroaryl group which have 1-5 heteroatoms independently selected from the group consisting of O, N and S;
and (iv) An 8 to 10 membered bicyclic heteroaryl group which have 1-6 heteroatoms independently selected from the group consisting of O, N and S;

Ring A can be illustrated but not limited to the following:

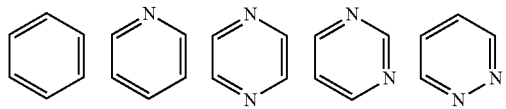

-continued

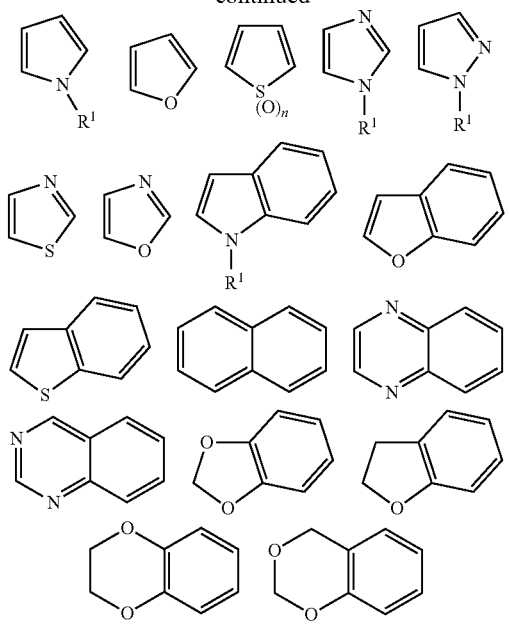

wherein
R¹ is independently selected from the group consisting of hydrogen, alkenyl, alkoxyalkyl, CF₃, alkyl, alkylcarbonyl, alkoxycarbonyl, aryl, heterocycloalkyl, hydroxyalkyl, and alkyl(NR²R³), wherein R² and R³ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively R² and R³ and may be taken together to form a 5-7 membered heterocyclic ring with N;

$R^{III}$ represents optionally 1-3 substituents independently selected from the group consisting of $C_1$-$C_5$ linear or branched alkyl, $C_1$-$C_5$ linear or branched haloalkyl, $C_1$-$C_5$ alkoxy, hydroxy, amino, $C_1$-$C_5$ alkylamino, C1-C6 dialkylamino, halogen, cyano, and nitro;

Z is selected from the group consisting of
(1') $(CH_2)_iN(R^7)C(O)N(R^8)(CH_2)_j$;
(2') $(CH_2)_iN(R^7)C(S)N(R^8)(CH_2)_j$;
(3') $(CH_2)_iN(R^7)C(O)$;
(4') $C(O)N(R^8)(CH_2)_j$;
(5') $(CH_2)_iN(R^7)S(O)_2$;
and (6') $S(O)_2N(R^8)(CH_2)_j$;
wherein
i is 0 or 1;
j is 0 or 1;
R⁷ and R⁸ are independently selected from the group consisting of hydrogen and alkyl;
Ring B is selected from the group consisting of:

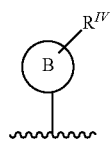

(i') Phenyl;
(ii') Naphthyl;
(iii') A 5 or 6 membered monocyclic heteroaryl group which have 1-3 heteroatoms independently selected from the group consisting of O, N and S;

and (iv') An 8 to 10 membered bicyclic heteroaryl group which have 1-3 heteroatoms independently selected from the group consisting of O, N and S;

Ring B can be illustrated but not limited to the following:

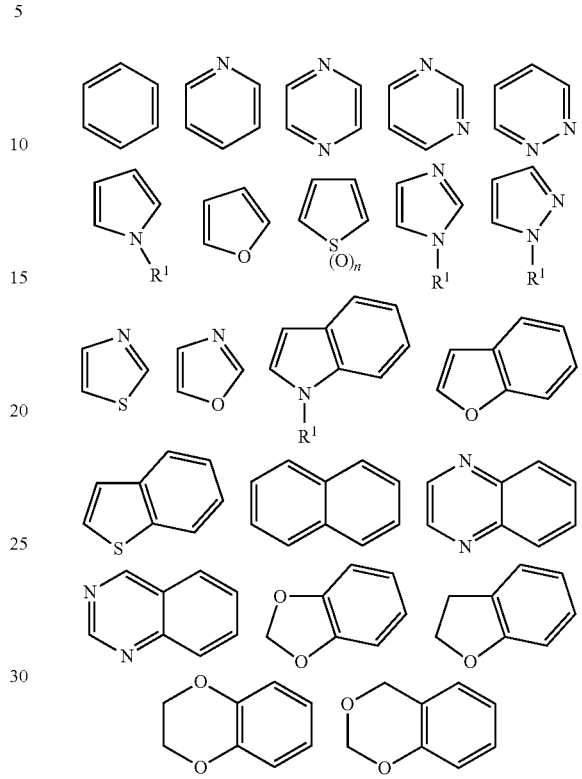

wherein
R¹ is independently selected from the group consisting of hydrogen, alkenyl, alkoxyalkyl, CF₃, alkyl, alkylcarbonyl, alkoxycarbonyl, aryl, heterocycloalkyl, hydroxyalkyl, and alkyl(NR²R³), wherein R² and R³ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively R² and R³ and may be taken together to form a 5-7 membered heterocyclic ring with N;

$R^{IV}$ represents optionally 1-3 substituents, independently selected from the group consisting of alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —NR⁹R¹⁰; wherein R⁹ and R¹⁰ are independently selected from the group consisting of hydrogen, alkyl, alkylcarbonyl, aryl, arylalkyl, cycloalkyl, cycloalkylalkyl, heterocyclyl, and heterocyclylalkyl;

and any pharmaceutical acceptable salt or prodrug.

(17) The compound according to paragraph 16, wherein Z is selected from the group consisting of $(CH_2)_iN(R^2)C(O)$, $C(O)N(R^8)(CH_2)_j$, $(CH_2)_iN(R^2)C(O)N(R^8)(CH_2)_j$ and $(CH_2)_iN(R^2)C(S)N(R^8)(CH_2)_j$.

(18) The compound according to paragraphs 16-17, wherein Y is selected from the group consisting of —(CH₂)g-O—(CH₂)h-; —(CH₂)g-NR¹—(CH₂)h-; —(CH₂)g-S(O)—, —(CH₂)h-; —(CH₂)g-SO₂NR²—(CH₂)h-; —(CH₂)g-NR²SO₂—(CH₂)h-; —(CH₂)g-CO—(CH₂)h-; —(CH₂)g-C(O)NR²—(CH₂)h-; —(CH₂)g-NR²C(O)—(CH₂)h-; —(CH₂)g-C≡C—(CH₂)h-; —(CH₂)g-NR²C(O)NR³—(CH₂)h and a single bond.

(19) The compound according to paragraphs 16-18, wherein Ring A and Ring B are independently selected from the group consisting of

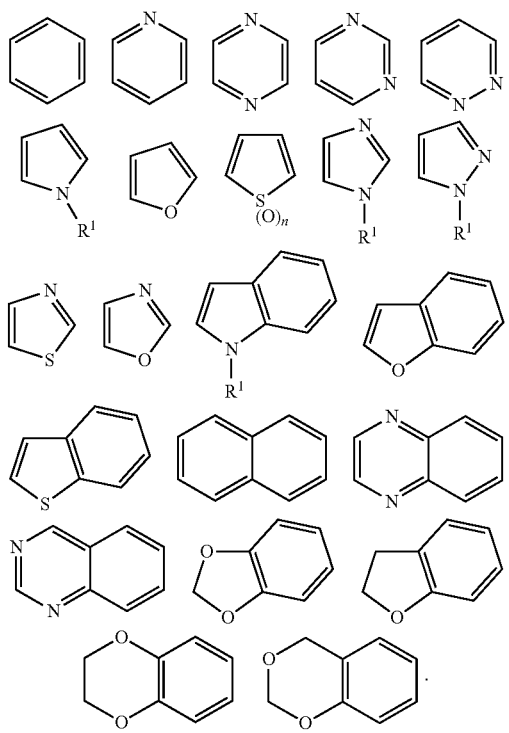

(20) The compound according to paragraphs 16-19, wherein W is C.
(21) A method of use of the compounds of paragraphs 1-20, wherein the compounds are used as tyrosine kinase modulators;
(22) Use of the compounds of paragraphs 1-20 in the preparation of a medicament for the treatment or prevention of diseases or conditions related with unregulated tyrosine kinase activities, comprising administering a therapeutically effective amount of the compound of paragraphs 1-20 together with a pharmaceutically acceptable carrier;
(23) The use of paragraph 22, wherein the diseases or conditions are selected from the group consisting of cell growth and metabolic disorders, blood vessel proliferative disorders, inflammatory disorders, neurodegenerative diseases, and immune disorders.
(24) The use of paragraphs 22-23 wherein the diseases or conditions are selected from the group consisting of colorectal cancer, lung cancer, hematological cancer, renal cancer, liver cancer, breast cancer, diabetic retinopathy, macular degeneration, age-related macular degeneration, retinopathy of prematurity, ocular angiogenesis, retinal edema, retinal ischemia, diabetic macular edema, cystoid macular edema, retinal vein occlusion, branch vein occlusion, preretinal neovascularization, laser-induced choroidal neovascularization, neovascularization associated with keratoplasty, glaucoma and ocular tumors, arthritis, restenosis, hepatic cirrhosis, atherosclerosis, psoriasis, diabetes mellitus, wound healing, inflammation, neurodegenerative diseases and immune disorders.
(25) The use of paragraphs 22-23 wherein the conditions and diseases are wound healing or to alleviate transplant rejection.
(26) A pharmaceutical composition comprising a therapeutic effective amount of a compound according to paragraphs 1-20 together with a pharmaceutically acceptable carrier which is suitable for systematic, parenteral, local or topical delivery.
(27) The pharmaceutical composition of paragraph 26, which are in the form selected from the group comprising of tablets, capsules, intravenous injections, intramuscular injections, local injections, topical creams, gels and ointments, eye drops, ophthalmic solutions, ophthalmic suspensions, ophthalmic emulsions, intravitreal injections, subtenon injections, ophthalmic bioerodible implant, and non-bioerodible ophthalmic inserts or depots.
(28) Use of the compounds of paragraphs 1-20 in the preparation of a medicament for the treatment of diseases and conditions, wherein the medicament contains pharmaceutical acceptable composition according to paragraphs 26 and 27.

DETAILED DESCRIPTION OF THE INVENTION

Figure 1:
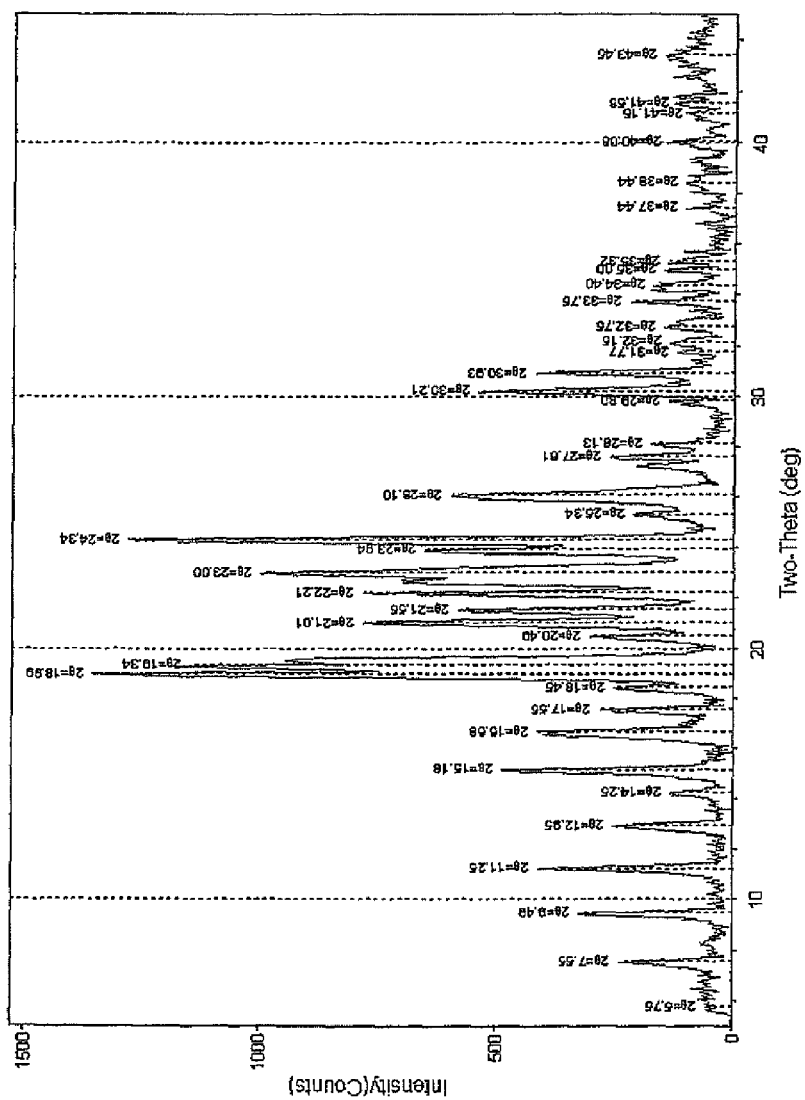
FIG. 1 shows a powder X-Ray Diffraction (XRPD) of Example 78.
Figure 2:
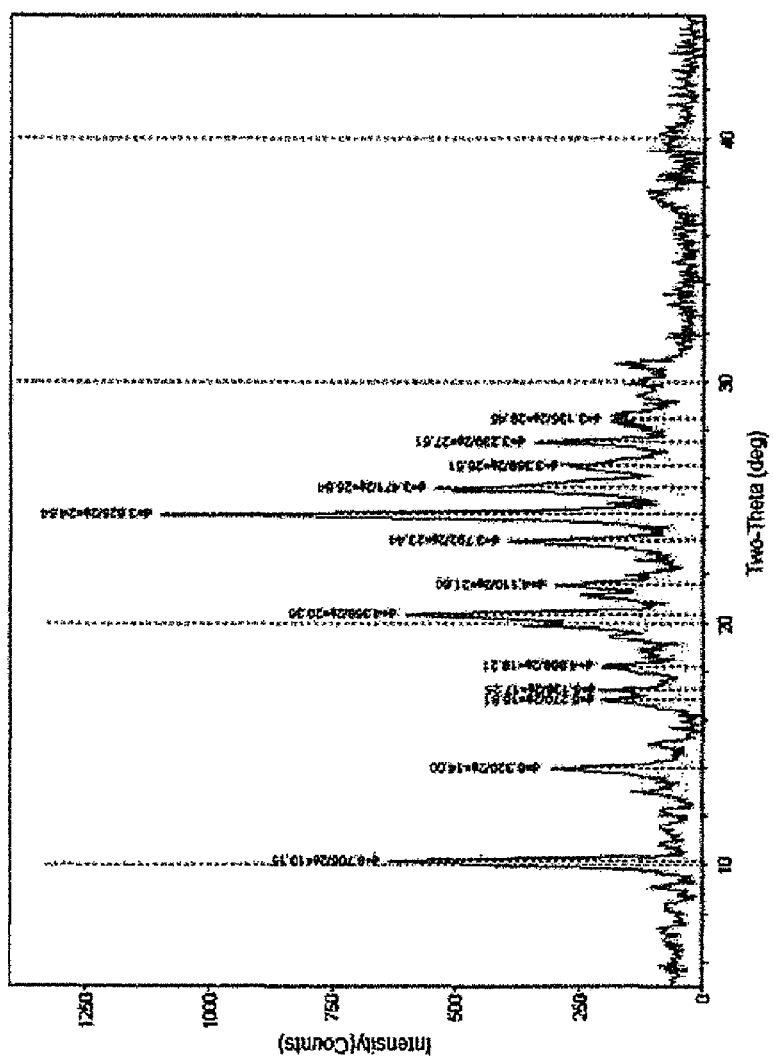
FIG. 2 shows a powder X-Ray Diffraction (XRPD) of Example 69.
Figure 3:
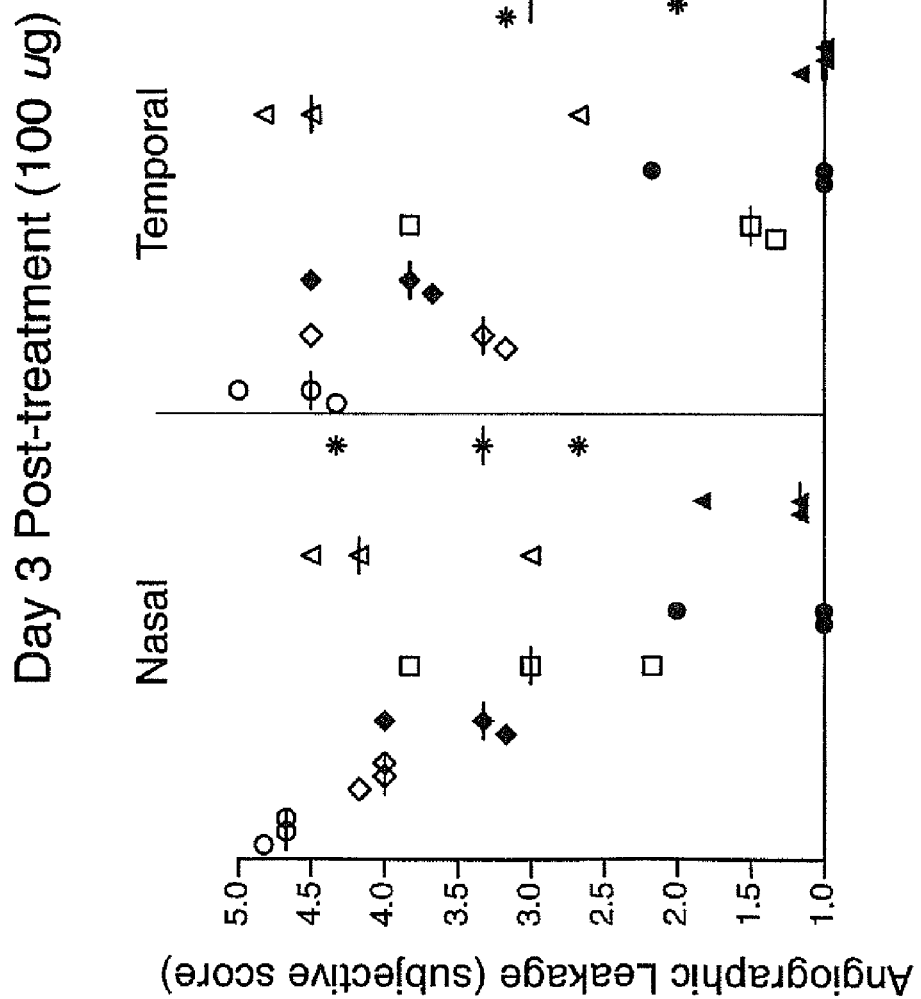
FIG. 3 shows a fluorescein angiography (blood-retinal barrier breakdown) of Example 121, Example 84 Sodium, Example 83, Example 78, Example 75 Sodium, Example 69, and Example 66.
Figure 4:
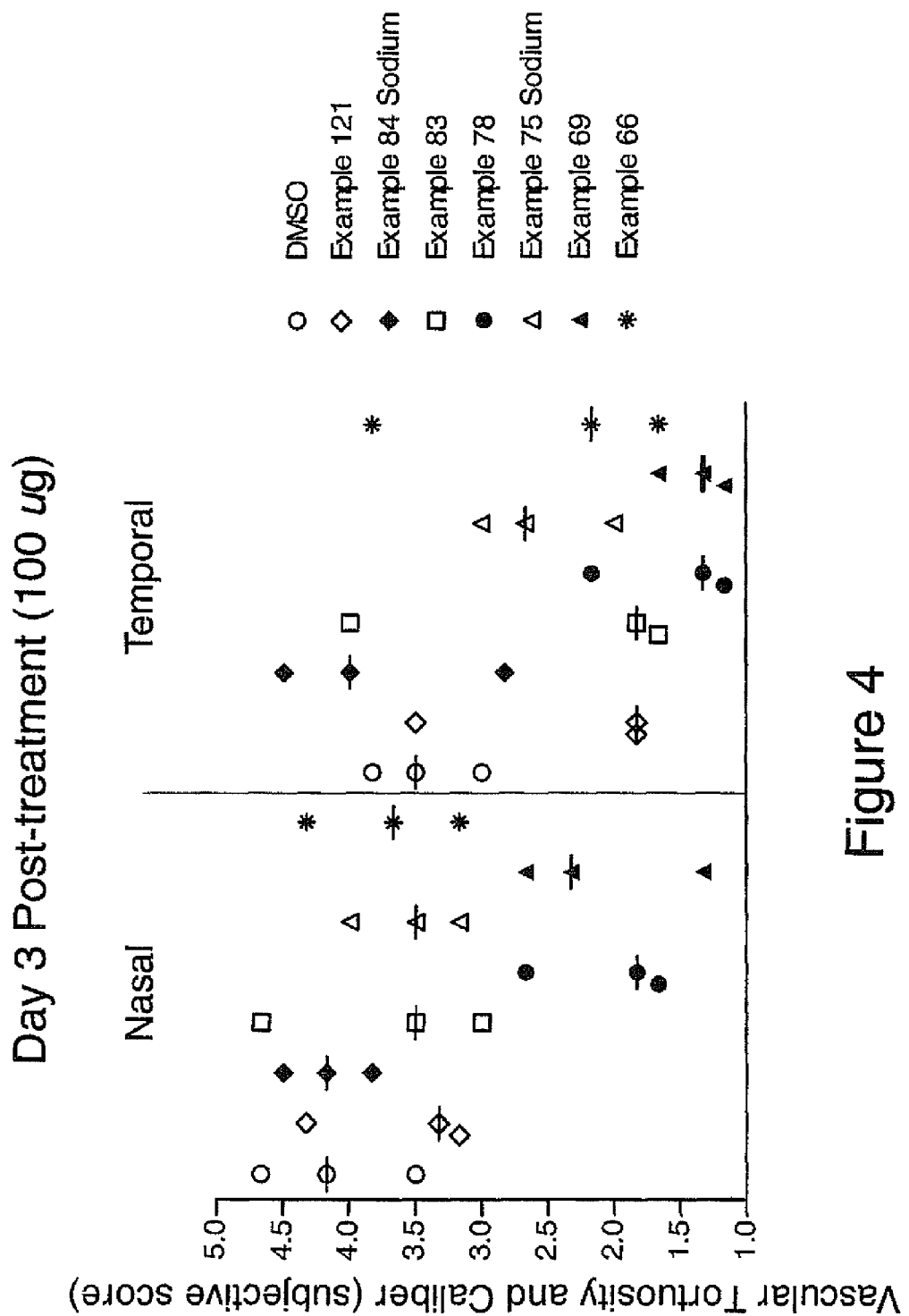
FIG. 4 shows a fundus photography (retinal vasodilation and vessel tortuosity) of Example 121, Example 84 Sodium, Example 83, Example 78, Example 75 Sodium, Example 69, and Example 66.

The present invention is directed to a series of compounds with multiple aromatic components useful as protein tyrosine kinase inhibitors. The compounds of the present invention are useful for treating diseases related to unregulated tyrosine kinase signal transduction, for example, cancer, blood vessel proliferative disorders, fibrotic disorders, and neurodegenerative diseases. In particular, compounds of the present invention are useful for the treatment of colorectal cancer, lung cancer, hematological cancer, renal cancer, liver cancer, breast cancer, diabetic retinopathy, macular degeneration, age-related macular degeneration, retinopathy of prematurity, ocular angiogenesis, retinal edema, retinal ischemia, diabetic macular edema, cystoid macular edema, retinal vein occlusion, branch vein occlusion, preretinal neovascularization, laser-induced choroidal neovascularization, neovascularization associated with keratoplasty, glaucoma and ocular tumors, arthritis, restenosis, hepatic cirrhosis, atherosclerosis, psoriasis, diabetes mellitus, wound healing, transplant rejection, inflammation, neurodegenerative diseases and immune disorders.

1. Compounds of the Invention

In one aspect of the invention, the compounds of the present invention can be represented by the general formula I:

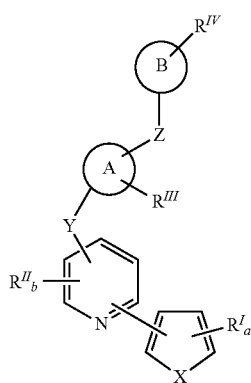

Formula I wherein

X is selected from the group consisting of NR¹, O, and S(O)$_n$;

n is 0 or an integer of from 1 to 2;

R¹ is independently selected from the group consisting of hydrogen, alkenyl, alkoxyalkyl, CF$_3$, alkyl, alkylcarbonyl, alkoxycarbonyl, aryl, heterocycloalkyl, hydroxyalkyl, and alkyl(NR²R³), wherein R² and R³ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively R² and R³ and may be taken together to form a 5-7 membered heterocyclic ring with N;

R$^I$ is selected from the group consisting of hydrogen, halogen, C$_1$ to C$_8$ alkyl, S(O)$_f$R⁴, (CR⁵R⁶)$_d$C(O)OR⁴, S(O)$_f$(CR⁵R⁶)$_d$C(O)OR⁴, (CR⁵R⁶)$_d$Ar, NR⁴(CR⁵R⁶)$_d$Ar, O(CR⁵R⁶)$_d$Ar, S(O)$_f$(CR⁵R⁶)$_d$Ar, (CR⁵R⁶)$_d$S(O)$_f$R⁴, NR⁴(CR⁵R⁶)$_d$S(O)$_f$R⁴, O(CR⁵R⁶)$_d$S(O)$_f$R⁴, S(O)$_f$(CR⁵R⁶)$_e$S(O)$_f$R⁴, (CR⁵R⁶)$_d$C(O)N(R⁴)$_2$, NR⁴(CR⁵R⁶)$_d$C(O)N(R⁴)$_2$, O(CR⁵R⁶)$_d$C(O)N(R⁴)$_2$, S(O)$_f$(CR⁵R⁶)$_e$C(O)N(R⁴)$_2$, (CR⁵R⁶)$_d$OR⁴, S(O)$_f$(CR⁵R⁶)$_d$OR⁴, (CR⁵R⁶)$_d$OSO$_2$R⁴, S(O)$_f$(CR⁵R⁶)$_e$OSO$_2$R⁴, (CR⁵R⁶)$_d$P(O)(OR⁴)$_2$, S(O)$_f$(CR⁵R⁶)$_e$P(O)(OR⁴)$_2$, OC(O)(CR⁵R⁶)$_d$N(R⁴)$_2$, C(O)(CR⁵R⁶)$_d$N(R⁴)$_2$, C(O)N=S(O)R⁵R⁶, NR²C(O)(CR⁵R⁶)$_d$N(R⁴)$_2$, (CR⁵R⁶)$_d$R⁵, S(O)$_f$(CR⁵R⁶)$_d$R⁵, HNC(O)R⁴, HN—C(O)OR⁴, (CR⁵R⁶)$_d$N(R⁴)$_2$, S(O)$_f$(CR⁵R⁶)$_d$N(R⁴)$_2$, OC(O)OR⁴, (CR⁵R⁶)$_d$C(O)(CR⁵R⁶)$_d$R⁴, (CR⁵R⁶)$_d$C(O)(CR⁵R⁶)$_d$OR⁴, and (CR⁵R⁶)$_d$C(O)(CR⁵R⁶)$_d$N(R⁴)$_2$, wherein each R⁴ is independently selected from the group consisting of hydrogen, hydroxyl, C$_1$-C$_8$ alkyl, aryl, C$_1$-C$_8$ hydroxyalkyl, C$_1$-C$_8$ alkoxyalkyl, (CR⁵R⁶)$_d$ and N(R⁴)$_2$ may form a 3-7 membered heterocyclic ring, comprising of aziridine, azetidine, pyrrolidine, 5-fluoropyrrolidine, piperidine, 6-fluoropiperidine, N-methylpiperazine, morpholine, 2,6-dimethylmorpholine, thiomorpholine, and wherein said heterocyclic ring may be optionally substituted with up to three of R⁵; wherein R⁵ and R⁶ are independently selected from the group consisting of hydrogen, halo, hydroxyl, C$_1$-C$_8$ alkyl, C$_1$-C$_8$ hydroxyalkyl, C$_1$-C$_8$ alkoxyalkyl, alkoxycarbonylalkyl, alkoxycarbonyl, hydroxycarbonyl, hydroxycarbonylalkyl, amide, alkylamide, amidoalkyl, sulfonate and CR⁵R⁶ may represent a carbocyclic or heterocyclic ring of from 5 to 6 carbons or alternatively, (CR⁵R⁶)$_d$ and (CR⁵R⁶)$_e$ may form a 3-7 membered carbocyclic or heterocyclic ring, wherein the ring may be optionally substituted with up to three of hydroxyl, halo, C$_1$-C$_8$ alkyl, C$_1$-C$_8$ hydroxyalkyl, C$_1$-C$_8$ alkoxyalkyl, alkoxycarbonylalkyl, alkoxycarbonyl, hydroxycarbonyl, hydroxycarbonylalkyl, amide, alkylamide, amidoalkyl and sulfonate;

a is 0 or an integer of from 1 to 3;
d is 0 or an integer of from 1 to 5;
e is an integer of from 1 to 4;
f is 0 or an integer of from 1 to 2;

R$^{II}$ is independently selected from the group consisting of hydrogen, alkoxy, alkoxyalkoxy, alkoxyalkyl, alkyl, aryloxy, aryloxyalkyl, halo, haloalkoxy, haloalkyl, hydroxy, hydroxyalkoxy, hydroxyalkyl, (NR²R³)alkoxy, (NR²R³)alkenyl, (NR²R³)alkyl, (NR²R³)carbonylalkenyl, and (NR²R³)carbonylalkyl, wherein R² and R³ are independently selected from the group consisting of hydrogen, alkyl, alkylcarbonyl, alkylsulfonyl, arylsulfonyl, haloalkylsulfonyl, and heterocyclylsulfonyl; alternatively R² and R³ and may be taken together to form a 5-7 membered heterocyclic ring with N;

b is 0 or an integer of from 1 to 2;

Y is selected from the group consisting of:
(1') —(CH$_2$)g-O—(CH$_2$)h-;
(2') —(CH$_2$)g-NR¹—(CH$_2$)h-;
(3') —(CH$_2$)g-S(O)$_n$—(CH$_2$)h-;
(4') —(CH$_2$)g-SO$_2$NR²—(CH$_2$)h-;
(5') —(CH$_2$)g-NR²SO$_2$—(CH$_2$)h-;
(6') —(CH$_2$)g-CO—(CH$_2$)h-;
(7') —(CH$_2$)g-C(O)NR²—(CH$_2$)h-;
(8') —(CH$_2$)g-NR²C(O)—(CH$_2$)h-;
(9') —(CH$_2$)g-C≡C—(CH$_2$)h-;
(10') —(CH$_2$)g-NR²C(O)NR³—(CH$_2$)h-;
(11') —(CH$_2$)g-(CH$_2$)h-;
(12') —(CH$_2$)g-CF$_2$—(CH$_2$)h-;
(13') —(CH$_2$)g-CCl$_2$—(CH$_2$)h-;
(14') —(CH$_2$)g-CHF—(CH$_2$)h-;
(15') —(CH$_2$)g-CH(OH)—(CH$_2$)h-;
(16') —(CH$_2$)g-CR²R³—(CH$_2$)h-;
(17') —(CH$_2$)g-C≡C—(CH$_2$)h-;
and (18') a single bond.

wherein
g is 0 or an integer of from 1 to 3;
h is 0 or an integer of from 1 to 3;

R¹ is independently selected from the group consisting of hydrogen, alkenyl, alkoxyalkyl, CF$_3$, alkyl, alkylcarbonyl, alkoxycarbonyl, aryl, heterocycloalkyl, hydroxyalkyl, and alkyl(NR²R³), wherein R² and R³ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively R² and R³ and may be taken together to form a 5-7 membered heterocyclic ring with N;

R² and R³ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively R² and R³ and may be taken together to form a 5-7 membered cyclic ring;

Ring A is selected from the group consisting of:

(i) Phenyl;
(ii) Naphthyl;

(iii) A 5 or 6 membered monocyclic heteroaryl group which have 1-5 heteroatoms independently selected from the group consisting of O, N and S;

and (iv) An 8 to 10 membered bicyclic heteroaryl group which have 1-6 heteroatoms independently selected from the group consisting of O, N and S;

Ring A can be illustrated but not limited to the following:

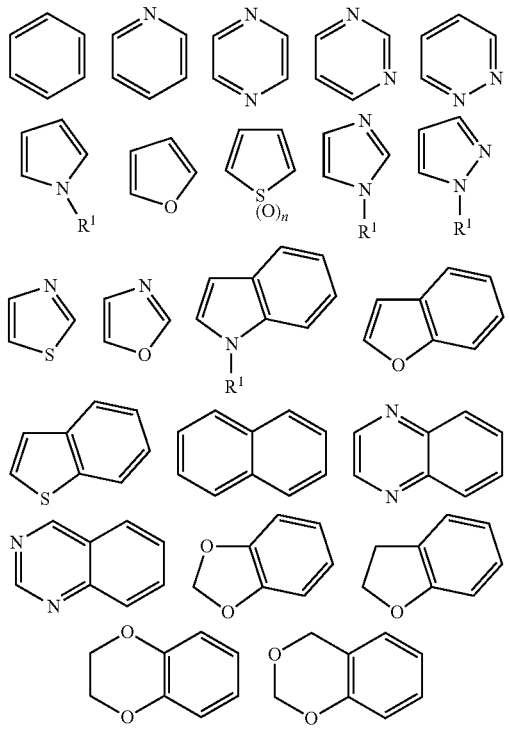

wherein
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl($NR^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N.

$R^{III}$ represents optionally 1-3 substituents independently selected from the group consisting of $C_1$-$C_5$ linear or branched alkyl, $C_1$-$C_5$ linear or branched haloalkyl, $C_1$-$C_5$ alkoxy, hydroxy, amino, $C_1$-$C_5$ alkylamino, $C_1$-$C_6$ dialkylamino, halogen, cyano, and nitro;

Z is selected from the group consisting of
(1') $(CH_2)_iN(R^7)C(O)N(R^8)(CH_2)_j$;
(2') $(CH_2)_iN(R^7)C(S)N(R^8)(CH_2)_j$;
(3') $(CH_2)_iN(R^7)C(O)$;
(4') $C(O)N(R^8)(CH_2)_j$;
(5') $(CH_2)_iN(R^7)S(O)_2$;
and (6') $S(O)_2N(R^8)(CH_2)_j$;

wherein
i is 0 or 1;
j is 0 or 1;
$R^7$ and $R^8$ are independently selected from the group consisting of hydrogen and alkyl;

Ring B is selected from the group consisting of:

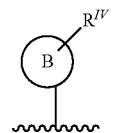

(i') Phenyl;
(ii') Naphthyl;
(iii') A 5 or 6 membered monocyclic heteroaryl group which have 1-3 heteroatoms independently selected from the group consisting of O, N and S;
and (iv') An 8 to 10 membered bicyclic heteroaryl group which have 1-3 heteroatoms independently selected from the group consisting of O, N and S;
Ring B can be illustrated but not limited to the following:

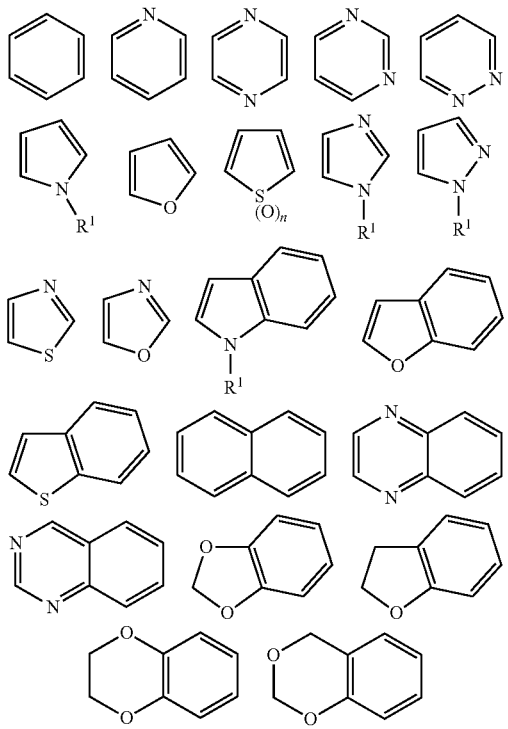

wherein
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl($NR^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;
$R^{IV}$ represents optionally 1-3 substituents, independently selected from the group consisting of hydrogen, alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —$NR^9R^{10}$; wherein $R^9$ and $R^{10}$ are independently selected from the group consisting of hydrogen, alkyl, alkylcarbonyl, aryl, arylalkyl, cycloalkyl, cycloalkylalkyl, heterocyclyl, and heterocyclylalkyl;

In another aspect of the invention, the compounds of the present invention can be represented by the general formula II:

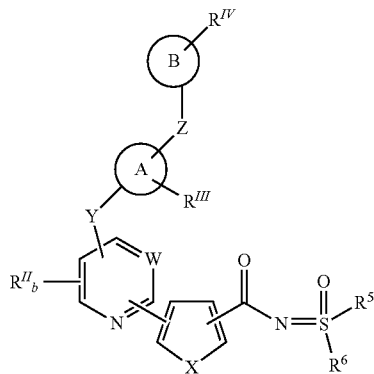

Formula II wherein
W is C or N;
X is selected from the group consisting of $NR^1$, O, and $S(O)_n$;
n is 0 or an integer of from 1 to 2;
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl($NR^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;
$R^5$ and $R^6$ are independently selected from the group consisting of hydrogen, halo, hydroxyl, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl, and sulfonate;
$R^{II}$ is independently selected from the group consisting of hydrogen, alkoxy, alkoxyalkoxy, alkoxyalkyl, alkyl, aryloxy, aryloxyalkyl, halo, haloalkoxy, haloalkyl, hydroxy, hydroxyalkoxy, hydroxyalkyl, $(NR^2R^3)$alkoxy, $(NR^2R^3)$alkenyl, $(NR^2R^3)$alkyl, $(NR^2R^3)$carbonylalkenyl, and $(NR^2R^3)$carbonylalkyl, wherein $R^2$ and $R^3$ are independently selected from the group consisting of hydrogen, alkyl, alkylcarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;
b is 0 or an integer of from 1 to 2;
Y is selected from the group consisting of:
  (1') —$(CH_2)$g-O—$(CH_2)$h-;
  (2') —$(CH_2)$g-$NR^1$—$(CH_2)$h-;
  (3') —$(CH_2)$g-$S(O)_n$—$(CH_2)$h-;
  (4') —$(CH_2)$g-$SO_2NR^2$—$(CH_2)$h-;
  (5') —$(CH_2)$g-$NR^2SO_2$—$(CH_2)$h-;
  (6') —$(CH_2)$g-CO—$(CH_2)$h-;
  (7') —$(CH_2)$g-$C(O)NR^2$—$(CH_2)$h-;
  (8') —$(CH_2)$g-$NR^2C(O)$—$(CH_2)$h-;
  (9') —$(CH_2)$g-C≡C—$(CH_2)$h-;
  (10') —$(CH_2)$g-$NR^2C(O)NR^3$—$(CH_2)$h-;
  (11') —$(CH_2)$g-$(CH_2)$h-;
  (12') —$(CH_2)$g-$CF_2$—$(CH_2)$h-;
  (13') —$(CH_2)$g-$CCl_2$—$(CH_2)$h-;
  (14') —$(CH_2)$g-CHF—$(CH_2)$h-;
  (15') —$(CH_2)$g-CH(OH)—$(CH_2)$h-;
  (16') —$(CH_2)$g-$CR^2R^3$—$(CH_2)$h-;
  (17') —$(CH_2)$g-C=C—$(CH_2)$h-;
  and (18') a single bond;
wherein
g is 0 or an integer of from 1 to 3;
h is 0 or an integer of from 1 to 3;
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl(N $R^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;
$R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered cyclic ring;
Ring A is selected from the group consisting of:

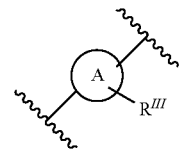

(i) Phenyl;
(ii) Naphthyl;
(iii) A 5 or 6 membered monocyclic heteroaryl group which have 1-5 heteroatoms independently selected from the group consisting of O, N and S;
and (iv) An 8 to 10 membered bicyclic heteroaryl group which have 1-6 heteroatoms independently selected from the group consisting of O, N and S;
Ring A can be illustrated but not limited to the following:

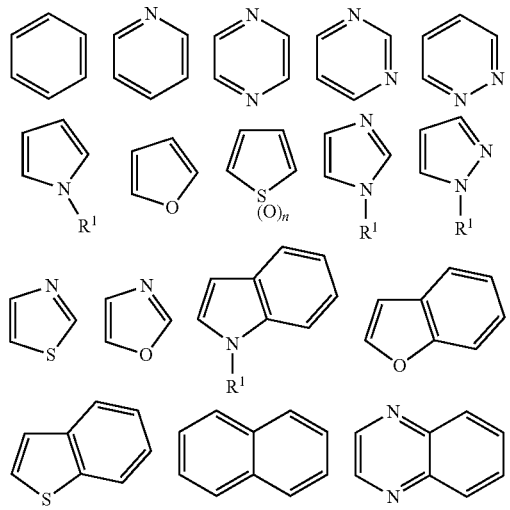

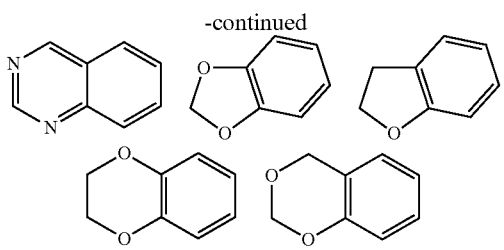

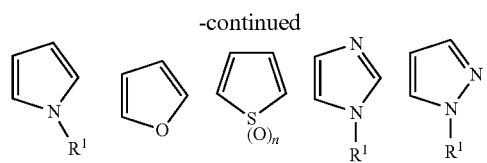

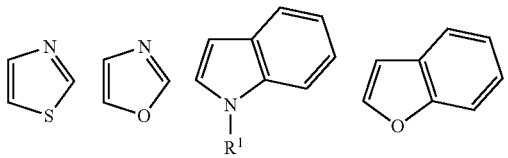

wherein
  R¹ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl($NR^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;
  $R^{III}$ represents optionally 1-3 substituents independently selected from the group consisting of $C_1$-$C_5$ linear or branched alkyl, $C_1$-$C_5$ linear or branched haloalkyl, $C_1$-$C_5$ alkoxy, hydroxy, amino, $C_1$-$C_5$ alkylamino, C1-C6 dialkylamino, halogen, cyano, and nitro;
  Z is selected from the group consisting of
    (1') $(CH_2)_iN(R^7)C(O)N(R^8)(CH_2)_j$;
    (2') $(CH_2)_iN(R^7)C(S)N(R^8)(CH_2)_j$;
    (3') $(CH_2)_iN(R^7)C(O)$;
    (4') $C(O)N(R^8)(CH_2)_j$;
    (5') $(CH_2)_iN(R^7)S(O)_2$;
    and (6') $S(O)_2N(R^8)(CH_2)_j$;
  wherein
    i is 0 or 1;
    j is 0 or 1;
    $R^7$ and $R^8$ are independently selected from the group consisting of hydrogen and alkyl.
  Ring B is selected from the group consisting of:

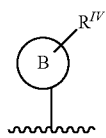

(i') Phenyl;
(ii') Naphthyl;
(iii') A 5 or 6 membered monocyclic heteroaryl group which have 1-3 heteroatoms independently selected from the group consisting of O, N and S;
and (iv') An 8 to 10 membered bicyclic heteroaryl group which have 1-3 heteroatoms independently selected from the group consisting of O, N and S;
  Ring B can be illustrated but not limited to the following:

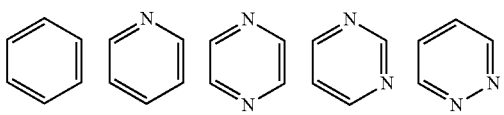

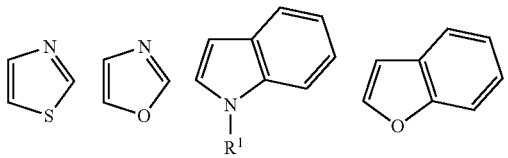

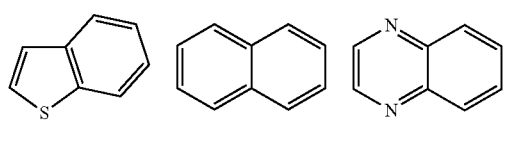

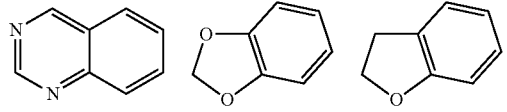

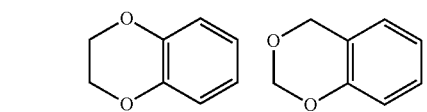

wherein
  R¹ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl(N $R^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;
  $R^{IV}$ represents optionally 1-3 substituents, independently selected from the group consisting of alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —$NR^9R^{10}$; wherein $R^9$ and $R^{10}$ are independently selected from the group consisting of hydrogen, alkyl, alkylcarbonyl, aryl, arylalkyl, cycloalkyl, cycloalkylalkyl, heterocyclyl, and heterocyclylalkyl; and including any pharmaceutically acceptable salt or prodrug.

Unless otherwise indicated, reference to a compound should be construed broadly to include compounds, pharmaceutically acceptable salts, prodrugs, tautomers, stereoisomers, diastereoisomers, alternate solid forms, crystal forms, polymorphic forms, hydrates, solvates, metabolites, mixtures of stereoisomers, mixtures of crystal forms, non-covalent complexes, and combinations thereof, of a chemical entity of a depicted structure or a chemical name. Whenever there is a conflict between chemical name and its structure drawing, the structure drawing should be used to interpret the compound of the present invention.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A "prodrug" is a compound, which when administered to the body of a subject (such as a mammal), breaks down in the subject's metabolic pathway to provide an active compound of Formula I. More specifically, a prodrug is an active or inactive "masked" compound that is modified chemically through in vivo physiological action, such as hydrolysis, metabolism and the like, into a compound of this invention following administration of the prodrug to a subject or patient. One common form of a prodrug is a masked carboxylic acid group. Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion. Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be amorphous forms, crystal forms, polymorphs, and the mixtures thereof.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

2. Uses, Formulation and Administration

The present invention is also directed to the use of the compounds as protein tyrosine kinase modulators and inhibitors. These compounds can be used to treat diseases related to unregulated tyrosine kinase signal transduction, for example, various cancers, blood vessel proliferative disorders, fibrotic disorders, and neurodegenerative diseases. In particular, compounds of the present invention are useful for the treatment and/or prevention of colorectal cancer, lung cancer, hematological cancer, renal cancer, liver cancer, breast cancer, diabetic retinopathy, macular degeneration, age-related macular degeneration, retinopathy of prematurity, ocular angiogenesis, retinal edema, retinal ischemia, diabetic macular edema, cystoid macular edema, retinal vein occlusion, branch vein occlusion, preretinal neovascularization, laser-induced choroidal neovascularization, neovascularization associated with keratoplasty, glaucoma and ocular tumors, arthritis, restenosis, hepatic cirrhosis, atherosclerosis, psoriasis, diabetes mellitus, wound healing, transplant rejection, inflammation, neurodegenerative diseases and immune disorders in the human being.

For the purposes of this disclosure, "treat," "treating," or "treatment" refer to the diagnosis, cure, mitigation, treatment, or prevention of disease or other undesirable condition.

The present invention is also directed to the preparation of a medicament for the treatment and prevention of diseases and conditions related with abnormal activities of tyrosine kinase receptors. The medicament contains a pharmaceutical acceptable composition, which comprises the therapeutic effective amount of the compounds of present invention, together with a pharmaceutical acceptable carrier.

The pharmaceutical acceptable compositions contain therapeutic effective amount of the compounds of the present invention. These compositions can be used as a medicament and administered to a mammal, such as a person, in need thereof. Different types of suitable dosage forms and medicaments are well known in the art, and can be readily adapted for delivery of the compounds of the present invention, such as, but not limited to, systematic, parenteral, local and topical delivery. The dosage forms can be tablets, capsules, intravenous injections, intramuscular injections, local injections, topical creams, gels and ointments, eye drops, ophthalmic solutions, ophthalmic suspensions, ophthalmic emulsions, intravitreal injections, subtenon injections, ophthalmic bioerodible implant, and non-bioerodible ophthalmic inserts or depots, nasal sprays and ointment, various rectal or vaginal preparations.

3. Examples

Some of the compounds of the present invention are listed in Table I.

TABLE 1

Exemplified Compounds of the Present Invention

| Example# | Chemical Structure | MW | Chemical Name |
|---|---|---|---|
| 1 | 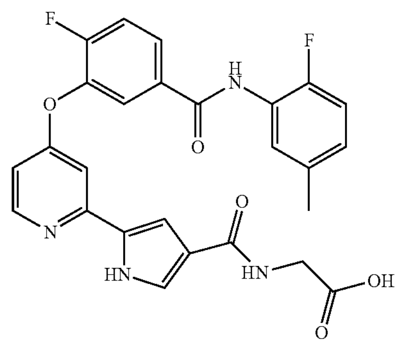 [SMILES: Cc1ccc(F)c(NC(=O)c2ccc(F)c(Oc3ccnc(-c4cc(C(=O)NCC(=O)O)c[nH]4)c3)c2)c1] | 506 | [({5-[4-(2-fluoro-5-{[(2-fluoro-5-methylphenyl)amino]carbonyl}phenoxy)-pyridin-2-yl]-1H-pyrrol-3-yl}carbonyl)amino]acetic acid |
| 2 | 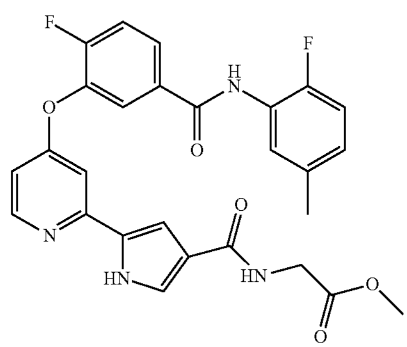 [SMILES: COC(=O)CNC(=O)c1c[nH]c(-c2cc(Oc3cc(C(=O)Nc4cc(C)ccc4F)ccc3F)ccn2)c1] | 520 | methyl [({5-[4-(2-fluoro-5-{[(2-fluoro-5-methylphenyl)amino]carbonyl}phenoxy)-pyridin-2-yl]-1H-pyrrol-3-yl}carbonyl)amino]acetate |
| 3 | 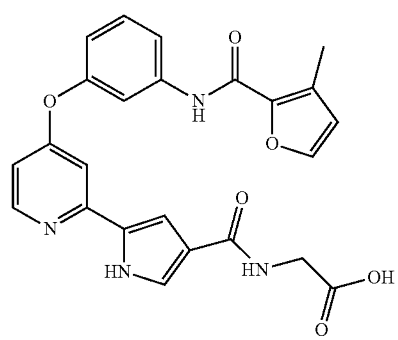 [SMILES: Cc1ccoc1C(=O)Nc1cccc(Oc2ccnc(-c3cc(C(=O)NCC(=O)O)c[nH]3)c2)c1] | 460 | ({[5-(4-{3-[(3-methyl-2-furoyl)amino]-phenoxy}pyridin-2-yl)-1H-pyrrol-3-yl]carbonyl}amino)acetic acid |
| 4 | 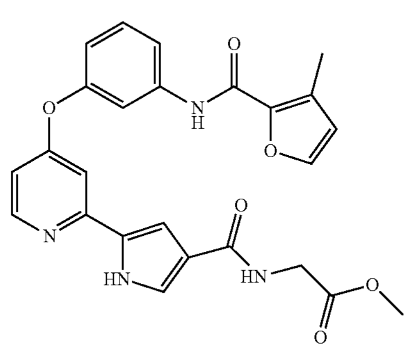 [SMILES: COC(=O)CNC(=O)c1c[nH]c(-c2cc(Oc3cccc(NC(=O)c4occc4C)c3)ccn2)c1] | 474 | methyl ({[5-(4-{3-[(3-methyl-2-furoyl)-amino]phenoxy}pyridin-2-yl)-1H-pyrrol-3-yl]carbonyl}amino)-acetate |

TABLE 1-continued

Exemplified Compounds of the Present Invention

| Example# | Chemical Structure | MW | Chemical Name |
|---|---|---|---|
| 5 | 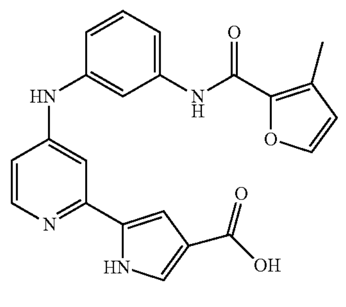 | 402 | 5-[4-({3-[(3-methyl-2-furoyl)amino]-phenyl}amino)pyridin-2-yl]-1H-pyrrole-3-carboxylic acid |
| 6 | 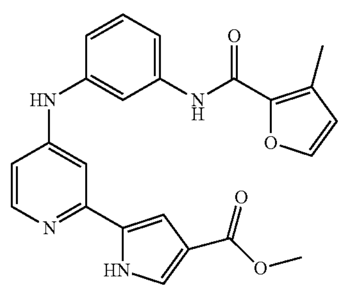 [SMILES: COC(=O)c1c[nH]c(-c2cc(Nc3cccc(NC(=O)c4occc4C)c3)ccn2)c1] | 416 | methyl 5-[4-({3-[(3-methyl-2-furoyl)-amino]phenyl}amino)pyridin-2-yl]-1H-pyrrole-3-carboxylate |
| 7 | 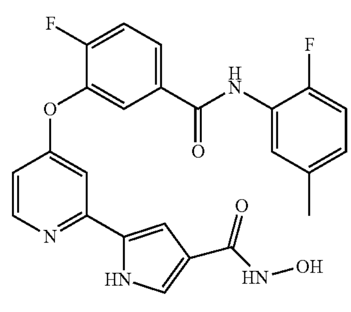 [SMILES: Cc1ccc(F)c(NC(=O)c2ccc(F)c(Oc3ccnc(-c4cc(C(=O)NO)c[nH]4)c3)c2)c1] | 464 | 5-[4-(2-fluoro-5-{[(2-fluoro-5-methylphenyl)amino]carbonyl}-phenoxy)pyridin-2-yl]-N-hydroxy-1H-pyrrole-3-carboxamide |
| 8 | 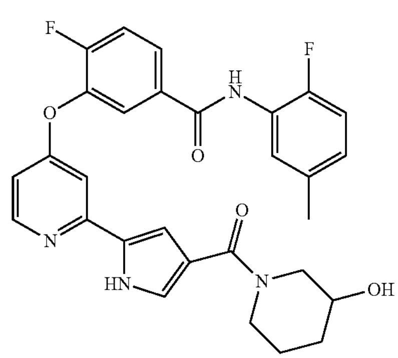 [SMILES: Cc1ccc(F)c(NC(=O)c2ccc(F)c(Oc3ccnc(-c4cc(C(=O)N5CCCC(O)C5)c[nH]4)c3)c2)c1] | 533 | 4-fluoro-N-(2-fluoro-5-methylphenyl)-3-[(2-{4-[(3-hydroxypiperidin-1-yl)-carbonyl]-1H-pyrrol-2-yl}pyridin-4-yl)oxy]benzamide |

TABLE 1-continued

Exemplified Compounds of the Present Invention

| Example# | Chemical Structure | MW | Chemical Name |
|---|---|---|---|
| 9 | 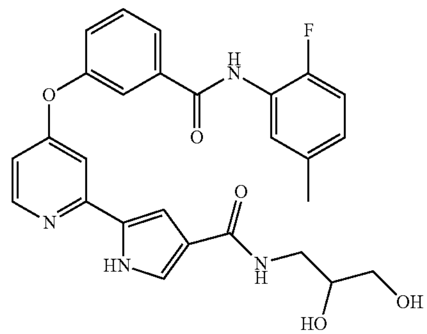 [SMILES: Cc1ccc(F)c(NC(=O)c2cccc(Oc3ccnc(-c4cc(C(=O)NCC(O)CO)c[nH]4)c3)c2)c1] | 505 | N-(2,3-dihydroxypropyl)-5-[4-(3-{[(2-fluoro-5-methylphenyl)amino]carbonyl}phenoxy)pyridin-2-yl]-1H-pyrrole-3-carboxamide |
| 10 | 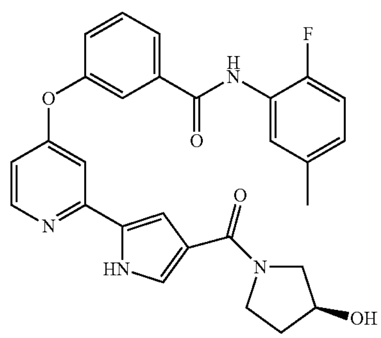 [SMILES: Cc1ccc(F)c(NC(=O)c2cccc(Oc3ccnc(-c4cc(C(=O)N5CC[C@H](O)C5)c[nH]4)c3)c2)c1] | 501 | N-(2-fluoro-5-methylphenyl)-3-[(2-{4-[(3-hydroxypyrrolidin-1-yl)carbonyl]-1H-pyrrol-2-yl}pyridin-4-yl)oxy]benzamide |
| 11 | 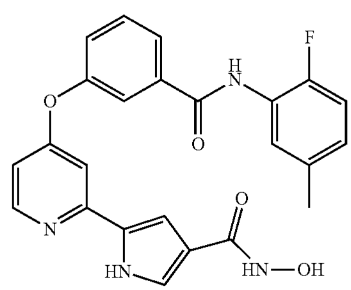 [SMILES: Cc1ccc(F)c(NC(=O)c2cccc(Oc3ccnc(-c4cc(C(=O)NO)c[nH]4)c3)c2)c1] | 446 | 5-[4-(3-{[(2-fluoro-5-methylphenyl)amino]carbonyl}phenoxy)-pyridin-2-yl]-N-hydroxy-1H-pyrrole-3-carboxamide |
| 12 | 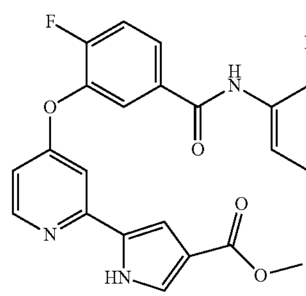 | 463 | methyl 5-[4-(2-fluoro-5-{[(2-fluoro-5-methylphenyl)amino]carbonyl}phenoxy)-pyridin-2-yl]-1H-pyrrole-3-carboxylate |

TABLE 1-continued

Exemplified Compounds of the Present Invention

| Example# | Chemical Structure | MW | Chemical Name |
|---|---|---|---|
| 13 | 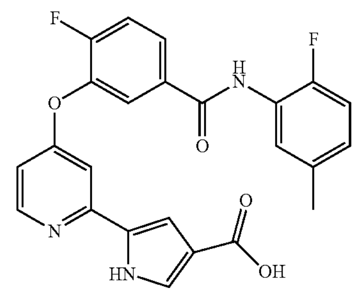 [SMILES: Cc1ccc(F)c(NC(=O)c2ccc(F)c(Oc3ccnc(-c4cc(C(=O)O)c[nH]4)c3)c2)c1] | 449 | 5-[4-(2-fluoro-5-{[(2-fluoro-5-methylphenyl)amino]carbonyl}phenoxy)-pyridin-2-yl]-1H-pyrrole-3-carboxylic acid |
| 14 | 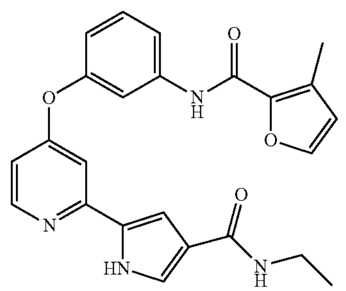 [SMILES: CCNC(=O)c1c[nH]c(-c2cc(Oc3cccc(NC(=O)c4occc4C)c3)ccn2)c1] | 430 | N-ethyl-5-(4-{3-[(3-methyl-2-furoyl)-amino]phenoxy}pyridin-2-yl)-1H-pyrrole-3-carboxamide |
| 15 | 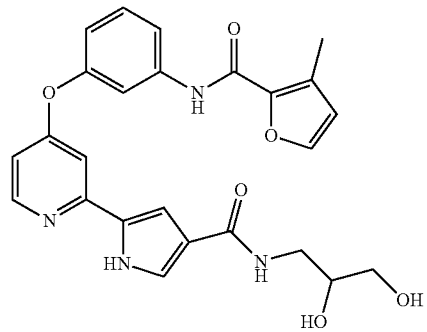 [SMILES: Cc1ccoc1C(=O)Nc1cccc(Oc2ccnc(-c3cc(C(=O)NCC(O)CO)c[nH]3)c2)c1] | 476 | N-(2,3-dihydroxypropyl)-5-(4-{3-[(3-methyl-2-furoyl)amino]phenoxy}-pyridin-2-yl)-1H-pyrrole-3-carboxamide |
| 16 | 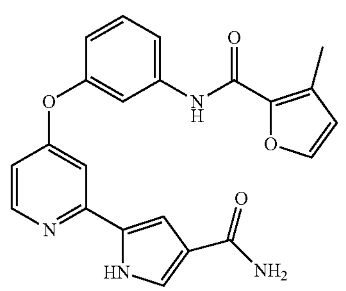 [SMILES: Cc1ccoc1C(=O)Nc1cccc(Oc2ccnc(-c3cc(C(N)=O)c[nH]3)c2)c1] | 402 | 5-(4-{3-[(3-methyl-2-furoyl)amino]-phenoxy}pyridin-2-yl)-1H-pyrrole-3-carboxamide |
| 17 | 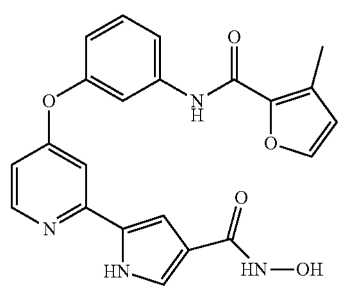 [SMILES: Cc1ccoc1C(=O)Nc1cccc(Oc2ccnc(-c3cc(C(=O)NO)c[nH]3)c2)c1] | 418 | N-hydroxy-5-(4-{3-[(3-methyl-2-furoyl)-amino]phenoxy}pyridin-2-yl)-1H-pyrrole-3-carboxamide |

TABLE 1-continued

Exemplified Compounds of the Present Invention

| Example# | Chemical Structure | MW | Chemical Name |
|---|---|---|---|
| 18 | 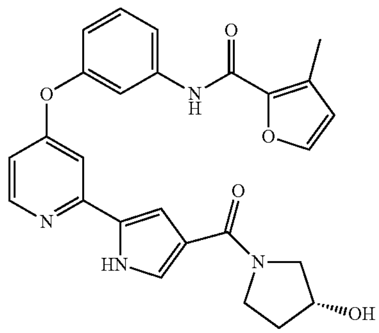 [SMILES: Cc1ccoc1C(=O)Nc1cccc(Oc2ccnc(-c3cc(C(=O)N4CC[C@@H](O)C4)c[nH]3)c2)c1] | 472 | N-(3-{[2-(4-{[(3R)-3-hydroxypyrrolidin-1-yl]carbonyl}-1H-pyrrol-2-yl)pyridin-4-yl]oxy}phenyl)-3-methyl-2-furamide |
| 19 | 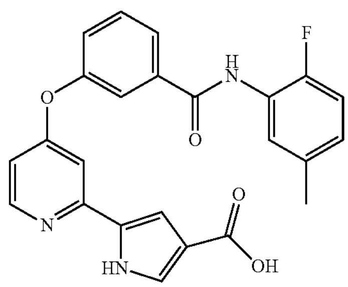 [SMILES: Cc1ccc(F)c(NC(=O)c2cccc(Oc3ccnc(-c4cc(C(=O)O)c[nH]4)c3)c2)c1] | 431 | 5-[4-(3-{[(2-fluoro-5-methylphenyl)amino]carbonyl}phenoxy)-pyridin-2-yl]-1H-pyrrole-3-carboxylic acid |
| 20 | 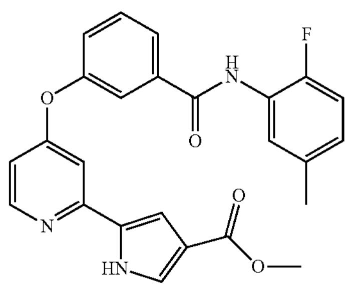 [SMILES: COC(=O)c1c[nH]c(-c2cc(Oc3cccc(C(=O)Nc4cc(C)ccc4F)c3)ccn2)c1] | 445 | methyl 5-[4-(3-{[(2-fluoro-5-methylphenyl)amino]carbonyl}phenoxy)-pyridin-2-yl]-1H-pyrrole-3-carboxylate |
| 21 | 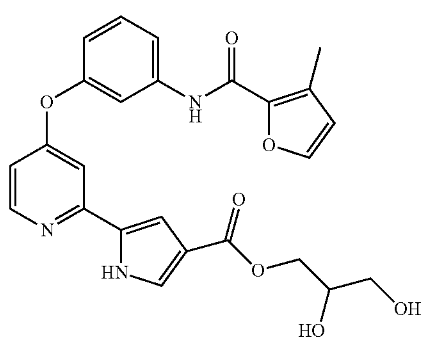 [SMILES: Cc1ccoc1C(=O)Nc1cccc(Oc2ccnc(-c3cc(C(=O)OCC(O)CO)c[nH]3)c2)c1] | 477 | 2,3-dihydroxypropyl 5-(4-{3-[(3-methyl-2-furoyl)amino]phenoxy}pyridin-2-yl)-1H-pyrrole-3-carboxylate |
| 22 | 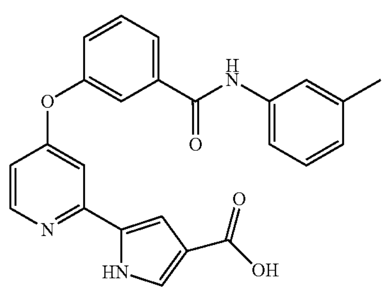 [SMILES: Cc1cccc(NC(=O)c2cccc(Oc3ccnc(-c4cc(C(=O)O)c[nH]4)c3)c2)c1] | 413 | 5-[4-(3-{[(3-methylphenyl)amino]-carbonyl}phenoxy)pyridin-2-yl]-1H-pyrrole-3-carboxylic acid |

TABLE 1-continued

Exemplified Compounds of the Present Invention

| Example# | Chemical Structure | MW | Chemical Name |
|---|---|---|---|
| 23 | 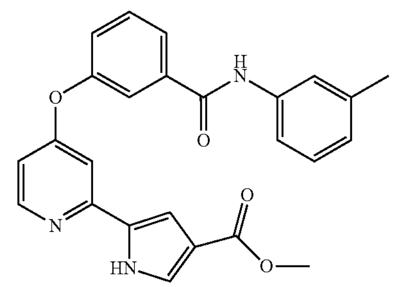 [SMILES: COC(=O)c1c[nH]c(-c2cc(Oc3cccc(C(=O)Nc4cccc(C)c4)c3)ccn2)c1] | 427 | methyl 5-[4-(3-{[(3-methylphenyl)amino]carbonyl}phenoxy)-pyridin-2-yl]-1H-pyrrole-3-carboxylate |
| 24 | 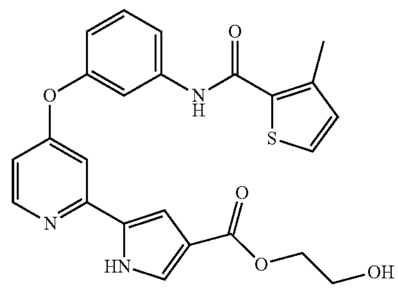 | 464 | 2-hydroxyethyl 5-[4-(3-{[(3-methyl-2-thienyl)carbonyl]amino}phenoxy)pyridin-2-yl]-1H-pyrrole-3-carboxylate |
| 25 | 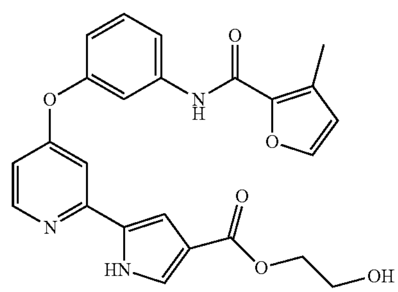 [SMILES: Cc1ccoc1C(=O)Nc1cccc(Oc2ccnc(-c3cc(C(=O)OCCO)c[nH]3)c2)c1] | 447 | 2-hydroxyethyl 5-(4-{3-[(3-methyl-2-furoyl)amino]phenoxy}pyridin-2-yl)-1H-pyrrole-3-carboxylate |
| 26 | 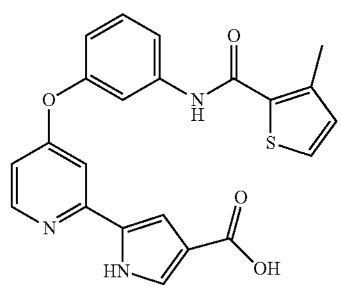 | 419 | 5-[4-(3-{[(3-methyl-2-thienyl)carbonyl]-amino}phenoxy)pyridin-2-yl]-1H-pyrrole-3-carboxylic acid |
| 27 | 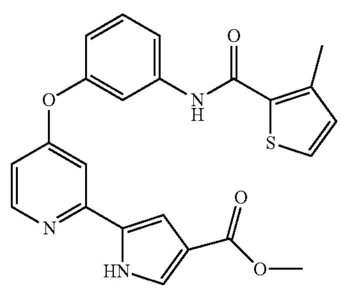 | 433 | methyl 5-[4-(3-{[(3-methyl-2-thienyl)carbonyl]amino}phenoxy)-pyridin-2-yl]-1H-pyrrole-3-carboxylate |

TABLE 1-continued

Exemplified Compounds of the Present Invention

| Example# | Chemical Structure | MW | Chemical Name |
|---|---|---|---|
| 28 | 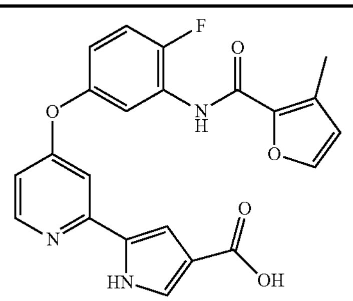 | 421 | 5-(4-{4-fluoro-3-[(3-methyl-2-furoyl)-amino]phenoxy}pyridin-2-yl)-1H-pyrrole-3-carboxylic acid |
| 29 | 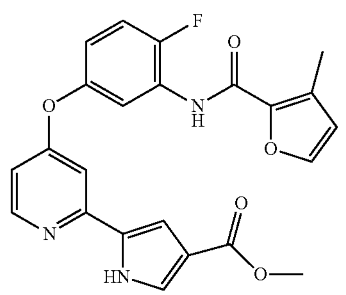 [SMILES: COC(=O)c1c[nH]c(-c2cc(Oc3ccc(F)c(NC(=O)c4occc4C)c3)ccn2)c1] | 435 | methyl 5-(4-{4-fluoro-3-[(3-methyl-2-furoyl)amino]phenoxy}pyridin-2-yl)-1H-pyrrole-3-carboxylate |
| 30 | 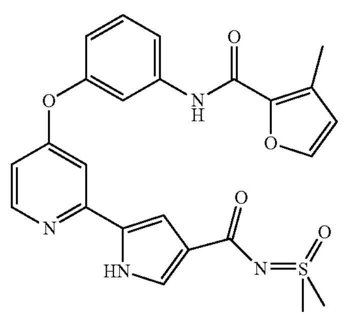 [SMILES: Cc1ccoc1C(=O)Nc1cccc(Oc2ccnc(-c3cc(C(=O)N=S(C)(C)=O)c[nH]3)c2)c1] | 479 | N-[dimethyl(oxido)-lambda~4~-sulfanylidene]-5-(4-{3-[(3-methyl-2-furoyl)amino]phenoxy}pyridin-2-yl)-1H-pyrrole-3-carboxamide |
| 31 | 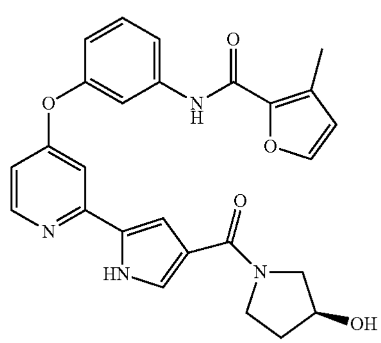 [SMILES: Cc1ccoc1C(=O)Nc1cccc(Oc2ccnc(-c3cc(C(=O)N4CC[C@H](O)C4)c[nH]3)c2)c1] | 472 | N-(3-{[2-(4-{[(3S)-3-hydroxypyrrolidin-1-yl]carbonyl}-1H-pyrrol-2-yl)pyridin-4-yl]oxy}phenyl)-3-methyl-2-furamide |
| 32 | 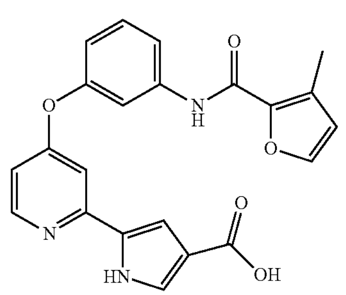 [SMILES: Cc1ccoc1C(=O)Nc1cccc(Oc2ccnc(-c3cc(C(=O)O)c[nH]3)c2)c1] | 403 | 5-(4-{3-[(3-methyl-2-furoyl)amino]-phenoxy}pyridin-2-yl)-1H-pyrrole-3-carboxylic acid |

TABLE 1-continued

Exemplified Compounds of the Present Invention

| Example# | Chemical Structure | MW | Chemical Name |
|---|---|---|---|
| 33 | 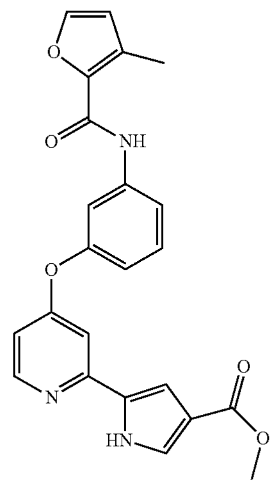 [SMILES: COC(=O)c1c[nH]c(-c2cc(Oc3cccc(NC(=O)c4occc4C)c3)ccn2)c1] | 417 | methyl 5-(4-{3-[(3-methyl-2-furoyl)-amino]phenoxy}pyridin-2-yl)-1H-pyrrole-3-carboxylate |
| 34 | 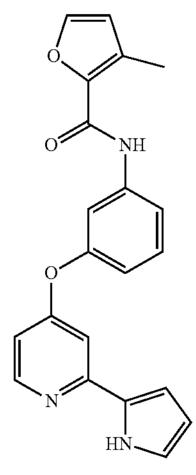 [SMILES: Cc1ccoc1C(=O)Nc1cccc(Oc2ccnc(-c3ccc[nH]3)c2)c1] | 359 | 3-methyl-N-(3-{[2-(1H-pyrrol-2-yl)-pyridin-4-yl]oxy}phenyl)-2-furamide |
| 35 | 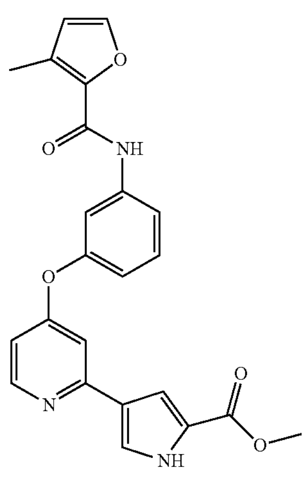 | 417 | methyl 4-(4-{3-[(3-methyl-2-furoyl)-amino]phenoxy}pyridin-2-yl)-1H-pyrrole-2-carboxylate |

TABLE 1-continued

Exemplified Compounds of the Present Invention

| Example# | Chemical Structure | MW | Chemical Name |
|---|---|---|---|
| 36 | 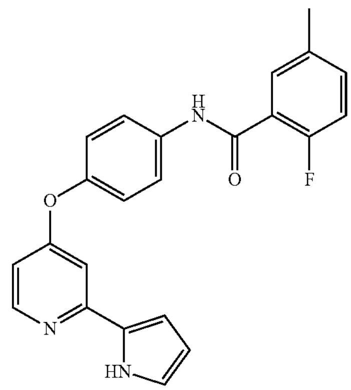 [SMILES: Cc1ccc(F)c(C(=O)Nc2ccc(Oc3ccnc(-c4ccc[nH]4)c3)cc2)c1] | 387 | 2-fluoro-5-methyl-N-(4-{[2-(1H-pyrrol-2-yl)pyridin-4-yl]oxy}phenyl)benzamide |
| 37 | 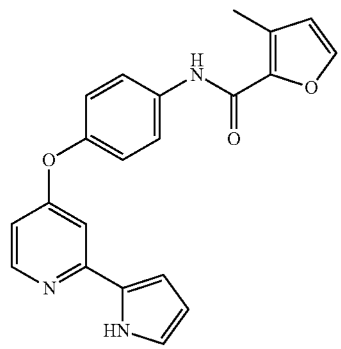 [SMILES: Cc1ccoc1C(=O)Nc1ccc(Oc2ccnc(-c3ccc[nH]3)c2)cc1] | 359 | 3-methyl-N-(4-{[2-(1H-pyrrol-2-yl)-pyridin-4-yl]oxy}phenyl)-2-furamide |
| 38 | 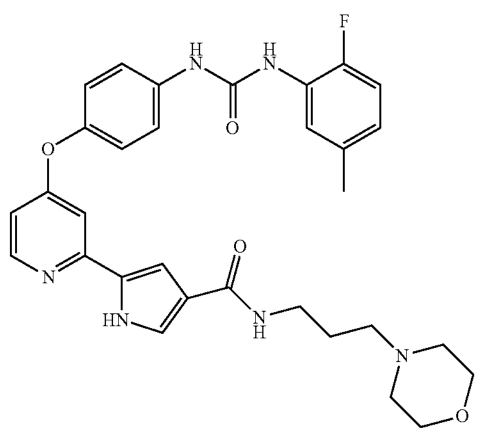 [SMILES: Cc1ccc(F)c(NC(=O)Nc2ccc(Oc3ccnc(-c4cc(C(=O)NCCCN5CCOCC5)c[nH]4)c3)cc2)c1] | 573 | 5-{4-[4-({[(2-fluoro-5-methylphenyl)amino]carbonyl}amino)-phenoxy]pyridin-2-yl}-N-(3-morpholin-4-ylpropyl)-1H-pyrrole-3-carboxamide |
| 39 | 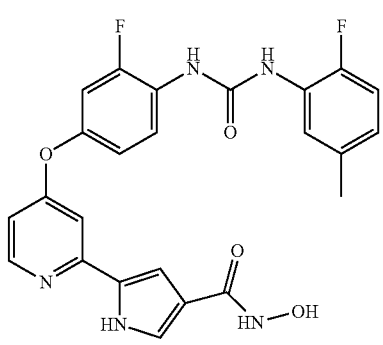 [SMILES: Cc1ccc(F)c(NC(=O)Nc2ccc(Oc3ccnc(-c4cc(C(=O)NO)c[nH]4)c3)cc2F)c1] | 479 | 5-{4-[3-fluoro-4-({[(2-fluoro-5-methylphenyl)amino]carbonyl}amino)-phenoxy]pyridin-2-yl}-N-hydroxy-1H-pyrrole-3-carboxamide |

TABLE 1-continued

Exemplified Compounds of the Present Invention

| Example# | Chemical Structure | MW | Chemical Name |
|---|---|---|---|
| 40 | 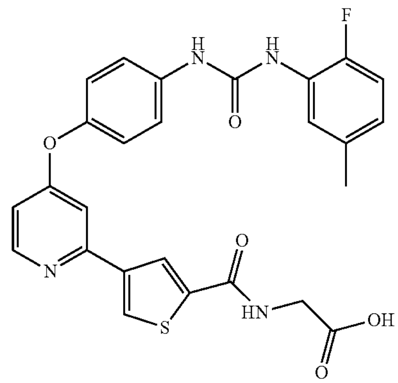 [SMILES: Cc1ccc(F)c(NC(=O)Nc2ccc(Oc3ccnc(-c4csc(C(=O)NCC(=O)O)c4)c3)cc2)c1] | 521 | {[(4-{4-[4-({[(2-fluoro-5-methylphenyl)amino]carbonyl}amino)-phenoxy]pyridin-2-yl}-2-thienyl)carbonyl]amino}acetic acid |
| 41 | 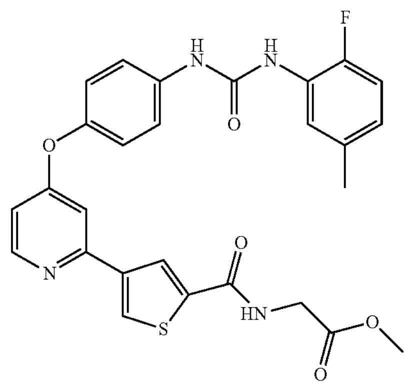 [SMILES: COC(=O)CNC(=O)c1cc(-c2cc(Oc3ccc(NC(=O)Nc4cc(C)ccc4F)cc3)ccn2)cs1] | 535 | methyl {[(4-{4-[4-({[(2-fluoro-5-methylphenyl)amino]carbonyl}amino)-phenoxy]pyridin-2-yl}-2-thienyl)carbonyl]amino}acetate |
| 42 | 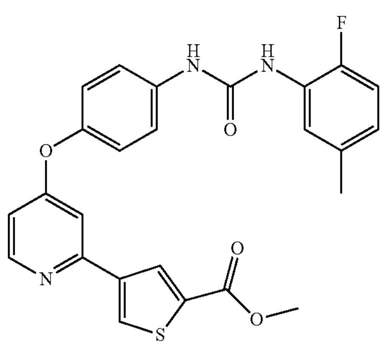 [SMILES: COC(=O)c1cc(-c2cc(Oc3ccc(NC(=O)Nc4cc(C)ccc4F)cc3)ccn2)cs1] | 478 | methyl 4-{4-[4-({[(2-fluoro-5-methylphenyl)amino]carbonyl}amino)-phenoxy]pyridin-2-yl}thiophene-2-carboxylate |
| 43 | 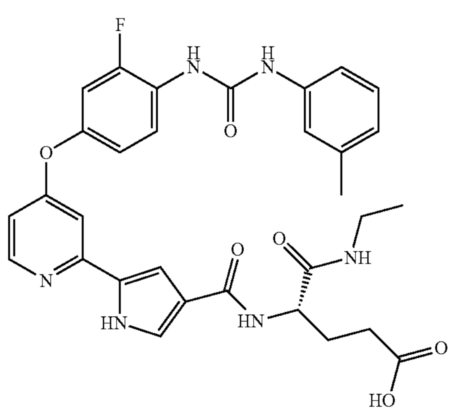 [SMILES: CCNC(=O)[C@H](CCC(=O)O)NC(=O)c1c[nH]c(-c2cc(Oc3ccc(NC(=O)Nc4cccc(C)c4)c(F)c3)ccn2)c1] | 603 | (4S)-5-(ethylamino)-4-{[(5-{4-[3-fluoro-4-({[(3-methylphenyl)amino]-carbonyl}amino)phenoxy]pyridin-2-yl}-1H-pyrrol-3-yl)carbonyl]amino}-5-oxopentanoic acid |

TABLE 1-continued

Exemplified Compounds of the Present Invention

| Example# | Chemical Structure | MW | Chemical Name |
|---|---|---|---|
| 44 | 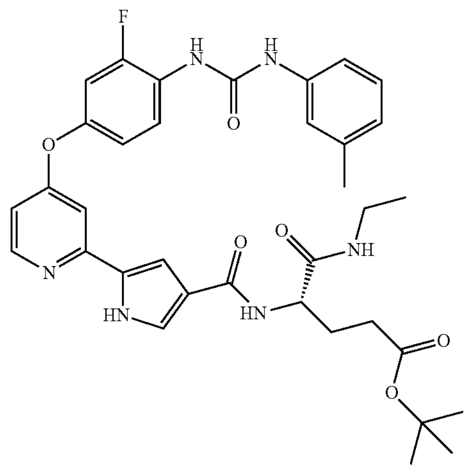 [SMILES: CCNC(=O)[C@H](CCC(=O)OC(C)(C)C)NC(=O)c1c[nH]c(-c2cc(Oc3ccc(NC(=O)Nc4cccc(C)c4)c(F)c3)ccn2)c1] | 659 | tert-butyl (4S)-5-(ethylamino)-4-{[(5-{4-[3-fluoro-4-({[(3-methylphenyl)-amino]carbonyl}amino)phenoxy]-pyridin-2-yl}-1H-pyrrol-3-yl)carbonyl]-amino}-5-oxopentanoate |
| 45 | 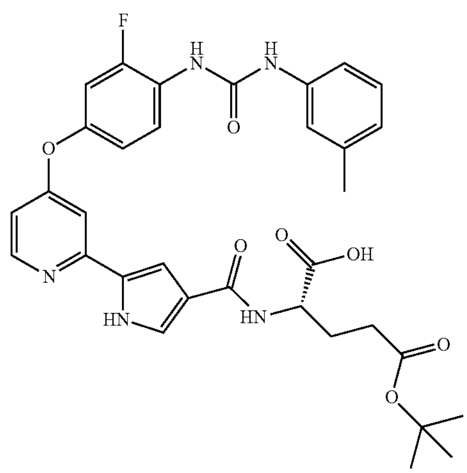 [SMILES: Cc1cccc(NC(=O)Nc2ccc(Oc3ccnc(-c4cc(C(=O)N[C@@H](CCC(=O)OC(C)(C)C)C(=O)O)c[nH]4)c3)cc2F)c1] | 632 | (2S)-5-tert-butoxy-2-{[(5-{4-[3-fluoro-4-({[(3-methylphenyl)amino]carbonyl}-amino)phenoxy]pyridin-2-yl}-1H-pyrrol-3-yl)carbonyl]amino}-5-oxopentanoic acid |
| 46 | 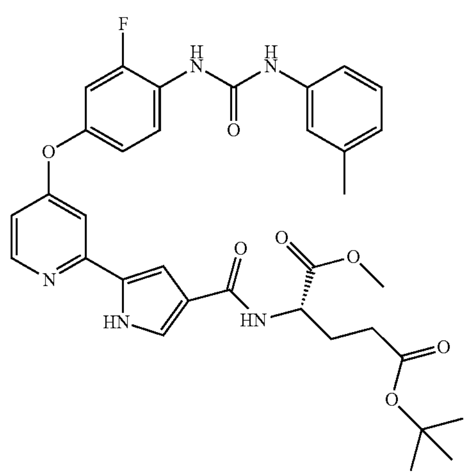 [SMILES: COC(=O)[C@H](CCC(=O)OC(C)(C)C)NC(=O)c1c[nH]c(-c2cc(Oc3ccc(NC(=O)Nc4cccc(C)c4)c(F)c3)ccn2)c1] | 646 | 5-tert-butyl 1-methyl 2-{[(5-{4-[3-fluoro-4-({[(3-methylphenyl)amino]carbonyl}-amino)phenoxy]pyridin-2-yl}-1H-pyrrol-3-yl)carbonyl]amino}pentanedioate |

TABLE 1-continued

Exemplified Compounds of the Present Invention

| Example# | Chemical Structure | MW | Chemical Name |
|---|---|---|---|
| 47 | 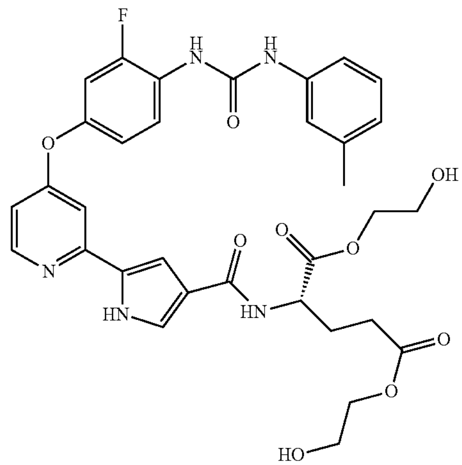 [SMILES: Cc1cccc(NC(=O)Nc2ccc(Oc3ccnc(-c4cc(C(=O)N[C@@H](CCC(=O)OCCO)C(=O)OCCO)c[nH]4)c3)cc2F)c1] | 664 | bis(2-hydroxyethyl) 2-{[(5-{4-[3-fluoro-4-({[(3-methylphenyl)amino]carbonyl}-amino)phenoxy]pyridin-2-yl}-1H-pyrrol-3-yl)carbonyl]amino}pentanedioate |
| 48 | 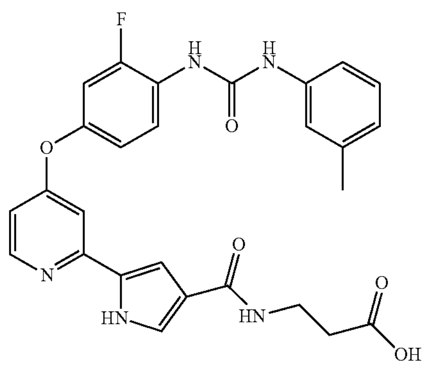 [SMILES: Cc1cccc(NC(=O)Nc2ccc(Oc3ccnc(-c4cc(C(=O)NCCC(=O)O)c[nH]4)c3)cc2F)c1] | 518 | 3-{[(5-{4-[3-fluoro-4-({[(3-methylphenyl)amino]carbonyl}amino)-phenoxy]pyridin-2-yl}-1H-pyrrol-3-yl)carbonyl]amino}propanoic acid |
| 49 | 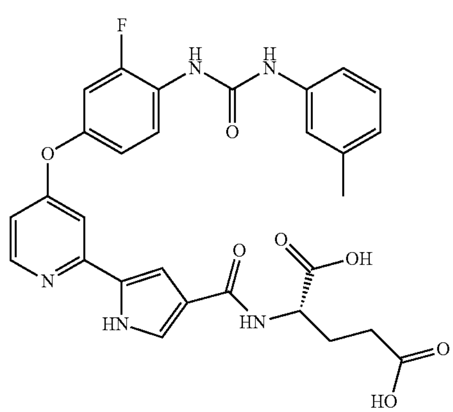 [SMILES: Cc1cccc(NC(=O)Nc2ccc(Oc3ccnc(-c4cc(C(=O)N[C@@H](CCC(=O)O)C(=O)O)c[nH]4)c3)cc2F)c1] | 576 | 2-{[(5-{4-[3-fluoro-4-({[(3-methylphenyl)amino]carbonyl}amino)-phenoxy]pyridin-2-yl}-1H-pyrrol-3-yl)carbonyl]amino}pentanedioic acid |

TABLE 1-continued

Exemplified Compounds of the Present Invention

| Example# | Chemical Structure | MW | Chemical Name |
|---|---|---|---|
| 50 | 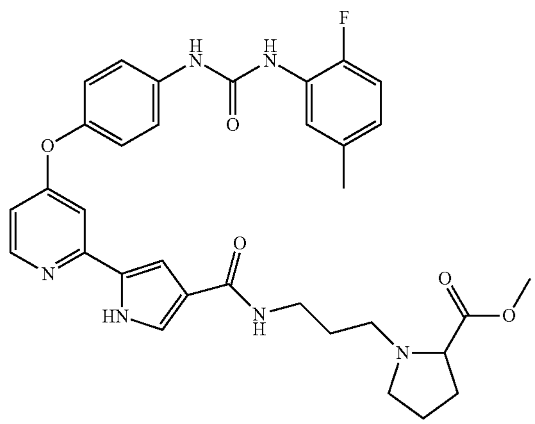 [SMILES: COC(=O)C1CCCN1CCCNC(=O)c1c[nH]c(-c2cc(Oc3ccc(NC(=O)Nc4cc(C)ccc4F)cc3)ccn2)c1] | 615 | methyl 1-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)-pyrrolidine-2-carboxylate |
| 51 | 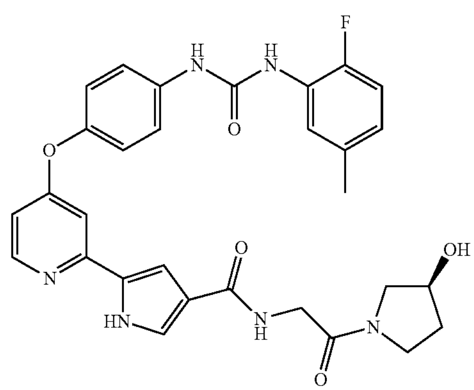 [SMILES: Cc1ccc(F)c(NC(=O)Nc2ccc(Oc3ccnc(-c4cc(C(=O)NCC(=O)N5CC[C@H](O)C5)c[nH]4)c3)cc2)c1] | 573 | 5-{4-[4-({[(2-fluoro-5-methylphenyl)amino]carbonyl}amino)phenoxy]pyridin-2-yl}-N-{2-[(3S)-3-hydroxypyrrolidin-1-yl]-2-oxoethyl}-1H-pyrrole-3-carboxamide |
| 52 | 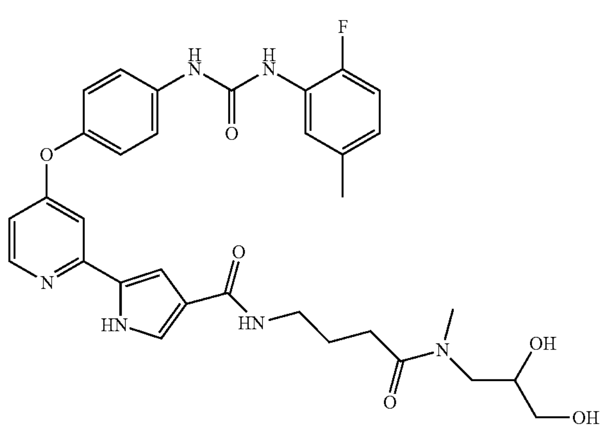 [SMILES: Cc1ccc(F)c(NC(=O)Nc2ccc(Oc3ccnc(-c4cc(C(=O)NCCCC(=O)N(C)CC(O)CO)c[nH]4)c3)cc2)c1] | 619 | N-{4-[(2,3-dihydroxypropyl)(methyl)amino]-4-oxobutyl}-5-{4-[4-({[(2-fluoro-5-methylphenyl)amino]carbonyl}amino)phenoxy]pyridin-2-yl}-1H-pyrrole-3-carboxamide |

TABLE 1-continued

Exemplified Compounds of the Present Invention

| Example# | Chemical Structure | MW | Chemical Name |
|---|---|---|---|
| 53 | 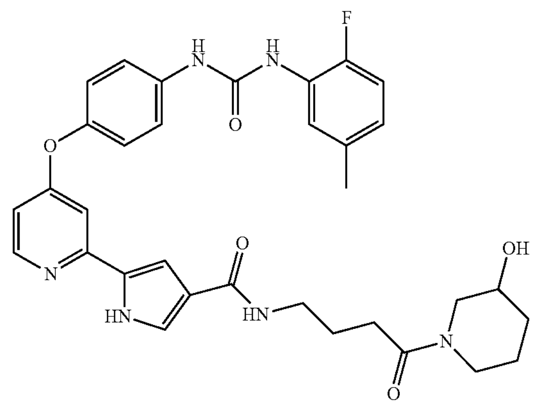 [SMILES: Cc1ccc(F)c(NC(=O)Nc2ccc(Oc3ccnc(-c4cc(C(=O)NCCCC(=O)N5CCCC(O)C5)c[nH]4)c3)cc2)c1] | 615 | 5-{4-[4-({[(2-fluoro-5-methylphenyl)amino]carbonyl}amino)phenoxy]pyridin-2-yl}-N-[4-(3-hydroxypiperidin-1-yl)-4-oxobutyl]-1H-pyrrole-3-carboxamide |
| 54 | 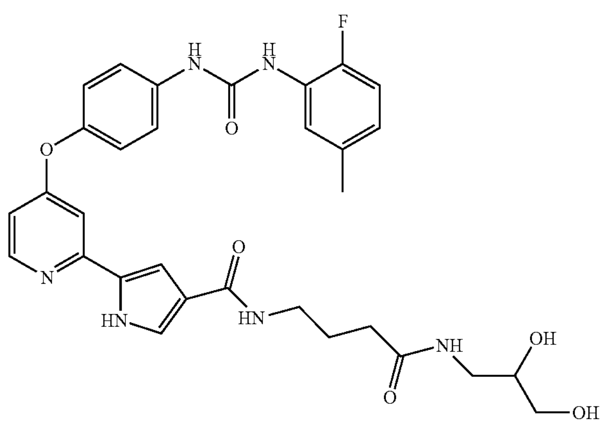 [SMILES: Cc1ccc(F)c(NC(=O)Nc2ccc(Oc3ccnc(-c4cc(C(=O)NCCCC(=O)NCC(O)CO)c[nH]4)c3)cc2)c1] | 605 | N-{4-[(2,3-dihydroxypropyl)amino]-4-oxobutyl}-5-{4-[4-({[(2-fluoro-5-methylphenyl)amino]carbonyl}amino)phenoxy]pyridin-2-yl}-1H-pyrrole-3-carboxamide |
| 55 | 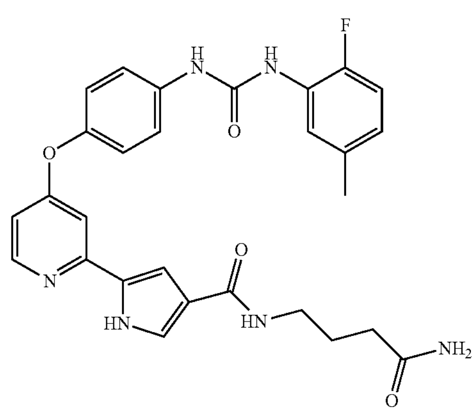 [SMILES: Cc1ccc(F)c(NC(=O)Nc2ccc(Oc3ccnc(-c4cc(C(=O)NCCCC(N)=O)c[nH]4)c3)cc2)c1] | 531 | N-(4-amino-4-oxobutyl)-5-{4-[4-({[(2-fluoro-5-methylphenyl)amino]carbonyl}amino)phenoxy]pyridin-2-yl}-1H-pyrrole-3-carboxamide |

TABLE 1-continued

Exemplified Compounds of the Present Invention

| Example# | Chemical Structure | MW | Chemical Name |
|---|---|---|---|
| 56 | 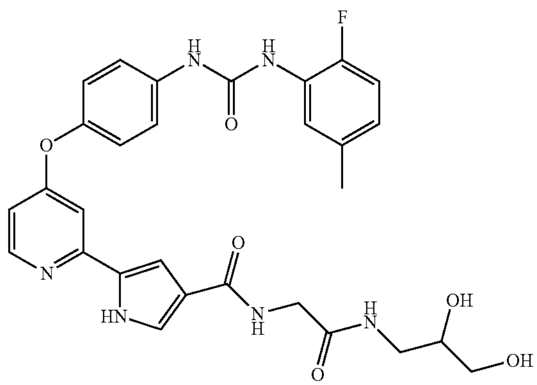 [SMILES: Cc1ccc(F)c(NC(=O)Nc2ccc(Oc3ccnc(-c4cc(C(=O)NCC(=O)NCC(O)CO)c[nH]4)c3)cc2)c1] | 577 | N-{2-[(2,3-dihydroxypropyl)amino]-2-oxoethyl}-5-{4-[4-({[(2-fluoro-5-methylphenyl)amino]carbonyl}amino)phenoxy]pyridin-2-yl}-1H-pyrrole-3-carboxamide |
| 57 | 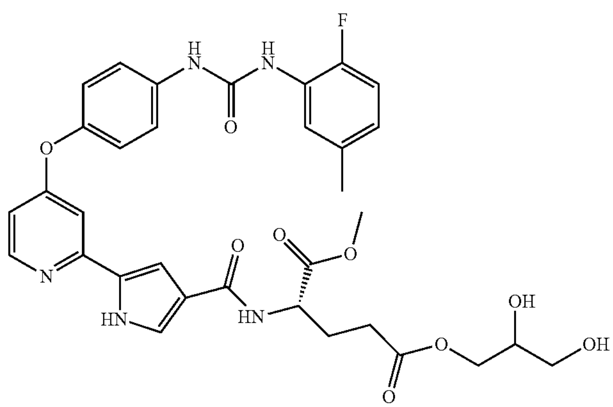 [SMILES: COC(=O)[C@H](CCC(=O)OCC(O)CO)NC(=O)c1c[nH]c(-c2cc(Oc3ccc(NC(=O)Nc4cc(C)ccc4F)cc3)ccn2)c1] | 664 | 5-(2,3-dihydroxypropyl) 1-methyl 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate |
| 58 | 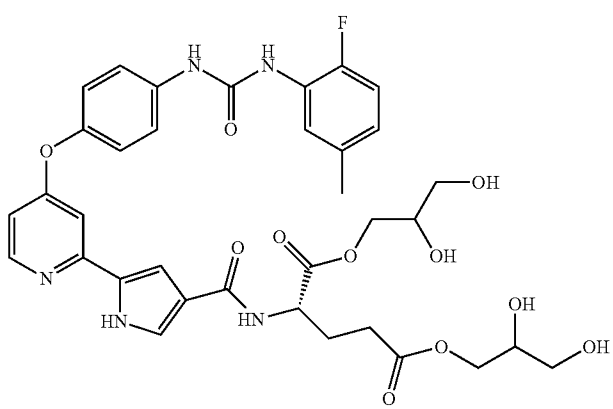 [SMILES: Cc1ccc(F)c(NC(=O)Nc2ccc(Oc3ccnc(-c4cc(C(=O)N[C@@H](CCC(=O)OCC(O)CO)C(=O)OCC(O)CO)c[nH]4)c3)cc2)c1] | 724 | bis(2,3-dihydroxypropyl) 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate |

TABLE 1-continued

Exemplified Compounds of the Present Invention

| Example# | Chemical Structure | MW | Chemical Name |
|---|---|---|---|
| 59 | 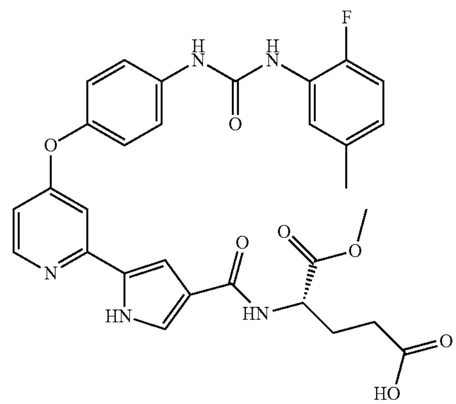 [SMILES: COC(=O)[C@H](CCC(=O)O)NC(=O)c1c[nH]c(-c2cc(Oc3ccc(NC(=O)Nc4cc(C)ccc4F)cc3)ccn2)c1] | 590 | 4-{[(5-{4-[4-({[(2-fluoro-5-methylphenyl)amino]carbonyl}amino)-phenoxy]pyridin-2-yl}-1H-pyrrol-3-yl)carbonyl]amino}-5-methoxy-5-oxopentanoic acid |
| 60 | 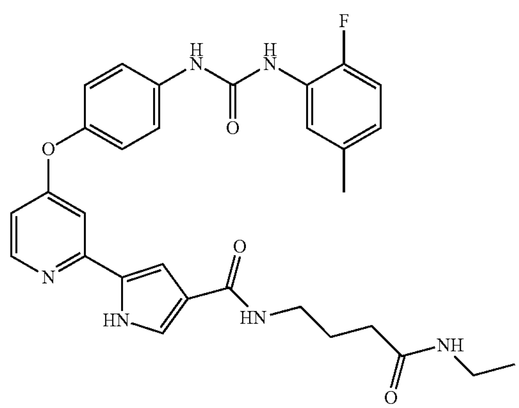 [SMILES: CCNC(=O)CCCNC(=O)c1c[nH]c(-c2cc(Oc3ccc(NC(=O)Nc4cc(C)ccc4F)cc3)ccn2)c1] | 559 | N-[4-(ethylamino)-4-oxobutyl]-5-{4-[4-({[(2-fluoro-5-methylphenyl)amino]-carbonyl}amino)phenoxy]pyridin-2-yl}-1H-pyrrole-3-carboxamide |
| 61 | 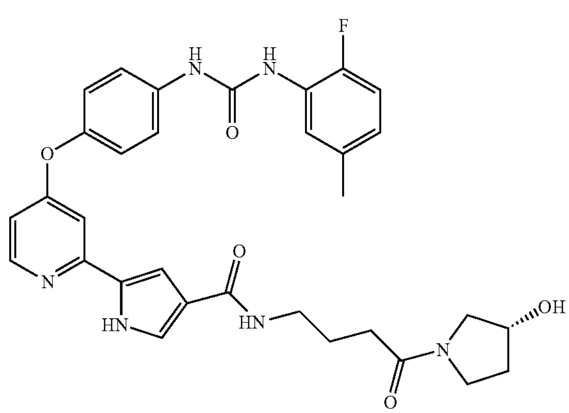 [SMILES: Cc1ccc(F)c(NC(=O)Nc2ccc(Oc3ccnc(-c4cc(C(=O)NCCCC(=O)N5CC[C@@H](O)C5)c[nH]4)c3)cc2)c1] | 601 | 5-{4-[4-({[(2-fluoro-5-methylphenyl)amino]carbonyl}amino)-phenoxy]pyridin-2-yl}-N-[4-(3-hydroxypyrrolidin-1-yl)-4-oxobutyl]-1H-pyrrole-3-carboxamide |

TABLE 1-continued

Exemplified Compounds of the Present Invention

| Example# | Chemical Structure | MW | Chemical Name |
|---|---|---|---|
| 62 | 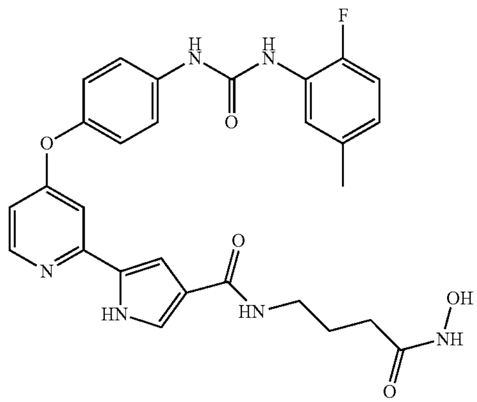 [SMILES: Cc1ccc(F)c(NC(=O)Nc2ccc(Oc3ccnc(-c4cc(C(=O)NCCCC(=O)NO)c[nH]4)c3)cc2)c1] | 547 | 5-{4-[4-({[(2-fluoro-5-methylphenyl)amino]carbonyl}amino)-phenoxy]pyridin-2-yl}-N-[4-(hydroxyamino)-4-oxobutyl]-1H-pyrrole-3-carboxamide |
| 63 | 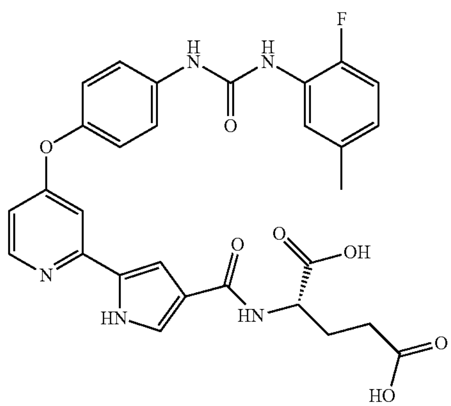 [SMILES: Cc1ccc(F)c(NC(=O)Nc2ccc(Oc3ccnc(-c4cc(C(=O)N[C@@H](CCC(=O)O)C(=O)O)c[nH]4)c3)cc2)c1] | 576 | 2-{[(5-{4-[4-({[(2-fluoro-5-methylphenyl)amino]carbonyl}amino)-phenoxy]pyridin-2-yl}-1H-pyrrol-3-yl)carbonyl]amino}pentanedioic acid |
| 64 | 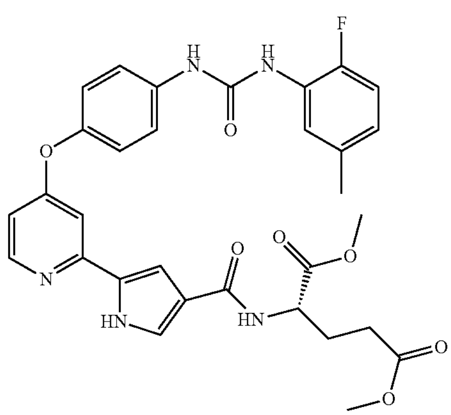 [SMILES: COC(=O)CC[C@H](NC(=O)c1c[nH]c(-c2cc(Oc3ccc(NC(=O)Nc4cc(C)ccc4F)cc3)ccn2)c1)C(=O)OC] | 604 | dimethyl 2-{[(5-{4-[4-({[(2-fluoro-5-methylphenyl)amino]carbonyl}amino)-phenoxy]pyridin-2-yl}-1H-pyrrol-3-yl)carbonyl]amino}-pentanedioate |

TABLE 1-continued

Exemplified Compounds of the Present Invention

| Example# | Chemical Structure | MW | Chemical Name |
|---|---|---|---|
| 65 | 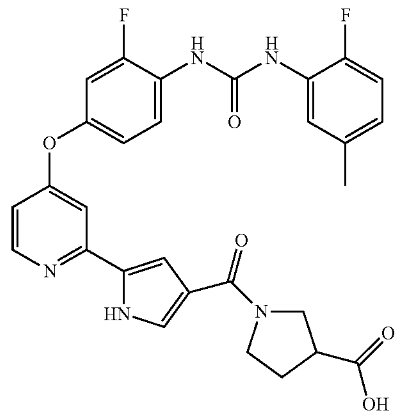 [SMILES: Cc1ccc(F)c(NC(=O)Nc2ccc(Oc3ccnc(-c4cc(C(=O)N5CCC(C(=O)O)C5)c[nH]4)c3)cc2F)c1] | 562 | 1-[(5-{4-[3-fluoro-4-({[(2-fluoro-5-methylphenyl)amino]carbonyl}amino)-phenoxy]pyridin-2-yl}-1H-pyrrol-3-yl)carbonyl]pyrrolidine-3-carboxylic acid |
| 66 | 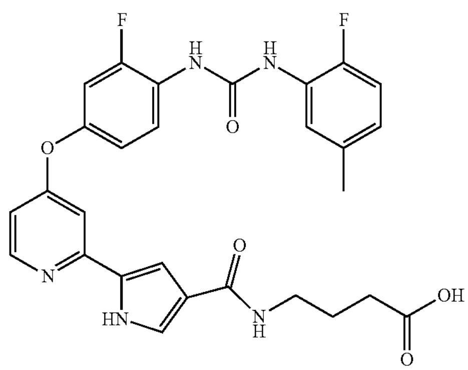 [SMILES: Cc1ccc(F)c(NC(=O)Nc2ccc(Oc3ccnc(-c4cc(C(=O)NCCCC(=O)O)c[nH]4)c3)cc2F)c1] | 550 | 4-{[(5-{4-[3-fluoro-4-({[(2-fluoro-5-methylphenyl)amino]carbonyl}amino)-phenoxy]pyridin-2-yl}-1H-pyrrol-3-yl)carbonyl]amino}butanoic acid |
| 67 | 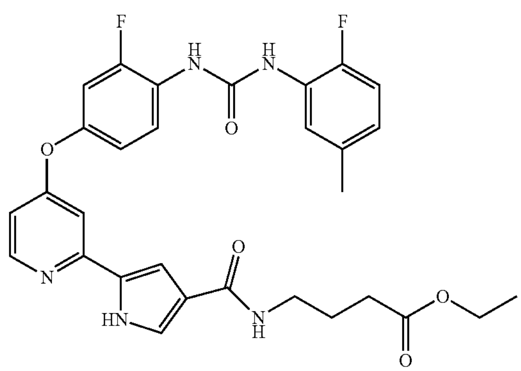 [SMILES: CCOC(=O)CCCNC(=O)c1c[nH]c(-c2cc(Oc3ccc(NC(=O)Nc4cc(C)ccc4F)c(F)c3)ccn2)c1] | 578 | ethyl 4-{[(5-{4-[3-fluoro-4-({[(2-fluoro-5-methylphenyl)amino]carbonyl}amino)-phenoxy]pyridin-2-yl}-1H-pyrrol-3-yl)carbonyl]amino}butanoate |
| 68 | 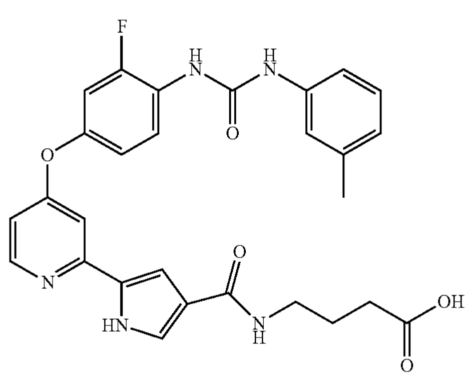 [SMILES: Cc1cccc(NC(=O)Nc2ccc(Oc3ccnc(-c4cc(C(=O)NCCCC(=O)O)c[nH]4)c3)cc2F)c1] | 532 | 4-{[(5-{4-[3-fluoro-4-({[(3-methylphenyl)amino]carbonyl}amino)-phenoxy]pyridin-2-yl}-1H-pyrrol-3-yl)carbonyl]amino}butanoic acid |

TABLE 1-continued

Exemplified Compounds of the Present Invention

| Example# | Chemical Structure | MW | Chemical Name |
|---|---|---|---|
| 69 | 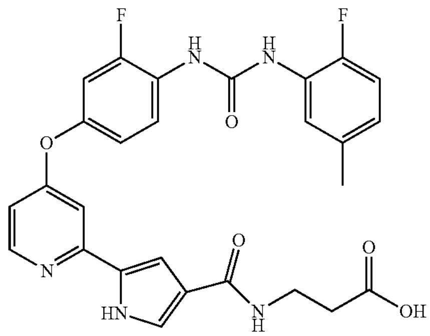 [SMILES: Cc1ccc(F)c(NC(=O)Nc2ccc(Oc3ccnc(-c4cc(C(=O)NCCC(=O)O)c[nH]4)c3)cc2F)c1] | 536 | 3-{[(5-{4-[3-fluoro-4-({[(2-fluoro-5-methylphenyl)amino]carbonyl}amino)-phenoxy]pyridin-2-yl}-1H-pyrrol-3-yl)carbonyl]amino}-propanoic acid |
| 70 | 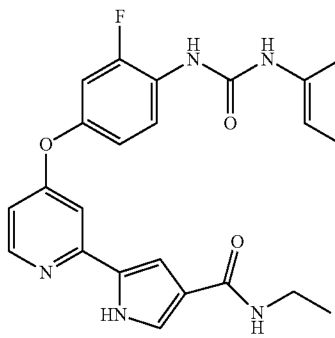 | 474 | N-ethyl-5-{4-[3-fluoro-4-({[(3-methylphenyl)amino]carbonyl}amino)-phenoxy]pyridin-2-yl}-1H-pyrrole-3-carboxamide |
| 71 | 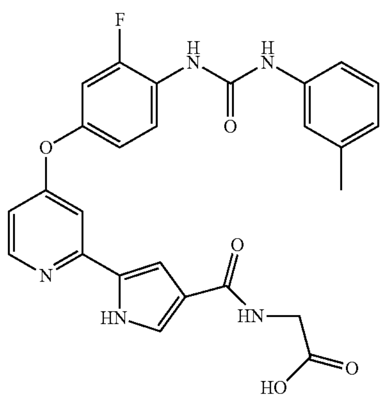 [SMILES: Cc1cccc(NC(=O)Nc2ccc(Oc3ccnc(-c4cc(C(=O)NCC(=O)O)c[nH]4)c3)cc2F)c1] | 503 | {[(5-{4-[3-fluoro-4-({[(3-methylphenyl)amino]carbonyl}amino)-phenoxy]pyridin-2-yl}-1H-pyrrol-3-yl)carbonyl]amino}acetic acid |
| 72 | 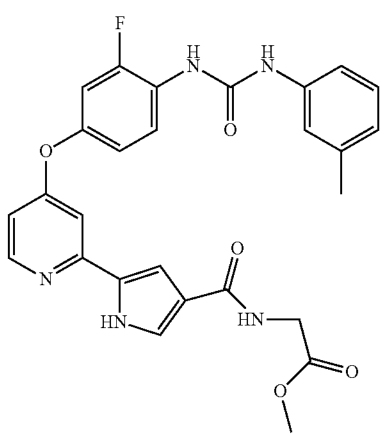 [SMILES: COC(=O)CNC(=O)c1c[nH]c(-c2cc(Oc3ccc(NC(=O)Nc4cccc(C)c4)c(F)c3)ccn2)c1] | 518 | methyl {[(5-{4-[3-fluoro-4-({[(3-methylphenyl)amino]carbonyl}amino)-phenoxy]pyridin-2-yl}-1H-pyrrol-3-yl)carbonyl]amino}acetate |

TABLE 1-continued

Exemplified Compounds of the Present Invention

| Example# | Chemical Structure | MW | Chemical Name |
|---|---|---|---|
| 73 | 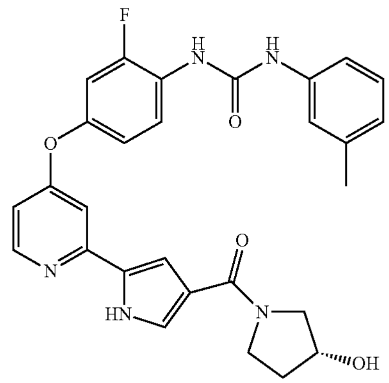 [SMILES: Cc1cccc(NC(=O)Nc2ccc(Oc3ccnc(-c4cc(C(=O)N5CC[C@@H](O)C5)c[nH]4)c3)cc2F)c1] | 516 | 1-(2-fluoro-4-{[2-(4-{[(3R)-3-hydroxypyrrolidin-1-yl]carbonyl}-1H-pyrrol-2-yl)pyridin-4-yl]oxy}phenyl)-3-(3-methylphenyl)urea |
| 74 | 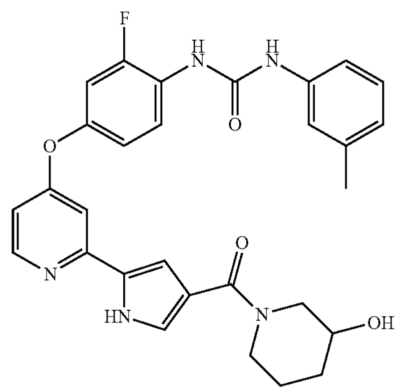 [SMILES: Cc1cccc(NC(=O)Nc2ccc(Oc3ccnc(-c4cc(C(=O)N5CCCC(O)C5)c[nH]4)c3)cc2F)c1] | 530 | 1-{2-fluoro-4-[(2-{4-[(3-hydroxy-piperidin-1-yl)carbonyl]-1H-pyrrol-2-yl}pyridin-4-yl)-oxy]phenyl}-3-(3-methylphenyl)urea |
| 75 | 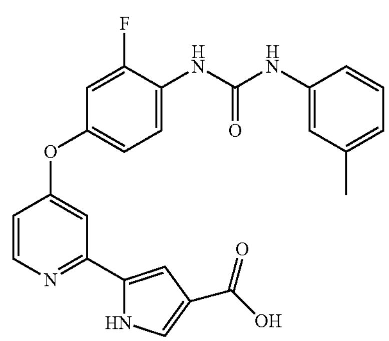 [SMILES: Cc1cccc(NC(=O)Nc2ccc(Oc3ccnc(-c4cc(C(=O)O)c[nH]4)c3)cc2F)c1] | 446 | 5-{4-[3-fluoro-4-({[(3-methylphenyl)amino]carbonyl}amino)-phenoxy]pyridin-2-yl}-1H-pyrrole-3-carboxylic acid |
| 76 | 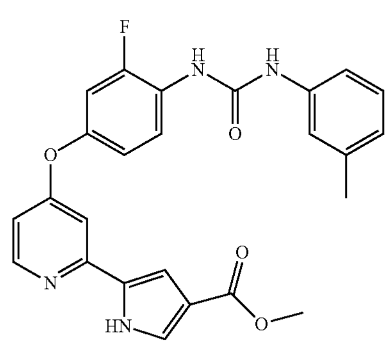 [SMILES: COC(=O)c1c[nH]c(-c2cc(Oc3ccc(NC(=O)Nc4cccc(C)c4)c(F)c3)ccn2)c1] | 460 | methyl 5-{4-[3-fluoro-4-({[(3-methylphenyl)amino]carbonyl}amino)-phenoxy]pyridin-2-yl}-1H-pyrrole-3-carboxylate |

TABLE 1-continued

Exemplified Compounds of the Present Invention

| Example# | Chemical Structure | MW | Chemical Name |
|---|---|---|---|
| 77 | 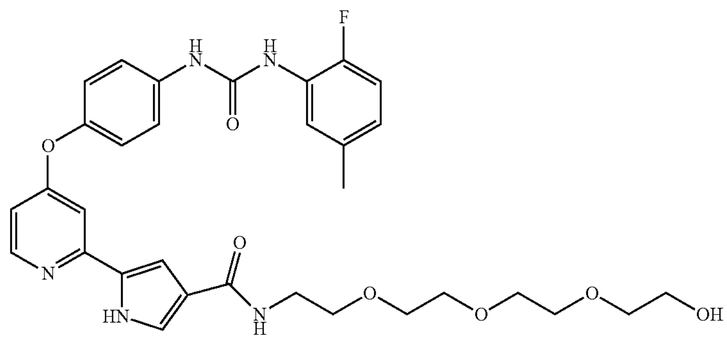 [SMILES: Cc1ccc(F)c(NC(=O)Nc2ccc(Oc3ccnc(-c4cc(C(=O)NCCOCCOCCOCCO)c[nH]4)c3)cc2)c1] | 622 | 5-{4-[4-({[(2-fluoro-5-methylphenyl)amino]carbonyl}amino)phenoxy]pyridin-2-yl}-N-(2-{2-[2-(2-hydroxyethoxy)ethoxy]ethoxy}ethyl)-1H-pyrrole-3-carboxamide |
| 78 | 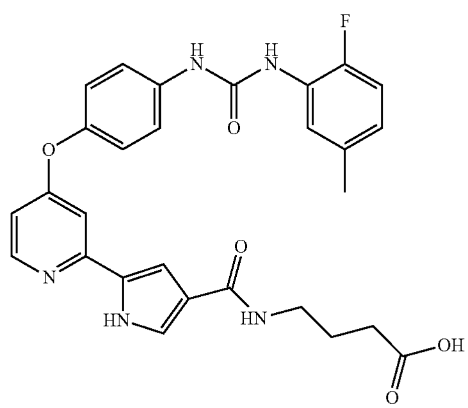 [SMILES: Cc1ccc(F)c(NC(=O)Nc2ccc(Oc3ccnc(-c4cc(C(=O)NCCCC(=O)O)c[nH]4)c3)cc2)c1] | 532 | 4-{[(5-{4-[4-({[(2-fluoro-5-methylphenyl)amino]carbonyl}amino)phenoxy]pyridin-2-yl}-1H-pyrrol-3-yl)carbonyl]amino}butanoic acid |
| 79 | 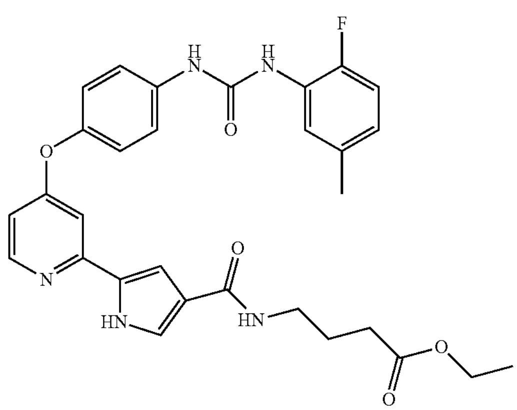 [SMILES: CCOC(=O)CCCNC(=O)c1c[nH]c(-c2cc(Oc3ccc(NC(=O)Nc4cc(C)ccc4F)cc3)ccn2)c1] | 560 | ethyl 4-{[(5-{4-[4-({[(2-fluoro-5-methylphenyl)amino]carbonyl}amino)phenoxy]pyridin-2-yl}-1H-pyrrol-3-yl)carbonyl]amino}butanoate |
| 80 | 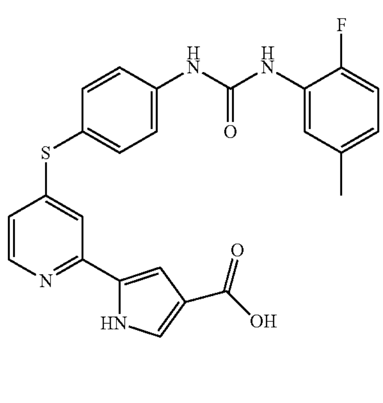 | 463 | 5-(4-{[4-({[(2-fluoro-5-methylphenyl)amino]carbonyl}amino)phenyl]thio}pyridin-2-yl)-1H-pyrrole-3-carboxylic acid |

TABLE 1-continued

Exemplified Compounds of the Present Invention

| Example# | Chemical Structure | MW | Chemical Name |
|---|---|---|---|
| 81 | 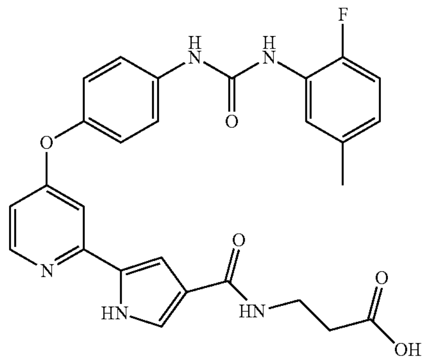 [SMILES: Cc1ccc(F)c(NC(=O)Nc2ccc(Oc3ccnc(-c4cc(C(=O)NCCC(=O)O)c[nH]4)c3)cc2)c1] | 518 | 3-{[(5-{4-[4-({[(2-fluoro-5-methylphenyl)amino]carbonyl}amino)-phenoxy]pyridin-2-yl}-1H-pyrrol-3-yl)carbonyl]amino}-propanoic acid |
| 82 | 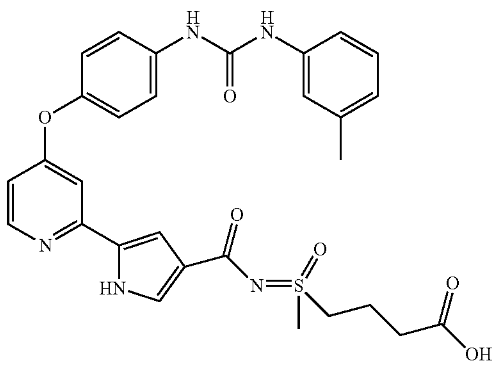 [SMILES: Cc1cccc(NC(=O)Nc2ccc(Oc3ccnc(-c4cc(C(=O)N=S(C)(=O)CCCC(=O)O)c[nH]4)c3)cc2)c1] | 576 | 4-{S-methyl-N-[(5-{4-[4-({[(3-methylphenyl)amino]carbonyl}amino)-phenoxy]pyridin-2-yl}-1H-pyrrol-3-yl)carbonyl]sulfonimidoyl}-butanoic acid |
| 83 | 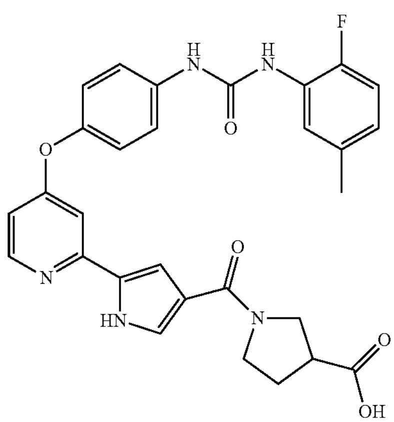 [SMILES: Cc1ccc(F)c(NC(=O)Nc2ccc(Oc3ccnc(-c4cc(C(=O)N5CCC(C(=O)O)C5)c[nH]4)c3)cc2)c1] | 544 | 1-[(5-{4-[4-({[(2-fluoro-5-methylphenyl)amino]carbonyl}amino)-phenoxy]pyridin-2-yl}-1H-pyrrol-3-yl)carbonyl]pyrrolidine-3-carboxylic acid |
| 84 | 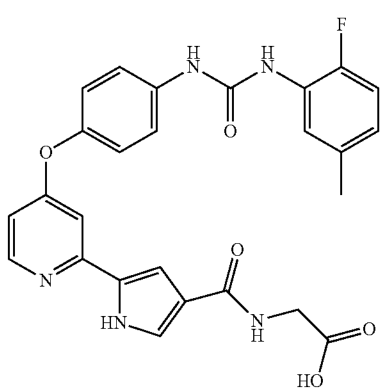 [SMILES: Cc1ccc(F)c(NC(=O)Nc2ccc(Oc3ccnc(-c4cc(C(=O)NCC(=O)O)c[nH]4)c3)cc2)c1] | 503 | {[(5-{4-[4-({[(2-fluoro-5-methylphenyl)amino]carbonyl}amino)-phenoxy]pyridin-2-yl}-1H-pyrrol-3-yl)carbonyl]amino}acetic acid |

TABLE 1-continued

Exemplified Compounds of the Present Invention

| Example# | Chemical Structure | MW | Chemical Name |
|---|---|---|---|
| 85 | 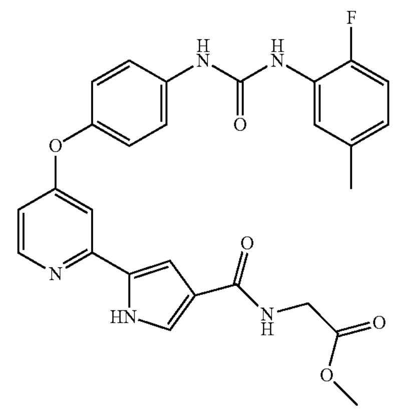 [SMILES: COC(=O)CNC(=O)c1c[nH]c(-c2cc(Oc3ccc(NC(=O)Nc4cc(C)ccc4F)cc3)ccn2)c1] | 518 | methyl {[(5-{4-[4-({[(2-fluoro-5-methylphenyl)amino]carbonyl}amino)-phenoxy]pyridin-2-yl}-1H-pyrrol-3-yl)carbonyl]amino}acetate |
| 86 | 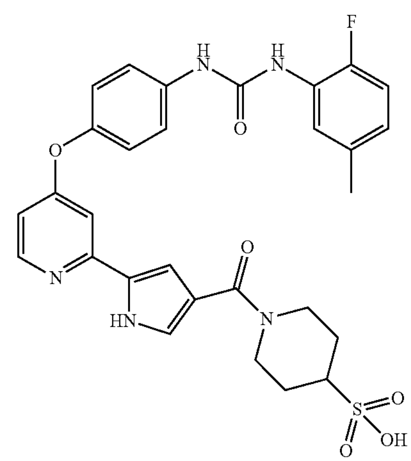 [SMILES: Cc1ccc(F)c(NC(=O)Nc2ccc(Oc3ccnc(-c4cc(C(=O)N5CCC(S(=O)(=O)O)CC5)c[nH]4)c3)cc2)c1] | 594 | 1-[(5-{4-[4-({[(2-fluoro-5-methylphenyl)amino]carbonyl}amino)-phenoxy]pyridin-2-yl}-1H-pyrrol-3-yl)carbonyl]piperidine-4-sulfonic acid |
| 87 | 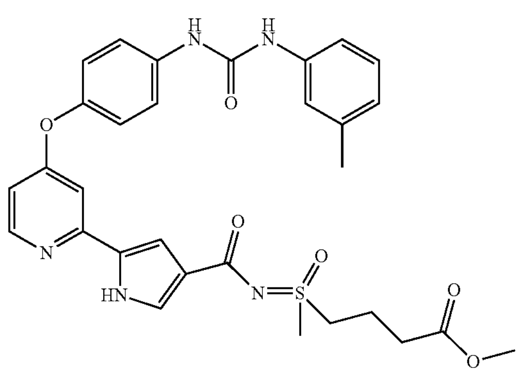 [SMILES: COC(=O)CCCS(C)(=O)=NC(=O)c1c[nH]c(-c2cc(Oc3ccc(NC(=O)Nc4cccc(C)c4)cc3)ccn2)c1] | 590 | methyl 4-{S-methyl-N-[(5-{4-[4-({[(3-methylphenyl)amino]carbonyl}amino)-phenoxy]pyridin-2-yl}-1H-pyrrol-3-yl)carbonyl]sulfonimidoyl}-butanoate |

TABLE 1-continued

Exemplified Compounds of the Present Invention

| Example# | Chemical Structure | MW | Chemical Name |
|---|---|---|---|
| 88 | 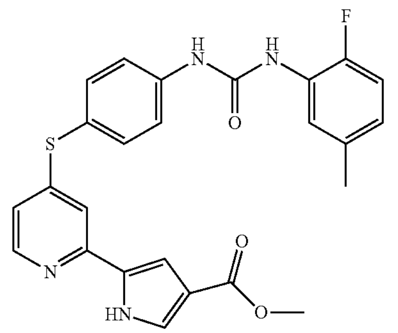 [SMILES: COC(=O)c1c[nH]c(-c2cc(Sc3ccc(NC(=O)Nc4cc(C)ccc4F)cc3)ccn2)c1] | 477 | methyl 5-(4-{[4-({[(2-fluoro-5-methylphenyl)amino]carbonyl}amino)-phenyl]thio}pyridin-2-yl)-1H-pyrrole-3-carboxylate |
| 89 | 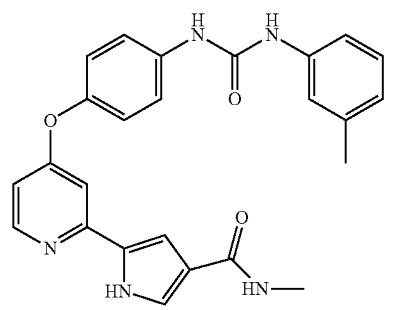 | 441 | N-methyl-5-{4-[4-({[(3-methylphenyl)amino]carbonyl}amino)-phenoxy]pyridin-2-yl}-1H-pyrrole-3-carboxamide |
| 90 | 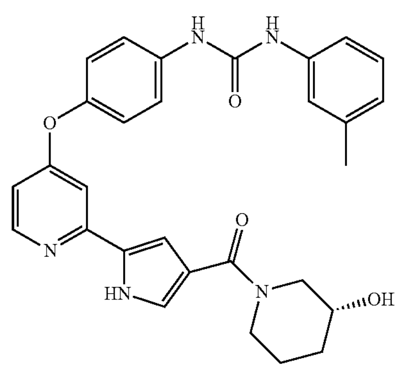 [SMILES: Cc1cccc(NC(=O)Nc2ccc(Oc3ccnc(-c4cc(C(=O)N5CCC[C@@H](O)C5)c[nH]4)c3)cc2)c1] | 512 | 1-{4-[(2-{4-[(3-hydroxypiperidin-1-yl)-carbonyl]-1H-pyrrol-2-yl}pyridin-4-yl)oxy]phenyl}-3-(3-methylphenyl)urea |
| 91 | 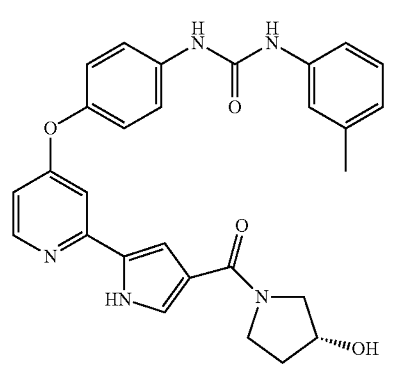 [SMILES: Cc1cccc(NC(=O)Nc2ccc(Oc3ccnc(-c4cc(C(=O)N5CC[C@@H](O)C5)c[nH]4)c3)cc2)c1] | 498 | 1-{4-[(2-{4-[(3-hydroxypyrrolidin-1-yl)-carbonyl]-1H-pyrrol-2-yl}pyridin-4-yl)oxy]phenyl}-3-{3-methylphenyl)urea |

TABLE 1-continued

Exemplified Compounds of the Present Invention

| Example # | Chemical Structure | MW | Chemical Name |
|---|---|---|---|
| 92 | 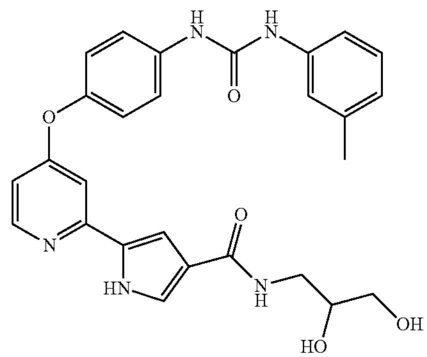 [SMILES: Cc1cccc(NC(=O)Nc2ccc(Oc3ccnc(-c4cc(C(=O)NCC(O)CO)c[nH]4)c3)cc2)c1] | 502 | N-(2,3-dihydroxypropyl)-5-{4-[4-({[(3-methylphenyl)amino]carbonyl}-amino)phenoxy]pyridin-2-yl}-1H-pyrrole-3-carboxamide |
| 93 | 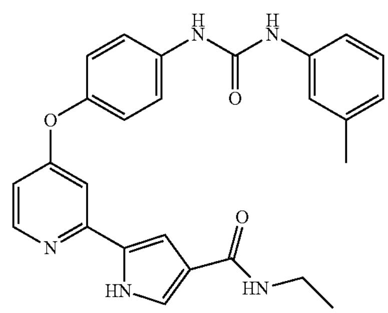 [SMILES: CCNC(=O)c1c[nH]c(-c2cc(Oc3ccc(NC(=O)Nc4cccc(C)c4)cc3)ccn2)c1] | 456 | N-ethyl-5-{4-[4-({[(3-methylphenyl)amino]carbonyl}amino)-phenoxy]pyridin-2-yl}-1H-pyrrole-3-carboxamide |
| 94 | 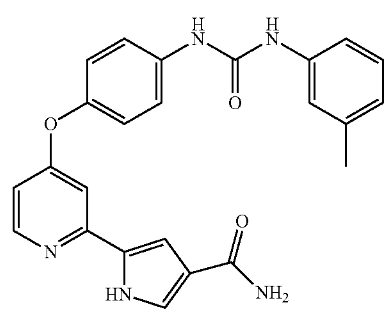 [SMILES: Cc1cccc(NC(=O)Nc2ccc(Oc3ccnc(-c4cc(C(N)=O)c[nH]4)c3)cc2)c1] | 427 | 5-{4-[4-({[(3-methylphenyl)amino]carbonyl}amino)-phenoxy]pyridin-2-yl}-1H-pyrrole-3-carboxamide |
| 95 | 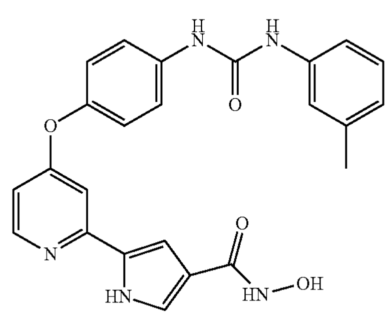 [SMILES: Cc1cccc(NC(=O)Nc2ccc(Oc3ccnc(-c4cc(C(=O)NO)c[nH]4)c3)cc2)c1] | 443 | N-hydroxy-5-{4-[4-({[(3-methylphenyl)amino]carbonyl}amino)-phenoxy]pyridin-2-yl}-1H-pyrrole-3-carboxamide |

TABLE 1-continued

Exemplified Compounds of the Present Invention

| Example# | Chemical Structure | MW | Chemical Name |
|---|---|---|---|
| 96 | 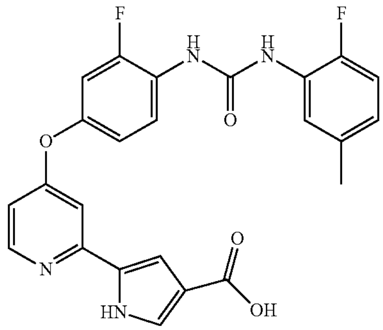 [SMILES: Cc1ccc(F)c(NC(=O)Nc2ccc(Oc3ccnc(-c4cc(C(=O)O)c[nH]4)c3)cc2F)c1] | 464 | 5-{4-[3-fluoro-4-({[(2-fluoro-5-methylphenyl)amino]carbonyl}amino)-phenoxy]pyridin-2-yl}-1H-pyrrole-3-carboxylic acid |
| 97 | 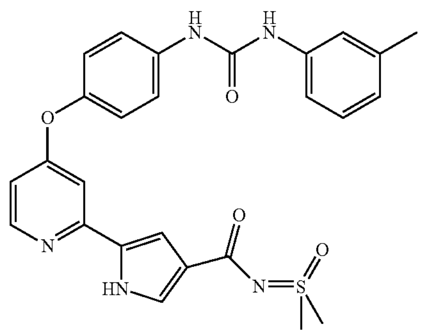 [SMILES: Cc1cccc(NC(=O)Nc2ccc(Oc3ccnc(-c4cc(C(=O)N=S(C)(C)=O)c[nH]4)c3)cc2)c1] | 504 | N-[dimethyl(oxido)-lambda~4~-sulfanylidene]-5-{4-[4-({[(3-methylphenyl)amino]carbonyl}amino)-phenoxy]pyridin-2-yl}-1H-pyrrole-3-carboxamide |
| 98 | 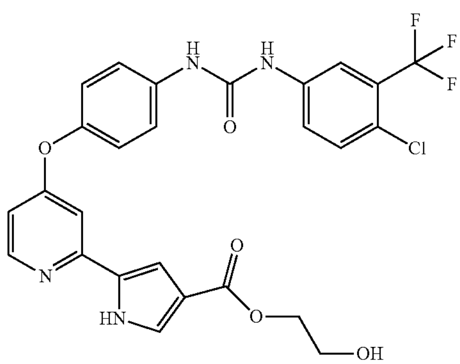 [SMILES: O=C(Nc1ccc(Oc2ccnc(-c3cc(C(=O)OCCO)c[nH]3)c2)cc1)Nc1ccc(Cl)c(C(F)(F)F)c1] | 561 | 2-hydroxyethyl 5-(4-{4-[({[4-chloro-3-(trifluoromethyl)phenyl]amino}-carbonyl)-amino]phenoxy}-pyridin-2-yl)-1H-pyrrole-3-carboxylate |
| 99 | 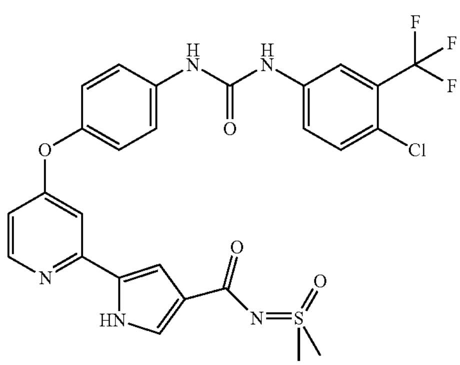 [SMILES: CS(C)(=O)=NC(=O)c1c[nH]c(-c2cc(Oc3ccc(NC(=O)Nc4ccc(Cl)c(C(F)(F)F)c4)cc3)ccn2)c1] | 592 | 5-(4-{4-[({[4-chloro-3-(tri-fluoromethyl)phenyl]amino}carbonyl)-amino]phenoxy}pyridin-2-yl)-N-[dimethyl(oxido)-lambda~4~-sulfanylidene]-1H-pyrrole-3-carboxamide |

TABLE 1-continued

Exemplified Compounds of the Present Invention

| Example# | Chemical Structure | MW | Chemical Name |
|---|---|---|---|
| 100 | 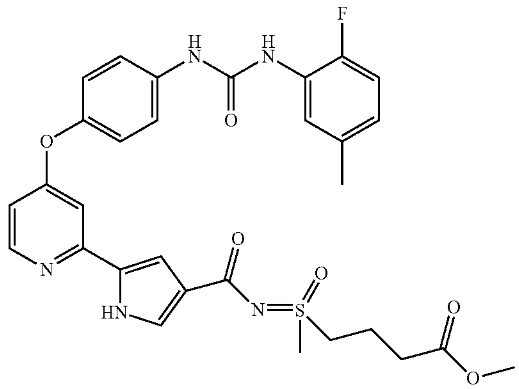 [SMILES: COC(=O)CCCS(C)(=O)=NC(=O)c1c[nH]c(-c2cc(Oc3ccc(NC(=O)Nc4cc(C)ccc4F)cc3)ccn2)c1] | 608 | methyl 4-{N-[(5-{4-[4-({[(2-fluoro-5-methylphenyl)amino]carbonyl}amino)-phenoxy]pyridin-2-yl}-1H-pyrrol-3-yl)carbonyl]-S-methylsulfonimidoyl}butanoate |
| 101 | 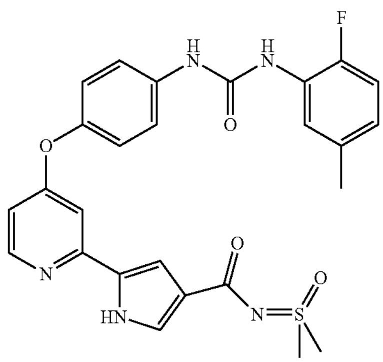 [SMILES: Cc1ccc(F)c(NC(=O)Nc2ccc(Oc3ccnc(-c4cc(C(=O)N=S(C)(C)=O)c[nH]4)c3)cc2)c1] | 522 | N-[dimethyl(oxido)-lambda~4~-sulfanylidene]-5-{4-[4-({[(2-fluoro-5-methylphenyl)amino]carbonyl}-amino)phenoxy]pyridin-2-yl}-1H-pyrrole-3-carboxamide |
| 102 | 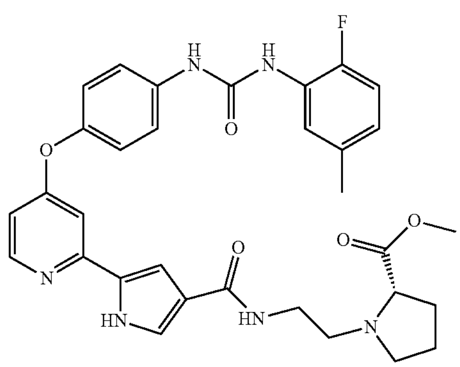 [SMILES: COC(=O)[C@@H]1CCCN1CCNC(=O)c1c[nH]c(-c2cc(Oc3ccc(NC(=O)Nc4cc(C)ccc4F)cc3)ccn2)c1] | 601 | methyl (2S)-1-(2-{[(5-{4-[4-({[(2-fluoro-5-methylphenyl)amino]carbonyl}amino)-phenoxy]pyridin-2-yl}-1H-pyrrol-3-yl)carbonyl]amino}ethyl)-pyrrolidine-2-carboxylate |
| 103 | 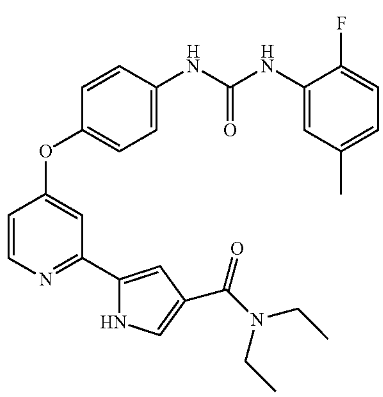 [SMILES: CCN(CC)C(=O)c1c[nH]c(-c2cc(Oc3ccc(NC(=O)Nc4cc(C)ccc4F)cc3)ccn2)c1] | 502 | N,N-diethyl-5-{4-[4-({[(2-fluoro-5-methylphenyl)amino]carbonyl}-amino)phenoxy]pyridin-2-yl}-1H-pyrrole-3-carboxamide |

TABLE 1-continued

Exemplified Compounds of the Present Invention

| Example# | Chemical Structure | MW | Chemical Name |
|---|---|---|---|
| 104 | 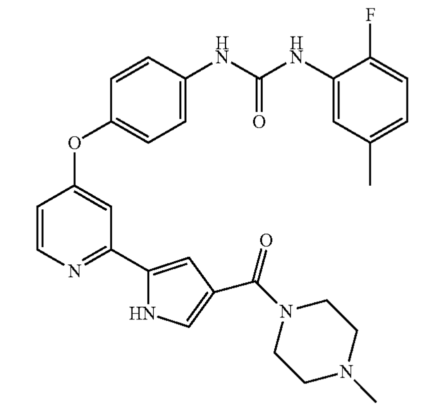 [SMILES: Cc1ccc(F)c(NC(=O)Nc2ccc(Oc3ccnc(-c4cc(C(=O)N5CCN(C)CC5)c[nH]4)c3)cc2)c1] | 529 | 1-(2-fluoro-5-methylphenyl)-3-{4-[(2-{4-[(4-methylpiperazin-1-yl)carbonyl]-1H-pyrrol-2-yl}pyridin-4-yl)oxy]-phenyl}urea |
| 105 | 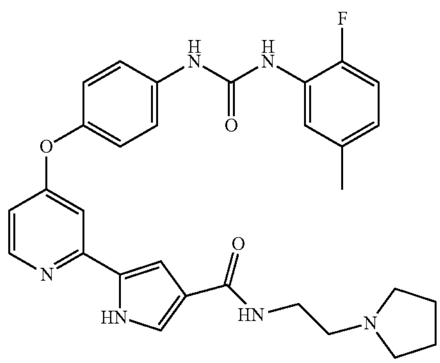 [SMILES: Cc1ccc(F)c(NC(=O)Nc2ccc(Oc3ccnc(-c4cc(C(=O)NCCN5CCCC5)c[nH]4)c3)cc2)c1] | 543 | 5-{4-[4-({[(2-fluoro-5-methylphenyl)amino]carbonyl}amino)-phenoxy]pyridin-2-yl}-N-(2-pyrrolidin-1-ylethyl)-1H-pyrrole-3-carboxamide |
| 106 | 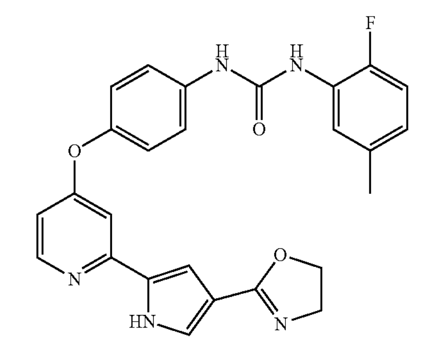 [SMILES: Cc1ccc(F)c(NC(=O)Nc2ccc(Oc3ccnc(-c4cc(C5=NCCO5)c[nH]4)c3)cc2)c1] | 471 | 1-[4-({2-[4-(aziridin-1-ylcarbonyl)-1H-pyrrol-2-yl]pyridin-4-yl}oxy)phenyl]-3-(2-fluoro-5-methylphenyl)urea |
| 107 | 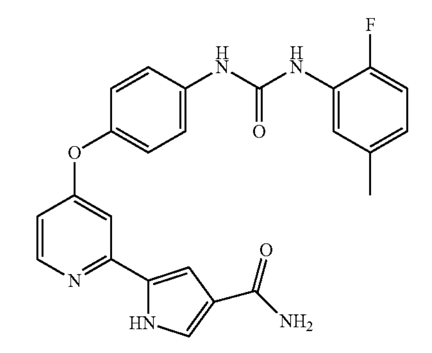 [SMILES: Cc1ccc(F)c(NC(=O)Nc2ccc(Oc3ccnc(-c4cc(C(N)=O)c[nH]4)c3)cc2)c1] | 445 | 5-{4-[4-({[(2-fluoro-5-methylphenyl)amino]carbonyl}amino)-phenoxy]pyridin-2-yl}-1H-pyrrole-3-carboxamide |

TABLE 1-continued

Exemplified Compounds of the Present Invention

| Example# | Chemical Structure | MW | Chemical Name |
|---|---|---|---|
| 108 | 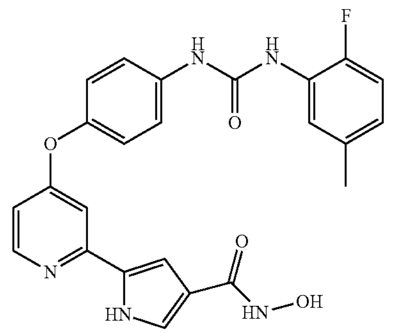 [SMILES: Cc1ccc(F)c(NC(=O)Nc2ccc(Oc3ccnc(-c4cc(C(=O)NO)c[nH]4)c3)cc2)c1] | 461 | 5-{4-[4-({[(2-fluoro-5-methylphenyl)amino]carbonyl}amino)-phenoxy]pyridin-2-yl}-N-hydroxy-1H-pyrrole-3-carboxamide |
| 109 | 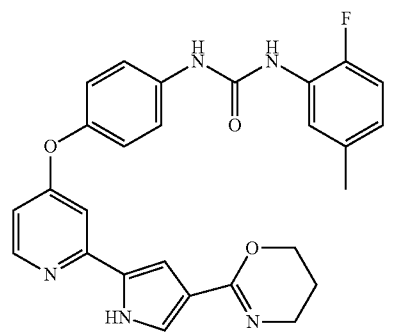 [SMILES: Cc1ccc(F)c(NC(=O)Nc2ccc(Oc3ccnc(-c4cc(C5=NCCCO5)c[nH]4)c3)cc2)c1] | 486 | 1-[4-({2-[4-(azetidin-1-ylcarbonyl)-1H-pyrrol-2-yl]pyridin-4-yl}oxy)phenyl]-3-(2-fluoro-5-methylphenyl)urea |
| 110 | 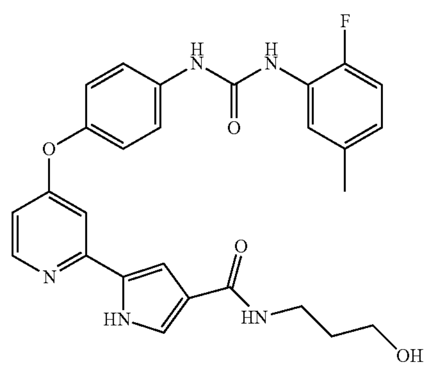 [SMILES: Cc1ccc(F)c(NC(=O)Nc2ccc(Oc3ccnc(-c4cc(C(=O)NCCCO)c[nH]4)c3)cc2)c1] | 504 | 5-{4-[4-({[(2-fluoro-5-methylphenyl)amino]carbonyl}amino)-phenoxy]pyridin-2-yl}-N-(3-hydroxypropyl)-1H-pyrrole-3-carboxamide |
| 111 | 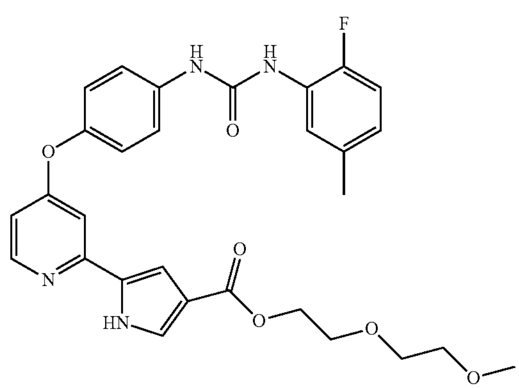 [SMILES: COCCOCCOC(=O)c1c[nH]c(-c2cc(Oc3ccc(NC(=O)Nc4cc(C)ccc4F)cc3)ccn2)c1] | 549 | 2-(2-methoxyethoxy)ethyl 5-{4-[4-({[(2-fluoro-5-methylphenyl)amino]-carbonyl}amino)phenoxy]pyridin-2-yl}-1H-pyrrole-3-carboxylate |

TABLE 1-continued

Exemplified Compounds of the Present Invention

| Example# | Chemical Structure | MW | Chemical Name |
|---|---|---|---|
| 112 | 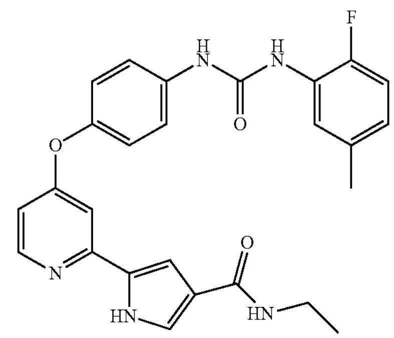 [SMILES: CCNC(=O)c1c[nH]c(-c2cc(Oc3ccc(NC(=O)Nc4cc(C)ccc4F)cc3)ccn2)c1] | 474 | N-ethyl-5-{4-[4-({[(2-fluoro-5-methylphenyl)amino]carbonyl}amino)-phenoxy]pyridin-2-yl}-1H-pyrrole-3-carboxamide |
| 113 | 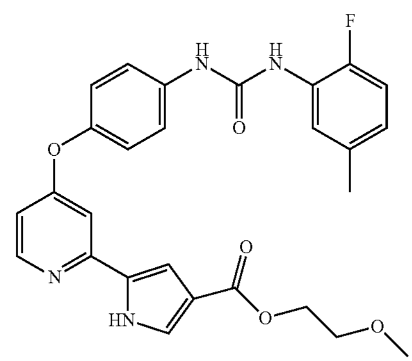 [SMILES: COCCOC(=O)c1c[nH]c(-c2cc(Oc3ccc(NC(=O)Nc4cc(C)ccc4F)cc3)ccn2)c1] | 505 | 2-methoxyethyl 5-{4-[4-({[(2-fluoro-5-methylphenyl)amino]carbonyl}amino)-phenoxy]pyridin-2-yl}-1H-pyrrole-3-carboxylate |
| 114 | 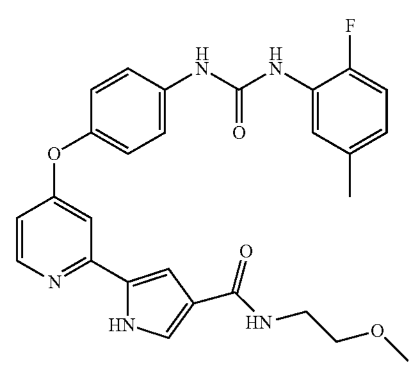 [SMILES: COCCNC(=O)c1c[nH]c(-c2cc(Oc3ccc(NC(=O)Nc4cc(C)ccc4F)cc3)ccn2)c1] | 504 | 5-{4-[4-({[(2-fluoro-5-methylphenyl)amino]carbonyl}amino)-phenoxy]pyridin-2-yl}-N-(2-methoxyethyl)-1H-pyrrole-3-carboxamide |
| 115 | 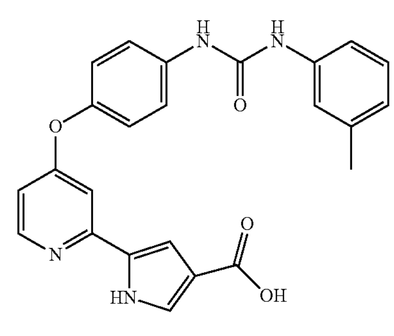 | 428 | 5-{4-[4-({[(3-methylphenyl)amino]carbonyl}amino)-phenoxy]pyridin-2-yl}-1H-pyrrole-3-carboxylic acid |

TABLE 1-continued

Exemplified Compounds of the Present Invention

| Example# | Chemical Structure | MW | Chemical Name |
|---|---|---|---|
| 116 | 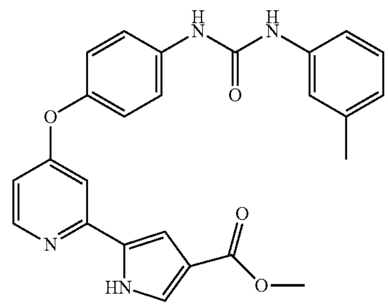 [SMILES: COC(=O)c1c[nH]c(-c2cc(Oc3ccc(NC(=O)Nc4cccc(C)c4)cc3)ccn2)c1] | 442 | methyl 5-{4-[4-({[(3-methylphenyl)amino]carbonyl}amino)-phenoxy]pyridin-2-yl}-1H-pyrrole-3-carboxylate |
| 117 | 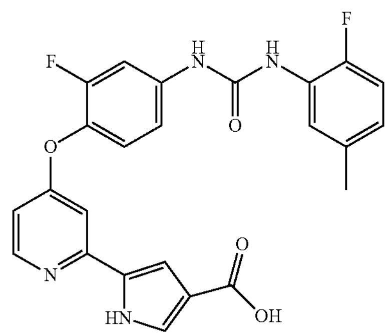 [SMILES: Cc1ccc(F)c(NC(=O)Nc2ccc(Oc3ccnc(-c4cc(C(=O)O)c[nH]4)c3)c(F)c2)c1] | 464 | 5-{4-[2-fluoro-4-({[(2-fluoro-5-methylphenyl)amino]carbonyl}amino)-phenoxy]pyridin-2-yl}-1H-pyrrole-3-carboxylic acid |
| 118 | 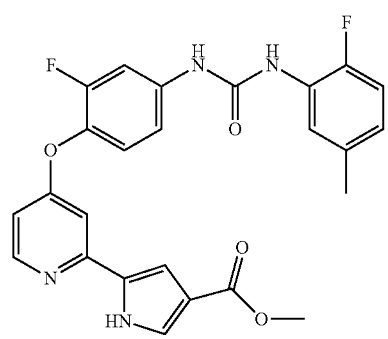 | 478 | methyl 5-{4-[2-fluoro-4-({[(2-fluoro-5-methylphenyl)amino]carbonyl}amino)-phenoxy]pyridin-2-yl}-1H-pyrrole-3-carboxylate |
| 119 | 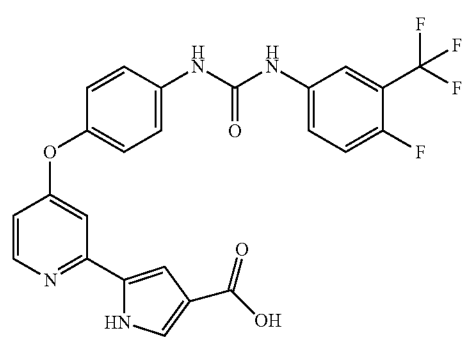 [SMILES: O=C(Nc1ccc(Oc2ccnc(-c3cc(C(=O)O)c[nH]3)c2)cc1)Nc1ccc(F)c(C(F)(F)F)c1] | 500 | 5-(4-{4-[({[4-fluoro-3-(trifluoromethyl)phenyl]amino}-carbonyl)-amino]phenoxy}pyridin-2-yl)-1H-pyrrole-3-carboxylic acid |

TABLE 1-continued

Exemplified Compounds of the Present Invention

| Example # | Chemical Structure | MW | Chemical Name |
|---|---|---|---|
| 120 | 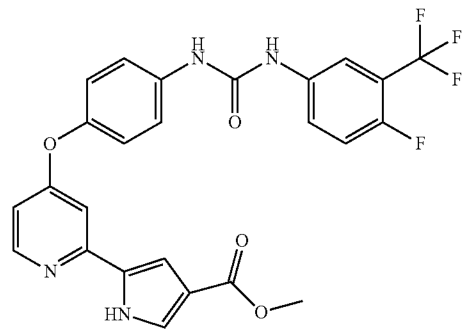 [SMILES: COC(=O)c1c[nH]c(-c2cc(Oc3ccc(NC(=O)Nc4ccc(F)c(C(F)(F)F)c4)cc3)ccn2)c1] | 514 | methyl 5-(4-{4-[({[4-fluoro-3-(trifluoromethyl)phenyl]amino}-carbonyl)-amino]phenoxy}pyridin-2-yl)-1H-pyrrole-3-carboxylate |
| 121 | 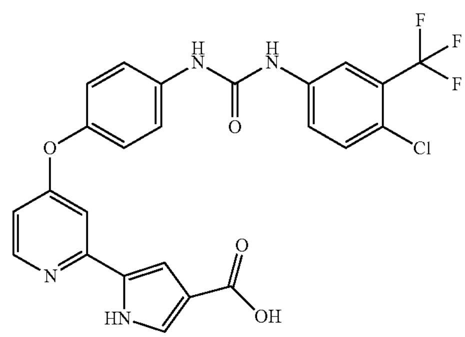 [SMILES: O=C(Nc1ccc(Oc2ccnc(-c3cc(C(=O)O)c[nH]3)c2)cc1)Nc1ccc(Cl)c(C(F)(F)F)c1] | 517 | 5-(4-{4-[({[4-chloro-3-(trifluoromethyl)phenyl]amino}-carbonyl)-amino]phenoxy}pyridin-2-yl)-1H-pyrrole-3-carboxylic acid |
| 122 | 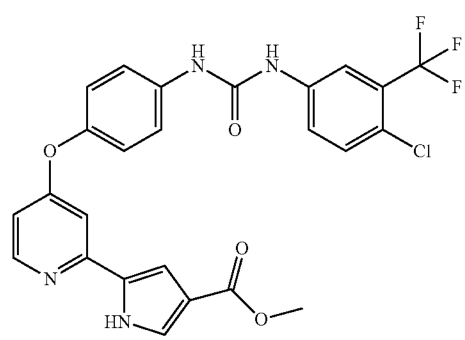 [SMILES: COC(=O)c1c[nH]c(-c2cc(Oc3ccc(NC(=O)Nc4ccc(Cl)c(C(F)(F)F)c4)cc3)ccn2)c1] | 531 | methyl 5-(4-{4-[({[4-chloro-3-(trifluoromethyl)phenyl]amino}-carbonyl)-amino]phenoxy}pyridin-2-y)-1H-pyrrole-3-carboxylate |
| 123 | 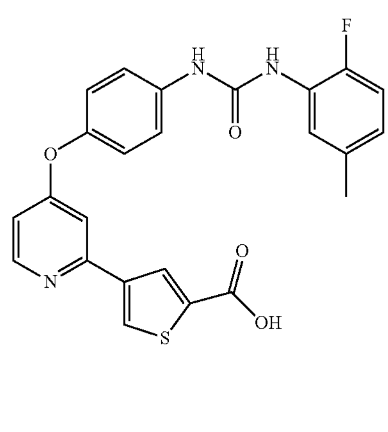 [SMILES: Cc1ccc(F)c(NC(=O)Nc2ccc(Oc3ccnc(-c4csc(C(=O)O)c4)c3)cc2)c1] | 463 | 4-{4-[4-({[(2-fluoro-5-methylphenyl)amino]carbonyl}-amino)phenoxy]pyridin-2-yl}thiophene-2-carboxylic acid |

TABLE 1-continued

Exemplified Compounds of the Present Invention

| Example# | Chemical Structure | MW | Chemical Name |
|---|---|---|---|
| 124 | 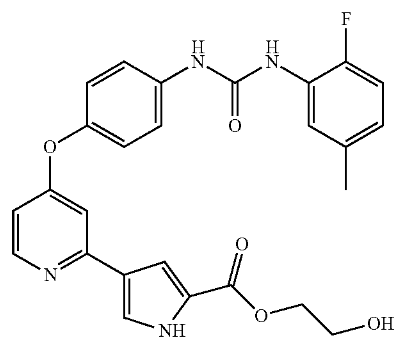 [SMILES: Cc1ccc(F)c(NC(=O)Nc2ccc(Oc3ccnc(-c4c[nH]c(C(=O)OCCO)c4)c3)cc2)c1] | 490 | 2-hydroxyethyl 4-{4-[4-({[(2-fluoro-5-methylphenyl)amino]carbonyl}amino)-phenoxy]pyridin-2-yl}-1H-pyrrole-2-carboxylate |
| 125 | 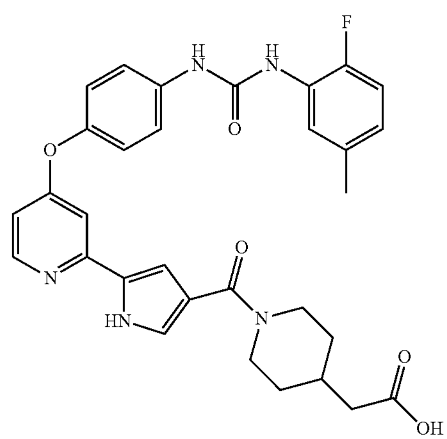 [SMILES: Cc1ccc(F)c(NC(=O)Nc2ccc(Oc3ccnc(-c4cc(C(=O)N5CCC(CC(=O)O)CC5)c[nH]4)c3)cc2)c1] | 572 | {1-[(5-{4-[4-({[(2-fluoro-5-methylphenyl)amino]carbonyl}amino)-phenoxy]pyridin-2-yl}-1H-pyrrol-3-yl)carbonyl]piperidin-4-yl}-acetic acid |
| 126 | 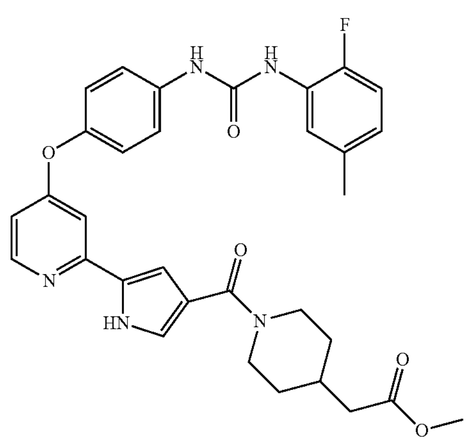 [SMILES: COC(=O)CC1CCN(C(=O)c2c[nH]c(-c3cc(Oc4ccc(NC(=O)Nc5cc(C)ccc5F)cc4)ccn3)c2)CC1] | 586 | methyl {1-[(5-{4-[4-({[(2-fluoro-5-methylphenyl)amino]carbonyl}amino)-phenoxy]pyridin-2-yl}-1H-pyrrol-3-yl)carbonyl]piperidin-4-yl}acetate |

TABLE 1-continued

Exemplified Compounds of the Present Invention

| Example# | Chemical Structure | MW | Chemical Name |
|---|---|---|---|
| 127 | 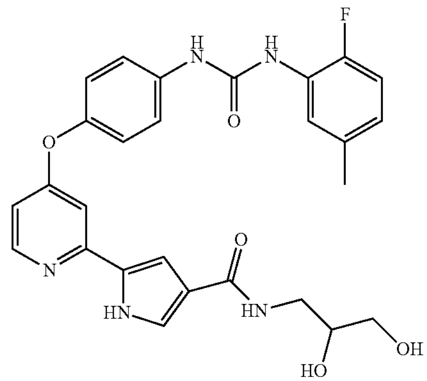 [SMILES: Cc1ccc(F)c(NC(=O)Nc2ccc(Oc3ccnc(-c4cc(C(=O)NCC(O)CO)c[nH]4)c3)cc2)c1] | 520 | N-(2,3-dihydroxypropyl)-5-{4-[4-({[(2-fluoro-5-methylphenyl)amino]-carbonyl}amino)phenoxy]pyridin-2-yl}-1H-pyrrole-3-carboxamide |
| 128 | 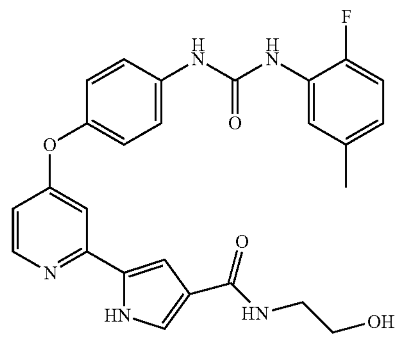 [SMILES: Cc1ccc(F)c(NC(=O)Nc2ccc(Oc3ccnc(-c4cc(C(=O)NCCO)c[nH]4)c3)cc2)c1] | 490 | 5-{4-[4-({[(2-fluoro-5-methylphenyl)amino]carbonyl}amino)-phenoxy]pyridin-2-yl}-N-(2-hydroxyethyl)-1H-pyrrole-3-carboxamide |
| 129 | 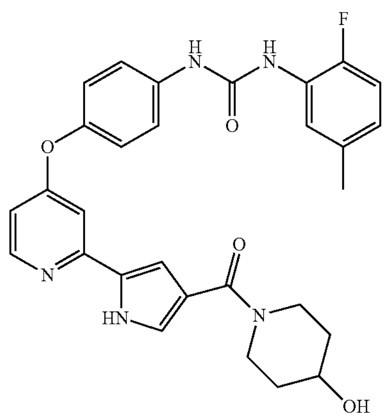 [SMILES: Cc1ccc(F)c(NC(=O)Nc2ccc(Oc3ccnc(-c4cc(C(=O)N5CCC(O)CC5)c[nH]4)c3)cc2)c1] | 530 | 1-(2-fluoro-5-methylphenyl)-3-{4-[(2-{4-[(4-hydroxypiperidin-1-yl)carbonyl]-1H-pyrrol-2-yl}pyridin-4-yl)oxy]phenyl}urea |
| 130 | 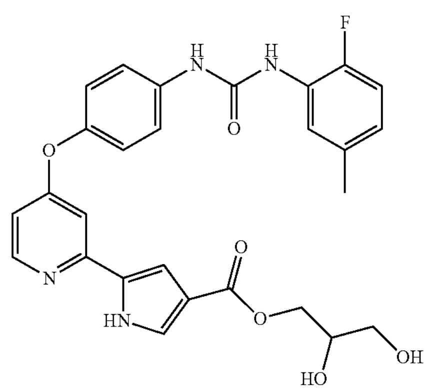 [SMILES: Cc1ccc(F)c(NC(=O)Nc2ccc(Oc3ccnc(-c4cc(C(=O)OCC(O)CO)c[nH]4)c3)cc2)c1] | 521 | 2,3-dihydroxypropyl 5-{4-[4-({[(2-fluoro-5-methylphenyl)-amino]carbonyl}amino)-phenoxy]pyridin-2-yl}-1H-pyrrole-3-carboxylate |

TABLE 1-continued

Exemplified Compounds of the Present Invention

| Example# | Chemical Structure | MW | Chemical Name |
|---|---|---|---|
| 131 | 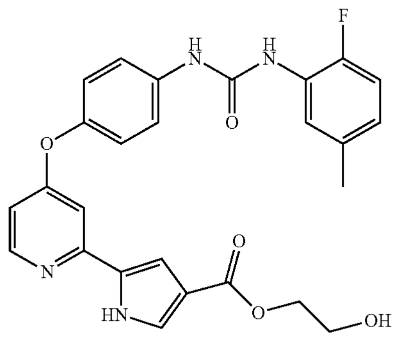 [SMILES: Cc1ccc(F)c(NC(=O)Nc2ccc(Oc3ccnc(-c4cc(C(=O)OCCO)c[nH]4)c3)cc2)c1] | 490 | 2-hydroxyethyl 5-{4-[4-({[(2-fluoro-5-methylphenyl)amino]carbonyl}amino)-phenoxy]pyridin-2-yl}-1H-pyrrole-3-carboxylate |
| 132 | 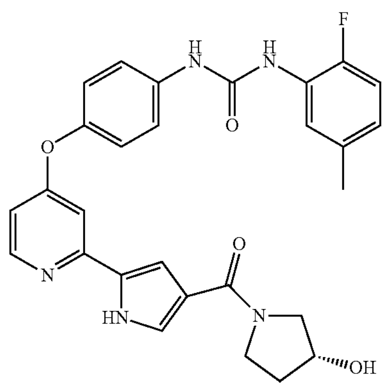 [SMILES: Cc1ccc(F)c(NC(=O)Nc2ccc(Oc3ccnc(-c4cc(C(=O)N5CC[C@@H](O)C5)c[nH]4)c3)cc2)c1] | 516 | 1-(2-fluoro-5-methylphenyl)-3-(4-{[2-(4-{[(3R)-3-hydroxypyrrolidin-1-yl]-carbonyl}-1H-pyrrol-2-yl)pyridin-4-yl]oxy}phenyl)urea |
| 133 | 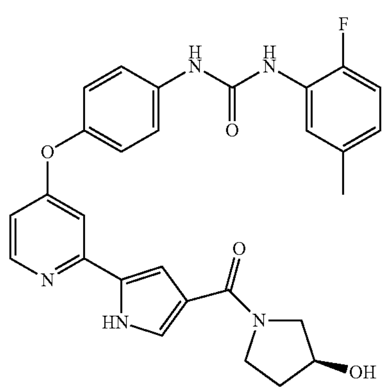 [SMILES: Cc1ccc(F)c(NC(=O)Nc2ccc(Oc3ccnc(-c4cc(C(=O)N5CC[C@H](O)C5)c[nH]4)c3)cc2)c1] | 516 | 1-(2-fluoro-5-methylphenyl)-3-(4-{[2-(4-{[(3S)-3-hydroxypyrrolidin-1-yl]-carbonyl}-1H-pyrrol-2-yl)pyridin-4-yl]oxy}phenyl)urea |
| 134 | 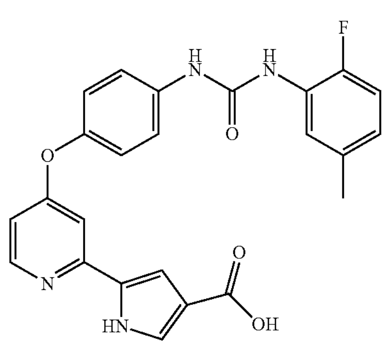 [SMILES: Cc1ccc(F)c(NC(=O)Nc2ccc(Oc3ccnc(-c4cc(C(=O)O)c[nH]4)c3)cc2)c1] | 446 | 5-{4-[4-({[(2-fluoro-5-methylphenyl)amino]carbonyl}amino)-phenoxy]pyridin-2-yl}-1H-pyrrole-3-carboxylic acid |

TABLE 1-continued

Exemplified Compounds of the Present Invention

| Example# | Chemical Structure | MW | Chemical Name |
|---|---|---|---|
| 135 | 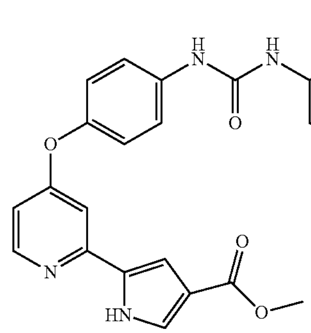 | 460 | methyl 5-{4-[4-({[(2-fluoro-5-methylphenyl)amino]carbonyl}amino)-phenoxy]pyridin-2-yl}-1H-pyrrole-3-carboxylate |
| 136 | 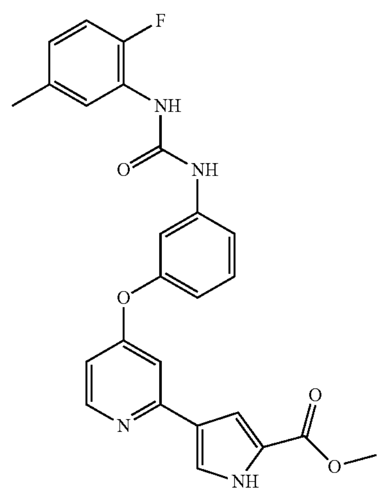 | 460 | methyl 4-{4-[3-({[(2-fluoro-5-methylphenyl)amino]carbonyl}amino)-phenoxy]pyridin-2-yl}-1H-pyrrole-2-carboxylate |
| 137 | 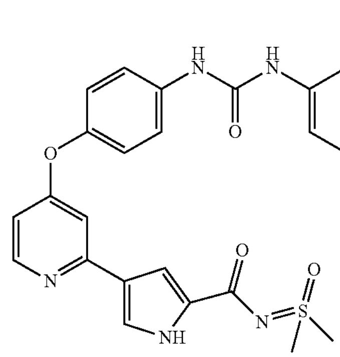 | 522 | N-[dimethyl(oxido)-lambda~4~-sulfanylidene]-4-{4-[4-({[(2-fluoro-5-methylphenyl)amino]carbonyl}amino)-phenoxy]pyridin-2-yl}-1H-pyrrole-2-carboxamide |
| 138 | 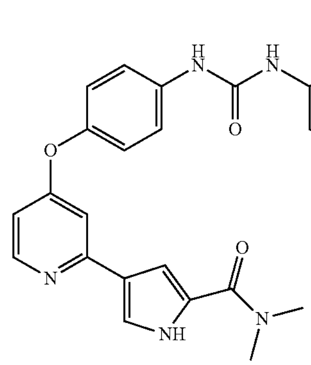 | 474 | 4-{4-[4-({[(2-fluoro-5-methylphenyl)amino]carbonyl}amino)-phenoxy]pyridin-2-yl}-N,N-dimelhyl-1H-pyrrole-2-carboxamide |

TABLE 1-continued

Exemplified Compounds of the Present Invention

| Example# | Chemical Structure | MW | Chemical Name |
|---|---|---|---|
| 139 | 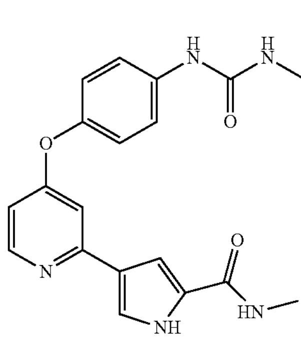 | 459 | 4-{4-[4-({[(2-fluoro-5-methylphenyl)amino]carbonyl}amino)-phenoxy]pyridin-2-yl}-N-methyl-1H-pyrrole-2-carboxamide |
| 140 | 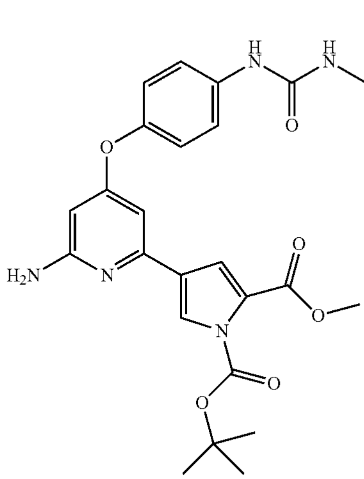 | 576 | 1-tert-butyl 2-methyl 4-{6-amino-4-[4-({[(2-fluoro-5-methylphenyl)-amino]carbonyl}amino)phenoxy]-pyridin-2-yl}-1H-pyrrole-1,2-dicarboxylate |
| 141 | 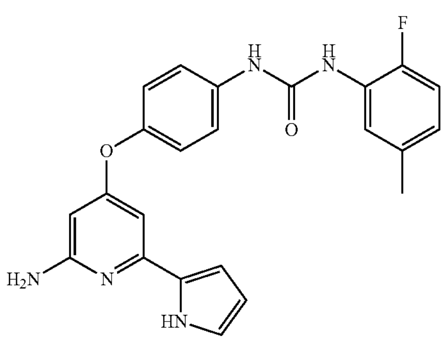 [SMILES: Cc1ccc(F)c(NC(=O)Nc2ccc(Oc3cc(N)nc(-c4ccc[nH]4)c3)cc2)c1] | 417 | 1-(4-{[2-amino-6-(1H-pyrrol-2-yl)-pyridin-4-yl]oxy}phenyl)-3-(2-fluoro-5-methylphenyl)urea |
| 142 | 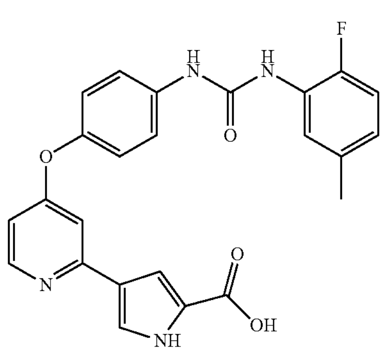 | 446 | 4-{4-[4-({[(2-fluoro-5-methylphenyl)amino]carbonyl}amino)-phenoxy]pyridin-2-yl}-1H-pyrrole-2-carboxylic acid |

TABLE 1-continued

Exemplified Compounds of the Present Invention

| Example# | Chemical Structure | MW | Chemical Name |
|---|---|---|---|
| 143 | 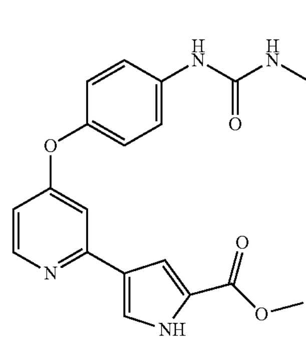 | 460 | methyl 4-{4-[4-({[(2-fluoro-5-methylphenyl)amino]carbonyl}amino)phenoxy]pyridin-2-yl}-1H-pyrrole-2-carboxylate |
| 144 | 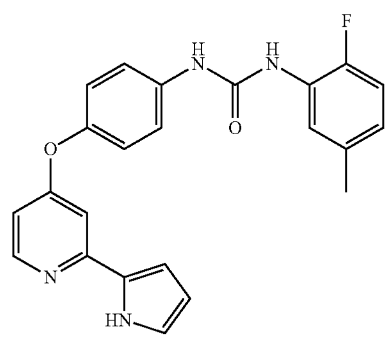 [SMILES: Cc1ccc(F)c(NC(=O)Nc2ccc(Oc3ccnc(-c4ccc[nH]4)c3)cc2)c1] | 402 | 1-(2-fluoro-5-methylphenyl)-3-(4-{[2-(1H-pyrrol-2-yl)pyridin-4-yl]oxy}phenyl)urea |
| 145 | 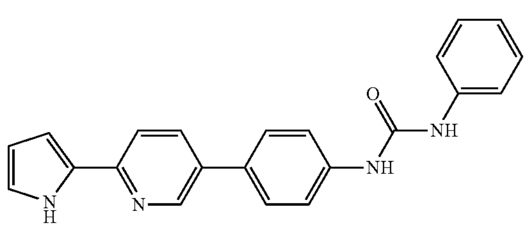 [SMILES: O=C(Nc1ccccc1)Nc1ccc(-c2ccc(-c3ccc[nH]3)nc2)cc1] | 354 | 1-phenyl-3-{4-[6-(1H-pyrrol-2-yl)pyridin-3-yl]phenyl}urea |
| 146 | 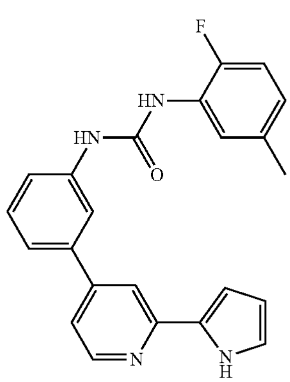 [SMILES: Cc1ccc(F)c(NC(=O)Nc2cccc(-c3ccnc(-c4ccc[nH]4)c3)c2)c1] | 386 | 1-(2-fluoro-5-methylphenyl)-3-{3-[2-(1H-pyrrol-2-yl)pyridin-4-yl]phenyl}urea |

TABLE 1-continued

Exemplified Compounds of the Present Invention

| Example # | Chemical Structure | MW | Chemical Name |
|---|---|---|---|
| 147 | 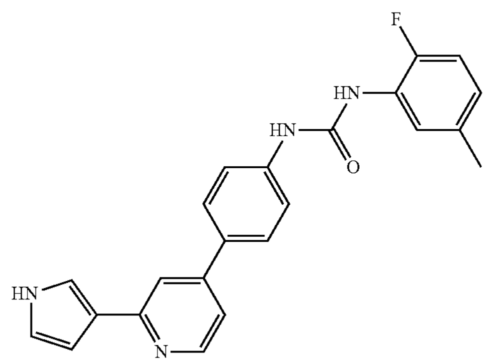 [SMILES: Cc1ccc(F)c(NC(=O)Nc2ccc(-c3ccnc(-c4cc[nH]c4)c3)cc2)c1] | 386 | 1-(2-fluoro-5-methylphenyl)-3-{4-[2-(1H-pyrrol-3-yl)pyridin-4-yl]phenyl)urea |
| 148 | 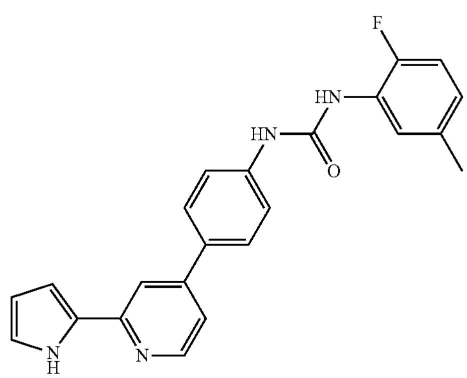 [SMILES: Cc1ccc(F)c(NC(=O)Nc2ccc(-c3ccnc(-c4ccc[nH]4)c3)cc2)c1] | 386 | 1-(2-fluoro-5-methylphenyl)-3-{4-[2-(1H-pyrrol-2-yl)pyridin-4-yl]phenyl}urea |

Additional compounds of the present invention are listed below.

| Example # | Chemical Structure | MW | Chemical Name |
|---|---|---|---|
| 149 | 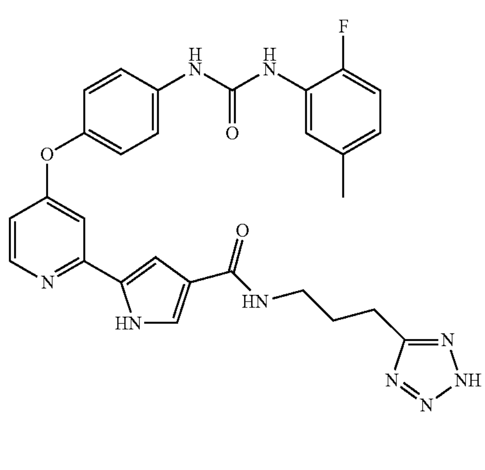 [SMILES: Cc1ccc(F)c(NC(=O)Nc2ccc(Oc3ccnc(-c4cc(C(=O)NCCCc5nn[nH]n5)c[nH]4)c3)cc2)c1] | 556 | 5-{4-[4-({[(2-fluoro-5-methylphenyl)amino]carbonyl}-amino)phenoxy]pyridin-2-yl}-N-[3-(2H-tetrazol-5-yl)propyl]-1H-pyrrole-3-carboxamide |

-continued

| Example # | Chemical Structure | MW | Chemical Name |
|---|---|---|---|
| 150 | 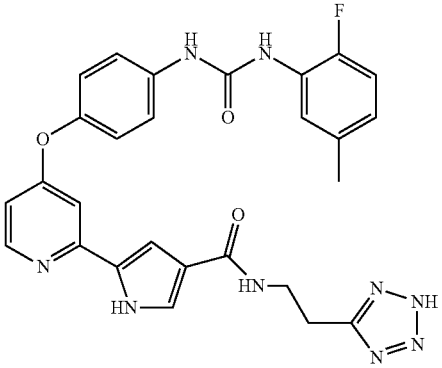 [SMILES: Cc1ccc(F)c(NC(=O)Nc2ccc(Oc3ccnc(-c4cc(C(=O)NCCc5nn[nH]n5)c[nH]4)c3)cc2)c1] | 542 | 5-{4-[4-({[(2-fluoro-5-methylphenyl)amino]carbonyl}-amino)phenoxy]pyridin-2-yl}-N-[2-(2H-tetrazol-5-yl)ethyl]-1H-pyrrole-3-carboxamide |
| 151 | 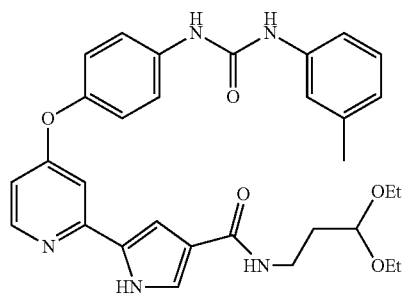 [SMILES: CCOC(CCNC(=O)c1c[nH]c(-c2cc(Oc3ccc(NC(=O)Nc4cccc(C)c4)cc3)ccn2)c1)OCC] | 558 | N-(3,3-diethoxypropyl)-5-{4-[4-({[(3-methylphenyl)amino]carbonyl}-amino)phenoxy]pyridin-2-yl}-1H-pyrrole-3-carboxamide |
| 152 | 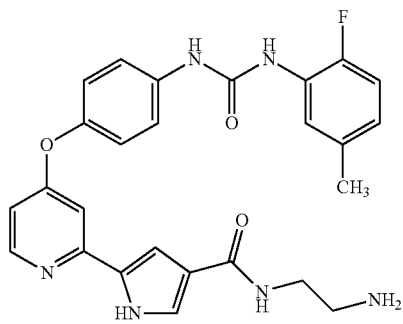 [SMILES: Cc1ccc(F)c(NC(=O)Nc2ccc(Oc3ccnc(-c4cc(C(=O)NCCN)c[nH]4)c3)cc2)c1] | 489 | N-(2-aminoethyl)-5-{4-[4-({[(2-fluoro-5-methylphenyl)amino]carbonyl}-amino)phenoxy]pyridin-2-yl}-1H-pyrrole-3-carboxamide |
| 153 | 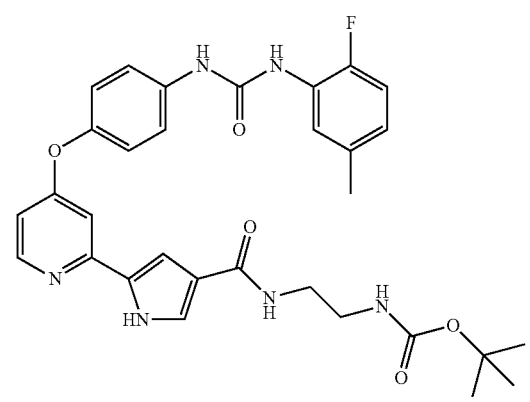 [SMILES: Cc1ccc(F)c(NC(=O)Nc2ccc(Oc3ccnc(-c4cc(C(=O)NCCNC(=O)OC(C)(C)C)c[nH]4)c3)cc2)c1] | 589 | tert-butyl (2-{[(5-{4-[4-({[(2-fluoro-5-methylphenyl)amino]carbonyl}-amino)phenoxy]pyridin-2-yl}-1H-pyrrol-3-yl)carbonyl]amino}ethyl)carbamate |

-continued

| Example # | Chemical Structure | MW | Chemical Name |
|---|---|---|---|
| 154 | 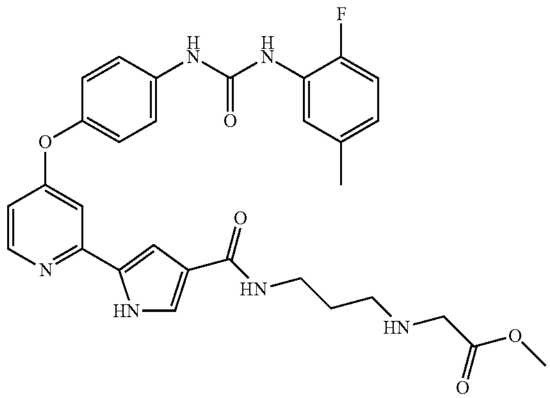 [SMILES: COC(=O)CNCCCNC(=O)c1c[nH]c(-c2cc(Oc3ccc(NC(=O)Nc4cc(C)ccc4F)cc3)ccn2)c1] | 575 | methyl [(3-{[(5-{4-[4-({[(2-fluoro-5-methylphenyl)amino]carbonyl}-amino)phenoxy]pyridin-2-yl}-1H-pyrrol-3-yl)carbonyl]amino}propyl)amino]acetate |
| 155 | 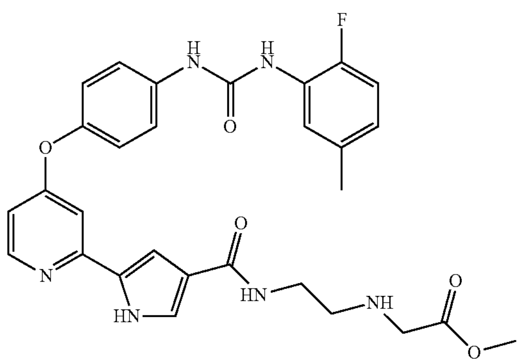 [SMILES: COC(=O)CNCCNC(=O)c1c[nH]c(-c2cc(Oc3ccc(NC(=O)Nc4cc(C)ccc4F)cc3)ccn2)c1] | 561 | methyl [(2-{[(5-{4-[4-({[(2-fluoro-5-methylphenyl)amino]carbonyl}-amino)phenoxy]pyridin-2-yl}-1H-pyrrol-3-yl)carbonyl]amino}ethyl)amino]acetate |
| 156 | 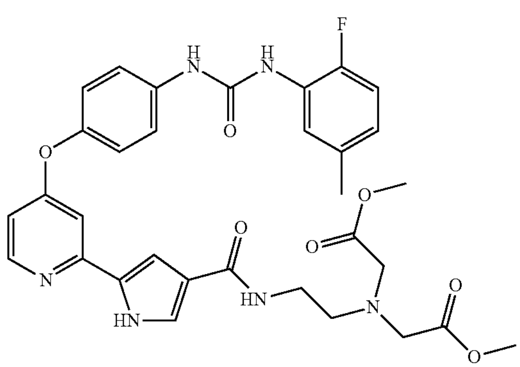 [SMILES: COC(=O)CN(CCNC(=O)c1c[nH]c(-c2cc(Oc3ccc(NC(=O)Nc4cc(C)ccc4F)cc3)ccn2)c1)CC(=O)OC] | 633 | dimethyl 2,2'-[(2-{[(5-{4-[4-({[(2-fluoro-5-methylphenyl)amino]carbonyl}-amino)phenoxy]pyridin-2-yl}-1H-pyrrol-3-yl)carbonyl]amino}ethyl)imino]diacetate |
| 157 | 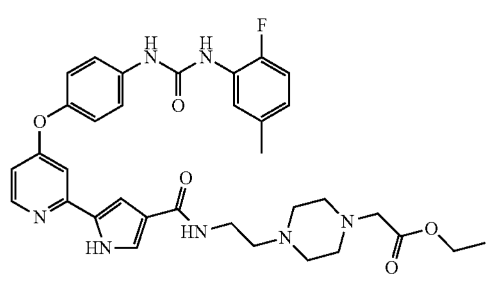 [SMILES: CCOC(=O)CN1CCN(CCNC(=O)c2c[nH]c(-c3cc(Oc4ccc(NC(=O)Nc5cc(C)ccc5F)cc4)ccn3)c2)CC1] | 644 | ethyl [4-(2-{[(5-{4-[4-({[(2-fluoro-5-methylphenyl)amino]carbonyl}-amino)phenoxy]pyridin-2-yl}-1H-pyrrol-3-yl)carbonyl]amino}ethyl)piperazin-1-yl]acetate |

-continued

| Example # | Chemical Structure | MW | Chemical Name |
|---|---|---|---|
| 158 | 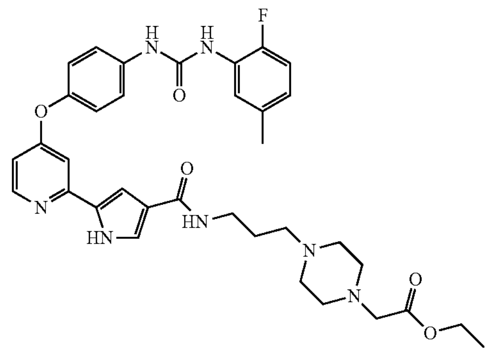 [SMILES: CCOC(=O)CN1CCN(CCCNC(=O)c2c[nH]c(-c3cc(Oc4ccc(NC(=O)Nc5cc(C)ccc5F)cc4)ccn3)c2)CC1] | 658 | ethyl [4-(3-{[(5-{4-[4-({[(2-fluoro-5-methylphenyl)amino]carbonyl}-amino)phenoxy]pyridin-2-yl}-1H-pyrrol-3-yl)carbonyl]amino}propyl)piperazin-1-yl]acetate |
| 159 | 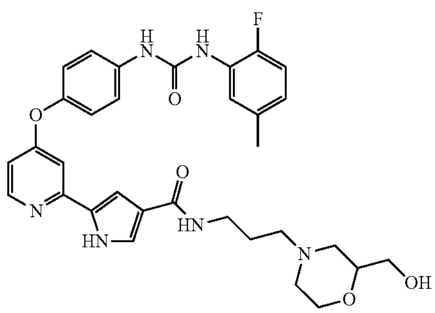 [SMILES: Cc1ccc(F)c(NC(=O)Nc2ccc(Oc3ccnc(-c4cc(C(=O)NCCCN5CCOC(CO)C5)c[nH]4)c3)cc2)c1] | 603 | 5-{4-[4-({[(2-fluoro-5-methylphenyl)amino]carbonyl}-amino)phenoxy]pyridin-2-yl}-N-{3-[2-(hydroxymethyl)morpholin-4-yl]propyl}-1H-pyrrole-3-carboxamide |
| 160 | 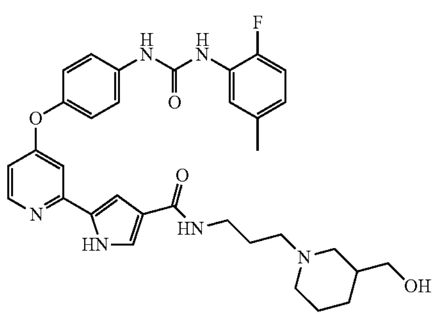 [SMILES: Cc1ccc(F)c(NC(=O)Nc2ccc(Oc3ccnc(-c4cc(C(=O)NCCCN5CCCC(CO)C5)c[nH]4)c3)cc2)c1] | 601 | 5-{4-[4-({[(2-fluoro-5-methylphenyl)amino]carbonyl}-amino)phenoxy]pyridin-2-yl}-N-{3-[3-(hydroxymethyl)piperidin-1-yl]propyl}-1H-pyrrole-3-carboxamide |
| 161 | 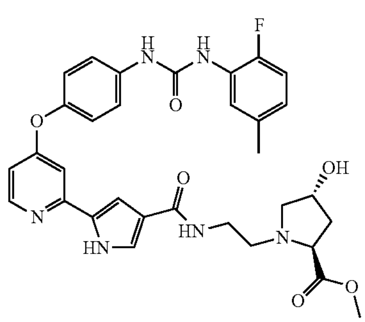 [SMILES: COC(=O)[C@@H]1C[C@@H](O)CN1CCNC(=O)c1c[nH]c(-c2cc(Oc3ccc(NC(=O)Nc4cc(C)ccc4F)cc3)ccn2)c1] | 617 | methyl rel-(2R,4S)-1-(2-{[(5-{4-[4-({[(2-fluoro-5-methylphenyl)amino]carbonyl}-amino)phenoxy]pyridin-2-yl}-1H-pyrrol-3-yl)carbonyl]amino}ethyl)-4-hydroxypyrrolidine-2-carboxylate |

| Example # | Chemical Structure | MW | Chemical Name |
|---|---|---|---|
| 162 | 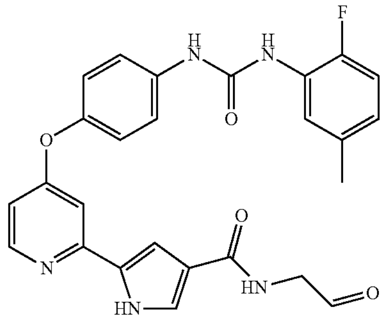 [SMILES: Cc1ccc(F)c(NC(=O)Nc2ccc(Oc3ccnc(-c4cc(C(=O)NCC=O)c[nH]4)c3)cc2)c1] | 487 | 5-{4-[4-({[(2-fluoro-5-methylphenyl)amino]carbonyl}-amino)phenoxy]pyridin-2-yl}-N-(2-oxoethyl)-1H-pyrrole-3-carboxamide |
| 163 | 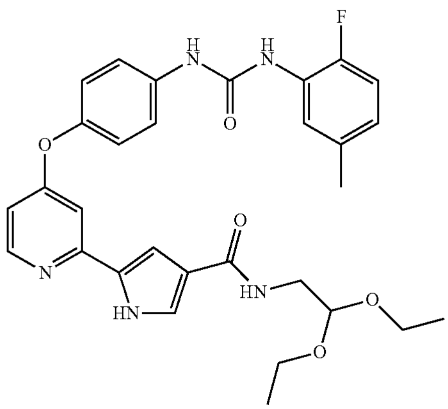 [SMILES: CCOC(CNC(=O)c1c[nH]c(-c2cc(Oc3ccc(NC(=O)Nc4cc(C)ccc4F)cc3)ccn2)c1)OCC] | 562 | N-(2,2-diethoxyethyl)-5-{4-[4-({[(2-fluoro-5-methylphenyl)amino]carbonyl}-amino)phenoxy]pyridin-2-yl}-1H-pyrrole-3-carboxamide |
| 164 | 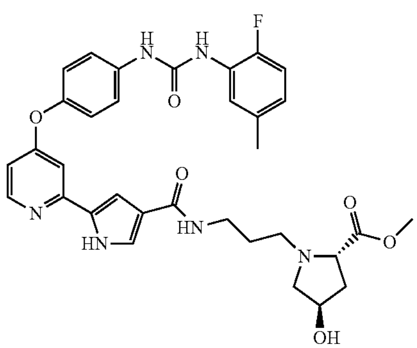 [SMILES: COC(=O)[C@@H]1C[C@@H](O)CN1CCCNC(=O)c1c[nH]c(-c2cc(Oc3ccc(NC(=O)Nc4cc(C)ccc4F)cc3)ccn2)c1] | 631 | methyl rel-(2R,4S)-1-(3-{[(5-{4-[4-({[(2-fluoro-5-methylphenyl)amino]carbonyl}-amino)phenoxy]pyridin-2-yl}-1H-pyrrol-3-yl)carbonyl]amino}propyl)-4-hydroxypyrrolidine-2-carboxylate |
| 165 | 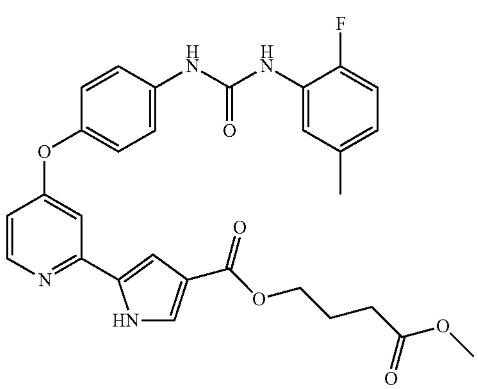 [SMILES: COC(=O)CCCOC(=O)c1c[nH]c(-c2cc(Oc3ccc(NC(=O)Nc4cc(C)ccc4F)cc3)ccn2)c1] | 547 | 4-methoxy-4-oxobutyl 5-{4-[4-({[(2-fluoro-5-methylphenyl)amino]carbonyl}-amino)phenoxy]pyridin-2-yl}-1H-pyrrole-3-carboxylate |

| Example # | Chemical Structure | MW | Chemical Name |
|---|---|---|---|
| 166 | 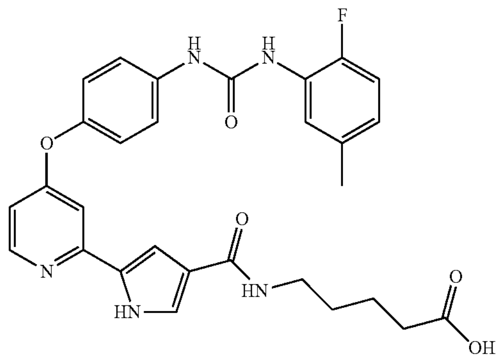 [SMILES: Cc1ccc(F)c(NC(=O)Nc2ccc(Oc3ccnc(-c4cc(C(=O)NCCCCC(=O)O)c[nH]4)c3)cc2)c1] | 546 | 5-{[(5-{4-[4-({[(2-fluoro-5-methylphenyl)amino]carbonyl}-amino)phenoxy]pyridin-2-yl}-1H-pyrrol-3-yl)carbonyl]amino}pentanoic acid |
| 167 | 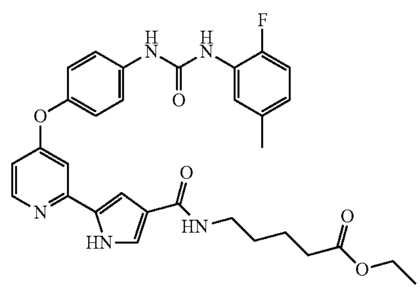 [SMILES: CCOC(=O)CCCCNC(=O)c1c[nH]c(-c2cc(Oc3ccc(NC(=O)Nc4cc(C)ccc4F)cc3)ccn2)c1] | 574 | ethyl 5-{[(5-{4-[4-({[(2-fluoro-5-methylphenyl)amino]carbonyl}-amino)phenoxy]pyridin-2-yl}-1H-pyrrol-3-yl)carbonyl]amino}pentanoate |
| 168 | 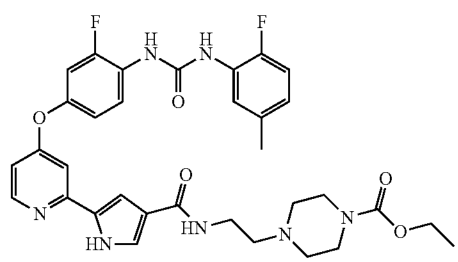 [SMILES: CCOC(=O)N1CCN(CCNC(=O)c2c[nH]c(-c3cc(Oc4ccc(NC(=O)Nc5cc(C)ccc5F)c(F)c4)ccn3)c2)CC1] | 648 | ethyl 4-(2-{[(5-{4-[3-fluoro-4-({[(2-fluoro-5-methylphenyl)amino]carbonyl}-amino)phenoxy]pyridin-2-yl}-1H-pyrrol-3-yl)carbonyl]amino}ethyl)-piperazine-1-carboxylate |
| 169 | 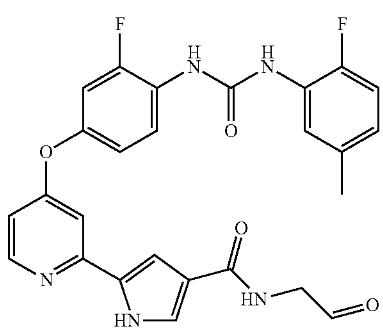 [SMILES: Cc1ccc(F)c(NC(=O)Nc2ccc(Oc3ccnc(-c4cc(C(=O)NCC=O)c[nH]4)c3)cc2F)c1] | 505 | 5-{4-[3-fluoro-4-({[(2-fluoro-5-methylphenyl)amino]carbonyl}-amino)phenoxy]pyridin-2-yl}-N-(2-oxoethyl)-1H-pyrrole-3-carboxamide |

-continued

| Example # | Chemical Structure | MW | Chemical Name |
|---|---|---|---|
| 170 | 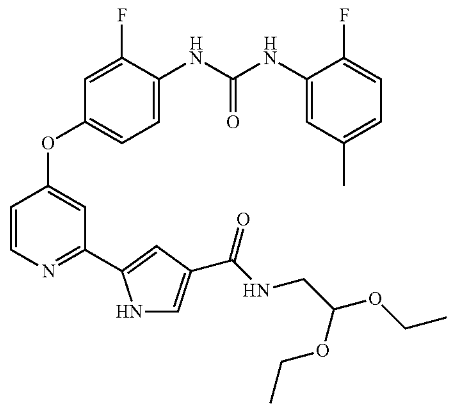 [SMILES: CCOC(CNC(=O)c1c[nH]c(-c2cc(Oc3ccc(NC(=O)Nc4cc(C)ccc4F)c(F)c3)ccn2)c1)OCC] | 580 | N-(2,2-diethoxyethyl)-5-{4-[3-fluoro-4-({[(2-fluoro-5-methylphenyl)amino]carbonyl}-amino)phenoxy]pyridin-2-yl}-1H-pyrrole-3-carboxamide |
| 171 | 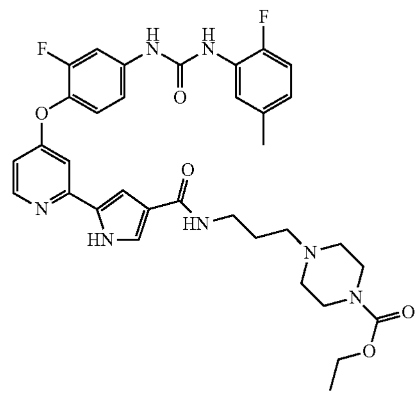 [SMILES: CCOC(=O)N1CCN(CCCNC(=O)c2c[nH]c(-c3cc(Oc4ccc(NC(=O)Nc5cc(C)ccc5F)cc4F)ccn3)c2)CC1] | 647 | ethyl 4-{3-[({5-[4-(2-fluoro-5-{[(2-fluoro-5-methylphenyl)amino]carbonyl}-phenoxy)pyridin-2-yl]-1H-pyrrol-3-yl}carbonyl)amino]propyl}piperazine-1-carboxylate |
| 172 | 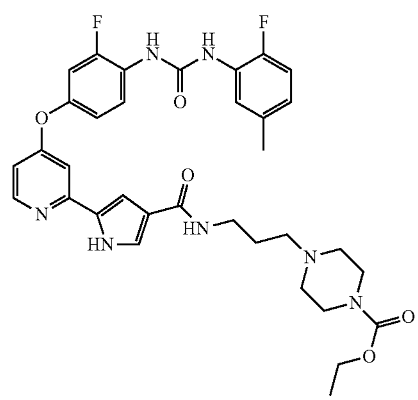 [SMILES: CCOC(=O)N1CCN(CCCNC(=O)c2c[nH]c(-c3cc(Oc4ccc(NC(=O)Nc5cc(C)ccc5F)c(F)c4)ccn3)c2)CC1] | 662 | ethyl 4-(3-{[(5-{4-[3-fluoro-4-[{[(2-fluoro-5-methylphenyl)amino]carbonyl}-amino)phenoxy]pyridin-2-yl}-1H-pyrrol-3-yl)carbonyl]amino}-propyl)piperazine-1-carboxylate |
| 173 | 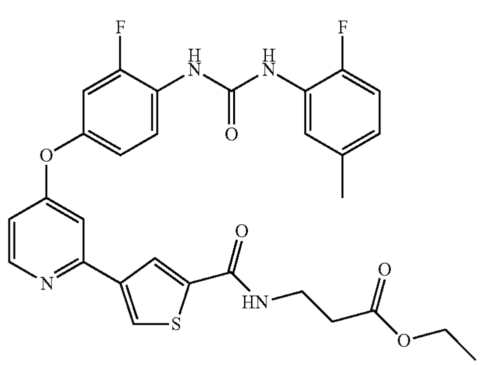 [SMILES: CCOC(=O)CCNC(=O)c1cc(-c2cc(Oc3ccc(NC(=O)Nc4cc(C)ccc4F)c(F)c3)ccn2)cs1] | 581 | ethyl 3-{[(4-{4-[3-fluoro-4-[{[(2-fluoro-5-methylphenyl)amino]carbonyl}-amino)phenoxy]pyridin-2-yl}-2-thienyl)carbonyl]amino}propanoate |

-continued

| Example # | Chemical Structure | MW | Chemical Name |
|---|---|---|---|
| 174 | 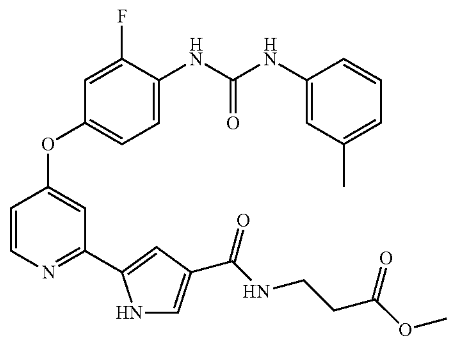 [SMILES: COC(=O)CCNC(=O)c1c[nH]c(-c2cc(Oc3ccc(NC(=O)Nc4cccc(C)c4)c(F)c3)ccn2)c1] | 532 | methyl 3-{[(5-{4-[3-fluoro-4-({[(3-methylphenyl)amino]carbonyl}-amino)phenoxy]pyridin-2-yl}-1H-pyrrol-3-yl)carbonyl]amino}propanoate |
| 175 | 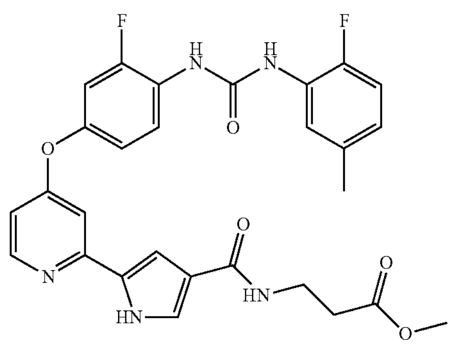 [SMILES: COC(=O)CCNC(=O)c1c[nH]c(-c2cc(Oc3ccc(NC(=O)Nc4cc(C)ccc4F)c(F)c3)ccn2)c1] | 550 | methyl 3-{[(5-{4-[3-fluoro-4-({[(2-fluoro-5-methylphenyl)amino]carbonyl}-amino)phenoxy]pyridin-2-yl}-1H-pyrrol-3-yl)carbonyl]amino}propanoate |
| 176 | 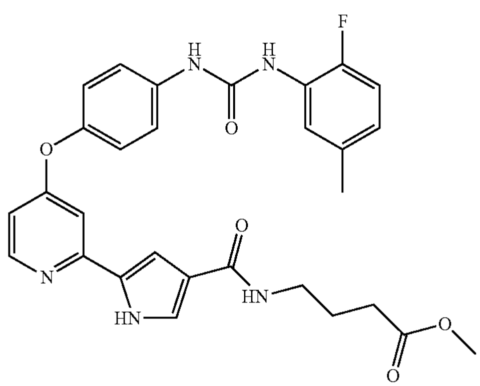 [SMILES: COC(=O)CCCNC(=O)c1c[nH]c(-c2cc(Oc3ccc(NC(=O)Nc4cc(C)ccc4F)cc3)ccn2)c1] | 546 | methyl 4-{[(5-{4-[4-({[(2-fluoro-5-methylphenyl)amino]carbonyl}-amino)phenoxy]pyridin-2-yl}-1H-pyrrol-3-yl)carbonyl]amino}butanoate |
| 177 | 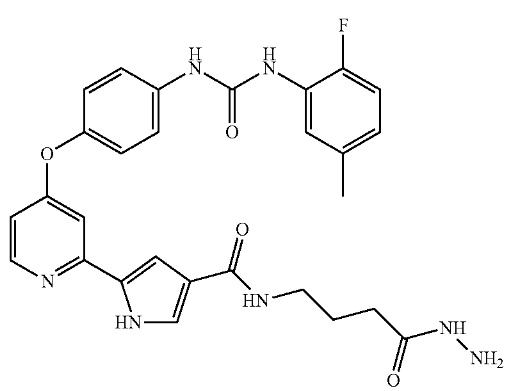 [SMILES: Cc1ccc(F)c(NC(=O)Nc2ccc(Oc3ccnc(-c4cc(C(=O)NCCCC(=O)NN)c[nH]4)c3)cc2)c1] | 546 | 5-{4-[4-({[(2-fluoro-5-methylphenyl)amino]carbonyl}-amino)phenoxy]pyridin-2-yl}-N-(4-hydrazino-4-oxobutyl)-1H-pyrrole-3-carboxamide |

-continued

| Example # | Chemical Structure | MW | Chemical Name |
|---|---|---|---|
| 178 | 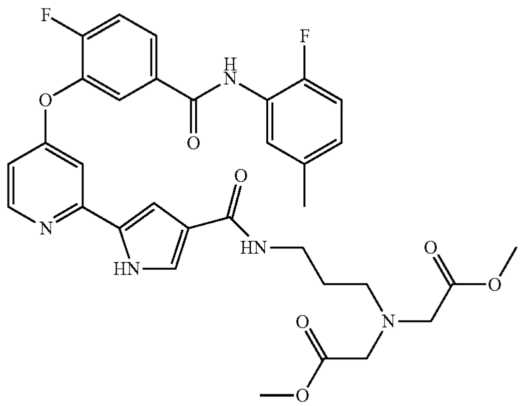 [SMILES: COC(=O)CN(CCCNC(=O)c1c[nH]c(-c2cc(Oc3cc(C(=O)Nc4cc(C)ccc4F)ccc3F)ccn2)c1)CC(=O)OC] | 650 | dimethyl 2,2'-({3-[({5-[4-(2-fluoro-5-{[(2-fluoro-5-methylphenyl)amino]carbonyl}-phenoxy)pyridin-2-yl]-1H-pyrrol-3-yl}carbonyl)amino]propyl}imino)diacetate |
| 179 | 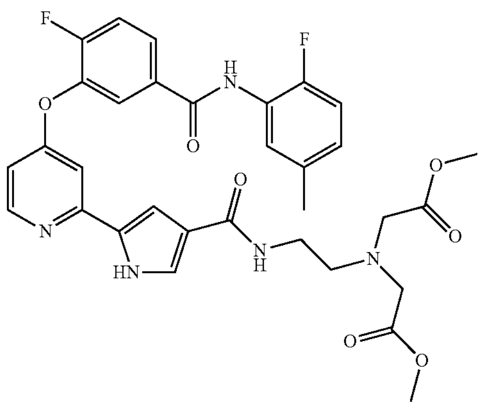 [SMILES: COC(=O)CN(CCNC(=O)c1c[nH]c(-c2cc(Oc3cc(C(=O)Nc4cc(C)ccc4F)ccc3F)ccn2)c1)CC(=O)OC] | 636 | dimethyl 2,2'-({2-[({5-[4-(2-fluoro-5-{[(2-fluoro-5-methylphenyl)amino]carbonyl}-phenoxy)pyridin-2-yl]-1H-pyrrol-3-yl}carbonyl)amino]ethyl}imino)diacetate |
| 180 | 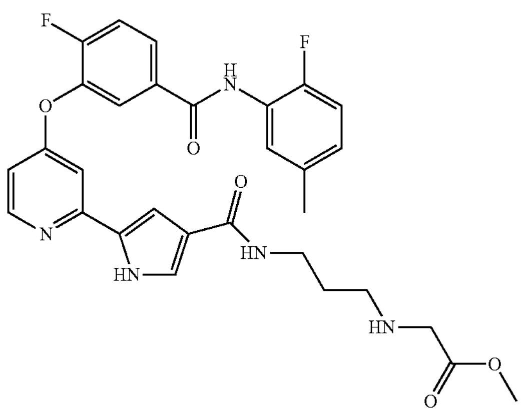 [SMILES: COC(=O)CNCCCNC(=O)c1c[nH]c(-c2cc(Oc3cc(C(=O)Nc4cc(C)ccc4F)ccc3F)ccn2)c1] | 578 | methyl ({3-[({5-[4-(2-fluoro-5-{[(2-fluoro-5-methylphenyl)amino]carbonyl}-phenoxy)pyridin-2-yl]-1H-pyrrol-3-yl}carbonyl)amino]propyl}amino)acetate |
| 181 | 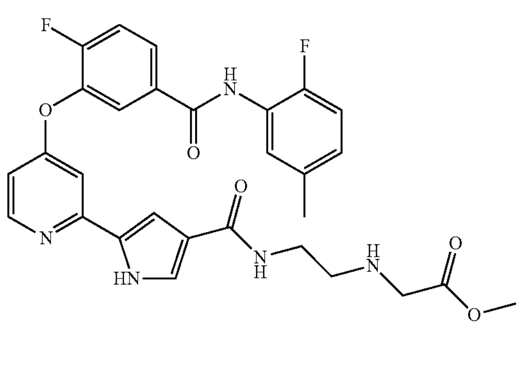 [SMILES: COC(=O)CNCCNC(=O)c1c[nH]c(-c2cc(Oc3cc(C(=O)Nc4cc(C)ccc4F)ccc3F)ccn2)c1] | 564 | methyl ({2-[({5-[4-(2-fluoro-5-{[(2-fluoro-5-methylphenyl)amino]carbonyl}-phenoxy)pyridin-2-yl]-1H-pyrrol-3-yl}carbonyl)amino]ethyl}amino)acetate |

-continued

| Example # | Chemical Structure | MW | Chemical Name |
|---|---|---|---|
| 182 | 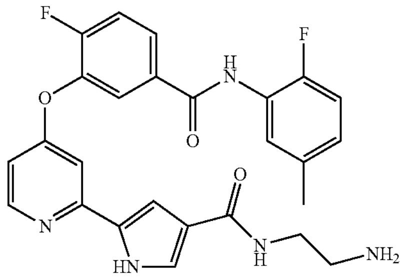 [SMILES: Cc1ccc(F)c(NC(=O)c2ccc(F)c(Oc3ccnc(-c4cc(C(=O)NCCN)c[nH]4)c3)c2)c1] | 491 | N-(2-aminoethyl)-5-[4-(2-fluoro-5-{[(2-fluoro-5-methylphenyl)amino]carbonyl}-phenoxy)pyridin-2-yl]-1H-pyrrole-3-carboxamide |
| 183 | 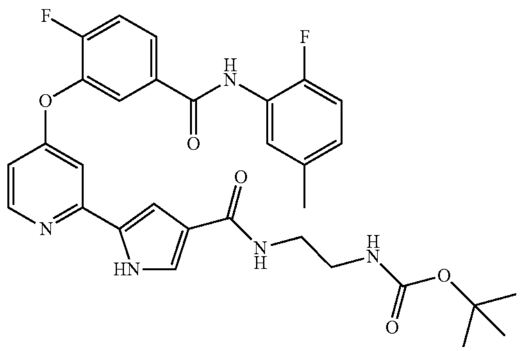 [SMILES: Cc1ccc(F)c(NC(=O)c2ccc(F)c(Oc3ccnc(-c4cc(C(=O)NCCNC(=O)OC(C)(C)C)c[nH]4)c3)c2)c1] | 592 | tert-butyl {2-[({5-[4-(2-fluoro-5-{[(2-fluoro-5-methylphenyl)amino]carbonyl}-phenoxy)pyridin-2-yl]-1H-pyrrol-3-yl}carbonyl)amino]ethyl}carbamate |
| 184 | 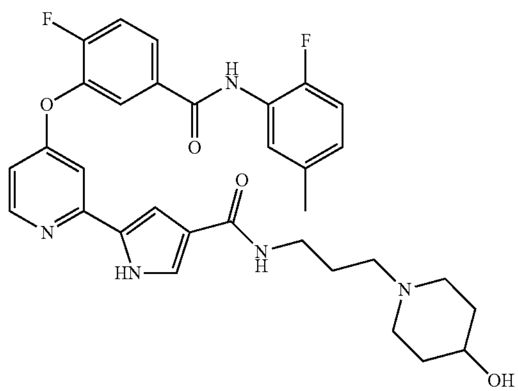 [SMILES: Cc1ccc(F)c(NC(=O)c2ccc(F)c(Oc3ccnc(-c4cc(C(=O)NCCCN5CCC(O)CC5)c[nH]4)c3)c2)c1] | 590 | 5-[4-(2-fluoro-5-{[(2-fluoro-5-methylphenyl)amino]carbonyl}-phenoxy)pyridin-2-yl]-N-[3-(4-hydroxypiperidin-1-yl)propyl]-1H-pyrrole-3-carboxamide |
| 185 | 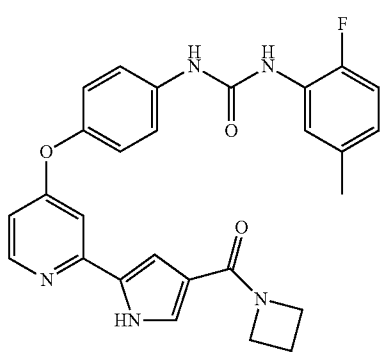 [SMILES: Cc1ccc(F)c(NC(=O)Nc2ccc(Oc3ccnc(-c4cc(C(=O)N5CCC5)c[nH]4)c3)cc2)c1] | 486 | 1-[4-({2-[4-(azetidin-1-ylcarbonyl)-1H-pyrrol-2-yl]pyridin-4-yl}oxy)phenyl]-3-(2-fluoro-5-methylphenyl)urea |

-continued

| Example # | Chemical Structure | MW | Chemical Name |
|---|---|---|---|
| 186 | 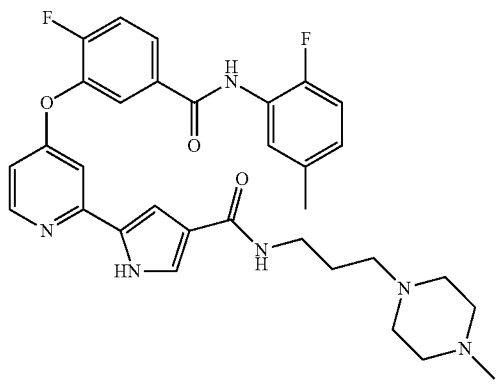 [SMILES: Cc1ccc(F)c(NC(=O)c2ccc(F)c(Oc3ccnc(-c4cc(C(=O)NCCCN5CCN(C)CC5)c[nH]4)c3)c2)c1] | 589 | 5-[4-(2-fluoro-5-{[(2-fluoro-5-methylphenyl)amino]carbonyl}-phenoxy)pyridin-2-yl]-N-[3-(4-methylpiperazin-1-yl)propyl]-1H-pyrrole-3-carboxamide |
| 187 | 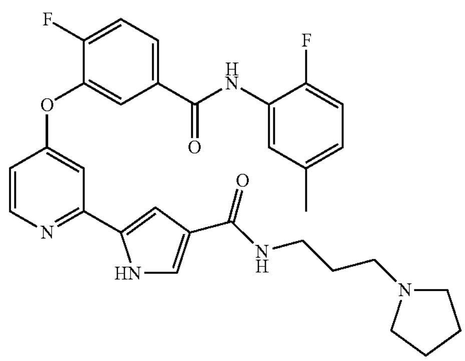 [SMILES: Cc1ccc(F)c(NC(=O)c2ccc(F)c(Oc3ccnc(-c4cc(C(=O)NCCCN5CCCC5)c[nH]4)c3)c2)c1] | 560 | 5-[4-(2-fluoro-5-{[(2-fluoro-5-methylphenyl)amino]carbonyl}-phenoxy)pyridin-2-yl]-N-(3-pyrrolidin-1-ylpropyl)-1H-pyrrole-3-carboxamide |
| 188 | 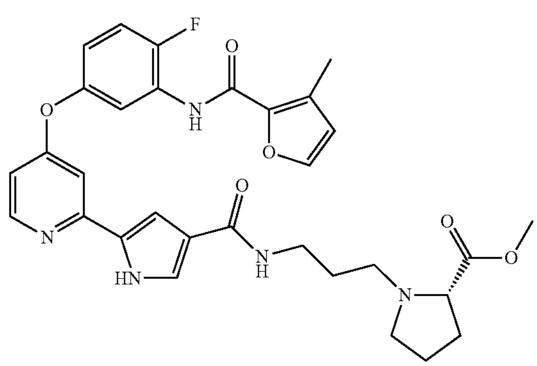 [SMILES: COC(=O)[C@@H]1CCCN1CCCNC(=O)c1c[nH]c(-c2cc(Oc3ccc(F)c(NC(=O)c4occc4C)c3)ccn2)c1] | 590 | methyl 1-[3-({[5-(4-{4-fluoro-3-[(3-methyl-2-furoyl)amino]phenoxy}pyridin-2-yl)-1H-pyrrol-3-yl]carbonyl}amino)propyl]pyrrolidine-2-carboxylate |
| 189 | 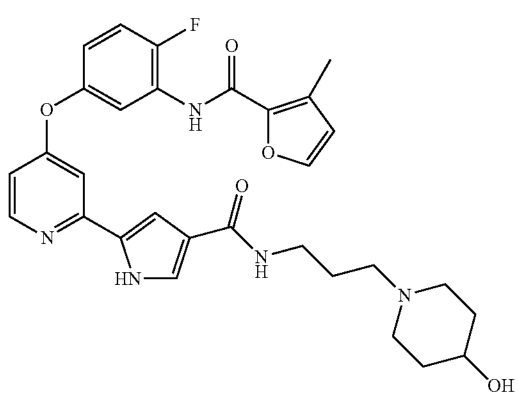 [SMILES: Cc1ccoc1C(=O)Nc1cc(Oc2ccnc(-c3cc(C(=O)NCCCN4CCC(O)CC4)c[nH]3)c2)ccc1F] | 562 | 5-(4-{4-fluoro-3-[(3-methyl-2-furoyl)amino]phenoxy}pyridin-2-yl)-N-[3-(4-hydroxypiperidin-1-yl)propyl]-1H-pyrrole-3-carboxamide |

| Example # | Chemical Structure | MW | Chemical Name |
|---|---|---|---|
| 190 | 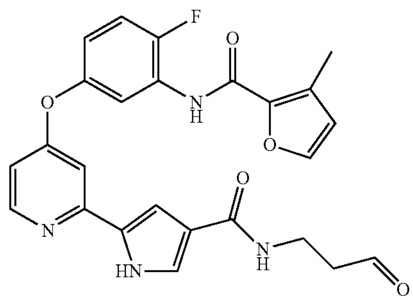 [SMILES: Cc1ccoc1C(=O)Nc1cc(Oc2ccnc(-c3cc(C(=O)NCCC=O)c[nH]3)c2)ccc1F] | 476 | 5-(4-{4-fluoro-3-[(3-methyl-2-furoyl)amino]phenoxy}pyridin-2-yl)-N-(3-oxopropyl)-1H-pyrrole-3-carboxamide (Last One for early filing in 2010) |
| 191 | 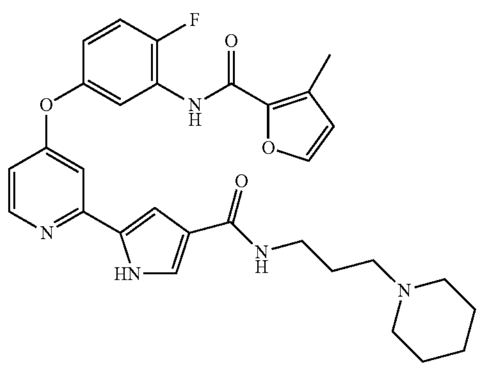 [SMILES: Cc1ccoc1C(=O)Nc1cc(Oc2ccnc(-c3cc(C(=O)NCCCN4CCCCC4)c[nH]3)c2)ccc1F] | 546 | 5-(4-{4-fluoro-3-[(3-methyl-2-furoyl)amino]phenoxy}pyridin-2-yl)-N-(3-piperidin-1-ylpropyl)-1H-pyrrole-3-carboxamide |
| 192 | 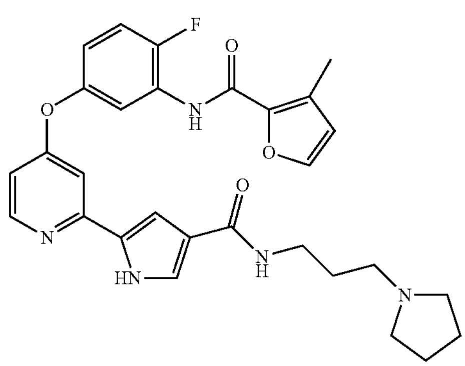 [SMILES: Cc1ccoc1C(=O)Nc1cc(Oc2ccnc(-c3cc(C(=O)NCCCN4CCCC4)c[nH]3)c2)ccc1F] | 532 | 5-(4-{4-fluoro-3-[(3-methyl-2-furoyl]amino]phenoxy}pyridin-2-yl)-N-(3-pyrrolidin-1-ylpropyl)-1H-pyrrole-3-carboxamide |
| 193 | 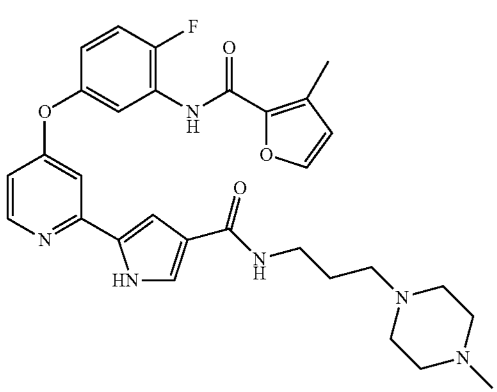 [SMILES: Cc1ccoc1C(=O)Nc1cc(Oc2ccnc(-c3cc(C(=O)NCCCN4CCN(C)CC4)c[nH]3)c2)ccc1F] | 561 | 5-(4-{4-fluoro-3-[(3-methyl-2-furoyl)amino]phenoxy}pyridin-2-yl)-N-[3-(4-methylpiperazin-1-yl)propyl]-1H-pyrrole-3-carboxamide |

| Example # | Chemical Structure | MW | Chemical Name |
|---|---|---|---|
| 194 | 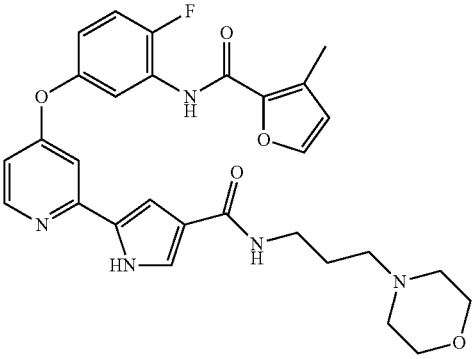 | 548 | 5-(4-{4-fluoro-3-[(3-methyl-2-furoyl)amino]phenoxy}pyridin-2-yl)-N-(3-morpholin-4-ylpropyl)-1H-pyrrole-3-carboxamide |
| 195 | 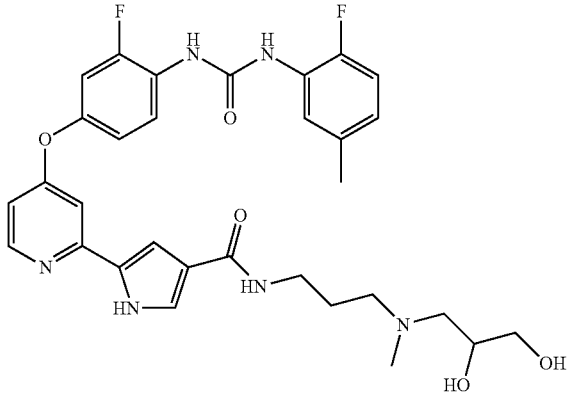 [SMILES: Cc1ccc(F)c(NC(=O)Nc2ccc(Oc3ccnc(-c4cc(C(=O)NCCCN(C)CC(O)CO)c[nH]4)c3)cc2F)c1] | 609 | N-{3-[(2,3-dihydroxypropyl)-(methyl)amino]propyl}-5-{4-[3-fluoro-4-({[(2-fluoro-5-methylphenyl)amino]carbonyl}-amino)phenoxy]pyridin-2-yl}-1H-pyrrole-3-carboxamide |
| 196 | 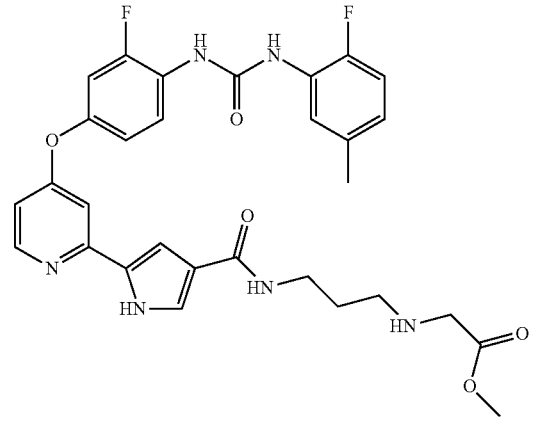 [SMILES: COC(=O)CNCCCNC(=O)c1c[nH]c(-c2cc(Oc3ccc(NC(=O)Nc4cc(C)ccc4F)c(F)c3)ccn2)c1] | 593 | methyl [(3-{[(5-{4-[3-fluoro-4-({[(2-fluoro-5-methylphenyl)amino]carbonyl}-amino)phenoxy]pyridin-2-yl}-1H-pyrrol-3-yl)carbonyl]amino}propyl)amino]acetate |
| 197 | 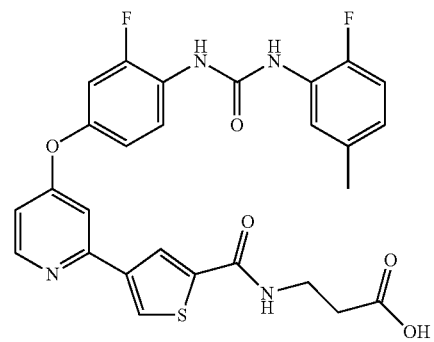 [SMILES: Cc1ccc(F)c(NC(=O)Nc2ccc(Oc3ccnc(-c4csc(C(=O)NCCC(=O)O)c4)c3)cc2F)c1] | 553 | 3-{[(4-{4-[3-fluoro-4-({[(2-fluoro-5-methylphenyl)amino]carbonyl}-amino)phenoxy]pyridin-2-yl}-2-thienyl)carbonyl]amino}propanoic acid |

| Example # | Chemical Structure | MW | Chemical Name |
|---|---|---|---|
| 198 | 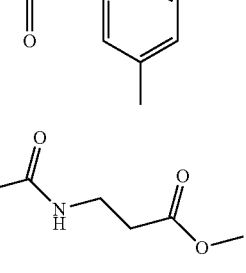 | 567 | methyl 3-{[(4-{4-[3-fluoro-4-({[(2-fluoro-5-methylphenyl)amino]carbonyl}-amino)phenoxy]pyridin-2-yl}-2-thienyl)carbonyl]amino}propanoate |
| 199 | 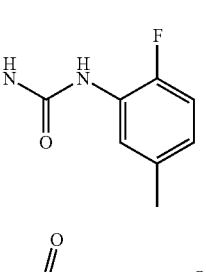 | 536 | 3-{[(4-{4-[3-fluoro-4-({[(2-fluoro-5-methylphenyl)amino]carbonyl}-amino)phenoxy]pyridin-2-yl}-1H-pyrrol-2-yl)carbonyl]amino}propanoic acid |
| 200 | 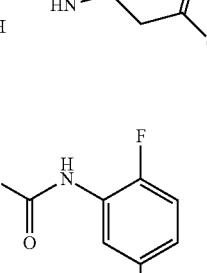 | 550 | methyl 3-{[(4-{4-[3-fluoro-4-({[(2-fluoro-5-methylphenyl)amino]carbonyl}-amino)phenoxy]pyridin-2-yl}-1H-pyrrol-2-yl)carbonyl]amino}propanoate |
| 201 | 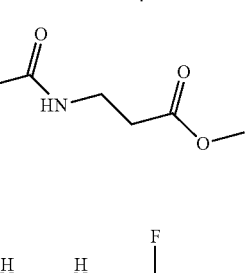 | 611 | N-(3,3-diethoxypropyl)-4-{4-[3-fluoro-4-({[(2-fluoro-5-methylphenyl)amino]carbonyl}amino)-phenoxy]pyridin-2-yl}thiophene-2-carboxamide |

-continued

| Example # | Chemical Structure | MW | Chemical Name |
|---|---|---|---|
| 202 | 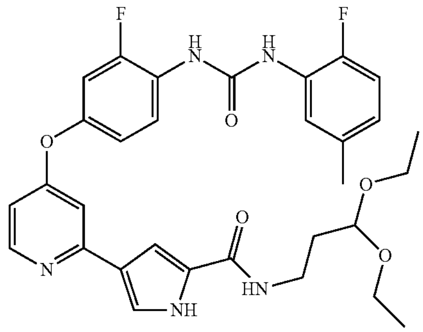 [SMILES: CCOC(CCNC(=O)c1cc(-c2cc(Oc3ccc(NC(=O)Nc4cc(C)ccc4F)c(F)c3)ccn2)c[nH]1)OCC] | 594 | N-(3,3-diethoxypropyl)-4-{4-[3-fluoro-4-({[(2-fluoro-5-methylphenyl)amino]carbonyl}-amino)phenoxy]pyridin-2-yl}-1H-pyrrole-2-carboxamide |
| 203 | 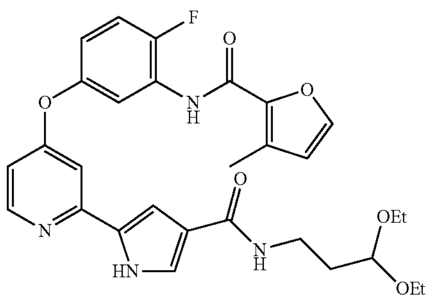 [SMILES: CCOC(CCNC(=O)c1c[nH]c(-c2cc(Oc3ccc(F)c(NC(=O)c4occc4C)c3)ccn2)c1)OCC] | 551 | N-(3,3-diethoxypropyl)-5-(4-{4-fluoro-3-[(3-methyl-2-furoyl)amino]phenoxy}-pyridin-2-yl)-1H-pyrrole-3-carboxamide |
| 204 | 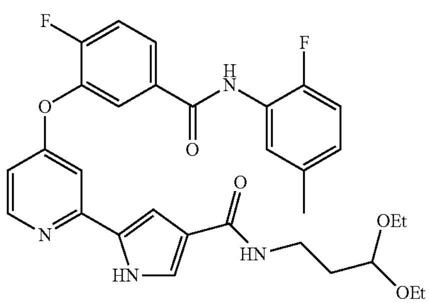 [SMILES: CCOC(CCNC(=O)c1c[nH]c(-c2cc(Oc3cc(C(=O)Nc4cc(C)ccc4F)ccc3F)ccn2)c1)OCC] | 579 | N-(3,3-diethoxypropyl)-5-[4-(2-fluoro-5-{[(2-fluoro-5-methylphenyl)amino]carbonyl}-phenoxy)pyridin-2-yl]-1H-pyrrole-3-carboxamide |
| 205 | 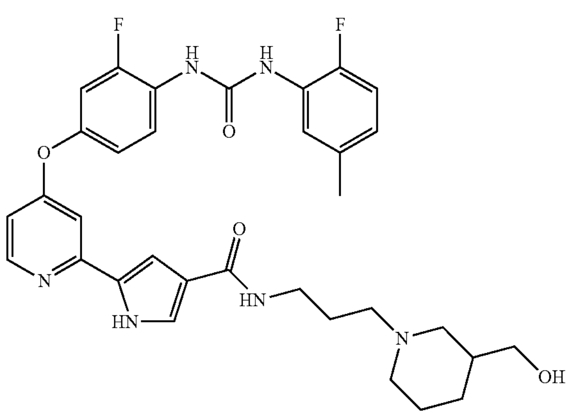 [SMILES: Cc1ccc(F)c(NC(=O)Nc2ccc(Oc3ccnc(-c4cc(C(=O)NCCCN5CCCC(CO)C5)c[nH]4)c3)cc2F)c1] | 619 | 5-{4-[3-fluoro-4-({[(2-fluoro-5-methylphenyl)amino]carbonyl}-amino)phenoxy]pyridin-2-yl}-N-{3-[3-(hydroxymethyl)piperidin-1-yl]propyl}-1H-pyrrole-3-carboxamide |

-continued

| Example # | Chemical Structure | MW | Chemical Name |
|---|---|---|---|
| 206 | 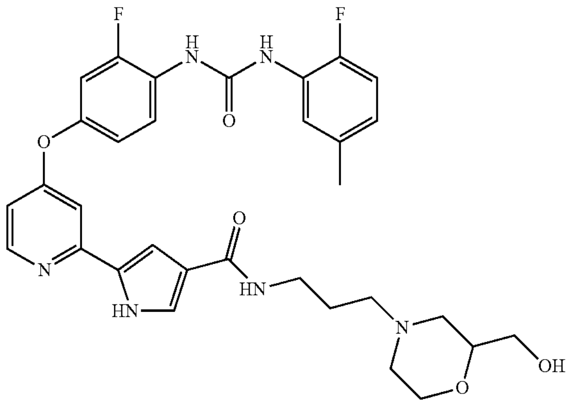 [SMILES: Cc1ccc(F)c(NC(=O)Nc2ccc(Oc3ccnc(-c4cc(C(=O)NCCCN5CCOC(CO)C5)c[nH]4)c3)cc2F)c1] | 621 | 5-{4-[3-fluoro-4-({[(2-fluoro-5-methylphenyl)amino]carbonyl}-amino)phenoxy]pyridin-2-yl}-N-{3-[2-(hydroxymethyl)morpholin-4-yl]propyl}-1H-pyrrole-3-carboxamide |
| 207 | 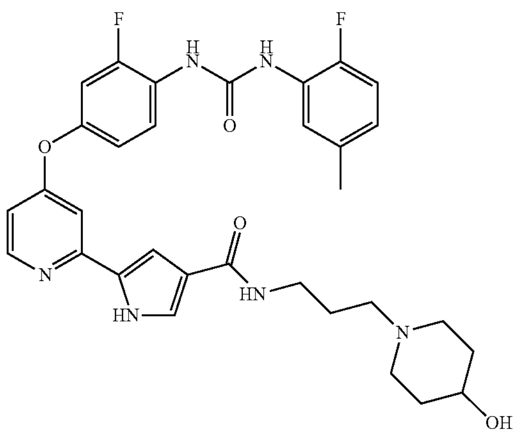 [SMILES: Cc1ccc(F)c(NC(=O)Nc2ccc(Oc3ccnc(-c4cc(C(=O)NCCCN5CCC(O)CC5)c[nH]4)c3)cc2F)c1] | 605 | 5-{4-[3-fluoro-4-({[(2-fluoro-5-methylphenyl)amino]carbonyl}-amino)phenoxy]pyridin-2-yl}-N-[3-(4-hydroxypiperidin-1-yl)propyl]-1H-pyrrole-3-carboxamide |
| 208 | 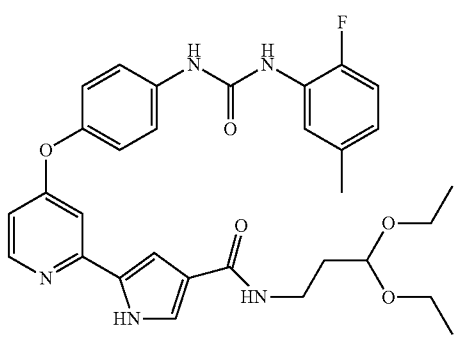 [SMILES: CCOC(CCNC(=O)c1c[nH]c(-c2cc(Oc3ccc(NC(=O)Nc4cc(C)ccc4F)cc3)ccn2)c1)OCC] | 576 | N-(3,3-diethoxypropyl)-5-{4-[4-({[(2-fluoro-5-methylphenyl)amino]carbonyl}-amino)phenoxy]pyridin-2-yl}-1H-pyrrole-3-carboxamide |
| 209 | 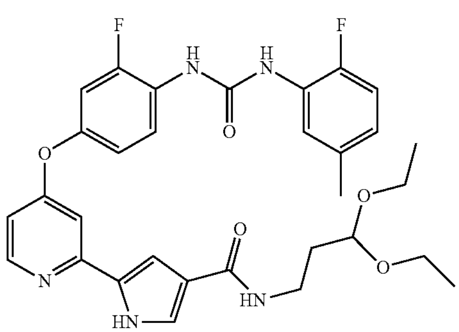 [SMILES: CCOC(CCNC(=O)c1c[nH]c(-c2cc(Oc3ccc(NC(=O)Nc4cc(C)ccc4F)c(F)c3)ccn2)c1)OCC] | 594 | N-(3,3-diethoxypropyl)-5-{4-[3-fluoro-4-({[(2-fluoro-5-methylphenyl)amino]carbonyl}-amino)phenoxy]pyridin-2-yl}-1H-pyrrole-3-carboxamide |

-continued

| Example # | Chemical Structure | MW | Chemical Name |
|---|---|---|---|
| 210 | 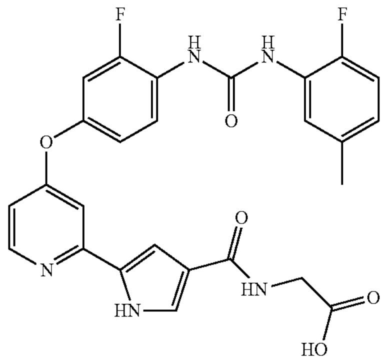 [SMILES: Cc1ccc(F)c(NC(=O)Nc2ccc(Oc3ccnc(-c4cc(C(=O)NCC(=O)O)c[nH]4)c3)cc2F)c1] | 521 | {[(5-{4-[3-fluoro-4-({[(2-fluoro-5-methylphenyl)amino]carbonyl}-amino)phenoxy]pyridin-2-yl}-1H-pyrrol-3-yl)carbonyl]amino}acetic acid |
| 211 | 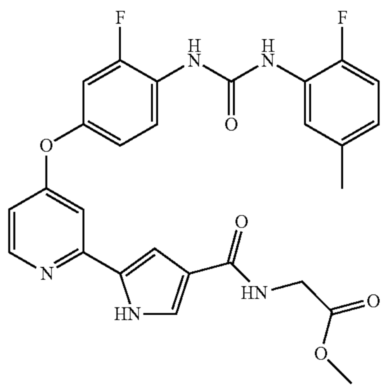 [SMILES: COC(=O)CNC(=O)c1c[nH]c(-c2cc(Oc3ccc(NC(=O)Nc4cc(C)ccc4F)c(F)c3)ccn2)c1] | 536 | methyl {[(5-{4-[3-fluoro-4-({[(2-fluoro-5-methylphenyl)amino]carbonyl}-amino)phenoxy]pyridin-2-yl}-1H-pyrrol-3-yl)carbonyl]amino}acetate |
| 212 | 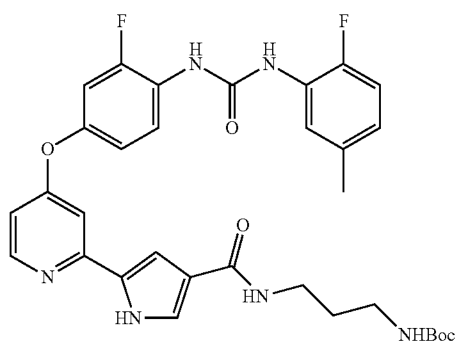 [SMILES: Cc1ccc(F)c(NC(=O)Nc2ccc(Oc3ccnc(-c4cc(C(=O)NCCCNC(=O)OC(C)(C)C)c[nH]4)c3)cc2F)c1] | 621 | tert-butyl (3-{[(5-{4-[3-fluoro-4-({[(2-fluoro-5-methylphenyl)amino]carbonyl}-amino)phenoxy]pyridin-2-yl}-1H-pyrrol-3-yl)carbonyl]amino}propyl)carbamate |
| 213 | 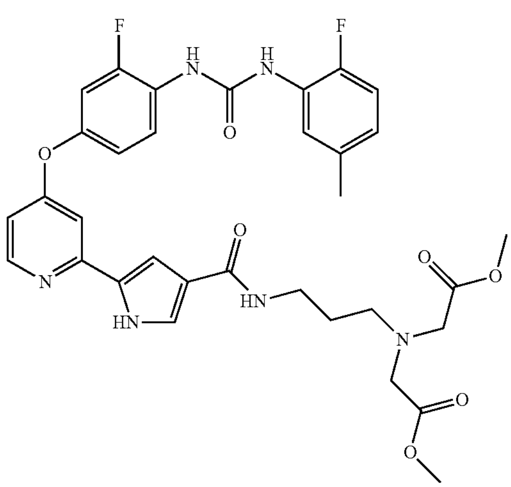 [SMILES: COC(=O)CN(CCCNC(=O)c1c[nH]c(-c2cc(Oc3ccc(NC(=O)Nc4cc(C)ccc4F)c(F)c3)ccn2)c1)CC(=O)OC] | 665 | dimethyl 2,2'-[(3-{[(5-{4-[3-fluoro-4-({[(2-fluoro-5-methylphenyl)amino]carbonyl}-amino)phenoxy]pyridin-2-yl}-1H-pyrrol-3-yl)carbonyl]amino}propyl)imino]diacetate |

-continued

| Example # | Chemical Structure | MW | Chemical Name |
|---|---|---|---|
| 214 | 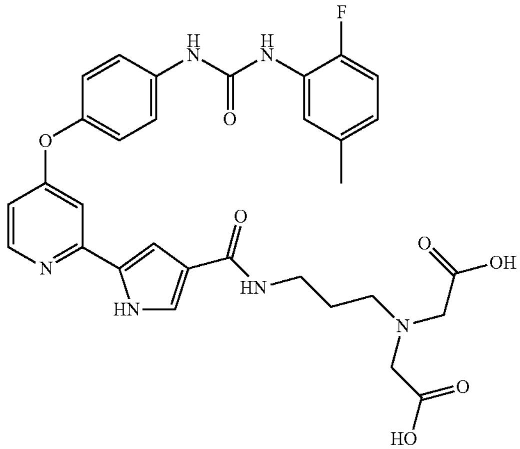 [SMILES: Cc1ccc(F)c(NC(=O)Nc2ccc(Oc3ccnc(-c4cc(C(=O)NCCCN(CC(=O)O)CC(=O)O)c[nH]4)c3)cc2)c1] | 619 | 2,2'-[(3-{[(5-{4-[4-({[(2-fluoro-5-methylphenyl)amino]carbonyl}-amino)phenoxy]pyridin-2-yl}-1H-pyrrol-3-yl)carbonyl]amino}propyl)imino]diacetic acid |
| 215 | 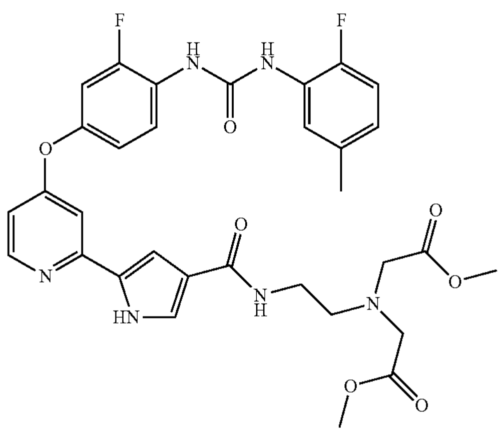 [SMILES: COC(=O)CN(CCNC(=O)c1c[nH]c(-c2cc(Oc3ccc(NC(=O)Nc4cc(C)ccc4F)c(F)c3)ccn2)c1)CC(=O)OC] | 651 | dimethyl 2,2'-[(2-{[(5-{4-[3-fluoro-4-({[(2-fluoro-5-methylphenyl)amino]carbonyl}-amino)phenoxy]pyridin-2-yl}-1H-pyrrol-3-yl)carbonyl]amino}ethyl)imino]diacetate |
| 216 | 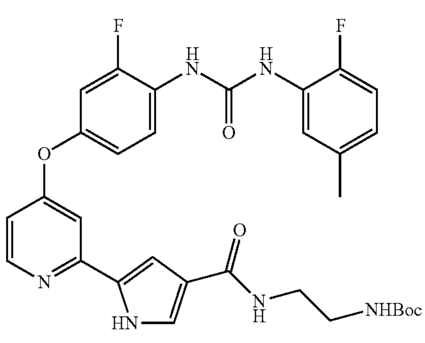 [SMILES: Cc1ccc(F)c(NC(=O)Nc2ccc(Oc3ccnc(-c4cc(C(=O)NCCNC(=O)OC(C)(C)C)c[nH]4)c3)cc2F)c1] | 607 | tert-butyl (2-{[(5-{4-[3-fluoro-4-({[(2-fluoro-5-methylphenyl)amino]carbonyl}-amino)phenoxy]pyridin-2-yl}-1H-pyrrol-3-yl)carbonyl]amino}ethyl)carbamate |

| Example # | Chemical Structure | MW | Chemical Name |
|---|---|---|---|
| 217 | 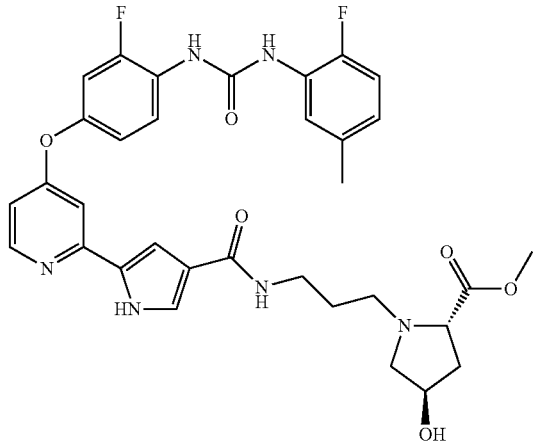 [SMILES: COC(=O)[C@@H]1C[C@@H](O)CN1CCCNC(=O)c1c[nH]c(-c2cc(Oc3ccc(NC(=O)Nc4cc(C)ccc4F)c(F)c3)ccn2)c1] | 649 | methyl rel-(2R,4S)-1-(3-{[(5-{4-[3-fluoro-4-({[(2-fluoro-5-methylphenyl)amino]carbonyl}-amino)phenoxy]pyridin-2-yl}-1H-pyrrol-3-yl)carbonyl]amino}propyl)-4-hydroxypyrrolidine-2-carboxylate |
| 218 | 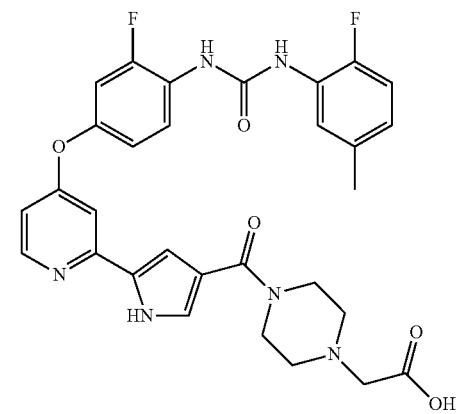 [SMILES: Cc1ccc(F)c(NC(=O)Nc2ccc(Oc3ccnc(-c4cc(C(=O)N5CCN(CC(=O)O)CC5)c[nH]4)c3)cc2F)c1] | 591 | {4-[(5-{4-[3-fluoro-4-({[(2-fluoro-5-methylphenyl)amino]carbonyl}-amino)phenoxy]pyridin-2-yl}-1H-pyrrol-3-yl)carbonyl]piperazin-1-yl}acetic acid |
| 219 | 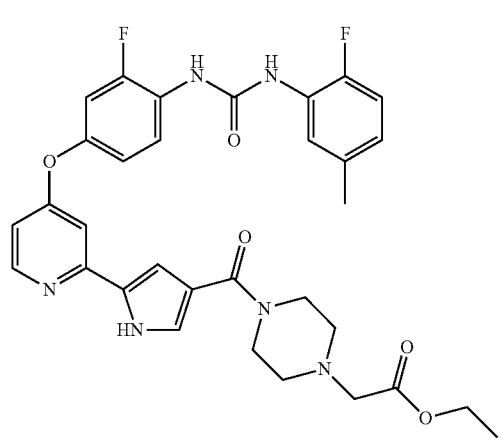 [SMILES: CCOC(=O)CN1CCN(C(=O)c2c[nH]c(-c3cc(Oc4ccc(NC(=O)Nc5cc(C)ccc5F)c(F)c4)ccn3)c2)CC1] | 619 | ethyl {4-[(5-{4-[3-fluoro-4-({[(2-fluoro-5-methylphenyl)amino]carbonyl}-amino)phenoxy]pyridin-2-yl}-1H-pyrrol-3-yl)carbonyl]piperazin-1-yl}acetate |

-continued

| Example # | Chemical Structure | MW | Chemical Name |
|---|---|---|---|
| 220 | 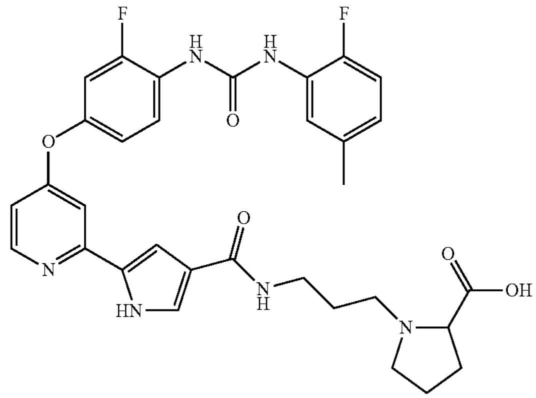 [SMILES: Cc1ccc(F)c(NC(=O)Nc2ccc(Oc3ccnc(-c4cc(C(=O)NCCCN5CCCC5C(=O)O)c[nH]4)c3)cc2F)c1] | 619 | 1-(3-{[(5-{4-[3-fluoro-4-({[(2-fluoro-5-methylphenyl)amino]carbonyl}-amino)phenoxy]pyridin-2-yl}-1H-pyrrol-3-yl)carbonyl]amino}propyl)-pyrrolidine-2-carboxylic acid |
| 221 | 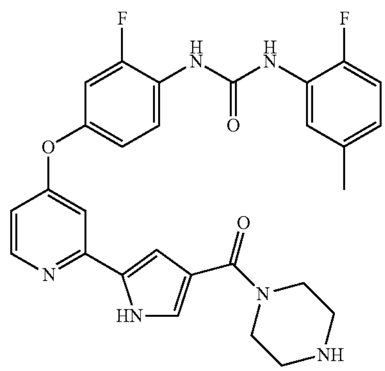 [SMILES: Cc1ccc(F)c(NC(=O)Nc2ccc(Oc3ccnc(-c4cc(C(=O)N5CCNCC5)c[nH]4)c3)cc2F)c1] | 533 | 1-(2-fluoro-5-methylphenyl)-3-[2-fluoro-4-({2-[4-(piperazin-1-ylcarbonyl)-1H-pyrrol-2-yl]pyridin-4-yl}oxy)-phenyl]urea |
| 222 | 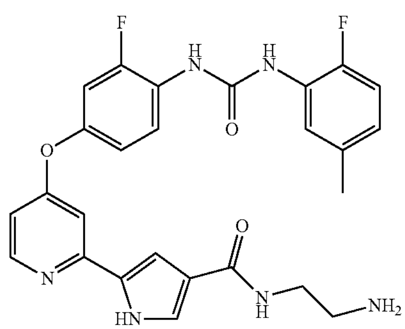 [SMILES: Cc1ccc(F)c(NC(=O)Nc2ccc(Oc3ccnc(-c4cc(C(=O)NCCN)c[nH]4)c3)cc2F)c1] | 507 | N-(2-aminoethyl)-5-{4-[3-fluoro-4-({[(2-fluoro-5-methylphenyl)amino]carbonyl}-amino)phenoxy]pyridin-2-yl}-1H-pyrrole-3-carboxamide |
| 223 | 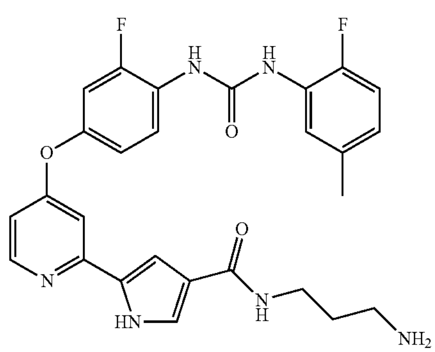 [SMILES: Cc1ccc(F)c(NC(=O)Nc2ccc(Oc3ccnc(-c4cc(C(=O)NCCCN)c[nH]4)c3)cc2F)c1] | 521 | N-(3-aminopropyl)-5-{4-[3-fluoro-4-({[(2-fluoro-5-methylphenyl)amino]carbonyl}-amino)phenoxy]pyridin-2-yl}-1H-pyrrole-3-carboxamide |

-continued

| Example # | Chemical Structure | MW | Chemical Name |
|---|---|---|---|
| 224 | 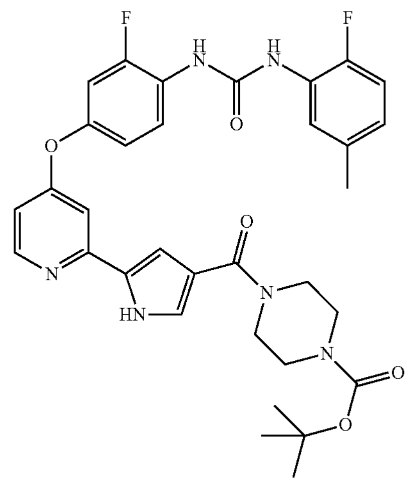 [SMILES: Cc1ccc(F)c(NC(=O)Nc2ccc(Oc3ccnc(-c4cc(C(=O)N5CCN(C(=O)OC(C)(C)C)CC5)c[nH]4)c3)cc2F)c1] | 633 | tert-butyl 4-[(5-{4-[3-fluoro-4-({[(2-fluoro-5-methylphenyl)amino]carbonyl}-amino)phenoxy]pyridin-2-yl}-1H-pyrrol-3-yl)carbonyl]piperazine-1-carboxylate |
| 225 | 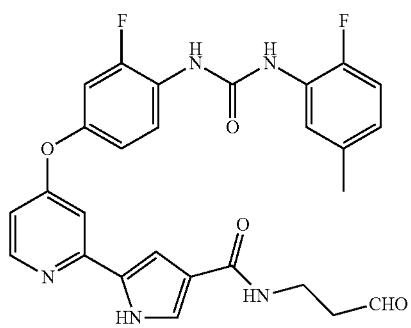 [SMILES: Cc1ccc(F)c(NC(=O)Nc2ccc(Oc3ccnc(-c4cc(C(=O)NCCC=O)c[nH]4)c3)cc2F)c1] | 520 | 5-{4-[3-fluoro-4-({[(2-fluoro-5-methylphenyl)amino]carbonyl}-amino)phenoxy]pyridin-2-yl}-N-(3-oxopropyl)-1H-pyrrole-3-carboxamide |
| 226 | 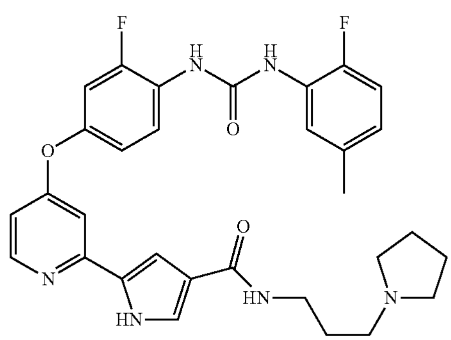 [SMILES: Cc1ccc(F)c(NC(=O)Nc2ccc(Oc3ccnc(-c4cc(C(=O)NCCCN5CCCC5)c[nH]4)c3)cc2F)c1] | 575 | 5-{4-[3-fluoro-4-({[(2-fluoro-5-methylphenyl)amino]carbonyl}-amino)phenoxy]pyridin-2-yl}-N-(3-pyrrolidin-1-ylpropyl)-1H-pyrrole-3-carboxamide |
| 227 | 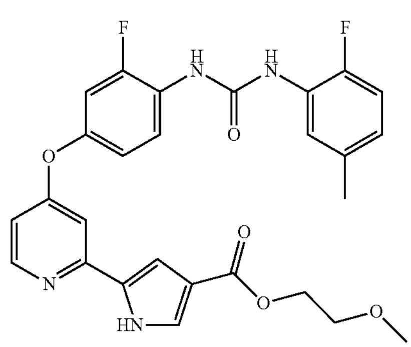 [SMILES: COCCOC(=O)c1c[nH]c(-c2cc(Oc3ccc(NC(=O)Nc4cc(C)ccc4F)c(F)c3)ccn2)c1] | 523 | 2-methoxyethyl 5-{4-[3-fluoro-4-({[(2-fluoro-5-methylphenyl)amino]carbonyl}-amino)phenoxy]pyridin-2-yl}-1H-pyrrole-3-carboxylate |

-continued

| Example # | Chemical Structure | MW | Chemical Name |
|---|---|---|---|
| 228 | 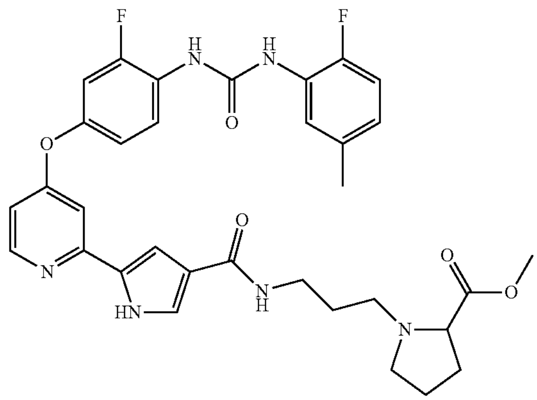 [SMILES: COC(=O)C1CCCN1CCCNC(=O)c1c[nH]c(-c2cc(Oc3ccc(NC(=O)Nc4cc(C)ccc4F)c(F)c3)ccn2)c1] | 633 | methyl 1-(3-{[(5-{4-[3-fluoro-4-({[(2-fluoro-5-methylphenyl)amino]carbonyl}-amino)phenoxy]pyridin-2-yl}-1H-pyrrol-3-yl)carbonyl]amino}-propyl)pyrrolidine-2-carboxylate |
| 229 | 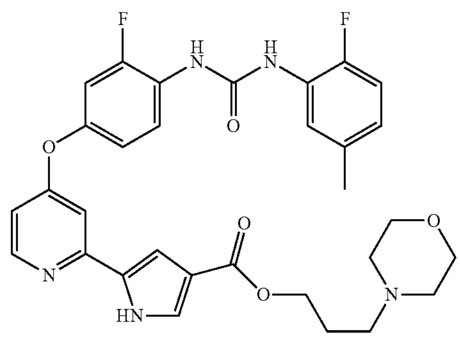 [SMILES: Cc1ccc(F)c(NC(=O)Nc2ccc(Oc3ccnc(-c4cc(C(=O)OCCCN5CCOCC5)c[nH]4)c3)cc2F)c1] | 592 | 3-morpholin-4-ylpropyl 5-{4-[3-fluoro-4-({[(2-fluoro-5-methylphenyl)amino]carbonyl}-amino)phenoxy]pyridin-2-yl}-1H-pyrrole-3-carboxylate |
| 230 | 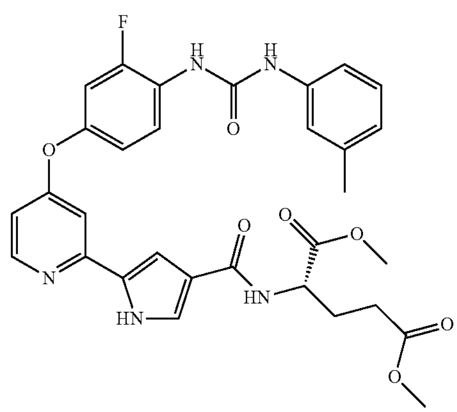 [SMILES: COC(=O)CC[C@H](NC(=O)c1c[nH]c(-c2cc(Oc3ccc(NC(=O)Nc4cccc(C)c4)c(F)c3)ccn2)c1)C(=O)OC] | 604 | dimethyl 2-{[(5-{4-[3-fluoro-4-({[(3-methylphenyl)amino]carbonyl}-amino)phenoxy]pyridin-2-yl}-1H-pyrrol-3-yl)carbonyl]amino}pentanedioate |
| 231 | 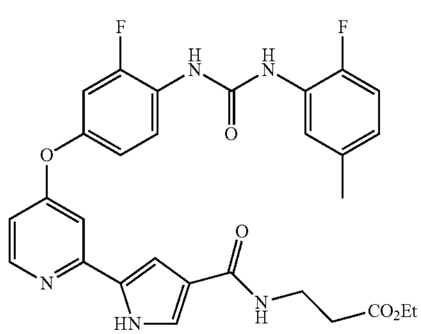 [SMILES: CCOC(=O)CCNC(=O)c1c[nH]c(-c2cc(Oc3ccc(NC(=O)Nc4cc(C)ccc4F)c(F)c3)ccn2)c1] | 564 | ethyl 3-{[(5-{4-[3-fluoro-4-({[(2-fluoro-5-methylphenyl)amino]carbonyl}-amino)phenoxy]pyridin-2-yl}-1H-pyrrol-3-yl)carbonyl]amino}propanoate |

-continued

| Example # | Chemical Structure | MW | Chemical Name |
|---|---|---|---|
| 232 | 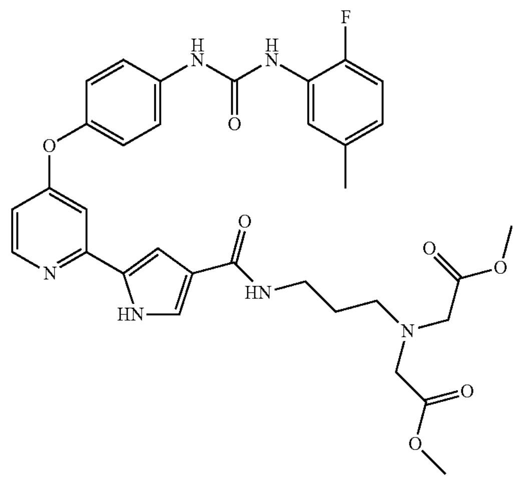 [SMILES: COC(=O)CN(CCCNC(=O)c1c[nH]c(-c2cc(Oc3ccc(NC(=O)Nc4cc(C)ccc4F)cc3)ccn2)c1)CC(=O)OC] | 647 | dimethyl 2,2'-[(3-{[(5-{4-[4-({[(2-fluoro-5-methylphenyl)amino]carbonyl}-amino)phenoxy]pyridin-2-yl}-1H-pyrrol-3-yl)carbonyl]amino}propyl)imino]diacetate |
| 233 | 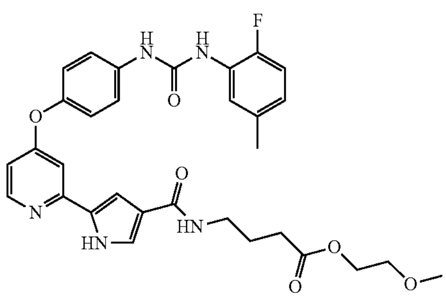 [SMILES: COCCOC(=O)CCCNC(=O)c1c[nH]c(-c2cc(Oc3ccc(NC(=O)Nc4cc(C)ccc4F)cc3)ccn2)c1] | 590 | 2-methoxyethyl 4-{[(5-{4-[4-({[(2-fluoro-5-methylphenyl)amino]carbonyl}-amino)phenoxy]pyridin-2-yl}-1H-pyrrol-3-yl)carbonyl]amino}butanoate |
| 234 | 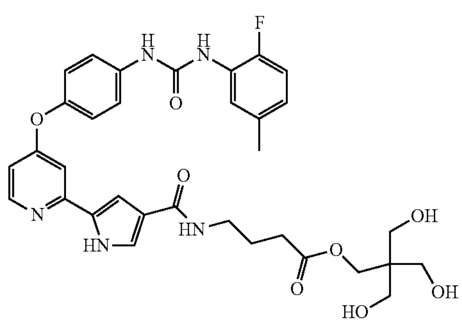 [SMILES: Cc1ccc(F)c(NC(=O)Nc2ccc(Oc3ccnc(-c4cc(C(=O)NCCCC(=O)OCC(CO)(CO)CO)c[nH]4)c3)cc2)c1] | 650 | 3-hydroxy-2,2-bis(hydroxymethyl)propyl 4-{[(5-{4-[4-({[(2-fluoro-5-methylphenyl)amino]carbonyl}-amino)phenoxy]pyridin-2-yl}-1H-pyrrol-3-yl)carbonyl]amino}butanoate |
| 235 | 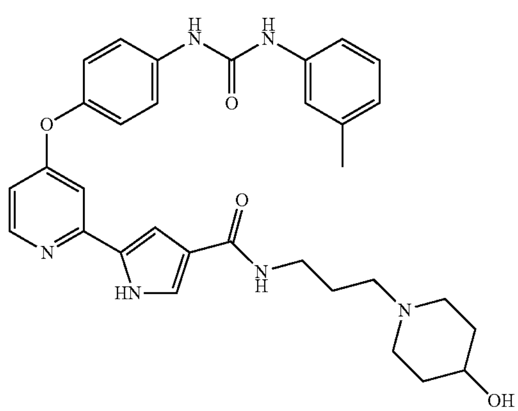 [SMILES: Cc1cccc(NC(=O)Nc2ccc(Oc3ccnc(-c4cc(C(=O)NCCCN5CCC(O)CC5)c[nH]4)c3)cc2)c1] | 569 | N-[3-(4-hydroxypiperidin-1-yl)propyl]-5-{4-[4-({[(3-methylphenyl)amino]carbonyl}-amino)phenoxy]pyridin-2-yl}-1H-pyrrole-3-carboxamide |

-continued

| Example # | Chemical Structure | MW | Chemical Name |
|---|---|---|---|
| 236 | 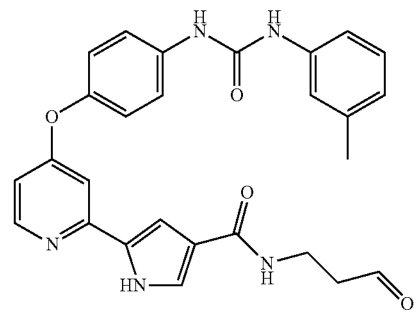 [SMILES: Cc1cccc(NC(=O)Nc2ccc(Oc3ccnc(-c4cc(C(=O)NCCC=O)c[nH]4)c3)cc2)c1] | 484 | 5-{4-[4-({[(3-methylphenyl)amino]-carbonyl}amino)phenoxy]pyridin-2-yl}-N-(3-oxopropyl)-1H-pyrrole-3-carboxamide |
| 237 | 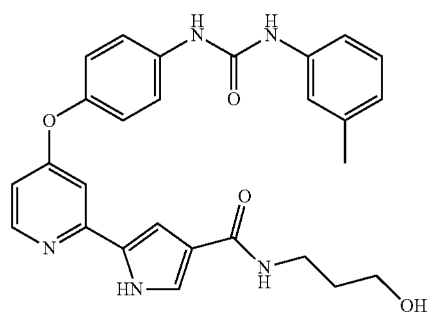 [SMILES: Cc1cccc(NC(=O)Nc2ccc(Oc3ccnc(-c4cc(C(=O)NCCCO)c[nH]4)c3)cc2)c1] | 486 | N-(3-hydroxypropyl)-5-{4-[4-({[(3-methylphenyl)amino]carbonyl}-amino)phenoxy]pyridin-2-yl}-1H-pyrrole-3-carboxamide |
| 238 | 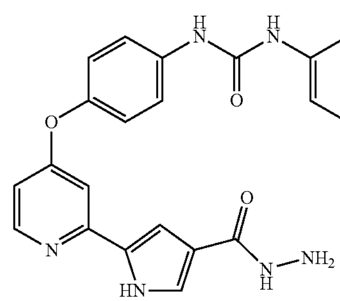 | 442 | 1-[4-({2-[4-(hydrazinocarbonyl)-1H-pyrrol-2-yl]pyridin-4-yl}oxy)phenyl]-3-(3-methylphenyl)urea |
| 239 | 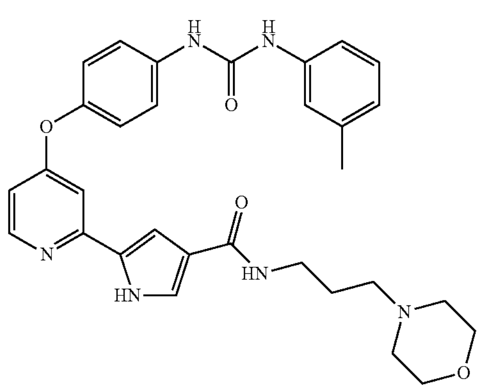 [SMILES: Cc1cccc(NC(=O)Nc2ccc(Oc3ccnc(-c4cc(C(=O)NCCCN5CCOCC5)c[nH]4)c3)cc2)c1] | 555 | 5-{4-[4-({[(3-methylphenyl)amino]-carbonyl}amino)phenoxy]pyridin-2-yl}-N-(3-morpholin-4-ylpropyl)-1H-pyrrole-3-carboxamide |

-continued

| Example # | Chemical Structure | MW | Chemical Name |
|---|---|---|---|
| 240 | 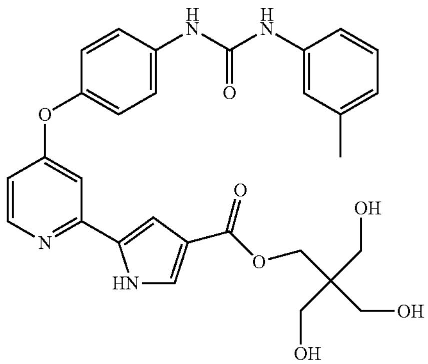 [SMILES: Cc1cccc(NC(=O)Nc2ccc(Oc3ccnc(-c4cc(C(=O)OCC(CO)(CO)CO)c[nH]4)c3)cc2)c1] | 547 | 3-hydroxy-2,2-bis(hydroxymethyl)propyl 5-{4-[4-({[(3-methylphenyl)amino]carbonyl}-amino)phenoxy]pyridin-2-yl}-1H-pyrrole-3-carboxylate |
| 241 | 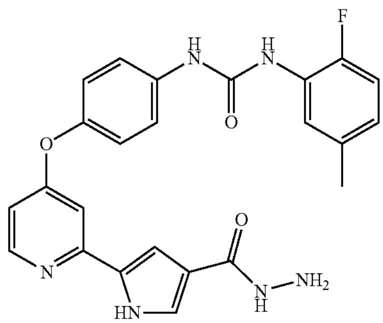 [SMILES: Cc1ccc(F)c(NC(=O)Nc2ccc(Oc3ccnc(-c4cc(C(=O)NN)c[nH]4)c3)cc2)c1] | 460 | 1-(2-fluoro-5-methylphenyl)-3-[4-({2-[4-(hydrazinocarbonyl)-1H-pyrrol-2-yl]pyridin-4-yl}oxy)phenyl]urea |
| 242 | 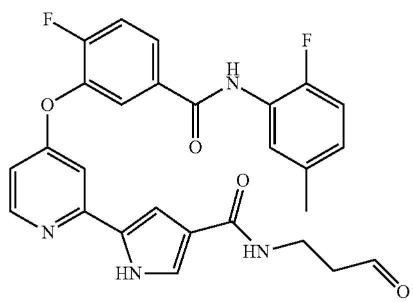 [SMILES: Cc1ccc(F)c(NC(=O)c2ccc(F)c(Oc3ccnc(-c4cc(C(=O)NCCC=O)c[nH]4)c3)c2)c1] | 504 | 5-[4-(2-fluoro-5-{[(2-fluoro-5-methylphenyl)amino]carbonyl}-phenoxy)pyridin-2-yl]-N-(3-oxopropyl)-1H-pyrrole-3-carboxamide |
| 243 | 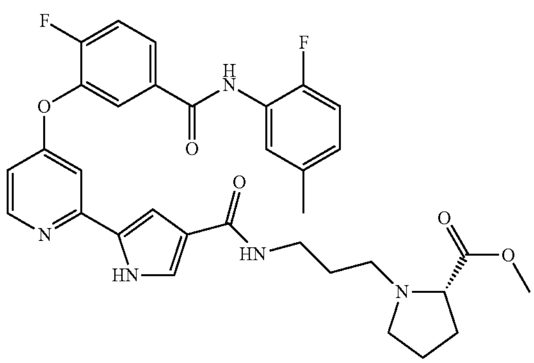 [SMILES: COC(=O)[C@@H]1CCCN1CCCNC(=O)c1c[nH]c(-c2cc(Oc3cc(C(=O)Nc4cc(C)ccc4F)ccc3F)ccn2)c1] | 618 | methyl (2S)-1-{3-[({5-[4-(2-fluoro-5-{[(2-fluoro-5-methylphenyl)amino]carbonyl}-phenoxy)pyridin-2-yl]-1H-pyrrol-3-yl}carbonyl)amino]propyl}pyrrolidine-2-carboxylate |

-continued

| Example # | Chemical Structure | MW | Chemical Name |
|---|---|---|---|
| 244 | 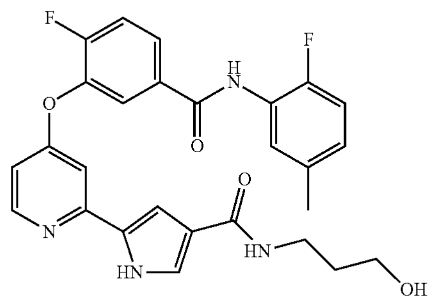 [SMILES: Cc1ccc(F)c(NC(=O)c2ccc(F)c(Oc3ccnc(-c4cc(C(=O)NCCCO)c[nH]4)c3)c2)c1] | 507 | 5-[4-(2-fluoro-5-{[(2-fluoro-5-methylphenyl)amino]carbonyl}-phenoxy)pyridin-2-yl]-N-(3-hydroxypropyl)-1H-pyrrole-3-carboxamide |
| 245 | 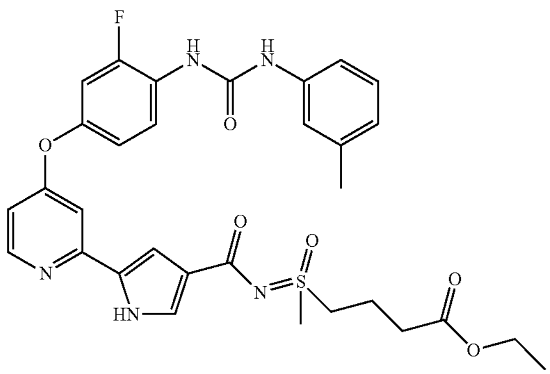 [SMILES: CCOC(=O)CCCS(C)(=O)=NC(=O)c1c[nH]c(-c2cc(Oc3ccc(NC(=O)Nc4cccc(C)c4)c(F)c3)ccn2)c1] | 622 | ethyl 4-{N-[(5-{4-[3-fluoro-4-({[(3-methylphenyl)amino]carbonyl}-amino)phenoxy]pyridin-2-yl}-1H-pyrrol-3-yl)carbonyl]-S-methylsulfonimidoyl}-butanoate |
| 246 | 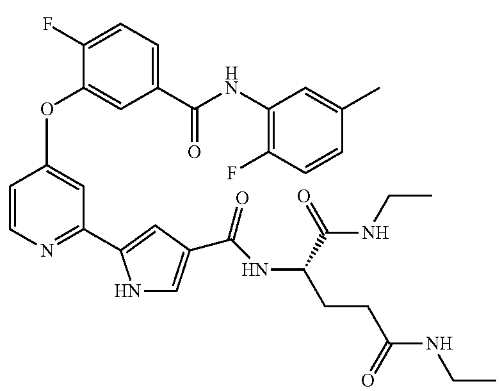 [SMILES: CCNC(=O)CC[C@H](NC(=O)c1c[nH]c(-c2cc(Oc3cc(C(=O)Nc4cc(C)ccc4F)ccc3F)ccn2)c1)C(=O)NCC] | 633 | N,N'-diethyl-2-[({5-[4-(2-fluoro-5-{[(2-fluoro-5-methylphenyl)amino]carbonyl}-phenoxy)pyridin-2-yl]-1H-pyrrol-3-yl}carbonyl)amino]pentanediamide |
| 247 | 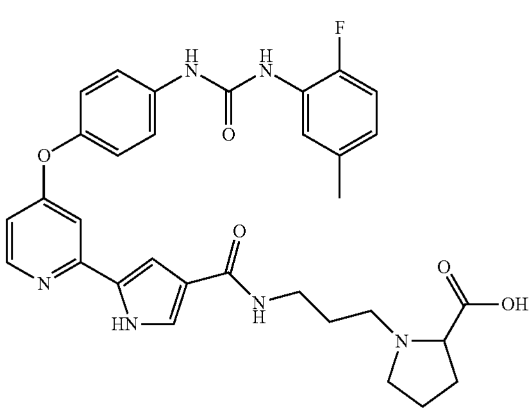 [SMILES: Cc1ccc(F)c(NC(=O)Nc2ccc(Oc3ccnc(-c4cc(C(=O)NCCCN5CCCC5C(=O)O)c[nH]4)c3)cc2)c1] | 601 | 1-(3-{[(5-{4-[4-({[(2-fluoro-5-methylphenyl)amino]carbonyl}-amino)phenoxy]pyridin-2-yl}-1H-pyrrol-3-yl)carbonyl]amino}propyl)-pyrrolidine-2-carboxylic acid |

| Example # | Chemical Structure | MW | Chemical Name |
|---|---|---|---|
| 248 | 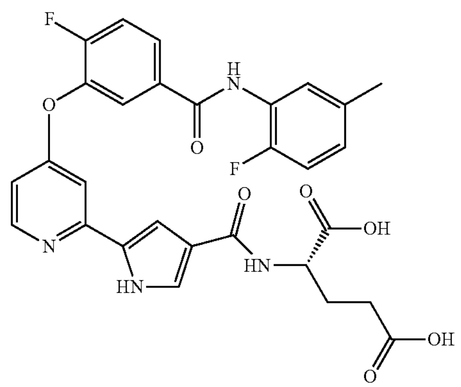 [SMILES: Cc1ccc(F)c(NC(=O)c2ccc(F)c(Oc3ccnc(-c4cc(C(=O)N[C@@H](CCC(=O)O)C(=O)O)c[nH]4)c3)c2)c1] | 579 | 2-[({5-[4-(2-fluoro-5-{[(2-fluoro-5-methylphenyl)amino]carbonyl}-phenoxy)pyridin-2-yl]-1H-pyrrol-3-yl}carbonyl)amino]pentanedioic acid |
| 249 | 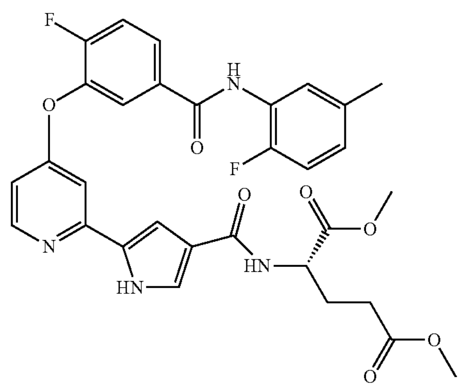 [SMILES: COC(=O)CC[C@H](NC(=O)c1c[nH]c(-c2cc(Oc3cc(C(=O)Nc4cc(C)ccc4F)ccc3F)ccn2)c1)C(=O)OC] | 607 | dimethyl 2-[({5-[4-(2-fluoro-5-{[(2-fluoro-5-methylphenyl)amino]carbonyl}-phenoxy)pyridin-2-yl]-1H-pyrrol-3-yl}carbonyl)amino]pentanedioate |
| 250 | 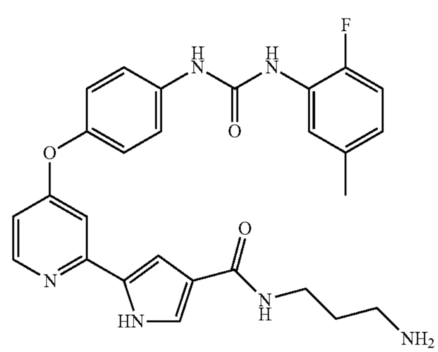 [SMILES: Cc1ccc(F)c(NC(=O)Nc2ccc(Oc3ccnc(-c4cc(C(=O)NCCCN)c[nH]4)c3)cc2)c1] | 503 | N-(3-aminopropyl)-5-{4-[4-({[(2-fluoro-5-methylphenyl)amino]carbonyl}-amino)phenoxy]pyridin-2-yl}-1H-pyrrole-3-carboxamide |
| 251 | 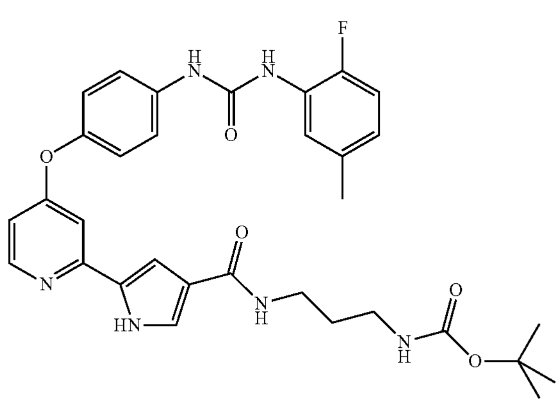 [SMILES: Cc1ccc(F)c(NC(=O)Nc2ccc(Oc3ccnc(-c4cc(C(=O)NCCCNC(=O)OC(C)(C)C)c[nH]4)c3)cc2)c1] | 603 | tert-butyl (3-{[(5-{4-[4-({[(2-fluoro-5-methylphenyl)amino]carbonyl}-amino)phenoxy]pyridin-2-yl}-1H-pyrrol-3-yl)carbonyl]amino}propyl)carbamate |

| Example # | Chemical Structure | MW | Chemical Name |
|---|---|---|---|
| 252 | 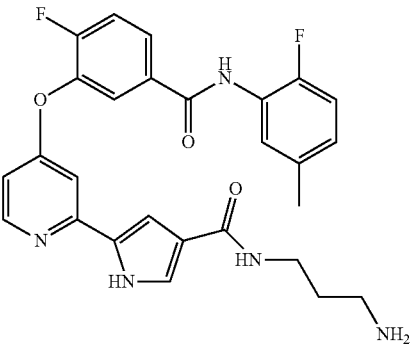 [SMILES: Cc1ccc(F)c(NC(=O)c2ccc(F)c(Oc3ccnc(-c4cc(C(=O)NCCCN)c[nH]4)c3)c2)c1] | 506 | N-(3-aminopropyl)-5-[4-(2-fluoro-5-{[(2-fluoro-5-methylphenyl)amino]carbonyl}phenoxy)pyridin-2-yl]-1H-pyrrole-3-carboxamide |
| 253 | 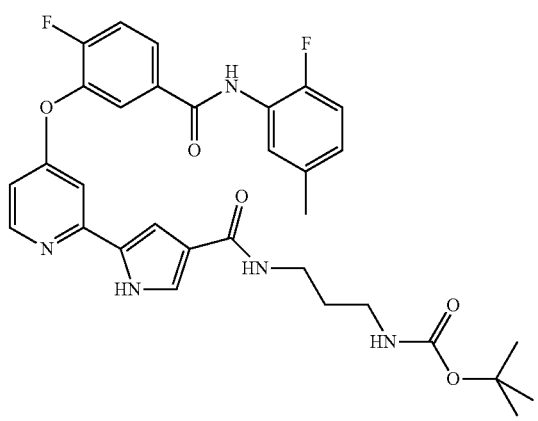 [SMILES: Cc1ccc(F)c(NC(=O)c2ccc(F)c(Oc3ccnc(-c4cc(C(=O)NCCCNC(=O)OC(C)(C)C)c[nH]4)c3)c2)c1] | 606 | tert-butyl {3-[({5-[4-(2-fluoro-5-{[(2-fluoro-5-methylphenyl)amino]carbonyl}-phenoxy)pyridin-2-yl]-1H-pyrrol-3-yl}carbonyl)amino]propyl}carbamate |
| 254 | 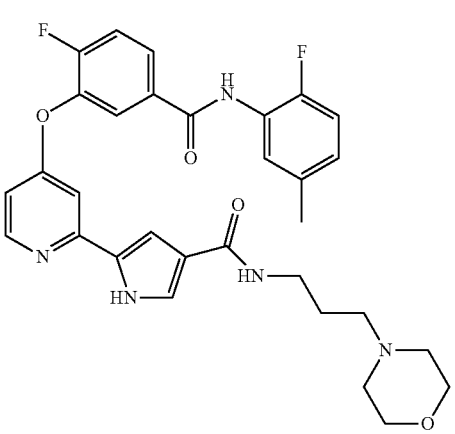 [SMILES: Cc1ccc(F)c(NC(=O)c2ccc(F)c(Oc3ccnc(-c4cc(C(=O)NCCCN5CCOCC5)c[nH]4)c3)c2)c1] | 576 | 5-[4-(2-fluoro-5-{[(2-fluoro-5-methylphenyl)amino]carbonyl}-phenoxy)pyridin-2-yl]-N-(3-morpholin-4-ylpropyl)-1H-pyrrole-3-carboxamide |
| 255 | 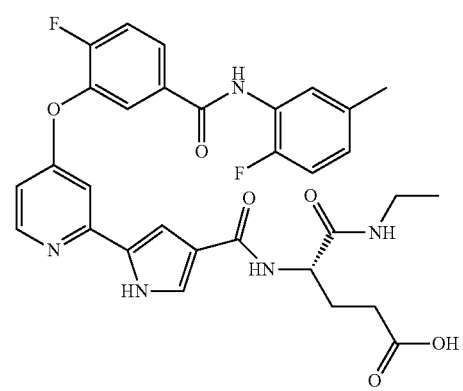 [SMILES: CCNC(=O)[C@H](CCC(=O)O)NC(=O)c1c[nH]c(-c2cc(Oc3cc(C(=O)Nc4cc(C)ccc4F)ccc3F)ccn2)c1] | 606 | 5-(ethylamino)-4-({5-[4-(2-fluoro-5-{[(2-fluoro-5-methylphenyl)amino]carbonyl}-phenoxy)pyridin-2-yl]-1H-pyrrol-3-yl}carbonyl)amino]-5-oxopentanoic acid |

| Example # | Chemical Structure | MW | Chemical Name |
|---|---|---|---|
| 256 | 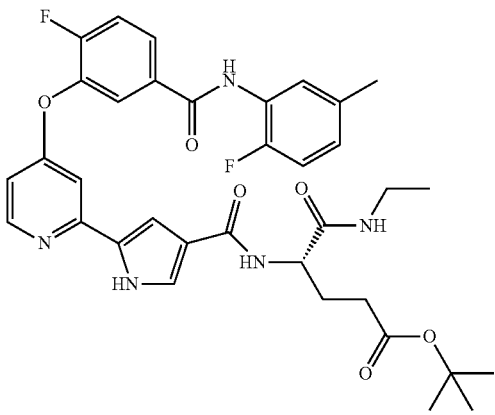 [SMILES: CCNC(=O)[C@H](CCC(=O)OC(C)(C)C)NC(=O)c1c[nH]c(-c2cc(Oc3cc(C(=O)Nc4cc(C)ccc4F)ccc3F)ccn2)c1] | 662 | tert-butyl 5-(ethylamino)-4-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoate |
| 257 | 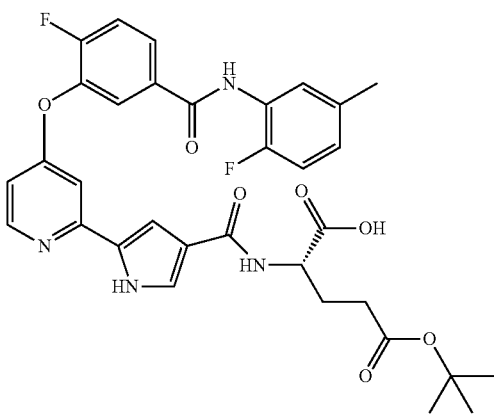 [SMILES: Cc1ccc(F)c(NC(=O)c2ccc(F)c(Oc3ccnc(-c4cc(C(=O)N[C@@H](CCC(=O)OC(C)(C)C)C(=O)O)c[nH]4)c3)c2)c1] | 635 | 5-tert-butoxy-2-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoic acid |
| 258 | 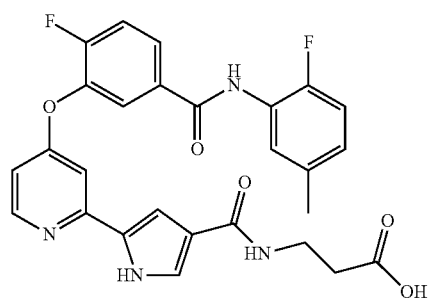 [SMILES: Cc1ccc(F)c(NC(=O)c2ccc(F)c(Oc3ccnc(-c4cc(C(=O)NCCC(=O)O)c[nH]4)c3)c2)c1] | 520 | 3-[({5-[4-(2-fluoro-5-{[(2-fluoro-5-methylphenyl)amino]carbonyl}phenoxy)pyridin-2-yl]-1H-pyrrol-3-yl}carbonyl)amino]propanoic acid |
| 259 | 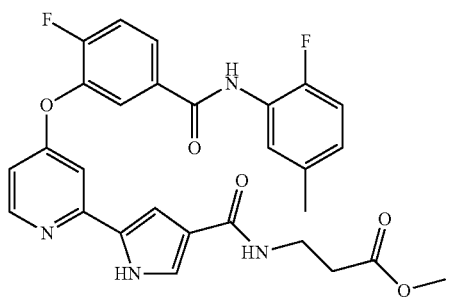 [SMILES: COC(=O)CCNC(=O)c1c[nH]c(-c2cc(Oc3cc(C(=O)Nc4cc(C)ccc4F)ccc3F)ccn2)c1] | 535 | methyl 3-[({5-[4-(2-fluoro-5-{[(2-fluoro-5-methylphenyl)amino]carbonyl}phenoxy)pyridin-2-yl]-1H-pyrrol-3-yl}carbonyl)amino]propanoate |

-continued

| Example # | Chemical Structure | MW | Chemical Name |
|---|---|---|---|
| 260 | 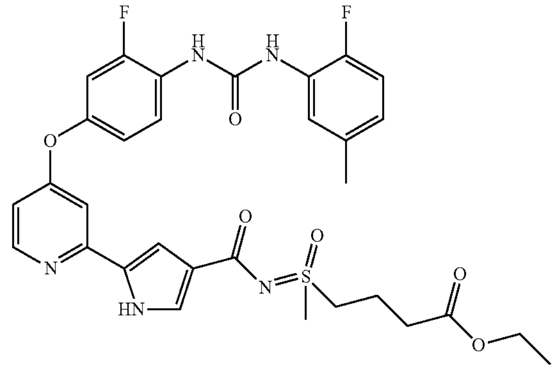 [SMILES: CCOC(=O)CCCS(C)(=O)=NC(=O)c1c[nH]c(-c2cc(Oc3ccc(NC(=O)Nc4cc(C)ccc4F)c(F)c3)ccn2)c1] | 640 | ethyl 4-{N-[(5-{4-[3-fluoro-4-({[(2-fluoro-5-methylphenyl)amino]carbonyl}-amino)phenoxy]pyridin-2-yl}-1H-pyrrol-3-yl)carbonyl]-S-methylsulfonimidoyl}-butanoate |
| 261 | 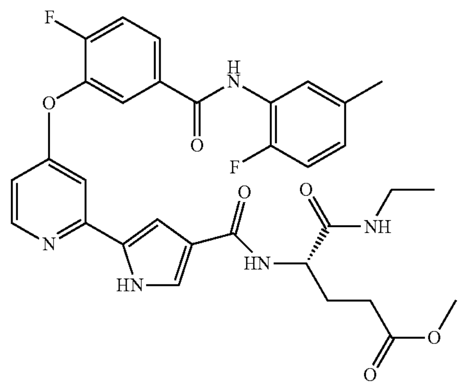 [SMILES: CCNC(=O)[C@H](CCC(=O)OC)NC(=O)c1c[nH]c(-c2cc(Oc3cc(C(=O)Nc4cc(C)ccc4F)ccc3F)ccn2)c1] | 620 | methyl 5-(ethylamino)-4-[({5-[4-(2-fluoro-5-{[(2-fluoro-5-methylphenyl)amino]carbonyl}-phenoxy)pyridin-2-yl]-1H-pyrrol-3-yl}carbonyl)amino]-5-oxopentanoate |
| 262 | 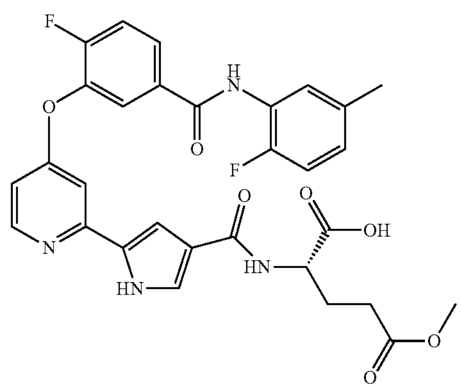 [SMILES: COC(=O)CC[C@H](NC(=O)c1c[nH]c(-c2cc(Oc3cc(C(=O)Nc4cc(C)ccc4F)ccc3F)ccn2)c1)C(=O)O] | 593 | 2-[({5-[4-(2-fluoro-5-{[(2-fluoro-5-methylphenyl)amino]carbonyl}-phenoxy)pyridin-2-yl]-1H-pyrrol-3-yl}carbonyl)amino]-5-methoxy-5-oxopentanoic acid |
| 263 | 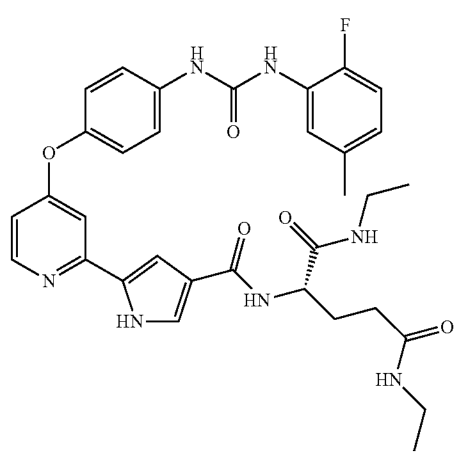 [SMILES: CCNC(=O)CC[C@H](NC(=O)c1c[nH]c(-c2cc(Oc3ccc(NC(=O)Nc4cc(C)ccc4F)cc3)ccn2)c1)C(=O)NCC] | 630 | N,N'-diethyl-2-{[(5-{4-[4-({[(2-fluoro-5-methylphenyl)amino]carbonyl}-amino)phenoxy]pyridin-2-yl}-1H-pyrrol-3-yl)carbonyl]amino}pentanediamide |

-continued

| Example # | Chemical Structure | MW | Chemical Name |
|---|---|---|---|
| 264 | 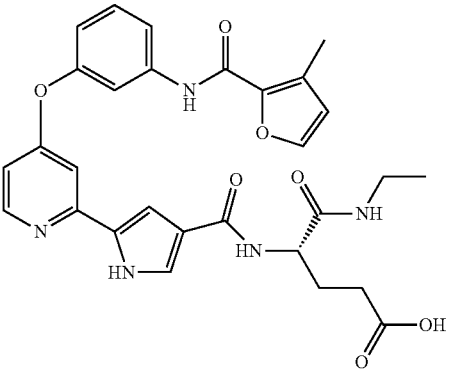 [SMILES: CCNC(=O)[C@H](CCC(=O)O)NC(=O)c1c[nH]c(-c2cc(Oc3cccc(NC(=O)c4occc4C)c3)ccn2)c1] | 560 | 5-(ethylamino)-4-({[5-(4-{3-[(3-methyl-2-furoyl)amino]phenoxy}pyridin-2-yl)-1H-pyrrol-3-yl]carbonyl}amino)-5-oxopentanoic acid |
| 265 | 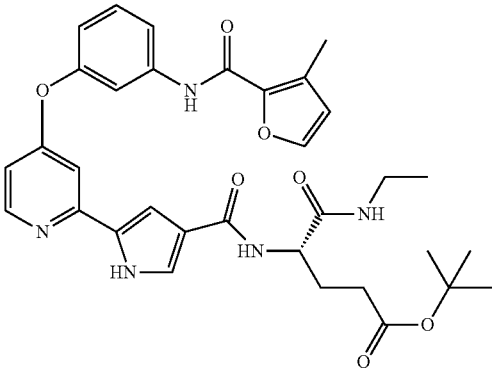 [SMILES: CCNC(=O)[C@H](CCC(=O)OC(C)(C)C)NC(=O)c1c[nH]c(-c2cc(Oc3cccc(NC(=O)c4occc4C)c3)ccn2)c1] | 616 | tert-butyl 5-(ethylamino)-4-({[5-(4-{3-[(3-methyl-2-furoyl)amino]phenoxy}pyridin-2-yl)-1H-pyrrol-3-yl]carbonyl}amino)-5-oxopentanoate |
| 266 | 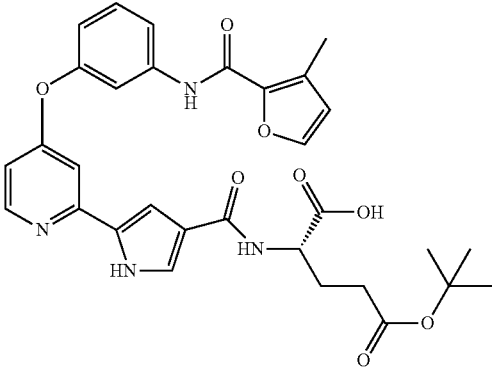 [SMILES: Cc1ccoc1C(=O)Nc1cccc(Oc2ccnc(-c3cc(C(=O)N[C@@H](CCC(=O)OC(C)(C)C)C(=O)O)c[nH]3)c2)c1] | 589 | 5-tert-butoxy-2-({[5-(4-{3-[(3-methyl-2-furoyl)amino]phenoxy}pyridin-2-yl)-1H-pyrrol-3-yl]carbonyl}amino)-5-oxopentanoic acid |
| 267 | 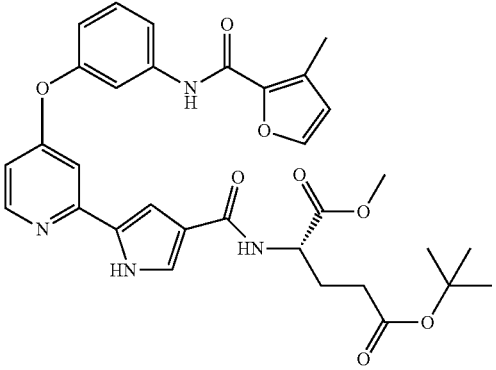 [SMILES: COC(=O)[C@H](CCC(=O)OC(C)(C)C)NC(=O)c1c[nH]c(-c2cc(Oc3cccc(NC(=O)c4occc4C)c3)ccn2)c1] | 603 | 5-tert-butyl 1-methyl 2-({[5-(4-{3-[(3-methyl-2-furoyl)amino]phenoxy}pyridin-2-yl)-1H-pyrrol-3-yl]carbonyl}amino)pentanedioate |

| Example # | Chemical Structure | MW | Chemical Name |
|---|---|---|---|
| 268 | 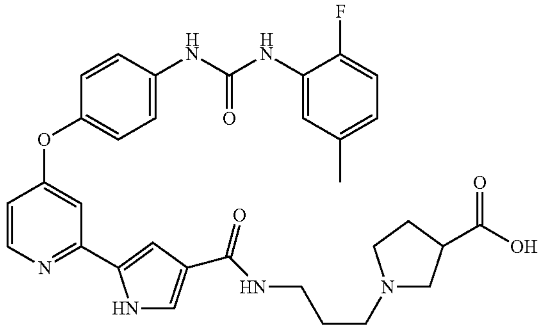 [SMILES: Cc1ccc(F)c(NC(=O)Nc2ccc(Oc3ccnc(-c4cc(C(=O)NCCCN5CCC(C(=O)O)C5)c[nH]4)c3)cc2)c1] | 601 | 1-(3-{[(5-{4-[4-({[(2-fluoro-5-methylphenyl)amino]carbonyl}-amino)phenoxy]pyridin-2-yl}-1H-pyrrol-3-yl)carbonyl]amino}propyl)-pyrrolidine-3-carboxylic acid |
| 269 | 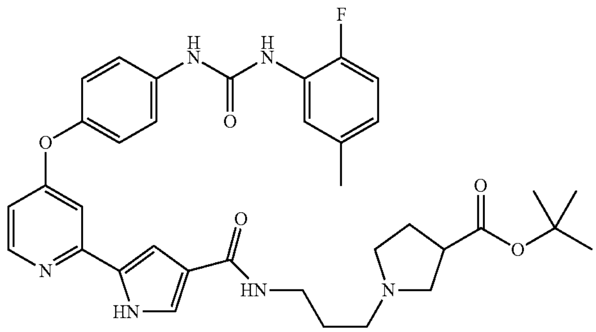 [SMILES: Cc1ccc(F)c(NC(=O)Nc2ccc(Oc3ccnc(-c4cc(C(=O)NCCCN5CCC(C(=O)OC(C)(C)C)C5)c[nH]4)c3)cc2)c1] | 657 | tert-butyl 1-(3-{[(5-{4-[4-({[(2-fluoro-5-methylphenyl)amino]carbonyl}-amino)phenoxy]pyridin-2-yl}-1H-pyrrol-3-yl)carbonyl]amino}-propyl)pyrrolidine-3-carboxylate |
| 270 | 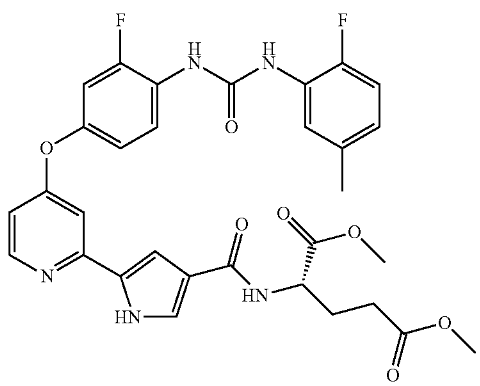 [SMILES: COC(=O)CC[C@H](NC(=O)c1c[nH]c(-c2cc(Oc3ccc(NC(=O)Nc4cc(C)ccc4F)c(F)c3)ccn2)c1)C(=O)OC] | 621 | dimethyl 2-{[(5-{4-[3-fluoro-4-({[(2-fluoro-5-methylphenyl)amino]carbonyl}-amino)phenoxy]pyridin-2-yl}-1H-pyrrol-3-yl)carbonyl]amino}pentanedioate |
| 271 | 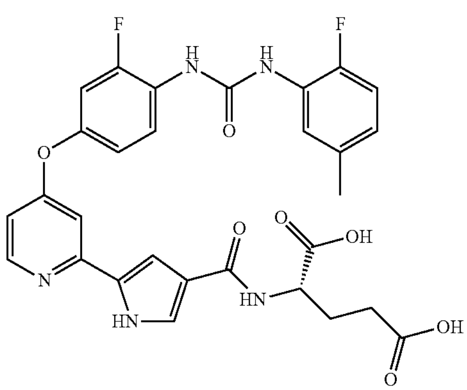 [SMILES: Cc1ccc(F)c(NC(=O)Nc2ccc(Oc3ccnc(-c4cc(C(=O)N[C@@H](CCC(=O)O)C(=O)O)c[nH]4)c3)cc2F)c1] | 594 | 5-tert-butoxy-2-{[(5-{4-[3-fluoro-4-({[(2-fluoro-5-methylphenyl)amino]carbonyl}-amino)phenoxy]pyridin-2-yl}-1H-pyrrol-3-yl)carbonyl]amino}-5-oxopentanoic acid |

| Example # | Chemical Structure | MW | Chemical Name |
|---|---|---|---|
| 272 | 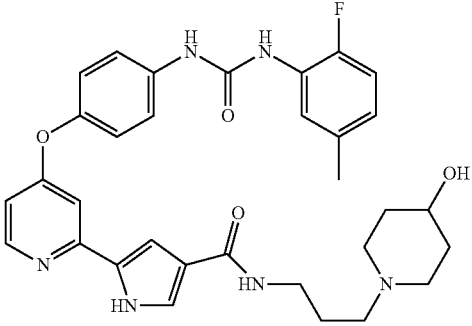 [SMILES: Cc1ccc(F)c(NC(=O)Nc2ccc(Oc3ccnc(-c4cc(C(=O)NCCCN5CCC(O)CC5)c[nH]4)c3)cc2)c1] | 587 | 5-{4-[4-({[(2-fluoro-5-methylphenyl)amino]carbonyl}-amino)phenoxy]pyridin-2-yl}-N-[3-(4-hydroxypiperidin-1-yl)propyl]-1H-pyrrole-3-carboxamide |
| 273 | 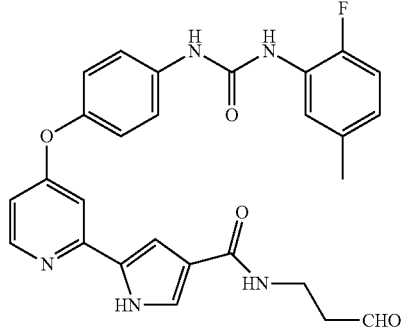 [SMILES: Cc1ccc(F)c(NC(=O)Nc2ccc(Oc3ccnc(-c4cc(C(=O)NCCC=O)c[nH]4)c3)cc2)c1] | 502 | 5-{4-[4-({[(2-fluoro-5-methylphenyl)amino]carbonyl}-amino)phenoxy]pyridin-2-yl}-N-(3-oxopropyl)-1H-pyrrole-3-carboxamide |
| 274 | 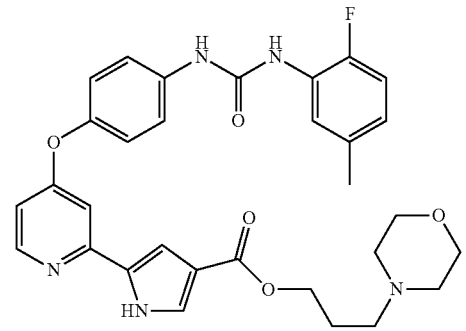 | 574 | 3-morpholin-4-ylpropyl 5-{4-[4-({[(2-fluoro-5-methylphenyl)amino]carbonyl}-amino)phenoxy]pyridin-2-yl}-1H-pyrrole-3-carboxylate |
| 275 | 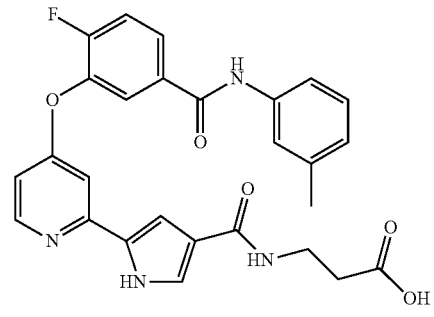 [SMILES: Cc1cccc(NC(=O)c2ccc(F)c(Oc3ccnc(-c4cc(C(=O)NCCC(=O)O)c[nH]4)c3)c2)c1] | 502 | 3-[({5-[4-(2-fluoro-5-{[(2-fluoro-5-methylphenyl)amino]carbonyl}-phenoxy)pyridin-2-yl]-1H-pyrrol-3-yl}carbonyl)amino]propanoic acid |

| Example # | Chemical Structure | MW | Chemical Name |
|---|---|---|---|
| 276 | 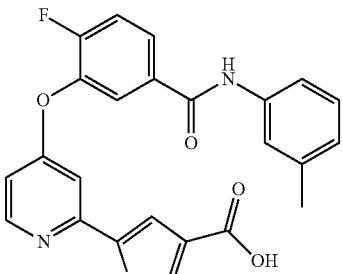 | 430 | 5-[4-(2-fluoro-5-{[(3-methylphenyl)amino]carbonyl}-phenoxy)pyridin-2-yl]-1H-pyrrole-3-carboxylic acid |
| 277 | 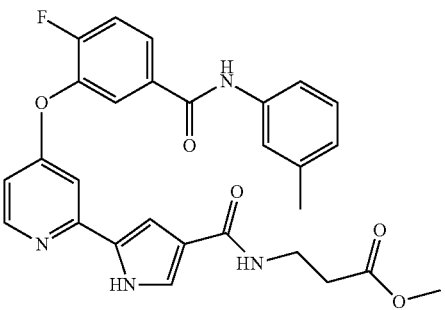 [SMILES: COC(=O)CCNC(=O)c1c[nH]c(-c2cc(Oc3cc(C(=O)Nc4cccc(C)c4)ccc3F)ccn2)c1] | 517 | methyl 3-[({5-[4-(2-fluoro-5-{[(2-fluoro-5-methylphenyl)amino]carbonyl}-phenoxy)pyridin-2-yl]-1H-pyrrol-3-yl}carbonyl)amino]propanoate |
| 278 | 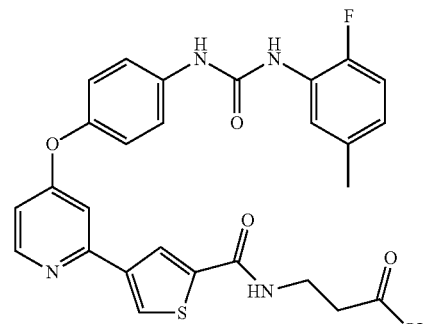 | 535 | 3-{[(4-{4-[4-({[(2-fluoro-5-methylphenyl)amino]carbonyl}-amino)phenoxy]pyridin-2-yl}-2-thienyl)carbonyl]amino}propanoic acid |
| 279 | 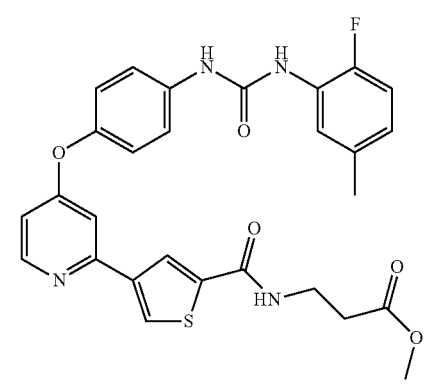 [SMILES: COC(=O)CCNC(=O)c1cc(-c2cc(Oc3ccc(NC(=O)Nc4cc(C)ccc4F)cc3)ccn2)cs1] | 549 | methyl 3-{[(4-{4-[4-({[(2-fluoro-5-methylphenyl)amino]carbonyl}-amino)phenoxy]pyridin-2-yl}-2-thienyl)carbonyl]amino}propanoate |

3.1 Compound Synthesis and Characterization

Preparation of methyl 5-(4,4,5,5-tetramethyl-1,3,2-dioxaborolan-2-yl)-1H-pyrrole-3-carboxylate

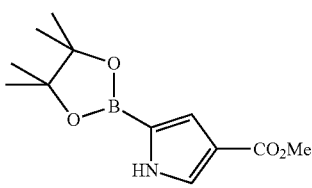 [SMILES: COC(=O)c1c[nH]c(B2OC(C)(C)C(C)(C)O2)c1]

To a mixture of methyl-1H-pyrrole-3-carboxylate (5.0 g, 39.9 mmol), bis(pinacolato)diboron (5.37 g, 21.1 mmol), 4,4'-di-tert-butyl-2,2'-bipyridine (0.054 g, 0.20 mmol) and [Ir(OMe)(COD)]$_2$ (0.067 g, 0.099 mmol) was added cyclohexane (60 mL). The mixture stirred at 90° C. for 5 hours. The mixture was cooled to room temperature and filtered, washing with ample amounts of water and twice with hexanes. The light orange solid was collected and dried in a vacuum oven at 55° C. to afford methyl 5-(4,4,5,5-tetramethyl-1,3,2-dioxaborolan-2-yl)-1H-pyrrole-3-carboxylate (6.99 g, 70% yield).

Preparation of 3-(2-Bromo-pyridin-4-yloxy)-benzoic acid

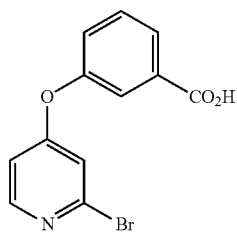 [SMILES: O=C(O)c1cccc(Oc2ccnc(Br)c2)c1]

A mixture of 2-bromo-4-chloro-pyridine (200 mg, 1.04 mmol), methyl-3-hydroxybenzoate (158 mg, 1.04 mmol), cesium carbonate (507 mg, 1.56 mmol) in 10 ml of anhydrous DMSO was heated at 66° C. for 5 hours. The mixture was diluted with ethyl acetate (100 ml), washed with brine (3×50 ml), dried over Na$_2$SO$_4$ and evaporated to give a colorless oil. The oil was dissolved in MeOH (8 ml), and 2M NaOH solution (4 ml, 8 mmol) was added. The mixture was heated at 60° C. for 20 minutes, poured into 50 ml of water, and acidified to pH=4. The precipitates were filtered, washed with water and dried in vacuo to give 3-(2-bromo-pyridin-4-yloxy)-benzoic acid as white solid. Yield: 170 mg, 56%.

$^1$H NMR (DMSO-d$_6$): 13.24 (br. s., 1H), 8.27 (d, J=5.9 Hz, 1H), 7.87 (d, J=7.6 Hz, 1H), 7.58-7.68 (m, 2H), 7.45-7.52 (m, 1H), 7.19 (d, J=2.1 Hz, 1H), 7.00 (dd, J=5.7, 2.2 Hz, 1H)

LR MS (ES−): 292 (M−H), 294

Preparation of 3-(2-Bromo-pyridin-4-yloxy)-N-m-tolyl-benzamide

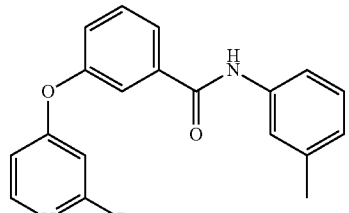

A mixture of 3-(2-bromo-pyridin-4-yloxy)-benzoic acid (170 mg, 0.58 mmol), HATU (265 mg, 0.69 mmol),) m-toluidine (93 mg, 0.87 mmol) and N,N-diisopropylethylamine (164 mg, 1.28 mmol) in anhydrous DMF (10 ml) was stirred at room temperature for 20 minutes. The mixture was poured into 100 ml of water. The precipitates were filtered, washed with water and dried in vacuo to give 3-(2-Bromo-pyridin-4-yloxy)-N-m-tolyl-benzamide as off-white solid. Yield: 150 mg, 68%.

$^1$H NMR (DMSO-d$_6$): 10.18 (s, 1H), 8.29 (d, J=5.9 Hz, 1H), 7.91 (d, J=7.6 Hz, 1H), 7.78 (s, 1H), 7.65 (t, J=7.9 Hz, 1H), 7.50-7.60 (m, 2H), 7.45 (dd, J=7.9, 1.8 Hz, 1H), 7.16-7.25 (m, 2H), 7.02 (dd, J=5.7, 2.2 Hz, 1H), 6.92 (d, J=7.6 Hz, 1H), 2.29 (s, 3H)

LR MS (ES+): 405 (M+Na$^+$), 407

LR MS (ES−): 381 (M−H), 383

Preparation of 3-(2-Bromo-pyridin-4-yloxy)-N-(2-fluoro-5-methyl-phenyl)-benzamide

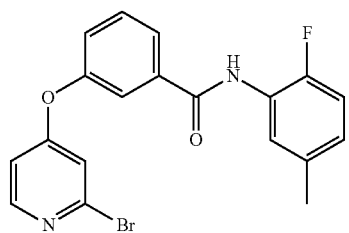 [SMILES: Cc1ccc(F)c(NC(=O)c2cccc(Oc3ccnc(Br)c3)c2)c1]

A mixture of 3-(2-bromo-pyridin-4-yloxy)-benzoic acid (200 mg, 0.68 mmol), HATU (312 mg, 0.82 mmol),) 2-fluoro-5-methylaniline (125 mg, 1.0 mmol) and N,N-diisopropylethylamine (193 mg, 1.5 mmol) in anhydrous DMF (10 ml) was stirred at 60° C. for 90 minutes. The mixture was poured into 100 ml of water. The precipitates were filtered, washed with water and dried in vacuo to give 3-(2-bromo-pyridin-4-yloxy)-N-(2-fluoro-5-methyl-phenyl)-benzamide as off-white solid. Yield: 200 mg, 74%.

Example 1

[({5-[4-(2-fluoro-5-{[(2-fluoro-5-methylphenyl)amino]carbonyl}phenoxy)pyridin-2-yl]-1H-pyrrol-3-yl}carbonyl)amino]acetic acid

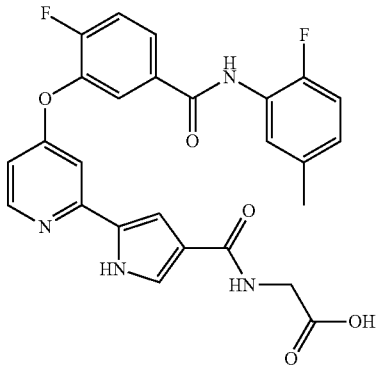 [SMILES: Cc1ccc(F)c(NC(=O)c2ccc(F)c(Oc3ccnc(-c4cc(C(=O)NCC(=O)O)c[nH]4)c3)c2)c1]

To a stirred solution of methyl [({5-[4-(2-fluoro-5-{[(2-fluoro-5-methylphenyl)amino]carbonyl}phenoxy)pyridin-2-yl]-1H-pyrrol-3-yl}carbonyl)amino]acetate (110 mg, 0.2 mmol) in a mixture of solvents THF/MeOH (5 ml/5 ml) was added 1M NaOH solution (1 ml, 1 mmol). The mixture was stirred at room temperature for 1 hour, and poured into 100 ml of water. 2M HCl was added until pH=4. The precipitates were filtered, washed with water and dried in vacuo to give [({5-[4-(2-fluoro-5-{[(2-fluoro-5-methylphenyl)amino]carbonyl}phenoxy)pyridin-2-yl]-1H-pyrrol-3-yl}carbonyl)amino]acetic acid as white solid. Yield: 100 mg, 93%.

$^1$H NMR (DMSO-$d_6$): 12.41 (br. s., 1H), 11.87 (br. s., 1H), 10.12 (s, 1H), 8.42 (d, J=5.6 Hz, 1H), 8.19 (t, J=6.0 Hz, 1H), 7.95-8.04 (m, 2H), 7.63 (dd, J=10.1, 8.7 Hz, 1H), 7.41 (dd, J=3.1, 1.6 Hz, 1H), 7.35 (dd, J=7.3, 1.8 Hz, 1H), 7.27 (d, J=2.3 Hz, 1H), 7.09-7.18 (m, 2H), 7.04 (td, J=5.3, 2.3 Hz, 1H), 6.81 (dd, J=5.9, 2.3 Hz, 1H), 3.82 (d, J=5.9 Hz, 2H), 2.27 (s, 3H)

LR MS (ES−): 505 (M−H)

Example 2 methyl [({5-[4-(2-fluoro-5-{[(2-fluoro-5-methylphenyl)amino]carbonyl}phenoxy)pyridin-2-yl]-1H-pyrrol-3-yl}carbonyl)amino]acetate

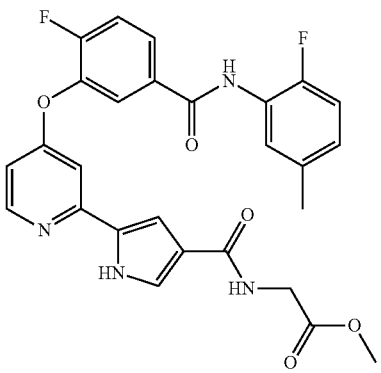 [SMILES: COC(=O)CNC(=O)c1c[nH]c(-c2cc(Oc3cc(C(=O)Nc4cc(C)ccc4F)ccc3F)ccn2)c1]

Similar procedure as Example 1.

$^1$H NMR (DMSO-$d_6$): 11.95 (br. s., 1H), 10.12 (s, 1H), 8.44 (d, J=5.9 Hz, 1H), 8.33 (t, J=5.9 Hz, 1H), 7.97-8.03 (m, 2H), 7.61-7.67 (m, 1H), 7.45 (br. s., 1H), 7.33-7.37 (m, 1H), 7.30 (s, 1H), 7.18 (br. s., 1H), 7.14 (dd, J=10.3, 8.5 Hz, 1H), 7.02-7.08 (m, 1H), 6.86 (br. s., 1H), 3.91 (d, J=5.9 Hz, 2H), 3.61 (s, 3H), 2.27 (s, 3H)

LR MS (ES+): 521 (MH), 543 (M+Na$^+$)

LR MS (ES−): 519 (M−H)

Preparation of 4-(3-Aminophenoxy)-2-chloropyridine

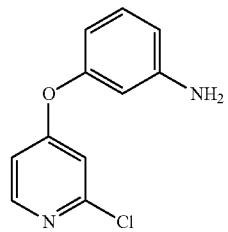 [SMILES: Nc1cccc(Oc2ccnc(Cl)c2)c1]

To a mixture of 3-aminophenol (3.7 g, 34.09 mmol) in DMSO (50 mL) was added Cs2CO3 (30.7 g, 94.46 mmol). The mixture stirred for 10 minutes and then 2,4-dichloropyridine (5.0 g, 33.79 mmol) was added. The mixture was stirred at 120° C. for 1.5 h. The mixture was cooled and diluted with water. The aqueous solution was extracted with EtOAc (3×100 mL). The organic extracts were combined, dried over MgSO4 and concentrated to afford a dark oil. The oil was purified via column chromatography, eluting with 30-40% EtOAc/hexanes, to afford 4-(3-Aminophenoxy)-2-chloropyridine (6.63 g, 89%) as a brown solid.

Preparation of methyl 5-[4-(3-aminophenoxy)pyridin-2-yl]-1H-pyrrole-3-carboxylate

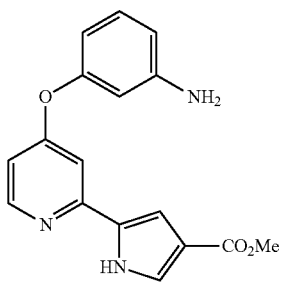 [SMILES: COC(=O)c1c[nH]c(-c2cc(Oc3cccc(N)c3)ccn2)c1]

A mixture of 4-(3-aminophenoxy)-2-chloropyridine (4.0 g, 18.13 mmol), methyl-(5-(4,4,5,5-tetramethyl-1,3,2-dioxaborolan-2-yl)-1H-pyrrole-3-carboxylate (6.82 g, 27.16 mmol) and Pd(PPh3)$_4$ (4.20 g, 3.63 mmol) was added to a thick walled reaction vessel and purged with N2. A solution of 2M K2CO3 (13.59 mL) was added, followed by DME (70 mL). The reaction vessel was sealed and the mixture stirred at 92° C. for 18 h. The reaction vessel was cooled to room temperature and the mixture was filtered over celite, washing with EtOAc. The filtrate was concentrated and the resultant dark oil was purified via column chromatography, eluting with 40-80% EtOAc/hexanes to afford methyl 5-[4-(3-aminophenoxy)pyridin-2-yl]-1H-pyrrole-3-carboxylate (2.85 g, 51% yield).

Example 3

({[5-(4-{3-[(3-methyl-2-furoyl)amino]phenoxy}pyridin-2-yl)-1H-pyrrol-3-yl]carbonyl}amino)acetic acid

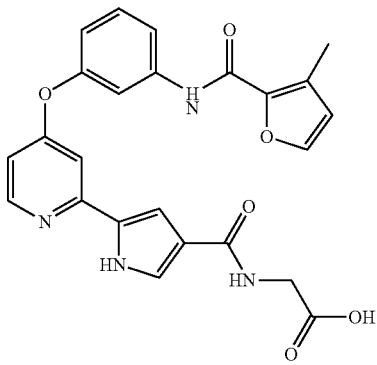 [SMILES: Cc1ccoc1C(=O)Nc1cccc(Oc2ccnc(-c3cc(C(=O)NCC(=O)O)c[nH]3)c2)c1]

Similar procedure as Example 1.

¹H NMR (DMSO-d₆): 12.42 (br. s., 1H), 11.91 (br. s., 1H), 10.20 (s, 1H), 8.41 (d, J=5.6 Hz, 1H), 8.21 (t, J=5.4 Hz, 1H), 7.76 (s, 1H), 7.65-7.73 (m, 2H), 7.36-7.47 (m, 2H), 7.26 (br. s., 1H), 7.12 (br. s., 1H), 6.86-6.98 (m, 1H), 6.77 (br. s., 1H), 6.56 (s, 1H), 3.81 (d, J=5.9 Hz, 2H), 2.29 (s, 3H)

LR MS (ES−): 459 (M−H)

Example 4 methyl ({[5-(4-{3-[(3-methyl-2-furoyl)amino]phenoxy}pyridin-2-yl)-1H-pyrrol-3-yl]carbonyl}amino)acetate

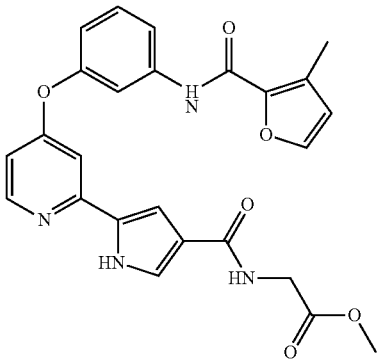 [SMILES: COC(=O)CNC(=O)c1c[nH]c(-c2cc(Oc3cccc(NC(=O)c4occc4C)c3)ccn2)c1]

Similar procedure as Example 3.

¹H NMR (DMSO-d₆): 11.88 (br. s., 1H), 10.19 (s, 1H), 8.40 (d, J=5.6 Hz, 1H), 8.32 (t, J=5.6 Hz, 1H), 7.76 (s, 1H), 7.65-7.72 (m, 2H), 7.36-7.44 (m, 2H), 7.23 (d, J=2.1 Hz, 1H), 7.08 (br. s., 1H), 6.90 (d, J=7.3 Hz, 1H), 6.75 (dd, J=5.6, 1.8 Hz, 1H), 6.56 (s, 1H), 3.89 (d, J=5.6 Hz, 2H), 3.60 (s, 3H), 2.29 (s, 3H)

LR MS (ES+): 475 (MH), 497 (M+Na⁺)
LR MS (ES−): 473 (M−H)

Preparation of 2-Chloro-N-(3-nitrophenyl)pyridine-4-amine

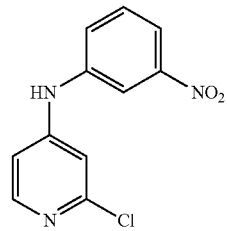 [SMILES: O=[N+]([O-])c1cccc(Nc2ccnc(Cl)c2)c1]

To a degassed (15 min, N₂) suspension of 2-chloro-4-iodopyridine (3.0 g, 12.53 mmol), 3-nitroaniline (1.82 g, 13.18 mmol), BINAP (0.39 g, 0.626 mmol) and Cs₂CO₃ (8.16 g, 25.04 mmol) in toluene (72 mL) was added Pd(OAc)₂ (0.084 g, 0.374 mmol). The reaction tube was sealed and the mixture stirred at 90° C. for 18 h. The mixture was cooled to rt and filtered, washing with EtOAc. The orange/yellow solid collected was washed with CH₂Cl₂ until all the product washed through into the filtrate. The filtrate was concentrated to afford 2-Chloro-N-(3-nitrophenyl)pyridine-4-amine as a bright yellow solid. Additional product was collected from the solid collected upon concentration of the previous filtrate, after washing with CH₂Cl₂. No further purification. Total amount of product collected was 2.85 g (91% yield).

Preparation of tert-Butyl 2-chloropyridin-4-yl(3-nitrophenyl)carbamate

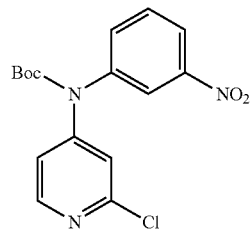 [SMILES: CC(C)(C)OC(=O)N(c1cccc([N+](=O)[O-])c1)c1ccnc(Cl)c1]

To a stirring solution of 2-Chloro-N-(3-nitrophenyl)pyridine-4-amine (2.70 g, 10.82 mmol) in THF (45 mL) was added Et₃N (6.32 mL, 45.3 mmol). The mixture was cooled to 0° C., and DMAP (0.0135 g, 0.110 mmol) and BOC₂O (2.84 g, 12.99 mmol) were added. The mixture was warmed to rt and stirred for 18 h. The mixture was quenched with ice and diluted with water. Extracted with EtOAc (3×200 mL), washed with brine and water, dried (MgSO₄), and concentrated. A dark oil was afforded, which was passed through a pad of silica gel, eluting with 1:1 EtOAc/hexanes. Concentrated and dried under high vacuum to afford tert-Butyl 2-chloropyridin-4-yl(3-nitrophenyl)carbamate (3.65 g, 96.5% yield).

Preparation of methyl 5-(4-(tert-butoxycarbonyl(3-nitrophenyl)amino)pyridine-2-yl)-1H-pyrrole-3-carboxylate

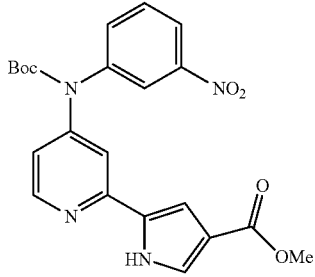 [SMILES: COC(=O)c1c[nH]c(-c2cc(N(C(=O)OC(C)(C)C)c3cccc([N+](=O)[O-])c3)ccn2)c1]

A mixture of tert-Butyl 2-chloropyridin-4-yl(3-nitrophenyl)carbamate (3.65 g, 10.43 mmol), methyl-(5-(4,4,5,5-tetramethyl-1,3,2-dioxaborolan-2-yl)-1H-pyrrole-3-carboxylate (5.48 g, 21.82 mmol), xantphos (0.72 g, 1.25 mmol) and Pd$_2$dba$_3$ (0.72 g, 0.79 mmol) was added to a thick walled reaction vessel and purged with N$_2$. A solution of 2M K$_2$CO$_3$ (8.76 mL) was added, followed by dioxane (67 mL). The reaction vessel was sealed and the mixture stirred at 105° C. for 18 h. The reaction vessel was cooled to rt and the mixture was filtered over celite, washing with EtOAc. The filtrate was concentrated to afford a dark oil, which was purified via column chromatography eluting with 30-50% EtOAc/hexanes to afford methyl 5-(4-(tert-butoxycarbonyl(3-nitrophenyl)amino)pyridine-2-yl)-1H-pyrrole-3-carboxylate (2.98 g, 65% yield) as an orange oil.

Preparation of methyl 5-(4-((3-nitrophenyl)amino)pyridin-2-yl)-1H-pyrrole-3-carboxylate

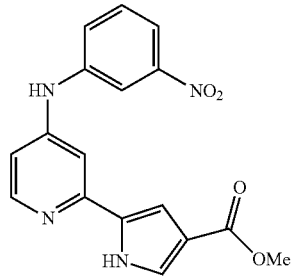 [SMILES: COC(=O)c1c[nH]c(-c2cc(Nc3cccc([N+](=O)[O-])c3)ccn2)c1]

Methyl 5-(4-(tert-butoxycarbonyl(3-nitrophenyl)amino)pyridine-2-yl)-1H-pyrrole-3-carboxylate (0.40 g, 0.91 mmol) was taken up in toluene (38 mL) and SiO$_2$ (9.0 g) was added. The mixture stirred at reflux for 20 h. The mixture was cooled to rt and filtered over celite, washing with EtOAc. The filtrate was concentrated to a bright orange color. The solid was taken up in hexanes and filtered. The solid was then washed with CH$_2$Cl$_2$/hexanes to afford methyl 5-(4-((3-nitrophenyl)amino)pyridin-2-yl)-1H-pyrrole-3-carboxylate (0.15 g, 49% yield) as a bright yellow solid.

Preparation of methyl 5-(4-((3-aminophenyl)amino)pyridin-2-yl)-1H-pyrrole-3-carboxylate

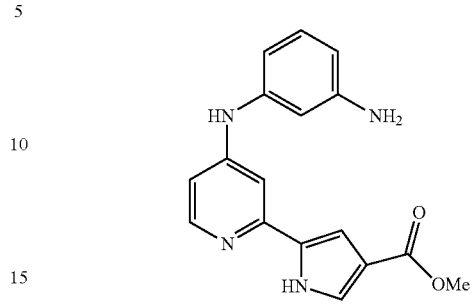

Methyl 5-(4-((3-nitrophenyl)amino)pyridin-2-yl)-1H-pyrrole-3-carboxylate (1.32 g, 3.9 mmol) was taken up in EtOAc/EtOH (1:1; 90 mL) and purged with N$_2$. Pd/C (10%, 0.145 g) was added and the mixture was stirred under an atmosphere of H$_2$ at rt for 18 h. The mixture was filtered over celite, washing with EtOAc/EtOH. The filtrate was concentrated, taken back up in EtOAc and filtered over celite again to remove any residual catalyst. The filtrate was concentrated again and taken back up in EtOAc. The solution was filtered and the filtrate was concentrated to afford a tan solid. The solid was washed with CH$_2$Cl$_2$/hexanes (1:2) and dried under high vacuum to afford methyl 5-(4-((3-aminophenyl)amino)pyridin-2-yl)-1H-pyrrole-3-carboxylate (1.15 g, 96% yield) as a tan solid.

Example 5

5-[4-({3-[(3-methyl-2-furoyl)amino]phenyl}amino)pyridin-2-yl]-1H-pyrrole-3-carboxylic acid

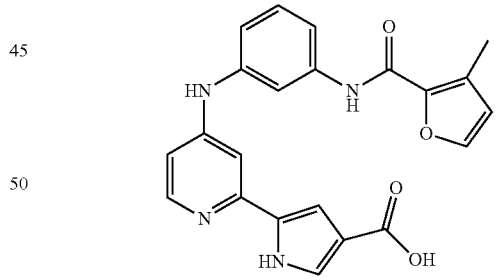

To a stirred solution of methyl 5-[4-({3-[(3-methyl-2-furoyl)amino]phenyl}amino)pyridin-2-yl]-1H-pyrrole-3-carboxylate (10 mg, 0.024 mmol) in a mixture of solvents THF/MeOH (5 ml/5 ml) was added 2 ml of 1M NaOH (2 mmol) solution. The mixture was heated in a 60° C. bath for 16 hours, cooled to room temperature and poured into 100 ml of water. 2M HCl was added until pH=5. The resulting precipitates were filtered, washed with water, and dried in vacuo to give 5-[4-({3-[(3-methyl-2-furoyl)amino]phenyl}amino)pyridin-2-yl]-1H-pyrrole-3-carboxylic acid as light brown solid. Yield: 2 mg.

Example 6 methyl 5-[4-({3-[(3-methyl-2-furoyl)amino]phenyl}amino)pyridin-2-yl]-1H-pyrrole-3-carboxylate

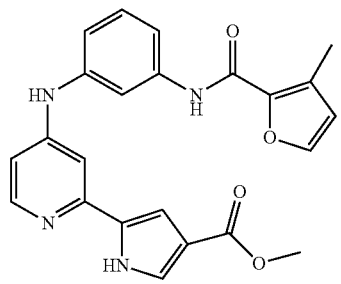 [SMILES: COC(=O)c1c[nH]c(-c2cc(Nc3cccc(NC(=O)c4occc4C)c3)ccn2)c1]

A mixture of 3-methyl-2-furoic acid (22 mg, 0.18 mmol), HATU (73 mg, 0.19 mmol) and N,N-diisopropylethylamine (45 mg, 0.35 mmol) in anhydrous DMF (10 ml) was stirred at room temperature for 10 minutes, followed by addition of methyl 5-(4-((3-aminophenyl)amino)pyridin-2-yl)-1H-pyrrole-3-carboxylate (50 mg, 0.16 mmol). The mixture was stirred at room temperature for 3 hours and poured into 100 ml of water. The precipitates were filtered, washed with water and dried in vacuo to give methyl 5-[4-({3-[(3-methyl-2-furoyl)amino]phenyl}amino)pyridin-2-yl]-1H-pyrrole-3-carboxylate as off-white solid. Yield: 10 mg, 15%.

$^1$H NMR (DMSO-$d_6$): 13.60 (br. s., 1H), 12.37 (br. s., 1H), 10.14 (s, 1H), 8.15 (d, J=6.5 Hz, 1H), 7.86 (t, J=1.9 Hz, 1H), 7.77 (d, J=1.8 Hz, 1H), 7.58 (br. s., 1H), 7.52 (d, J=7.6 Hz, 1H), 7.32-7.38 (m, 2H), 7.22 (br. s., 1H), 6.97 (d, J=7.6 Hz, 1H), 6.86 (dd, J=6.2, 2.1 Hz, 1H), 6.57 (d, J=1.8 Hz, 1H), 3.71 (s, 3H), 2.32 (s, 3H)

LR MS (ES+): 417 (MH)
LR MS (ES−): 415 (M−H)

Example 7

5-[4-(2-fluoro-5-{[(2-fluoro-5-methylphenyl)amino]carbonyl}phenoxy)pyridin-2-yl]-N-hydroxy-1H-pyrrole-3-carboxamide

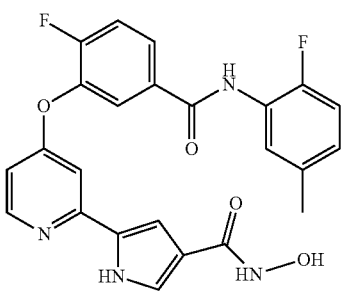 [SMILES: Cc1ccc(F)c(NC(=O)c2ccc(F)c(Oc3ccnc(-c4cc(C(=O)NO)c[nH]4)c3)c2)c1]

Similar procedure as Example 1.

$^1$H NMR (DMSO-$d_6$): 11.85 (br. s., 1H), 10.56 (br. s., 1H), 10.12 (s, 1H), 8.66 (br. s., 1H), 8.41 (d, J=5.6 Hz, 1H), 7.99 (d, J=7.3 Hz, 2H), 7.63 (t, J=9.4 Hz, 1H), 7.30-7.40 (m, 2H), 7.27 (br. s., 1H), 7.10-7.18 (m, 1H), 7.01-7.10 (m, 2H), 6.75-6.85 (m, 1H), 2.26 (s, 3H)

LR MS (ES+): 487 (M+Na$^+$)
LR MS (ES−): 463 (M−H)

Example 8

4-fluoro-N-(2-fluoro-5-methylphenyl)-3-[(2-{4-[(3-hydroxypiperidin-1-yl)carbonyl]-1H-pyrrol-2-yl}pyridin-4-yl)oxy]benzamide

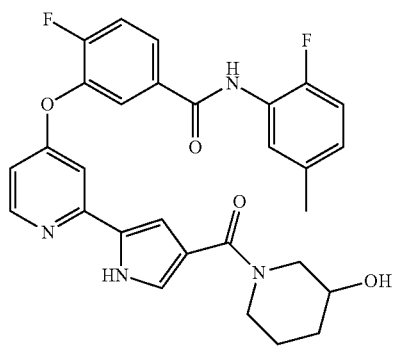 [SMILES: Cc1ccc(F)c(NC(=O)c2ccc(F)c(Oc3ccnc(-c4cc(C(=O)N5CCCC(O)C5)c[nH]4)c3)c2)c1]

Similar procedure as Example 1.

LR MS (ES+): 533 (MH), 555 (M+Na$^+$)
LR MS (ES−): 531 (M−H)

Example 9

N-(2,3-dihydroxypropyl)-5-[4-(3-{[(2-fluoro-5-methylphenyl)amino]carbonyl}phenoxy)pyridin-2-yl]-1H-pyrrole-3-carboxamide

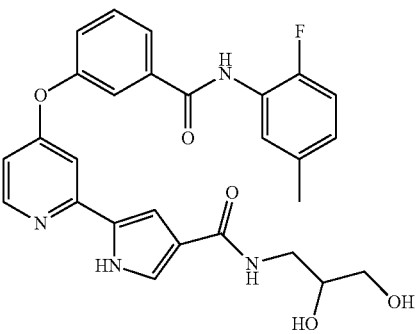 [SMILES: Cc1ccc(F)c(NC(=O)c2cccc(Oc3ccnc(-c4cc(C(=O)NCC(O)CO)c[nH]4)c3)c2)c1]

Similar procedure as Example 1.

$^1$H NMR (DMSO-$d_6$): 11.83 (br. s., 1H), 10.11 (s, 1H), 8.41 (d, J=5.6 Hz, 1H), 7.89 (d, J=7.0 Hz, 1H), 7.83 (t, J=5.6 Hz, 1H), 7.77 (s, 1H), 7.63 (t, J=7.9 Hz, 1H), 7.42-7.46 (m, 1H), 7.39 (d, J=1.5 Hz, 1H), 7.35 (d, J=7.3 Hz, 1H), 7.25 (d, J=2.1 Hz, 1H), 7.09-7.16 (m, 2H), 7.02-7.06 (m, 1H), 6.76 (dd, J=5.7, 2.5 Hz, 1H), 4.77 (d, J=5.0 Hz, 1H), 4.53 (t, J=6.0 Hz, 1H), 3.50-3.56 (m, 1H), 3.25-3.30 (m, 3H), 3.08-3.14 (m, 1H), 2.27 (s, 3H)

LR MS (ES+): 505 (MH), 527 (M+Na$^+$)
LR MS (ES−): 503 (M−H)

Example 10

N-(2-fluoro-5-methylphenyl)-3-[(2-{4-[(3-hydroxy-pyrrolidin-1-yl)carbonyl]-1H-pyrrol-2-yl}pyridin-4-yl)oxy]benzamide

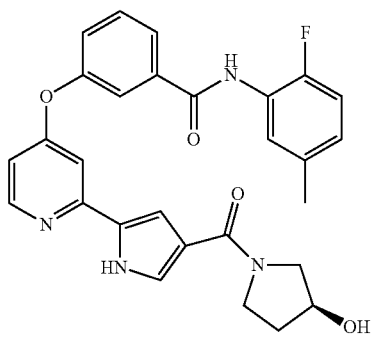 [SMILES: Cc1ccc(F)c(NC(=O)c2cccc(Oc3ccnc(-c4cc(C(=O)N5CC[C@H](O)C5)c[nH]4)c3)c2)c1]

A mixture of 5-{4-[3-(2-Fluoro-5-methyl-phenylcarbamoyl)-phenoxy]-pyridin-2-yl}-1H-pyrrole-3-carboxylic acid (50 mg, 0.12 mmol), HATU (55 mg, 0.14 mmol) and N,N-diisopropylethylamine (34 mg, 0.26 mmol) in anhydrous DMF (8 ml) was stirred at room temperature for 10 minutes, followed by addition of (S)-3-pyrrolidinol (16 mg, 0.18 mmol). The mixture was stirred for another 10 minutes and poured into 100 ml of water. The precipitates were filtered, washed with water and dried in vacuo to give N-(2-fluoro-5-methylphenyl)-3-[(2-{4-[(3-hydroxypyrrolidin-1-yl)carbonyl]-1H-pyrrol-2-yl}pyridin-4-yl)oxy]benzamide as white solid. Yield: 40 mg, 69%.

$^1$H NMR (DMSO-d$_6$): 11.91 (br. s., 1H), 10.12 (s, 1H), 8.42 (d, J=5.6 Hz, 1H), 7.89 (d, J=7.6 Hz, 1H), 7.76 (s, 1H), 7.63 (t, J=7.9 Hz, 1H), 7.32-7.51 (m, 3H), 7.26 (d, J=6.7 Hz, 1H), 6.99-7.20 (m, 3H), 6.73 (dd, 1H), 4.91 (br. s., 1H), 4.30 (br. s., 1H), 3.76 (br. s., 2H), 3.50 (br. s., 2H), 2.28 (s, 3H), 1.86 (br. s., 2H)

LR MS (ES+): 501 (MH), 523 (M+Na$^+$)
LR MS (ES−): 499 (M−H)

Example 11

5-[4-(3-{[(2-fluoro-5-methylphenyl)amino]carbonyl}phenoxy)pyridin-2-yl]-N-hydroxy-1H-pyrrole-3-carboxamide

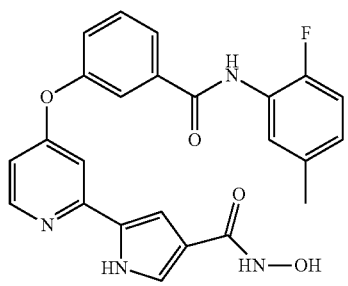 [SMILES: Cc1ccc(F)c(NC(=O)c2cccc(Oc3ccnc(-c4cc(C(=O)NO)c[nH]4)c3)c2)c1]

Similar procedure as Example 10.

$^1$H NMR (DMSO-d$_6$): 11.84 (br. s., 1H), 10.56 (br. s., 1H), 10.10 (s, 1H), 8.65 (br. s., 1H), 8.40 (d, J=5.6 Hz, 1H), 7.89 (d, J=7.6 Hz, 1H), 7.76 (br. s., 1H), 7.63 (t, J=7.9 Hz, 1H), 7.44 (dd, J=7.9, 1.5 Hz, 1H), 7.35 (d, J=6.7 Hz, 1H), 7.31 (br. s., 1H), 7.25 (d, J=1.8 Hz, 1H), 7.13 (dd, J=10.3, 8.5 Hz, 1H), 7.01-7.07 (m, 2H), 6.75 (dd, J=5.7, 2.2 Hz, 1H), 2.27 (s, 3H)

LR MS (ES+): 469 (M+Na$^+$)
LR MS (ES−): 445 (M−H)

Preparation of
3-(2-Chloropyridin-4-yloxy)-4-fluorobenzoic acid methyl ester

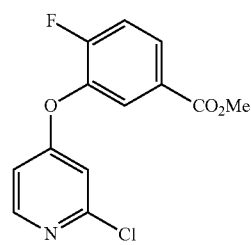 [SMILES: COC(=O)c1ccc(F)c(Oc2ccnc(Cl)c2)c1]

4-Fluoro-3-hydroxybenzoic acid methyl ester (1.70 g, 10.0 mmol) was dissolved in dimethylformamide (9 mL) under nitrogen at room temperature. Sodium hydride (60% oil dispersion, 0.48 g, 12 mmol) was added in portions over 30 min. The reaction was stirred for 90 minutes and then cooled in an ice bath. 2-Chloro-4-nitropyridine (1.58 g, 10.0 mmol) was added in small portions over 50 min. The reaction was stirred at room temperature for 17.5 h. Water (200 ml) was added and the mixture stirred until a brown lump formed. The water was decanted and the residue dissolved in EtOAc (150 mL). The solution was washed with brine, dried (MgSO$_4$), filtered and evaporated to give 3-(2-Chloropyridin-4-yloxy)-4-fluorobenzoic acid methyl ester. Yield: 3.10 g.

Preparation of
3-(2-Chloropyridin-4-yloxy)-4-fluorobenzoic acid

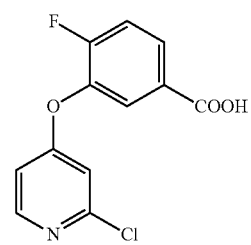 [SMILES: O=C(O)c1ccc(F)c(Oc2ccnc(Cl)c2)c1]

3-(2-Chloropyridin-4-yloxy)-4-fluorobenzoic acid methyl ester (2.81 g, 10.0 mmol) was dissolved in tetrahydrofuran (15 mL) and mixed with 2M lithium hydroxide (15 mL, 30 mmol). The suspension was stirred for 5 h. To the reaction was added water, then extracted with EtOAc. The aqueous layer was treated with 6M HCl (5 mL, 30 mmol) and then extracted with EtOAc (3×25 mL). The extract was dried (MgSO$_4$), filtered and evaporated to 3-(2-Chloropyridin-4-yloxy)-4-fluorobenzoic acid. Yield: 2.22 g, 83%.

Preparation of 3-(2-Chloropyridin-4-yloxy)-4-fluoro-N-(2-fluoro-5-methylphenyl)benzamide

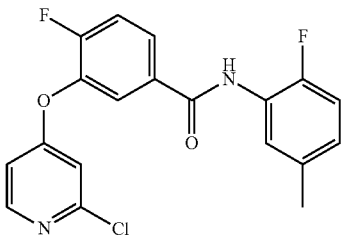 [SMILES: Cc1ccc(F)c(NC(=O)c2ccc(F)c(Oc3ccnc(Cl)c3)c2)c1]

A solution of 3-(2-Chloropyridin-4-yloxy)-4-fluorobenzoic acid (2.22 g, 8.29 mmol), 2-fluoro-5-methylaniline (1.56 g, 12.4 mmol), O-(7-azabenzotriazol-1-yl)-N,N,N',N'-tetramethyluronium hexafluorophosphate (HATU, 3.78 g, 9.95 mmol) and N-methylmorpholine (2.00 mL, 18.2 mmol) in dimethylformamide (22 mL) was heated at 90° C. for 2 h. The solvent was evaporated in vacuo at 50° C. To the residue was added water resulting in a thick oil. The water was decanted and the oil dissolved in EtOAc then extracted twice with water, 1M hydrochloric acid and brine. The organic layer was dried (MgSO$_4$), filtered and evaporated to crude 6 (3.37 g). Trituration with dichloromethane (25 mL) gave 3-(2-Chloropyridin-4-yloxy)-4-fluoro-N-(2-fluoro-5-methylphenyl)benzamide as white solid. Yield: 1.788 g, 58%.

Example 12 methyl 5-[4-(2-fluoro-5-{[(2-fluoro-5-methylphenyl)amino]carbonyl}phenoxy)pyridin-2-yl]-1H-pyrrole-3-carboxylate

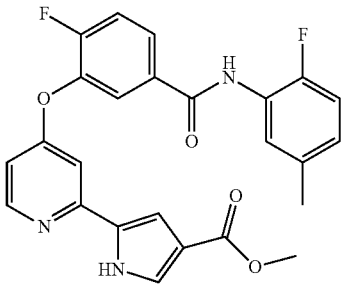 [SMILES: COC(=O)c1c[nH]c(-c2cc(Oc3cc(C(=O)Nc4cc(C)ccc4F)ccc3F)ccn2)c1]

A mixture of 3-(2-Chloropyridin-4-yloxy)-4-fluoro-N-(2-fluoro-5-methylphenyl)benzamide (1.217 g, 3.25 mmol), methyl 5-(4,4,5,5-tetramethyl-1,3,2-dioxaborolan-2-yl)-1H-pyrrole-3-carboxylate (1.63 g, 6.50 mmol) and potassium carbonate (0.67 g, 4.87 mmol) in water (2.5 mL) and dioxane (15 mL) was purged with nitrogen for several minutes. To the mixture was added tetrakis-triphenylphosphine palladium(0) (0.18 g, (0.16 mmol). The reaction was sealed under nitrogen and heated at 100° C. for 15 h. The cooled reaction was mixed with dichloromethane and filtered through Celite. The red solution was evaporated. The resulting oil was dissolved in dichloromethane, put on a column of silica gel (80 g) and eluted with hexane/EtOAc (1:1) to afford methyl 5-[4-(2-fluoro-5-{[(2-fluoro-5-methylphenyl)amino]carbonyl}phenoxy)pyridin-2-yl]-1H-pyrrole-3-carboxylate as white solid. Yield: 1.162 g, 77%.

Example 13

5-[4-(2-fluoro-5-{[(2-fluoro-5-methylphenyl)amino]carbonyl}phenoxy)pyridin-2-yl]-1H-pyrrole-3-carboxylic acid

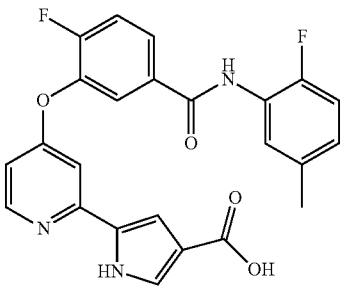 [SMILES: Cc1ccc(F)c(NC(=O)c2ccc(F)c(Oc3ccnc(-c4cc(C(=O)O)c[nH]4)c3)c2)c1]

Similar procedure as Example 12.
$^1$H NMR (DMSO-d$_6$): 12.03 (br. s., 1H), 11.85 (br. s., 1H), 10.11 (s, 1H), 8.42 (d, J=5.6 Hz, 1H), 7.98 (d, J=6.2 Hz, 2H), 7.62 (t, J=9.4 Hz, 1H), 7.43 (br. s., 1H), 7.30-7.39 (m, 2H), 7.08-7.19 (m, 2H), 7.04 (br. s., 1H), 6.79 (d, J=3.2 Hz, 1H), 2.26 (s, 3H)
LR MS (ES−): 448 (M−H)

Example 14

N-ethyl-5-(4-{3-[(3-methyl-2-furoyl)amino]phenoxy}pyridin-2-yl)-1H-pyrrole-3-carboxamide

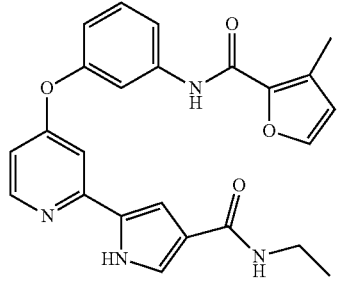 [SMILES: CCNC(=O)c1c[nH]c(-c2cc(Oc3cccc(NC(=O)c4occc4C)c3)ccn2)c1]

Similar procedure as Example 31.
LR MS (ES+): 453 (M+Na$^+$)

Example 15

N-(2,3-dihydroxypropyl)-5-(4-{3-[(3-methyl-2-furoyl)amino]phenoxy}pyridin-2-yl)-1H-pyrrole-3-carboxamide

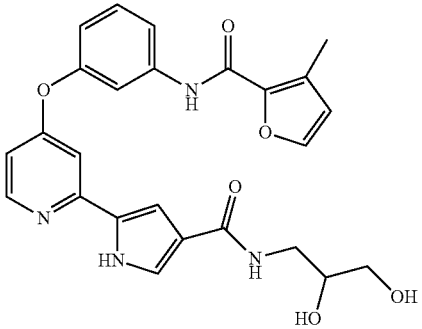

Similar procedure as Example 31.

$^1$H NMR (DMSO-d$_6$): 11.83 (br. s., 1H), 10.21 (s, 1H), 8.40 (d, J=5.9 Hz, 1H), 7.85 (t, J=6.0 Hz, 1H), 7.78 (s, 1H), 7.63-7.74 (m, 2H), 7.35-7.48 (m, 2H), 7.23 (d, J=2.1 Hz, 1H), 7.10 (s, 1H), 6.85-6.96 (m, 1H), 6.75 (dd, J=5.7, 2.2 Hz, 1H), 6.57 (s, 1H), 4.78 (d, J=4.7 Hz, 1H), 4.53 (t, J=5.9 Hz, 1H), 3.48-3.61 (m, 1H), 3.24-3.33 (m, 3H), 3.04-3.19 (m, 1H), 2.30 (s, 3H)

LR MS (ES+): 499 (M+Na$^+$)
LR MS (ES−): 475 (M−H)

Example 16

5-(4-{3-[(3-methyl-2-furoyl)amino]phenoxy}pyridin-2-yl)-1H-pyrrole-3-carboxamide

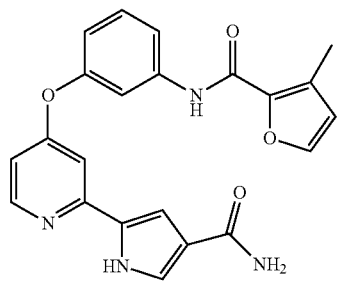 [SMILES: Cc1ccoc1C(=O)Nc1cccc(Oc2ccnc(-c3cc(C(N)=O)c[nH]3)c2)c1]

Similar procedure as Example 31.

$^1$H NMR (DMSO-d$_6$): 11.83 (br. s., 1H), 10.21 (s, 1H), 8.40 (d, J=5.9 Hz, 1H), 7.77 (s, 1H), 7.65-7.74 (m, 2H), 7.31-7.48 (m, 3H), 7.23 (d, J=1.2 Hz, 1H), 7.07 (br. s., 1H), 6.86-6.95 (m, 1H), 6.75 (d, J=3.5 Hz, 2H), 6.57 (s, 1H), 2.30 (s, 3H)

LR MS (ES−): 401 (M−H)

Example 17

N-hydroxy-5-(4-{3-[(3-methyl-2-furoyl)amino]phenoxy}pyridin-2-yl)-1H-pyrrole-3-carboxamide

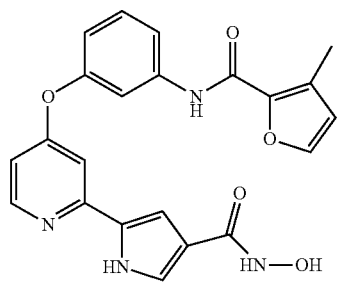 [SMILES: Cc1ccoc1C(=O)Nc1cccc(Oc2ccnc(-c3cc(C(=O)NO)c[nH]3)c2)c1]

Similar procedure as Example 31.

$^1$H NMR (DMSO-d$_6$): 11.84 (br. s., 1H), 10.49-10.64 (m, 1H), 10.20 (s, 1H), 8.60-8.74 (m, 1H), 8.39 (d, J=5.9 Hz, 1H), 7.65-7.81 (m, 3H), 7.41 (t, J=7.9 Hz, 1H), 7.32 (br. s., 1H), 7.23 (s, 1H), 7.02 (br. s., 1H), 6.85-6.94 (m, 1H), 6.69-6.78 (m, 1H), 6.57 (s, 1H), 2.30 (s, 3H)

LR MS (ES−): 417 (M−H)

Example 18

N-(3-{[2-(4-{[(3R)-3-hydroxypyrrolidin-1-yl]carbonyl}-1H-pyrrol-2-yl)pyridin-4-yl]oxy}phenyl)-3-methyl-2-furamide

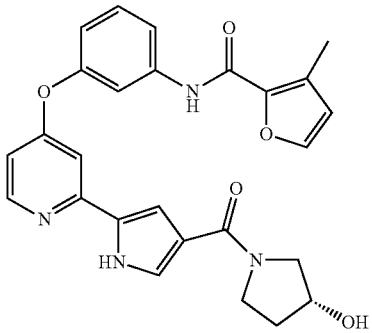 [SMILES: Cc1ccoc1C(=O)Nc1cccc(Oc2ccnc(-c3cc(C(=O)N4CC[C@@H](O)C4)c[nH]3)c2)c1]

Similar procedure as Example 31.

$^1$H NMR (DMSO-d$_6$): 11.90 (br. s., 1H), 10.20 (s, 1H), 8.40 (d, J=5.6 Hz, 1H), 7.77 (d, J=1.5 Hz, 1H), 7.64-7.73 (m, 2H), 7.36-7.46 (m, 2H), 7.21-7.30 (m, 1H), 7.03-7.13 (m, 1H), 6.85-6.93 (m, 1H), 6.70 (dd, J=5.7, 2.2 Hz, 1H), 6.57 (d, J=1.5 Hz, 1H), 4.90 (br. s., 1H), 4.30 (m, 1H), 3.76 (m, 1H), 3.49 (m, 2H), 2.30 (s, 3H), 1.86 (m, 2H)

LR MS (ES−): 471 (M−H)

Example 19

5-{4-[3-(2-Fluoro-5-methyl-phenylcarbamoyl)-phenoxy]-pyridin-2-yl}-1H-pyrrole-3-carboxylic acid

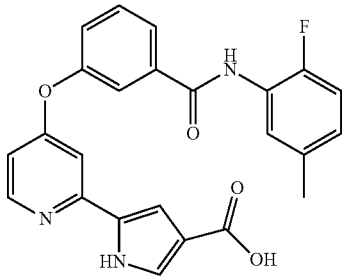 [SMILES: Cc1ccc(F)c(NC(=O)c2cccc(Oc3ccnc(-c4cc(C(=O)O)c[nH]4)c3)c2)c1]

To a stirred solution of 5-{4-[3-(2-Fluoro-5-methyl-phenylcarbamoyl)-phenoxy]-pyridin-2-yl}-1H-pyrrole-3-carboxylic acid methyl ester (140 mg, 0.31 mmol) in THF (8 ml) was added 5M NaOH solution (1 ml, 5 mmol). The mixture was heated at 70° C. for 3 hours, cooled to room temp, and poured into 100 ml of water. 2M HCl was added until pH=4. The precipitates were filtered, washed with water, and dried to give 5-{4-[3-(2-Fluoro-5-methyl-phenylcarbamoyl)-phenoxy]-pyridin-2-yl}-1H-pyrrole-3-carboxylic acid as white solid. Yield: 120 mg, 92%.

$^1$H NMR (d$_6$-DMSO): 12.03 (br. s., 1H), 11.89 (br. s., 1H), 10.11 (s, 1H), 8.42 (d, J=5.6 Hz, 1H), 7.89 (d, J=7.3 Hz, 1H), 7.77 (s, 1H), 7.56-7.71 (m, 1H), 7.30-7.54 (m, 4H), 6.97-7.23 (m, 3H), 6.75 (dd, J=5.6, 2.1 Hz, 1H), 2.28 (s, 3H)

LR MS (ES+): 454 (M+Na$^+$)
LR MS (ES−): 430 (M−H)

Example 20

5-{4-[3-(2-Fluoro-5-methyl-phenylcarbamoyl)-phenoxy]-pyridin-2-yl}-1H-pyrrole-3-carboxylic acid methyl ester

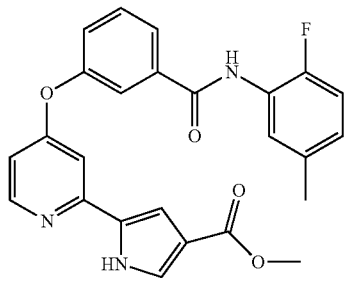 [SMILES: COC(=O)c1c[nH]c(-c2cc(Oc3cccc(C(=O)Nc4cc(C)ccc4F)c3)ccn2)c1]

A mixture of 3-(2-bromo-pyridin-4-yloxy)-N-(2-fluoro-5-methyl-phenyl)-benzamide (200 mg, 0.50 mmol), methyl-(5-(4,4,5,5-tetramethyl-1,3,2-dioxaborolan-2-yl)-1H-pyrrole-3-carboxylate (251 mg, 1.0 mmol) and $PdCl_2(dppf) \cdot CH_2Cl_2$ (10 mg, 0.012 mmol) was added to a thick-walled reaction vessel and purged with $N_2$. A solution of 2M $Na_2CO_3$ (0.5 mL) was added, followed by DMSO (8 mL). The reaction vessel was sealed and the mixture stirred at 95° C. for 16 h. The reaction vessel was cooled to room temperature and the mixture was poured into 100 ml of water. The precipitates were filtered, washed with water and dried to give the crude, which was purified via column chromatography eluting with 30-40% EtOAc/hexanes to afford 5-{4-[3-(2-Fluoro-5-methyl-phenylcarbamoyl)-phenoxy]-pyridin-2-yl}-1H-pyrrole-3-carboxylic acid methyl ester (150 mg, 58% yield).

$^1$H NMR ($d_6$-DMSO): 12.14 (br. s., 1H), 10.11 (s, 1H), 8.43 (d, J=5.6 Hz, 1H), 7.89 (d, J=7.9 Hz, 1H), 7.77 (s, 1H), 7.64 (t, J=7.9 Hz, 1H), 7.41-7.50 (m, 3H), 7.35 (s, 1H), 7.09-7.21 (m, 2H), 7.06 (dd, J=5.1, 1.9 Hz, 1H), 6.76 (dd, J=5.6, 2.3 Hz, 1H), 3.70 (s, 3H), 2.28 (s, 3H)

LR MS (ES+): 468 (M+Na$^+$)

LR MS (ES−): 444 (M−H)

Example 21

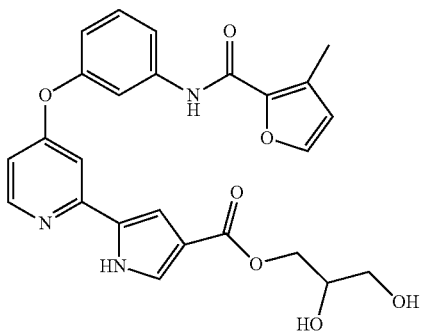 [SMILES: Cc1ccoc1C(=O)Nc1cccc(Oc2ccnc(-c3cc(C(=O)OCC(O)CO)c[nH]3)c2)c1]

Similar procedure as Example 25.

2,3-dihydroxypropyl 5-(4-{3-[(3-methyl-2-furoyl)amino]phenoxy}pyridin-2-yl)-1H-pyrrole-3-carboxylate

Example 22

5-[4-(3-m-Tolylcarbamoyl-phenoxy)-pyridin-2-yl]-1H-pyrrole-3-carboxylic acid

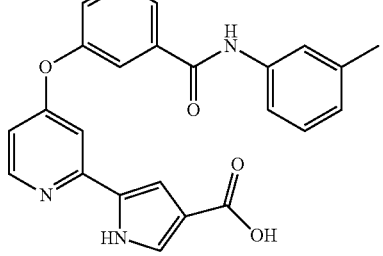

Similar procedure as Example 19.

$^1$H NMR (DMSO-$d_6$): 12.03 (br. s., 1H), 11.86 (br. s., 1H), 10.19 (s, 1H), 8.42 (d, J=5.6 Hz, 1H), 7.88 (d, J=7.9 Hz, 1H), 7.78 (s, 1H), 7.50-7.69 (m, 3H), 7.32-7.46 (m, 3H), 7.21 (t, J=7.8 Hz, 1H), 7.06 (s, 1H), 6.91 (d, J=7.3 Hz, 1H), 6.74 (dd, J=5.6, 2.3 Hz, 1H), 2.28 (s, 3H)

Example 23

5-[4-(3-m-Tolylcarbamoyl-phenoxy)-pyridin-2-yl]-1H-pyrrole-3-carboxylic acid methyl ester

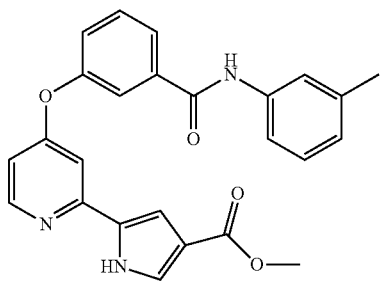 [SMILES: COC(=O)c1c[nH]c(-c2cc(Oc3cccc(C(=O)Nc4cccc(C)c4)c3)ccn2)c1]

Similar procedure as Example 20.

$^1$H NMR (DMSO-$d_6$): 12.14 (br. s., 1H), 10.18 (s, 1H), 8.43 (d, J=5.6 Hz, 1H), 7.89 (d, J=7.9 Hz, 1H), 7.78 (s, 1H), 7.50-7.68 (m, 3H), 7.38-7.48 (m, 3H), 7.21 (t, J=7.8 Hz, 1H), 7.12 (s, 1H), 6.91 (d, J=7.6 Hz, 1H), 6.75 (dd, J=5.7, 2.2 Hz, 1H), 3.70 (s, 3H), 2.28 (s, 3H)

LR MS (ES+): 450 (M+Na$^+$)

LR MS (ES−): 426 (M−H)

Example 24

2-hydroxyethyl 5-[4-(3-{[(3-methyl-2-thienyl)carbonyl]amino}phenoxy)pyridin-2-yl]-1H-pyrrole-3-carboxylate

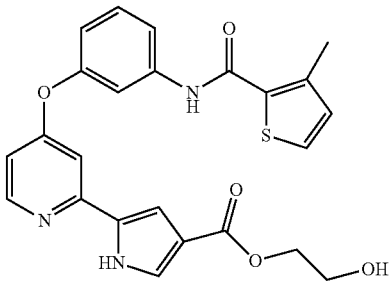 [SMILES: Cc1ccoc1C(=O)Nc1cccc(Oc2ccnc(-c3cc(C(=O)OCCO)c[nH]3)c2)c1]

Similar procedure as Example 25.

$^1$H NMR (d$_6$-DMSO): 12.13 (br. s., 1H), 10.13 (s, 1H), 8.43 (d, J=5.9 Hz, 1H), 7.68 (d, J=5.0 Hz, 1H), 7.56-7.64 (m, 2H), 7.40-7.52 (m, 3H), 7.14 (s, 1H), 7.03 (d, J=5.0 Hz, 1H), 6.89-6.98 (m, 1H), 6.76 (dd, J=5.7, 2.2 Hz, 1H), 4.83 (t, J=5.9 Hz, 1H), 4.15 (t, J=5.1 Hz, 2H), 3.64 (q, J=5.6 Hz, 2H), 2.44 (s, 3H)

LR MS (ES+): 486 (M+Na$^+$)
LR MS (ES−): 462 (M−H)

Example 25

2-hydroxyethyl 5-(4-{3-[(3-methyl-2-furoyl)amino]phenoxy}pyridin-2-yl)-1H-pyrrole-3-carboxylate

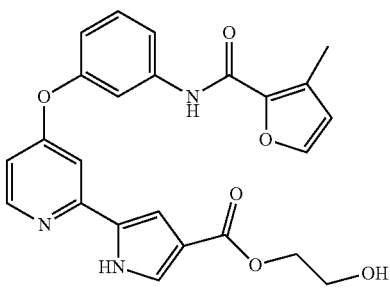

A mixture of 5-(4-{3-[(3-methyl-2-furoyl)amino]phenoxy}pyridin-2-yl)-1H-pyrrole-3-carboxylic acid (70 mg, 0.17 mmol), ethylene glycol (1 ml), 1-ethyl-3-(3-dimethylaminopropyl)carbodiimide hydrochloride (EDC.HCl, 40 mg, 0.21 mmol) and 4-dimethylaminopyridine (DMAP, 10 mg, 0.08 mmol) in anhydrous DMF (10 ml) was stirred at 70° C. for 3 hours then room temperature for 16 hours. The mixture was poured into 100 ml of water. Saturated NaHCO$_3$ solution was added until pH=9. The precipitates were filtered, washed with water and dried in vacuo to give the crude, which was purified by silica gel chromatography eluting with a gradient of 3~4% MeOH/CHCl$_3$ to give 2-hydroxyethyl 5-(4-{3-[(3-methyl-2-furoyl)amino]phenoxy}pyridin-2-yl)-1H-pyrrole-3-carboxylate as white solid. Yield: 40 mg, 51%.

$^1$H NMR (d$_6$-DMSO): 12.13 (br. s., 1H), 10.22 (s, 1H), 8.43 (d, J=5.9 Hz, 1H), 7.79 (s, 1H), 7.70 (s, 2H), 7.36-7.54 (m, 3H), 7.13 (br. s., 1H), 6.86-6.97 (m, 1H), 6.72-6.80 (m, 1H), 6.59 (s, 1H), 5.75 (s, 1H), 4.83 (t, J=5.3 Hz, 1H), 4.14 (t, J=4.7 Hz, 2H), 3.58-3.69 (m, 2H), 2.32 (s, 3H)

LR MS (ES+): 470 (M+Na$^+$)
LR MS (ES−): 446 (M−H)

Example 26

5-[4-(3-{[(3-methyl-2-thienyl)carbonyl]amino}phenoxy)pyridin-2-yl]-1H-pyrrole-3-carboxylic acid

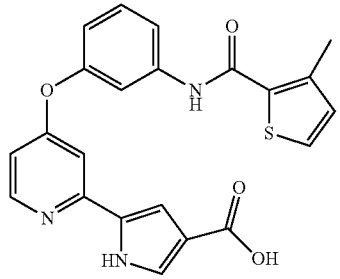

Similar procedure as Example 32.

$^1$H NMR (d$_6$-DMSO): 12.04 (br. s., 1H), 11.87 (s, 1H), 10.13 (s, 1H), 8.42 (d, J=6.2 Hz, 1H), 7.68 (d, J=4.7 Hz, 1H), 7.57-7.64 (m, 2H), 7.40-7.49 (m, 2H), 7.38 (dd, J=3.2, 1.5 Hz, 1H), 7.05-7.09 (m, 1H), 7.03 (d, J=5.0 Hz, 1H), 6.90-6.97 (m, 1H), 6.75 (dd, J=5.7, 2.5 Hz, 1H), 2.44 (s, 3H)

LR MS (ES+): 442 (M+Na$^+$)
LR MS (ES−): 418 (M−H)

Example 27 methyl 5-[4-(3-{[(3-methyl-2-thienyl)carbonyl]amino}phenoxy)pyridin-2-yl]-1H-pyrrole-3-carboxylate

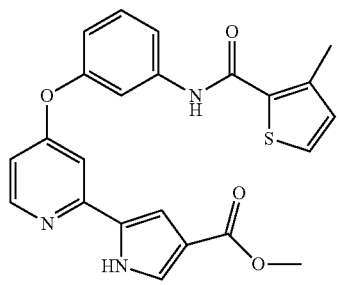

Similar procedure as Example 33.

$^1$H NMR (DMSO-d$_6$): 12.12 (br. s., 1H), 10.10 (s, 1H), 8.35-8.45 (m, 1H), 7.65 (d, J=5.0 Hz, 1H), 7.55-7.60 (m, 2H), 7.37-7.45 (m, 3H), 7.10 (s, 1H), 7.00 (d, J=5.0 Hz, 1H), 6.87-6.93 (m, 1H), 6.73 (dd, J=5.6, 2.3 Hz, 1H), 3.69 (s, 3H), 2.41 (s, 3H)

LR MS (ES+): 456 (M+Na$^+$)
LR MS (ES−): 432 (M−H)

Example 28

5-(4-{4-fluoro-3-[(3-methyl-2-furoyl)amino]phenoxy}pyridin-2-yl)-1H-pyrrole-3-carboxylic acid

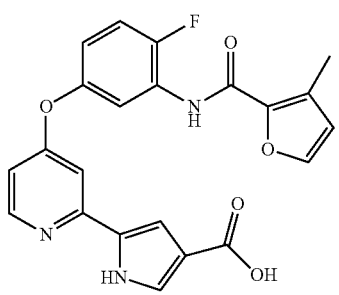 [SMILES: Cc1ccoc1C(=O)Nc1cc(Oc2ccnc(-c3cc(C(=O)O)c[nH]3)c2)ccc1F]

To a stirred solution of methyl 5-(4-{4-fluoro-3-[(3-methyl-2-furoyl)amino]phenoxy}pyridin-2-yl)-1H-pyrrole-3-carboxylate (20 mg, 0.046 mmol) in a mixture of solvents THF/MeOH (5 ml/5 ml) was added 3 ml of 1M NaOH (3 mmol) solution. The mixture was heated in a 72° C. bath for 3 hours, cooled to room temperature and poured into 50 ml of water. 2M HCl was added until pH=4. The resulting precipitates were filtered, washed with water, and dried in vacuo to give 5-(4-{4-fluoro-3-[(3-methyl-2-furoyl)amino]phenoxy}pyridin-2-yl)-1H-pyrrole-3-carboxylic acid as light gray solid.

Yield: 19 mg, 100%.

LR MS (ES−): 420 (M−H)

Example 29 methyl 5-(4-{4-fluoro-3-[(3-methyl-2-furoyl)amino]phenoxy}pyridin-2-yl)-1H-pyrrole-3-carboxylate

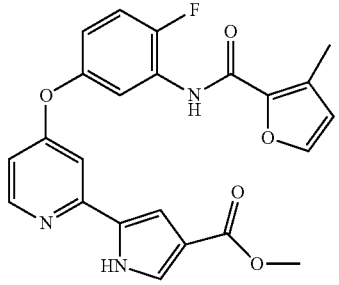 [SMILES: COC(=O)c1c[nH]c(-c2cc(Oc3ccc(F)c(NC(=O)c4occc4C)c3)ccn2)c1]

Similar procedure as Example 33.

$^1$H NMR (d$_6$-DMSO): 12.15 (br. s., 1H), 9.74 (s, 1H), 8.43 (d, J=5.6 Hz, 1H), 7.81 (d, J=1.8 Hz, 1H), 7.60 (dd, J=6.4, 2.9 Hz, 1H), 7.34-7.50 (m, 3H), 7.02-7.18 (m, 2H), 6.75 (dd, J=5.6, 2.3 Hz, 1H), 6.60 (d, J=1.5 Hz, 1H), 3.72 (s, 3H), 2.31 (s, 3H)

LR MS (ES+): 458 (M+Na$^+$)

LR MS (ES−): 434 (M−H)

Example 30

N-[dimethyl(oxido)-lambda~4~sulfanylidene]-5-(4-{3-[(3-methyl-2-furoyl)amino]phenoxy}pyridin-2-yl)-1H-pyrrole-3-carboxamide

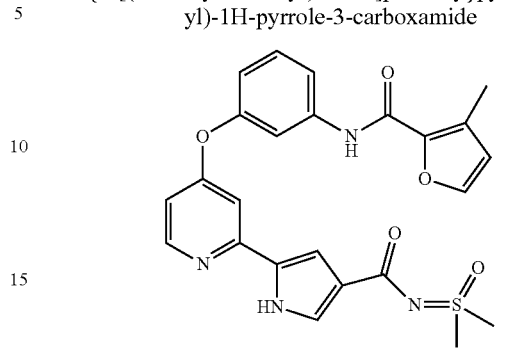

Similar procedure as Example 101.

$^1$H NMR (d$_6$-DMSO): 11.83 (br. s., 1H), 10.20 (s, 1H), 8.39 (d, J=5.6 Hz, 1H), 7.77 (d, J=1.5 Hz, 1H), 7.65-7.72 (m, 2H), 7.37-7.45 (m, 1H), 7.32 (d, J=2.1 Hz, 1H), 7.27 (dd, J=2.9, 1.5 Hz, 1H), 6.96-6.99 (m, 1H), 6.87-6.92 (m, 1H), 6.71 (dd, J=5.6, 2.3 Hz, 1H), 6.57 (d, J=1.8 Hz, 1H), 3.35 (s, 6H), 2.30 (s, 3H)

LR MS (ES+): 501 (M+Na$^+$)

LR MS (ES−): 477 (M−H)

Example 31

N-(3-{[2-(4-{[(3S)-3-hydroxypyrrolidin-1-yl]carbonyl}-1H-pyrrol-2-yl)pyridin-4-yl]oxy}phenyl)-3-methyl-2-furamide

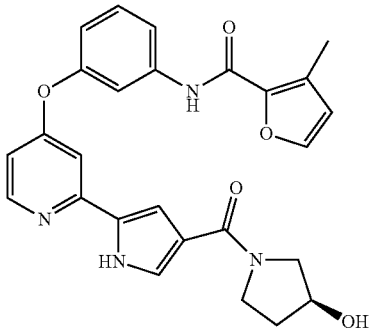 [SMILES: Cc1ccoc1C(=O)Nc1cccc(Oc2ccnc(-c3cc(C(=O)N4CC[C@H](O)C4)c[nH]3)c2)c1]

A mixture of 5-(4-{3-[(3-methyl-2-furoyl)amino]phenoxy}pyridin-2-yl)-1H-pyrrole-3-carboxylic acid (60 mg, 0.15 mmol), HATU (68 mg, 0.18 mmol) and N,N-diisopropylethylamine (43 mg, 0.33 mmol) in anhydrous DMF (10 ml) was stirred at room temperature for 10 minutes, followed by addition of (S)-3-pyrrolidinol (16 mg, 0.18 mmol). The mixture was stirred for another 10 minutes and poured into 100 ml of water. 2M HCl was added dropwise until pH=4~5. The precipitates were filtered, washed with water and dried in vacuo to give N-(3-{[2-(4-{[(3S)-3-hydroxypyaolidin-1-yl]carbonyl}-1H-pyrrol-2-yl)pyridin-4-yl]oxy}phenyl)-3-methyl-2-furamide as white solid. Yield: 40 mg, 56%.

$^1$H NMR (d$_6$-DMSO): 11.95 (br. s., 1H), 10.21 (s, 1H), 8.41 (d, J=5.6 Hz, 1H), 7.77 (d, J=1.8 Hz, 1H), 7.64-7.74 (m, 2H), 7.35-7.51 (m, 2H), 7.29 (br. s., 1H), 7.12 (br. s., 1H), 6.90 (dd, J=8.1, 1.3 Hz, 1H), 6.73 (dd, J=5.7, 2.2 Hz, 1H), 6.57 (d, J=1.8 Hz, 1H), 4.20-4.36 (m, 1H), 3.66-3.88 (m, 2H), 3.42-3.60 (m, 3H), 2.30 (s, 3H), 1.66-2.03 (m, 2H)

LR MS (ES+): 495 (M+Na$^+$)

LR MS (ES−): 471 (M−H)

Example 32

5-(4-{3-[(3-methyl-2-furoyl)amino]phenoxy}pyridin-2-yl)-1H-pyrrole-3-carboxylic acid

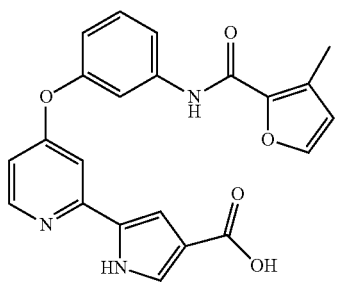 [SMILES: Cc1ccoc1C(=O)Nc1cccc(Oc2ccnc(-c3cc(C(=O)O)c[nH]3)c2)c1]

To a stirred solution of methyl 5-(4-{3-[(3-methyl-2-furoyl)amino]phenoxy}pyridin-2-yl)-1H-pyrrole-3-carboxylate (1.30 g, 3.12 mmol) in a mixture of solvents THF/MeOH (10 ml/10 ml) was added 2 ml of 5M NaOH (10 mmol) solution. The mixture was heated in a 68° C. bath for 8 hours, cooled to room temperature and poured into 200 ml of water. 2M HCl was added until pH=3. The resulting precipitates were filtered, washed with water, and dried in vacuo to give 5-(4-{3-[(3-methyl-2-furoyl)amino]phenoxy}pyridin-2-yl)-1H-pyrrole-3-carboxylic acid as white solid. Yield: 1.20 g, 95%.

$^1$H NMR (d$_6$-DMSO): 11.98 (br. s., 1H), 10.22 (s, 1H), 8.42 (d, J=5.6 Hz, 1H), 7.79 (d, J=1.2 Hz, 1H), 7.61-7.76 (m, 2H), 7.27-7.51 (m, 3H), 7.04 (br. s., 1H), 6.85-6.98 (m, 1H), 6.73 (dd, J=5.7, 2.2 Hz, 1H), 6.59 (d, J=1.5 Hz, 1H), 2.32 (s, 3H)

LR MS (ES−): 402 (M−H)

Example 33 methyl 5-(4-{3-[(3-methyl-2-furoyl)amino]phenoxy}pyridin-2-yl)-1H-pyrrole-3-carboxylate

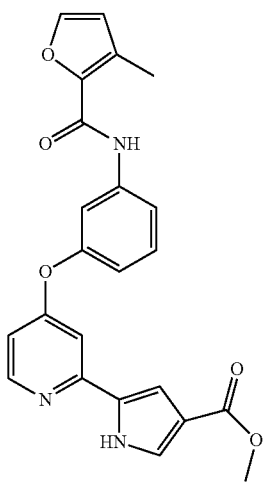 [SMILES: COC(=O)c1c[nH]c(-c2cc(Oc3cccc(NC(=O)c4occc4C)c3)ccn2)c1]

A mixture of 3-methyl-2-furoic acid (490 mg, 3.88 mmol), HATU (1.71 g, 4.5 mmol) and N,N-diisopropylethylamine (1.0 g, 7.8 mmol) in anhydrous DMF (10 ml) was stirred at room temperature for 10 minutes, followed by addition of methyl 5-[4-(3-aminophenoxy)pyridin-2-yl]-1H-pyrrole-3-carboxylate (1.0 g, 3.24 mmol). The mixture was stirred at 50° C. for 2 hours and poured into 100 ml of water. 2M HCl was added dropwise until pH=4~5. The precipitates were filtered, washed with water and dried in vacuo to give methyl 5-(4-{3-[(3-methyl-2-furoyl)amino]phenoxy}pyridin-2-yl)-1H-pyrrole-3-carboxylate as white solid. Yield: 1.30 g, 96%.

$^1$H NMR (d$_6$-DMSO): 12.15 (br. s., 1H), 10.22 (s, 1H), 8.43 (d, J=5.9 Hz, 1H), 7.79 (d, J=1.5 Hz, 1H), 7.68-7.74 (m, 2H), 7.38-7.47 (m, 3H), 7.09-7.14 (m, 1H), 6.88-6.94 (m, 1H), 6.75 (dd, J=5.6, 2.3 Hz, 1H), 6.59 (d, J=1.5 Hz, 1H), 3.72 (s, 3H), 2.32 (s, 3H)

LR MS (ES+): 440 (M+Na$^+$)

LR MS (ES−): 416 (M−H)

Example 34

3-methyl-N-(3-{[2-(1H-pyrrol-2-yl)pyridin-4-yl]oxy}phenyl)-2-furamide

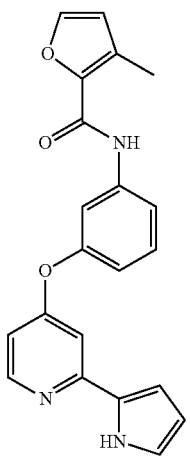 [SMILES: Cc1ccoc1C(=O)Nc1cccc(Oc2ccnc(-c3ccc[nH]3)c2)c1]

A mixture of 3-methyl-2-furoic acid (60 mg, 0.48 mmol), HBTU (198 mg, 0.52 mmol) and N,N-diisopropylethylamine (129 mg, 1.0 mmol) in anhydrous DMF (10 ml) was stirred at room temperature for 10 minutes, followed by addition of 3-{[2-(1H-pyrrol-2-yl)pyridin-4-yl]oxy}aniline (100 mg, 0.40 mmol). The mixture was stirred at 70° C. for 3 hours and poured into 100 ml of water. The precipitates were filtered, washed with water and dried in vacuo to give the crude, which was purified by silica gel chromatography eluting with 3-5% MeOH/CHCl$_3$ to give 3-methyl-N-(3-{[2-(1H-pyrrol-2-yl)pyridin-4-yl]oxy}phenyl)-2-furamide as white solid. Yield: 52 mg, 36%.

$^1$H NMR (d$_6$-DMSO): 11.46 (br. s., 1H), 10.19 (s, 1H), 8.36 (d, J=6.2 Hz, 1H), 7.77 (d, J=1.8 Hz, 1H), 7.64-7.72 (m, 2H), 7.35-7.44 (m, 1H), 7.28 (d, J=2.1 Hz, 1H), 6.86-6.91 (m, 1H), 6.81-6.86 (m, 1H), 6.68-6.74 (m, 1H), 6.65 (dd, J=5.7, 2.5 Hz, 1H), 6.57 (d, J=1.8 Hz, 1H), 6.06-6.13 (m, 1H), 2.30 (s, 3H)

LR MS (ES+): 360 (M+H)

LR MS (ES−): 358 (M−H)

Example 35 methyl 4-(4-{3-[(3-methyl-2-furoyl)amino]phenoxy}pyridin-2-yl)-1H-pyrrole-2-carboxylate

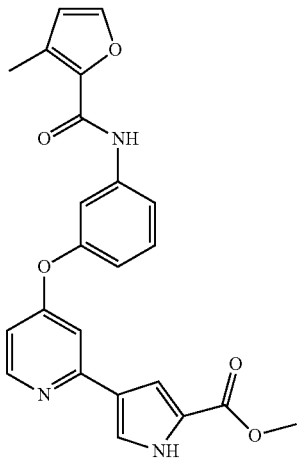 [SMILES: COC(=O)c1cc(-c2cc(Oc3cccc(NC(=O)c4occc4C)c3)ccn2)c[nH]1]

Similar procedure as Example 33.

¹H NMR (d₆-DMSO): 12.18 (br. s., 1H), 10.19 (s, 1H), 8.37 (d, J=5.6 Hz, 1H), 7.77 (d, J=1.8 Hz, 1H), 7.59-7.72 (m, 3H), 7.33-7.44 (m, 2H), 7.25-7.32 (m, 1H), 6.83-6.93 (m, 1H), 6.66 (dd, J=5.6, 2.3 Hz, 1H), 6.57 (d, J=1.2 Hz, 1H), 3.76 (s, 3H), 2.30 (s, 3H)

LR MS (ES+): 440 (M+Na⁺)
LR MS (ES−): 416 (M−H)

Example 36

2-fluoro-5-methyl-N-(4-{[2-(1H-pyrrol-2-yl)pyridin-4-yl]oxy}phenyl)benzamide

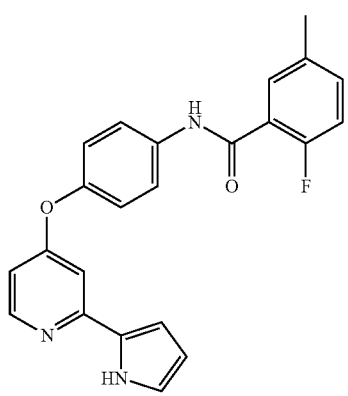 [SMILES: Cc1ccc(F)c(C(=O)Nc2ccc(Oc3ccnc(-c4ccc[nH]4)c3)cc2)c1]

Similar procedure as Example 37.

¹H NMR (d₆-DMSO): 11.44 (br. s., 1H), 10.47 (s, 1H), 8.33 (d, J=5.6 Hz, 1H), 7.76-7.86 (m, 2H), 7.46 (dd, J=6.4, 2.1 Hz, 1H), 7.36 (ddd, J=7.9, 5.3, 2.1 Hz, 1H), 7.13-7.27 (m, 4H), 6.80-6.87 (m, 1H), 6.66-6.73 (m, 1H), 6.60 (dd, J=5.6, 2.3 Hz, 1H), 6.06-6.15 (m, 1H), 2.34 (s, 3H)

LR MS (ES+): 388 (M+H)
LR MS (ES−): 386 (M−H)

Example 37

3-methyl-N-(4-{[2-(1H-pyrrol-2-yl)pyridin-4-yl]oxy}phenyl)-2-furamide

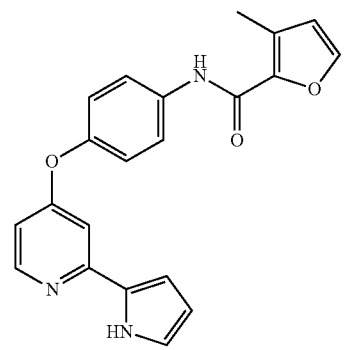 [SMILES: Cc1ccoc1C(=O)Nc1ccc(Oc2ccnc(-c3ccc[nH]3)c2)cc1]

A mixture of 3-methyl-2-furoic acid (70 mg, 0.55 mmol), HATU (243 mg, 0.64 mmol,) tert-butyl 2-[4-(4-aminophenoxy)pyridin-2-yl]-1H-pyrrole-1-carboxylate (160 mg, 0.46 mmol) and N,N-diisopropylethylamine (148 mg, 1.15 mmol) in anhydrous DMF (10 ml) was stirred at 45° C. for 2 hours. The mixture was poured into 100 ml of water. The precipitates were filtered, washed with water and dried in vacuo to give the crude, which was dissolved in 5 ml of methylene chloride, followed by addition of trifluoroacetic acid (3 ml). The mixture was stirred at room temperature for 16 hours. The solvents were evaporated under reduced pressure. The residue was purified by reversed-phase chromatography with a gradient of 10~50% acetonitrile/water to give 3-methyl-N-(4-{[2-(1H-pyrrol-2-yl)pyridin-4-yl]oxy}phenyl)-2-furamide as white solid. Yield: 56 mg, 34%.

LR MS (ES+): 360 (M+H)
LR MS (ES−): 358 (M−H)

Preparation of 4-((2-chloropyridin-4-yl)oxy)aniline

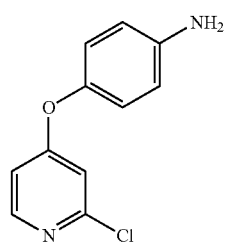 [SMILES: Nc1ccc(Oc2ccnc(Cl)c2)cc1]

A stirred solution of 4-aminophenol (740 mg, 6.8 mmol) in anhydrous DMSO (8 ml) was flushed with nitrogen and treated with 1M KOBuᵗ/THF solution (10 ml, 10 mmol). The mixture was stirred at room temperature under nitrogen for 10 minutes. 2,4-dichloropyridine (1.0 g, 6.8 mmol) was added and the mixture was heated at 60° C. for 30 minutes, cooled to room temperature and poured into 100 ml of water. The resulting precipitates were filtered, washed with water and dried to give 4-((2-chloropyridin-4-yl)oxy)aniline as light brown solid. The material was used for the following reactions without further purification. Yield: 1.15 g, 77%.

¹H NMR (d₆-DMSO): 8.21 (d, 1H), 6.77-6.91 (m, 4H), 6.54-6.68 (m, 2H), 5.16 (s, 2H)

Preparation of methyl 5-[4-(4-aminophenoxy)pyridin-2-yl]-1H-pyrrole-3-carboxylate

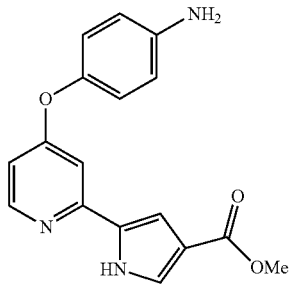 [SMILES: COC(=O)c1c[nH]c(-c2cc(Oc3ccc(N)cc3)ccn2)c1]

A mixture of 4-((2-chloropyridin-4-yl)oxy)aniline (2.6 g, 11.78 mmol), methyl-(5-(4,4,5,5-tetramethyl-1,3,2-dioxaborolan-2-yl)-1H-pyrrole-3-carboxylate (6.0 g, 23.90 mmol) and Pd(PPh3)4 (2.72 g, 2.35 mmol) was added to a thick walled reaction vessel and purged with N₂. A solution of 2M K₂CO₃ (17.68 mL) was added, followed by DME (90 mL). The reaction vessel was sealed and the mixture stirred at 92° C. for 18 h. The reaction vessel was cooled to room temperature and the mixture was filtered over celite, washing with EtOAc. The filtrate was concentrated to afford a dark oil, which was purified via column chromatography eluting with 40-80% EtOAc/hexanes to afford methyl 5-[4-(4-aminophenoxy)pyridin-2-yl]-1H-pyrrole-3-carboxylate (2.4 g, 65% yield).

Example 38

5-{4-[4-({[(2-fluoro-5-methylphenyl)amino]carbonyl}amino)phenoxy]pyridin-2-yl}-N-(3-morpholin-4-ylpropyl)-1H-pyrrole-3-carboxamide

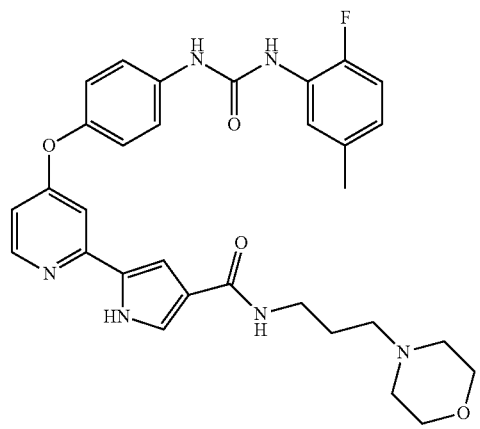 [SMILES: Cc1ccc(F)c(NC(=O)Nc2ccc(Oc3ccnc(-c4cc(C(=O)NCCCN5CCOCC5)c[nH]4)c3)cc2)c1]

Similar procedure as Example 132.
LR MS (ES+): 573 (MH)

Example 39

5-{4-[3-fluoro-4-({[(2-fluoro-5-methylphenyl)amino]carbonyl}amino)phenoxy]pyridin-2-yl}-N-hydroxy-1H-pyrrole-3-carboxamide

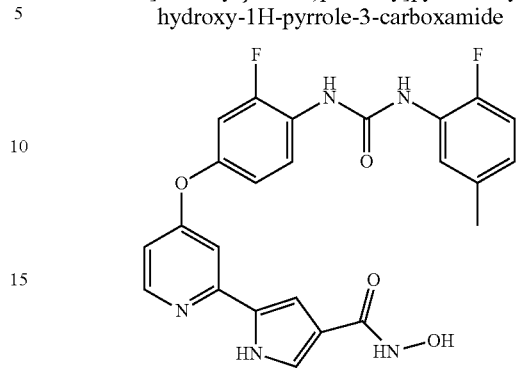

Similar procedure as Example 132.
¹H NMR (DMSO-d₆): 11.82 (br. s., 1H), 10.55 (br. s., 1H), 9.05 (d, J=1.8 Hz, 1H), 8.94 (d, J=2.3 Hz, 1H), 8.64 (br. s., 1H), 8.37 (d, J=5.6 Hz, 1H), 8.23 (t, J=9.2 Hz, 1H), 7.98 (dd, J=7.8, 1.9 Hz, 1H), 7.31 (br. s., 1H), 7.26 (dd, J=11.7, 2.6 Hz, 1H), 7.19 (d, J=2.3 Hz, 1H), 7.09 (dd, J=11.3, 8.4 Hz, 1H), 6.98-7.05 (m, 2H), 6.76-6.83 (m, 1H), 6.73 (dd, J=5.7, 2.5 Hz, 1H), 2.25 (s, 3H)
LR MS (ES-): 478 (M-H)

Example 40

{[(4-{4-[4-({[(2-fluoro-5-methylphenyl)amino]carbonyl}amino)phenoxy]pyridin-2-yl}-2-thienyl)carbonyl]amino}acetic acid

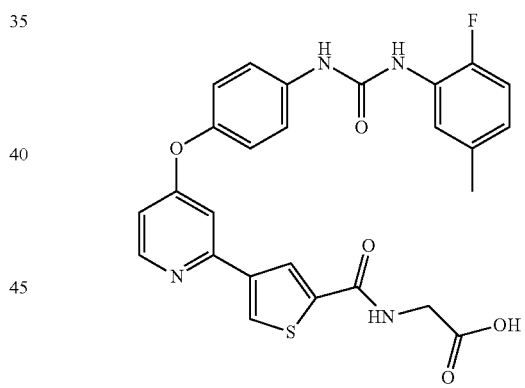

To a stirred solution of methyl {[(4-{4-[4-({[(2-fluoro-5-methylphenyl)amino]carbonyl}amino)phenoxy]pyridin-2-yl}-2-thienyl)carbonyl]amino}acetate (60 mg, 0.11 mmol) in a mixture of solvents THF/MeOH (5 ml/5 ml) was added 1 ml of 1M NaOH (1.0 mmol) solution. The mixture was stirred at room temperature for 1 hour and poured into 100 ml of water. 2M HCl was added until pH=3. The resulting precipitates were filtered, washed with water, and dried in vacuo to give {[(4-{4-[4-({[(2-fluoro-5-methylphenyl)amino]carbonyl}amino)phenoxy]pyridin-2-yl}-2-thienyl)carbonyl]amino}acetic acid as white solid. Yield: 50 mg, 86%.
¹H NMR (DMSO-d₆): 12.61 (br s, 1H), 9.15 (s, 1H), 8.98 (t, J=5.9 Hz, 1H), 8.43-8.48 (m, 2H), 8.40 (d, J=1.5 Hz, 1H), 8.36 (d, J=1.2 Hz, 1H), 7.95 (dd, J=7.6, 1.8 Hz, 1H), 7.50-7.58 (m, 2H), 7.40 (d, J=2.3 Hz, 1H), 7.12-7.19 (m, 2H), 7.08 (dd, J=11.3, 8.4 Hz, 1H), 6.73-6.81 (m, 2H), 3.88 (d, J=5.9 Hz, 2H), 2.25 (s, 3H)
LR MS (ES-): 519 (M-H)

Example 41 methyl {[(4-{4-[4-({[(2-fluoro-5-methylphenyl)amino]carbonyl}amino)phenoxy]pyridin-2-yl}-2-thienyl)carbonyl]amino}acetate

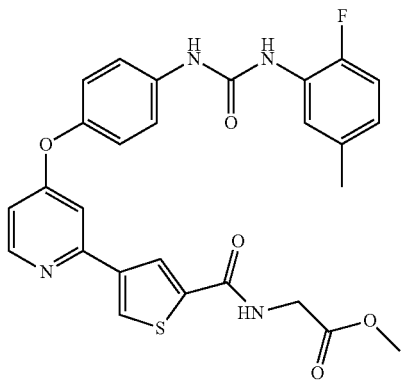 [SMILES: COC(=O)CNC(=O)c1cc(-c2cc(Oc3ccc(NC(=O)Nc4cc(C)ccc4F)cc3)ccn2)cs1]

A mixture of 4-{4-[4-({[(2-fluoro-5-methylphenyl)amino]carbonyl}amino)phenoxy]pyridin-2-yl}thiophene-2-carboxylic acid (100 mg, 0.22 mmol), HATU (100 mg, 0.26 mmol) and N,N-diisopropylethylamine (85 mg, 0.66 mmol) in anhydrous DMF (10 ml) was stirred at room temperature for 10 minutes, followed by addition of glycine methyl ester hydrochloride (41 mg, 0.33 mmol). The mixture was stirred for another 10 minutes and poured into 100 ml of water. 2M HCl was added dropwise until pH=4~5. The precipitates were filtered, washed with water and dried in vacuo to give methyl {[(4-{4-[4-({[(2-fluoro-5-methylphenyl)amino]carbonyl}amino)phenoxy]pyridin-2-yl}-2-thienyl)carbonyl]amino}acetate as white solid. Yield: 90 mg, 78%.

$^1$H NMR (DMSO-d$_6$): 9.17 (s, 1H), 9.10 (t, J=5.9 Hz, 1H), 8.44-8.49 (m, 2H), 8.37-8.42 (m, 2H), 7.92-7.98 (m, 1H), 7.55 (d, J=8.8 Hz, 2H), 7.43 (d, J=2.1 Hz, 1H), 7.16 (d, J=8.8 Hz, 2H), 7.08 (dd, J=11.3, 8.4 Hz, 1H), 6.75-6.84 (m, 2H), 3.98 (d, J=5.9 Hz, 2H), 3.63 (s, 3H), 2.25 (s, 3H)

LR MS (ES+): 557 (M+Na$^+$)
LR MS (ES−): 533 (M−H)

Preparation of methyl 4-(4-(4-aminophenoxy)pyridine-2-yl)thiophene-2-carboxylate

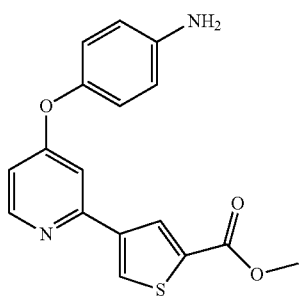 [SMILES: COC(=O)c1cc(-c2cc(Oc3ccc(N)cc3)ccn2)cs1]

A mixture of 4-(4-aminophenoxy)-2-chloropyridine (5.0 g, 22.66 mmol), methyl-(4-(4,4,5,5-tetramethyl-1,3,2-dioxaborolan-2-yl)-thiophene-2-carboxylate (9.73 g, 36.25 mmol) and Pd(PPh3)4 (5.24 g, 4.53 mmol) was added to a thick walled reaction vessel and purged with N2. A solution of 2M K2CO3 (17.0 mL) was added, followed by dioxane (120 mL). The reaction vessel was sealed and the mixture stirred at 92° C. for 18 h. The reaction vessel was cooled to room temperature and the mixture was filtered over celite, washing with EtOAc. The filtrate was concentrated and the resultant dark oil was purified via column chromatography, eluting with 40-60% EtOAc/hexanes to afford methyl 4-(4-(4-aminophenoxy)pyridine-2-yl)thiophene-2-carboxylate (6.1 g, 82% yield).

Example 42 methyl 4-{4-[4-({[(2-fluoro-5-methylphenyl)amino]carbonyl}amino)phenoxy]pyridin-2-yl}thiophene-2-carboxylate

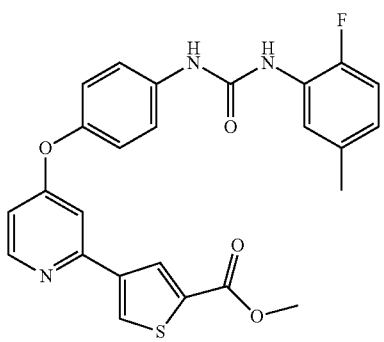 [SMILES: COC(=O)c1cc(-c2cc(Oc3ccc(NC(=O)Nc4cc(C)ccc4F)cc3)ccn2)cs1]

To a stirred solution of methyl 4-[4-(4-aminophenoxy)pyridin-2-yl]thiophene-2-carboxylate (500 mg, 1.53 mmol) in anhydrous THF (10 ml) was added 2-fluoro-5-methyl-phenylisocyanate (255 mg, 1.68 mmol). The mixture was stirred at room temperature for one hour and poured into 200 ml of water. The resulting precipitates were filtered, washed with water and dried in vacuo to give the crude, which was purified by silica gel chromatography eluting with 3-5% MeOH/CHCl$_3$ to give methyl 4-{4-[4-({[(2-fluoro-5-methylphenyl)amino]carbonyl}amino)phenoxy]pyridin-2-yl}thiophene-2-carboxylate as off-white solid. Yield: 560 mg, 76%.

$^1$H NMR (DMSO-d$_6$): 9.14 (s, 1H), 8.51 (d, J=1.5 Hz, 1H), 8.41-8.47 (m, 2H), 8.33 (d, J=1.8 Hz, 1H), 7.96 (d, J=6.2 Hz, 1H), 7.48-7.57 (m, 3H), 7.13 (d, J=9.1 Hz, 2H), 7.08 (dd, J=11.4, 8.5 Hz, 1H), 6.76-6.81 (m, 1H), 6.74 (dd, J=5.6, 2.3 Hz, 1H), 3.83 (s, 3H), 2.25 (s, 3H)

LR MS (ES+): 500 (M+Na$^+$)
LR MS (ES−): 476 (M−H)

Example 43

(4S)-5-(ethylamino)-4-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoic acid

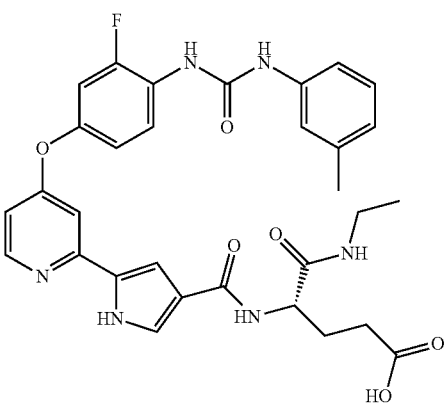 [SMILES: CCNC(=O)[C@H](CCC(=O)O)NC(=O)c1c[nH]c(-c2cc(Oc3ccc(NC(=O)Nc4cccc(C)c4)c(F)c3)ccn2)c1]

To a stirred solution of tert-butyl (4S)-5-(ethylamino)-4-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoate (30 mg, 0.046 mmol) in 5 ml of methylene chloride was added 2 ml of TFA. The mixture was stirred at room temperature for 1 hour, and evaporated to dryness. The residue was dissolved in MeOH (3 ml), which was added dropwise into 100 ml of water with vigorous stirring. The precipitates were filtered, washed with water and dried to give (4S)-5-(ethylamino)-4-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoic acid as white solid. Yield: 20 mg, 74%.

$^1$H NMR (DMSO-$d_6$): 12.04 (br. s., 1H), 11.86 (br. s., 1H), 8.97 (s, 1H), 8.57 (d, J=2.1 Hz, 1H), 8.39 (d, J=5.9 Hz, 1H), 8.20 (t, J=9.1 Hz, 1H), 7.82 (t, J=5.6 Hz, 1H), 7.79 (d, J=8.2 Hz, 1H), 7.46 (br. s., 1H), 7.12-7.29 (m, 5H), 6.99-7.04 (m, 1H), 6.79 (d, J=7.3 Hz, 1H), 6.74 (d, J=4.7 Hz, 1H), 4.31 (td, J=8.6, 5.4 Hz, 1H), 2.97-3.11 (m, 2H), 2.26 (s, 3H), 2.17-2.25 (m, 2H), 1.87-1.98 (m, 1H), 1.74-1.84 (m, 1H), 0.97 (t, J=7.2 Hz, 3H)

LR MS (ES−): 601 (M−H)

Example 44 tert-butyl (4S)-5-(ethylamino)-4-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoate

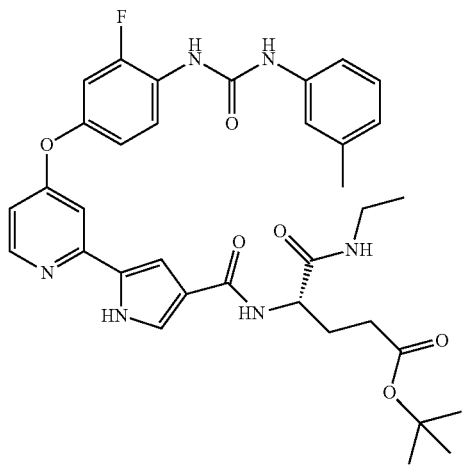 [SMILES: CCNC(=O)[C@H](CCC(=O)OC(C)(C)C)NC(=O)c1c[nH]c(-c2cc(Oc3ccc(NC(=O)Nc4cccc(C)c4)c(F)c3)ccn2)c1]

A mixture of (2S)-5-tert-butoxy-2-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoic acid (80 mg, 0.13 mmol), HATU (57 mg, 0.15 mmol) and N,N-diisopropylethylamine (49 mg, 0.38 mmol) in anhydrous DMF (8 ml) was stirred at room temperature for 10 minutes, followed by addition of 2-Methylamine in THF solution (0.1 ml, 0.2 mmol). The mixture was stirred for another 10 minutes and poured into 100 ml of water. 2M HCl was added dropwise until pH=5. The precipitates were filtered, washed with water and dried in vacuo to give the crude, which was purified by silica gel chromatography eluting with 4~5% MeOH/CHCl$_3$ to give tert-butyl (4S)-5-(ethylamino)-4-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoate as white solid. Yield: 40 mg, 48%.

$^1$H NMR (DMSO-$d_6$): 11.83 (br. s., 1H), 8.95 (s, 1H), 8.56 (br. s., 1H), 8.38 (d, J=5.6 Hz, 1H), 8.20 (t, J=9.1 Hz, 1H), 7.81 (t, J=5.3 Hz, 1H), 7.77 (d, J=8.2 Hz, 1H), 7.45 (d, J=1.5 Hz, 1H), 7.23-7.30 (m, 2H), 7.18-7.23 (m, 2H), 7.12-7.18 (m, 2H), 6.98-7.04 (m, 1H), 6.79 (d, J=7.6 Hz, 1H), 6.73 (dd, J=5.6, 2.3 Hz, 1H), 4.27-4.35 (m, 1H), 3.01-3.08 (m, 2H), 2.26 (s, 3H), 2.17-2.23 (m, 2H), 1.87-1.95 (m, 1H), 1.78 (m, 1H), 1.34 (s, 9H), 0.97 (t, J=7.2 Hz, 3H)

LR MS (ES+): 681 (M+Na$^+$)
LR MS (ES−): 657 (M−H)

Example 45

(2S)-5-tert-butoxy-2-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoic acid

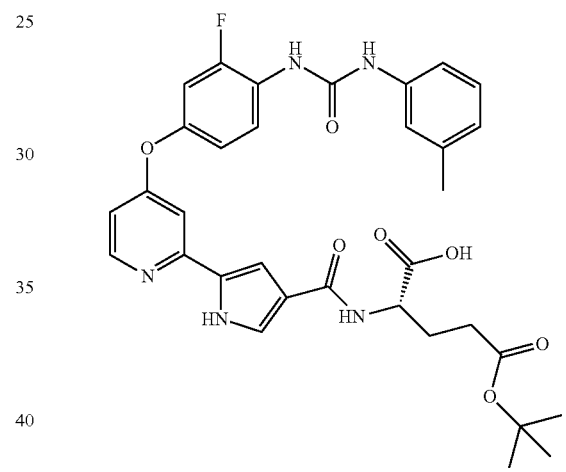

To a stirred solution of (S)-5-tert-butyl 1-methyl 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioate (120 mg, 0.19 mmol) in a mixture of solvents THF/MeOH (5 ml/5 ml) was added 1 ml of 1M NaOH (1 mmol) solution. The mixture was stirred at room temperature for 30 minutes, and poured into 100 ml of water. 2M HCl was added dropwise until pH=4. The resulting precipitates were filtered, washed with water, and dried in vacuo to give (2S)-5-tert-butoxy-2-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoic acid as white solid. Yield: 100 mg, 85%.

$^1$H NMR (DMSO-$d_6$): 12.49 (br. s., 1H), 11.84 (br. s., 1H), 8.98 (s, 1H), 8.58 (d, J=2.3 Hz, 1H), 8.38 (d, J=5.6 Hz, 1H), 8.20 (t, J=9.1 Hz, 1H), 7.89 (br. s., 1H), 7.42 (br. s., 1H), 7.28 (s, 1H), 7.25 (dd, J=11.7, 2.6 Hz, 1H), 7.20-7.23 (m, 2H), 7.11-7.18 (m, 2H), 7.01 (dd, J=9.0, 1.6 Hz, 1H), 6.79 (d, J=7.3 Hz, 1H), 6.73 (dd, J=5.6, 2.3 Hz, 1H), 4.23-4.34 (m, 1H), 2.23-2.28 (m, 2H), 2.26 (s, 3H), 1.95-2.03 (m, 1H), 1.80-1.88 (m, 1H), 1.35 (s, 9H)

LR MS (ES+): 654 (M+Na$^+$)
LR MS (ES−): 630 (M−H)

Example 46

(S)-5-tert-butyl 1-methyl 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioate

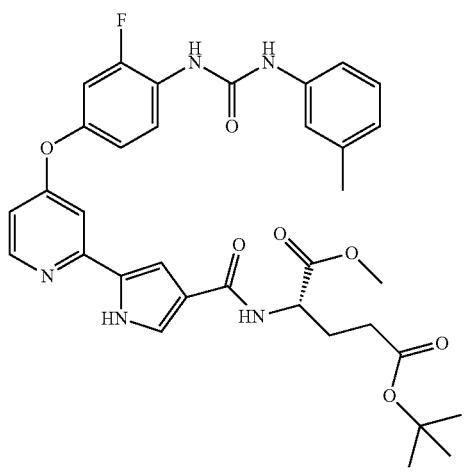 [SMILES: COC(=O)[C@H](CCC(=O)OC(C)(C)C)NC(=O)c1c[nH]c(-c2cc(Oc3ccc(NC(=O)Nc4cccc(C)c4)c(F)c3)ccn2)c1]

A mixture of 5-{4-[3-fluoro-4-({[(3-methylphenyl)amino] carbonyl}amino)phenoxy]pyridin-2-yl}-1H-pyrrole-3-carboxylic acid (500 mg, 1.1 mmol), HATU (500 mg, 1.32 mmol) and N,N-diisopropylethylamine (426 mg, 3.3 mmol) in anhydrous DMF (8 ml) was stirred at room temperature for 10 minutes, followed by addition of L-Glutamic acid 5-tert-butyl 1-methyl ester hydrochloride (334 mg, 1.32 mmol). The mixture was stirred for another 10 minutes and poured into 200 ml of water. 2M HCl was added dropwise until pH=5. The precipitates were filtered, washed with water and dried in vacuo to give the crude, which was purified by silica gel chromatography eluting with 3~5% MeOH/CHCl$_3$ to give (S)-5-tert-butyl 1-methyl 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioate as off-white solid. Yield: 380 mg, 52%.

$^1$H NMR (DMSO-d$_6$): 11.87 (br. s., 1H), 8.96 (s, 1H), 8.56 (br. s., 1H), 8.38 (d, J=5.6 Hz, 1H), 8.20 (t, J=8.9 Hz, 1H), 8.08 (d, J=7.0 Hz, 1H), 7.44 (br. s., 1H), 7.23-7.29 (m, 2H), 7.18-7.23 (m, 2H), 7.11-7.17 (m, 2H), 7.01 (d, J=8.8 Hz, 1H), 6.79 (d, J=7.0 Hz, 1H), 6.70-6.76 (m, 1H), 4.32-4.41 (m, 1H), 3.60 (s, 3H), 2.23-2.31 (m, 5H), 1.93-2.03 (m, 1H), 1.81-1.91 (m, 1H), 1.35 (s, 9H)

LR MS (ES+): 646 (MH), 668 (M+Na$^+$)

LR MS (ES−): 644 (M−H)

Example 47 bis(2-hydroxyethyl) 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioate

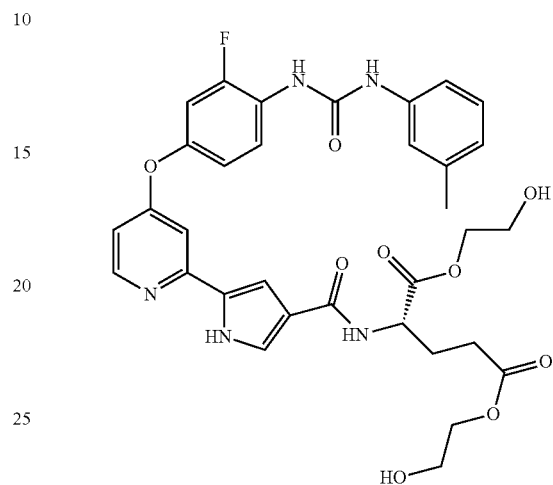

Similar procedure as Example 131.

LR MS (ES+): 686 (M+Na$^+$)

LR MS (ES−): 662 (M−H), 561

Example 48

3-{[(5-{4-[3-fluoro-4-({[(3-methylphenyl)amino]carbonyl}amino)phenoxy]pyridin-2-yl}-1H-pyrrol-3-yl)carbonyl]amino}propanoic acid

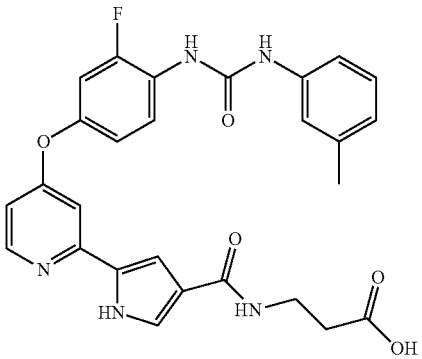 [SMILES: Cc1cccc(NC(=O)Nc2ccc(Oc3ccnc(-c4cc(C(=O)NCCC(=O)O)c[nH]4)c3)cc2F)c1]

Similar procedure as Example 132.

$^1$H NMR (DMSO-d$_6$): 11.90 (br. s., 1H), 8.99 (s, 1H), 8.59 (br. s., 1H), 8.40 (d, J=5.9 Hz, 1H), 8.22 (t, J=9.0 Hz, 1H), 7.90-7.96 (m, 1H), 7.40 (br. s., 1H), 7.25-7.30 (m, 2H), 7.21 (d, J=7.0 Hz, 2H), 7.15 (t, J=7.8 Hz, 2H), 7.03 (d, J=9.1 Hz, 1H), 6.79 (d, J=7.0 Hz, 2H), 3.32-3.37 (m, 2H), 2.43 (t, J=7.0 Hz, 2H), 2.26 (s, 3H)

LR MS (ES−): 516 (M−H)

Example 49

2-{[(5-{-4-[3-fluoro-4-({[(3-methylphenyl)amino]carbonyl}amino)phenoxy]pyridin-2-yl}-1H-pyrrol-3-yl)carbonyl]amino}pentanedioic acid

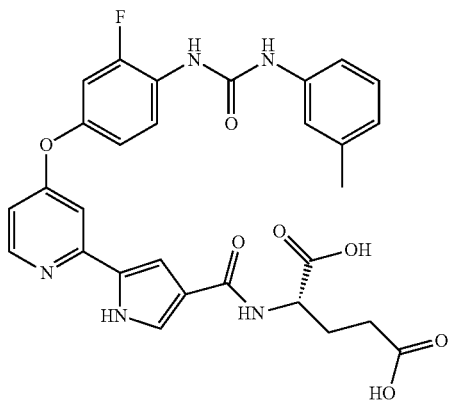 [SMILES: Cc1cccc(NC(=O)Nc2ccc(Oc3ccnc(-c4cc(C(=O)N[C@@H](CCC(=O)O)C(=O)O)c[nH]4)c3)cc2F)c1]

¹H NMR (DMSO-d₆): 12.43 (br. s., 2H), 11.89 (br. s., 1H), 8.97 (br. s., 1H), 8.57 (br. s., 1H), 8.39 (d, J=5.3 Hz, 1H), 8.20 (t, J=8.8 Hz, 1H), 7.97 (d, J=7.6 Hz, 1H), 7.46 (br. s., 1H), 7.11-7.31 (m, 4H), 7.02 (d, J=9.1 Hz, 1H), 6.79 (d, J=7.0 Hz, 1H), 6.75 (br. s., 1H), 4.32 (br. s., 1H), 2.30 (t, J=7.2 Hz, 2H), 2.26 (s, 3H), 2.01 (m, 2H), 1.86 (m, 2H)

LR MS (ES−): 574 (M−H)

Example 50 methyl 1-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)pyrrolidine-2-carboxylate

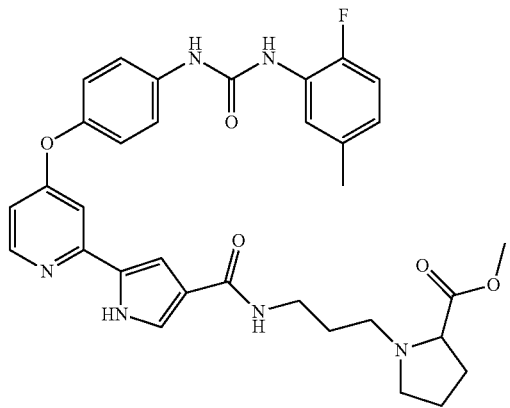 [SMILES: COC(=O)C1CCCN1CCCNC(=O)c1c[nH]c(-c2cc(Oc3ccc(NC(=O)Nc4cc(C)ccc4F)cc3)ccn2)c1]

Similar procedure as Example 132
LR MS (ES+): 615 (MH), 637 (M+Na⁺)
LR MS (ES−): 613 (M−H)

Example 51

5-{4-[4-({[(2-fluoro-5-methylphenyl)amino]carbonyl}amino)phenoxy]pyridin-2-yl}-N-{2-[(3S)-3-hydroxypyrrolidin-1-yl]-2-oxoethyl}-1H-pyrrole-3-carboxamide

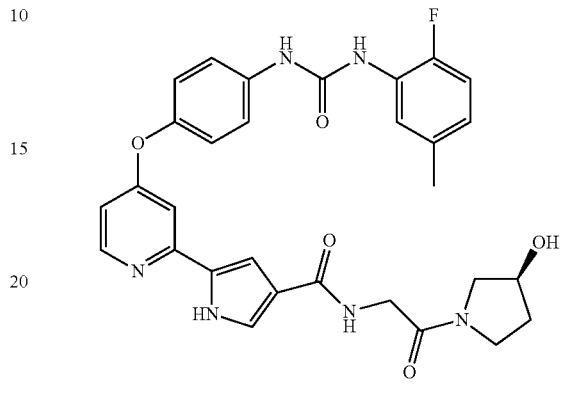

Similar procedure as Example 132.
LR MS (ES+): 573 (MH), 595 (M+Na⁺)
LR MS (ES−): 571 (M−H)

Example 52

N-{4-[(2,3-dihydroxypropyl)(methyl)amino]-4-oxobutyl}-5-{4-[4-({[(2-fluoro-5-methylphenyl)amino]carbonyl}amino)phenoxy]pyridin-2-yl}-1H-pyrrole-3-carboxamide

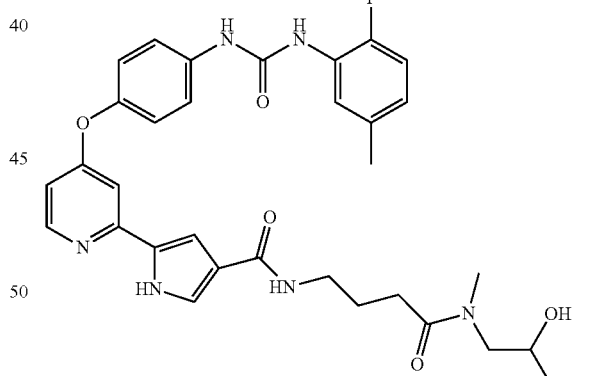

Similar procedure as Example 61.
¹H NMR (DMSO-d₆): 11.70-11.82 (m, 1H), 9.24 (s, 1H), 8.50 (d, J=2.1 Hz, 1H), 8.35 (d, J=5.9 Hz, 1H), 7.93-7.98 (m, 1H), 7.85 (dt, J=14.5, 5.5 Hz, 1H), 7.54 (d, J=9.1 Hz, 2H), 7.34 (br. s., 1H), 7.10-7.15 (m, 3H), 7.08 (dd, J=11.2, 8.5 Hz, 1H), 7.01-7.05 (m, 1H), 6.73-6.82 (m, 1H), 6.67 (dd, J=5.6, 2.3 Hz, 1H), 4.87 (d, J=5.3 Hz, 1H), 4.60-4.69 (m, 1H), 4.46 (t, J=5.9 Hz, 1H), 3.55-3.65 (m, 2H), 3.20-3.27 (m, 2H), 3.10-3.19 (m, 1H), 2.96 (s, 1H), 2.79 (s, 2H), 2.27-2.35 (m, 1H), 2.24 (s, 3H), 1.62-1.72 (m, 2H)
LR MS (ES+): 619 (MH), 641 (M+Na⁺)
LR MS (ES−): 617 (M−H)

Example 53

5-{4-[4-({[(2-fluoro-5-methylphenyl)amino]carbonyl}amino)phenoxy]pyridin-2-yl}-N-[4-(3-hydroxypiperidin-1-yl)-4-oxobutyl]-1H-pyrrole-3-carboxamide

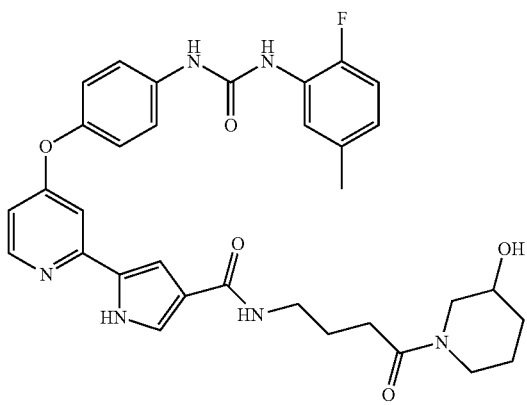 [SMILES: Cc1ccc(F)c(NC(=O)Nc2ccc(Oc3ccnc(-c4cc(C(=O)NCCCC(=O)N5CCCC(O)C5)c[nH]4)c3)cc2)c1]

Similar procedure as Example 61.
LR MS (ES+): 637 (M+Na⁺)
LR MS (ES−): 613 (M−H)

Example 54

N-{4-[(2,3-dihydroxypropyl)amino]-4-oxobutyl}-5-{4-[4-({[(2-fluoro-5-methylphenyl)amino]carbonyl}amino)phenoxy]pyridin-2-yl}-1H-pyrrole-3-carboxamide

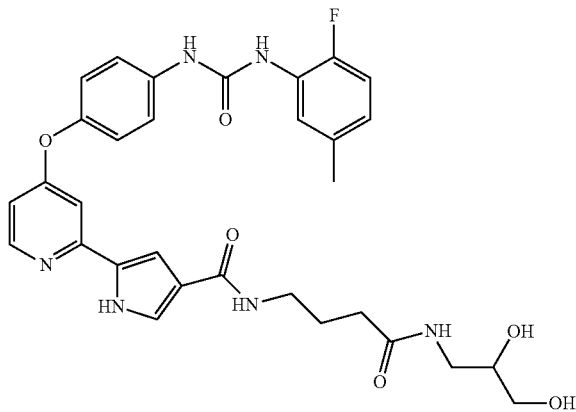 [SMILES: Cc1ccc(F)c(NC(=O)Nc2ccc(Oc3ccnc(-c4cc(C(=O)NCCCC(=O)NCC(O)CO)c[nH]4)c3)cc2)c1]

Similar procedure as Example 61.
¹H NMR (DMSO-d₆): 11.77 (br. s., 1H), 9.14 (s, 1H), 8.46 (d, J=2.3 Hz, 1H), 8.35 (d, J=5.9 Hz, 1H), 7.96 (dd, J=7.9, 2.1 Hz, 1H), 7.84 (t, J=5.6 Hz, 1H), 7.77 (t, J=5.9 Hz, 1H), 7.51-7.57 (m, 2H), 7.33 (dd, J=3.1, 1.6 Hz, 1H), 7.11-7.16 (m, 3H), 7.08 (dd, J=11.3, 8.4 Hz, 1H), 7.01-7.05 (m, 1H), 6.75-6.82 (m, 1H), 6.68 (dd, J=5.7, 2.5 Hz, 1H), 4.68 (d, J=5.0 Hz, 1H), 4.46 (t, J=5.9 Hz, 1H), 3.41-3.47 (m, 1H), 3.20-3.26 (m, 2H), 3.09-3.19 (m, 3H), 2.90-2.97 (m, 1H), 2.25 (s, 3H), 2.10 (t, J=7.6 Hz, 2H), 1.66 (quin, J=7.3 Hz, 2H)
LR MS (ES+): 605 (MH), 627 (M+Na⁺)
LR MS (ES−): 603 (M−H)

Example 55

N-(4-amino-4-oxobutyl)-5-{4-[4-({[(2-fluoro-5-methylphenyl)amino]carbonyl}amino)phenoxy]pyridin-2-yl}-1H-pyrrole-3-carboxamide

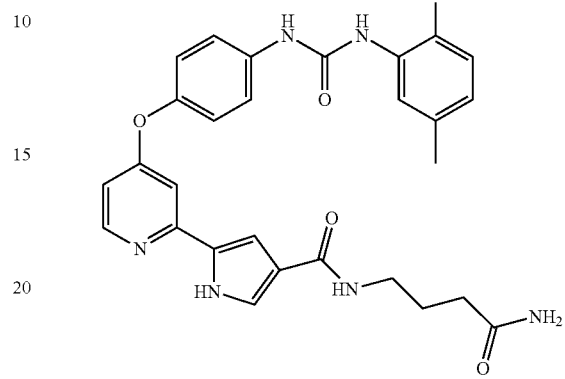

Similar procedure as Example 61.
¹H NMR (DMSO-d₆): 11.92 (br. s., 1H), 9.20 (br. s., 1H), 8.48 (d, J=1.8 Hz, 1H), 8.39 (d, J=5.9 Hz, 1H), 7.95 (dd, J=7.8, 1.9 Hz, 1H), 7.89 (br. s., 1H), 7.56 (d, J=8.8 Hz, 2H), 7.42 (br. s., 1H), 7.18-7.28 (m, 2H), 7.15 (d, J=8.8 Hz, 2H), 7.08 (dd, J=11.4, 8.5 Hz, 1H), 6.78 (ddd, J=7.5, 5.0, 2.2 Hz, 2H), 6.68 (br. s., 1H), 3.14 (q, J=6.7 Hz, 2H), 2.25 (s, 3H), 2.05 (t, J=7.5 Hz, 2H), 1.66 (quin, J=7.3 Hz, 2H)
LR MS (ES+): 553 (M+Na⁺)
LR MS (ES−): 529 (M−H)

Example 56

N-{2-[(2,3-dihydroxypropyl)amino]-2-oxoethyl}-5-{4-[4-({[(2-fluoro-5-methylphenyl)amino]carbonyl}amino)phenoxy]pyridin-2-yl}-1H-pyrrole-3-carboxamide

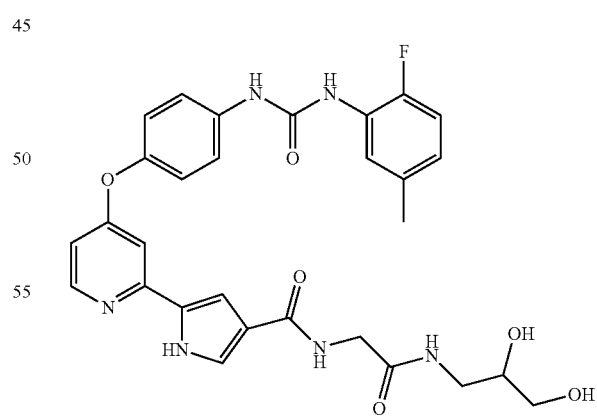

Similar procedure as Example 132.
¹H NMR (DMSO-d₆): 11.83 (br. s., 1H), 9.15 (s, 1H), 8.46 (br. s., 1H), 8.36 (d, J=5.9 Hz, 1H), 8.14 (t, J=6.0 Hz, 1H), 7.95 (d, J=7.6 Hz, 1H), 7.67 (t, J=5.6 Hz, 1H), 7.54 (d, J=8.8 Hz, 2H), 7.38 (br. s., 1H), 7.13 (d, J=8.8 Hz, 3H), 7.03-7.11 (m, 2H), 6.75-6.82 (m, 1H), 6.69 (dd, J=5.6, 2.3 Hz, 1H), 4.70

(d, J=5.0 Hz, 1H), 4.47 (t, J=5.7 Hz, 1H), 3.76 (d, J=5.6 Hz, 2H), 3.45 (dq, J=11.2, 5.5 Hz, 1H), 3.16-3.27 (m, 3H), 2.93-3.00 (m, 1H), 2.25 (s, 3H)
LR MS (ES+): 577 (MH), 599 (M+Na+)
LR MS (ES−): 575 (M−H)

Example 57

5-(2,3-dihydroxypropyl) 1-methyl 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate

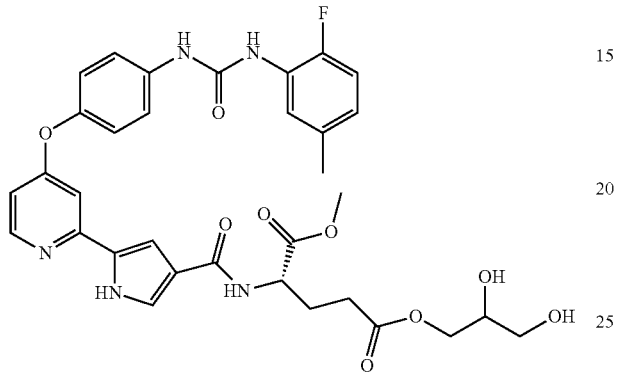

Similar procedure as Example 58.
$^1$H NMR (DMSO-d$_6$): 11.86 (br. s., 1H), 9.14 (s, 1H), 8.46 (d, J=2.3 Hz, 1H), 8.36 (d, J=5.6 Hz, 1H), 8.08-8.17 (m, 1H), 7.96 (dd, J=7.9, 1.8 Hz, 1H), 7.54 (d, J=8.5 Hz, 2H), 7.43 (br. s., 1H), 7.04-7.21 (m, 4H), 6.78 (dt, J=5.7, 2.7 Hz, 1H), 6.68 (dd, J=5.6, 2.3 Hz, 1H), 4.83 (d, J=5.3 Hz, 1H), 4.58 (t, J=5.7 Hz, 1H), 4.36-4.45 (m, 1H), 3.95-4.06 (m, 2H), 3.88 (dd, J=11.0, 6.6 Hz, 1H), 3.60 (s, 3H), 3.28-3.35 (m, 2H), 2.40 (t, J=7.6 Hz, 2H), 2.25 (s, 3H), 1.99-2.10 (m, 1H), 1.88-1.95 (m, 1H), 1.15 (t, J=7.0 Hz, 1H)
LR MS (ES+): 664 (MH), 686 (M+Na+)

Example 58 bis(2,3-dihydroxypropyl) 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate

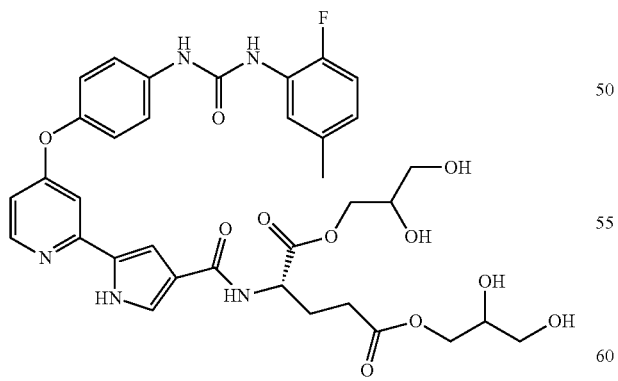

A mixture of 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioic acid (60 mg, 0.10 mmol), glycerol (0.5 ml), 1-Ethyl-3-(3-dimethylaminopropyl)carbodiimide hydrochloride (EDC.HCl, 37 mg, 0.19 mmol) and 4-dimethylaminopyridine (DMAP, 5 mg, 0.04 mmol) in anhydrous THF (10 ml) was stirred at 60° C. for 3 hours. The mixture was cooled to room temperature, concentrated and purified by silica gel chromatography eluting with a gradient of 10~15% MeOH/CHCl$_3$ to give bis(2,3-dihydroxypropyl) 2-{[(5-{-4-[4-({[(2-fluoro-5-methylphenyl)amino]carbonyl}amino)phenoxy]pyridin-2-yl}-1H-pyrrol-3-yl)carbonyl]amino}pentanedioate as colorless oil. Yield: 40 mg, 53%.
LR MS (ES+): 746 (M+Na+)
LR MS (ES−): 722 (M−H)

Example 59

4-{[(5-{4-[4-({[(2-fluoro-5-methylphenyl)amino]carbonyl}amino)phenoxy]pyridin-2-yl}-1H-pyrrol-3-yl)carbonyl]amino}-5-methoxy-5-oxopentanoic acid

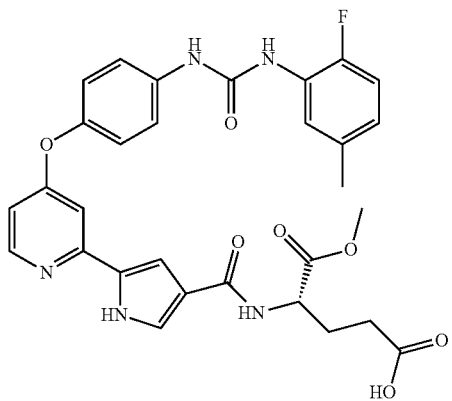 [SMILES: COC(=O)[C@H](CCC(=O)O)NC(=O)c1c[nH]c(-c2cc(Oc3ccc(NC(=O)Nc4cc(C)ccc4F)cc3)ccn2)c1]

Similar procedure as Example 132.
$^1$H NMR (DMSO-d$_6$): 11.98 (br. s., 1H), 9.19 (s, 1H), 8.48 (d, J=2.6 Hz, 1H), 8.39 (d, J=5.9 Hz, 1H), 8.13 (d, J=7.3 Hz, 1H), 7.95 (dd, J=7.8, 1.9 Hz, 1H), 7.53-7.57 (m, 2H), 7.47-7.52 (m, 1H), 7.24 (br. s., 1H), 7.19 (br. s., 1H), 7.15 (d, J=8.8 Hz, 2H), 7.08 (dd, J=11.3, 8.4 Hz, 1H), 6.72-6.81 (m, 2H), 4.38 (ddd, J=9.5, 7.5, 5.3 Hz, 1H), 3.60 (s, 3H), 2.31 (t, J=7.6 Hz, 2H), 2.25 (s, 3H), 1.95-2.05 (m, 1H), 1.82-1.93 (m, J=14.0, 9.6, 7.0, 7.0 Hz, 1H)
LR MS (ES−): 588 (M−H)

Example 60

N-[4-(ethylamino)-4-oxobutyl]-5-{4-[4-({[(2-fluoro-5-methylphenyl)amino]carbonyl}amino)phenoxy]pyridin-2-yl}-1H-pyrrole-3-carboxamide

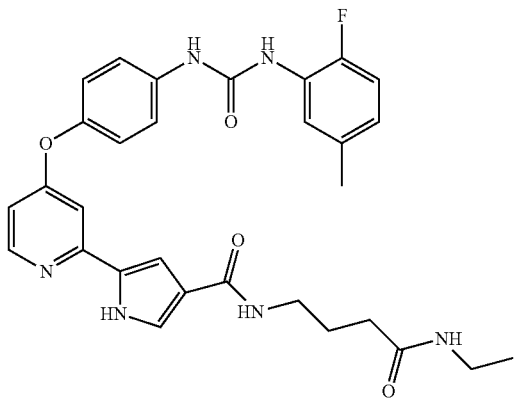 [SMILES: CCNC(=O)CCCNC(=O)c1c[nH]c(-c2cc(Oc3ccc(NC(=O)Nc4cc(C)ccc4F)cc3)ccn2)c1]

Similar procedure as Example 61.

¹H NMR (DMSO-d₆): 11.96 (br. s., 1H), 9.20 (s, 1H), 8.48 (d, J=2.6 Hz, 1H), 8.39 (d, J=5.9 Hz, 1H), 7.95 (dd, J=7.8, 1.9 Hz, 1H), 7.89 (br. s., 1H), 7.76 (t, J=5.3 Hz, 1H), 7.53-7.58 (m, 2H), 7.44 (br. s., 1H), 7.23 (br. s., 1H), 7.13-7.19 (m, 3H), 7.08 (dd, J=11.3, 8.4 Hz, 1H), 6.75-6.84 (m, 2H), 3.11-3.17 (m, 2H), 3.01 (qd, J=7.2, 5.6 Hz, 2H), 2.25 (s, 3H), 2.05 (t, J=7.5 Hz, 2H), 1.66 (quin, J=7.3 Hz, 2H), 0.96 (t, J=7.2 Hz, 3H)

LR MS (ES+): 559 (MH), 581 (M+Na⁺)

LR MS (ES−): 557 (M−H)

Example 61

5-{4-[4-({[(2-fluoro-5-methylphenyl)amino]carbonyl}amino)phenoxy]pyridin-2-yl}-N-[4-(3-hydroxypyrrolidin-1-yl)-4-oxobutyl]-1H-pyrrole-3-carboxamide

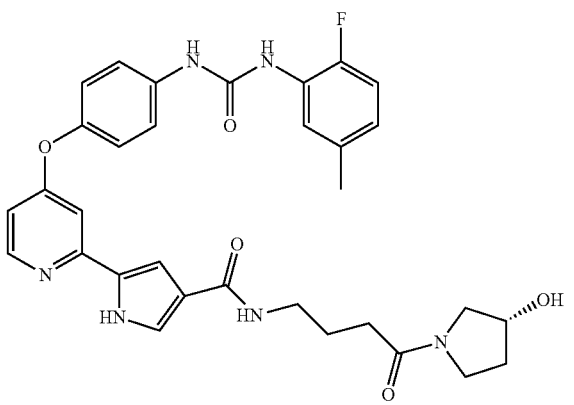 [SMILES: Cc1ccc(F)c(NC(=O)Nc2ccc(Oc3ccnc(-c4cc(C(=O)NCCCC(=O)N5CC[C@@H](O)C5)c[nH]4)c3)cc2)c1]

A mixture of 4-{[(5-{4-[4-({[(2-fluoro-5-methylphenyl)amino]carbonyl}amino)phenoxy]pyridin-2-yl}-1H-pyrrol-3-yl)carbonyl]amino}butanoic acid (60 mg, 0.11 mmol), HATU (50 mg, 0.13 mmol) and N,N-diisopropylethylamine (43 mg, 0.33 mmol) in anhydrous DMF (8 ml) was stirred at room temperature for 10 minutes, followed by addition of (R)-3-pyrrolidinol (14 mg, 0.16 mmol). The mixture was stirred for another 10 minutes and poured into 100 ml of water. 2M HCl was added dropwise until pH=4~5. The precipitates were filtered, washed with water and dried in vacuo to give 5-{4-[4-({[(2-fluoro-5-methylphenyl)amino]carbonyl}amino)phenoxy]pyridin-2-yl}-N-[4-(3-hydroxypyrrolidin-1-yl)-4-oxobutyl]-1H-pyrrole-3-carboxamide as white solid. Yield: 40 mg, 59%.

¹H NMR (DMSO-d₆): 11.97 (br. s., 1H), 9.31 (s, 1H), 8.53 (d, J=2.3 Hz, 1H), 8.39 (d, J=5.9 Hz, 1H), 7.95 (dd, J=7.8, 1.9 Hz, 1H), 7.91 (d, J=4.4 Hz, 1H), 7.54-7.59 (m, 2H), 7.42-7.48 (m, 1H), 7.24 (br. s., 1H), 7.16 (d, J=8.8 Hz, 2H), 7.05-7.10 (m, 1H), 6.78 (ddd, J=7.5, 5.0, 2.2 Hz, 2H), 4.24-4.28 (m, 0H), 4.16-4.21 (m, 1H), 3.40-3.48 (m, 2H), 3.35 (ddd, J=11.6, 8.4, 3.5 Hz, 1H), 3.25-3.30 (m, 1H), 3.14-3.25 (m, 4H), 2.25 (s, 3H), 2.23-2.27 (m, 1H), 2.20 (t, J=7.9 Hz, 1H), 1.84-1.92 (m, 1H), 1.75-1.82 (m, 1H), 1.65-1.73 (m, 2H)

LR MS (ES+): 601 (MH), 623 (M+Na⁺)

LR MS (ES−): 599 (M−H)

Example 62

5-{4-[4-({[(2-fluoro-5-methylphenyl)amino]carbonyl}amino)phenoxy]pyridin-2-yl}-N-[4-(hydroxyamino)-4-oxobutyl]-1H-pyrrole-3-carboxamide

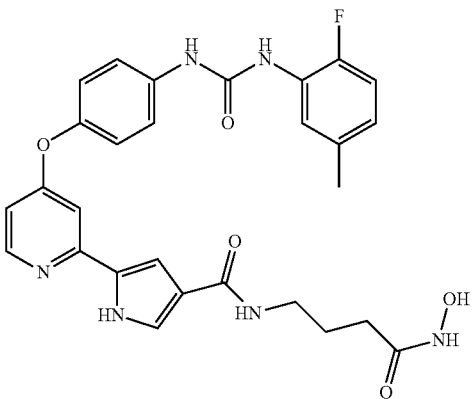 [SMILES: Cc1ccc(F)c(NC(=O)Nc2ccc(Oc3ccnc(-c4cc(C(=O)NCCCC(=O)NO)c[nH]4)c3)cc2)c1]

Similar procedure as Example 61.

¹H NMR (DMSO-d₆): 11.92 (br. s., 1H), 10.33 (s, 1H), 9.18 (s, 1H), 8.47 (d, J=2.6 Hz, 1H), 8.39 (d, J=5.9 Hz, 1H), 7.95 (dd, J=7.9, 1.8 Hz, 1H), 7.87-7.92 (m, 1H), 7.51-7.58 (m, 2H), 7.38-7.46 (m, 1H), 7.21 (br. s., 1H), 7.11-7.18 (m, 3H), 7.05-7.11 (m, 1H), 6.72-6.82 (m, 2H), 3.14 (q, J=6.7 Hz, 2H), 2.25 (s, 3H), 1.96 (t, J=7.6 Hz, 2H), 1.66 (quin, J=7.3 Hz, 2H)

LR MS (ES+): 547 (MH), 569 (M+Na⁺)

LR MS (ES−): 545 (M−H)

Example 63

2-{[(5-{4-[4-({[(2-fluoro-5-methylphenyl)amino]carbonyl}amino)phenoxy]pyridin-2-yl}-1H-pyrrol-3-yl)carbonyl]amino}pentanedioic acid

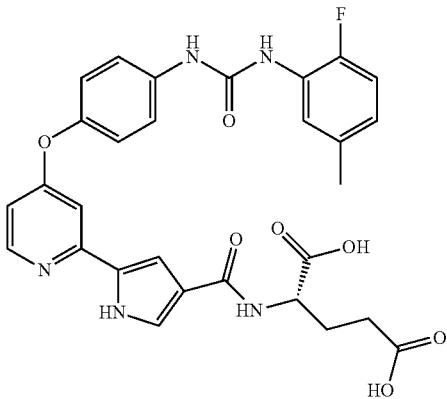 [SMILES: Cc1ccc(F)c(NC(=O)Nc2ccc(Oc3ccnc(-c4cc(C(=O)N[C@@H](CCC(=O)O)C(=O)O)c[nH]4)c3)cc2)c1]

Similar procedure as Example 132.

¹H NMR (DMSO-d₆): 12.42 (br. s., 1H), 12.12 (br. s., 1H), 11.86 (br. s., 1H), 9.15 (s, 1H), 8.46 (d, J=2.6 Hz, 1H), 8.37 (d, J=5.6 Hz, 1H), 7.93-8.01 (m, 2H), 7.51-7.58 (m, 2H), 7.44 (br. s., 1H), 7.18 (s, 1H), 7.11-7.16 (m, 3H), 7.08 (dd, J=11.3, 8.4 Hz, 1H), 6.75-6.82 (m, 1H), 6.69 (d, J=3.8 Hz, 1H), 4.32 (ddd, J=9.7, 7.9, 5.0 Hz, 1H), 2.30 (t, J=7.6 Hz, 2H), 2.25 (s, 3H), 1.96-2.05 (m, 1H), 1.80-1.91 (m, J=14.0, 9.8, 7.2, 7.2 Hz, 1H)

LR MS (ES−): 574 (M−H)

Example 64 dimethyl 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate

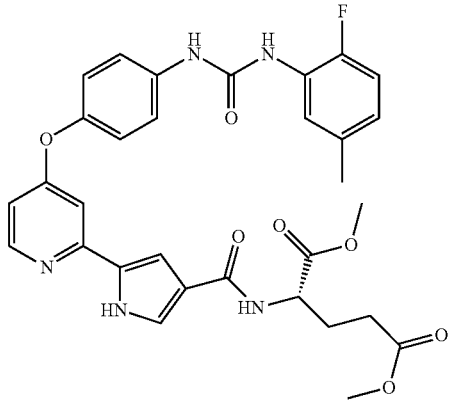 [SMILES: COC(=O)CC[C@H](NC(=O)c1c[nH]c(-c2cc(Oc3ccc(NC(=O)Nc4cc(C)ccc4F)cc3)ccn2)c1)C(=O)OC]

Similar procedure as Example 132.
$^1$H NMR (DMSO-d$_6$): 12.27 (br. s., 1H), 9.33 (br. s., 1H), 8.50-8.57 (m, 1H), 8.44 (d, J=6.2 Hz, 1H), 8.23 (d, J=6.7 Hz, 1H), 7.95 (d, J=6.5 Hz, 1H), 7.64 (br. s., 1H), 7.58 (d, J=8.8 Hz, 2H), 7.39 (br. s., 2H), 7.19 (d, J=8.8 Hz, 2H), 7.08 (dd, J=11.2, 8.2 Hz, 1H), 6.92 (br. s., 1H), 6.79 (d, J=5.6 Hz, 1H), 4.35-4.43 (m, 1H), 3.60 (s, 3H), 3.55 (s, 3H), 2.40 (t, J=7.5 Hz, 2H), 2.22-2.28 (m, 3H), 2.00-2.10 (m, 1H), 1.88-1.97 (m, 1H)
LR MS (ES+): 626 (M+Na$^+$)
LR MS (ES−): 602 (M−H)

Example 65

1-[(5-{4-[3-fluoro-4-({[(2-fluoro-5-methylphenyl)amino]carbonyl}amino)phenoxy]pyridin-2-yl}-1H-pyrrol-3-yl)carbonyl]pyrrolidine-3-carboxylic acid

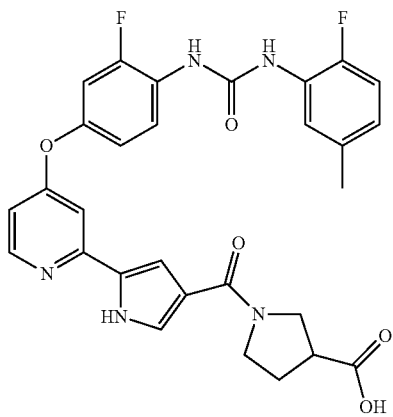 [SMILES: Cc1ccc(F)c(NC(=O)Nc2ccc(Oc3ccnc(-c4cc(C(=O)N5CCC(C(=O)O)C5)c[nH]4)c3)cc2F)c1]

Similar procedure as Example 132.
$^1$H NMR (DMSO-d$_6$): 12.47 (br. s., 1H), 11.85-12.01 (m, 1H), 9.05 (d, J=1.8 Hz, 1H), 8.94 (d, J=2.3 Hz, 1H), 8.39 (d, J=5.9 Hz, 1H), 8.22 (t, J=9.1 Hz, 1H), 7.98 (dd, J=7.8, 1.9 Hz, 1H), 7.41 (br. s., 1H), 7.21-7.32 (m, 2H), 7.06-7.14 (m, 2H), 7.01 (dd, J=9.0, 1.6 Hz, 1H), 6.79 (ddd, J=7.6, 5.1, 1.9 Hz, 1H), 6.65-6.76 (m, 1H), 2.97-3.93 (m, 5H), 2.25 (s, 3H), 1.93-2.19 (m, 2H)
LR MS (ES+): 562 (MH), 584 (M+Na$^+$)
LR MS (ES−): 560 (M−H)

Example 66

4-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}butanoic acid

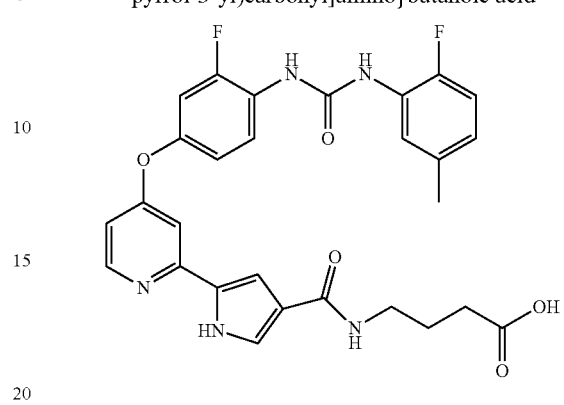

To a stirred solution of ethyl 4-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}butanoate (45 mg, 0.078 mmol) in 10 ml of THF was added 3 ml of 1M NaOH (3.0 mmol). The mixture was heated at 60° C. for 3 hours, cooled to room temperature and poured into 100 ml of water. 2M HCl was added until pH=5. The precipitates were filtered, washed with water, and dried to give 4-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}butanoic acid as grey solid. Yield: 40 mg, 93%.
$^1$H NMR (DMSO-d$_6$): 11.99 (br. s., 1H), 11.82 (br. s., 1H), 9.06 (d, J=2.1 Hz, 1H), 8.94 (d, J=2.6 Hz, 1H), 8.38 (d, J=5.9 Hz, 1H), 8.23 (t, J=9.1 Hz, 1H), 7.98 (dd, J=7.9, 2.1 Hz, 1H), 7.85 (t, J=5.7 Hz, 1H), 7.37 (br. s., 1H), 7.27 (dd, J=11.7, 2.6 Hz, 1H), 7.19 (s, 1H), 7.09 (dd, J=11.3, 8.4 Hz, 2H), 7.02 (dd, J=8.9, 1.6 Hz, 1H), 6.77-6.82 (m, 1H), 6.73-6.77 (m, 1H), 3.16 (q, J=6.7 Hz, 2H), 2.25 (s, 3H), 2.22 (t, J=7.3 Hz, 2H), 1.67 (quin, J=7.2 Hz, 2H)
LR MS (ES−): 548 (M−H)

Example 67 ethyl 4-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}butanoate

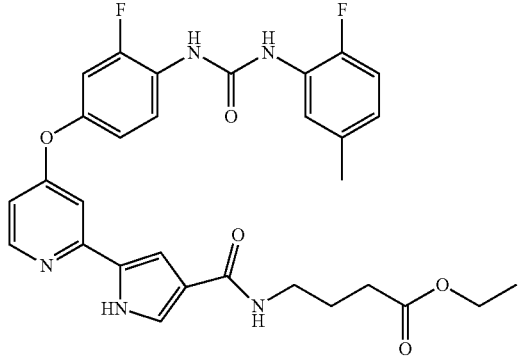 [SMILES: CCOC(=O)CCCNC(=O)c1c[nH]c(-c2cc(Oc3ccc(NC(=O)Nc4cc(C)ccc4F)c(F)c3)ccn2)c1]

Similar procedure as Example 132.
$^1$H NMR (DMSO-d$_6$): 11.99 (br. s., 1H), 9.09 (d, J=1.5 Hz, 1H), 8.96 (d, J=2.3 Hz, 1H), 8.42 (d, J=6.2 Hz, 1H), 8.26 (t, J=9.1 Hz, 1H), 7.98 (dd, J=7.8, 2.2 Hz, 1H), 7.86-7.94 (m, 1H), 7.46 (br. s., 1H), 7.25-7.34 (m, 2H), 7.22 (br. s., 1H), 7.09 (dd, J=11.3, 8.4 Hz, 1H), 7.02-7.07 (m, 1H), 6.87 (br. s., 1H), 6.76-6.82 (m, 1H), 4.01 (q, J=7.1 Hz, 2H), 3.13-3.21 (m, 2H), 2.30 (t, J=7.5 Hz, 2H), 2.25 (s, 3H), 1.70 (quin, J=7.2 Hz, 2H), 1.14 (t, J=7.04 Hz, 3H)

LR MS (ES+): 578 (MH), 600 (M+Na$^+$)

LR MS (ES−): 576 (M−H)

Example 68

4-{[(5-{4-[3-fluoro-4-({[(3-methylphenyl)amino]carbonyl}amino)phenoxy]pyridin-2-yl}-1H-pyrrol-3-yl)carbonyl]amino}butanoic acid

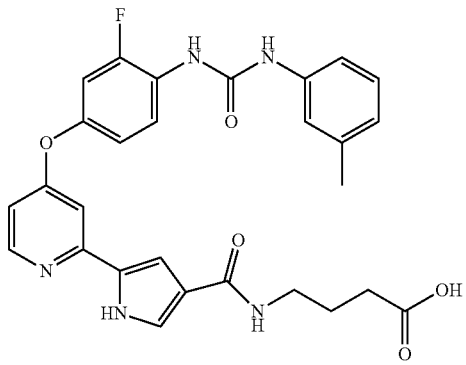 [SMILES: Cc1cccc(NC(=O)Nc2ccc(Oc3ccnc(-c4cc(C(=O)NCCCC(=O)O)c[nH]4)c3)cc2F)c1]

Similar procedure as Example 66.

$^1$H NMR (DMSO-d$_6$): 12.00 (br. s., 1H), 11.82 (br. s., 1H), 8.97 (s, 1H), 8.57 (d, J=2.3 Hz, 1H), 8.38 (d, J=5.9 Hz, 1H), 8.21 (t, J=9.1 Hz, 1H), 7.85 (t, J=5.7 Hz, 1H), 7.37 (br. s., 1H), 7.24-7.29 (m, 2H), 7.17-7.23 (m, 2H), 7.13-7.17 (m, 1H), 7.10 (br. s., 1H), 7.02 (dd, J=8.8, 1.8 Hz, 1H), 6.79 (d, J=7.3 Hz, 1H), 6.75 (br. s., 1H), 3.16 (q, J=6.7 Hz, 2H), 2.26 (s, 3H), 2.22 (t, J=7.3 Hz, 2H), 1.67 (quin, J=7.2 Hz, 2H)

LR MS (ES+): 532 (MH), 554 (M+Na$^+$)

LR MS (ES−): 530 (M−H)

Example 69

3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propanoic acid

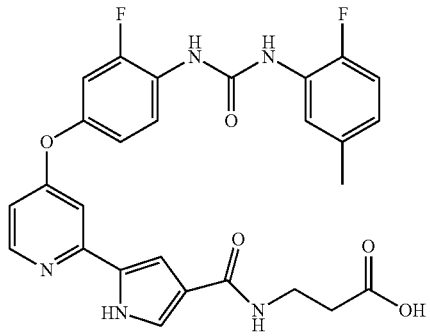 [SMILES: Cc1ccc(F)c(NC(=O)Nc2ccc(Oc3ccnc(-c4cc(C(=O)NCCC(=O)O)c[nH]4)c3)cc2F)c1]

Similar procedure as Example 66.

$^1$H NMR (DMSO-d$_6$): 11.93 (br. s., 2H), 9.08 (br. s., 1H), 8.96 (d, J=1.8 Hz, 1H), 8.41 (d, J=5.9 Hz, 1H), 8.25 (t, J=8.9 Hz, 1H), 7.98 (d, J=7.9 Hz, 1H), 7.94 (br. s., 1H), 7.43 (d, J=2.1 Hz, 1H), 7.29 (d, J=10.3 Hz, 1H), 7.24 (br. s., 1H), 7.17 (br. s., 1H), 7.09 (dd, J=11.3, 8.4 Hz, 1H), 7.04 (d, J=8.5 Hz, 1H), 6.83 (br. s., 1H), 6.76-6.81 (m, 1H), 3.33-3.38 (m, 2H), 2.44 (t, J=7.0 Hz, 2H), 2.25 (s, 3H)

LR MS (ES−): 534 (M−H)

Example 70

N-ethyl-5-{4-[3-fluoro-4-({[(3-methylphenyl)amino]carbonyl}amino)phenoxy]pyridin-2-yl}-1H-pyrrole-3-carboxamide

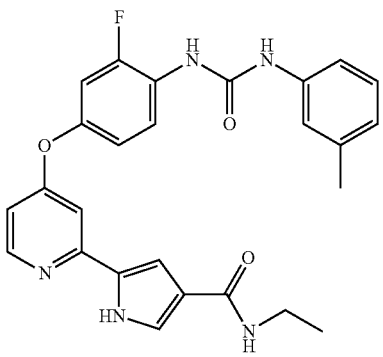 [SMILES: CCNC(=O)c1c[nH]c(-c2cc(Oc3ccc(NC(=O)Nc4cccc(C)c4)c(F)c3)ccn2)c1]

Similar procedure as Example 132.

$^1$H NMR (DMSO-d$_6$): 11.98 (br. s., 1H), 9.11 (s, 1H), 8.67 (br. s., 1H), 8.41 (d, J=5.9 Hz, 1H), 8.23 (t, J=9.1 Hz, 1H), 7.87 (t, J=5.0 Hz, 1H), 7.44 (br. s., 1H), 7.25-7.32 (m, 3H), 7.18-7.25 (m, 2H), 7.12-7.17 (m, 1H), 7.04 (dd, J=9.0, 1.6 Hz, 1H), 6.85 (br. s., 1H), 6.79 (d, J=7.3 Hz, 1H), 3.15-3.22 (m, 2H), 2.26 (s, 3H), 1.05 (t, J=7.2 Hz, 3H)

LR MS (ES+): 474 (MH), 496 (M+Na$^+$)

LR MS (ES−): 472 (M−H)

Example 71

{[(5-{4-[3-fluoro-4-({[(3-methylphenyl)amino]carbonyl}amino)phenoxy]pyridin-2-yl}-1H-pyrrol-3-yl)carbonyl]amino}acetic acid

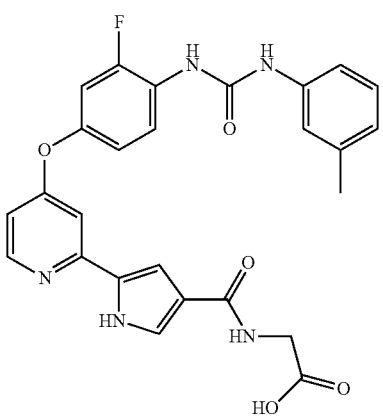 [SMILES: Cc1cccc(NC(=O)Nc2ccc(Oc3ccnc(-c4cc(C(=O)NCC(=O)O)c[nH]4)c3)cc2F)c1]

Similar procedure as Example 66.

$^1$H NMR (DMSO-d$_6$): 11.84 (br. s., 1H), 9.23 (s, 1H), 8.73 (d, J=1.5 Hz, 1H), 8.38 (d, J=5.6 Hz, 1H), 8.18 (t, J=9.1 Hz, 1H), 8.12 (t, J=5.4 Hz, 1H), 7.38 (dd, J=2.9, 1.8 Hz, 1H), 7.28 (s, 1H), 7.21-7.26 (m, 2H), 7.19 (d, J=2.3 Hz, 1H), 7.14 (t, J=7.8 Hz, 1H), 7.08-7.11 (m, 1H), 7.01 (dd, J=9.0, 2.5 Hz, 1H), 6.78 (d, J=7.3 Hz, 1H), 6.73 (dd, J=5.9, 2.3 Hz, 1H), 3.78 (d, J=5.9 Hz, 2H), 2.25 (s, 3H)

LR MS (ES−): 502 (M−H)

Example 72 methyl {[(5-{4-[3-fluoro-4-({[(3-methylphenyl)amino]carbonyl}amino)phenoxy]pyridin-2-yl}-1H-pyrrol-3-yl)carbonyl]amino}acetate

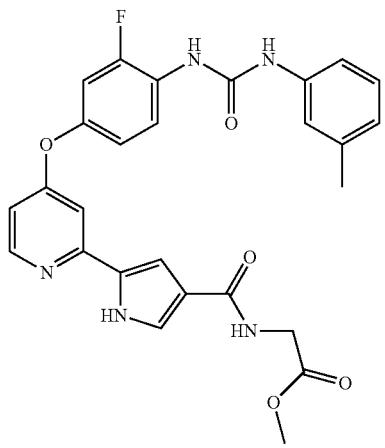 [SMILES: COC(=O)CNC(=O)c1c[nH]c(-c2cc(Oc3ccc(NC(=O)Nc4cccc(C)c4)c(F)c3)ccn2)c1]

Similar procedure as Example 132.
$^1$H NMR (DMSO-d$_6$): 11.87 (br. s., 1H), 8.96 (s, 1H), 8.56 (d, J=2.3 Hz, 1H), 8.38 (d, J=5.9 Hz, 1H), 8.31 (t, J=6.0 Hz, 1H), 8.20 (t, J=9.1 Hz, 1H), 7.39 (dd, J=3.2, 1.8 Hz, 1H), 7.24-7.29 (m, 2H), 7.21 (d, J=8.2 Hz, 1H), 7.19 (d, J=2.3 Hz, 1H), 7.13-7.17 (m, 1H), 7.08-7.10 (m, 1H), 7.01 (dd, J=8.5, 2.1 Hz, 1H), 6.79 (d, J=7.3 Hz, 1H), 6.74 (dd, J=5.9, 2.3 Hz, 1H), 3.90 (d, J=5.9 Hz, 2H), 3.60 (s, 3H), 2.26 (s, 3H)
LR MS (ES+): 518 (MH), 540 (M+Na$^+$)
LR MS (ES−): 516 (M−H)

Example 73

1-(2-fluoro-4-{[2-(4-{[(3R)-3-hydroxypyrrolidin-1-yl]carbonyl}-1H-pyrrol-2-yl)pyridin-4-yl]oxy}phenyl)-3-(3-methylphenyl)urea

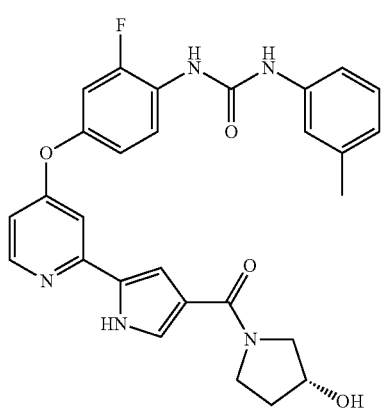 [SMILES: Cc1cccc(NC(=O)Nc2ccc(Oc3ccnc(-c4cc(C(=O)N5CC[C@@H](O)C5)c[nH]4)c3)cc2F)c1]

Similar procedure as Example 132.
$^1$H NMR (DMSO-d$_6$): 11.87 (br. s., 1H), 8.97 (s, 1H), 8.56 (d, J=2.1 Hz, 1H), 8.37 (d, J=5.9 Hz, 1H), 8.18 (t, J=9.1 Hz, 1H), 7.38 (d, J=2.3 Hz, 1H), 7.18-7.30 (m, 4H), 7.12-7.17 (m, 1H), 7.08 (d, J=18.8 Hz, 1H), 6.99 (dt, J=7.6, 1.5 Hz, 1H), 6.78 (d, J=7.6 Hz, 1H), 6.68 (dd, J=5.6, 2.3 Hz, 1H), 4.90 (d, J=9.4 Hz, 1H), 4.30 (br. s., 1H), 3.68-3.82 (m, 2H), 3.42-3.54 (m, 2H), 2.26 (s, 3H), 1.72-1.97 (m, 2H)
LR MS (ES+): 516 (MH), 538 (M+Na$^+$)
LR MS (ES−): 514 (M−H)

Example 74

1-{2-fluoro-4-[(2-{4-[(3-hydroxypiperidin-1-yl)carbonyl]-1H-pyrrol-2-yl}pyridin-4-yl)oxy]phenyl}-3-(3-methylphenyl)urea

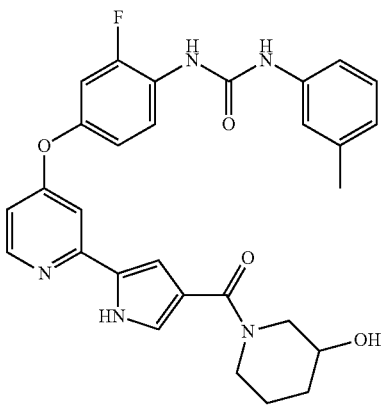 [SMILES: Cc1cccc(NC(=O)Nc2ccc(Oc3ccnc(-c4cc(C(=O)N5CCCC(O)C5)c[nH]4)c3)cc2F)c1]

Similar procedure as Example 132.
$^1$H NMR (DMSO-d$_6$): 11.83 (br. s., 1H), 8.96 (s, 1H), 8.55 (d, J=2.3 Hz, 1H), 8.37 (d, J=5.6 Hz, 1H), 8.19 (t, J=9.1 Hz, 1H), 7.34 (d, J=2.3 Hz, 1H), 7.27 (s, 1H), 7.19-7.25 (m, 2H), 7.15 (t, J=7.8 Hz, 1H), 7.12 (br. s., 1H), 6.97-7.01 (m, 1H), 6.90 (s, 1H), 6.79 (d, J=7.6 Hz, 1H), 6.68 (dd, J=5.7, 2.2 Hz, 1H), 4.87 (br. s., 1H), 4.04 (br. s., 1H), 3.85 (br. s., 1H), 3.41-3.52 (m, 1H), 3.07 (t, J=10.1 Hz, 1H), 2.26 (s, 3H), 1.78-1.90 (m, 1H), 1.67 (td, J=8.8, 4.7 Hz, 1H), 1.30-1.43 (m, 2H)
LR MS (ES+): 530 (MH), 552 (M+Na$^+$)
LR MS (ES−): 528 (M−H)

Example 75

5-{4-[3-fluoro-4-({[(3-methylphenyl)amino]carbonyl}amino)phenoxy]pyridin-2-yl}-1H-pyrrole-3-carboxylic acid

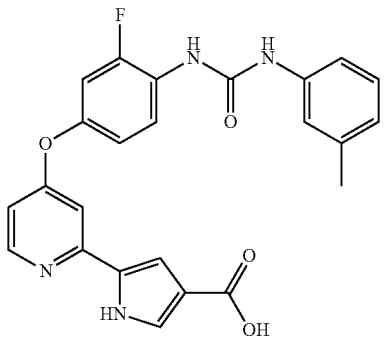 [SMILES: Cc1cccc(NC(=O)Nc2ccc(Oc3ccnc(-c4cc(C(=O)O)c[nH]4)c3)cc2F)c1]

Similar procedure as Example 134.
$^1$H NMR (DMSO-d$_6$): 12.04 (br. s., 1H), 11.87 (br. s., 1H), 8.97 (br. s., 1H), 8.56 (br. s., 1H), 8.39 (d, J=5.9 Hz, 1H), 8.20 (t, J=9.1 Hz, 1H), 7.36 (br. s., 2H), 7.19-7.30 (m, 3H), 7.12-7.17 (m, 1H), 7.08 (br. s., 1H), 7.00 (d, J=8.8 Hz, 1H), 6.79 (d, J=7.3 Hz, 1H), 6.73 (br. s., 1H), 2.26 (s, 3H)
LR MS (ES+): 469 (MH)

Example 76 methyl 5-{4-[3-fluoro-4-({[(3-methylphenyl)amino]carbonyl}amino)phenoxy]pyridin-2-yl}-1H-pyrrole-3-carboxylate

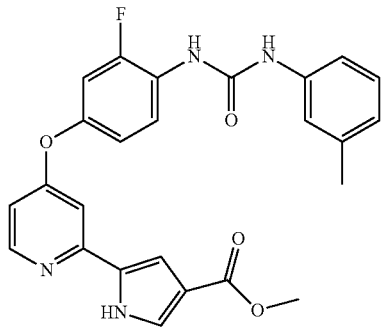 [SMILES: COC(=O)c1c[nH]c(-c2cc(Oc3ccc(NC(=O)Nc4cccc(C)c4)c(F)c3)ccn2)c1]

Similar procedure as Example 135.

$^1$H NMR (DMSO-d$_6$): 12.11 (br. s., 1H), 8.96 (s, 1H), 8.55 (s, 1H), 8.38 (d, J=5.9 Hz, 1H), 8.19 (t, J=9.1 Hz, 1H), 7.42 (dd, J=3.1, 1.6 Hz, 1H), 7.37 (d, J=2.1 Hz, 1H), 7.28 (s, 1H), 7.19-7.26 (m, 2H), 7.12-7.17 (m, 1H), 7.09-7.12 (m, 1H), 7.00 (dd, J=9.1, 2.3 Hz, 1H), 6.79 (d, J=7.3 Hz, 1H), 6.72 (dd, J=5.6, 2.3 Hz, 1H), 3.69 (s, 3H), 2.26 (s, 3H)

LR MS (ES+): 461 (MH), 483 (M+Na$^+$)

LR MS (ES−): 459 (M−H)

Example 77

5-{4-[4-({[(2-fluoro-5-methylphenyl)amino]carbonyl}amino)phenoxy]pyridin-2-yl}-N-(2-{2-[2-(2-hydroxyethoxy)ethoxy]ethoxy}ethyl)-1H-pyrrole-3-carboxamide

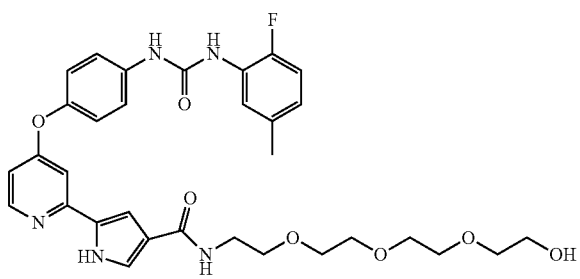 [SMILES: Cc1ccc(F)c(NC(=O)Nc2ccc(Oc3ccnc(-c4cc(C(=O)NCCOCCOCCOCCO)c[nH]4)c3)cc2)c1]

Similar procedure as Example 132.

$^1$H NMR (DMSO-d$_6$): 11.92 (br. s., 1H), 9.20 (s, 1H), 8.48 (br. s., 1H), 8.38 (d, J=5.6 Hz, 1H), 7.96 (d, J=7.9 Hz, 1H), 7.92 (br. s., 1H), 7.55 (d, J=8.8 Hz, 2H), 7.43 (br. s., 1H), 7.20 (br. s., 1H), 7.11-7.17 (m, 3H), 7.08 (dd, J=11.2, 8.5 Hz, 1H), 6.73-6.81 (m, 2H), 3.41-3.48 (m, 12H), 3.34-3.39 (m, 2H), 3.31 (q, J=5.8 Hz, 2H), 2.25 (s, 3H)

LR MS (ES+): 622 (MH), 644 (M+Na$^+$)

LR MS (ES−): 620 (M−H)

Example 78

4-{[(5-{4-[4-({[(2-fluoro-5-methylphenyl)amino]carbonyl}amino)phenoxy]pyridin-2-yl}-1H-pyrrol-3-yl)carbonyl]amino}butanoic acid

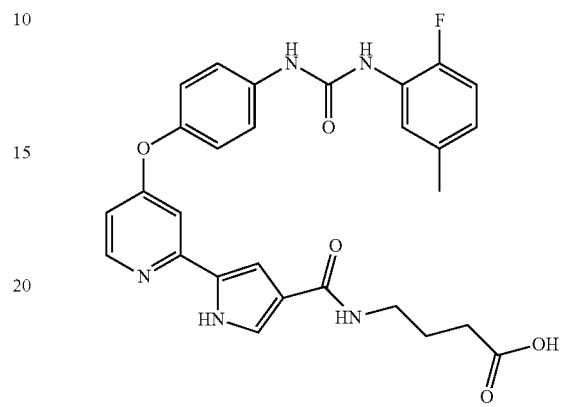

Similar procedure as Example 66.

$^1$H NMR (DMSO-d$_6$): 11.83 (br. s., 1H), 9.17 (s, 1H), 8.49 (d, J=2.3 Hz, 1H), 8.39 (d, J=5.9 Hz, 1H), 7.95-8.02 (m, 1H), 7.88 (t, J=5.6 Hz, 1H), 7.57 (d, J=9.1 Hz, 2H), 7.38 (br. s., 1H), 7.16 (d, J=9.1 Hz, 2H), 7.06-7.17 (m, 3H), 6.77-6.85 (m, 1H), 6.67-6.76 (m, 1H), 3.16-3.22 (m, 2H), 2.28 (s, 3H), 2.25 (t, J=7.3 Hz, 2H), 1.70 (quin, J=7.2 Hz, 2H)

LR MS (ES+): 532 (MH)

LR MS (ES−): 530 (M−H)

Example 79 ethyl 4-{[(5-{4-[4-({[(2-fluoro-5-methylphenyl)amino]carbonyl}amino)phenoxy]pyridin-2-yl}-1H-pyrrol-3-yl)carbonyl]amino}butanoate

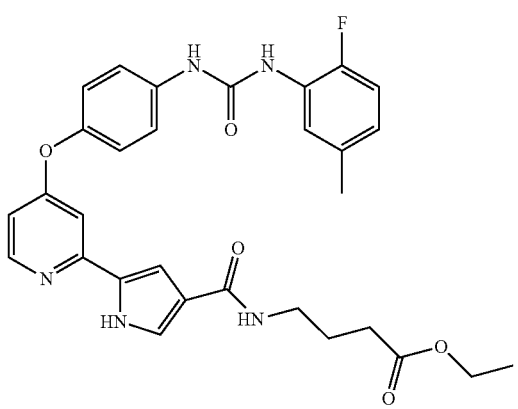 [SMILES: CCOC(=O)CCCNC(=O)c1c[nH]c(-c2cc(Oc3ccc(NC(=O)Nc4cc(C)ccc4F)cc3)ccn2)c1]

Similar procedure as Example 132.

LR MS (ES+): 560 (MH), 582 (M+Na$^+$)

LR MS (ES−): 558 (M−H)

Preparation of 4-(2-Chloro-pyridin-4-ylsulfanyl)-phenylamine

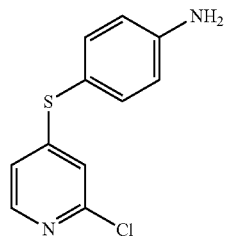 [SMILES: Nc1ccc(Sc2ccnc(Cl)c2)cc1]

2,4-Dichloropyrdine (4.44 g, 30.0 mmol) and potassium carbonate (8.28 g, 60.0 mmol) in dimethylformamide (60 mL) was purged with nitrogen for 10 min. 4-Aminothiophenol (3.76 g, 30.0 mmol) was added and the mixture stirred under nitrogen at room temperature for 18 h. Water (300 mL) was added and the slurry stirred for 30 min. The resulting solid was filtered, washed with water and vacuum dried at room temperature. Recrystallization from ethyl acetate (35 mL), filtered hot, then cooled gave 4-(2-Chloro-pyridin-4-ylsulfanyl)-phenylamine (3.946 g, 56% yield).

Preparation of 1-[4-(2-Chloro-pyridin-4-ylsulfanyl)-phenyl]-3-(2-fluoro-5-methyl-phenyl)-urea

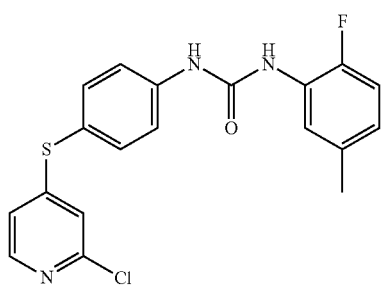 [SMILES: Cc1ccc(F)c(NC(=O)Nc2ccc(Sc3ccnc(Cl)c3)cc2)c1]

To a stirred solution of 4-(2-Chloro-pyridin-4-ylsulfanyl)-phenylamine (300 mg, 1.27 mmol) in anhydrous THF (10 ml) was added 2-fluoro-5-methyl-phenylisocyanate (210 mg, 1.39 mmol). The mixture was stirred at 60° C. for 5 hours, and poured into 100 ml of water. The precipitates were filtered, washed with water (50 ml), and dried to give the crude, which was purified by silica gel chromatography eluting with 2-3% MeOH/CHCl$_3$ to give 1-[4-(2-Chloro-pyridin-4-ylsulfanyl)-phenyl]-3-(2-fluoro-5-methyl-phenyl)-urea as white solid. Yield: 410 mg, 83%.

$^1$H NMR (DMSO-d$_6$): 9.37 (s, 1H), 8.57 (d, J=2.1 Hz, 1H), 8.17 (d, J=5.9 Hz, 1H), 7.89-8.01 (m, 1H), 7.58-7.70 (m, 2H), 7.47-7.59 (m, 2H), 7.10 (dd, J=11.4, 8.2 Hz, 1H), 6.94-7.03 (m, 2H), 6.82 (dd, J=4.8, 2.2 Hz, 1H), 2.26 (s, 3H)

Example 80

5-(4-{[4-({[(2-fluoro-5-methylphenyl)amino]carbonyl}amino)phenyl]thio}pyridin-2-yl)-1H-pyrrole-3-carboxylic acid

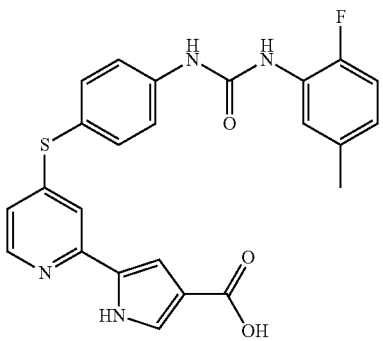 [SMILES: Cc1ccc(F)c(NC(=O)Nc2ccc(Sc3ccnc(-c4cc(C(=O)O)c[nH]4)c3)cc2)c1]

To a stirred solution of methyl 5-(4-{[4-({[(2-fluoro-5-methylphenyl)amino]carbonyl}amino)phenyl]thio}pyridin-2-yl)-1H-pyrrole-3-carboxylate (86 mg, 0.18 mmol) in a mixture of solvents THF/MeOH (5 ml/5 ml) was added 2 ml of 1M NaOH (2 mmol) solution. The mixture was heated in a 66° C. bath for 7 hours, cooled to room temperature and poured into 100 ml of water. 2M HCl was added until pH=3. The resulting precipitates were filtered, washed with water, and dried in vacuo to give 5-(4-{[4-({[(2-fluoro-5-methylphenyl)amino]carbonyl}amino)phenyl]thio}pyridin-2-yl)-1H-pyrrole-3-carboxylic acid as light brown solid. Yield: 73 mg, 88%.

$^1$H NMR (DMSO-d$_6$): 12.01 (br. s., 1H), 9.37 (s, 1H), 8.56 (d, J=1.8 Hz, 1H), 8.27 (d, J=5.6 Hz, 1H), 7.95 (s, 1H), 7.44-7.68 (m, 5H), 7.36 (br. s., 1H), 7.10 (dd, J=11.1, 8.5 Hz, 1H), 6.94 (br. s., 1H), 6.81 (br. s., 1H), 6.69 (d, J=5.3 Hz, 1H), 2.26 (s, 3H).

LR MS (ES−): 461 (M−H)

Example 81

3-{[(5-{4-[4-({[(2-fluoro-5-methylphenyl)amino]carbonyl}amino)phenoxy]pyridin-2-yl}-1H-pyrrol-3-yl)carbonyl]amino}propanoic acid

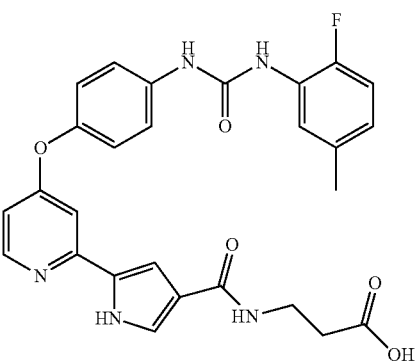 [SMILES: Cc1ccc(F)c(NC(=O)Nc2ccc(Oc3ccnc(-c4cc(C(=O)NCCC(=O)O)c[nH]4)c3)cc2)c1]

Similar procedure as Example 66.

$^1$H NMR (DMSO-d$_6$): 12.12 (br. s., 1H), 11.81 (br. s., 1H), 9.15 (s, 1H), 8.46 (br. s., 1H), 8.36 (d, J=5.6 Hz, 1H), 7.96 (d, J=7.6 Hz, 1H), 7.92 (t, J=5.3 Hz, 1H), 7.54 (d, J=8.8 Hz, 2H), 7.35 (br. s., 1H), 7.13 (dd, J=6.6, 2.2 Hz, 3H), 7.08 (dd, J=11.2, 8.5 Hz, 1H), 7.04 (br. s., 1H), 6.75-6.82 (m, 1H), 6.70 (d, J=3.2 Hz, 1H), 3.32-3.41 (m, 2H), 2.43 (t, J=7.0 Hz, 2H), 2.25 (s, 3H)

LR MS (ES+): 518 (MH), 540 (M+Na⁺)
LR MS (ES−): 516 (M−H)

Example 82

4-{S-methyl-N-[(5-{4-[4-({[(3-methylphenyl)amino]carbonyl}amino)phenoxy]pyridin-2-yl}-1H-pyrrol-3-yl)carbonyl]sulfonimidoyl}butanoic acid

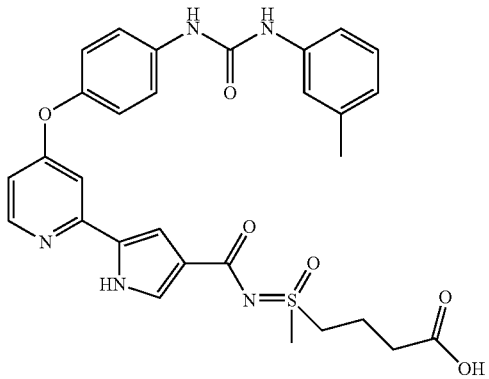 [SMILES: Cc1cccc(NC(=O)Nc2ccc(Oc3ccnc(-c4cc(C(=O)N=S(C)(=O)CCCC(=O)O)c[nH]4)c3)cc2)c1]

To a stirred solution of methyl 4-{S-methyl-N-[(5-{4-[4-({[(3-methylphenyl)amino]carbonyl}amino)phenoxy]pyridin-2-yl}-1H-pyrrol-3-yl)carbonyl]sulfonimidoyl}butanoate (5 mg, 0.0087 mol) in MeOH (3 ml) was added 1M NaOH (0.5 ml, 0.5 mmol). The mixture was stirred at room temperature for 30 minutes, and poured into 30 ml of water. 2M HCl was added dropwise until pH=4. The precipitates were filtered, washed with water and dried to give 4-{S-methyl-N-[(5-{4-[4-({[(3-methylphenyl)amino]carbonyl}amino)phenoxy]pyridin-2-yl}-1H-pyrrol-3-yl)carbonyl]sulfonimidoyl}butanoic acid as off-white solid. Yield: 5 mg, 100%.

LR MS (ES+): 576 (MH), 598 (M+Na⁺)
LR MS (ES−): 574 (M−H)

Example 83

1-[(5-{4-[4-({[(2-fluoro-5-methylphenyl)amino]carbonyl}amino)phenoxy]pyridin-2-yl}-1H-pyrrol-3-yl)carbonyl]pyrrolidine-3-carboxylic acid

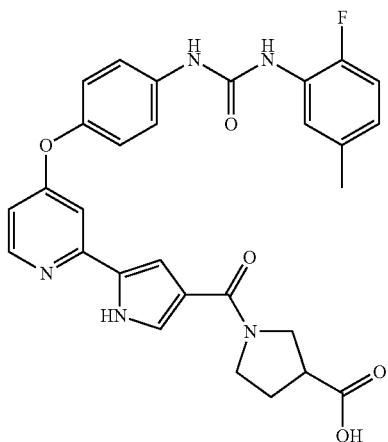 [SMILES: Cc1ccc(F)c(NC(=O)Nc2ccc(Oc3ccnc(-c4cc(C(=O)N5CCC(C(=O)O)C5)c[nH]4)c3)cc2)c1]

Similar procedure as Example 132.
¹H NMR (DMSO-d₆): 12.04 (br. s., 1H), 9.16 (s, 1H), 8.46 (d, J=2.3 Hz, 1H), 8.39 (d, J=5.6 Hz, 1H), 7.93-7.99 (m, 1H), 7.54 (d, J=9.1 Hz, 2H), 7.41 (br. s., 1H), 7.33 (br. s., 1H), 7.14 (d, J=8.8 Hz, 2H), 7.08 (dd, J=11.3, 8.4 Hz, 1H), 6.75-6.82 (m, 1H), 6.72 (br. s., 1H), 2.98-3.93 (m, 5H), 2.25 (s, 3H), 1.93-2.19 (m, 2H)

LR MS (ES+): 544 (MH), 566 (M+Na⁺)
LR MS (ES−): 542 (M−H)

Example 84

{[(5-{4-[4-({[(2-fluoro-5-methylphenyl)amino]carbonyl}amino)phenoxy]pyridin-2-yl}-1H-pyrrol-3-yl)carbonyl]amino}acetic acid

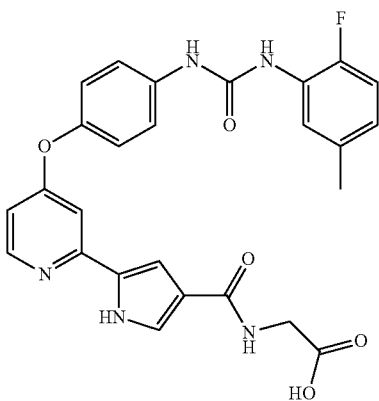 [SMILES: Cc1ccc(F)c(NC(=O)Nc2ccc(Oc3ccnc(-c4cc(C(=O)NCC(=O)O)c[nH]4)c3)cc2)c1]

Similar procedure as Example 66.
¹H NMR (DMSO-d₆): 12.42 (br. s., 1H), 11.85 (br. s., 1H), 9.15 (s, 1H), 8.47 (d, J=2.1 Hz, 1H), 8.37 (d, J=5.9 Hz, 1H), 8.21 (t, J=6.0 Hz, 1H), 7.90-8.03 (m, 1H), 7.55 (d, J=8.8 Hz, 2H), 7.38 (br. s., 1H), 7.02-7.21 (m, 5H), 6.74-6.84 (m, 1H), 6.70 (dd, J=5.6, 2.3 Hz, 1H), 3.82 (d, J=5.9 Hz, 2H), 2.26 (s, 3H)

LR MS (ES+): 504 (MH), 526 (M+Na⁺)
LR MS (ES−): 502 (M−H)

Example 85 methyl {[(5-{4-[4-({[(2-fluoro-5-methylphenyl)amino]carbonyl}amino)phenoxy]pyridin-2-yl}-1H-pyrrol-3-yl)carbonyl]amino}acetate

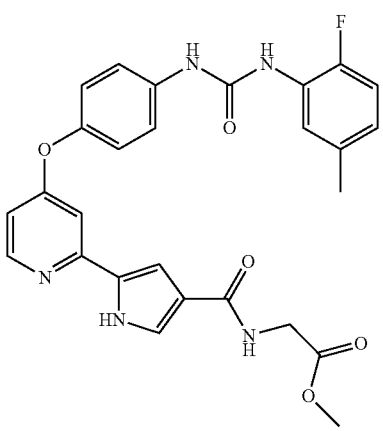 [SMILES: COC(=O)CNC(=O)c1c[nH]c(-c2cc(Oc3ccc(NC(=O)Nc4cc(C)ccc4F)cc3)ccn2)c1]

Similar procedure as Example 132.
¹H NMR (DMSO-d₆): 12.00 (br. s., 1H), 9.18 (s, 1H), 8.48 (d, J=2.1 Hz, 1H), 8.29-8.44 (m, 2H), 7.97 (d, J=7.9 Hz, 1H), 7.56 (d, J=9.1 Hz, 2H), 7.46 (br. s., 1H), 7.02-7.27 (m, 5H), 6.79 (d, J=2.1 Hz, 2H), 3.91 (d, J=6.2 Hz, 2H), 3.61 (s, 3H), 2.26 (s, 3H)

LR MS (ES+): 518 (MH), 540 (M+Na⁺)
LR MS (ES−): 516 (M−H)

Example 86

1-[(5-{4-[4-({[(2-fluoro-5-methylphenyl)amino]carbonyl}amino)phenoxy]pyridin-2-yl}-1H-pyrrol-3-yl)carbonyl]piperidine-4-sulfonic acid

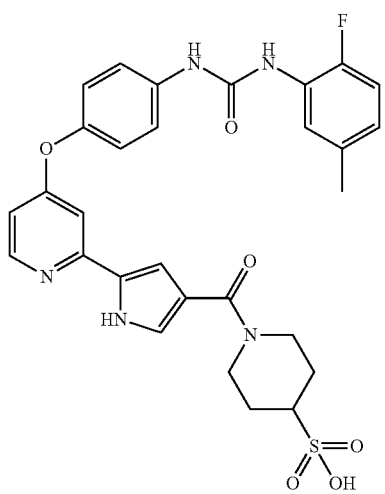 [SMILES: Cc1ccc(F)c(NC(=O)Nc2ccc(Oc3ccnc(-c4cc(C(=O)N5CCC(S(=O)(=O)O)CC5)c[nH]4)c3)cc2)c1]

Similar procedure as Example 132.

$^1$H NMR (DMSO-$d_6$): 12.41 (br. s., 1H), 9.24 (s, 1H), 8.46-8.53 (m, 2H), 7.91-7.98 (m, 1H), 7.54-7.64 (m, 3H), 7.45 (br. s., 1H), 7.30 (br. s., 1H), 7.22 (d, J=8.8 Hz, 2H), 7.08 (dd, J=11.2, 8.2 Hz, 1H), 7.02 (br. s., 1H), 6.75-6.82 (m, 1H), 4.29 (br. s., 2H), 3.52 (br. s., 2H), 2.48-2.56 (m, 1H), 2.25 (s, 3H), 1.93 (d, J=12.6 Hz, 2H), 1.45 (br. s., 2H)

LR MS (ES+): 616 (M+Na$^+$)

LR MS (ES−): 592 (M−H)

Example 87 methyl 4-{S-methyl-N-[(5-{4-[4-({[(3-methylphenyl)amino]carbonyl}amino)phenoxy]pyridin-2-yl}-1H-pyrrol-3-yl)carbonyl]sulfonimidoyl}butanoate

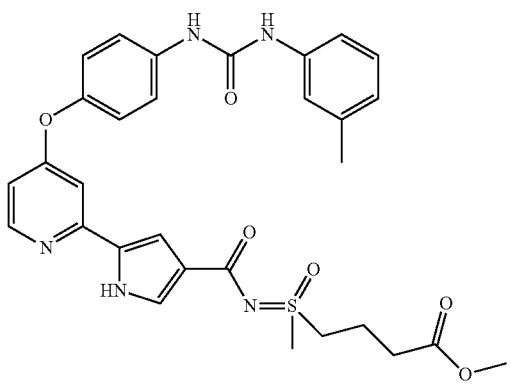 [SMILES: COC(=O)CCCS(C)(=O)=NC(=O)c1c[nH]c(-c2cc(Oc3ccc(NC(=O)Nc4cccc(C)c4)cc3)ccn2)c1]

Similar procedure as Example 101.

LR MS (ES+): 590 (MH), 612 (M+Na$^+$)

Example 88 methyl 5-(4-{[4-({[(2-fluoro-5-methylphenyl)amino]carbonyl}amino)phenyl]thio}pyridin-2-yl)-1H-pyrrole-3-carboxylate

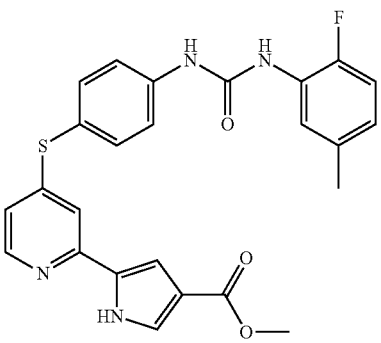 [SMILES: COC(=O)c1c[nH]c(-c2cc(Sc3ccc(NC(=O)Nc4cc(C)ccc4F)cc3)ccn2)c1]

A mixture of 1-[4-(2-Chloro-pyridin-4-ylsulfanyl)-phenyl]-3-(2-fluoro-5-methyl-phenyl)-urea (410 mg, 1.06 mmol), methyl-(5-(4,4,5,5-tetramethyl-1,3,2-dioxaborolan-2-yl)-1H-pyrrole-3-carboxylate (532 mg, 2.12 mmol) and PdCl$_2$(dppf).CH$_2$Cl$_2$ (10 mg, 0.012 mmol) was added to a thick-walled reaction vessel and purged with N$_2$. A solution of 2M Na$_2$CO$_3$ (1.0 mL) was added, followed by DMSO (10 mL). The reaction vessel was sealed and the mixture stirred at 95° C. for 16 h. The reaction vessel was cooled to room temperature and the mixture was poured into 100 ml of water. The precipitates were filtered, washed with water and dried to give the crude, which was purified via silica gel chromatography eluting with 2-5% MeOH/CHCl$_3$ to afford methyl 5-(4-{[4-({[(2-fluoro-5-methylphenyl)amino]carbonyl}amino)phenyl]thio}pyridin-2-yl)-1H-pyrrole-3-carboxylate as off-white solid. Yield: 100 mg, 20% yield.

LR MS (ES+): 477 (MH), 499 (M+Na$^+$)

Example 89

N-methyl-5-{4-[4-({[(3-methylphenyl)amino]carbonyl}amino)phenoxy]pyridin-2-yl}-1H-pyrrole-3-carboxamide

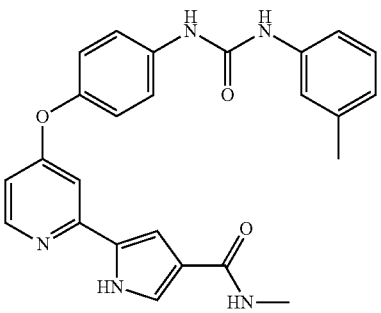 [SMILES: CNC(=O)c1c[nH]c(-c2cc(Oc3ccc(NC(=O)Nc4cccc(C)c4)cc3)ccn2)c1]

Similar procedure as Example 132.

$^1$H NMR (DMSO-$d_6$): 11.88 (br. s., 1H), 8.89 (s, 1H), 8.69 (s, 1H), 8.37 (d, J=5.9 Hz, 1H), 7.82 (d, J=4.4 Hz, 1H), 7.52-7.58 (m, 2H), 7.37 (br. s., 1H), 7.27 (s, 1H), 7.22 (d, J=8.2 Hz, 1H), 7.18 (br. s., 1H), 7.11-7.15 (m, 3H), 7.08 (br. s., 1H), 6.71-6.80 (m, 2H), 2.67 (d, J=4.7 Hz, 3H), 2.25 (s, 3H)

Example 90

1-{4-[(2-{4-[(3-hydroxypiperidin-1-yl)carbonyl]-1H-pyrrol-2-yl}pyridin-4-yl)oxy]phenyl}-3-(3-methylphenyl)urea

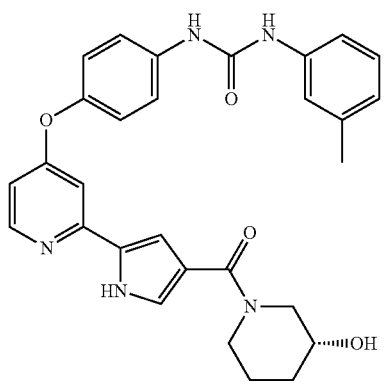 [SMILES: Cc1cccc(NC(=O)Nc2ccc(Oc3ccnc(-c4cc(C(=O)N5CCC[C@@H](O)C5)c[nH]4)c3)cc2)c1]

Similar procedure as Example 132.

LR MS (ES+): 512 (MH), 534 (M+Na⁺)

LR MS (ES−): 510 (M−H)

Example 91

1-{4-[(2-{4-[(3-hydroxypyrrolidin-1-yl)carbonyl]-1H-pyrrol-2-yl}pyridin-4-yl)oxy]phenyl}-3-(3-methylphenyl)urea

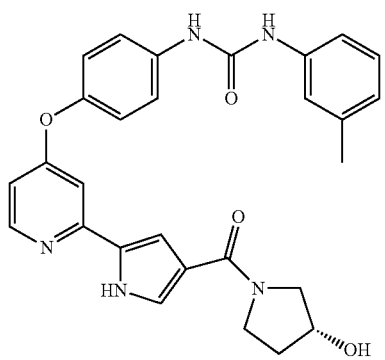 [SMILES: Cc1cccc(NC(=O)Nc2ccc(Oc3ccnc(-c4cc(C(=O)N5CC[C@@H](O)C5)c[nH]4)c3)cc2)c1]

Similar procedure as Example 132.

$^1$H NMR (DMSO-d$_6$): 11.88 (br. s., 1H), 8.74 (s, 1H), 8.58 (s, 1H), 8.36 (d, J=5.6 Hz, 1H), 7.54 (d, J=8.8 Hz, 2H), 6.99-7.39 (m, 8H), 6.78 (d, J=7.0 Hz, 1H), 6.62 (dd, J=5.6, 2.3 Hz, 1H), 4.91 (br. s., 1H), 4.31 (br. s., 1H), 3.67-3.87 (m, 2H), 3.49 (br. s., 2H), 2.26 (s, 3H), 1.88 (br. s., 2H)

LR MS (ES+): 520 (M+Na⁺)

Example 92

N-(2,3-dihydroxypropyl)-5-{4-[4-({[(3-methylphenyl)amino]carbonyl}amino)phenoxy]pyridin-2-yl}-1H-pyrrole-3-carboxamide

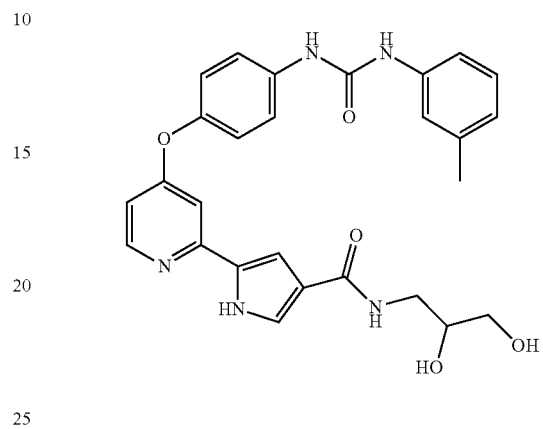

Similar procedure as Example 132.

$^1$H NMR (DMSO-d$_6$): 11.86 (br. s., 1H), 8.78 (s, 1H), 8.61 (s, 1H), 8.37 (d, J=5.9 Hz, 1H), 7.87 (t, J=5.7 Hz, 1H), 7.55 (d, J=8.8 Hz, 2H), 7.41 (br. s., 1H), 7.05-7.32 (m, 7H), 6.75 (dd, J=17.7, 6.6 Hz, 2H), 3.49-3.61 (m, 1H), 3.22-3.35 (m, 3H), 3.04-3.18 (m, 1H), 2.26 (s, 3H) LR MS (ES+): 524 (M+Na⁺)

Example 93

N-ethyl-5-{4-[4-({[(3-methylphenyl)amino]carbonyl}amino)phenoxy]pyridin-2-yl}-1H-pyrrole-3-carboxamide

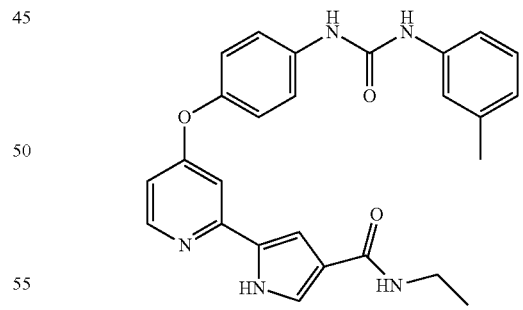

Similar procedure as Example 132.

$^1$H NMR (DMSO-d$_6$): 12.09 (br. s., 1H), 8.98 (s, 1H), 8.76 (s, 1H), 8.42 (d, J=5.9 Hz, 1H), 7.91 (br. s., 1H), 7.45-7.65 (m, 3H), 7.05-7.38 (m, 7H), 6.82-6.94 (m, 1H), 6.78 (d, J=7.6 Hz, 1H), 3.09-3.27 (m, 2H), 2.26 (s, 3H), 1.06 (t, J=7.2 Hz, 3H)

LR MS (ES+): 478 (M+Na⁺)

LR MS (ES−): 454 (M−H)

Example 94

5-{4-[4-({[(3-methylphenyl)amino]carbonyl}amino)phenoxy]pyridin-2-yl}-1H-pyrrole-3-carboxamide

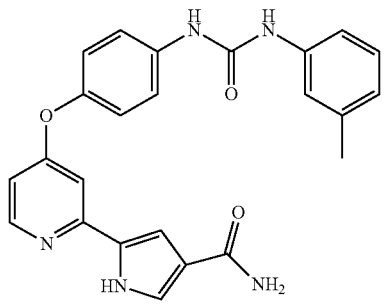 [SMILES: Cc1cccc(NC(=O)Nc2ccc(Oc3ccnc(-c4cc(C(N)=O)c[nH]4)c3)cc2)c1]

Similar procedure as Example 132.

¹H NMR (d₆-DMSO, 300 MHz): 11.81 (br. s., 1H), 8.76 (s, 1H), 8.59 (s, 1H), 8.37 (d, J=5.6 Hz, 1H), 7.55 (d, J=9.1 Hz, 2H), 7.37 (br. s., 2H), 7.28 (s, 1H), 7.19-7.26 (m, 1H), 7.09-7.18 (m, 4H), 7.04 (br. s., 1H), 6.78 (d, J=7.3 Hz, 2H), 6.69 (dd, J=5.4, 1.9 Hz, 1H), 2.26 (s, 3H)

LR MS (ES+): 428 (MH), 450 (M+Na⁺)

LR MS (ES−): 426 (M−H)

Example 95

N-hydroxy-5-{4-[4-({[(3-methylphenyl)amino]carbonyl}amino)phenoxy]pyridin-2-yl}-1H-pyrrole-3-carboxamide

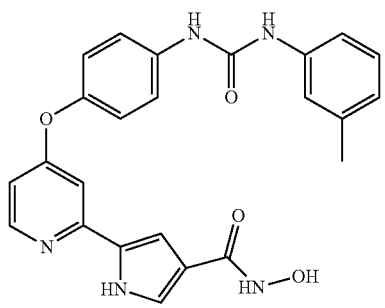 [SMILES: Cc1cccc(NC(=O)Nc2ccc(Oc3ccnc(-c4cc(C(=O)NO)c[nH]4)c3)cc2)c1]

Similar procedure as Example 132.

¹H NMR (d₆-DMSO, 300 MHz): 11.98 (br. s., 1H), 10.62 (br. s., 1H), 8.87 (s, 1H), 8.68 (s, 1H), 8.41 (d, J=5.6 Hz, 1H), 7.58 (d, J=9.1 Hz, 2H), 7.04-7.46 (m, 8H), 6.80 (d, J=7.6 Hz, 2H), 2.28 (s, 3H)

LR MS (ES+): 444 (MH), 466 (M+Na⁺)

LR MS (ES−): 442 (M−H)

Example 96

5-{4-[3-fluoro-4-({[(2-fluoro-5-methylphenyl)amino]carbonyl}amino)phenoxy]pyridin-2-yl}-1H-pyrrole-3-carboxylic acid

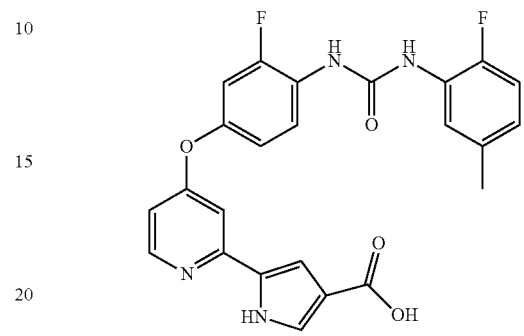

Similar procedure as Example 134.

¹H NMR (d₆-DMSO, 300 MHz): 12.04 (br. s., 1H), 11.88 (br. s., 1H), 9.08 (s, 1H), 8.97 (s, 1H), 8.41 (d, J=5.6 Hz, 1H), 8.25 (t, J=9.2 Hz, 1H), 8.01 (d, J=7.6 Hz, 1H), 7.38 (s, 2H), 7.27 (dd, J=11.9, 2.5 Hz, 1H), 6.95-7.18 (m, 3H), 6.78-6.88 (m, 1H), 6.74 (dd, J=5.6, 2.1 Hz, 1H), 2.28 (s, 3H)

LR MS (ES+): 465 (MH), 487 (M+Na⁺)

LR MS (ES−): 463 (M−H)

Example 97

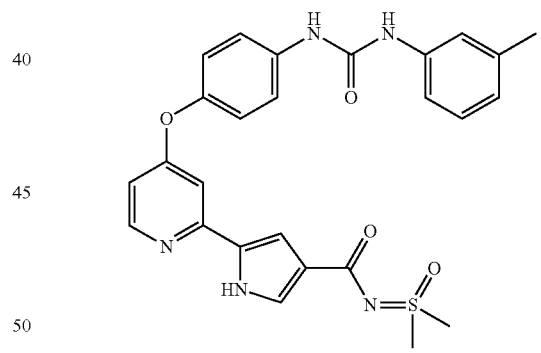

N-[dimethyl(oxido)-lambda~4~-sulfanylidene]-5-{4-[4-({[(3-methylphenyl)amino]carbonyl}amino)phenoxy]pyridin-2-yl}-1H-pyrrole-3-carboxamide Similar procedure as Example 101.

¹H NMR (d₆-DMSO, 300 MHz): 11.82 (none, 1H), 11.83 (br. s., 1H), 8.76 (s, 1H), 8.60 (s, 1H), 8.37 (d, J=5.9 Hz, 1H), 7.56 (d, J=9.1 Hz, 2H), 7.21-7.35 (m, 4H), 7.08-7.20 (m, 3H), 6.95 (s, 1H), 6.79 (d, J=7.0 Hz, 1H), 6.66 (dd, J=5.6, 2.3 Hz, 1H), 3.37 (s, 6H), 2.28 (s, 3H)

LR MS (ES+): 526 (M+Na⁺)

LR MS (ES−): 502 (M−H)

Example 98

2-hydroxyethyl 5-{4-[4-({[(4-chloro-3-(trifluoromethyl)phenyl)amino]carbonyl}amino)phenoxy]pyridin-2-yl}-1H-pyrrole-3-carboxylate

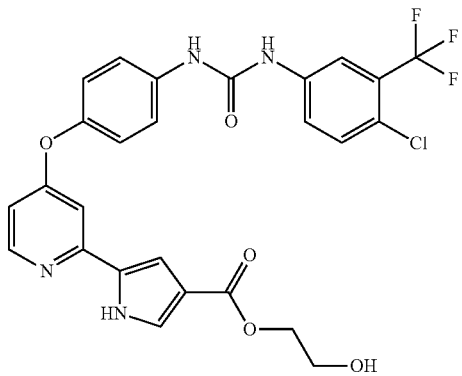 [SMILES: O=C(Nc1ccc(Oc2ccnc(-c3cc(C(=O)OCCO)c[nH]3)c2)cc1)Nc1ccc(Cl)c(C(F)(F)F)c1]

Similar procedure as Example 131.

¹H NMR (d₆-DMSO, 300 MHz): 12.12 (br. s., 1H), 9.19 (s, 1H), 8.97 (s, 1H), 8.40 (d, J=5.9 Hz, 1H), 8.12 (d, J=2.1 Hz, 1H), 7.53-7.70 (m, 4H), 7.48 (dd, J=3.1, 1.6 Hz, 1H), 7.35 (d, J=2.1 Hz, 1H), 7.16 (d, J=9.1 Hz, 2H), 7.09 (d, J=2.3 Hz, 1H), 6.68 (dd, J=5.6, 2.3 Hz, 1H), 4.83 (t, J=5.9 Hz, 1H), 4.15 (t, J=5.0 Hz, 2H), 3.59-3.69 (m, 2H)

LR MS (ES+): 583 (M+Na⁺), 585
LR MS (ES−): 559 (M−H), 561

Example 99

N-[dimethyl(oxido)-lambda~4~-sulfanylidene]-5-{4-[4-({[(4-chloro-3-(trifluoromethyl)phenyl)amino]carbonyl}amino)phenoxy]pyridin-2-yl}-1H-pyrrole-3-carboxamide

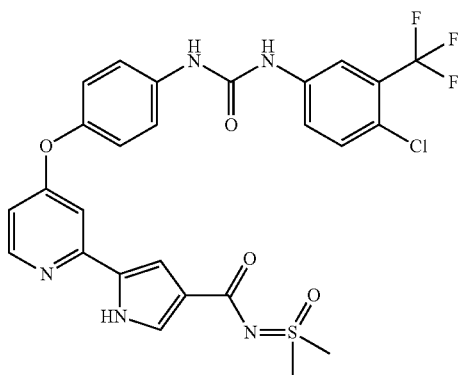 [SMILES: CS(C)(=O)=NC(=O)c1c[nH]c(-c2cc(Oc3ccc(NC(=O)Nc4ccc(Cl)c(C(F)(F)F)c4)cc3)ccn2)c1]

Similar procedure as Example 101.

¹H NMR (d₆-DMSO, 300 MHz) 11.83 (br. s., 1H), 9.19 (s, 1H), 8.97 (s, 1H), 8.37 (d, J=5.9 Hz, 1H), 8.12 (d, J=2.3 Hz, 1H), 7.54-7.69 (m, 4H), 7.23-7.31 (m, 2H), 7.12-7.19 (m, 2H), 6.93-6.97 (m, 1H), 6.67 (dd, J=5.9, 2.3 Hz, 6H)

LR MS (ES−): 590 (M−H)

Example 100 methy 4-(N-5-{4-[4-({[(2-fluoro-5-methylphenyl)amino]carbonyl}amino)phenoxy]pyridin-2-yl}-1H-pyrrole-3-carboxyl)-S-methylsulfonimidoyl)butanoate

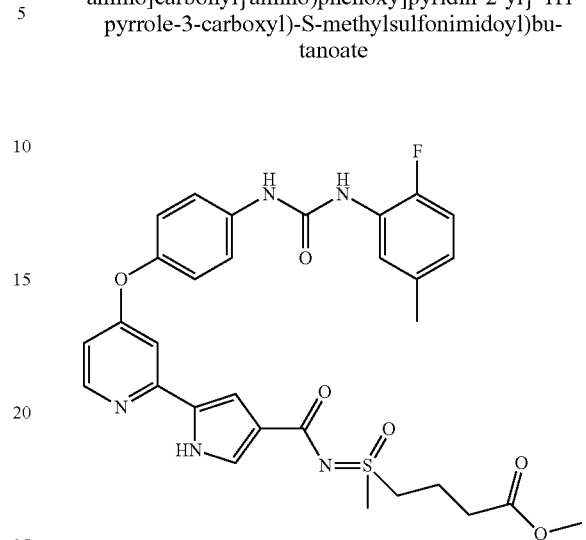

Similar procedure as Example 101.
LR MS (ES+): 630 (M+Na⁺)
LR MS (ES−): 606 (M−H)

Example 101

N-[dimethyl(oxido)-lambda~4~-sulfanylidene]-5-{4-[4-({[(2-fluoro-5-methylphenyl)amino]carbonyl}amino)phenoxy]pyridin-2-yl}-1H-pyrrole-3-carboxamide

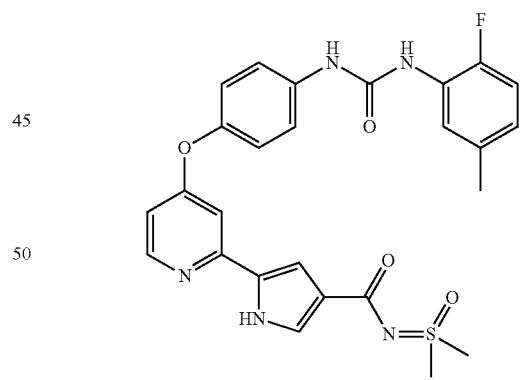

A mixture of 5-{4-[4-({[(2-fluoro-5-methylphenyl)amino]carbonyl}amino)phenoxy]pyridin-2-yl}-1H-pyrrole-3-carboxylic acid (60 mg, 0.13 mmol), HATU (60 mg, 0.16 mmol), sulfonimidoyldimethane (24 mg, 0.26 mmol), N,N-diisopropylethylamine (37 mg, 0.29 mmol), 200 mg of 4 Å molecular sieves and 5 ml of anhydrous 1,4-dioxane was added to a thick walled reaction vessel and purged with N₂. The reaction vessel was sealed and the mixture stirred at 90° C. for 18 hours. The reaction vessel was cooled to room temperature and the mixture was poured into 100 ml of water. The precipitates were filtered, washed with water and dried to give the crude, which was purified by silica gel chromatography eluting with 3~5% MeOH/CHCl$_3$ to give N-[dimethyl(oxido)-lambda~4~-sulfanylidene]-5-{4-[4-({[(2-fluoro-5-methylphenyl)amino]carbonyl}amino)phenoxy]pyridin-2-yl}-1H-pyrrole-3-carboxamide as white solid. Yield: 38 mg, 54%.
$^1$H NMR (d$_6$-DMSO): 11.83 (br. s., 1H), 9.16 (s, 1H), 8.48 (br. s., 1H), 8.37 (d, J=5.9 Hz, 1H), 7.98 (d, J=6.7 Hz, 1H), 7.56 (d, J=8.8 Hz, 2H), 7.26 (dd, J=8.6, 1.6 Hz, 2H), 7.05-7.19 (m, 3H), 6.96 (s, 1H), 6.75-6.85 (m, 1H), 6.66 (dd, J=5.4, 1.6 Hz, 1H), 3.37 (s, 6H), 2.27 (s, 3H)
LR MS (ES+): 544 (M+Na$^+$)
LR MS (ES−): 520 (M−H)

Example 102 methyl (2S)-1-(2-{[(5-{4-[4-({[(2-fluoro-5-methylphenyl)amino]carbonyl}amino)phenoxy]pyridin-2-yl}-1H-pyrrol-3-yl)carbonyl]amino}ethyl)pyrrolidine-2-carboxylate

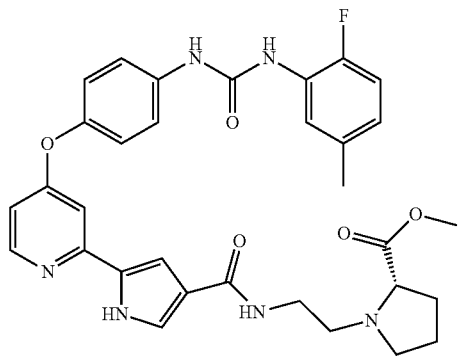 [SMILES: COC(=O)[C@@H]1CCCN1CCNC(=O)c1c[nH]c(-c2cc(Oc3ccc(NC(=O)Nc4cc(C)ccc4F)cc3)ccn2)c1]

Similar procedure as Example 132.
LR MS (ES+): 623 (M+Na$^+$)
LR MS (ES−): 599 (M−H)

Example 103

N,N-diethyl-5-{4-[4-({[(2-fluoro-5-methylphenyl)amino]carbonyl}amino)phenoxy]pyridin-2-yl}-1H-pyrrole-3-carboxamide

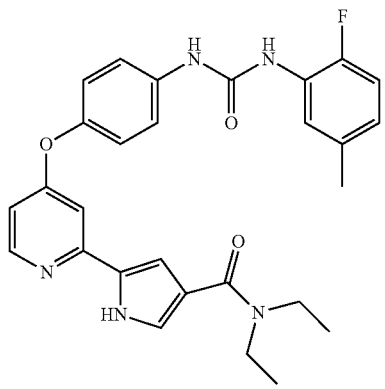 [SMILES: CCN(CC)C(=O)c1c[nH]c(-c2cc(Oc3ccc(NC(=O)Nc4cc(C)ccc4F)cc3)ccn2)c1]

Similar procedure as Example 132.
$^1$H NMR (d$_6$-DMSO): 11.97 (br. s., 1H), 9.19 (s, 1H), 8.49 (d, J=2.6 Hz, 1H), 8.40 (d, J=6.2 Hz, 1H), 7.98 (dd, J=7.8, 1.9 Hz, 1H), 7.53-7.61 (m, 2H), 7.40 (d, J=1.5 Hz, 1H), 7.05-7.25 (m, 4H), 7.01 (br. s., 1H), 6.76-6.86 (m, 1H), 6.67-6.76 (m, 1H), 3.26-3.64 (m, 4H), 2.27 (s, 3H), 1.13 (t, J=7.0 Hz, 6H)
LR MS (ES+): 524 (M+Na$^+$)
LR MS (ES−): 500 (M−H)

Example 104

1-(2-fluoro-5-methylphenyl)-3-{4-[(2-{4-[(4-methylpiperazin-1-yl)carbonyl]-1H-pyrrol-2-yl}pyridin-4-yl)oxy]phenyl}urea

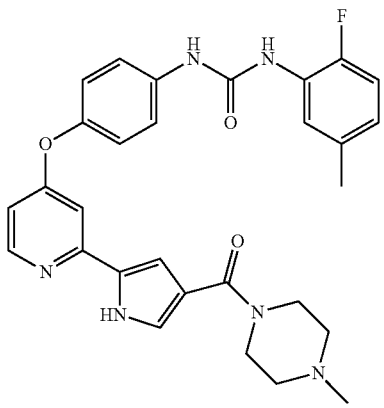 [SMILES: Cc1ccc(F)c(NC(=O)Nc2ccc(Oc3ccnc(-c4cc(C(=O)N5CCN(C)CC5)c[nH]4)c3)cc2)c1]

Similar procedure as Example 132.
$^1$H NMR (d$_6$-DMSO): 11.87 (br. s., 1H), 9.16 (s, 1H), 8.47 (d, J=2.6 Hz, 1H), 8.37 (d, J=5.6 Hz, 1H), 7.98 (dd, J=8.1, 1.9 Hz, 1H), 7.50-7.59 (m, 2H), 7.35 (d, J=2.3 Hz, 1H), 7.08-7.19 (m, 4H), 6.87-6.95 (m, 1H), 6.80 (ddd, J=7.7, 5.1, 2.2 Hz, 1H), 6.63 (dd, J=5.9, 2.3 Hz, 1H), 3.60 (d, J=4.1 Hz, 4H), 2.23-2.35 (m, 7H), 2.18 (s, 3H)
LR MS (ES+): 551 (M+Na$^+$)
LR MS (ES−): 527 (M−H)

Example 105

5-{4-[4-({[(2-fluoro-5-methylphenyl)amino]carbonyl}amino)phenoxy]pyridin-2-yl}-N-(2-pyrrolidin-1-ylethyl)-1H-pyrrole-3-carboxamide

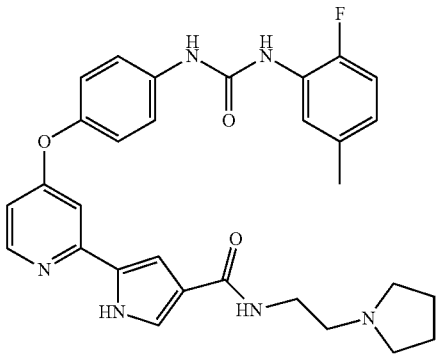 [SMILES: Cc1ccc(F)c(NC(=O)Nc2ccc(Oc3ccnc(-c4cc(C(=O)NCCN5CCCC5)c[nH]4)c3)cc2)c1]

Similar procedure as Example 132.
$^1$H NMR (d$_6$-DMSO): 11.80 (br. s., 1H), 9.17 (s, 1H), 8.48 (d, J=2.6 Hz, 1H), 8.37 (d, J=5.6 Hz, 1H), 7.98 (dd, J=7.9, 2.1 Hz, 1H), 7.82 (t, J=5.7 Hz, 1H), 7.50-7.63 (m, 2H), 7.35 (dd, J=2.9, 1.8 Hz, 1H), 7.00-7.20 (m, 5H), 6.80 (dt, J=7.9, 2.2 Hz, 1H), 6.70 (dd, J=5.9, 2.3 Hz, 1H), 3.21-3.35 (m, 2H), 2.37-2.57 (m, 6H), 2.27 (s, 3H), 1.65 (dt, J=6.6, 3.1 Hz, 4H)

LR MS (ES+): 565 (M+Na⁺)

LR MS (ES−): 541 (M−H)

Example 106

1-(4-((2-(4-(4,5-dihydrooxazol-2-yl)-1H-pyrrol-2-yl)pyridin-4-yl)oxy)phenyl)-3-(2-fluoro-5-methylphenyl)urea

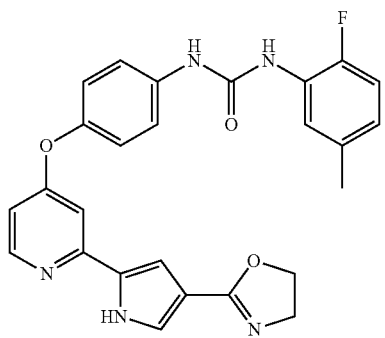 [SMILES: Cc1ccc(F)c(NC(=O)Nc2ccc(Oc3ccnc(-c4cc(C5=NCCO5)c[nH]4)c3)cc2)c1]

Similar procedure as Example 132.

$^1$H NMR (d$_6$-DMSO): 11.90 (br. s., 1H), 9.15 (s, 1H), 8.47 (d, J=2.6 Hz, 1H), 8.36 (d, J=5.9 Hz, 1H), 7.97 (dd, J=8.2, 2.1 Hz, 1H), 7.50-7.58 (m, 2H), 7.28 (d, J=2.1 Hz, 1H), 7.23 (br. s., 1H), 7.04-7.17 (m, 3H), 6.97 (br. s., 1H), 6.79 (ddd, J=7.5, 5.1, 2.3 Hz, 1H), 6.65 (dd, J=5.7, 2.5 Hz, 1H), 4.17-4.31 (m, 2H), 3.82 (t, J=9.2 Hz, 2H), 2.26 (s, 3H)

LR MS (ES+): 494 (M+Na⁺)

LR MS (ES−): 470 (M−H)

Example 107

5-{4-[4-({[(2-fluoro-5-methylphenyl)amino]carbonyl}amino)phenoxy]pyridin-2-yl}-1H-pyrrole-3-carboxamide

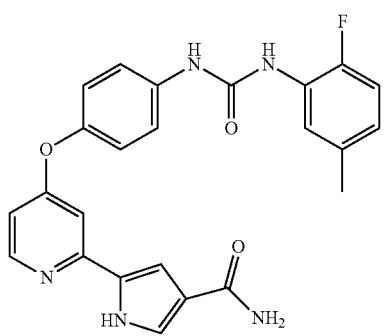

Similar procedure as Example 132.

$^1$H NMR (d$_6$-DMSO): 11.89 (br. s., 1H), 9.21 (s, 1H), 8.50 (d, J=2.3 Hz, 1H), 8.39 (d, J=5.9 Hz, 1H), 7.98 (dd, J=8.1, 1.9 Hz, 1H), 7.53-7.62 (m, 2H), 7.43 (br. s., 2H), 7.05-7.24 (m, 5H), 6.71-6.86 (m, 3H), 2.27 (s, 3H)

LR MS (ES+): 468 (M+Na⁺)

LR MS (ES−): 444 (M−H)

Example 108

5-{4-[4-({[(2-fluoro-5-methylphenyl)amino]carbonyl}amino)phenoxy]pyridin-2-yl}-N-hydroxy-1H-pyrrole-3-carboxamide

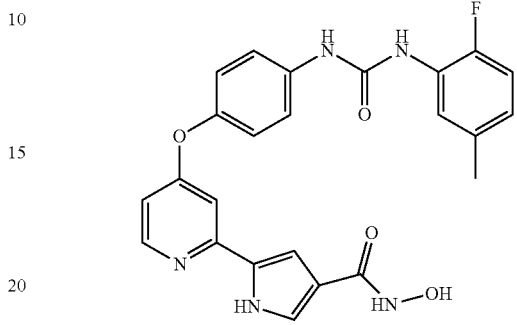

Similar procedure as Example 132.

$^1$H NMR (d$_6$-DMSO): 12.10 (br. s., 1H), 10.66 (br. s., 1H), 9.29 (s, 1H), 8.53 (br. s., 1H), 8.43 (d, J=6.2 Hz, 1H), 7.93-8.03 (m, 1H), 7.59 (d, J=8.8 Hz, 2H), 7.39-7.50 (m, 1H), 7.30 (br. s., 1H), 7.05-7.26 (m, 4H), 6.75-6.91 (m, 2H), 2.27 (s, 3H)

LR MS (ES+): 484 (M+Na⁺)

LR MS (ES−): 460 (M−H)

Example 109

1-(4-((2-(4-(5,6-dihydro-4H-1,3-oxazin-2-yl)-1H-pyrrol-2-yl)pyridin-4-yl)oxy)phenyl)-3-(2-fluoro-5-methylphenyl)urea

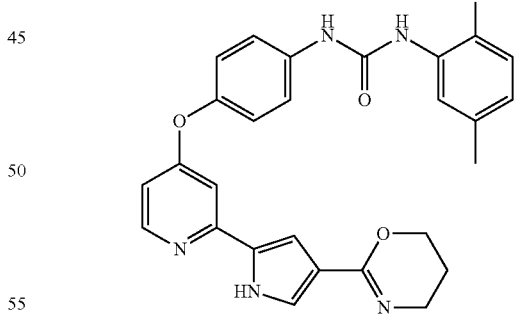

Similar procedure as Example 132.

$^1$H NMR (d$_6$-DMSO): 11.67 (br. s., 1H), 9.16 (s, 1H), 8.47 (d, J=2.1 Hz, 1H), 8.34 (d, J=5.6 Hz, 1H), 7.97 (d, J=5.9 Hz, 1H), 7.54 (d, J=9.1 Hz, 2H), 7.02-7.23 (m, 5H), 6.86 (br. s., 1H), 6.74-6.83 (m, 1H), 6.64 (dd, J=5.9, 2.3 Hz, 1H), 4.14-4.28 (m, 2H), 3.33-3.42 (m, 2H), 2.26 (s, 3H), 1.83 (br. s., 2H)

LR MS (ES+): 486 (M+H)

LR MS (ES−): 484 (M−H)

Example 110

5-{4-[4-({[(2-fluoro-5-methylphenyl)amino]carbonyl}amino)phenoxy]pyridin-2-yl}-N-(3-hydroxypropyl)-1H-pyrrole-3-carboxamide

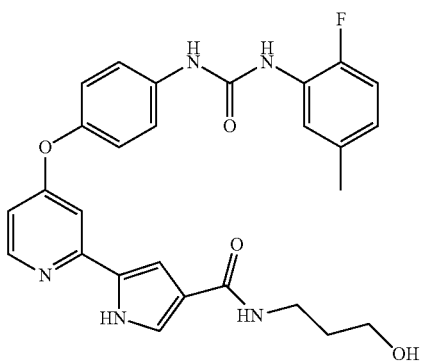 [SMILES: Cc1ccc(F)c(NC(=O)Nc2ccc(Oc3ccnc(-c4cc(C(=O)NCCCO)c[nH]4)c3)cc2)c1]

Similar procedure as Example 132.

$^1$H NMR (d$_6$-DMSO): 11.78 (br. s., 1H), 9.20 (s, 1H), 8.51 (d, J=2.1 Hz, 1H), 8.36 (d, J=5.6 Hz, 1H), 7.96 (dd, J=7.9, 1.8 Hz, 1H), 7.83 (t, J=5.7 Hz, 1H), 7.55 (d, J=9.1 Hz, 2H), 7.32-7.36 (m, 1H), 7.02-7.17 (m, 5H), 6.78 (td, J=5.3, 2.6 Hz, 1H), 6.69 (dd, J=5.6, 2.3 Hz, 1H), 4.42 (t, J=5.3 Hz, 1H), 3.41 (q, J=6.2 Hz, 2H), 3.15-3.26 (m, 2H), 2.26 (s, 3H), 1.60 (quin, J=6.7 Hz, 2H)

LR MS (ES+): 526 (M+Na$^+$)
LR MS (ES−): 502 (M−H)

Example 111

2-(2-methoxyethoxy)ethyl 5-{4-[4-({[(2-fluoro-5-methylphenyl)amino]carbonyl}amino)phenoxy]pyridin-2-yl}-1H-pyrrole-3-carboxylate

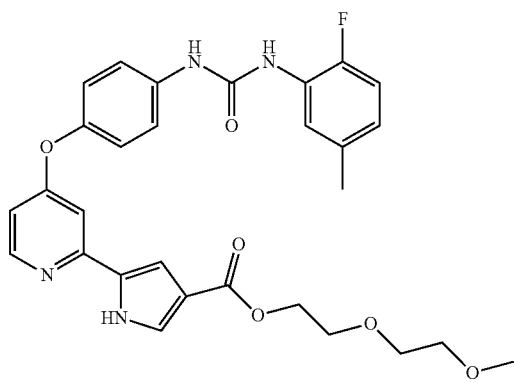 [SMILES: COCCOCCOC(=O)c1c[nH]c(-c2cc(Oc3ccc(NC(=O)Nc4cc(C)ccc4F)cc3)ccn2)c1]

Similar procedure as Example 131.

$^1$H NMR (d$_6$-DMSO): 12.12 (br. s., 1H), 9.15 (s, 1H), 8.47 (d, J=2.3 Hz, 1H), 8.38 (d, J=5.9 Hz, 1H), 7.97 (dd, J=8.1, 1.9 Hz, 1H), 7.49-7.59 (m, 2H), 7.41 (dd, J=3.1, 1.6 Hz, 1H), 7.34 (d, J=2.3 Hz, 1H), 7.03-7.17 (m, 4H), 6.74-6.84 (m, 1H), 6.67 (dd, J=5.7, 2.5 Hz, 1H), 4.20-4.28 (m, 2H), 3.62-3.70 (m, 2H), 3.51-3.59 (m, 2H), 3.39-3.46 (m, 2H), 3.18-3.24 (m, 3H), 2.26 (s, 3H)

LR MS (ES+): 571 (M+Na$^+$)
LR MS (ES−): 547 (M−H)

Example 112

N-ethyl-5-{4-[4-({[(2-fluoro-5-methylphenyl)amino]carbonyl}amino)phenoxy]pyridin-2-yl}-1H-pyrrole-3-carboxamide

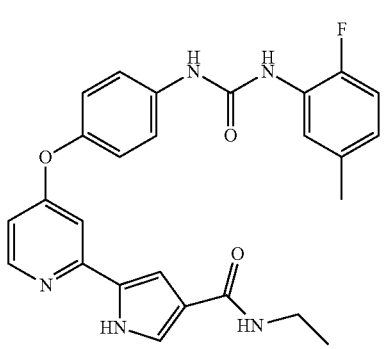 [SMILES: CCNC(=O)c1c[nH]c(-c2cc(Oc3ccc(NC(=O)Nc4cc(C)ccc4F)cc3)ccn2)c1]

Similar procedure as Example 132.

$^1$H NMR (d$_6$-DMSO): 11.93 (br. s., 1H), 9.23 (s, 1H), 8.50 (d, J=2.3 Hz, 1H), 8.39 (d, J=6.2 Hz, 1H), 7.96 (dd, J=7.9, 1.8 Hz, 1H), 7.87 (t, J=5.6 Hz, 1H), 7.57 (d, J=8.8 Hz, 2H), 7.42 (br. s., 1H), 7.02-7.27 (m, 5H), 6.72-6.86 (m, 2H), 3.09-3.25 (m, 2H), 2.26 (s, 3H), 1.06 (t, J=7.2 Hz, 3H)

LR MS (ES+): 496 (M+Na$^+$)
LR MS (ES−): 472 (M−H)

Example 113

2-methoxyethyl 5-{4-[4-({[(2-fluoro-5-methylphenyl)amino]carbonyl}amino)phenoxy]pyridin-2-yl}-1H-pyrrole-3-carboxylate

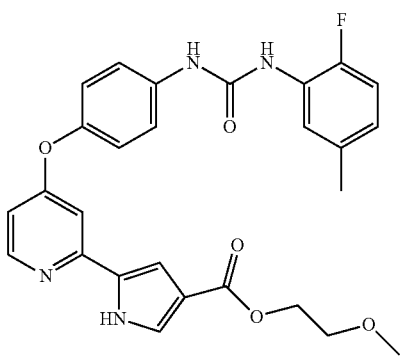 [SMILES: COCCOC(=O)c1c[nH]c(-c2cc(Oc3ccc(NC(=O)Nc4cc(C)ccc4F)cc3)ccn2)c1]

Similar procedure as Example 131.

$^1$H NMR (d$_6$-DMSO): 12.12 (br. s., 1H), 9.15 (s, 1H), 8.46 (br. s., 1H), 8.38 (d, J=5.6 Hz, 1H), 7.98 (s, 1H), 7.54 (d, J=8.8 Hz, 2H), 7.41 (d, J=1.2 Hz, 1H), 7.35 (d, J=1.8 Hz, 1H), 7.01-7.19 (m, 4H), 6.78 (d, J=5.9 Hz, 1H), 6.66 (dd, J=5.9, 2.1 Hz, 1H), 4.17-4.32 (m, 2H), 3.51-3.65 (m, 2H), 3.29 (s, 3H), 2.26 (s, 3H)

LR MS (ES+): 527 (M+Na$^+$)
LR MS (ES−): 503 (M−H)

Example 114

5-{4-[4-({[(2-fluoro-5-methylphenyl)amino]carbonyl}amino)phenoxy]pyridin-2-yl}-N-(2-methoxyethyl)-1H-pyrrole-3-carboxamide

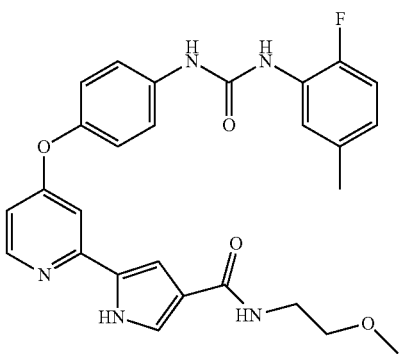

Similar procedure as Example 132.

$^1$H NMR (d$_6$-DMSO): 11.86 (br. s., 1H), 9.17 (s, 1H), 8.48 (d, J=2.3 Hz, 1H), 8.38 (d, J=5.9 Hz, 1H), 7.86-8.02 (m, 2H), 7.56 (d, J=8.8 Hz, 2H), 7.40 (br. s., 1H), 7.02-7.21 (m, 5H), 6.67-6.84 (m, 2H), 3.26-3.50 (m, 7H), 2.26 (s, 3H)

LR MS (ES+): 526 (M+Na$^+$)

LR MS (ES−): 502 (M−H)

Example 115

5-{4-[4-({[(3-methylphenyl)amino]carbonyl}amino)phenoxy]pyridin-2-yl}-1H-pyrrole-3-carboxylic acid

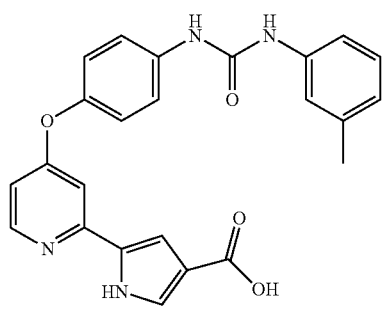 [SMILES: Cc1cccc(NC(=O)Nc2ccc(Oc3ccnc(-c4cc(C(=O)O)c[nH]4)c3)cc2)c1]

Similar procedure as Example 134.

$^1$H NMR (d$_6$-DMSO): 12.05 (br. s., 1H), 8.79 (s, 1H), 8.62 (s, 1H), 8.39 (d, J=5.6 Hz, 1H), 7.52-7.61 (m, 2H), 7.39 (dd, J=3.1, 1.6 Hz, 1H), 7.34 (d, J=2.3 Hz, 1H), 7.30 (s, 1H), 7.21-7.27 (m, 1H), 7.10-7.20 (m, 3H), 7.05 (s, 1H), 6.79 (d, J=7.3 Hz, 1H), 6.68 (dd, J=5.6, 2.3 Hz, 1H), 2.28 (s, 3H)

LR MS (ES−): 427 (M−H)

Example 116 methyl 5-{4-[4-({[(3-methylphenyl)amino]carbonyl}amino)phenoxy]pyridin-2-yl}-1H-pyrrole-3-carboxylate

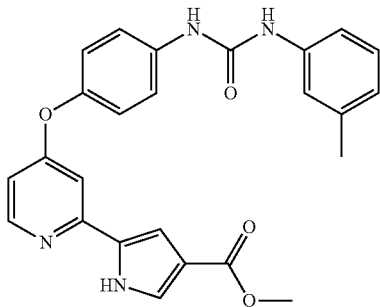 [SMILES: COC(=O)c1c[nH]c(-c2cc(Oc3ccc(NC(=O)Nc4cccc(C)c4)cc3)ccn2)c1]

Similar procedure as Example 135.

$^1$H NMR (d$_6$-DMSO): 12.12 (br. s., 1H), 9.02 (br. s., 1H), 8.85 (br. s., 1H), 8.36 (d, J=5.6 Hz, 1H), 7.50-7.59 (m, 2H), 7.41 (d, J=1.5 Hz, 1H), 7.33 (d, J=2.3 Hz, 1H), 7.29 (s, 1H), 7.24 (d, J=7.9 Hz, 1H), 7.08-7.18 (m, 3H), 7.06 (d, J=1.5 Hz, 1H), 6.77 (d, J=7.6 Hz, 1H), 6.65 (dd, J=5.6, 2.3 Hz, 1H), 3.69 (s, 3H), 2.26 (s, 3H)

LR MS (ES+): 465 (M+Na$^+$)

LR MS (ES−): 441 (M−H)

Example 117

5-{4-[2-fluoro-4-({[(2-fluoro-5-methylphenyl)amino]carbonyl}amino)phenoxy]pyridin-2-yl}-1H-pyrrole-3-carboxylic acid

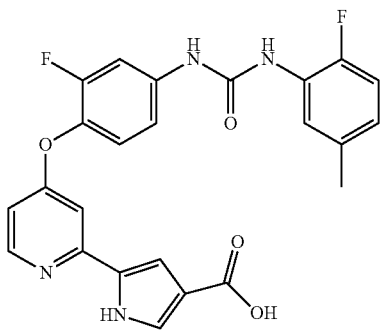 [SMILES: Cc1ccc(F)c(NC(=O)Nc2ccc(Oc3ccnc(-c4cc(C(=O)O)c[nH]4)c3)c(F)c2)c1]

Similar procedure as Example 134.

$^1$H NMR (d$_6$-DMSO): 12.03 (br. s., 1H), 11.86 (br. s., 1H), 9.62 (s, 1H), 8.65 (s, 1H), 8.38 (d, J=5.6 Hz, 1H), 7.94 (dd, J=7.9, 1.8 Hz, 1H), 7.72 (dd, J=13.2, 2.3 Hz, 1H), 7.26-7.40 (m, 3H), 7.15-7.24 (m, 1H), 7.01-7.14 (m, 2H), 6.81 (td, J=5.3, 2.3 Hz, 1H), 6.68 (dd, J=5.7, 2.2 Hz, 1H), 2.26 (s, 3H)

LR MS (ES+): 487 (M+Na$^+$)

LR MS (ES−): 463 (M−H)

Example 118 methyl 5-{4-[2-fluoro-4-({[(2-fluoro-5-methylphenyl)amino]carbonyl}amino)phenoxy]pyridin-2-yl}-1H-pyrrole-3-carboxylate

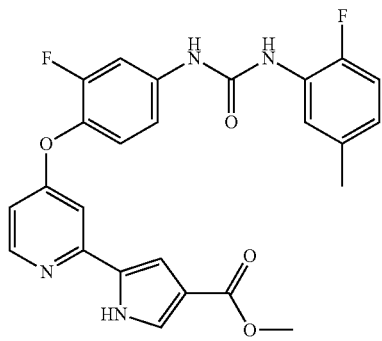 [SMILES: COC(=O)c1c[nH]c(-c2cc(Oc3ccc(NC(=O)Nc4cc(C)ccc4F)cc3F)ccn2)c1]

Similar procedure as Example 135.

$^1$H NMR (d$_6$-DMSO): 12.13 (br. s., 1H), 9.34 (s, 1H), 8.55 (d, J=2.3 Hz, 1H), 8.39 (d, J=5.9 Hz, 1H), 7.94 (dd, J=7.8, 1.6 Hz, 1H), 7.72 (dd, J=13.5, 2.3 Hz, 1H), 7.43 (dd, J=3.2, 1.8 Hz, 1H), 7.37 (d, J=2.3 Hz, 1H), 7.26-7.36 (m, 1H), 7.18 (dd, J=8.9, 1.6 Hz, 1H), 7.05-7.15 (m, 2H), 6.77-6.87 (m, 1H), 6.70 (dd, J=5.6, 2.3 Hz, 1H), 3.70 (s, 3H), 2.26 (s, 3H)

LR MS (ES+): 501 (M+Na$^+$)

LR MS (ES−): 477 (M−H)

Example 119

5-(4-{4-[({[4-fluoro-3-(trifluoromethyl)phenyl]amino}carbonyl)amino]phenoxy}pyridin-2-yl)-1H-pyrrole-3-carboxylic acid

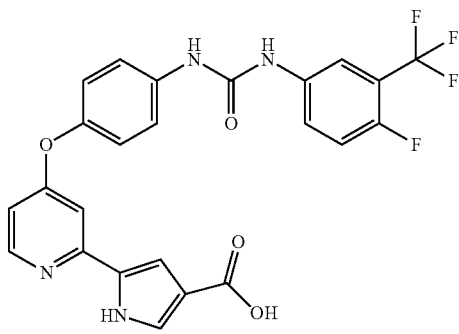 [SMILES: O=C(Nc1ccc(Oc2ccnc(-c3cc(C(=O)O)c[nH]3)c2)cc1)Nc1ccc(Cl)c(C(F)(F)F)c1]

Similar procedure as Example 134.

$^1$H NMR (d$_6$-DMSO): 12.05 (d, 1H), 9.11 (s, 1H), 8.96 (s, 1H), 8.38 (d, J=5.6 Hz, 1H), 7.99 (dd, J=6.4, 2.3 Hz, 1H), 7.60-7.72 (m, 1H), 7.56 (d, J=9.1 Hz, 2H), 7.27-7.49 (m, 3H), 7.14 (d, J=9.1 Hz, 2H), 7.03 (br. s., 1H), 6.67 (dd, J=5.7, 2.2 Hz, 1H)

LR MS (ES−): 499 (M−H)

Example 120 methyl 5-(4-{4-[({[4-fluoro-3-(trifluoromethyl)phenyl]amino}carbonyl)amino]phenoxy}pyridin-2-yl)-1H-pyrrole-3-carboxylate

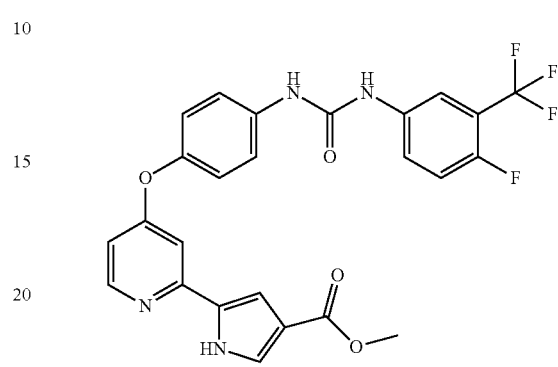

Similar procedure as Example 135.

$^1$H NMR (d$_6$-DMSO): 12.12 (br. s., 1H), 9.04 (s, 1H), 8.91 (s, 1H), 8.37 (d, J=6.2 Hz, 1H), 7.99 (dd, J=6.4, 2.6 Hz, 1H), 7.60-7.69 (m, 1H), 7.51-7.61 (m, 2H), 7.37-7.49 (m, 2H), 7.34 (d, J=2.1 Hz, 1H), 7.09-7.18 (m, 2H), 7.01-7.09 (m, 1H), 6.66 (dd, J=5.6, 2.3 Hz, 1H), 3.70 (s, 3H)

LR MS (ES+): 537 (M+Na$^+$)

LR MS (ES−): 513 (M−H)

Example 121

5-(4-{4-[({[4-chloro-3-(trifluoromethyl)phenyl]amino}carbonyl)amino]phenoxy}pyridin-2-yl)-1H-pyrrole-3-carboxylic acid

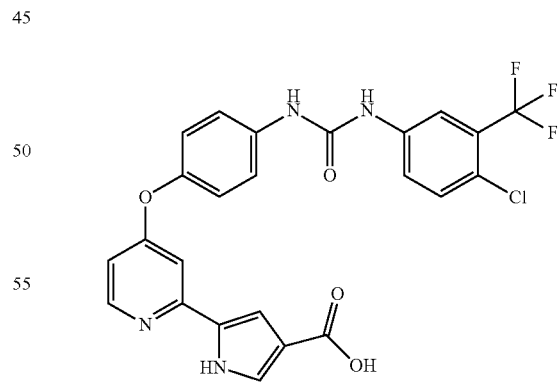

Similar procedure as Example 134.

$^1$H NMR (d$_6$-DMSO): 12.08 (br. s., 1H), 9.23 (s, 1H), 9.00 (s, 1H), 8.39 (d, J=5.6 Hz, 1H), 8.10 (s, 1H), 7.48-7.72 (m, 4H), 7.27-7.47 (m, 2H), 7.00-7.23 (m, 3H), 6.69 (br. s., 1H)

LR MS (ES−): 515 (M−H)

Example 122 methyl 5-(4-{4-[({[4-chloro-3-(trifluoromethyl)phenyl]amino}carbonyl)amino]phenoxy}pyridin-2-yl)-1H-pyrrole-3-carboxylate

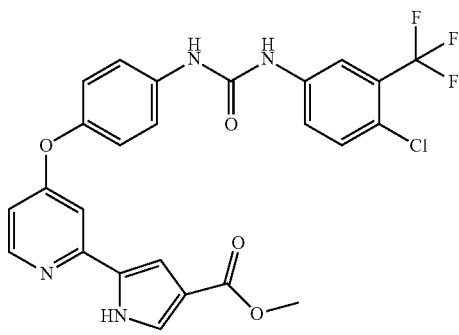 [SMILES: COC(=O)c1c[nH]c(-c2cc(Oc3ccc(NC(=O)Nc4ccc(Cl)c(C(F)(F)F)c4)cc3)ccn2)c1]

Similar procedure as Example 135.
$^1$H NMR (d$_6$-DMSO): 12.12 (br. s., 1H), 9.17 (s, 1H), 8.94 (s, 1H), 8.38 (d, J=5.9 Hz, 1H), 8.10 (d, J=2.1 Hz, 1H), 7.51-7.69 (m, 4H), 7.42 (dd, J=3.2, 1.8 Hz, 1H), 7.34 (d, J=2.3 Hz, 1H), 7.10-7.18 (m, 2H), 7.03-7.09 (m, 1H), 6.66 (dd, J=5.9, 2.3 Hz, 1H), 3.70 (s, 3H)
LR MS (ES+): 553 (M+Na$^+$)
LR MS (ES–): 529 (M–H)

Example 123

4-{4-[4-({[(2-fluoro-5-methylphenyl)amino]carbonyl}amino)phenoxy]pyridin-2-yl}thiophene-2-carboxylic acid

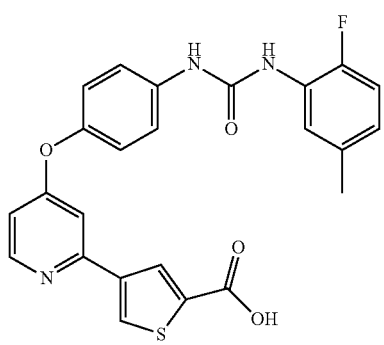 [SMILES: Cc1ccc(F)c(NC(=O)Nc2ccc(Oc3ccnc(-c4csc(C(=O)O)c4)c3)cc2)c1]

To a stirred solution of methyl 4-{4-[4-({[(2-fluoro-5-methylphenyl)amino]carbonyl}amino)phenoxy]pyridin-2-yl}thiophene-2-carboxylate (550 mg, 1.15 mmol) in a mixture of solvents—THF/MeOH (20 ml/20 ml) was added 1 ml of 5M NaOH (5 mmol) solution. The mixture was heated in a 66° C. bath for 2 hours, cooled to room temperature and poured into 200 ml of water. 2M HCl was added until pH=5. The resulting precipitates were filtered, washed with water, and dried in vacuo to give 4-{4-[4-({[(2-fluoro-5-methylphenyl)amino]carbonyl}amino)phenoxy]pyridin-2-yl}thiophene-2-carboxylic acid as off-white solid. Yield: 520 mg, 97%.
$^1$H NMR (d$_6$-DMSO): 9.30 (s, 1H), 8.59 (d, J=2.6 Hz, 1H), 8.43 (d, J=5.9 Hz, 1H), 8.35 (br. s., 1H), 8.13 (br. s., 1H), 7.95 (dd, J=7.8, 1.9 Hz, 1H), 7.51-7.59 (m, 2H), 7.45 (s, 1H), 7.03-7.18 (m, 3H), 6.75-6.83 (m, 1H), 6.72 (dd, J=5.6, 2.3 Hz, 1H), 2.25 (s, 3H)
LR MS (ES–): 462 (M–H)

Example 124

2-hydroxyethyl 4-{4-[4-({[(2-fluoro-5-methylphenyl)amino]carbonyl}amino)phenoxy]pyridin-2-yl}-1H-pyrrole-2-carboxylate

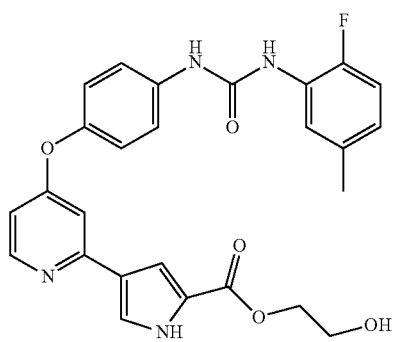 [SMILES: Cc1ccc(F)c(NC(=O)Nc2ccc(Oc3ccnc(-c4c[nH]c(C(=O)OCCO)c4)c3)cc2)c1]

Similar procedure as Example 131.
$^1$H NMR (DMSO-d$_6$) δ: 12.11 (br. s., 1H), 9.15 (s, 1H), 8.47 (d, J=2.1 Hz, 1H), 8.33 (d, J=5.6 Hz, 1H), 7.97 (dd, J=7.9, 1.8 Hz, 1H), 7.63 (dd, J=2.9, 1.8 Hz, 1H), 7.53 (d, J=8.8 Hz, 2H), 7.22-7.37 (m, 2H), 7.01-7.18 (m, 3H), 6.72-6.85 (m, 1H), 6.58 (dd, J=5.6, 2.3 Hz, 1H), 4.83 (t, J=5.9 Hz, 1H), 4.19 (t, J=5.1 Hz, 2H), 3.57-3.73 (m, 2H), 2.25 (s, 3H)
LR MS (ES+): 491 (MH), 513 (M+Na$^+$)
LR MS (ES–): 489 (M–H)

Example 125

{1-[(5-{4-[4-({[(2-fluoro-5-methylphenyl)amino]carbonyl}amino)phenoxy]pyridin-2-yl}-1H-pyrrol-3-yl)carbonyl]piperidin-4-yl}acetic acid

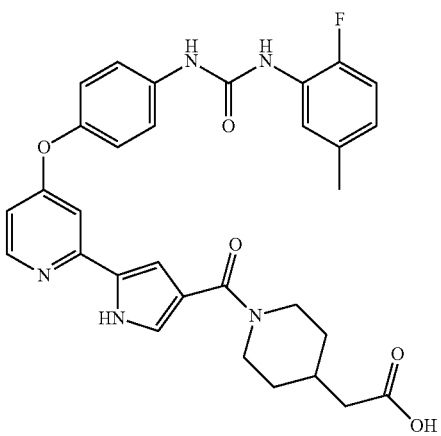 [SMILES: Cc1ccc(F)c(NC(=O)Nc2ccc(Oc3ccnc(-c4cc(C(=O)N5CCC(CC(=O)O)CC5)c[nH]4)c3)cc2)c1]

To a stirred solution of methyl {1-[(5-{4-[4-({[(2-fluoro-5-methylphenyl)amino]carbonyl}amino)phenoxy]pyridin-2-yl}-1H-pyrrol-3-yl)carbonyl]piperidin-4-yl}acetate (50 mg, 0.085 mmol) in THF/MeOH (5 ml/5 ml) was added 1M NaOH solution (3 ml, 3 mmol). The mixture was stirred at room temperature for one hour, and poured into 50 ml of water. 2M HCl was added until pH=4. The resulting precipitates were filtered, washed with water, and dried in vacuo to give {1-[(5-{4-[4-({[(2-fluoro-5-methylphenyl)amino]carbonyl}amino)phenoxy]pyridin-2-yl}-1H-pyrrol-3-yl)carbonyl]piperidin-4-yl}acetic acid as white solid. Yield: 47 mg, 96%.
LR MS (ES−): 570 (M−H)

Example 126 methyl {1-[(5-{4-[4-({[(2-fluoro-5-methylphenyl)amino]carbonyl}amino)phenoxy]pyridin-2-yl}-1H-pyrrol-3-yl)carbonyl]piperidin-4-yl}acetate

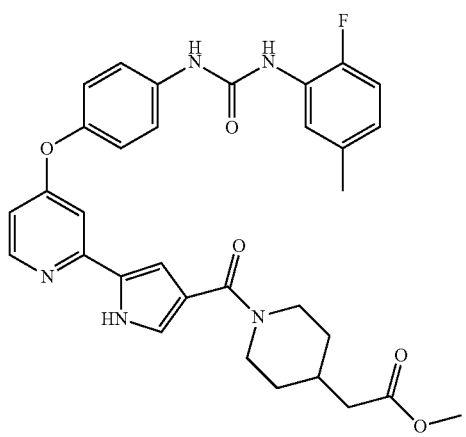 [SMILES: COC(=O)CC1CCN(C(=O)c2c[nH]c(-c3cc(Oc4ccc(NC(=O)Nc5cc(C)ccc5F)cc4)ccn3)c2)CC1]

Similar procedure as Example 132.
$^1$H NMR (d$_6$-DMSO): 11.83 (br. s., 1H), 9.14 (s, 1H), 8.46 (br. s., 1H), 8.35 (d, J=5.6 Hz, 1H), 7.97 (d, J=8.2 Hz, 1H), 7.53 (d, J=8.8 Hz, 2H), 7.33 (d, J=1.8 Hz, 1H), 7.01-7.18 (m, 4H), 6.86 (s, 1H), 6.80 (d, J=4.4 Hz, 1H), 6.61 (dd, J=5.9, 2.1 Hz, 1H), 4.26 (br. s., 1H), 3.57 (s, 3H), 2.87 (br. s., 2H), 2.18-2.32 (m, 5H), 1.93 (br. s., 1H), 1.65 (br. s., 2H), 1.14 (br. s., 2H)
LR MS (ES+): 608 (M+Na$^+$)
LR MS (ES−): 584 (M−H)

Example 127

N-(2,3-dihydroxypropyl)-5-{4-[4-({[(2-fluoro-5-methylphenyl)amino]carbonyl}amino)phenoxy]pyridin-2-yl}-1H-pyrrole-3-carboxamide

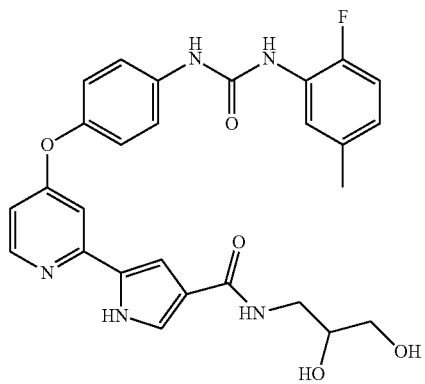

Similar procedure as Example 132.
$^1$H NMR (d$_6$-DMSO): 11.81 (br. s., 1H), 9.17 (s, 1H), 8.48 (d, J=2.3 Hz, 1H), 8.36 (d, J=5.6 Hz, 1H), 7.97 (dd, J=7.8, 1.9 Hz, 1H), 7.86 (t, J=5.7 Hz, 1H), 7.51-7.60 (m, 2H), 7.38 (dd, J=3.1, 1.6 Hz, 1H), 7.10-7.19 (m, 3H), 7.07 (td, J=4.3, 2.5 Hz, 2H), 6.74-6.84 (m, 1H), 6.69 (dd, J=5.6, 2.3 Hz, 1H), 4.78 (d, J=5.0 Hz, 1H), 4.54 (t, J=5.9 Hz, 1H), 3.48-3.60 (m, 1H), 3.23-3.36 (m, 3H), 3.05-3.18 (m, 1H), 2.26 (s, 3H)
LR MS (ES+): 542 (M+Na$^+$)
LR MS (ES−): 518 (M−H)

Example 128

5-{4-[4-({[(2-fluoro-5-methylphenyl)amino]carbonyl}amino)phenoxy]pyridin-2-yl}-N-(2-hydroxyethyl)-1H-pyrrole-3-carboxamide

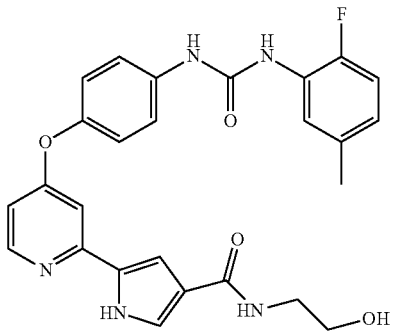 [SMILES: Cc1ccc(F)c(NC(=O)Nc2ccc(Oc3ccnc(-c4cc(C(=O)NCCO)c[nH]4)c3)cc2)c1]

Similar procedure as Example 132.
$^1$H NMR (d$_6$-DMSO): 11.79 (br. s., 1H), 9.30 (s, 1H), 8.57 (d, J=1.5 Hz, 1H), 8.36 (d, J=5.6 Hz, 1H), 7.95 (dd, J=7.9, 1.8 Hz, 1H), 7.84 (t, J=5.6 Hz, 1H), 7.50-7.63 (m, 2H), 7.35 (d, J=1.5 Hz, 1H), 7.00-7.21 (m, 5H), 6.79 (td, J=5.3, 2.5 Hz, 1H), 6.69 (dd, J=5.6, 2.3 Hz, 1H), 4.66 (t, J=5.6 Hz, 1H), 3.38-3.51 (m, 2H), 3.22 (q, J=6.1 Hz, 2H), 2.25 (s, 3H)
LR MS (ES+): 512 (M+Na$^+$)
LR MS (ES−): 488 (M−H)

Example 129

1-(2-fluoro-5-methylphenyl)-3-{4-[(2-{4-[(4-hydroxypiperidin-1-yl)carbonyl]-1H-pyrrol-2-yl}pyridin-4-yl)oxy]phenyl}urea

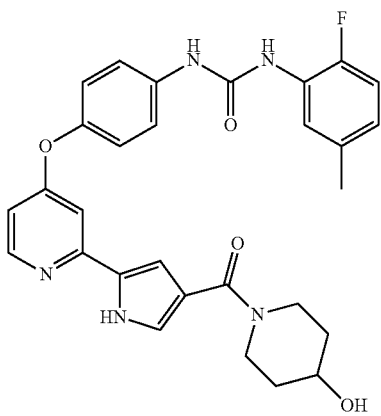 [SMILES: Cc1ccc(F)c(NC(=O)Nc2ccc(Oc3ccnc(-c4cc(C(=O)N5CCC(O)CC5)c[nH]4)c3)cc2)c1]

Similar procedure as Example 132.
$^1$H NMR (d$_6$-DMSO): 11.84 (br. s., 1H), 9.17 (s, 1H), 8.48 (d, J=2.3 Hz, 1H), 8.37 (d, J=5.6 Hz, 1H), 7.99 (dd, J=7.9, 1.8 Hz, 1H), 7.55 (d, J=8.8 Hz, 2H), 7.36 (d, J=2.3 Hz, 1H), 7.04-7.20 (m, 4H), 6.89 (s, 1H), 6.81 (td, J=5.3, 2.3 Hz, 1H), 6.63 (dd, J=5.9, 2.3 Hz, 1H), 4.73 (d, J=4.1 Hz, 1H), 3.90-4.06 (m, 2H), 3.71 (dt, J=8.4, 4.3 Hz, 1H), 3.25 (d, J=2.6 Hz, 2H), 2.27 (s, 3H), 1.73 (d, J=4.1 Hz, 2H), 1.21-1.44 (m, 2H)
LR MS (ES+): 552 (M+Na$^+$)
LR MS (ES−): 528 (M−H)

Example 130

2,3-dihydroxypropyl 5-{4-[4-({[(2-fluoro-5-methylphenyl)amino]carbonyl}amino)phenoxy]pyridin-2-yl}-1H-pyrrole-3-carboxylate

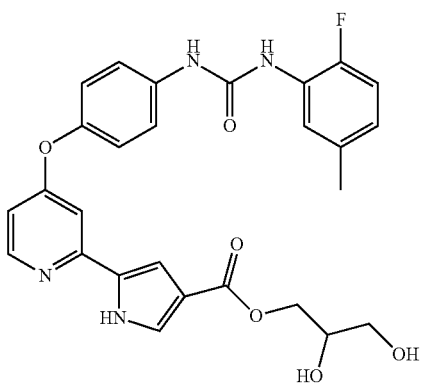 [SMILES: Cc1ccc(F)c(NC(=O)Nc2ccc(Oc3ccnc(-c4cc(C(=O)OCC(O)CO)c[nH]4)c3)cc2)c1]

Similar procedure as Example 131.

$^1$H NMR (d$_6$-DMSO): 12.12 (br. s., 1H), 9.24 (s, 1H), 8.54 (d, J=2.3 Hz, 1H), 8.39 (d, J=5.9 Hz, 1H), 7.98 (dd, J=7.8, 1.9 Hz, 1H), 7.51-7.62 (m, 2H), 7.48 (dd, J=3.1, 1.6 Hz, 1H), 7.34-7.40 (m, 1H), 7.05-7.20 (m, 4H), 6.75-6.87 (m, 1H), 6.68 (dd, J=5.9, 2.3 Hz, 1H), 4.92 (d, J=5.3 Hz, 1H), 4.64 (t, J=5.7 Hz, 1H), 4.11-4.22 (m, 1H), 3.97-4.09 (m, 1H), 3.67-3.79 (m, 1H), 3.38-3.46 (m, 2H), 2.28 (s, 3H)

LR MS (ES+): 543 (M+Na$^+$)

LR MS (ES−): 519 (M−H)

Example 131

2-hydroxyethyl 5-{4-[4-({[(2-fluoro-5-methylphenyl)amino]carbonyl}amino)phenoxy]pyridin-2-yl}-1H-pyrrole-3-carboxylate

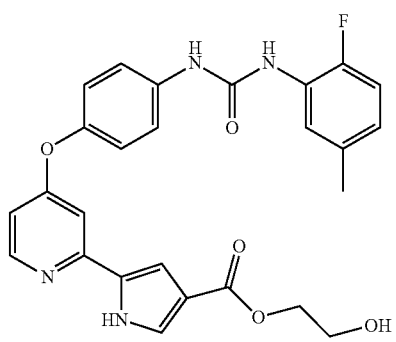 [SMILES: Cc1ccc(F)c(NC(=O)Nc2ccc(Oc3ccnc(-c4cc(C(=O)OCCO)c[nH]4)c3)cc2)c1]

A mixture of 5-{4-[4-({[(2-fluoro-5-methylphenyl)amino]carbonyl}amino)phenoxy]pyridin-2-yl}-1H-pyrrole-3-carboxylic acid (50 mg, 0.11 mmol), ethylene glycol (1 ml), 1-Ethyl-3-(3-dimethyllaminopropyl)carbodiimide hydrochloride (EDC.HCl, 25 mg, 0.13 mmol) and 4-dimethylaminopyridine (DMAP, 5 mg, 0.04 mmol) in anhydrous THF (10 ml) was stirred at 60° C. for 16 hours. The mixture was poured into 100 ml of water. 2M HCl was added dropwise until pH=4. The precipitates were filtered, washed with water and dried in vacuo to give the crude, which was purified by silica gel chromatography with a gradient of 3-5% MeOH/CHCl$_3$ to give 2-hydroxyethyl 5-{4-[4-({[(2-fluoro-5-methylphenyl)amino]carbonyl}amino)phenoxy]pyridin-2-yl}-1H-pyrrole-3-carboxylate as white solid. Yield: 36 mg, 67%.

$^1$H NMR (d$_6$-DMSO): 12.12 (br. s., 1H), 9.18 (s, 1H), 8.49 (d, J=1.8 Hz, 1H), 8.39 (d, J=5.6 Hz, 1H), 7.94-8.05 (m, 1H), 7.56 (d, J=9.1 Hz, 2H), 7.48 (d, J=1.5 Hz, 1H), 7.35 (d, J=2.1 Hz, 1H), 7.03-7.23 (m, 4H), 6.75-6.86 (m, 1H), 6.69 (dd, J=5.7, 2.2 Hz, 1H), 4.83 (t, J=5.7 Hz, 1H), 4.15 (t, J=5.1 Hz, 2H), 3.64 (q, J=5.4 Hz, 2H), 2.27 (s, 3H)

LR MS (ES+): 513 (M+Na$^+$)

LR MS (ES−): 489 (M−H)

Example 132

1-(2-fluoro-5-methylphenyl)-3-(4-{[2-(4-{[(3R)-3-hydroxypyrrolidin-1-yl]carbonyl}-1H-pyrrol-2-yl)pyridin-4-yl]oxy}phenyl)urea

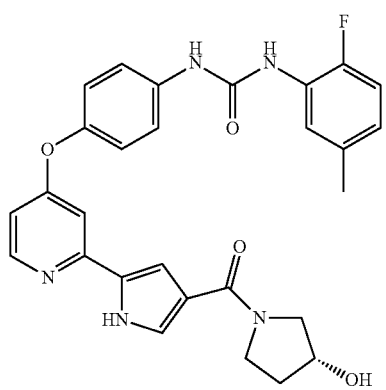 [SMILES: Cc1ccc(F)c(NC(=O)Nc2ccc(Oc3ccnc(-c4cc(C(=O)N5CC[C@@H](O)C5)c[nH]4)c3)cc2)c1]

A mixture of 5-{4-[4-({[(2-fluoro-5-methylphenyl)amino]carbonyl}amino)phenoxy]pyridin-2-yl}-1H-pyrrole-3-carboxylic acid (50 mg, 0.11 mmol), HATU (51 mg, 0.13 mmol) and N,N-diisopropylethylamine (31 mg, 0.24 mmol) in anhydrous DMF (10 ml) was stirred at room temperature for 10 minutes, followed by addition of (R)-3-pyrrolidinol (14 mg, 0.16 mmol). The mixture was stirred for another 10 minutes and poured into 100 ml of water. 2M HCl was added dropwise until pH=4~5. The precipitates were filtered, washed with water and dried in vacuo to give 1-(2-fluoro-5-methylphenyl)-3-(4-{[2-(4-{[(3R)-3-hydroxypyrrolidin-1-yl]carbonyl}-1H-pyrrol-2-yl)pyridin-4-yl]oxy}phenyl)urea as white solid. Yield: 40 mg, 71%.

$^1$H NMR (d$_6$-DMSO): 11.90 (br. s., 1H), 9.17 (s, 1H), 8.49 (d, J=2.6 Hz, 1H), 8.38 (d, J=5.9 Hz, 1H), 7.99 (dd, J=7.8, 1.9 Hz, 1H), 7.51-7.62 (m, 2H), 7.37 (d, J=2.3 Hz, 1H), 7.25 (br. s., 1H), 7.02-7.19 (m, 4H), 6.76-6.86 (m, 1H), 6.64 (dd, J=5.6, 2.3 Hz, 1H), 4.93 (br. s., 1H), 4.22-4.38 (m, 1H), 3.69-3.87 (m, 1H), 3.43-3.59 (m, 2H), 3.35-3.42 (m, 1H), 2.27 (s, 3H), 1.90 (br. s., 2H)

LR MS (ES+): 538 (M+Na$^+$)

LR MS (ES−): 514 (M−H)

Example 133

1-(2-fluoro-5-methylphenyl)-3-(4-{[2-(4-{[(3S)-3-hydroxypyrrolidin-1-yl]carbonyl}-1H-pyrrol-2-yl)pyridin-4-yl]oxy}phenyl)urea

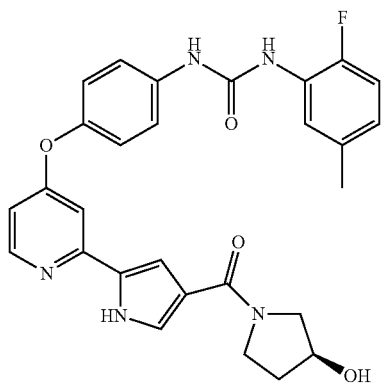 [SMILES: Cc1ccc(F)c(NC(=O)Nc2ccc(Oc3ccnc(-c4cc(C(=O)N5CC[C@H](O)C5)c[nH]4)c3)cc2)c1]

Similar procedure as Example 132.
LR MS (ES+): 538 (M+Na⁺)
LR MS (ES−): 514 (M−H)

Example 134

5-{4-[4-({[(2-fluoro-5-methylphenyl)amino]carbonyl}amino)phenoxy]pyridin-2-yl}-1H-pyrrole-3-carboxylic acid

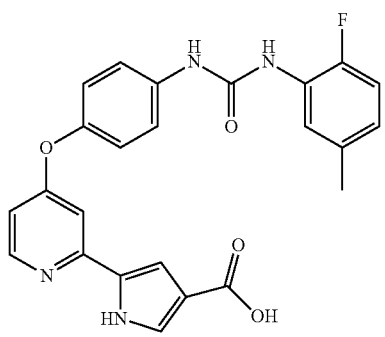 [SMILES: Cc1ccc(F)c(NC(=O)Nc2ccc(Oc3ccnc(-c4cc(C(=O)O)c[nH]4)c3)cc2)c1]

To a stirred solution of methyl 5-{4-[4-({[(2-fluoro-5-methylphenyl)amino]carbonyl}amino)phenoxy]pyridin-2-yl}-1H-pyrrole-3-carboxylate (1.38 g, 3.00 mmol) in a mixture of solvents THF/MeOH (20 ml/20 ml) was added 2 ml of 5M NaOH (10 mmol) solution. The mixture was heated in a 72° C. bath for 5 hours, cooled to room temperature and poured into 200 ml of water. 2M HCl was added until pH=3. The resulting precipitates were filtered, washed with water, and dried in vacuo to give 5-{4-[4-({[(2-fluoro-5-methylphenyl)amino]carbonyl}amino)phenoxy]pyridin-2-yl}-1H-pyrrole-3-carboxylic acid as light brown solid. Yield: 1.28 g, 96%.
¹H NMR (d₆-DMSO): 12.04 (br. s., 1H), 11.88 (br. s., 1H), 9.18 (s, 1H), 8.49 (d, J=2.3 Hz, 1H), 8.39 (d, J=5.6 Hz, 1H), 7.94-8.05 (m, 1H), 7.56 (d, J=9.1 Hz, 2H), 7.31-7.42 (m, 2H), 7.01-7.21 (m, 4H), 6.81 (td, J=5.2, 2.2 Hz, 1H), 6.68 (dd, J=5.6, 2.3 Hz, 1H), 2.27 (s, 3H)
LR MS (ES−): 467 (M−H)

Example 135 methyl 5-{4-[4-({[(2-fluoro-5-methylphenyl)amino]carbonyl}amino)phenoxy]pyridin-2-yl}-1H-pyrrole-3-carboxylate

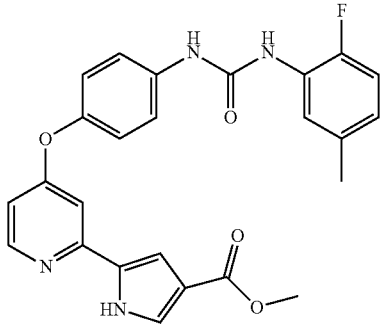 [SMILES: COC(=O)c1c[nH]c(-c2cc(Oc3ccc(NC(=O)Nc4cc(C)ccc4F)cc3)ccn2)c1]

To a stirred solution of methyl 5-[4-(4-aminophenoxy)pyridin-2-yl]-1H-pyrrole-3-carboxylate (1.0 g, 3.23 mmol) in anhydrous THF (10 ml) was added 2-fluoro-5-methyl-phenylisocyanate (488 mg, 3.23 mmol). The mixture was stirred at room temperature for one hour and poured into 200 ml of 0.02M HCl solution with vigorous stirring. The resulting precipitates were filtered, washed with water, and dried in vacuo to give methyl 5-{4-[4-({[(2-fluoro-5-methylphenyl)amino]carbonyl}amino)phenoxy]pyridin-2-yl}-1H-pyrrole-3-carboxylate as white solid. Yield: 1.38 g, 93%.
¹H NMR (d₆-DMSO): 12.14 (br. s., 1H), 9.17 (s, 1H), 8.49 (d, J=2.3 Hz, 1H), 8.39 (d, J=5.9 Hz, 1H), 7.99 (dd, J=7.9, 1.8 Hz, 1H), 7.53-7.59 (m, 2H), 7.44 (dd, J=3.2, 1.5 Hz, 1H), 7.36 (d, J=2.3 Hz, 1H), 7.06-7.18 (m, 4H), 6.77-6.85 (m, 1H), 6.68 (dd, J=5.6, 2.3 Hz, 1H), 3.72 (s, 3H), 2.28 (s, 3H)
LR MS (ES+): 483 (M+Na⁺)
LR MS (ES−): 459 (M−H)

Preparation of 1-tert-butyl 2-methyl 4-[4-(3-aminophenoxy)pyridin-2-yl]-1H-pyrrole-1,2-dicarboxylate

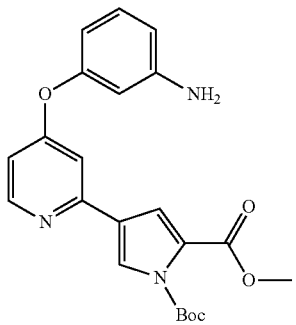 [SMILES: COC(=O)c1cc(-c2cc(Oc3cccc(N)c3)ccn2)cn1C(=O)OC(C)(C)C]

Similar procedure as 1-tert-butyl 2-methyl 4-[4-(4-aminophenoxy)pyridin-2-yl]-1H-pyrrole-1,2-dicarboxylate.
¹H NMR (d₆-DMSO): 8.38 (d, 1H), 8.01 (d, J=1.5 Hz, 1H), 7.45 (d, J=2.1 Hz, 1H), 7.37 (d, J=1.5 Hz, 1H), 7.06 (t, J=7.9 Hz, 1H), 6.67 (dd, J=5.7, 2.2 Hz, 1H), 6.43 (d, J=7.9 Hz, 1H), 6.20-6.33 (m, 2H), 5.32 (br. s., 2H), 3.72-3.85 (m, 3H), 1.53 (s, 9H)
LR MS (ES+): 432 (M+Na⁺)

Example 136 methyl 4-{4-[3-({[(2-fluoro-5-methylphenyl)amino]carbonyl}amino)phenoxy]pyridin-2-yl}-1H-pyrrole-2-carboxylate

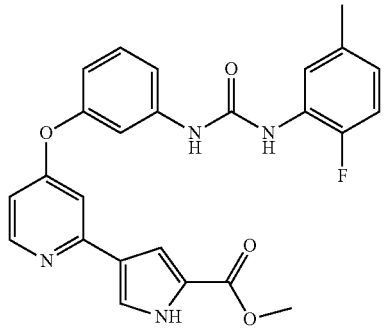 [SMILES: COC(=O)c1cc(-c2cc(Oc3cccc(NC(=O)Nc4cc(C)ccc4F)c3)ccn2)c[nH]1]

To a stirred solution of 1-tert-butyl 2-methyl 4-[4-(3-aminophenoxy)pyridin-2-yl]-1H-pyrrole-1,2-dicarboxylate (150 mg, 0.37 mmol) in anhydrous THF (10 ml) was added 2-fluoro-5-methyl-phenylisocyanate (67 mg, 0.44 mmol). The mixture was stirred at room temperature for 3 hours and poured into 100 ml of water. The resulting precipitates were filtered, washed with water, and dried in vacuo to give the Boc-protected intermediate as brown solid. This intermediate was dissolved in 5 ml of methylene chloride, and 3 ml of trifluoroacetic acid was added. Stirring was continued for 20 minutes. The mixture was evaporated to dryness to give the crude product, which was purified by silica gel chromatography eluting with 5% MeOH/CHCl$_3$ to give methyl 4-{4-[3-({[(2-fluoro-5-methylphenyl)amino]carbonyl}amino)phenoxy]pyridin-2-yl}-1H-pyrrole-2-carboxylate as white solid. Yield: 67 mg, 39%.

$^1$H NMR (d$_6$-DMSO): 12.18 (br. s., 1H), 9.23 (s, 1H), 8.47 (br. s., 1H), 8.36 (d, J=5.6 Hz, 1H), 7.91 (d, J=7.6 Hz, 1H), 7.63 (br. s., 1H), 7.25-7.47 (m, 4H), 7.16 (d, J=7.9 Hz, 1H), 7.07 (dd, J=11.4, 8.5 Hz, 1H), 6.72-6.85 (m, 2H), 6.65 (dd, J=5.6, 2.1 Hz, 1H), 3.76 (s, 3H), 2.22 (s, 3H)

LR MS (ES+): 483 (M+Na$^+$)
LR MS (ES−): 459 (M−H)

Example 137

N-[dimethyl(oxido)-lambda~4~-sulfanylidene]-4-{4-[4-({[(2-fluoro-5-methylphenyl)amino]carbonyl}amino)phenoxy]pyridin-2-yl}-1H-pyrrole-2-carboxamide

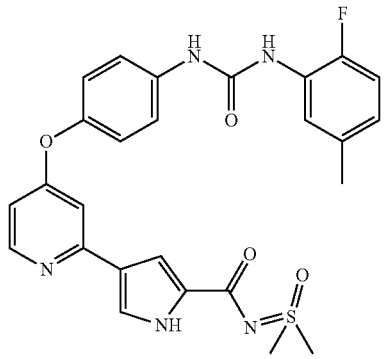 [SMILES: Cc1ccc(F)c(NC(=O)Nc2ccc(Oc3ccnc(-c4c[nH]c(C(=O)N=S(C)(C)=O)c4)c3)cc2)c1]

Similar procedure as Example 101.
LR MS (ES+): 544 (M+Na$^+$)
LR MS (ES−): 520 (M−H)

Example 138

4-{4-[4-({[(2-fluoro-5-methylphenyl)amino]carbonyl}amino)phenoxy]pyridin-2-yl}-N,N-dimethyl-1H-pyrrole-2-carboxamide

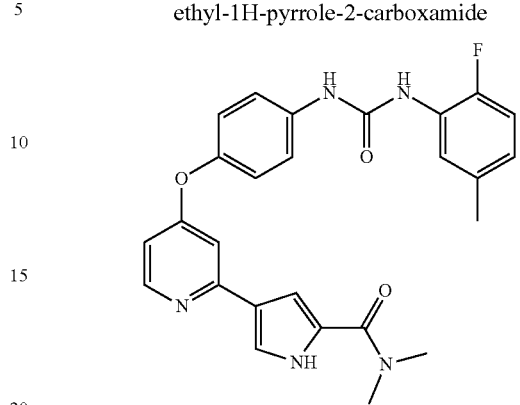

The title compound was isolated as a side product in the synthesis of Example 137.
LR MS (ES+): 474 (M+H)
LR MS (ES−): 472 (M−H

Example 139

4-{4-[4-({[(2-fluoro-5-methylphenyl)amino]carbonyl}amino)phenoxy]pyridin-2-yl}-N-methyl-1H-pyrrole-2-carboxamide

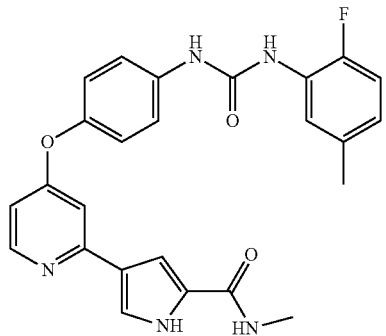

A mixture of 4-{4-[4-({[(2-fluoro-5-methylphenyl)amino]carbonyl}amino)phenoxy]pyridin-2-yl}-1H-pyrrole-2-carboxylic acid (50 mg, 0.11 mmol), HATU (50 mg, 0.13 mmol), 2M methylamine/THF solution (0.1 ml, 0.2 mmol) and N,N-diisopropylethylamine (31 mg, 0.24 mmol) in anhydrous DMF (8 ml) was stirred at room temperature for 10 minutes. The mixture was poured into 100 ml of water. The precipitates were filtered, washed with water and dried to give the crude, which was purified by silica gel chromatography with 3~5% MeOH/CHCl$_3$ to give 4-{4-[4-({[(2-fluoro-5-methylphenyl)amino]carbonyl}amino)phenoxy]pyridin-2-yl}-N-methyl-1H-pyrrole-2-carboxamide as white solid. Yield: 21 mg, 41%.

$^1$H NMR (d$_6$-DMSO): 11.69 (br. s., 1H), 9.17 (s, 1H), 8.48 (d, J=2.3 Hz, 1H), 8.32 (d, J=5.6 Hz, 1H), 8.01-8.12 (m, 1H), 7.96 (dd, J=7.8, 1.9 Hz, 1H), 7.48-7.61 (m, 2H), 7.43 (dd, J=2.9, 1.5 Hz, 1H), 7.03-7.23 (m, 5H), 6.79 (dt, J=8.1, 2.3 Hz, 1H), 6.61 (dd, J=5.6, 2.3 Hz, 1H), 2.71 (d, J=4.7 Hz, 3H), 2.26 (s, 3H)

LR MS (ES+): 482 (M+Na⁺)

LR MS (ES−): 458 (M−H)

Preparation of 4-(4-aminophenoxy)-6-chloropyridin-2-amine

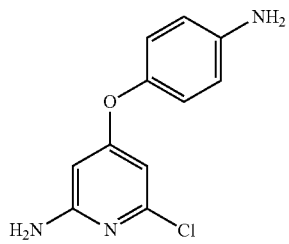 [SMILES: Nc1ccc(Oc2cc(N)nc(Cl)c2)cc1]

A stirred solution of 4-aminophenol (335 mg, 3.1 mmol) in anhydrous DMSO (8 ml) was flushed with nitrogen and treated with 1M KOBu$^t$/THF solution (3.1 ml, 3.1 mmol). The mixture was stirred at room temperature under nitrogen for 10 minutes. 4,6-dichloropyridin-2-ylamine (500 mg, 3.1 mmol) was added and the mixture was heated at 88° C. for 16 hours, cooled to room temperature and poured into 100 ml of water. The resulting precipitates were filtered, washed with water and dried to give the crude product, which was purified by silica gel chromatography with 2~5% MeOH/CHCl₃ to give 4-(4-aminophenoxy)-6-chloropyridin-2-amine as light brown solid. Yield: 350 mg, 49%.

Example 140

1-tert-butyl 2-methyl 4-{6-amino-4-[4-({[(2-fluoro-5-methylphenyl)amino]carbonyl}amino)phenoxy]pyridin-2-yl}-1H-pyrrole-1,2-dicarboxylate

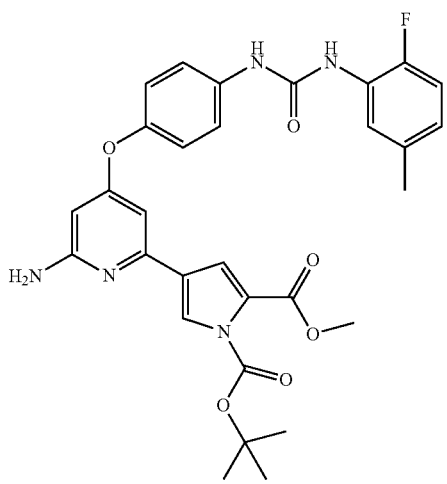 [SMILES: COC(=O)c1cc(-c2cc(Oc3ccc(NC(=O)Nc4cc(C)ccc4F)cc3)cc(N)n2)cn1C(=O)OC(C)(C)C]

Similar procedure as Example 148.

LR MS (ES+): 598 (M+Na⁺)

Example 141

1-(4-{[2-amino-6-(1H-pyrrol-2-yl)pyridin-4-yl]oxy}phenyl)-3-(2-fluoro-5-methylphenyl)urea

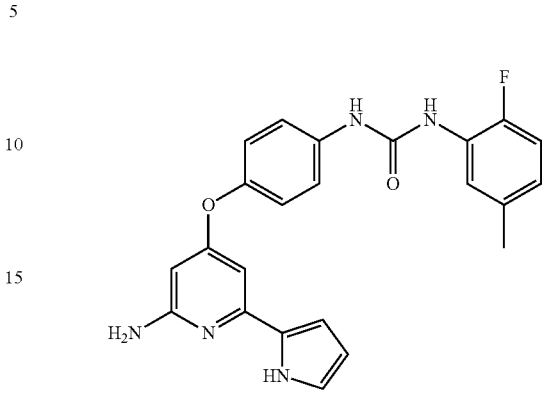

Similar procedure as Example 148.

¹H NMR (d₆-DMSO): 11.02 (br. s., 1H), 9.11 (s, 1H), 8.44 (br. s., 1H), 7.97 (d, 1H), 7.50 (d, J=8.8 Hz, 2H), 6.98-7.17 (m, 3H), 6.78 (br. s., 2H), 6.53 (br. s., 2H), 6.05 (br. s., 1H), 5.74 (br. s., 2H), 5.61 (s, 1H), 2.25 (s, 3H)

LR MS (ES+): 418 (M+H)

LR MS (ES−): 416 (M−H)

Example 142

4-{4-[4-({[(2-fluoro-5-methylphenyl)amino]carbonyl}amino)phenoxy]pyridin-2-yl}-1H-pyrrole-2-carboxylic acid

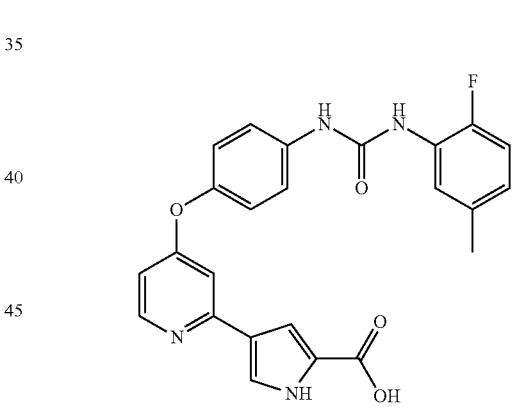

To a stirred solution of methyl 4-{4-[4-({[(2-fluoro-5-methylphenyl)amino]carbonyl}amino)phenoxy]pyridin-2-yl}-1H-pyrrole-2-carboxylate (220 mg, 0.48 mmol) in THF/MeOH (3 ml/10 ml) was added 1M NaOH (4.0 ml, 4.0 mmol). The mixture was heated at 70° C. for 2 hours, cooled to room temperature and poured into 100 ml of water. 1M HCl was added until pH=4 and the resulting precipitates were filtered, washed with water and dried in vacuo to give 4-{4-[4-({[(2-fluoro-5-methylphenyl)amino]carbonyl}amino)phenoxy]pyridin-2-yl}-1H-pyrrole-2-carboxylic acid.

Yield: 200 mg, 94%.

¹H NMR (d₆-DMSO): 12.38 (br. s., 1H), 12.04 (br. s., 1H), 9.14-9.23 (m, 1H), 8.48 (d, J=2.3 Hz, 1H), 8.34 (d, J=5.6 Hz, 1H), 7.97 (dd, J=7.9, 2.1 Hz, 1H), 7.60 (br. s., 1H), 7.50-7.58 (m, 2H), 7.30 (d, J=2.1 Hz, 1H), 7.22 (s, 1H), 7.03-7.18 (m, 3H), 6.73-6.84 (m, 1H), 6.60 (dd, J=5.6, 2.3 Hz, 1H), 2.25 (s, 3H)

LR MS (ES−): 445 (M−H)

Preparation of 1-tert-butyl 2-methyl 4-[4-(4-aminophenoxy)pyridin-2-yl]-1H-pyrrole-1,2-dicarboxylate

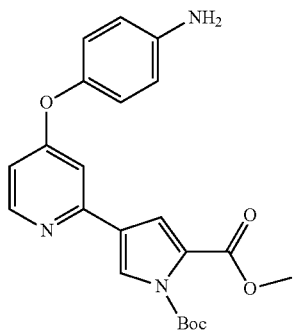 [SMILES: COC(=O)c1cc(-c2cc(Oc3ccc(N)cc3)ccn2)cn1C(=O)OC(C)(C)C]

A 100 ml flask was charged with 4-((2-chloropyridin-4-yl)oxy)aniline (150 mg, 0.68 mmol), 1-tert-butyl 2-methyl 4-(4,4,5,5-tetramethyl-1,3,2-dioxaborolan-2-yl)-1H-pyrrole-1,2-dicarboxylate (260 mg, 0.81 mmol), 2M Na$_2$CO$_3$ solution (0.5 ml, 1.0 mmol), PdCl$_2$(PPh$_3$)$_2$ (5 mg, 0.007 mmol), 10 ml of 1,4-dioxane and 3 ml of water. The mixture was flushed with nitrogen and heated at 70° C. for 30 minutes. The mixture was cooled to room temperature and poured into 100 ml of water. The precipitates were filtered and dried to give the crude, which was further purified by silica gel chromatography eluting with 2-3% MeOH/CHCl$_3$ to give 1-tert-butyl 2-methyl 4-[4-(4-aminophenoxy)pyridin-2-yl]-1H-pyrrole-1,2-dicarboxylate as light brown oil.
Yield: 240 mg, 86%.

Example 143

Methyl 4-{4-[4-({[(2-fluoro-5-methylphenyl)amino]carbonyl}amino)phenoxy]pyridin-2-yl}-1H-pyrrole-2-carboxylate

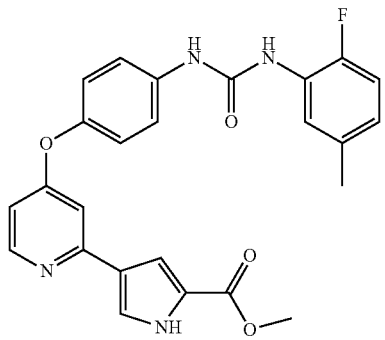 [SMILES: COC(=O)c1cc(-c2cc(Oc3ccc(NC(=O)Nc4cc(C)ccc4F)cc3)ccn2)c[nH]1]

To a stirred solution of 1-tert-butyl 2-methyl 4-[4-(4-aminophenoxy)pyridin-2-yl]-1H-pyrrole-1,2-dicarboxylate (240 mg, 0.59 mmol) in anhydrous THF (10 ml) was added 2-fluoro-5-methyl-phenylisocyanate (107 mg, 0.71 mmol). The mixture was stirred at room temperature for 30 minutes and poured into 100 ml of water. The resulting precipitates were filtered, washed with water and dried to give a brown oil. Purification by silica gel chromatography eluting with 2-3% MeOH/CHCl$_3$ gave the Boc-protected intermediate as light green oil, which was dissolved in 5 ml of methylene chloride, followed by addition of 3 ml of trifluoroacetic acid. The mixture was stirred at room temperature for 10 minutes, evaporated to dryness, and purified by silica gel chromatography eluting with 2-5% MeOH/CHCl$_3$ to give methyl 4-{4-[4-({[(2-fluoro-5-methylphenyl)amino]carbonyl}amino)phenoxy]pyridin-2-yl}-1H-pyrrole-2-carboxylate as white solid. Yield: 135 mg, 50%.

$^1$H NMR (d$_6$-DMSO): 12.17 (br. s., 1H), 9.14 (s, 1H), 8.46 (d, J=2.3 Hz, 1H), 8.33 (d, J=5.9 Hz, 1H), 7.91-8.04 (m, 1H), 7.61 (dd, J=3.1, 1.6 Hz, 1H), 7.53 (d, J=9.1 Hz, 2H), 7.22-7.31 (m, 2H), 7.02-7.17 (m, 3H), 6.73-6.85 (m, 1H), 6.58 (dd, J=5.7, 2.5 Hz, 1H), 3.76 (s, 3H), 2.26 (s, 3H)
LR MS (ES+): 483 (M+Na$^+$)
LR MS (ES−): 459 (M−H)

Preparation of tert-butyl 2-[4-(4-aminophenoxy)pyridin-2-yl]-1H-pyrrole-1-carboxylate

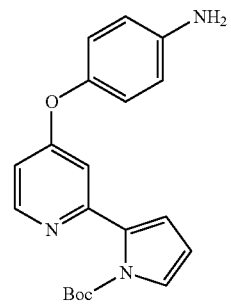 [SMILES: CC(C)(C)OC(=O)n1cccc1-c1cc(Oc2ccc(N)cc2)ccn1]

To a stirred mixture of N-Boc-pyrrole-2-boronic acid (114 mg, 0.54 mmol) and 4-((2-chloropyridin-4-yl)oxy)aniline (100 mg, 0.45 mmol) in 8 ml of 1,4-dioxane, was added PdCl$_2$(PPh$_3$)$_2$ (10 mg, 0.014 mmol) and 1M Na$_2$CO$_3$ aqueous solution (0.5 ml, 1.0 mmol). The mixture was heated at 72° C. under N$_2$ for one hour, cooled to room temperature and poured into 100 ml of water. The resulting mixture was extracted with EtOAc (2×50 ml). The organic layers were combined, washed with brine (50 ml), dried over Na$_2$SO$_4$, and evaporated to give a brown oil, which was purified by silica gel chromatography with a gradient of 20~50% EtOAc/hexanes to give tert-butyl 2-[4-(4-aminophenoxy)pyridin-2-yl]-1H-pyrrole-1-carboxylate as colorless oil. Yield: 110 mg, 70%.

Example 144

1-(2-fluoro-5-methylphenyl)-3-(4-{[2-(1H-pyrrol-2-yl)pyridin-4-yl]oxy}phenyl)urea

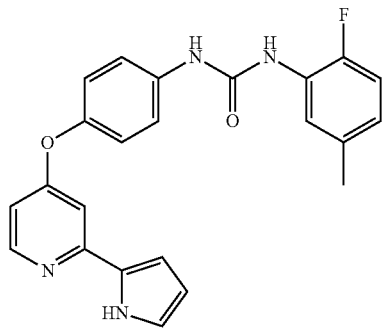 [SMILES: Cc1ccc(F)c(NC(=O)Nc2ccc(Oc3ccnc(-c4ccc[nH]4)c3)cc2)c1]

To a stirred solution of tert-butyl 2-[4-(4-aminophenoxy)pyridin-2-yl]-1H-pyrrole-1-carboxylate (100 mg, 0.28 mmol) in anhydrous THF (10 ml) was added 2-fluoro-5-methyl-phenylisocyanate (51 mg, 0.34 mmol). The mixture was stirred at room temperature for one hour and poured into 100 ml of water. The resulting mixture was extracted with EtOAc (2×50 ml). The organic layers were combined, washed with brine (50 ml), dried over Na₂SO₄, and evaporated to give a brown oil, which was purified by silica gel chromatography with 2-5% MeOH/CHCl₃ to give the Boc-protected intermediate as light green oil. The oil was dissolved in 5 ml of methylene chloride, and 3 ml of trifluoroacetic acid was added. Stirring was continued for 10 hours, and the mixture was evaporated to dryness. The brown residue was dissolved in methanol (5 ml). This methanol solution was then added dropwise into 100 ml of 1M NaHCO₃ solution with stirring. The resulting precipitates were filtered, washed with water, and dried in vacuo to give 1-(2-fluoro-5-methylphenyl)-3-(4-{[2-(1H-pyrrol-2-yl)pyridin-4-yl]oxy}phenyl)urea as light grey solid.

¹H NMR (d₆-DMSO): 11.43 (br. s., 1H), 9.14 (s, 1H), 8.46 (d, J=2.6 Hz, 1H), 8.32 (d, J=5.6 Hz, 1H), 7.96 (dd, J=7.9, 1.8 Hz, 1H), 7.48-7.58 (m, 2H), 7.20 (d, J=2.1 Hz, 1H), 7.04-7.16 (m, 3H), 6.75-6.86 (m, 2H), 6.67 (dt, J=3.8, 1.9 Hz, 1H), 6.57 (dd, J=5.9, 2.3 Hz, 1H), 6.05-6.13 (m, 1H), 2.25 (s, 3H)

Example 145

1-phenyl-3-{4-[6-(1H-pyrrol-2-yl)pyridin-3-yl]phenyl}urea

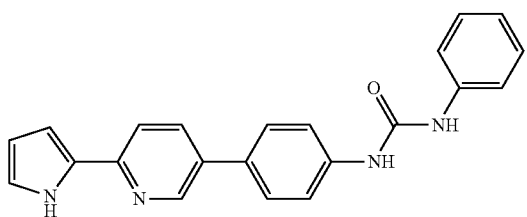 [SMILES: O=C(Nc1ccccc1)Nc1ccc(-c2ccc(-c3ccc[nH]3)nc2)cc1]

Similar procedure as Example 148.
¹H NMR (DMSO-d₆): 11.46 (br. s., 1H), 8.79 (s, 1H), 8.75 (d, J=1.8 Hz, 1H), 8.67 (s, 1H), 7.98 (dd, J=8.4, 2.5 Hz, 1H), 7.70 (d, J=8.2 Hz, 1H), 7.67 (d, J=8.5 Hz, 2H), 7.56 (d, J=8.5 Hz, 2H), 7.45 (d, J=7.6 Hz, 2H), 7.27 (t, J=7.9 Hz, 2H), 6.96 (t, J=7.3 Hz, 1H), 6.84-6.88 (m, 1H), 6.77 (t, J=3.8 Hz, 1H), 6.11-6.16 (m, 1H)

Example 146

1-(2-fluoro-5-methylphenyl)-3-{3-[2-(1H-pyrrol-2-yl)pyridin-4-yl]phenyl}urea

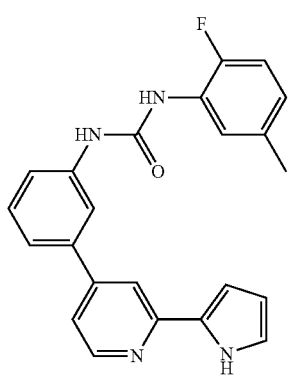 [SMILES: Cc1ccc(F)c(NC(=O)Nc2cccc(-c3ccnc(-c4ccc[nH]4)c3)c2)c1]

Similar procedure as Example 148
LR MS (ES+): 387 (M+H⁺)

Example 147

1-(2-fluoro-5-methylphenyl)-3-{4-[2-(1H-pyrrol-3-yl)pyridin-4-yl]phenyl}urea

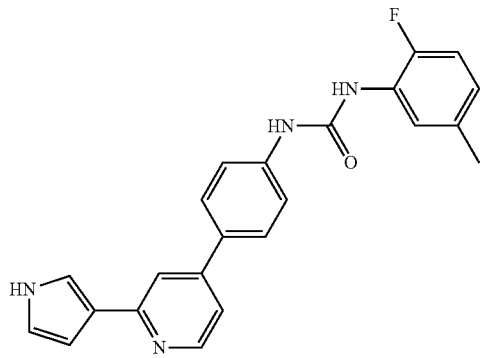 [SMILES: Cc1ccc(F)c(NC(=O)Nc2ccc(-c3ccnc(-c4cc[nH]c4)c3)cc2)c1]

Similar procedure as Example 148.
¹H NMR (d₆-DMSO): 11.72 (br. s., 1H), 9.49 (br. s., 1H), 8.63 (s, 1H), 8.53 (d, J=6.4 Hz, 1H), 8.38 (br. s., 1H), 8.07 (d, J=8.5 Hz, 2H), 8.00-8.04 (m, 1H), 7.97 (dd, J=7.9, 1.8 Hz, 1H), 7.81-7.90 (m, 1H), 7.69 (d, J=8.8 Hz, 2H), 7.13 (dd, J=11.3, 8.4 Hz, 1H), 7.03 (d, J=2.1 Hz, 1H), 6.98 (br. s., 1H), 6.84 (ddd, J=7.8, 5.3, 2.1 Hz, 1H), 2.21-2.36 (m, 3H)
LR MS (ES+): 387 (M+H)

tert-butyl (4-(2-chloropyridin-4-yl)phenyl)carbamate

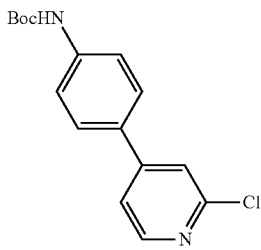 [SMILES: CC(C)(C)OC(=O)Nc1ccc(-c2ccnc(Cl)c2)cc1]

To a mixture of (4-boc-aminophenyl)boronic acid (200 mg, 0.84 mmol) and 2-chloro-4-bromopyridine (162 mg, 0.84 mmol) in 10 ml of 1,4-dioxane, was added PdCl₂(PPh₃)₂ (10 mg, 0.014 mmol) and 1M Na₂CO₃ aqueous solution (0.5 ml, 1.0 mmol). The mixture was heated at 70° C. under N₂ for 2 hours, cooled to room temperature and poured into 100 ml of water. The brown precipitates were filtered, washed with water and dried to give tert-butyl (4-(2-chloropyridin-4-yl)phenyl)carbamate as the crude product.

4-(2-(1H-pyrrol-2-yl)pyridin-4-yl)aniline

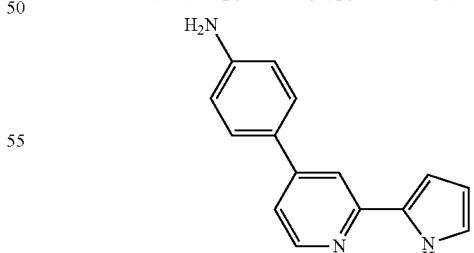

To a mixture of N-Boc-pyrrole-2-boronic acid (210 mg, 1.0 mmol) and tert-butyl (4-(2-chloropyridin-4-yl)phenyl)carbamate (250 mg, 0.82 mmol) in 10 ml of 1,4-dioxane, was added PdCl₂(PPh₃)₂ (10 mg, 0.014 mmol) and 1M Na₂CO₃ aqueous solution (0.75 ml, 1.5 mmol). The mixture was heated at 60° C. under N₂ for 3 hours, cooled to room temperature and poured into 100 ml of water. The precipitates were filtered, dried and purified by silica gel chromatography with 1-5% MeOH/CHCl₃ to give the intermediate as light yellow oil. This intermediate was dissolved in 10 ml of methylene chloride and 3 ml of trifluoroacetic acid was added. The mixture was stirred at room temperature for 16 hours and evaporated to dryness to give 4-(2-(1H-pyrrol-2-yl)pyridin-4-yl)aniline TFA salt as light brown solid. Yield: 290 mg, 100%.

Example 148

1-(2-fluoro-5-methylphenyl)-3-{4-[2-(1H-pyrrol-2-yl)pyridin-4-yl]phenyl}urea

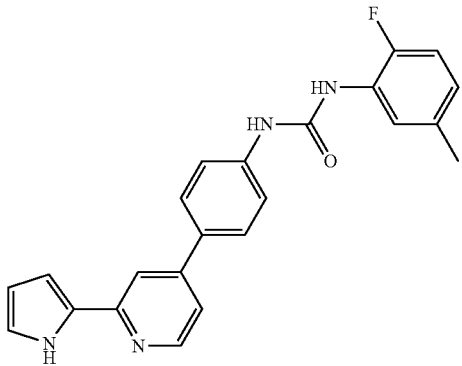 [SMILES: Cc1ccc(F)c(NC(=O)Nc2ccc(-c3ccnc(-c4ccc[nH]4)c3)cc2)c1]

To a stirred suspension of 4-(2-(1H-pyrrol-2-yl)pyridin-4-yl)aniline TFA salt (60 mg, 0.17 mmol) in anhydrous THF (10 ml) was added 2-fluoro-5-methyl-phenylisocyanate (48 mg, 0.32 mmol) and N,N-diisopropylethylamine (40 mg, 0.31 mmol). After 1 hour, the reaction mixture was evaporated and purified by silica gel chromatography with 2-3% MeOH/CHCl₃ to give 1-(2-fluoro-5-methylphenyl)-3-{4-[2-(1H-pyrrol-2-yl)pyridin-4-yl]phenyl}urea as off-white solid. Yield: 28 mg.

¹H NMR (d₆-DMSO): 11.49 (br. s., 1H), 9.29 (br. s., 1H), 8.52-8.60 (m, 1H), 8.48 (d, J=5.3 Hz, 1H), 7.94-8.04 (m, 2H), 7.84 (d, J=8.5 Hz, 2H), 7.62 (d, J=8.5 Hz, 2H), 7.42 (dd, J=5.3, 1.5 Hz, 1H), 7.12 (dd, J=11.4, 8.2 Hz, 1H), 6.89 (s, 2H), 6.82 (dt, J=5.4, 2.6 Hz, 1H), 6.16 (t, J=2.9 Hz, 1H), 2.29 (s, 3H)

LR MS (ES+): 409 (M+Na⁺)
LR MS (ES−): 385 (M−H)

Synthesis and characterization of additional compounds are listed below.

Example 149

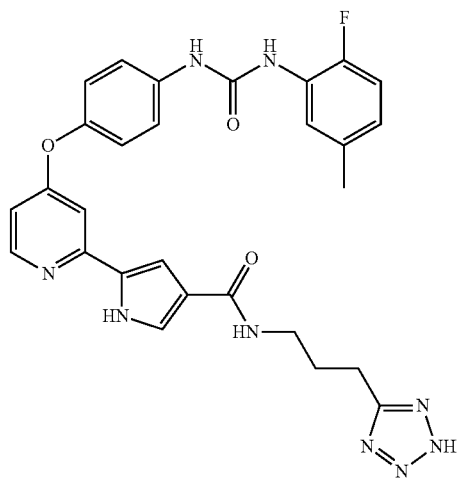 [SMILES: Cc1ccc(F)c(NC(=O)Nc2ccc(Oc3ccnc(-c4cc(C(=O)NCCCc5nn[nH]n5)c[nH]4)c3)cc2)c1]

5-{4-[4-({[(2-fluoro-5-methylphenyl)amino] carbonyl}amino)phenoxy]pyridin-2-yl}-N-[3-(2H-tetrazol-5-yl)propyl]-1H-pyrrole-3-carboxamide To a stirred solution of 5-{4-[4-({[(2-fluoro-5-methylphenyl)amino]carbonyl}amino)phenoxy]pyridin-2-yl}-1H-pyrrole-3-carboxylic acid (100 mg, 0.22 mmol) in 10 ml of anhydrous DMF were added HATU (91 mg, 0.24 mmol) and N,N-diisopropylethylamine (85 mg, 0.66 mmol). The mixture was stirred at room temperature for 10 minutes, followed by addition of 3-(1H-tetrazol-5-yl)propan-1-amine hydrochloride (54 mg, 0.33 mmol). The mixture was stirred at room temperature for another 60 minutes and poured into 100 ml of water with vigorous stirring. 1M HCl was added dropwise until pH=5. The precipitates were filtered, washed with water and dried in vacuo to give 5-{4-[4-({[(2-fluoro-5-methylphenyl)amino]carbonyl}amino)phenoxy]pyridin-2-yl}-N-[3-(2H-tetrazol-5-yl)propyl]-1H-pyrrole-3-carboxamide as light brown solid. Yield: 105 mg, 85%.

¹H NMR (DMSO-d₆): 11.83 (t, J=2.9 Hz, 1H), 9.17 (s, 1H), 8.49 (d, J=2.9 Hz, 1H), 8.38 (d, J=5.9 Hz, 1H), 7.98-8.00 (m, 2H), 7.55-7.58 (m, 2H), 7.37 (dd, J=3.2, 1.8 Hz, 1H), 7.14-7.17 (m, 3H), 7.11 (dd, J=11.4, 8.2 Hz, 1H), 7.06-7.07 (m, 1H), 6.80-6.82 (m, 1H), 6.71 (dd, J=5.6, 2.3 Hz, 1H), 3.24-3.27 (m, 2H), 2.90 (t, J=7.8 Hz, 2H), 2.28 (s, 3H), 1.91 (quin, J=7.3 Hz, 2H)

LR MS (ES−): 554 (M−H)

The following Example 150 was prepared using the experiment procedure described in Example 149, but with the appropriate reagent, reaction conditions and reactant substitutions that will be readily realized by those of ordinary skill in this art without the exercise of undue experimentation.

Example 150

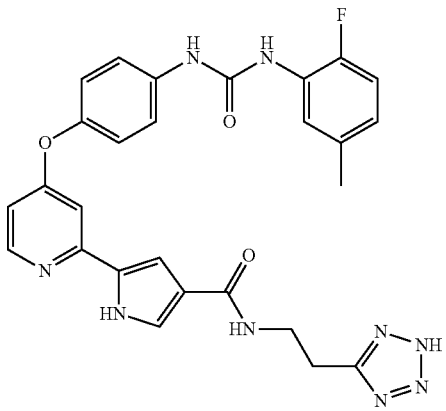 [SMILES: Cc1ccc(F)c(NC(=O)Nc2ccc(Oc3ccnc(-c4cc(C(=O)NCCc5nn[nH]n5)c[nH]4)c3)cc2)c1]

5-{4-[4-({[(2-fluoro-5-methylphenyl)amino] carbonyl}amino)phenoxy]pyridin-2-yl}-N-[2-(2H-tetrazol-5-yl)ethyl]-1H-pyrrole-3-carboxamide ¹H NMR (DMSO-d₆): 11.92 (br. s., 1H), 9.22 (s, 1H), 8.51 (d, J=2.6 Hz, 1H), 8.40 (d, J=5.9 Hz, 1H), 8.10 (t, J=5.7 Hz, 1H), 7.98 (dd, J=8.4, 1.9 Hz, 1H), 7.56-7.59 (m, 2H), 7.40 (br. s., 1H), 7.20 (br. s., 1H), 7.16-7.19 (m, 2H), 7.11 (dd, J=11.3, 8.4 Hz, 1H), 7.09 (br. s., 1H), 6.80-6.83 (m, 1H), 6.77 (br. s., 1H), 3.54-3.57 (m, 2H), 3.10 (t, J=7.0 Hz, 2H), 2.28 (s, 3H)

LR MS (ES+): 542 (MH+)
LR MS (ES−): 540 (M−H)

Example 151

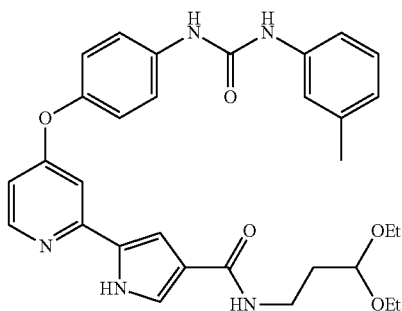 [SMILES: CCOC(CCNC(=O)c1c[nH]c(-c2cc(Oc3ccc(NC(=O)Nc4cccc(C)c4)cc3)ccn2)c1)OCC]

N-(3,3-diethoxypropyl)-5-{4-[4-({[(3-methylphenyl)amino]carbonyl}amino)phenoxy]pyridin-2-yl}-1H-pyrrole-3-carboxamide To a stirred solution of 5-{4-[4-({[(3-methylphenyl)amino]carbonyl}amino)phenoxy]pyridin-2-yl}-1H-pyrrole-3-carboxylic acid (Example 115) (700 mg, 1.64 mmol) in 10 ml of anhydrous DMF were added HATU (684 mg, 1.84 mmol) and N,N-diisopropylethylamine (426 mg, 3.3 mmol). The mixture was stirred at room temperature for 10 minutes, followed by addition of 1-amino-3,3-diethoxypropane (294 mg, 2.0 mmol). The mixture was stirred at room temperature for another 10 minutes and poured into 150 ml of water with vigorous stirring. The precipitates were filtered, washed with water and dried in vacuo to give N-(3,3-diethoxypropyl)-5-{4-[4-({[(3-methylphenyl)amino]carbonyl}amino)phenoxy]pyridin-2-yl}-1H-pyrrole-3-carboxamide as white solid. Yield: 910 mg, 100%.

$^1$H NMR (DMSO-$d_6$): 11.81 (br. s., 1H), 8.77 (s, 1H), 8.60 (s, 1H), 8.38 (d, J=5.6 Hz, 1H), 7.82 (t, J=5.7 Hz, 1H), 7.53-7.60 (m, 2H), 7.35 (dd, J=3.1, 1.6 Hz, 1H), 7.30 (s, 1H), 7.12-7.26 (m, 5H), 7.03 (t, J=2.2 Hz, 1H), 6.80 (d, J=7.3 Hz, 1H), 6.70 (dd, J=5.9, 2.3 Hz, 1H), 4.53 (t, J=5.4 Hz, 1H), 3.51-3.63 (m, 2H), 3.43 (dq, J=9.7, 7.0 Hz, 2H), 3.16-3.24 (m, 2H), 2.28 (s, 3H), 1.68-1.78 (m, 2H), 1.11 (t, J=7.0 Hz, 6H)

LR MS (ES-): 556 (M-H)

Example 152

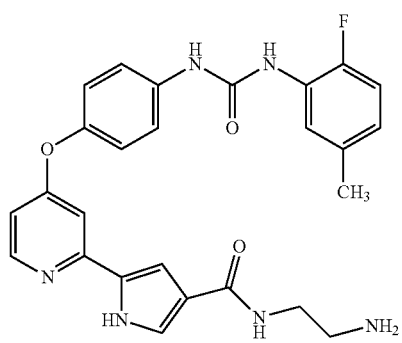 [SMILES: Cc1ccc(F)c(NC(=O)Nc2ccc(Oc3ccnc(-c4cc(C(=O)NCCN)c[nH]4)c3)cc2)c1]

N-(2-aminoethyl)-5-{4-[4-({[(2-fluoro-5-methylphenyl)amino]carbonyl}amino)phenoxy]pyridin-2-yl}-1H-pyrrole-3-carboxamide To a stirred suspension of tert-butyl (2-{[(5-{4-[4-({[(2-fluoro-5-methylphenyl)amino]carbonyl}amino)phenoxy]pyridin-2-yl}-1H-pyrrol-3-yl)carbonyl]amino}ethyl)carbamate (355 mg, 0.60 mmol) in 10 ml of methylene chloride was added 5 ml of trifluoroacetic acid. The mixture was stirred at room temperature for 30 minutes and evaporated to dryness under reduced pressure. The residue was re-dissolved in MeOH (5 ml) and poured into 100 ml of water with vigorous stirring. Saturated NaHCO3 solution was added until pH=8~9. The precipitates were filtered, washed with water and dried in vacuo to give N-(2-aminoethyl)-5-{4-[4-({[(2-fluoro-5-methylphenyl)amino]carbonyl}amino)phenoxy]pyridin-2-yl}-1H-pyrrole-3-carboxamide as brown solid. Yield: 260 mg, 88%.

LR MS (ES+): 489 (MH+)

Example 153

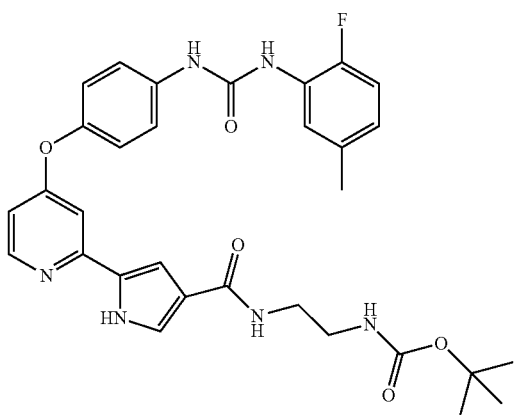 [SMILES: Cc1ccc(F)c(NC(=O)Nc2ccc(Oc3ccnc(-c4cc(C(=O)NCCNC(=O)OC(C)(C)C)c[nH]4)c3)cc2)c1]

tert-butyl (2-{[(5-{4-[4-({[(2-fluoro-5-methylphenyl)amino]carbonyl}amino)phenoxy]pyridin-2-yl}-1H-pyrrol-3-yl)carbonyl]amino}ethyl)carbamate A mixture of 5-{4-[4-({[(2-fluoro-5-methylphenyl)amino]carbonyl}amino)phenoxy]pyridin-2-yl}-1H-pyrrole-3-carboxylic acid (300 mg, 0.67 mmol), HATU (280 mg, 0.74 mmol) and N,N-diisopropylethylamine (190 mg, 1.47 mmol) in anhydrous DMF (10 ml) was stirred at room temperature for 10 minutes, followed by addition of tert-butyl (2-aminoethyl)carbamate (128 mg, 0.80 mmol). The mixture was stirred for another 10 minutes and poured into 100 ml of water. The precipitates were filtered, washed with water and dried in vacuo to give tert-butyl (2-{[(5-{4-[4-({[(2-fluoro-5-methylphenyl)amino]carbonyl}amino)phenoxy]pyridin-2-yl}-1H-pyrrol-3-yl)carbonyl]amino}ethyl)carbamate as white solid. Yield: 355 mg, 90%.

$^1$H NMR (DMSO-$d_6$): 11.84 (br. s., 1H), 9.18 (s, 1H), 8.49 (d, J=2.6 Hz, 1H), 8.39 (d, J=5.6 Hz, 1H), 7.99 (dd, J=7.8, 2.2 Hz, 1H), 7.89 (t, J=5.4 Hz, 1H), 7.54-7.60 (m, 2H), 7.35-7.38 (m, 1H), 7.08-7.19 (m, 4H), 7.05 (s, 1H), 6.78-6.87 (m, 2H), 6.73 (dd, J=5.9, 2.3 Hz, 1H), 3.17-3.24 (m, 2H), 3.00-3.08 (m, 2H), 2.27 (s, 3H), 1.36 (s, 9H)

LR MS (ES+): 611 (M+Na$^+$)

LR MS (ES-): 587 (M-H)

Example 154

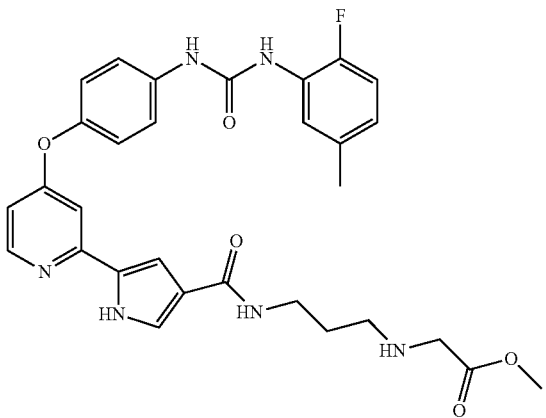 [SMILES: COC(=O)CNCCCNC(=O)c1c[nH]c(-c2cc(Oc3ccc(NC(=O)Nc4cc(C)ccc4F)cc3)ccn2)c1]

methyl [(3-{[(5-{4-[4-({[(2-fluoro-5-methylphenyl)amino]carbonyl}amino)phenoxy]pyridin-2-yl}-1H-pyrrol-3-yl)carbonyl]amino}propyl)amino]acetate To a stirred solution of N-(3-aminopropyl)-5-{4-[4-({[(2-fluoro-5-methylphenyl)amino]carbonyl}amino)phenoxy]pyridin-2-yl}-1H-pyrrole-3-carboxamide (260 mg, 0.52 mmol) and N,N-diisopropylethylamine (134 mg, 1.04 mmol) in 10 ml of anhydrous DMF was added methyl bromoacetate (80 mg, 0.52 mmol). The mixture was stirred at room temperature for 40 minutes and poured into 100 ml of water with vigorous stirring. The precipitates were filtered and dried in vacuo to give the crude, which was purified by silica gel chromatography eluting with a gradient of 3~10% MeOH/CHCl$_3$ to afford methyl [(3-{[(5-{4-[4-({[(2-fluoro-5-methylphenyl)amino]carbonyl}amino)phenoxy]pyridin-2-yl}-1H-pyrrol-3-yl)carbonyl]amino}propyl)amino]acetate as white solid. Yield: 100 mg, 34%.

$^1$H NMR (DMSO-d$_6$): 11.80 (br. s., 1H), 9.19 (s, 1H), 8.50 (d, J=2.9 Hz, 1H), 8.38 (d, J=5.6 Hz, 1H), 7.99 (dd, J=7.9, 2.1 Hz, 1H), 7.88 (t, J=5.7 Hz, 1H), 7.55-7.58 (m, 2H), 7.35 (dd, J=3.2, 1.8 Hz, 1H), 7.14-7.18 (m, 3H), 7.11 (dd, J=11.3, 8.4 Hz, 1H), 7.05 (dd, J=2.5, 1.9 Hz, 1H), 6.79-6.82 (m, 1H), 6.70 (dd, J=5.6, 2.3 Hz, 1H), 3.61 (s, 3H), 3.32 (br. s., 2H), 3.19-3.23 (m, 2H), 2.53 (t, J=6.9 Hz, 2H), 2.27 (s, 3H), 1.59 (quin, J=6.9 Hz, 2H)

LR MS (ES+): 575 (MH+)
LR MS (ES−): 573 (M−H)

Example 155

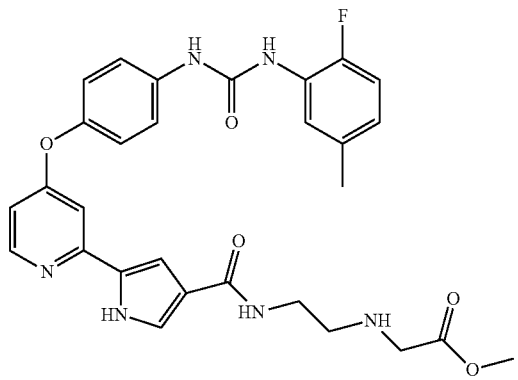 [SMILES: COC(=O)CNCCNC(=O)c1c[nH]c(-c2cc(Oc3ccc(NC(=O)Nc4cc(C)ccc4F)cc3)ccn2)c1]

methyl [(2-{[(5-{4-[4-({[(2-fluoro-5-methylphenyl)amino]carbonyl}amino)phenoxy]pyridin-2-yl}-1H-pyrrol-3-yl)carbonyl]amino}ethyl)amino]acetate To a stirred solution of N-(2-aminoethyl)-5-{4-[4-({[(2-fluoro-5-methylphenyl)amino]carbonyl}amino)phenoxy]pyridin-2-yl}-1H-pyrrole-3-carboxamide (200 mg, 0.41 mmol) in 10 ml of anhydrous DMF, were added N,N-diisopropylethylamine (137 mg, 1.06 mmol) and methyl bromoacetate (82 mg, 0.54 mmol). The mixture was stirred at room temperature for 1 hour and poured into 100 ml of water. The precipitates were filtered, washed with water, and dried in vacuo to give the crude, which was purified by silica gel chromatography eluting with a gradient of 3~8% of methanol in chloroform to give methyl [(2-{[(5-{4-[4-({[(2-fluoro-5-methylphenyl)amino]carbonyl}amino)phenoxy]pyridin-2-yl}-1H-pyrrol-3-yl)carbonyl]amino}ethyl)amino]acetate as white solid. Yield: 100 mg, 43%.

$^1$H NMR (DMSO-d$_6$): 11.82 (br. s., 1H), 9.20 (s, 1H), 8.50 (d, J=2.6 Hz, 1H), 8.38 (d, J=5.9 Hz, 1H), 7.99 (dd, J=7.9, 2.3 Hz, 1H), 7.85 (t, J=5.7 Hz, 1H), 7.56-7.59 (m, 2H), 7.37 (dd, J=3.1, 1.6 Hz, 1H), 7.15-7.17 (m, 3H), 7.11 (dd, J=11.3, 8.4 Hz, 1H), 7.05-7.06 (m, 1H), 6.79-6.82 (m, 1H), 6.71 (dd, J=5.6, 2.3 Hz, 1H), 3.61 (s, 3H), 3.36 (s, 2H), 3.25 (q, J=6.3 Hz, 2H), 2.64 (t, J=6.5 Hz, 2H), 2.27 (s, 3H)

LR MS (ES+): 561 (MH+)
LR MS (ES−): 559 (M−H)

Example 156

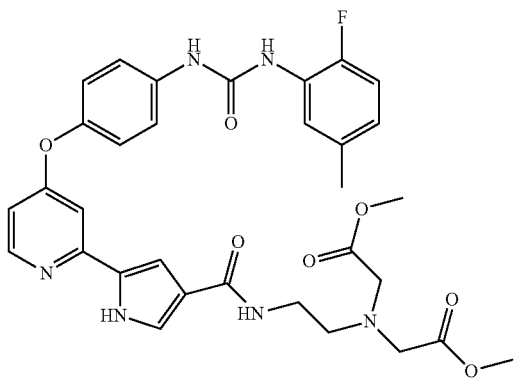 [SMILES: COC(=O)CN(CCNC(=O)c1c[nH]c(-c2cc(Oc3ccc(NC(=O)Nc4cc(C)ccc4F)cc3)ccn2)c1)CC(=O)OC]

dimethyl 2,2'-[(2-{[(5-{4-[4-({[(2-fluoro-5-methylphenyl)amino]carbonyl}amino)phenoxy]pyridin-2-yl}-1H-pyrrol-3-yl)carbonyl]amino}ethyl)imino]diacetate Example 156 was isolated from the preparation of Example 155.

$^1$H NMR (DMSO-d$_6$): 11.82 (t, J=2.9 Hz, 1H), 9.18 (s, 1H), 8.49 (d, J=2.9 Hz, 1H), 8.38 (d, J=5.6 Hz, 1H), 7.99 (dd, J=8.4, 1.9 Hz, 1H), 7.77 (t, J=5.4 Hz, 1H), 7.55-7.58 (m, 2H), 7.34 (dd, J=2.9, 1.8 Hz, 1H), 7.14-7.18 (m, 3H), 7.11 (dd, J=11.3, 8.4 Hz, 1H), 7.04 (dd, J=2.3, 1.8 Hz, 1H), 6.79-6.82 (m, 1H), 6.71 (dd, J=5.6, 2.3 Hz, 1H), 3.59 (s, 6H), 3.56 (s, 4H), 3.22-3.27 (m, 2H), 2.78 (t, J=6.7 Hz, 2H), 2.27 (s, 3H)

LR MS (ES+): 633 (MH+)
LR MS (ES−): 631 (M−H)

Example 157

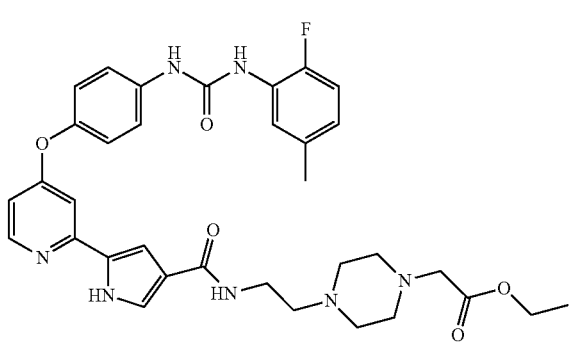 [SMILES: CCOC(=O)CN1CCN(CCNC(=O)c2c[nH]c(-c3cc(Oc4ccc(NC(=O)Nc5cc(C)ccc5F)cc4)ccn3)c2)CC1]

ethyl [4-(2-{[(5-{4-[4-({[(2-fluoro-5-methylphenyl)amino]carbonyl}amino)phenoxy]pyridin-2-yl}-1H-pyrrol-3-yl)carbonyl]amino}ethyl)piperazin-1-yl]acetate To a stirred solution of 5-{4-[4-({[(2-fluoro-5-methylphenyl)amino]carbonyl}amino)phenoxy]pyridin-2-yl}-N-(2-oxoethyl)-1H-pyrrole-3-carboxamide (200 mg, 0.41 mmol) and ethyl piperazinoacetate (141 mg, 0.82 mmol) in anhydrous DMF (10 ml) was added acetic acid (10 mg, 0.17 mmol). The mixture was stirred under nitrogen for 30 minutes, followed by addition of 1M sodium cyanoborohydride solution in THF (0.8 ml, 0.8 mmol). The reaction mixture was stirred for another hour, and poured into 100 ml of water with vigorous stirring. The precipitates were filtered, washed with water, and dried in vacuo to give the crude, which was purified by silica gel chromatography eluting with a gradient of 8~12% methanol/chloroform solution to give ethyl [4-(2-{[(5-{4-[4-({[(2-fluoro-5-methylphenyl)amino]carbonyl}amino)phenoxy]pyridin-2-yl}-1H-pyrrol-3-yl)carbonyl]amino}ethyl)piperazin-1-yl]acetate as white solid. Yield: 90 mg, 34%.

$^1$H NMR (DMSO-$d_6$): 11.81 (t, J=2.9 Hz, 1H), 9.20 (s, 1H), 8.50 (d, J=2.6 Hz, 1H), 8.38 (d, J=5.9 Hz, 1H), 7.99 (dd, J=7.3, 2.1 Hz, 1H), 7.81 (t, J=5.7 Hz, 1H), 7.56-7.58 (m, 2H), 7.35 (dd, J=3.2, 1.8 Hz, 1H), 7.14-7.17 (m, 3H), 7.11 (dd, J=11.3, 8.4 Hz, 1H), 7.05 (dd, J=2.5, 1.9 Hz, 1H), 6.79-6.82 (m, 1H), 6.70-6.71 (m, 1H), 4.07 (q, J=7.2 Hz, 2H), 3.26-3.30 (m, 2H), 3.17 (s, 2H), 2.38-2.53 (m, 10H), 2.27 (s, 3H), 1.18 (t, J=7.0 Hz, 3H)

LR MS (ES+): 644 (MH+)
LR MS (ES−): 642 (M−H)

The following Example 158 through 159 were prepared using the experiment procedure described in Example 160, but with the appropriate reagent, reaction conditions and reactant substitutions that will be readily realized by those of ordinary skill in this art without the exercise of undue experimentation.

Example 158

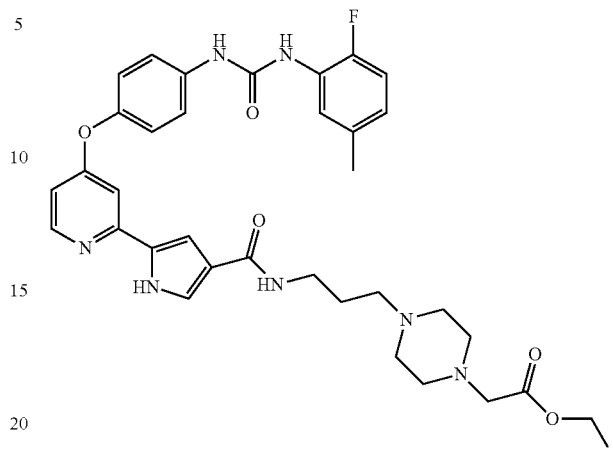

ethyl [4-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)piperazin-1-yl]acetate $^1$H NMR (DMSO-$d_6$): 11.81 (t, J=3.1 Hz, 1H), 9.19 (s, 1H), 8.50 (d, J=2.9 Hz, 1H), 8.38 (d, J=5.6 Hz, 1H), 7.99 (dd, J=7.9, 2.6 Hz, 1H), 7.88 (t, J=5.6 Hz, 1H), 7.55-7.58 (m, 2H), 7.35 (dd, J=3.2, 1.8 Hz, 1H), 7.14-7.17 (m, 3H), 7.11 (dd, J=11.3, 8.4 Hz, 1H), 7.05 (dd, J=2.5, 1.9 Hz, 1H), 6.79-6.82 (m, 1H), 6.71 (dd, J=5.6, 2.3 Hz, 1H), 4.07 (q, J=7.1 Hz, 2H), 3.18-3.21 (m, 2H), 3.17 (s, 2H), 2.30-2.54 (m, 10H), 2.27 (s, 3H), 1.62 (quin, J=7.0 Hz, 2H), 1.17 (t, J=7.2 Hz, 3H)

LR MS (ES+): 658 (MH+)
LR MS (ES−): 656 (M−H)

Example 159

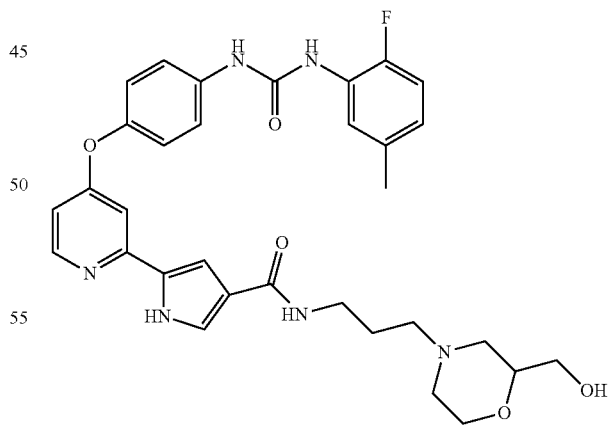

5-{4-[4-({[(2-fluoro-5-methylphenyl)amino]carbonyl}amino)phenoxy]pyridin-2-yl}-N-{3-[2-(hydroxymethyl)morpholin-4-yl]propyl}-1H-pyrrole-3-carboxamide

LR MS (ES+): 603 (MH+)

Example 160

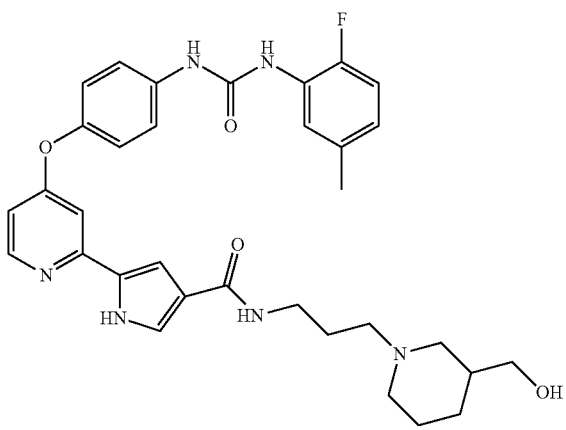 [SMILES: Cc1ccc(F)c(NC(=O)Nc2ccc(Oc3ccnc(-c4cc(C(=O)NCCCN5CCCC(CO)C5)c[nH]4)c3)cc2)c1]

5-{4-[4-({[(2-fluoro-5-methylphenyl)amino]
carbonyl}amino)phenoxy]pyridin-2-yl}-N-{3-[3-
(hydroxymethyl)piperidin-1-yl]propyl}-1H-pyrrole-
3-carboxamide To a stirred solution of 5-{4-[4-({[(2-fluoro-5-methylphenyl)amino]carbonyl}amino)phenoxy]pyridin-2-yl}-N-(3-oxopropyl)-1H-pyrrole-3-carboxamide (120 mg, 0.24 mmol) and 3-piperidinemethanol (56 mg, 0.49 mmol) in anhydrous DMF (10 ml) was added acetic acid (10 mg, 0.17 mmol). The mixture was stirred under nitrogen for 30 minutes, followed by addition of 1M sodium cyanoborohydride solution in THF (0.5 ml, 0.5 mmol). The reaction mixture was stirred for another hour, and poured into 100 ml of water with vigorous stirring. The precipitates were filtered, washed with water, and dried in vacuo to give the crude, which was purified by silica gel chromatography eluting with a gradient of 10~20% methanol/chloroform solution to give 5-{4-[4-({[(2-fluoro-5-methylphenyl)amino]carbonyl}amino)phenoxy]pyridin-2-yl}-N-{3-[3-(hydroxymethyl)piperidin-1-yl]propyl}-1H-pyrrole-3-carboxamide as white solid. Yield: 58 mg, 40%.

LR MS (ES+): 601 (MH+)
LR MS (ES−): 599 (M−H)

The following Example 161 was prepared using the experiment procedure described in Example 157, but with the appropriate reagent, reaction conditions and reactant substitutions that will be readily realized by those of ordinary skill in this art without the exercise of undue experimentation.

Example 161

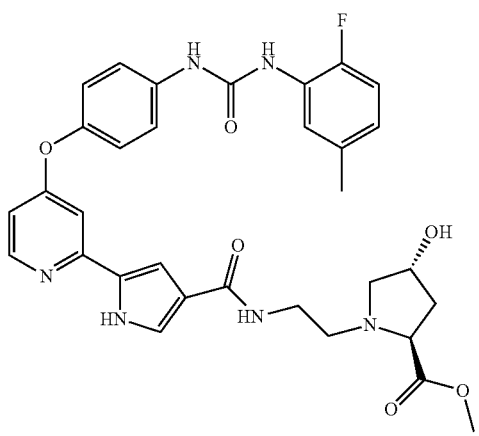 [SMILES: COC(=O)[C@@H]1C[C@@H](O)CN1CCNC(=O)c1c[nH]c(-c2cc(Oc3ccc(NC(=O)Nc4cc(C)ccc4F)cc3)ccn2)c1]

methyl rel-(2R,4S)-1-(2-{[(5-{4-[4-({[(2-fluoro-5-
methylphenyl)amino]carbonyl}amino)phenoxy]pyri-
din-2-yl}-1H-pyrrol-3-yl)carbonyl]amino}ethyl)-4-
hydroxypyrrolidine-2-carboxylate $^1$H NMR (DMSO-d$_6$): 11.81 (t, J=2.9 Hz, 1H), 9.17 (s, 1H), 8.49 (d, J=2.9 Hz, 1H), 8.38 (d, J=5.6 Hz, 1H), 7.99 (dd, J=8.4, 1.9 Hz, 1H), 7.77 (t, J=5.6 Hz, 1H), 7.55-7.58 (m, 2H), 7.34 (dd, J=3.2, 1.8 Hz, 1H), 7.14-7.18 (m, 3H), 7.11 (dd, J=11.3, 8.4 Hz, 1H), 7.04 (dd, J=2.5, 1.9 Hz, 1H), 6.79-6.82 (m, 1H), 6.70-6.72 (m, 1H), 4.88 (d, J=4.4 Hz, 1H), 4.19-4.24 (m, 1H), 3.59 (s, 3H), 3.46 (t, J=7.6 Hz, 1H), 3.26-3.31 (m, 2H), 3.15-3.21 (m, 1H), 2.75 (dt, J=11.8, 7.4 Hz, 1H), 2.53-2.57 (m, 1H), 2.34 (dd, J=9.7, 4.1 Hz, 1H), 2.28 (s, 3H), 1.95 (dt, J=12.8, 7.3 Hz, 1H), 1.84-1.89 (m, 1H)

LR MS (ES+): 617 (MH+)
LR MS (ES−): 615 (M−H)

Example 162

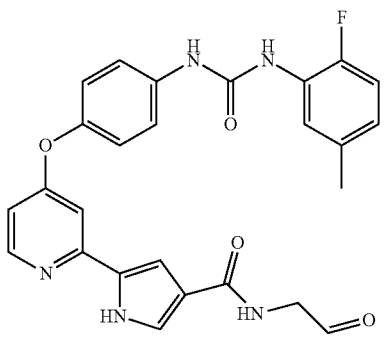 [SMILES: Cc1ccc(F)c(NC(=O)Nc2ccc(Oc3ccnc(-c4cc(C(=O)NCC=O)c[nH]4)c3)cc2)c1]

5-{4-[4-({[(2-fluoro-5-methylphenyl)amino]
carbonyl}amino)phenoxy]pyridin-2-yl}-N-(2-oxoet-
hyl)-1H-pyrrole-3-carboxamide To a stirred solution of N-(2,2-diethoxyethyl)-5-{4-[4-({[(2-fluoro-5-methylphenyl)amino]carbonyl}amino)phenoxy]pyridin-2-yl}1H-pyrrole-3-carboxamide (580 mg, 1.03 mmol) in 10 ml of THF was added 1 ml of 2M HCl. The mixture was heated under nitrogen at 60 C. for 2 hours, cooled to room temperature, and poured into 100 ml of water. Saturated NaHCO3 solution was added until pH=8. The precipitates were filtered, washed with water, and dried in vacuo to give 5-{4-[4-({[(2-fluoro-5-methylphenyl)amino]carbonyl}amino)phenoxy]pyridin-2-yl}-N-(2-oxoethyl)-1H-pyrrole-3-carboxamide as light brown solid. Yield: 450 mg, 90%.

LR MS (ES+): 488 (MH+)
LR MS (ES−): 486 (M−H)

Example 163

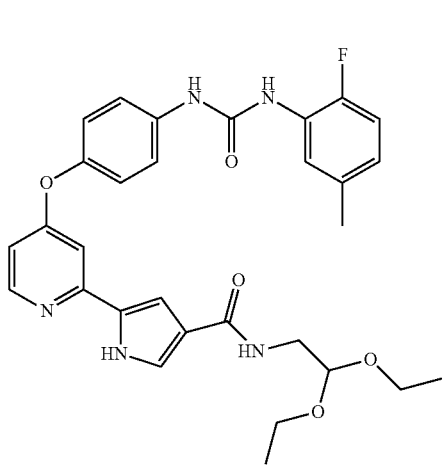 [SMILES: CCOC(CNC(=O)c1c[nH]c(-c2cc(Oc3ccc(NC(=O)Nc4cc(C)ccc4F)cc3)ccn2)c1)OCC]

N-(2,2-diethoxyethyl)-5-{4-[4-({[(2-fluoro-5-methylphenyl)amino]carbonyl}amino)phenoxy]pyridin-2-yl}-1H-pyrrole-3-carboxamide A mixture of 5-{4-[4-({[(2-fluoro-5-methylphenyl)amino]carbonyl}amino)phenoxy]pyridin-2-yl}-1H-pyrrole-3-carboxylic acid (500 mg, 1.12 mmol), HATU (467 mg, 1.23 mmol) and N,N-diisopropylethylamine (322 mg, 2.5 mmol) in anhydrous DMF (10 ml) was stirred at room temperature for 10 minutes, followed by addition of aminoacetaldehyde diethyl acetal (194 mg, 1.46 mmol). The mixture was stirred for another 10 minutes and poured into 100 ml of water. The precipitates were filtered, washed with water and dried in vacuo to give N-(2,2-diethoxyethyl)-5-{4-[4-({[(2-fluoro-5-methylphenyl)amino]carbonyl}amino)phenoxy]pyridin-2-yl}-1H-pyrrole-3-carboxamide as white solid. Yield: 580 mg, 92%.

$^1$H NMR (DMSO-$d_6$): 11.83 (br. s., 1H), 9.18 (s, 1H), 8.49 (d, J=2.9 Hz, 1H), 8.38 (d, J=5.6 Hz, 1H), 7.99 (dd, J=7.9, 2.3 Hz, 1H), 7.94 (t, J=6.0 Hz, 1H), 7.54-7.60 (m, 2H), 7.40 (dd, J=3.1, 1.6 Hz, 1H), 7.10-7.19 (m, 4H), 7.08 (t, J=2.2 Hz, 1H), 6.78-6.84 (m, 1H), 6.71 (dd, J=5.6, 2.3 Hz, 1H), 4.56 (t, J=5.6 Hz, 1H), 3.62 (dq, J=9.7, 7.0 Hz, 2H), 3.47 (dq, J=9.7, 7.0 Hz, 2H), 3.24 (t, J=5.7 Hz, 2H), 2.28 (s, 3H), 1.11 (t, J=7.0 Hz, 6H)

LR MS (ES+): 562 (MH+)

LR MS (ES−): 560 (M−H)

The following Example 164 was prepared using the experiment procedure described in Example 160, but with the appropriate reagent, reaction conditions and reactant substitutions that will be readily realized by those of ordinary skill in this art without the exercise of undue experimentation.

Example 164

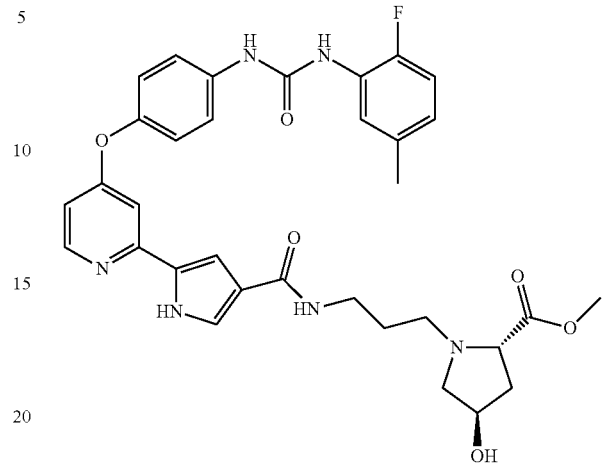

methyl rel-(2R,4S)-1-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)-4-hydroxypyrrolidine-2-carboxylate $^1$H NMR (DMSO-$d_6$): 11.80 (t, J=3.1 Hz, 1H), 9.17 (s, 1H), 8.49 (d, J=2.9 Hz, 1H), 8.38 (d, J=5.9 Hz, 1H), 7.99 (dd, J=7.9, 2.3 Hz, 1H), 7.85 (t, J=5.7 Hz, 1H), 7.55-7.58 (m, 2H), 7.34 (dd, J=3.2, 1.8 Hz, 1H), 7.14-7.17 (m, 3H), 7.11 (dd, J=11.3, 8.4 Hz, 1H), 7.04 (dd, J=2.5, 1.9 Hz, 1H), 6.79-6.82 (m, 1H), 6.71 (dd, J=5.7, 2.5 Hz, 1H), 4.87 (d, J=4.4 Hz, 1H), 4.18-4.23 (m, 1H), 3.59 (s, 3H), 3.36 (t, J=7.8 Hz, 1H), 3.17-3.25 (m, 3H), 2.64 (dt, J=12.1, 7.9 Hz, 1H), 2.39-2.44 (m, 1H), 2.28 (s, 3H), 2.23 (dd, J=9.5, 4.5 Hz, 1H), 1.96 (dt, J=12.8, 7.2 Hz, 1H), 1.83-1.89 (m, 1H), 1.54-1.60 (m, 2H)

LR MS (ES+): 653 (M+Na$^+$)

LR MS (ES−): 629 (M−H)

Example 165

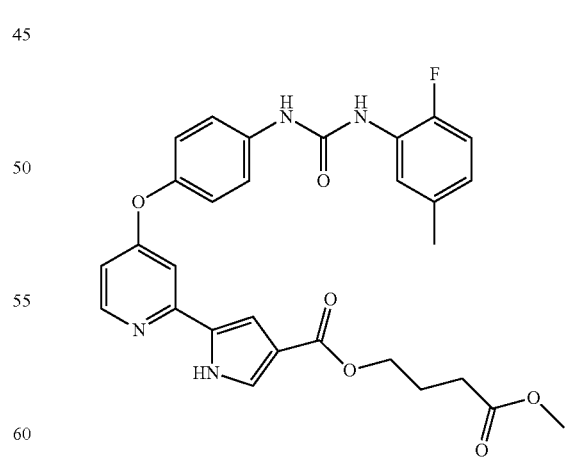

4-methoxy-4-oxobutyl 5-{4-[4-({[(2-fluoro-5-methylphenyl)amino]carbonyl}amino)phenoxy]pyridin-2-yl}-1H-pyrrole-3-carboxylate To a stirred solution of 5-{4-[4-({[(2-fluoro-5-methylphenyl)amino]carbonyl}amino)phenoxy]pyridin-2-yl}-1H-pyrrole-3-carboxylic acid (150 mg, 0.34 mmol) in 10 ml of anhydrous DMF were added methyl 4-bromobutanoate (123 mg, 0.68 mmol) and potassium carbonate (94 mg, 0.68 mmol). The mixture was heated at 60 C. for 2 hours, cooled to room temperature, and poured into 100 ml of water with vigorous stirring. The precipitates were filtered, washed with water and dried in vacuo to give the crude, which was purified by silica gel chromatography eluting with 2~3% of methanol in chloroform to give 4-methoxy-4-oxobutyl 5-{4-[4-({[(2-fluoro-5-methylphenyl)amino]carbonyl}amino)phenoxy]pyridin-2-yl}-1H-pyrrole-3-carboxylate as off-white solid. Yield: 130 mg, 71%.

$^1$H NMR (DMSO-d$_6$): 12.13 (br. s., 1H), 9.17 (s, 1H), 8.48 (d, J=2.6 Hz, 1H), 8.39 (d, J=5.9 Hz, 1H), 7.99 (dd, J=7.9, 2.3 Hz, 1H), 7.54-7.57 (m, 2H), 7.43 (dd, J=3.2, 1.8 Hz, 1H), 7.37 (d, J=2.3 Hz, 1H), 7.13-7.16 (m, 2H), 7.11 (dd, J=11.3, 8.4 Hz, 1H), 7.08 (dd, J=2.5, 1.9 Hz, 1H), 6.79-6.82 (m, 1H), 6.68 (dd, J=5.7, 2.5 Hz, 1H), 4.15 (t, J=6.5 Hz, 2H), 3.58 (s, 3H), 2.45 (t, J=7.3 Hz, 2H), 2.27 (s, 3H), 1.92 (quin, J=6.8 Hz, 2H)

LR MS (ES+): 547 (MH+)

LR MS (ES−): 545 (M−H)

Example 166

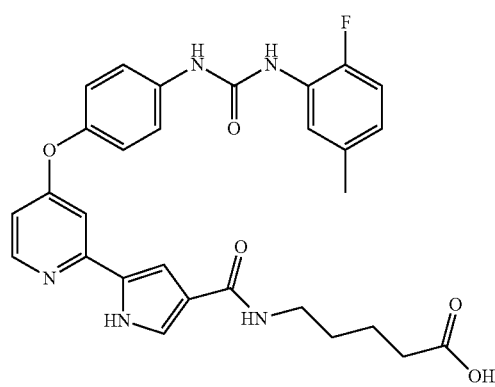 [SMILES: Cc1ccc(F)c(NC(=O)Nc2ccc(Oc3ccnc(-c4cc(C(=O)NCCCCC(=O)O)c[nH]4)c3)cc2)c1]

5-{[(5-{4-[4-({[(2-fluoro-5-methylphenyl)amino]carbonyl}amino)phenoxy]pyridin-2-yl}-1H-pyrrol-3-yl)carbonyl]amino}pentanoic acid To a stirred solution of ethyl 5-{[(5-{4-[4-({[(2-fluoro-5-methylphenyl)amino]carbonyl}amino)phenoxy]pyridin-2-yl}-1H-pyrrol-3-yl)carbonyl]amino}pentanoate (150 mg, 0.26 mmol) in 10 ml of THF was added 2 ml of 1M NaOH solution. The mixture was heated at 55 C. for 3 hours, cooled to room temperature and poured into 100 ml of water. 2M HCl was added dropwise with vigorous stirring until pH=4. The precipitates were filtered, washed with water, and dried in vacuo to give 5-{[(5-{4-[4-({[(2-fluoro-5-methylphenyl)amino]carbonyl}amino)phenoxy]pyridin-2-yl}-1H-pyrrol-3-yl)carbonyl]amino}pentanoic acid as white solid. Yield: 130 mg, 91%.

$^1$H NMR (DMSO-d$_6$): 11.96 (br. s., 1H), 11.82 (br. s., 1H), 9.18 (s, 1H), 8.49 (d, J=2.9 Hz, 1H), 8.38 (d, J=5.6 Hz, 1H), 7.99 (dd, J=7.9, 2.3 Hz, 1H), 7.85 (t, J=5.7 Hz, 1H), 7.56-7.58 (m, 2H), 7.37 (br. s., 1H), 7.15-7.18 (m, 3H), 7.11 (dd, J=11.4, 8.2 Hz, 1H), 7.07 (br. s., 1H), 6.79-6.83 (m, 1H), 6.72 (dd, J=5.6, 2.3 Hz, 1H), 3.17 (q, J=6.5 Hz, 2H), 2.28 (s, 3H), 2.23 (t, J=7.2 Hz, 2H), 1.44-1.55 (m, 4H)

LR MS (ES+): 546 (MH+)

LR MS (ES−): 544 (M−H)

Example 167

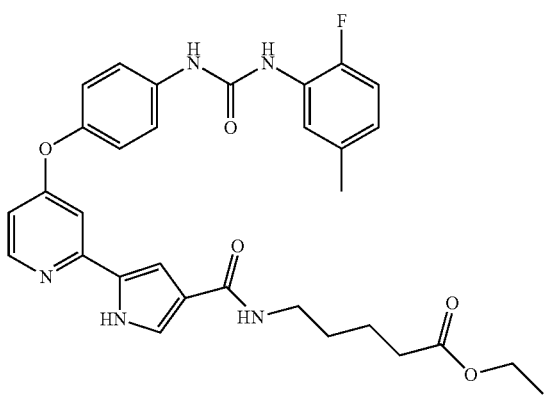 [SMILES: CCOC(=O)CCCCNC(=O)c1c[nH]c(-c2cc(Oc3ccc(NC(=O)Nc4cc(C)ccc4F)cc3)ccn2)c1]

ethyl 5-{[(5-{4-[4-({[(2-fluoro-5-methylphenyl)amino]carbonyl}amino)phenoxy]pyridin-2-yl}-1H-pyrrol-3-yl)carbonyl]amino}pentanoate A mixture of 5-{4-[4-({[(2-fluoro-5-methylphenyl)amino]carbonyl}amino)phenoxy]pyridin-2-yl}-1H-pyrrole-3-carboxylic acid (300 mg, 0.67 mmol), HATU (281 mg, 0.74 mmol) and N,N-diisopropylethylamine (258 mg, 2.0 mmol) in anhydrous DMF (10 ml) was stirred at room temperature for 10 minutes, followed by addition of ethyl 5-aminovalerate hydrochloride (145 mg, 0.80 mmol). The mixture was stirred for another 10 minutes and poured into 100 ml of water. 2M HCl was added dropwise until pH=4. The precipitates were filtered, washed with water and dried in vacuo to give the crude, which was purified by silica gel chromatography eluting with 3~5% of methanol in chloroform to give ethyl 5-{[(5-{4-[4-({[(2-fluoro-5-methylphenyl)amino]carbonyl}amino)phenoxy]pyridin-2-yl}-1H-pyrrol-3-yl)carbonyl]amino}pentanoate as white solid. Yield: 288 mg, 75%.

$^1$H NMR (DMSO-d$_6$): 11.79 (t, J=3.1 Hz, 1H), 9.17 (s, 1H), 8.49 (d, J=2.9 Hz, 1H), 8.38 (d, J=5.6 Hz, 1H), 7.98 (dd, J=8.1, 2.2 Hz, 1H), 7.84 (t, J=5.9 Hz, 1H), 7.55-7.58 (m, 2H), 7.35 (dd, J=3.2, 1.8 Hz, 1H), 7.14-7.17 (m, 3H), 7.11 (dd, J=11.3, 8.4 Hz, 1H), 7.05 (dd, J=2.6, 1.8 Hz, 1H), 6.79-6.82 (m, 1H), 6.70-6.72 (m, 1H), 4.03 (q, J=7.2 Hz, 2H), 3.15-3.18 (m, 2H), 2.30 (t, J=7.3 Hz, 2H), 2.27 (s, 3H), 1.51-1.56 (m, 2H), 1.44-1.50 (m, 2H), 1.16 (t, J=7.2 Hz, 3H)

LR MS (ES+): 574 (MH+)

LR MS (ES−): 572 (M−H)

Example 168

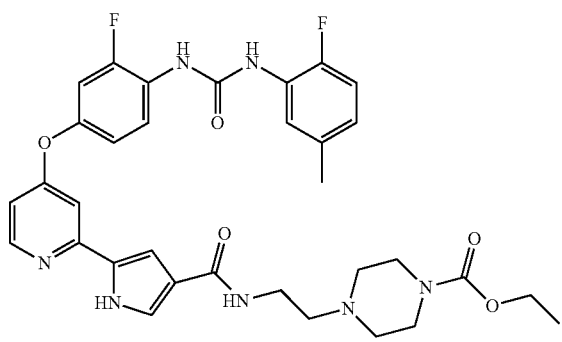 [SMILES: CCOC(=O)N1CCN(CCNC(=O)c2c[nH]c(-c3cc(Oc4ccc(NC(=O)Nc5cc(C)ccc5F)c(F)c4)ccn3)c2)CC1]

ethyl 4-(2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}ethyl)piperazine-1-carboxylate To a stirred solution of 5-{4-[3-fluoro-4-({[(2-fluoro-5-methylphenyl)amino]carbonyl}amino)phenoxy]pyridin-2-yl}-N-(2-oxoethyl)-1H-pyrrole-3-carboxamide (200 mg, 0.40 mmol) and 1-ethoxycarbonylpiperazine (158 mg, 1.0 mmol) in anhydrous DMF (10 ml) was added acetic acid (10 mg, 0.17 mmol). The mixture was stirred under nitrogen for 60 minutes, followed by addition of 1M sodium cyanoborohydride solution in THF (1.0 ml, 1.0 mmol). The reaction mixture was stirred for another hour, and poured into 100 ml of water with vigorous stirring. The precipitates were filtered, washed with water, and dried in vacuo to give the crude, which was purified by silica gel chromatography eluting with 5% methanol/chloroform solution to give ethyl 4-(2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}ethyl)piperazine-1-carboxylate as white solid. Yield: 77 mg, 30%.

$^1$H NMR (DMSO-$d_6$): 11.83 (br. s., 1H), 9.08 (d, J=2.6 Hz, 1H), 8.97 (d, J=2.6 Hz, 1H), 8.40 (d, J=5.6 Hz, 1H), 8.26 (t, J=9.1 Hz, 1H), 8.01 (dd, J=7.9, 2.6 Hz, 1H), 7.82 (t, J=5.9 Hz, 1H), 7.37 (dd, J=3.2, 1.8 Hz, 1H), 7.29 (dd, J=11.9, 2.8 Hz, 1H), 7.20 (d, J=2.3 Hz, 1H), 7.12 (dd, J=10.7, 7.8 Hz, 1H), 7.08-7.10 (m, 1H), 7.02-7.07 (m, 1H), 6.79-6.85 (m, 1H), 6.76 (dd, J=5.7, 2.5 Hz, 1H), 4.02 (q, J=7.0 Hz, 2H), 3.26-3.39 (m, 6H), 2.44 (t, J=6.9 Hz, 2H), 2.33-2.41 (m, 4H), 2.28 (s, 3H), 1.17 (t, J=7.0 Hz, 3H)

LR MS (ES+): 648 (MH+)
LR MS (ES−): 646 (M−H)

Example 169

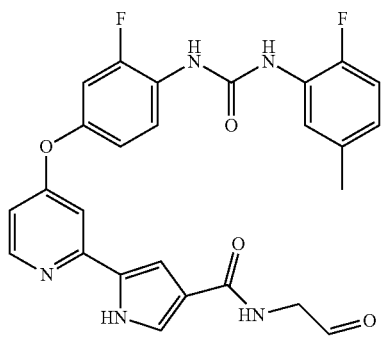 [SMILES: Cc1ccc(F)c(NC(=O)Nc2ccc(Oc3ccnc(-c4cc(C(=O)NCC=O)c[nH]4)c3)cc2F)c1]

5-{4-[3-fluoro-4-({[(2-fluoro-5-methylphenyl)amino]carbonyl}amino)phenoxy]pyridin-2-yl}-N-(2-oxoethyl)-1H-pyrrole-3-carboxamide To a stirred solution of N-(2,2-diethoxyethyl)-5-{4-[3-fluoro-4-({[(2-fluoro-5-methylphenyl)amino]carbonyl}amino)phenoxy]pyridin-2-yl}-1H-pyrrole-3-carboxamide (550 mg, 0.95 mmol) in 10 ml of THF was added 2 ml of 2M HCl. The mixture was stirred at room temperature under nitrogen for overnight, and poured into 100 ml of water with vigorous stirring. Saturated NaHCO3 solution was added until pH=8. The precipitates were filtered, washed with water, and dried to give 5-{4-[3-fluoro-4-({[(2-fluoro-5-methylphenyl)amino]carbonyl}amino)phenoxy]pyridin-2-yl}-N-(2-oxoethyl)-1H-pyrrole-3-carboxamide as off-white solid. Yield: 475 mg, 99%.

LR MS (ES+): 506 (MH+)
LR MS (ES−): 504 (M−H)

Example 170

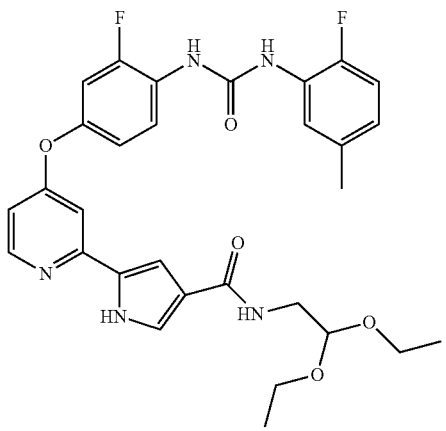 [SMILES: CCOC(CNC(=O)c1c[nH]c(-c2cc(Oc3ccc(NC(=O)Nc4cc(C)ccc4F)c(F)c3)ccn2)c1)OCC]

N-(2,2-diethoxyethyl)-5-{4-[3-fluoro-4-({[(2-fluoro-5-methylphenyl)amino]carbonyl}amino)phenoxy]pyridin-2-yl}-1H-pyrrole-3-carboxamide A mixture of 5-{4-[3-fluoro-4-({[(2-fluoro-5-methylphenyl)amino]carbonyl}amino)phenoxy]pyridin-2-yl}-1H-pyrrole-3-carboxylic acid (500 mg, 1.08 mmol), HATU (456 mg, 1.20 mmol) and N,N-diisopropylethylamine (278 mg, 2.16 mmol) in anhydrous DMF (10 ml) was stirred at room temperature for 10 minutes, followed by addition of aminoacetaldehyde diethyl acetal (173 mg, 1.30 mmol). The mixture was stirred for another 10 minutes and poured into 100 ml of water. The precipitates were filtered, washed with water and dried in vacuo to give N-(2,2-diethoxyethyl)-5-{4-[3-fluoro-4-({[(2-fluoro-5-methylphenyl)amino]carbonyl}amino)phenoxy]pyridin-2-yl}-1H-pyrrole-3-carboxamide as white solid. Yield: 550 mg, 88%.

$^1$H NMR (DMSO-$d_6$): 11.85 (br. s., 1H), 9.08 (d, J=2.3 Hz, 1H), 8.97 (d, J=2.6 Hz, 1H), 8.41 (d, J=5.6 Hz, 1H), 8.26 (t, J=9.1 Hz, 1H), 8.01 (dd, J=7.9, 2.3 Hz, 1H), 7.94 (t, J=6.0 Hz, 1H), 7.41 (dd, J=3.1, 1.6 Hz, 1H), 7.29 (dd, J=11.7, 2.6 Hz, 1H), 7.21 (d, J=2.3 Hz, 1H), 7.08-7.16 (m, 2H), 7.05 (ddd, J=9.1, 2.8, 1.3 Hz, 1H), 6.79-6.85 (m, 1H), 6.77 (dd, J=5.7, 2.5 Hz, 1H), 4.54-4.59 (m, 1H), 3.57-3.68 (m, 2H), 3.47 (dq, J=9.7, 7.0 Hz, 2H), 3.24 (t, J=5.7 Hz, 2H), 2.28 (s, 3H), 1.11 (t, J=7.0 Hz, 6H)

LR MS (ES+): 580 (MH+)
LR MS (ES−): 578 (M−H)

The following Example 171 was prepared using the experiment procedure described in Example 184, but with the appropriate reagent, reaction conditions and reactant substitutions that will be readily realized by those of ordinary skill in this art without the exercise of undue experimentation.

Example 171

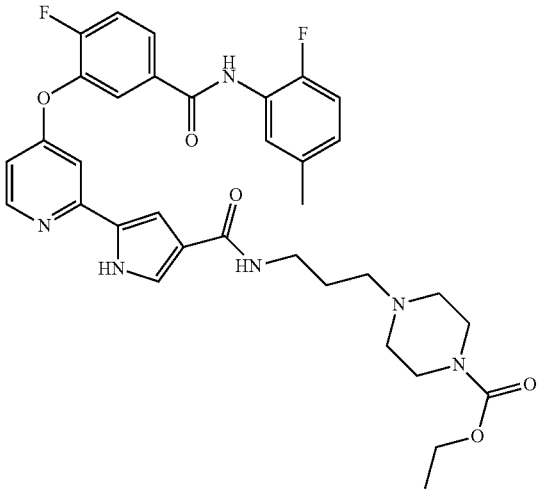 [SMILES: CCOC(=O)N1CCN(CCCNC(=O)c2c[nH]c(-c3cc(Oc4cc(C(=O)Nc5cc(C)ccc5F)ccc4F)ccn3)c2)CC1]

ethyl 4-{3-[({5-[4-(2-fluoro-5-{[(2-fluoro-5-methylphenyl)amino]carbonyl}phenoxy)pyridin-2-yl]-1H-pyrrol-3-yl}carbonyl)amino]propyl}piperazine-1-carboxylate $^1$H NMR (DMSO-d$_6$): 11.84 (br. s., 1H), 10.15 (s, 1H), 8.44 (d, J=5.9 Hz, 1H), 7.98-8.04 (m, 2H), 7.86 (t, J=5.6 Hz, 1H), 7.66 (t, J=9.7 Hz, 1H), 7.35-7.40 (m, 2H), 7.28 (d, J=2.3 Hz, 1H), 7.13-7.20 (m, 2H), 7.04-7.10 (m, 1H), 6.83 (dd, J=5.9, 2.3 Hz, 1H), 4.02 (q, J=7.0 Hz, 2H), 3.31-3.38 (m, 4H), 3.16-3.24 (m, 2H), 2.29 (s, 3H), 2.28-2.35 (m, 6H), 1.63 (quin, J=7.2 Hz, 2H), 1.17 (t, J=7.0 Hz, 3H)
LR MS (ES+): 647 (MH+)
LR MS (ES−): 645 (M−H)

The following Example 172 was prepared using the experiment procedure described in Example 212, but with the appropriate reagent, reaction conditions and reactant substitutions that will be readily realized by those of ordinary skill in this art without the exercise of undue experimentation.

Example 172

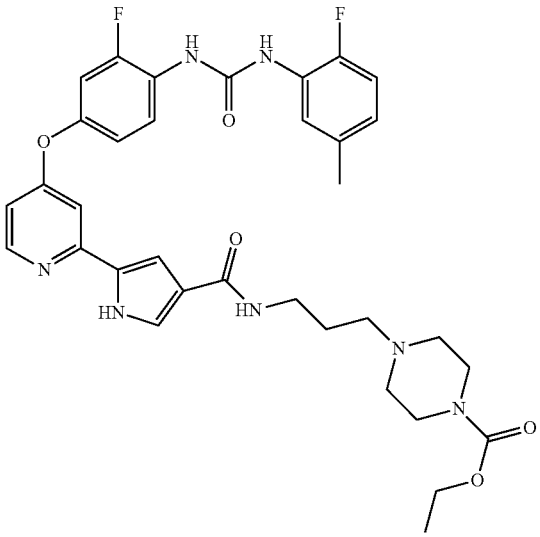 [SMILES: CCOC(=O)N1CCN(CCCNC(=O)c2c[nH]c(-c3cc(Oc4ccc(NC(=O)Nc5cc(C)ccc5F)c(F)c4)ccn3)c2)CC1]

ethyl 4-(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)piperazine-1-carboxylate $^1$H NMR (DMSO-d$_6$): 11.81 (br. s., 1H), 9.08 (d, J=2.6 Hz, 1H), 8.97 (d, J=2.3 Hz, 1H), 8.40 (d, J=5.9 Hz, 1H), 8.25 (t, J=9.2 Hz, 1H), 7.99-8.03 (m, 1H), 7.86 (t, J=5.6 Hz, 1H), 7.36 (dd, J=2.9, 1.8 Hz, 1H), 7.29 (dd, J=11.7, 2.6 Hz, 1H), 7.20 (d, J=2.3 Hz, 1H), 7.08-7.15 (m, 2H), 7.04 (ddd, J=9.1, 2.8, 1.3 Hz, 1H), 6.79-6.85 (m, 1H), 6.76 (dd, J=5.6, 2.3 Hz, 1H), 4.02 (q, J=7.0 Hz, 2H), 3.34 (dd, J=5.6, 4.4 Hz, 4H), 3.16-3.24 (m, 2H), 2.29-2.34 (m, 6H), 2.28 (s, 3H), 1.63 (quin, J=7.1 Hz, 2H), 1.16 (t, J=7.2 Hz, 3H)
LR MS (ES+): 662 (MH+)
LR MS (ES−): 660 (M−H)

Example 173

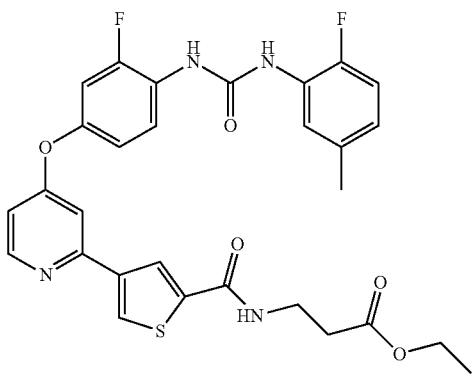 [SMILES: CCOC(=O)CCNC(=O)c1cc(-c2cc(Oc3ccc(NC(=O)Nc4cc(C)ccc4F)c(F)c3)ccn2)cs1]

ethyl 3-{[(4-{4-[3-fluoro-4-({[(2-fluoro-5-methylphenyl)amino]carbonyl}amino)phenoxy]pyridin-2-yl}-2-thienyl)carbonyl]amino}propanoate Example 174

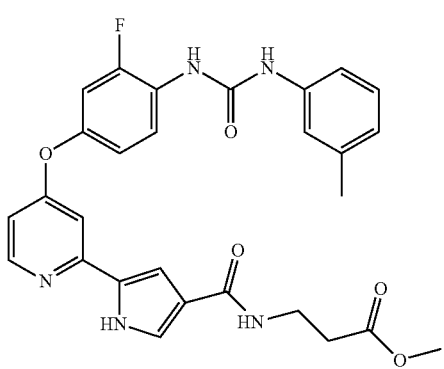 [SMILES: COC(=O)CCNC(=O)c1c[nH]c(-c2cc(Oc3ccc(NC(=O)Nc4cccc(C)c4)c(F)c3)ccn2)c1]

methyl 3-{[(5-{4-[3-fluoro-4-({[(3-methylphenyl)amino]carbonyl}amino)phenoxy]pyridin-2-yl}-1H-pyrrol-3-yl)carbonyl]amino}propanoate A mixture of 5-{4-[3-fluoro-4-({[(3-methylphenyl)amino]carbonyl}amino)phenoxy]pyridin-2-yl}-1H-pyrrole-3-carboxylic acid (Example 75) (1.50 g, 3.36 mmol), HATU (1.41 g, 3.70 mmol) and N,N-diisopropylethylamine (1.29 g, 10 mmol) in anhydrous DMF (15 ml) was stirred at room temperature for 10 minutes, followed by addition of β-alanine methyl ester hydrochloride (558 mg, 4.0 mmol). The mixture was stirred for another 10 minutes and poured into 200 ml of water with vigorous stirring. 2M HCl was added dropwise until pH=4. The precipitates were filtered, washed with water and dried in vacuo to give the crude, which was purified by silica gel chromatography eluting with 3% of methanol in chloroform to give methyl 3-{[(5-{4-[3-fluoro-4-({[(3-methylphenyl)amino]carbonyl}amino)phenoxy]pyridin-2-yl}-1H-pyrrol-3-yl)carbonyl]amino}propanoate as off-white solid. Yield: 1.18 g, 66%.

$^1$H NMR (DMSO-d$_6$): 11.83 (br. s., 1H), 8.99 (s, 1H), 8.59 (d, J=2.1 Hz, 1H), 8.40 (d, J=5.9 Hz, 1H), 8.23 (t, J=9.1 Hz, 1H), 7.96 (t, J=5.7 Hz, 1H), 7.37 (dd, J=3.2, 1.8 Hz, 1H), 7.30 (s, 1H), 7.28 (dd, J=11.7, 2.6 Hz, 1H), 7.23-7.25 (m, 1H), 7.20 (d, J=2.6 Hz, 1H), 7.16-7.19 (m, 1H), 7.09 (t, J=2.3 Hz, 1H), 7.04 (dd, J=9.0, 3.1 Hz, 1H), 6.82 (d, J=7.6 Hz, 1H), 6.76 (dd, J=5.7, 2.5 Hz, 1H), 3.60 (s, 3H), 3.39-3.42 (m, 2H), 2.54 (t, J=7.0 Hz, 2H), 2.29 (s, 3H)

LR MS (ES+): 532 (MH+)

LR MS (ES−): 530 (M−H)

Example 175

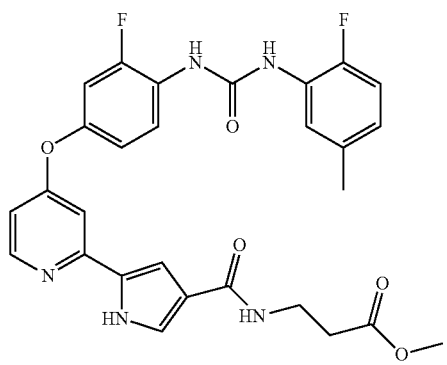 [SMILES: COC(=O)CCNC(=O)c1c[nH]c(-c2cc(Oc3ccc(NC(=O)Nc4cc(C)ccc4F)c(F)c3)ccn2)c1]

methyl 3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propanoate A mixture of 5-{4-[3-fluoro-4-({[(2-fluoro-5-methylphenyl)amino]carbonyl}amino)phenoxy]pyridin-2-yl}-1H-pyrrole-3-carboxylic acid (Example 96) (200 mg, 0.43 mmol), HATU (179 mg, 0.47 mmol) and N,N-diisopropylethylamine (166 mg, 1.29 mmol) in anhydrous DMF (10 ml) was stirred at room temperature for 10 minutes, followed by addition of β-alanine methyl ester hydrochloride (91 mg, 0.65 mmol). The mixture was stirred for another 10 minutes and poured into 100 ml of water with vigorous stirring. 2M HCl was added dropwise until pH=4. The precipitates were filtered, washed with water and dried in vacuo to give methyl 3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propanoate as brown solid. Yield: 180 mg, 76%.

$^1$H NMR (DMSO-d$_6$): 11.89 (br. s., 1H), 9.09 (d, J=1.8 Hz, 1H), 8.97 (d, J=2.6 Hz, 1H), 8.41 (d, J=5.9 Hz, 1H), 8.26 (t, J=9.1 Hz, 1H), 8.01 (dd, J=7.5, 2.2 Hz, 1H), 7.98 (t, J=5.7 Hz, 1H), 7.40 (br. s., 1H), 7.30 (dd, J=11.9, 2.8 Hz, 1H), 7.23 (br. s., 1H), 7.10-7.14 (m, 2H), 7.04-7.07 (m, 1H), 6.79-6.83 (m, 2H), 3.59 (s, 3H), 3.39-3.42 (m, 2H), 2.54 (t, J=7.0 Hz, 2H), 2.27 (s, 3H)

LR MS (ES+): 550 (MH+)

LR MS (ES−): 548 (M−H)

Example 176

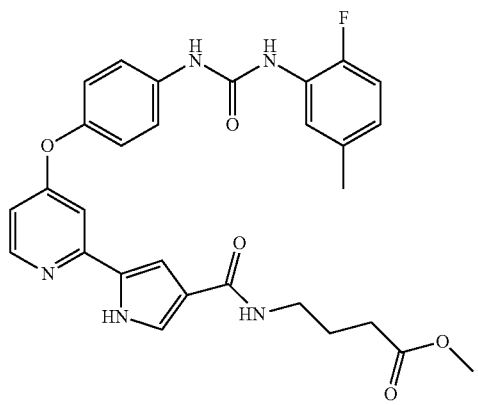 [SMILES: COC(=O)CCCNC(=O)c1c[nH]c(-c2cc(Oc3ccc(NC(=O)Nc4cc(C)ccc4F)cc3)ccn2)c1]

methyl 4-{[(5-{4-[4-({[(2-fluoro-5-methylphenyl)amino]carbonyl}amino)phenoxy]pyridin-2-yl}-1H-pyrrol-3-yl)carbonyl]amino}butanoate To a stirred solution of 5-{4-[4-({[(2-fluoro-5-methylphenyl)amino]carbonyl}amino)phenoxy]pyridin-2-yl}-1H-pyrrole-3-carboxylic acid (Example 115) (200 mg, 0.45 mmol) in 10 ml of anhydrous DMF were added HATU (190 mg, 0.50 mmol) and N,N-diisopropylethylamine (174 mg, 1.35 mmol). The mixture was stirred at room temperature for 10 minutes, followed by addition of methyl 4-aminobutyrate hydrochloride (104 mg, 0.68 mmol). The mixture was stirred for another 10 minutes and poured into 100 ml of water with vigorous stirring. 1M HCl was added slowly until pH=4. The precipitates were filtered, washed with water and dried in vacuo to give methyl 4-{[(5-{4-[4-({[(2-fluoro-5-methylphenyl)amino]carbonyl}amino)phenoxy]pyridin-2-yl}-1H-pyrrol-3-yl)carbonyl]amino}butanoate as white solid. Yield: 220 mg, 90%.

$^1$H NMR (DMSO-d$_6$): 11.84 (br. s., 1H), 9.18 (s, 1H), 8.49 (d, J=2.6 Hz, 1H), 8.39 (d, J=5.6 Hz, 1H), 7.99 (dd, J=7.6, 2.3 Hz, 1H), 7.89 (t, J=5.6 Hz, 1H), 7.56-7.59 (m, 2H), 7.38 (br. s., 1H), 7.15-7.18 (m, 3H), 7.11 (dd, J=11.3, 8.4 Hz, 1H), 7.08 (br. s., 1H), 6.80-6.83 (m, 1H), 6.72-6.74 (m, 1H), 3.58 (s, 3H), 3.17-3.21 (m, 2H), 2.34 (t, J=7.3 Hz, 2H), 2.28 (s, 3H), 1.73 (quin, J=7.2 Hz, 2H)

LR MS (ES+): 546 (MH+)

LR MS (ES−): 544 (M−H)

Example 177

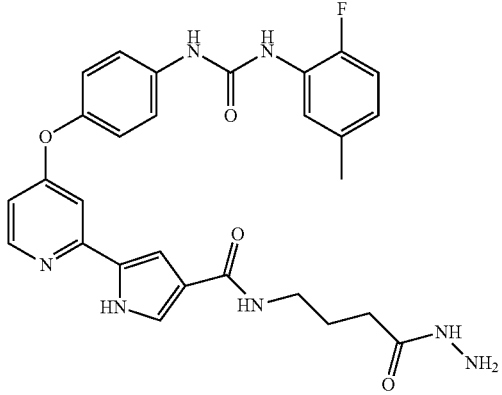 [SMILES: Cc1ccc(F)c(NC(=O)Nc2ccc(Oc3ccnc(-c4cc(C(=O)NCCCC(=O)NN)c[nH]4)c3)cc2)c1]

5-{4-[4-({[(2-fluoro-5-methylphenyl)amino]carbonyl}amino)phenoxy]pyridin-2-yl}-N-(4-hydrazino-4-oxobutyl)-1H-pyrrole-3-carboxamide A mixture of 4-{[(5-{4-[4-({[(2-fluoro-5-methylphenyl)amino]carbonyl}amino)phenoxy]pyridin-2-yl}-1H-pyrrol-3-yl)carbonyl]amino}butanoic acid (Example 78) (120 mg, 0.23 mmol), HATU (95 mg, 0.25 mmol) and N,N-diisopropylethylamine (59 mg, 0.46 mmol) in anhydrous DMF (10 ml) was stirred at room temperature for 10 minutes, followed by addition of hydrazine monohydrate (0.125 ml, 2.6 mmol). The mixture was stirred for another 10 minutes and poured into 100 ml of water. The precipitates were filtered, washed with water and dried in vacuo to give the crude, which was purified by silica gel chromatography eluting with 10~12% of methanol in chloroform to give 5-{4-[4-({[(2-fluoro-5-methylphenyl)amino]carbonyl}amino)phenoxy]pyridin-2-yl}-N-(4-hydrazino-4-oxobutyl)-1H-pyrrole-3-carboxamide as white solid. Yield: 60 mg, 49%.

$^1$H NMR (DMSO-$d_6$): 11.81 (br. s., 1H), 9.17 (s, 1H), 8.95 (br. s., 1H), 8.49 (d, J=2.3 Hz, 1H), 8.38 (d, J=5.6 Hz, 1H), 7.99 (dd, J=7.9, 2.3 Hz, 1H), 7.88 (t, J=5.9 Hz, 1H), 7.55-7.58 (m, 2H), 7.36-7.37 (m, 1H), 7.14-7.17 (m, 3H), 7.11 (dd, J=11.4, 8.2 Hz, 1H), 7.06 (t, J=2.3 Hz, 1H), 6.79-6.83 (m, 1H), 6.71 (dd, J=5.7, 2.5 Hz, 1H), 4.13-4.15 (m, 2H), 3.16 (q, J=6.7 Hz, 2H), 2.28 (s, 3H), 2.04 (t, J=7.5 Hz, 2H), 1.69 (quin, J=7.3 Hz, 2H)

LR MS (ES+): 546 (MH+)
LR MS (ES−): 544 (M−H)

Example 178

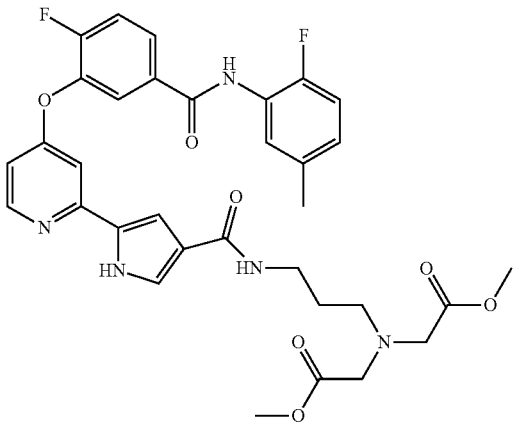 [SMILES: COC(=O)CN(CCCNC(=O)c1c[nH]c(-c2cc(Oc3cc(C(=O)Nc4cc(C)ccc4F)ccc3F)ccn2)c1)CC(=O)OC]

dimethyl 2,2'-({3-[({5-[4-(2-fluoro-5-{[(2-fluoro-5-methylphenyl)amino]carbonyl}phenoxy)pyridin-2-yl]-1H-pyrrol-3-yl}carbonyl)amino]propyl}imino)diacetate To a stirred solution of N-(3-aminopropyl)-5-[4-(2-fluoro-5-{[(2-fluoro-5-methylphenyl)amino]carbonyl}phenoxy)pyridin-2-yl]-1H-pyrrole-3-carboxamide (85 mg, 0.17 mmol) and N,N-diisopropylethylamine (100 mg, 0.78 mmol) in 10 ml of anhydrous DMF was added methyl bromoacetate (100 mg, 0.65 mmol). The mixture was heated at 55° C. for 30 minutes and poured into 100 ml of water with vigorous stirring. The precipitates were filtered and dried in vacuo to give the crude, which was purified by silica gel chromatography eluting with 3~5% of MeOH in CHCl$_3$ to afford dimethyl 2,2'-({3-[({5-[4-(2-fluoro-5-{[(2-fluoro-5-methylphenyl)amino]carbonyl}phenoxy)pyridin-2-yl]-1H-pyrrol-3-yl]carbonyl)amino]propyl}imino)diacetate as white solid. Yield: 70 mg, 64%.

$^1$H NMR (DMSO-$d_6$): 11.81 (br. s., 1H), 10.13 (s, 1H), 8.41 (d, J=5.9 Hz, 1H), 7.99 (d, J=6.2 Hz, 1H), 7.96-7.99 (m, 1H), 7.80 (t, J=5.7 Hz, 1H), 7.63 (t, J=9.5 Hz, 1H), 7.33-7.37 (m, 2H), 7.26 (d, J=2.6 Hz, 1H), 7.13 (dd, J=10.4, 8.1 Hz, 1H), 7.10-7.12 (m, 1H), 7.02-7.06 (m, 1H), 6.79 (dd, J=5.7, 2.5 Hz, 1H), 3.57 (s, 6H), 3.49 (s, 4H), 3.17 (q, J=6.7 Hz, 2H), 2.63 (t, J=6.9 Hz, 2H), 2.26 (s, 3H), 1.55 (quin, J=6.9 Hz, 2H)

LR MS (ES+): 650 (MH+)
LR MS (ES−): 648 (M−H)

Example 179

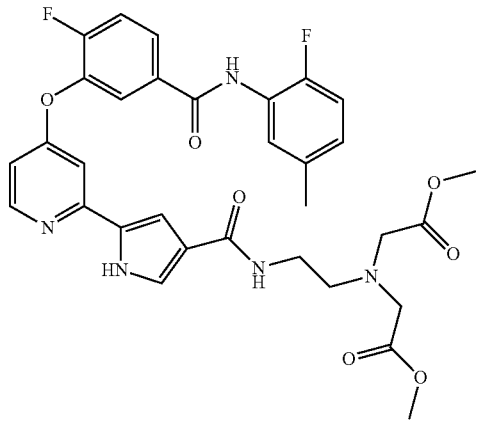 [SMILES: COC(=O)CN(CCNC(=O)c1c[nH]c(-c2cc(Oc3cc(C(=O)Nc4cc(C)ccc4F)ccc3F)ccn2)c1)CC(=O)OC]

dimethyl 2,2'-({2-[({5-[4-(2-fluoro-5-{[(2-fluoro-5-methylphenyl)amino]carbonyl}phenoxy)pyridin-2-yl]-1H-pyrrol-3-yl}carbonyl)amino]ethyl}imino)diacetate To a stirred solution of N-(2-aminoethyl)-5-[4-(2-fluoro-5-{[(2-fluoro-5-methylphenyl)amino]carbonyl}phenoxy)pyridin-2-yl]-1H-pyrrole-3-carboxamide (100 mg, 0.20 mmol) and N,N-diisopropylethylamine (129 mg, 1.0 mmol) in 10 ml of anhydrous DMF was added methyl bromoacetate (77 mg, 0.50 mmol). The mixture was heated at 55° C. for 30 minutes and poured into 100 ml of water with vigorous stirring. The precipitates were filtered and dried in vacuo to give the crude, which was purified by silica gel chromatography eluting with 2-3% of MeOH in CHCl$_3$ to afford dimethyl 2,2'-({2-[({5-[4-(2-fluoro-5-{[(2-fluoro-5-methylphenyl)amino]carbonyl}phenoxy)pyridin-2-yl]-1H-pyrrol-3-yl}carbonyl)amino]ethyl}imino)diacetate as off-white solid. Yield: 80 mg, 62%.

¹H NMR (DMSO-d₆): 11.83 (br. s., 1H), 10.12 (s, 1H), 8.41 (d, J=5.9 Hz, 1H), 7.95-8.01 (m, 2H), 7.73 (t, J=5.6 Hz, 1H), 7.60-7.65 (m, 1H), 7.32-7.37 (m, 2H), 7.25 (d, J=2.6 Hz, 1H), 7.14 (dd, J=10.4, 8.4 Hz, 1H), 7.09 (t, J=2.2 Hz, 1H), 7.02-7.07 (m, 1H), 6.80 (dd, J=5.7, 2.5 Hz, 1H), 3.57 (s, 6H), 3.54 (s, 4H), 3.21 (q, J=6.5 Hz, 2H), 2.75 (t, J=6.7 Hz, 2H), 2.26 (s, 3H)

LR MS (ES+): 636 (MH+)
LR MS (ES−): 634 (M−H)

Example 180

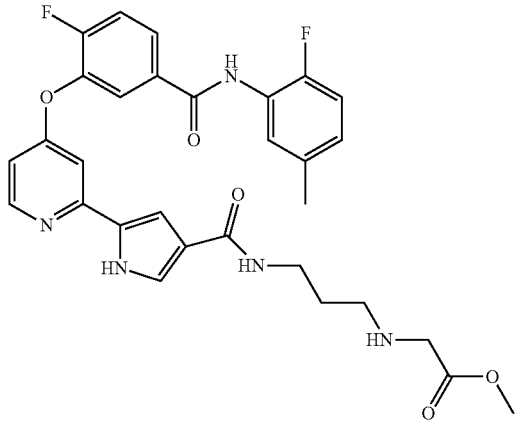 [SMILES: COC(=O)CNCCCNC(=O)c1c[nH]c(-c2cc(Oc3cc(C(=O)Nc4cc(C)ccc4F)ccc3F)ccn2)c1]

methyl ({3-[({5-[4-(2-fluoro-5-{[(2-fluoro-5-methylphenyl)amino]carbonyl}phenoxy)pyridin-2-yl]-1H-pyrrol-3-yl}carbonyl)amino]propyl}amino)acetate To a stirred solution of N-(3-aminopropyl)-5-[4-(2-fluoro-5-{[(2-fluoro-5-methylphenyl)amino]carbonyl}phenoxy)pyridin-2-yl]-1H-pyrrole-3-carboxamide (100 mg, 0.20 mmol) and N,N-diisopropylethylamine (52 mg, 0.40 mmol) in 10 ml of anhydrous DMF was added methyl bromoacetate (30 mg, 0.20 mmol). The mixture was stirred at room temperature for 50 minutes and poured into 100 ml of water with vigorous stirring. The precipitates were filtered and dried in vacuo to give the crude, which was purified by silica gel chromatography eluting with 2~3% of MeOH in CHCl₃ to afford methyl ({3-[({5-[4-(2-fluoro-5-{[(2-fluoro-5-methylphenyl)amino]carbonyl}phenoxy)pyridin-2-yl]-1H-pyrrol-3-yl}carbonyl)amino]propyl}amino)acetate as white solid. Yield: 40 mg, 35%.

LR MS (ES+): 578 (MH+)
LR MS (ES−): 576 (M−H)

Example 181

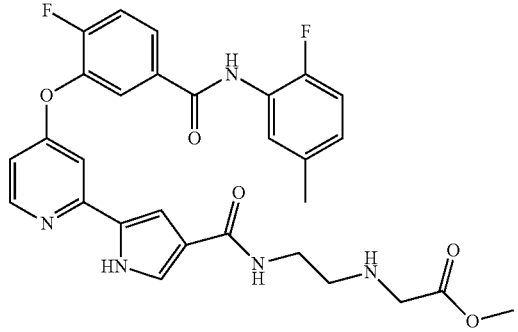 [SMILES: COC(=O)CNCCNC(=O)c1c[nH]c(-c2cc(Oc3cc(C(=O)Nc4cc(C)ccc4F)ccc3F)ccn2)c1]

methyl ({2-[({5-[4-(2-fluoro-5-{[(2-fluoro-5-methylphenyl)amino]carbonyl}phenoxy)pyridin-2-yl]-1H-pyrrol-3-yl}carbonyl)amino]ethyl}amino)acetate To a stirred solution of N-(2-aminoethyl)-5-[4-(2-fluoro-5-{[(2-fluoro-5-methylphenyl)amino]carbonyl}phenoxy)pyridin-2-yl]-1H-pyrrole-3-carboxamide (80 mg, 0.16 mmol) in 10 ml of anhydrous DMF, were added N,N-diisopropylethylamine (60 mg, 0.47 mmol) and methyl bromoacetate (30 mg, 0.20 mmol). The mixture was stirred at room temperature for 1 hour and poured into 100 ml of water. The precipitates were filtered, washed with water, and dried in vacuo to give the crude, which was purified by silica gel chromatography eluting with a gradient of 3~5% of methanol in chloroform to give methyl ({2-[({5-[4-(2-fluoro-5-{[(2-fluoro-5-methylphenyl)amino]carbonyl}phenoxy)pyridin-2-yl]-1H-pyrrol-3-yl}carbonyl)amino]ethyl}amino)acetate as white solid. Yield: 38 mg, 41%.

¹H NMR (DMSO-d₆): 11.82 (br. s., 1H), 10.13 (s, 1H), 8.41 (d, J=5.9 Hz, 1H), 7.96-8.02 (m, 2H), 7.81 (t, J=5.7 Hz, 1H), 7.63 (t, J=9.7 Hz, 1H), 7.33-7.39 (m, 2H), 7.26 (d, J=1.8 Hz, 1H), 7.10-7.16 (m, 2H), 7.01-7.06 (m, 1H), 6.80 (dd, J=5.7, 2.5 Hz, 1H), 3.58 (s, 3H), 3.34 (s, 2H), 3.22 (q, J=6.5 Hz, 2H), 2.61 (t, J=6.5 Hz, 2H), 2.26 (s, 3H)

LR MS (ES+): 564 (MH+)
LR MS (ES−): 562 (M−H)

Example 182

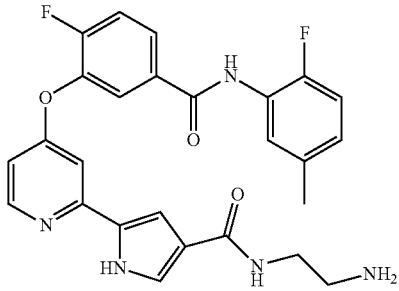 [SMILES: Cc1ccc(F)c(NC(=O)c2ccc(F)c(Oc3ccnc(-c4cc(C(=O)NCCN)c[nH]4)c3)c2)c1]

N-(2-aminoethyl)-5-[4-(2-fluoro-5-{[(2-fluoro-5-methylphenyl)amino]carbonyl}phenoxy)pyridin-2-yl]-1H-pyrrole-3-carboxamide To a stirred suspension of tert-butyl {2-[({5-[4-(2-fluoro-5-{[(2-fluoro-5-methylphenyl)amino]carbonyl}phenoxy)pyridin-2-yl]-1H-pyrrol-3-yl}carbonyl)amino]ethyl}carbamate (360 mg, 0.61 mmol) in 5 ml of methylene chloride was added 3 ml of trifluoroacetic acid. The mixture was stirred at room temperature for 20 minutes and evaporated to dryness under reduced pressure. The residue was re-dissolved in MeOH (5 ml) and poured into 100 ml of water with vigorous stirring. Saturated NaHCO₃ solution was added until pH=8-9. The precipitates were filtered, washed with water and dried in vacuo to give N-(2-aminoethyl)-5-[4-(2-fluoro-5-{[(2-fluoro-5-methylphenyl)amino]carbonyl}phenoxy)pyridin-2-yl]-1H-pyrrole-3-carboxamide as beige solid. Yield: 280 mg, 94%.

LR MS (ES+): 492 (MH+)
LR MS (ES−): 490 (M−H)

Example 183

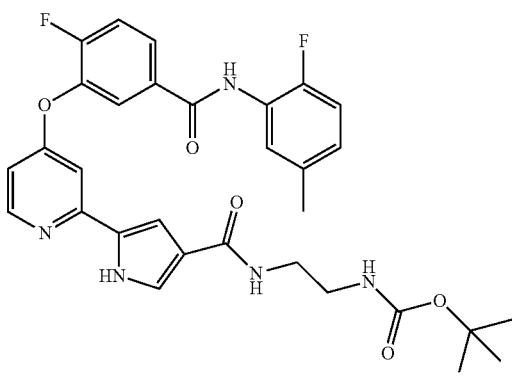 [SMILES: Cc1ccc(F)c(NC(=O)c2ccc(F)c(Oc3ccnc(-c4cc(C(=O)NCCNC(=O)OC(C)(C)C)c[nH]4)c3)c2)c1]

tert-butyl {2-[({5-[4-(2-fluoro-5-{[(2-fluoro-5-methylphenyl)amino]carbonyl}phenoxy)pyridin-2-yl]-1H-pyrrol-3-yl}carbonyl)amino]ethyl}carbamate A mixture of 5-[4-(2-fluoro-5-{[(2-fluoro-5-methylphenyl)amino]carbonyl}phenoxy)pyridin-2-yl]-1H-pyrrole-3-carboxylic acid (Example 13) (300 mg, 0.67 mmol), HATU (281 mg, 0.74 mmol) and N,N-diisopropylethylamine (190 mg, 1.47 mmol) in anhydrous DMF (10 ml) was stirred at room temperature for 10 minutes, followed by addition of tert-butyl (2-aminoethyl)carbamate (160 mg, 1.0 mmol). The mixture was stirred for another 10 minutes and poured into 100 ml of water. The precipitates were filtered, washed with water and dried in vacuo to give tert-butyl {2-[({5-[4-(2-fluoro-5-{[(2-fluoro-5-methylphenyl)amino]carbonyl}phenoxy)pyridin-2-yl]-1H-pyrrol-3-yl}carbonyl)amino]ethyl}carbamate as white solid. Yield: 395 mg, 100%.

$^1$H NMR (DMSO-d$_6$): 11.83 (br. s., 1H), 10.12 (s, 1H), 8.42 (d, J=5.6 Hz, 1H), 7.95-8.01 (m, 2H), 7.85 (t, J=5.7 Hz, 1H), 7.60-7.66 (m, 1H), 7.36 (dd, J=2.9, 1.8 Hz, 1H), 7.34 (dd, J=7.3, 2.3 Hz, 1H), 7.25 (d, J=2.3 Hz, 1H), 7.14 (dd, J=10.6, 8.2 Hz, 1H), 7.10 (t, J=2.2 Hz, 1H), 7.02-7.06 (m, 1H), 6.82-6.85 (m, 1H), 6.80 (dd, J=5.7, 2.5 Hz, 1H), 3.18 (q, J=6.5 Hz, 2H), 3.02 (q, J=6.4 Hz, 2H), 2.26 (s, 3H), 1.34 (s, 9H)

LR MS (ES+): 592 (MH+)
LR MS (ES−): 590 (M−H)

Example 184

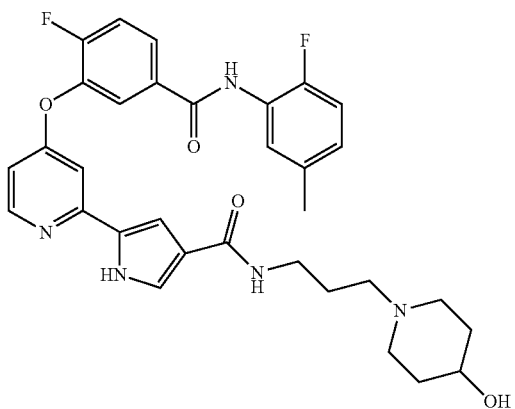 [SMILES: Cc1ccc(F)c(NC(=O)c2ccc(F)c(Oc3ccnc(-c4cc(C(=O)NCCCN5CCC(O)CC5)c[nH]4)c3)c2)c1]

5-[4-(2-fluoro-5-{[(2-fluoro-5-methylphenyl)amino]carbonyl}phenoxy)pyridin-2-yl]-N-[3-(4-hydroxypiperidin-1-yl)propyl]-1H-pyrrole-3-carboxamide To a stirred solution of 5-[4-(2-fluoro-5-{[(2-fluoro-5-methylphenyl)amino]carbonyl}phenoxy)pyridin-2-yl]-N-(3-oxopropyl)-1H-pyrrole-3-carboxamide (205 mg, 0.41 mmol) in 10 ml of anhydrous DMF were added 4-hydroxypiperidine (83 mg, 0.82 mmol) and acetic acid (10 mg, 0.17 mmol). The mixture was stirred at room temperature for 30 minutes, followed by addition of 1M sodium cyanoborohydride solution in THF (0.80 ml, 0.80 mmol) and stirring was continued for one more hour. The mixture was poured into 100 ml of water. The precipitates were filtered, washed with water and dried to give the crude, which was purified by silica gel flash chromatography eluting with 20% of MeOH in CHCl$_3$ to give 5-[4-(2-fluoro-5-{[(2-fluoro-5-methylphenyl)amino]carbonyl}phenoxy)pyridin-2-yl]-N-[3-(4-hydroxypiperidin-1-yl)propyl]-1H-pyrrole-3-carboxamide as white solid. Yield: 85 mg, 35%.

$^1$H NMR (DMSO-d$_6$): 11.81 (br. s., 1H), 10.12 (s, 1H), 8.41 (d, J=5.9 Hz, 1H), 7.96-8.01 (m, 2H), 7.84 (br. s., 1H), 7.63 (t, J=9.5 Hz, 1H), 7.32-7.37 (m, 2H), 7.25 (d, J=2.1 Hz, 1H), 7.14 (dd, J=10.3, 8.5 Hz, 1H), 7.10 (s, 1H), 7.02-7.07 (m, 1H), 6.80 (dd, J=5.6, 2.1 Hz, 1H), 4.47 (br. s., 1H), 3.39 (br. s., 1H), 3.16 (br. s., 2H), 2.65 (br. s., 2H), 2.26 (s, 3H), 2.23 (br. s., 2H), 1.92 (br. s., 2H), 1.66 (br. s., 2H), 1.58 (br. s., 2H), 1.34 (br. s., 2H)

LR MS (ES+): 590 (MH+)

Example 185

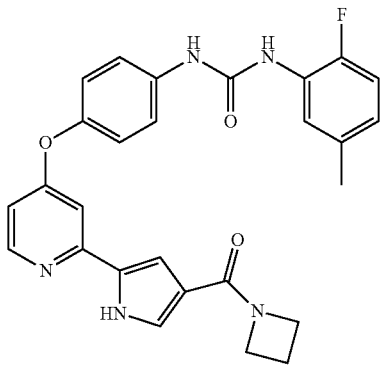 [SMILES: Cc1ccc(F)c(NC(=O)Nc2ccc(Oc3ccnc(-c4cc(C(=O)N5CCC5)c[nH]4)c3)cc2)c1]

1-[4-({2-[4-(azetidin-1-ylcarbonyl)-1H-pyrrol-2-yl]pyridin-4-yl}oxy)phenyl]-3-(2-fluoro-5-methylphenyl)urea A mixture of 5-{4-[4-({[(2-fluoro-5-methylphenyl)amino]carbonyl}amino)phenoxy]pyridin-2-yl}-1H-pyrrole-3-carboxylic acid (100 mg, 0.22 mmol), HATU (99 mg, 0.26 mmol) and N,N-diisopropylethylamine (62 mg, 0.48 mmol) in anhydrous DMF (10 ml) was stirred at room temperature for 10 minutes, followed by addition of azetidine (20 mg, 0.35 mmol). The mixture was stirred for another 5 minutes and poured into 100 ml of water. 2M HCl was added dropwise until pH=4~5. The precipitates were filtered, washed with water and dried in vacuo to give 1-[4-({2-[4-(azetidin-1-ylcarbonyl)-1H-pyrrol-2-yl]pyridin-4-yl}oxy)phenyl]-3-(2-fluoro-5-methylphenyl)urea as light brown solid. Yield: 95 mg, 87%.

$^1$H NMR (DMSO-d6): 12.18 (br. s., 1H), 9.28 (s, 1H), 8.53 (d, J=2.1 Hz, 1H), 8.43 (d, J=5.9 Hz, 1H), 7.96-8.01 (m, 1H), 7.58 (d, J=8.8 Hz, 2H), 7.48 (br. s., 1H), 7.34 (br. s., 1H), 7.08-7.22 (m, 4H), 6.81 (td, J=5.3, 2.6 Hz, 2H), 4.39 (br. s., 2H), 3.97 (br. s., 2H), 2.22-2.31 (m, 5H)

LR MS (ES+): 508 (M+Na+)
LR MS (ES−): 484 (M−H)

The following Example 186 was prepared using the experiment procedure described in Example 187, but with the appropriate reagent, reaction conditions and reactant substitutions that will be readily realized by those of ordinary skill in this art without the exercise of undue experimentation.

Example 186

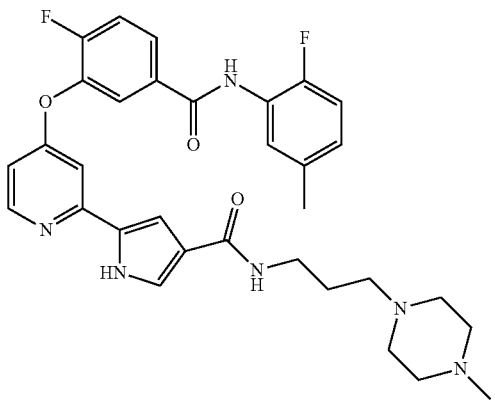 [SMILES: Cc1ccc(F)c(NC(=O)c2ccc(F)c(Oc3ccnc(-c4cc(C(=O)NCCCN5CCN(C)CC5)c[nH]4)c3)c2)c1]

5-[4-(2-fluoro-5-{[(2-fluoro-5-methylphenyl)amino] carbonyl}phenoxy)pyridin-2-yl]-N-[3-(4-methylpiperazin-1-yl)propyl]-1H-pyrrole-3-carboxamide $^1$H NMR (DMSO-d$_6$): 11.82 (br. s., 1H), 10.12 (s, 1H), 8.41 (d, J=5.9 Hz, 1H), 7.94-8.03 (m, 2H), 7.84 (t, J=5.4 Hz, 1H), 7.63 (t, J=9.5 Hz, 1H), 7.32-7.39 (m, 2H), 7.25 (d, J=2.3 Hz, 1H), 7.14 (dd, J=10.3, 8.5 Hz, 1H), 7.08-7.11 (m, 1H), 7.04 (dt, J=8.2, 2.3 Hz, 1H), 6.80 (dd, J=5.6, 2.3 Hz, 1H), 3.17 (q, J=6.7 Hz, 2H), 2.20-2.45 (br. s., 10H), 2.26 (s, 3H), 2.12 (s, 3H), 1.55-1.62 (m, 2H)

LR MS (ES+): 589 (MH+)
LR MS (ES−): 587 (M−H)

Example 187

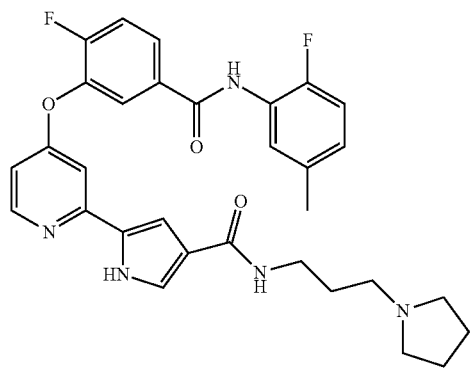 [SMILES: Cc1ccc(F)c(NC(=O)c2ccc(F)c(Oc3ccnc(-c4cc(C(=O)NCCCN5CCCC5)c[nH]4)c3)c2)c1]

5-[4-(2-fluoro-5-{[(2-fluoro-5-methylphenyl)amino] carbonyl}phenoxy)pyridin-2-yl]-N-(3-pyrrolidin-1-ylpropyl)-1H-pyrrole-3-carboxamide To a stirred solution of 5-[4-(2-fluoro-5-{[(2-fluoro-5-methylphenyl)amino]carbonyl}phenoxy)pyridin-2-yl]-1H-pyrrole-3-carboxylic acid (150 mg, 0.33 mmol) in 10 ml of anhydrous DMF were added HATU (152 mg, 0.40 mmol) and N,N-diisopropylethylamine (94 mg, 0.73 mmol). The mixture was stirred at room temperature for 10 minutes, followed by addition of N-(3-aminopropyl)pyrrolidine (85 mg, 0.66 mmol), and stirring was continued for another 10 minutes. The mixture was poured into 50 ml of water with vigorous stirring. The precipitates were filtered, washed with water and dried in vacuo to give 5-[4-(2-fluoro-5-{[(2-fluoro-5-methylphenyl)amino]carbonyl}phenoxy)pyridin-2-yl]-N-(3-pyrrolidin-1-ylpropyl)-1H-pyrrole-3-carboxamide as white solid. Yield: 160 mg, 86%.

$^1$H NMR (DMSO-d$_6$): 11.81 (br. s., 1H), 10.12 (s, 1H), 8.41 (d, J=5.6 Hz, 1H), 7.99 (d, J=6.2 Hz, 1H), 7.97 (br. s., 1H), 7.89 (t, J=5.6 Hz, 1H), 7.63 (t, J=9.5 Hz, 1H), 7.32-7.38 (m, 2H), 7.24 (d, J=2.1 Hz, 1H), 7.14 (dd, J=10.3, 8.5 Hz, 1H), 7.08 (s, 1H), 7.01-7.07 (m, 1H), 6.80 (dd, J=5.6, 2.3 Hz, 1H), 3.19 (q, J=6.7 Hz, 2H), 2.40 (br. s., 6H), 2.26 (s, 3H), 1.64 (br. s., 4H), 1.58-1.63 (m, 2H)

LR MS (ES+): 560 (MH+)
LR MS (ES−): 558 (M−H)

Example 188

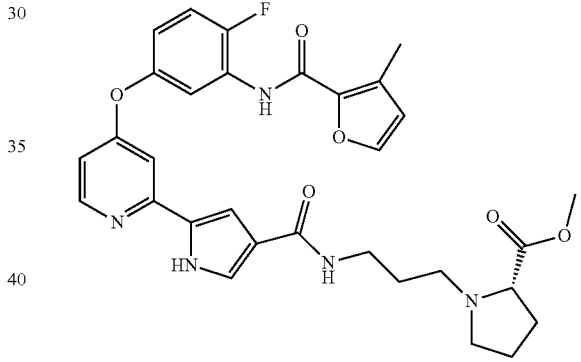

methyl 1-[3-({[5-(4-{4-fluoro-3-[(3-methyl-2-furoyl) amino]phenoxy}pyridin-2-yl)-1H-pyrrol-3-yl] carbonyl}amino)propyl]pyrrolidine-2-carboxylate To a stirred solution of 5-(4-{4-fluoro-3-[(3-methyl-2-furoyl)amino]phenoxy}pyridin-2-yl)-N-(3-oxopropyl)-1H-pyrrole-3-carboxamide (140 mg, 0.29 mmol) in 10 ml of anhydrous DMF were added L-proline methyl ester hydrochloride (96 mg, 0.58 mmol) and triethylamine (58 mg, 0.58 mmol). The mixture was stirred at room temperature for 30 minutes, followed by addition of 1M sodium cyanoborohydride solution in THF (0.60 ml, 0.60 mmol) and stirring was continued for another 30 minutes. The mixture was poured into 100 ml of water. The precipitates were filtered, washed with water and dried to give the crude, which was purified by silica gel flash chromatography eluting with 5% of MeOH in CHCl$_3$ to give methyl 1-[3-({[5-(4-{4-fluoro-3-[(3-methyl-2-furoyl)amino]phenoxy}pyridin-2-yl)-1H-pyrrol-3-yl] carbonyl}amino)propyl]pyrrolidine-2-carboxylate as light beige solid. Yield: 70 mg, 40%.

LR MS (ES+): 590 (MH+)
LR MS (ES−): 588 (M−H)

The following Example 189 was prepared using the experiment procedure described in Example 188, but with the appropriate reagent, reaction conditions and reactant substitutions that will be readily realized by those of ordinary skill in this art without the exercise of undue experimentation.

Example 189

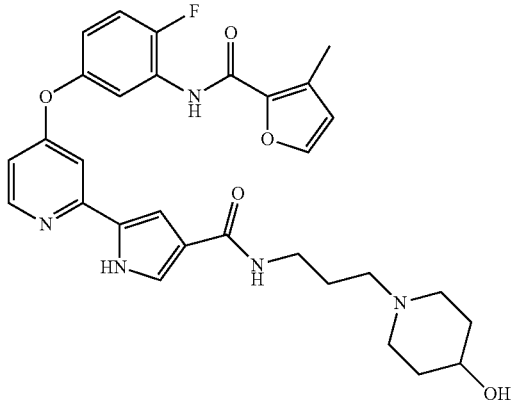 [SMILES: Cc1ccoc1C(=O)Nc1cc(Oc2ccnc(-c3cc(C(=O)NCCCN4CCC(O)CC4)c[nH]3)c2)ccc1F]

5-(4-{4-fluoro-3-[(3-methyl-2-furoyl)amino]phenoxy}pyridin-2-yl)-N-[3-(4-hydroxypiperidin-1-yl)propyl]-1H-pyrrole-3-carboxamide

LR MS (ES+): 562 (MH+)
LR MS (ES−): 560 (M−H)

Example 190

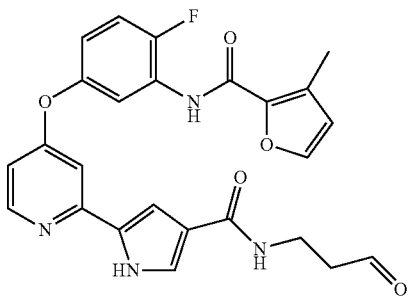 [SMILES: Cc1ccoc1C(=O)Nc1cc(Oc2ccnc(-c3cc(C(=O)NCCC=O)c[nH]3)c2)ccc1F]

5-(4-{4-fluoro-3-[(3-methyl-2-furoyl)amino]phenoxy}pyridin-2-yl)-N-(3-oxopropyl)-1H-pyrrole-3-carboxamide To a stirred solution of N-(3,3-diethoxypropyl)-5-(4-{4-fluoro-3-[(3-methyl-2-furoyl)amino]phenoxy}pyridin-2-yl)-1H-pyrrole-3-carboxamide (380 mg, 0.69 mmol) in 15 ml of tetrahydrofuran was added 1 ml of 2M HCl (2.0 mmol). The mixture was stirred at room temperature for 90 minutes and poured into 100 ml of water. 1M NaOH solution was added slowly until pH=7~8. The precipitates were filtered, washed with water and dried in vacuo to give 5-(4-{4-fluoro-3-[(3-methyl-2-furoyl)amino]phenoxy}pyridin-2-yl)-N-(3-oxopropyl)-1H-pyrrole-3-carboxamide as white solid. Yield: 270 mg, 82%.

$^1$H NMR(CHLOROFORM-d): 10.50 (br. s., 1H), 9.84 (s, 1H), 8.36-8.44 (m, 2H), 8.30 (d, J=6.2 Hz, 1H), 7.43 (s, 1H), 7.40 (br. s., 1H), 7.22 (t, J=9.5 Hz, 1H), 7.06 (br. s., 1H), 6.80-6.88 (m, 2H), 6.73-6.79 (m, 1H), 6.42 (s, 1H), 6.23 (t, J=5.7 Hz, 1H), 3.69 (q, J=5.8 Hz, 2H), 2.84 (t, J=5.7 Hz, 2H), 2.42 (s, 3H)
LR MS (ES+): 477 (MH+)
LR MS (ES−): 475 (M−H)

Example 191

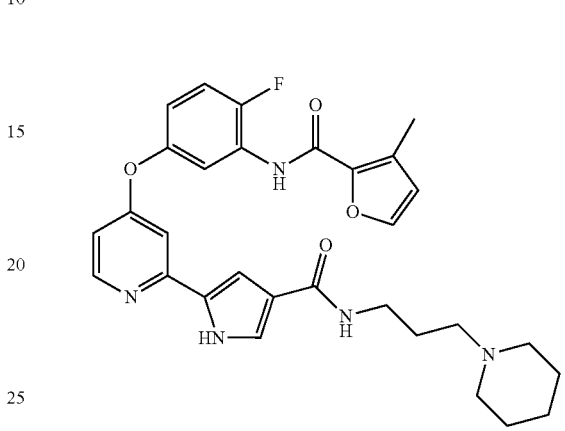

5-(4-{4-fluoro-3-[(3-methyl-2-furoyl)amino]phenoxy}pyridin-2-yl)-N-(3-piperidin-1-ylpropyl)-1H-pyrrole-3-carboxamide $^1$H NMR (DMSO-d$_6$): 11.79 (br. s., 1H), 9.71 (s, 1H), 8.39 (d, 1H), 7.85 (br. s., 1H), 7.79 (d, J=1.5 Hz, 1H), 7.58 (dd, J=6.5, 2.9 Hz, 1H), 7.39 (t, J=9.5 Hz, 1H), 7.34 (br. s., 1H), 7.19 (d, J=2.3 Hz, 1H), 7.06-7.09 (m, 1H), 7.04-7.06 (m, 1H), 6.72 (dd, J=5.6, 2.3 Hz, 1H), 6.57 (d, 1H), 3.16 (q, J=6.1 Hz, 2H), 2.28 (s, 3H), 2.21-2.30 (m, 6H), 1.59 (br. s., 2H), 1.45 (br. s., 4H), 1.33 (br. s., 2H)
LR MS (ES+): 546 (MH+)
LR MS (ES−): 544 (M−H)

Example 192

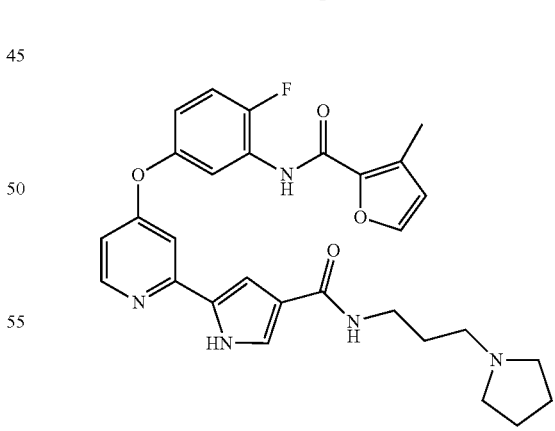

5-(4-{4-fluoro-3-[(3-methyl-2-furoyl)amino]phenoxy}pyridin-2-yl)-N-(3-pyrrolidin-1-ylpropyl)-1H-pyrrole-3-carboxamide $^1$H NMR (DMSO-d$_6$): 11.79 (br. s., 1H), 9.71 (s, 1H), 8.39 (d, J=5.9 Hz, 1H), 7.89 (t, J=5.4 Hz, 1H), 7.79 (d, J=1.5 Hz, 1H), 7.58 (dd, J=6.2, 2.9 Hz, 1H), 7.39 (t, J=9.5 Hz, 1H), 7.33 (dd, J=2.9, 1.8 Hz, 1H), 7.19 (d, J=2.3 Hz, 1H), 7.07 (dt, J=8.9, 3.5 Hz, 1H), 7.01-7.05 (m, 1H), 6.72 (dd, J=5.6, 2.3 Hz, 1H), 6.57 (d, J=1.2 Hz, 1H), 3.19 (q, J=6.7 Hz, 2H), 2.42 (br. s., 6H), 2.28 (s, 3H), 1.58-1.69 (m, 6H)

LR MS (ES+): 532 (MH+)

LR MS (ES−): 530 (M−H)

Example 193

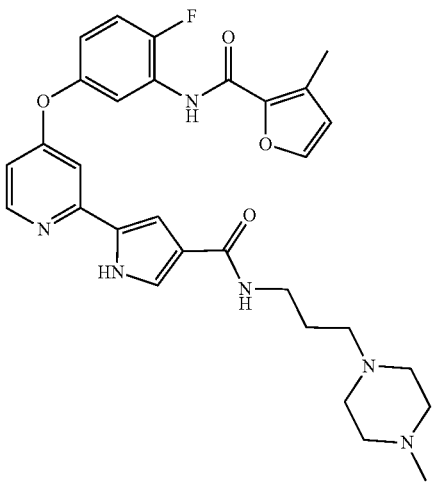 [SMILES: Cc1ccoc1C(=O)Nc1cc(Oc2ccnc(-c3cc(C(=O)NCCCN4CCN(C)CC4)c[nH]3)c2)ccc1F]

5-(4-{4-fluoro-3-[(3-methyl-2-furoyl)amino] phenoxy}pyridin-2-yl)-N-[3-(4-methylpiperazin-1-yl)propyl]-1H-pyrrole-3-carboxamide $^1$H NMR (DMSO-d$_6$): 11.80 (br. s., 1H), 9.71 (s, 1H), 8.39 (d, J=5.6 Hz, 1H), 7.85 (t, J=5.6 Hz, 1H), 7.78 (d, J=1.5 Hz, 1H), 7.57 (dd, J=6.5, 2.9 Hz, 1H), 7.39 (t, J=9.5 Hz, 1H), 7.34 (br. s., 1H), 7.20 (d, J=2.3 Hz, 1H), 7.06-7.09 (m, 1H), 7.05-7.06 (m, 1H), 6.72 (dd, J=5.7, 2.2 Hz, 1H), 6.57 (s, 1H), 3.16 (q, J=6.5 Hz, 2H), 2.31 (br. s., 10H), 2.28 (s, 3H), 2.13 (s, 3H), 1.59 (quin, J=7.0 Hz, 2H)

LR MS (ES+): 561 (MH+)

LR MS (ES−): 559 (M−H)

Example 194

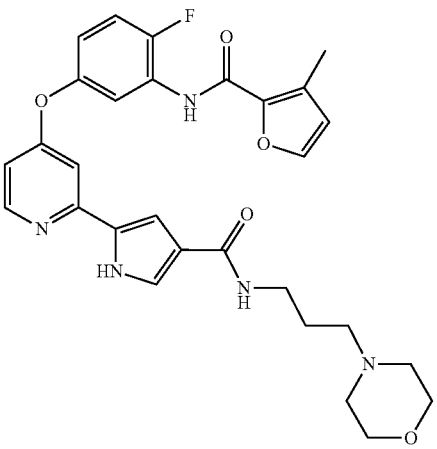 [SMILES: Cc1ccoc1C(=O)Nc1cc(Oc2ccnc(-c3cc(C(=O)NCCCN4CCOCC4)c[nH]3)c2)ccc1F]

5-(4-{4-fluoro-3-[(3-methyl-2-furoyl)amino] phenoxy}pyridin-2-yl)-N-(3-morpholin-4-ylpropyl)-1H-pyrrole-3-carboxamide To a stirred solution of 5-(4-{4-fluoro-3-[(3-methyl-2-furoyl)amino]phenoxy}pyridin-2-yl)-1H-pyrrole-3-carboxylic acid (Example 28) (150 mg, 0.36 mmol) in 10 ml of anhydrous DMF were added HATU (163 mg, 0.43 mmol) and N,N-diisopropylethylamine (102 mg, 0.79 mmol). The mixture was stirred at room temperature for 10 minutes, followed by addition of 3-morpholinopropylamine (104 mg, 0.72 mmol). The mixture was stirred for another 10 minutes and poured into 100 ml of water. The precipitates were filtered, washed with water and dried in vacuo to give the crude, which was purified by silica gel chromatography eluting with 10% methanol in chloroform to give 5-(4-{4-fluoro-3-[(3-methyl-2-furoyl)amino]phenoxy}pyridin-2-yl)-N-(3-morpholin-4-ylpropyl)-1H-pyrrole-3-carboxamide as white solid. Yield: 110 mg, 56%.

$^1$H NMR (DMSO-d$_6$): 11.79 (br. s., 1H), 9.71 (s, 1H), 8.39 (d, J=5.9 Hz, 1H), 7.84 (t, J=5.6 Hz, 1H), 7.78 (d, J=1.5 Hz, 1H), 7.58 (dd, J=6.5, 2.9 Hz, 1H), 7.39 (t, J=9.5 Hz, 1H), 7.33-7.36 (m, 1H), 7.19 (d, J=2.3 Hz, 1H), 7.07-7.09 (m, 1H), 7.05-7.07 (m, 1H), 6.72 (dd, J=5.7, 2.2 Hz, 1H), 6.57 (d, J=1.5 Hz, 1H), 3.53 (t, J=4.5 Hz, 4H), 3.17 (q, J=6.7 Hz, 2H), 2.30 (br. s., 4H), 2.28 (s, 3H), 2.26 (t, J=7.3 Hz, 2H), 1.60 (quin, J=7.0 Hz, 2H)

LR MS (ES+): 548 (MH+)

LR MS (ES−): 546 (M−H)

The following Examples 195 and 196 were prepared using the experiment procedure described in Example 212, but with the appropriate reagent, reaction conditions and reactant substitutions that will be readily realized by those of ordinary skill in this art without the exercise of undue experimentation.

Example 195

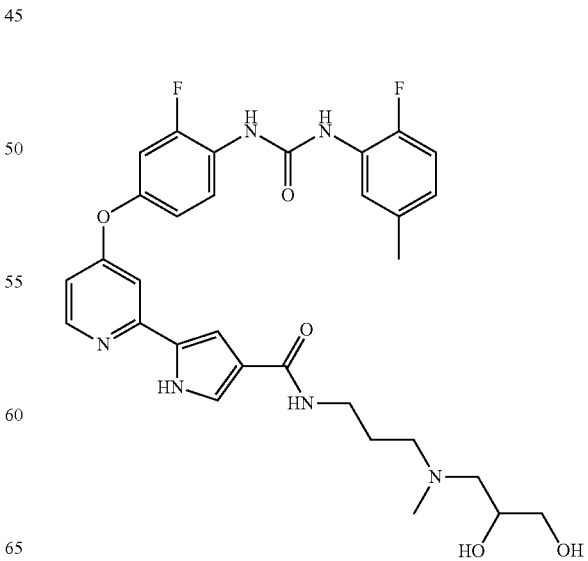

291

N-{3-[(2,3-dihydroxypropyl)(methyl)amino]propyl}-5-{4-[3-fluoro-4-({[(2-fluoro-5-methylphenyl)amino]carbonyl}amino)phenoxy]pyridin-2-yl}-1H-pyrrole-3-carboxamide

LR MS (ES+): 609 (MH+)
LR MS (ES−): 607 (M−H)

Example 196

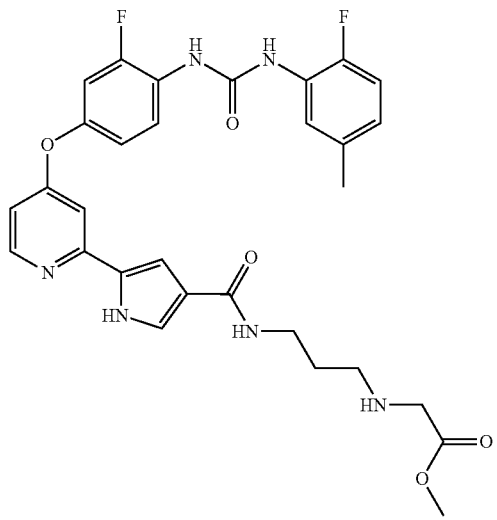 [SMILES: COC(=O)CNCCCNC(=O)c1c[nH]c(-c2cc(Oc3ccc(NC(=O)Nc4cc(C)ccc4F)c(F)c3)ccn2)c1]

methyl [(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)amino]acetate $^1$H NMR (DMSO-d$_6$): 11.80 (br. s., 1H), 9.12 (d, J=2.3 Hz, 1H), 9.01 (d, J=2.6 Hz, 1H), 8.37 (d, J=5.9 Hz, 1H), 8.22 (t, J=9.1 Hz, 1H), 7.97 (dd, J=7.0, 1.8 Hz, 1H), 7.88 (t, J=5.7 Hz, 1H), 7.34 (dd, J=3.1, 1.9 Hz, 1H), 7.25 (dd, J=11.7, 2.9 Hz, 1H), 7.17-7.20 (m, 1H), 7.05-7.11 (m, 2H), 7.01 (dt, J=9.3, 1.5 Hz, 1H), 6.77-6.81 (m, 1H), 6.73 (dd, J=5.6, 2.3 Hz, 1H), 3.59 (s, 3H), 3.36 (s, 2H), 3.19 (q, J=6.7 Hz, 2H), 2.54 (t, J=7.0 Hz, 2H), 2.25 (s, 3H), 1.58 (quin, J=7.0 Hz, 2H)
LR MS (ES+): 593 (MH+)
LR MS (ES−): 591 (M−H)

Example 197

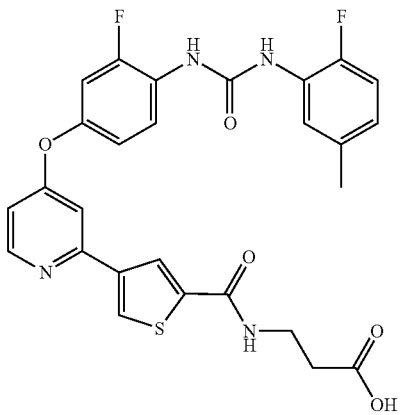 [SMILES: Cc1ccc(F)c(NC(=O)Nc2ccc(Oc3ccnc(-c4csc(C(=O)NCCC(=O)O)c4)c3)cc2F)c1]

292

3-{[(4-{4-[3-fluoro-4-({[(2-fluoro-5-methylphenyl)amino]carbonyl}amino)phenoxy]pyridin-2-yl}-2-thienyl)carbonyl]amino}propanoic acid $^1$H NMR (DMSO-d$_6$): 9.14 (d, J=2.34 Hz, 1H) 9.01 (d, J=2.34 Hz, 1H) 8.72 (t, J=5.42 Hz, 1H) 8.54 (d, J=6.15 Hz, 1H) 8.47 (s, 1H) 8.41 (d, J=1.17 Hz, 1H) 8.27 (t, J=9.08 Hz, 1H) 8.00 (dd, J=7.62, 1.76 Hz, 1H) 7.54 (d, J=2.34 Hz, 1H) 7.33 (dd, J=11.87, 2.78 Hz, 1H) 7.05-7.16 (m, 2H) 6.95 (dd, J=5.86, 2.34 Hz, 1H) 6.79-6.85 (m, 1H) 3.40-3.49 (m, 2H) 2.50-2.55 (m, 2H) 2.28 (s, 3H)
LR MS (ES−): 551 (M−H)

Example 198

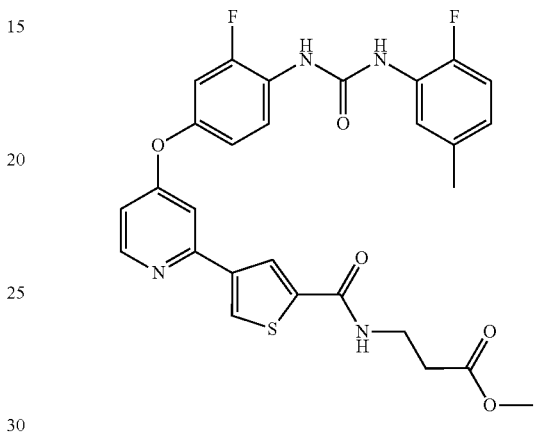

methyl 3-{[(4-{4-[3-fluoro-4-({[(2-fluoro-5-methylphenyl)amino]carbonyl}amino)phenoxy]pyridin-2-yl}-2-thienyl)carbonyl]amino}propanoate $^1$H NMR (DMSO-d$_6$): 9.08 (d, J=2.05 Hz, 1H) 8.97 (d, J=2.64 Hz, 1H) 8.72 (t, J=5.57 Hz, 1H) 8.49 (d, J=5.86 Hz, 1H) 8.39 (br. s, 2H) 8.25 (t, J=9.08 Hz, 1H) 8.01 (dd, J=7.76, 1.90 Hz, 1H) 7.46 (d, J=2.34 Hz, 1H) 7.30 (dd, J=11.87, 2.78 Hz, 1H) 7.12 (dd, J=11.43, 8.20 Hz, 1H) 7.05 (ddd, J=9.01, 2.71, 1.17 Hz, 1H) 6.85 (dd, J=5.86, 2.34 Hz, 1H) 6.81 (m, 1H) 3.61 (s, 3H) 3.43-3.52 (m, 2H) 2.60 (t, J=6.89 Hz, 2H) 2.28 (s, 3H)
LR MS (ES+): 589 (M+Na$^+$)
LR MS (ES−): 565 (M−H)

Example 199

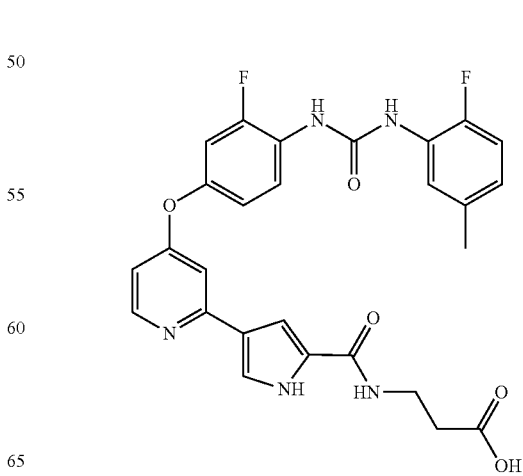

3-{[(4-{4-[3-fluoro-4-({[(2-fluoro-5-methylphenyl)amino]carbonyl}amino)phenoxy]pyridin-2-yl}-1H-pyrrol-2-yl)carbonyl]amino}propanoic acid ¹H NMR (DMSO-d₆): 11.93 (br. s., 1H) 9.13 (d, J=1.47 Hz, 1H) 9.01 (d, J=1.76 Hz, 1H) 8.42 (d, J=5.86 Hz, 1H) 8.21-8.31 (m, 2H) 8.01 (dd, J=7.76, 1.61 Hz, 1H) 7.65 (br. s., 1H) 7.29-7.35 (m, 2H) 7.24 (d, J=1.76 Hz, 1H) 7.05-7.17 (m, 2H) 6.79-6.86 (m, 2H) 3.38-3.47 (m, 2H) 2.47-2.51 (m, 2H) 2.29 (s, 3H)

LR MS (ES−): 534 (M−H)

Example 200

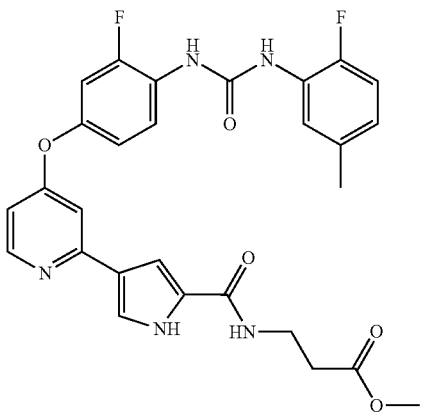 [SMILES: COC(=O)CCNC(=O)c1cc(-c2cc(Oc3ccc(NC(=O)Nc4cc(C)ccc4F)c(F)c3)ccn2)c[nH]1]

methyl 3-{[(4-{4-[3-fluoro-4-({[(2-fluoro-5-methylphenyl)amino]carbonyl}amino)phenoxy]pyridin-2-yl}-1H-pyrrol-2-yl)carbonyl]amino}propanoate ¹H NMR (DMSO-d₆): 11.74 (br. s., 1H) 9.06 (d, J=2.05 Hz, 1H) 8.96 (d, J=2.64 Hz, 1H) 8.36 (d, J=5.86 Hz, 1H) 8.18-8.27 (m, 2H) 8.01 (dd, J=7.62, 2.05 Hz, 1H) 7.50 (dd, J=3.08, 1.61 Hz, 1H) 7.23-7.29 (m, 2H) 7.08-7.16 (m, 2H) 7.02 (ddd, J=9.01, 2.56, 1.32 Hz, 1H) 6.82 (m, 1H) 6.69 (dd, J=5.71, 2.49 Hz, 1H) 3.60 (s, 3H) 3.40-3.49 (m, 2H) 2.57 (t, J=7.03 Hz, 2H) 2.28 (s, 3H)

LR MS (ES+): 572 (M+Na⁺)
LR MS (ES−): 548 (M−H)

Example 201

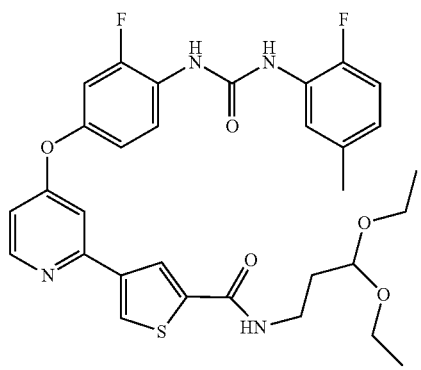 [SMILES: CCOC(CCNC(=O)c1cc(-c2cc(Oc3ccc(NC(=O)Nc4cc(C)ccc4F)c(F)c3)ccn2)cs1)OCC]

N-(3,3-diethoxypropyl)-4-{4-[3-fluoro-4-({[(2-fluoro-5-methylphenyl)amino]carbonyl}amino)phenoxy]pyridin-2-yl}thiophene-2-carboxamide ¹H NMR (DMSO-d₆): 9.08 (d, J=2.05 Hz, 1H) 8.97 (d, J=2.34 Hz, 1H) 8.59 (t, J=5.42 Hz, 1H) 8.49 (d, J=5.57 Hz, 1H) 8.37-8.39 (m, 2H) 8.25 (t, J=9.08 Hz, 1H) 8.01 (dd, J=7.91, 1.76 Hz, 1H) 7.46 (d, J=2.34 Hz, 1H) 7.30 (dd, J=11.72, 2.64 Hz, 1H) 7.12 (dd, J=11.43, 8.50 Hz, 1H) 7.05 (ddd, J=9.01, 2.71, 1.17 Hz, 1H) 6.85 (dd, J=5.71, 2.49 Hz, 1H) 6.79-6.83 (m, 1H) 4.56 (t, J=5.57 Hz, 1H) 3.52-3.64 (m, 2H) 3.45 (dq, J=9.67, 7.13 Hz, 2H) 3.24-3.31 (m, 2H) 2.28 (s, 3H) 1.74-1.83 (m, 2H) 1.11 (t, J=7.03 Hz, 6H)

LR MS (ES+): 633 (M+Na⁺)
LR MS (ES−): 609 (M−H)

Example 202

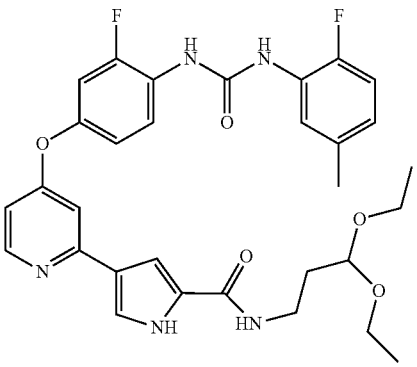 [SMILES: CCOC(CCNC(=O)c1cc(-c2cc(Oc3ccc(NC(=O)Nc4cc(C)ccc4F)c(F)c3)ccn2)c[nH]1)OCC]

N-(3,3-diethoxypropyl)-4-{4-[3-fluoro-4-({[(2-fluoro-5-methylphenyl)amino]carbonyl}amino)phenoxy]pyridin-2-yl}-1H-pyrrole-2-carboxamide ¹H NMR (DMSO-d₆): 11.75 (br. s., 1H) 9.07 (d, J=1.76 Hz, 1H) 8.96 (d, J=2.34 Hz, 1H) 8.38 (d, J=5.86 Hz, 1H) 8.24 (t, J=9.08 Hz, 1H) 8.08 (t, J=5.57 Hz, 1H) 8.01 (dd, J=7.76, 1.90 Hz, 1H) 7.49-7.55 (m, 1H) 7.27 (m, 2H) 7.08-7.18 (m, 2H) 7.03 (m, 1H) 6.82 (m, 1H) 6.69-6.73 (m, 1H) 4.55 (t, J=5.57 Hz, 1H) 3.58 (dq, J=9.38, 7.03 Hz, 2H) 3.44 (dq, J=9.67, 7.03 Hz, 2H) 3.19-3.29 (m, 2H) 2.27 (s, 3H) 1.75 (q, J=6.45 Hz, 2H) 1.11 (t, J=7.03 Hz, 6H)

LR MS (ES+): 616 (M+Na⁺)
LR MS (ES−): 592 (M−H)

Example 203

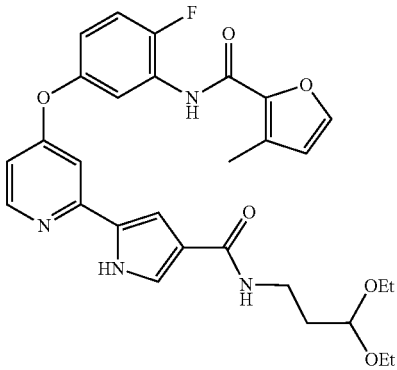 [SMILES: CCOC(CCNC(=O)c1c[nH]c(-c2cc(Oc3ccc(F)c(NC(=O)c4occc4C)c3)ccn2)c1)OCC]

N-(3,3-diethoxypropyl)-5-(4-{4-fluoro-3-[(3-methyl-2-furoyl)amino]phenoxy}pyridin-2-yl)-1H-pyrrole-3-carboxamide To a stirred solution of 5-(4-{4-fluoro-3-[(3-methyl-2-furoyl)amino]phenoxy}pyridin-2-yl)-1H-pyrrole-3-carboxylic acid (300 mg, 0.71 mmol) in 10 ml of anhydrous DMF were added HATU (324 mg, 0.85 mmol) and N,N-diisopropylethylamine (200 mg, 1.55 mmol). The mixture was stirred at room temperature for 10 minutes, followed by addition of 1-amino-3,3-diethoxypropane (157 mg, 1.06 mmol), and stirring was continued for another 10 minutes. The mixture was poured into 100 ml of water with vigorous stirring. The precipitates were filtered, washed with water and dried in vacuo to give N-(3,3-diethoxypropyl)-5-(4-{4-fluoro-3-[(3-methyl-2-furoyl)amino]phenoxy}pyridin-2-yl)-1H-pyrrole-3-carboxamide as white solid. Yield: 380 mg, 97%.

$^1$H NMR (DMSO-d$_6$): 11.79 (br. s., 1H), 9.71 (s, 1H), 8.39 (d, J=5.6 Hz, 1H), 7.79 (t, J=5.6 Hz, 1H), 7.78 (d, J=1.8 Hz, 1H), 7.57 (dd, J=6.3, 3.1 Hz, 1H), 7.39 (t, J=9.4 Hz, 1H), 7.34 (dd, J=2.8, 1.6 Hz, 1H), 7.19 (d, J=2.3 Hz, 1H), 7.06-7.09 (m, 1H), 7.04-7.06 (m, 1H), 6.72 (dd, J=5.6, 2.3 Hz, 1H), 6.57 (d, J=1.8 Hz, 1H), 4.51 (t, J=5.6 Hz, 1H), 3.54 (dq, J=9.5, 7.1 Hz, 2H), 3.41 (dq, J=9.4, 7.1 Hz, 2H), 3.18 (q, J=7.0 Hz, 2H), 2.28 (s, 3H), 1.71 (q, J=6.5 Hz, 2H), 1.08 (t, J=7.0 Hz, 6H)

LR MS (ES+): 551 (MH+)
LR MS (ES−): 549 (M−H)

Example 204

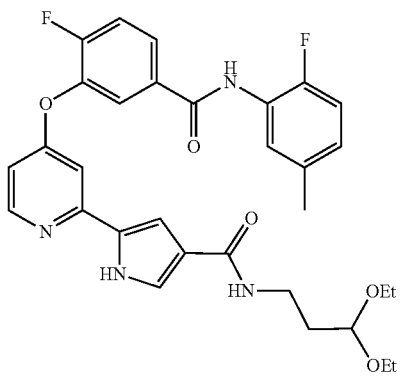 [SMILES: CCOC(CCNC(=O)c1c[nH]c(-c2cc(Oc3cc(C(=O)Nc4cc(C)ccc4F)ccc3F)ccn2)c1)OCC]

N-(3,3-diethoxypropyl)-5-[4-(2-fluoro-5-{[(2-fluoro-5-methylphenyl)amino]carbonyl}phenoxy)pyridin-2-yl]-1H-pyrrole-3-carboxamide To a stirred solution of 5-[4-(2-fluoro-5-{[(2-fluoro-5-methylphenyl)amino]carbonyl}phenoxy)pyridin-2-yl]-1H-pyrrole-3-carboxylic acid (200 mg, 0.45 mmol) in 10 ml of anhydrous DMF were added HATU (205 mg, 0.54 mmol) and N,N-diisopropylethylamine (128 mg, 0.99 mmol). The mixture was stirred at room temperature for 10 minutes, followed by addition of 1-amino-3,3-diethoxypropane (100 mg, 0.68 mmol), and stirring was continued for another 10 minutes. The mixture was poured into 100 ml of water with vigorous stirring. The precipitates were filtered, washed with water and dried in vacuo to give N-(3,3-diethoxypropyl)-5-[4-(2-fluoro-5-{[(2-fluoro-5-methylphenyl)amino]carbonyl}phenoxy)pyridin-2-yl]-1H-pyrrole-3-carboxamide as white solid.

Yield: 250 mg, 97%.

$^1$H NMR (DMSO-d$_6$): 11.81 (br. s., 1H), 10.12 (s, 1H), 8.41 (d, J=5.9 Hz, 1H), 7.99 (d, J=6.2 Hz, 1H), 7.96-7.98 (m, 1H), 7.79 (t, J=5.6 Hz, 1H), 7.63 (t, J=9.5 Hz, 1H), 7.36 (dd, J=2.8, 1.9 Hz, 1H), 7.33-7.35 (m, 1H), 7.25 (d, J=2.3 Hz, 1H), 7.14 (dd, J=10.3, 8.5 Hz, 1H), 7.10 (s, 1H), 7.01-7.07 (m, 1H), 6.80 (dd, J=5.9, 2.3 Hz, 1H), 4.51 (t, J=5.4 Hz, 1H), 3.54 (dq, J=9.4, 7.0 Hz, 2H), 3.41 (dq, J=9.4, 7.1 Hz, 2H), 3.15-3.21 (m, 2H), 2.26 (s, 3H), 1.65-1.76 (m, 2H), 1.08 (t, J=7.0 Hz, 6H)

LR MS (ES−): 577 (M−H)

The following Examples 205 and 206 were prepared using the experiment procedure described in Example 207, but with the appropriate reagent, reaction conditions and reactant substitutions that will be readily realized by those of ordinary skill in this art without the exercise of undue experimentation.

Example 205

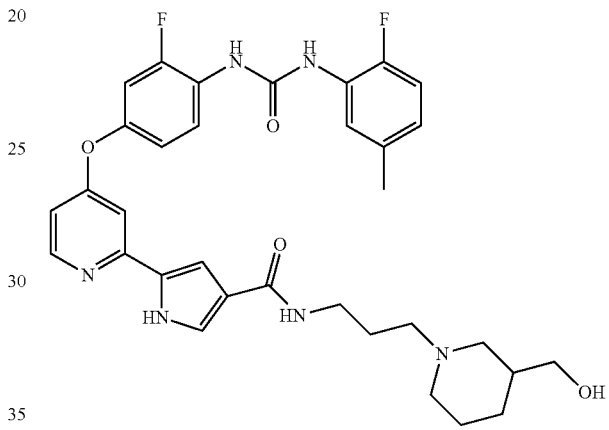

5-{4-[3-fluoro-4-({[(2-fluoro-5-methylphenyl)amino]carbonyl}amino)phenoxy]pyridin-2-yl}-N-{3-[3-(hydroxymethyl)piperidin-1-yl]propyl}-1H-pyrrole-3-carboxamide

LR MS (ES+): 619 (MH+)
LR MS (ES−): 617 (M−H)

Example 206

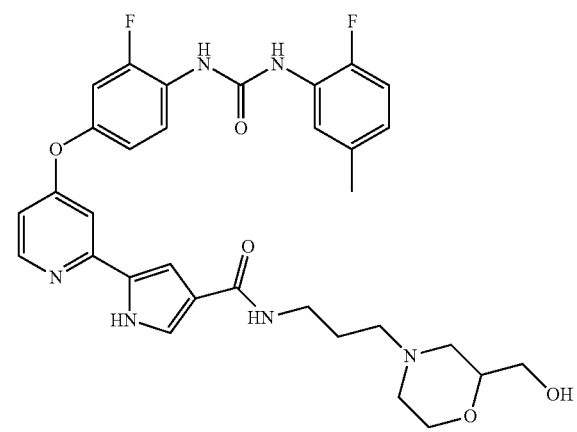

5-{4-[3-fluoro-4-({[(2-fluoro-5-methylphenyl)
amino]carbonyl}amino)phenoxy]pyridin-2-yl}-N-
{3-[2-(hydroxymethyl)morpholin-4-yl]propyl}-1H-
pyrrole-3-carboxamide

LR MS (ES+): 621 (MH+)
LR MS (ES-): 619 (M-H)

Example 207

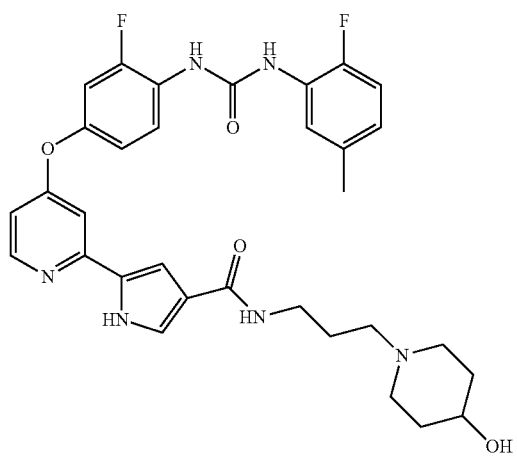 [SMILES: Cc1ccc(F)c(NC(=O)Nc2ccc(Oc3ccnc(-c4cc(C(=O)NCCCN5CCC(O)CC5)c[nH]4)c3)cc2F)c1]

5-{4-[3-fluoro-4-({[(2-fluoro-5-methylphenyl)
amino]carbonyl}amino)phenoxy]pyridin-2-yl}-N-[3-
(4-hydroxypiperidin-1-yl)propyl]-1H-pyrrole-3-car-
boxamide To a stirred solution of 5-{4-[3-fluoro-4-({[(2-fluoro-5-methylphenyl)amino]carbonyl}amino)phenoxy]pyridin-2-yl}-N-(3-oxopropyl)-1H-pyrrole-3-carboxamide (150 mg, 0.29 mmol) in 10 ml of anhydrous DMF were added 4-hydroxypiperidine (59 mg, 0.58 mmol) and acetic acid (10 mg, 0.17 mmol). The mixture was stirred at room temperature for 30 minutes, followed by addition of 1M sodium cyanoborohydride solution in THF (0.60 ml, 0.60 mmol) and stirring was continued for another 60 minutes. The mixture was poured into 50 ml of water. The precipitates were filtered, washed with water and dried to give the crude, which was purified by silica gel flash chromatography eluting with 20% of MeOH in CHCl$_3$ to give 5-{4-[3-fluoro-4-({[(2-fluoro-5-methylphenyl)amino]carbonyl}amino)phenoxy]pyridin-2-yl}-N-[3-(4-hydroxypiperidin-1-yl)propyl]-1H-pyrrole-3-carboxamide as white solid. Yield: 110 mg, 63%.

LR MS (ES+): 605 (MH+)
LR MS (ES-): 603 (M-H)

The following Example 208 was prepared using the experiment procedure described in Example 163, but with the appropriate reagent, reaction conditions and reactant substitutions that will be readily realized by those of ordinary skill in this art without the exercise of undue experimentation.

Example 208

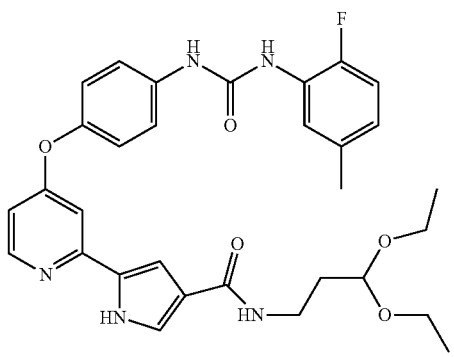 [SMILES: CCOC(CCNC(=O)c1c[nH]c(-c2cc(Oc3ccc(NC(=O)Nc4cc(C)ccc4F)cc3)ccn2)c1)OCC]

N-(3,3-diethoxypropyl)-5-{4-[4-({[(2-fluoro-5-methylphenyl)amino]carbonyl}amino)phenoxy]pyridin-2-yl}-1H-pyrrole-3-carboxamide The following Example 209 was prepared using the experiment procedure described in Example 170, but with the appropriate reagent, reaction conditions and reactant substitutions that will be readily realized by those of ordinary skill in this art without the exercise of undue experimentation.

Example 209

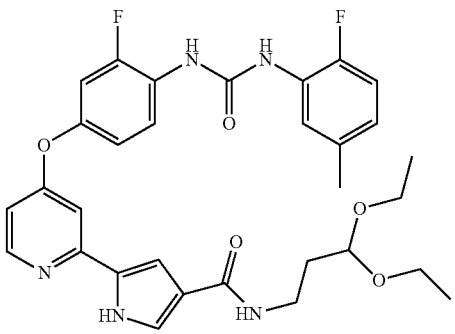 [SMILES: CCOC(CCNC(=O)c1c[nH]c(-c2cc(Oc3ccc(NC(=O)Nc4cc(C)ccc4F)c(F)c3)ccn2)c1)OCC]

N-(3,3-diethoxypropyl)-5-{4-[3-fluoro-4-({[(2-
fluoro-5-methylphenyl)amino]carbonyl}amino)phe-
noxy]pyridin-2-yl}-pyrrole-3-carboxamide Example 210

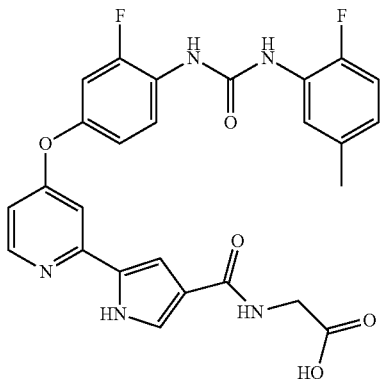 [SMILES: Cc1ccc(F)c(NC(=O)Nc2ccc(Oc3ccnc(-c4cc(C(=O)NCC(=O)O)c[nH]4)c3)cc2F)c1]

{[(5-{4-[3-fluoro-4-({[(2-fluoro-5-methylphenyl)amino]carbonyl}amino)phenoxy]pyridin-2-yl}-1H-pyrrol-3-yl)carbonyl]amino}acetic acid To a stirred solution of methyl {[(5-{4-[3-fluoro-4-({[(2-fluoro-5-methylphenyl)amino]carbonyl}amino)phenoxy]pyridin-2-yl}-1H-pyrrol-3-yl)carbonyl]amino}acetate (100 mg, 0.19 mmol) in 10 ml of MeOH was added 1M NaOH solution (1 ml, 1 mmol). The mixture was stirred at room temperature for one hour and poured into 100 ml of water. 1M HCl was added dropwise with vigorous stirring until pH=4. The precipitates were filtered, washed with water and dried in vacuo to give {[(5-{4-[3-fluoro-4-({[(2-fluoro-5-methylphenyl)amino]carbonyl}amino)phenoxy]pyridin-2-yl}-1H-pyrrol-3-yl)carbonyl]amino}acetic acid as white solid. Yield: 95 mg, 98%.

$^1$H NMR (DMSO-$d_6$): 12.41 (br. s., 1H), 11.86 (br. s., 1H), 9.06 (d, J=2.1 Hz, 1H), 8.94 (d, J=2.6 Hz, 1H), 8.39 (d, J=5.6 Hz, 1H), 8.23 (t, J=9.1 Hz, 1H), 8.20 (t, J=6.0 Hz, 1H), 7.98 (dd, J=7.6, 2.1 Hz, 1H), 7.40 (dd, J=3.1, 1.6 Hz, 1H), 7.27 (dd, J=11.9, 2.8 Hz, 1H), 7.20 (d, J=2.3 Hz, 1H), 7.11 (s, 1H), 7.07-7.12 (m, 1H), 7.03 (dd, J=9.1, 1.8 Hz, 1H), 6.77-6.82 (m, 1H), 6.75 (dd, J=5.6, 2.3 Hz, 1H), 3.81 (d, J=5.9 Hz, 2H), 2.25 (s, 3H)

LR MS (ES−): 520 (M−H)

The following Examples 211 was prepared using the experiment procedure described in Example 175, but with the appropriate reagent, reaction conditions and reactant substitutions that will be readily realized by those of ordinary skill in this art without the exercise of undue experimentation.

Example 211

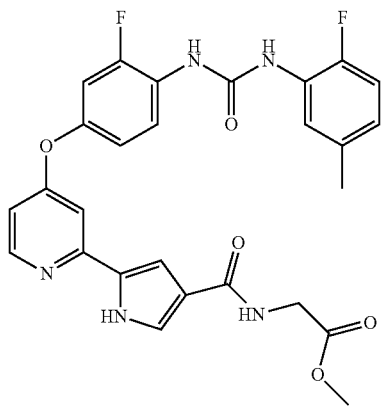 [SMILES: COC(=O)CNC(=O)c1c[nH]c(-c2cc(Oc3ccc(NC(=O)Nc4cc(C)ccc4F)c(F)c3)ccn2)c1]

methyl {[(5-{4-[3-fluoro-4-({[(2-fluoro-5-methylphenyl)amino]carbonyl}amino)phenoxy]pyridin-2-yl}-1H-pyrrol-3-yl)carbonyl]amino}acetate $^1$H NMR (DMSO-$d_6$): 11.87 (t, J=2.9 Hz, 1H), 9.06 (d, J=2.1 Hz, 1H), 8.94 (d, J=2.6 Hz, 1H), 8.39 (d, J=5.6 Hz, 1H), 8.32 (t, J=5.9 Hz, 1H), 8.23 (t, J=9.1 Hz, 1H), 7.98 (dd, J=7.9, 2.3 Hz, 1H), 7.39 (dd, J=3.2, 1.8 Hz, 1H), 7.27 (dd, J=11.9, 2.8 Hz, 1H), 7.19 (d, J=2.3 Hz, 1H), 7.06-7.12 (m, 2H), 7.02 (ddd, J=9.0, 2.9, 1.0 Hz, 1H), 6.77-6.81 (m, 1H), 6.74 (dd, J=5.6, 2.3 Hz, 1H), 3.90 (d, J=5.9 Hz, 2H), 3.61 (s, 3H), 2.25 (s, 3H)

LR MS (ES+): 558 (M+Na+)
LR MS (ES−): 534 (M−H)

Example 212

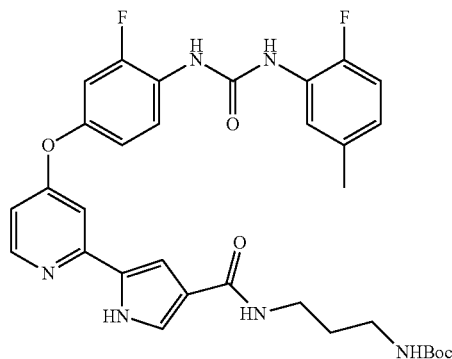 [SMILES: Cc1ccc(F)c(NC(=O)Nc2ccc(Oc3ccnc(-c4cc(C(=O)NCCCNC(=O)OC(C)(C)C)c[nH]4)c3)cc2F)c1]

tert-butyl (3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)carbamate A mixture of 5-{4-[3-fluoro-4-({[(2-fluoro-5-methylphenyl)amino]carbonyl}amino)phenoxy]pyridin-2-yl}-1H-pyrrole-3-carboxylic acid (400 mg, 0.86 mmol), HATU (380 mg, 1.0 mmol) and N,N-diisopropylethylamine (244 mg, 1.9 mmol) in anhydrous DMF (10 ml) was stirred at room temperature for 10 minutes, followed by addition of N-Boc-1,3-propanediamine (174 mg, 1.0 mmol). The mixture was stirred for another 10 minutes and poured into 100 ml of water with vigorous stirring. 1M HCl was added dropwise until pH=5. The precipitates were filtered, washed with water and dried in vacuo to give tert-butyl (3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)carbamate as white solid. Yield: 500 mg, 94%.

$^1$H NMR (DMSO-$d_6$): 11.86 (br. s., 1H), 9.07 (d, J=2.1 Hz, 1H), 8.95 (d, J=2.6 Hz, 1H), 8.39 (d, J=5.9 Hz, 1H), 8.24 (t, J=9.2 Hz, 1H), 7.98 (dd, J=7.6, 2.3 Hz, 1H), 7.82 (t, J=5.7 Hz, 1H), 7.37 (br. s., 1H), 7.28 (dd, J=11.7, 2.6 Hz, 1H), 7.20 (br. s., 1H), 7.11 (br. s., 1H), 7.09 (dd, J=11.3, 8.4 Hz, 1H), 7.03 (dd, J=9.1, 1.8 Hz, 1H), 6.77-6.81 (m, 2H), 6.75 (t, J=5.6 Hz, 1H), 3.14 (q, J=6.7 Hz, 2H), 2.91 (q, J=6.9 Hz, 2H), 2.25 (s, 3H), 1.54 (quin, J=7.0 Hz, 2H), 1.34 (s, 9H)

LR MS (ES+): 643 (M+Na+)
LR MS (ES−): 619 (M−H)

Example 213

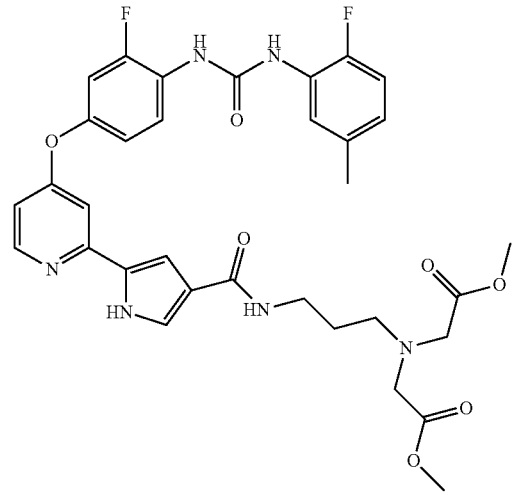 [SMILES: COC(=O)CN(CCCNC(=O)c1c[nH]c(-c2cc(Oc3ccc(NC(=O)Nc4cc(C)ccc4F)c(F)c3)ccn2)c1)CC(=O)OC]

dimethyl 2,2'-[(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)imino]diacetate To a stirred suspension of N-(3-aminopropyl)-5-{4-[3-fluoro-4-({[(2-fluoro-5-methylphenyl)amino]carbonyl}amino)phenoxy]pyridin-2-yl}-1H-pyrrole-3-carboxamide (240 mg, 0.46 mmol) in 10 ml of anhydrous THF were added N,N-diisopropylethylamine (1 ml, 5.6 mmol) and methyl bromoacetate (300 mg, 2.0 mmol). The mixture was heated at 55° C. for 3 hours and poured into 100 ml of water with vigorous stirring. The precipitates were filtered and dried in vacuo to give the crude, which was purified by silica gel chromatography eluting with 3~4% of MeOH in CHCl$_3$ to afford dimethyl 2,2'-[(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)imino]diacetate as white solid. Yield: 160 mg, 52%.

$^1$H NMR (DMSO-d$_6$): 11.79 (br. s., 1H), 9.05 (d, J=2.6 Hz, 1H), 8.94 (d, J=2.6 Hz, 1H), 8.37 (d, J=5.6 Hz, 1H), 8.23 (t, J=9.2 Hz, 1H), 7.98 (dd, J=7.9, 2.3 Hz, 1H), 7.79 (t, J=5.7 Hz, 1H), 7.33 (dd, J=3.2, 1.8 Hz, 1H), 7.26 (dd, J=11.7, 2.6 Hz, 1H), 7.18 (d, J=2.6 Hz, 1H), 7.08-7.12 (m, 1H), 7.07 (dd, J=2.5, 1.9 Hz, 1H), 7.01 (ddd, J=9.0, 2.9, 1.0 Hz, 1H), 6.77-6.81 (m, 1H), 6.73 (dd, J=5.9, 2.3 Hz, 1H), 3.56 (s, 6H), 3.49 (s, 4H), 3.12-3.21 (m, 2H), 2.63 (t, J=7.0 Hz, 2H), 2.25 (s, 3H), 1.49-1.60 (m, 2H)

LR MS (ES+): 687 (M+Na+)
LR MS (ES−): 663 (M−H)

Example 214

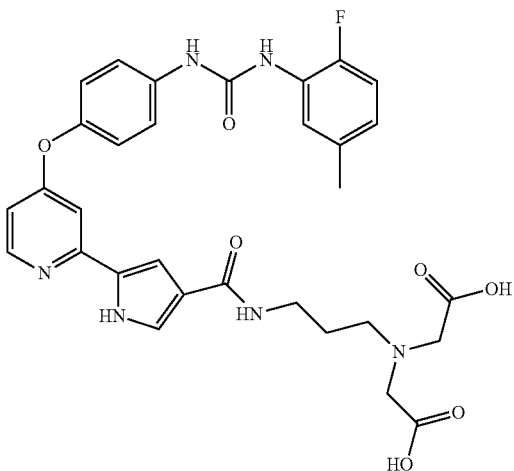 [SMILES: Cc1ccc(F)c(NC(=O)Nc2ccc(Oc3ccnc(-c4cc(C(=O)NCCCN(CC(=O)O)CC(=O)O)c[nH]4)c3)cc2)c1]

2,2'-[(3-{[(5-{4-[4-({[(2-fluoro-5-methylphenyl)amino]carbonyl}amino)phenoxy]pyridin-2-yl}-1H-pyrrol-3-yl)carbonyl]amino}propyl)imino]diacetic acid To a stirred solution of dimethyl 2,2'-[(3-{[(5-{4-[4-({[(2-fluoro-5-methylphenyl)amino]carbonyl}amino)phenoxy]pyridin-2-yl}-1H-pyrrol-3-yl)carbonyl]amino}propyl)imino]diacetate (100 mg, 0.15 mmol) in a mixture of THF/MeOH (5 ml/5 ml) was added 1M NaOH solution (1 ml, 1 mmol). The mixture was stirred at room temperature for 4 hours and poured into 50 ml of water. 1M HCl was added dropwise with vigorous stirring until pH=5. The precipitates were filtered, washed with water and dried in vacuo to give 2,2'-[(3-{[(5-{4-[4-({[(2-fluoro-5-methylphenyl)amino]carbonyl}amino)phenoxy]pyridin-2-yl}-1H-pyrrol-3-yl)carbonyl]amino}propyl)imino]diacetic acid as white solid. Yield: 82 mg, 78%.

$^1$H NMR (DMSO-d$_6$): 12.23 (br. s., 1H), 11.77 (br. s., 1H), 9.16 (s, 1H), 8.48 (d, J=2.3 Hz, 1H), 8.35 (d, J=5.6 Hz, 1H), 7.96 (dd, J=7.9, 2.6 Hz, 1H), 7.84 (t, J=5.7 Hz, 1H), 7.54 (d, J=9.1 Hz, 2H), 7.52-7.55 (m, 1H), 7.32 (dd, J=2.9, 1.8 Hz, 1H), 7.13 (d, J=8.8 Hz, 2H), 7.11-7.15 (m, 1H), 7.08 (dd, J=11.4, 8.2 Hz, 1H), 7.02 (t, J=2.2 Hz, 1H), 6.76-6.80 (m, 1H), 6.67 (dd, J=5.6, 2.3 Hz, 1H), 3.38 (s, 4H), 3.14-3.20 (m, 2H), 2.65 (t, J=7.3 Hz, 2H), 2.25 (s, 3H), 1.56 (quin, J=7.0 Hz, 2H)

LR MS (ES−): 617 (M−H)

Example 215

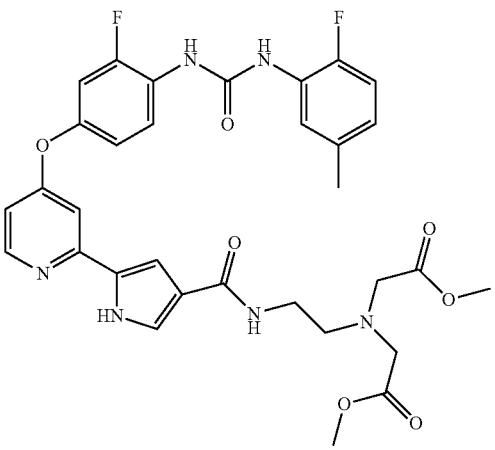 [SMILES: COC(=O)CN(CCNC(=O)c1c[nH]c(-c2cc(Oc3ccc(NC(=O)Nc4cc(C)ccc4F)c(F)c3)ccn2)c1)CC(=O)OC]

dimethyl 2,2'-[(2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}ethyl)imino]diacetate To a stirred suspension of N-(2-aminoethyl)-5-{4-[3-fluoro-4-({[(2-fluoro-5-methylphenyl)amino]carbonyl}amino)phenoxy]pyridin-2-yl}-1H-pyrrole-3-carboxamide (120 mg, 0.24 mmol) in 10 ml of anhydrous THF were added N,N-diisopropylethylamine (1 ml, 5.6 mmol) and methyl bromoacetate (300 mg, 2.0 mmol). The mixture was heated at 55° C. for 2 hours and poured into 100 ml of water with vigorous stirring. The precipitates were filtered and dried in vacuo to give the crude, which was purified by silica gel chromatography eluting with 3~4% of MeOH in CHCl$_3$ to afford dimethyl 2,2'-[(2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}ethyl)imino]diacetate as white solid. Yield: 110 mg, 71%.

$^1$H NMR (DMSO-d$_6$): 11.80 (t, J=2.9 Hz, 1H), 9.05 (s, 1H), 8.94 (d, J=2.3 Hz, 1H), 8.38 (d, J=5.6 Hz, 1H), 8.22 (t, J=9.1 Hz, 1H), 7.97-8.00 (m, 1H), 7.73 (t, J=5.4 Hz, 1H), 7.32 (dd, J=3.1, 1.6 Hz, 1H), 7.26 (dd, J=11.7, 2.9 Hz, 1H), 7.17 (d, J=2.3 Hz, 1H), 7.09 (dd, J=11.4, 8.2 Hz, 1H), 7.04-7.06 (m, 1H), 7.02 (dt, J=9.1, 1.5 Hz, 1H), 6.77-6.82 (m, 1H), 6.74 (dd, J=5.9, 2.3 Hz, 1H), 3.56 (s, 6H), 3.54 (s, 4H), 3.21 (q, J=6.3 Hz, 2H), 2.75 (t, J=6.7 Hz, 2H), 2.25 (s, 3H)

LR MS (ES+): 673 (M+Na+)
LR MS (ES−): 649 (M−H)

Example 216

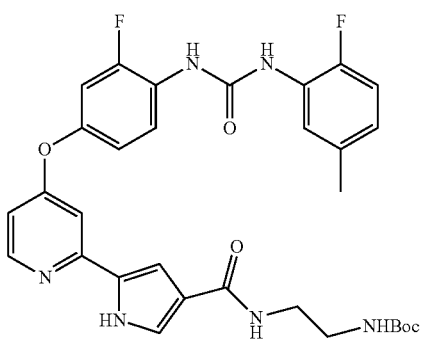 [SMILES: Cc1ccc(F)c(NC(=O)Nc2ccc(Oc3ccnc(-c4cc(C(=O)NCCNC(=O)OC(C)(C)C)c[nH]4)c3)cc2F)c1]

tert-butyl (2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}ethyl)carbamate A mixture of 5-{4-[3-fluoro-4-({[(2-fluoro-5-methylphenyl)amino]carbonyl}amino)phenoxy]pyridin-2-yl}-1H-pyrrole-3-carboxylic acid (300 mg, 0.65 mmol), HATU (296 mg, 0.78 mmol) and N,N-diisopropylethylamine (185 mg, 1.43 mmol) in anhydrous DMF (10 ml) was stirred at room temperature for 10 minutes, followed by addition of tert-butyl (2-aminoethyl)carbamate (125 mg, 0.78 mmol). The mixture was stirred for another 10 minutes and poured into 100 ml of water. 1M HCl was added dropwise until pH=5. The precipitates were filtered, washed with water and dried in vacuo to give tert-butyl (2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}ethyl)carbamate as white solid. Yield: 350 mg, 89%.

$^1$H NMR (DMSO-$d_6$): 11.88 (br. s., 1H), 9.07 (d, J=1.5 Hz, 1H), 8.95 (d, J=2.6 Hz, 1H), 8.40 (d, J=5.9 Hz, 1H), 8.25 (t, J=9.1 Hz, 1H), 7.98 (dd, J=7.9, 2.3 Hz, 1H), 7.84-7.90 (m, 1H), 7.38 (br. s., 1H), 7.26-7.30 (m, 1H), 7.20 (br. s., 1H), 7.11 (br. s., 1H), 7.09 (dd, J=11.3, 8.4 Hz, 1H), 7.03 (dd, J=8.8, 1.8 Hz, 1H), 6.82 (t, J=5.7 Hz, 1H), 6.77-6.81 (m, 2H), 3.16-3.20 (m, 2H), 3.02 (q, J=6.4 Hz, 2H), 2.25 (s, 3H), 1.34 (s, 9H)

LR MS (ES+): 629 (M+Na+)
LR MS (ES−): 605 (M−H)

The following Example 217 was prepared using the experimental procedure described in Example 207, but with the appropriate reagent, reaction conditions and reactant substitutions that will be readily realized by those of ordinary skill in this art without the exercise of undue experimentation.

Example 217

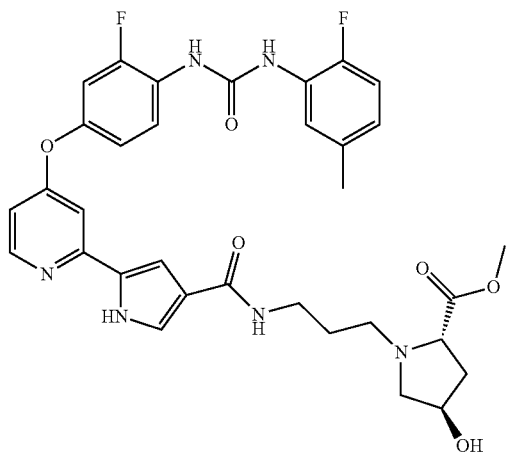 [SMILES: COC(=O)[C@@H]1C[C@@H](O)CN1CCCNC(=O)c1c[nH]c(-c2cc(Oc3ccc(NC(=O)Nc4cc(C)ccc4F)c(F)c3)ccn2)c1]

methyl rel-(2R,4S)-1-(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)-4-hydroxypyrrolidine-2-carboxylate $^1$H NMR (DMSO-$d_6$): 11.78 (br. s., 1H), 9.05 (s, 1H), 8.94 (d, J=2.1 Hz, 1H), 8.37 (d, J=5.6 Hz, 1H), 8.22 (t, J=9.1 Hz, 1H), 7.97-8.00 (m, 1H), 7.82 (t, J=5.7 Hz, 1H), 7.30-7.34 (m, 1H), 7.26 (dd, J=11.7, 2.9 Hz, 1H), 7.17 (d, J=2.1 Hz, 1H), 7.09 (dd, J=11.3, 8.4 Hz, 1H), 7.05-7.07 (m, 1H), 7.01 (dt, J=9.0, 1.5 Hz, 1H), 6.76-6.82 (m, 1H), 6.73 (dd, J=5.7, 2.5 Hz, 1H), 4.84 (d, J=4.4 Hz, 1H), 4.14-4.21 (m, 1H), 3.57 (s, 3H), 3.33 (t, J=7.6 Hz, 1H), 3.12-3.23 (m, 3H), 2.57-2.65 (m, 1H), 2.36-2.42 (m, 1H), 2.25 (s, 3H), 2.20 (dd, J=9.7, 4.4 Hz, 1H), 1.93 (dt, J=12.8, 7.2 Hz, 1H), 1.79-1.88 (m, 1H), 1.49-1.59 (m, 2H)

LR MS (ES+): 649 (MH+)
LR MS (ES−): 647 (M−H)

Example 218

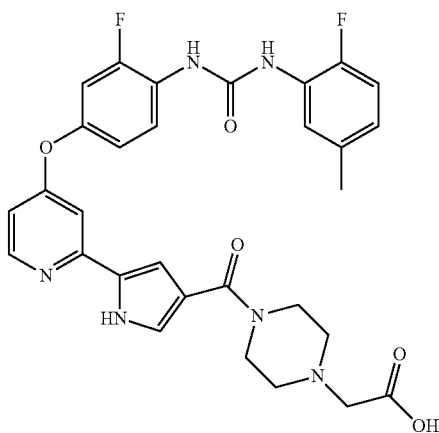 [SMILES: Cc1ccc(F)c(NC(=O)Nc2ccc(Oc3ccnc(-c4cc(C(=O)N5CCN(CC(=O)O)CC5)c[nH]4)c3)cc2F)c1]

{4-[(5-{4-[3-fluoro-4-({[(2-fluoro-5-methylphenyl)amino]carbonyl}amino)phenoxy]pyridin-2-yl}-1H-pyrrol-3-yl)carbonyl]piperazin-1-yl}acetic acid To a stirred solution of ethyl {4-[(5-{4-[3-fluoro-4-({[(2-fluoro-5-methylphenyl)amino]carbonyl}amino)phenoxy]pyridin-2-yl}-1H-pyrrol-3-yl)carbonyl]piperazin-1-yl}acetate (175 mg, 0.28 mmol) in MeOH (8 ml) was added 1M NaOH solution (1 ml, 1 mmol). The mixture was stirred at room temperature for 16 hours and poured into 50 ml of water. 1M HCl was added dropwise with vigorous stirring until pH=7. The precipitates were filtered, washed with water and dried in vacuo to give {4-[5-{4-[3-fluoro-4-({[(2-fluoro-5-methylphenyl)amino]carbonyl}amino)phenoxy]pyridin-2-yl}-1H-pyrrol-3-yl)carbonyl]piperazin-1-yl}acetic acid as white solid. Yield: 160 mg, 96%.

$^1$H NMR (DMSO-$d_6$): 11.87 (br. s., 1H), 9.05 (d, J=2.1 Hz, 1H), 8.94 (d, J=2.1 Hz, 1H), 8.37 (d, J=5.6 Hz, 1H), 8.21 (t, J=9.1 Hz, 1H), 7.98 (dd, J=7.8, 1.6 Hz, 1H), 7.37 (d, J=2.3 Hz, 1H), 7.24 (dd, J=11.7, 2.6 Hz, 1H), 7.13 (dd, J=2.9, 1.8 Hz, 1H), 7.09 (dd, J=11.3, 8.4 Hz, 1H), 7.00 (dd, J=9.0, 1.6 Hz, 1H), 6.93 (dd, J=2.5, 1.9 Hz, 1H), 6.76-6.82 (m, 1H), 6.68 (dd, J=5.7, 2.5 Hz, 1H), 3.61 (br. s., 4H), 3.15 (s, 2H), 2.53 (t, J=4.8 Hz, 4H), 2.25 (s, 3H)

LR MS (ES−): 589 (M−H)

Example 219

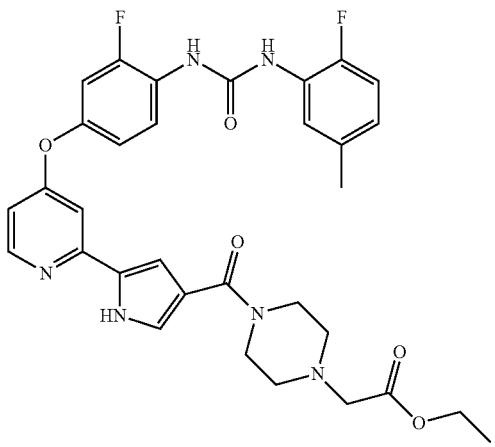 [SMILES: CCOC(=O)CN1CCN(C(=O)c2c[nH]c(-c3cc(Oc4ccc(NC(=O)Nc5cc(C)ccc5F)c(F)c4)ccn3)c2)CC1]

ethyl {4-[(5-{4-[3-fluoro-4-({[(2-fluoro-5-methylphenyl)amino]carbonyl}amino)phenoxy]pyridin-2-yl}-1H-pyrrol-3-yl)carbonyl]piperazin-1-yl}acetate A mixture of 5-{4-[3-fluoro-4-({[(2-fluoro-5-methylphenyl)amino]carbonyl}amino)phenoxy]pyridin-2-yl}-1H-pyrrole-3-carboxylic acid (300 mg, 0.65 mmol), HATU (296 mg, 0.78 mmol) and N,N-diisopropylethylamine (185 mg, 1.43 mmol) in anhydrous DMF (10 ml) was stirred at room temperature for 10 minutes, followed by addition of ethyl piperazinoacetate (168 mg, 0.98 mmol). The mixture was stirred for another 10 minutes and poured into 100 ml of water with vigorous stirring. The precipitates were filtered, washed with water and dried to give to the crude, which was purified by silica gel chromatography eluting with 5-8% of methanol in chloroform to afford ethyl {4-[(5-{4-[3-fluoro-4-({[(2-fluoro-5-methylphenyl)amino]carbonyl}amino)phenoxy]pyridin-2-yl}-1H-pyrrol-3-yl)carbonyl]piperazin-1-yl}acetate as white solid. Yield: 250 mg, 63%.

$^1$H NMR (DMSO-$d_6$): 11.86 (br. s., 1H), 9.04 (d, J=2.3 Hz, 1H), 8.93 (d, J=2.6 Hz, 1H), 8.37 (d, J=5.6 Hz, 1H), 8.21 (t, J=9.1 Hz, 1H), 7.98 (dd, J=7.9, 2.3 Hz, 1H), 7.37 (d, J=2.3 Hz, 1H), 7.24 (dd, J=11.7, 2.6 Hz, 1H), 7.12 (dd, J=3.2, 1.8 Hz, 1H), 7.09 (dd, J=11.3, 8.4 Hz, 1H), 7.00 (ddd, J=8.9, 2.8, 1.2 Hz, 1H), 6.92 (dd, J=2.5, 1.9 Hz, 1H), 6.77-6.81 (m, 1H), 6.68 (dd, J=5.6, 2.3 Hz, 1H), 4.06 (q, J=7.1 Hz, 2H), 3.60 (br. s., 4H), 3.23 (s, 2H), 2.48-2.52 (m, 4H), 2.25 (s, 3H), 1.16 (t, J=7.0 Hz, 3H)

LR MS (ES+): 641 (M+Na+)
LR MS (ES−): 617 (M−H)

Example 220

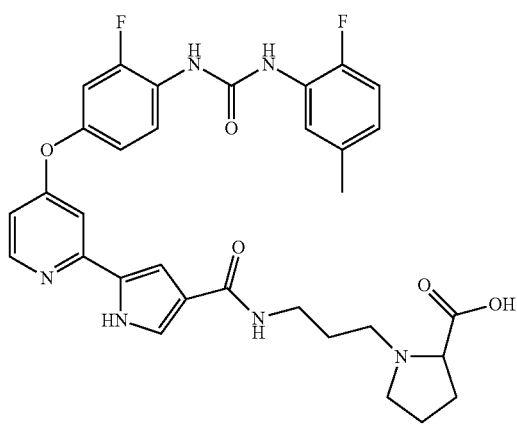 [SMILES: Cc1ccc(F)c(NC(=O)Nc2ccc(Oc3ccnc(-c4cc(C(=O)NCCCN5CCCC5C(=O)O)c[nH]4)c3)cc2F)c1]

1-(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)pyrrolidine-2-carboxylic acid To a stirred suspension of methyl 1-(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)pyrrolidine-2-carboxylate (100 mg, 0.16 mmol) in 1 ml of MeOH was added 0.2N NaOH solution (2 ml, 0.4 mmol). The mixture was heated at 50° C. for 16 hours and cooled to room temperature. 1M HCl was added dropwise with vigorous stirring until pH=7. The precipitates were filtered, washed with water and dried in vacuo to give 1-(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)pyrrolidine-2-carboxylic acid as white solid. Yield: 72 mg, 73%.

$^1$H NMR (DMSO-$d_6$): 11.83 (t, J=2.9 Hz, 1H), 9.14 (d, J=1.8 Hz, 1H), 9.02 (d, J=2.6 Hz, 1H), 8.38 (d, J=5.6 Hz, 1H), 8.21 (t, J=9.1 Hz, 1H), 7.93-8.00 (m, 2H), 7.35 (dd, J=3.1, 1.6 Hz, 1H), 7.26 (dd, J=11.7, 2.6 Hz, 1H), 7.16 (d, J=2.6 Hz, 1H), 7.08 (dd, J=11.2, 8.2 Hz, 1H), 7.05-7.07 (m, 1H), 7.01 (dd, J=9.0, 1.9 Hz, 1H), 6.77-6.81 (m, 1H), 6.74 (dd, J=5.7, 2.5 Hz, 1H), 3.46-3.52 (m, 2H), 3.25 (td, J=13.3, 6.6 Hz, 1H), 3.15-3.22 (m, 1H), 3.04 (ddd, J=12.4, 9.0, 6.5 Hz, 1H), 2.89 (ddd, J=12.5, 9.1, 6.6 Hz, 1H), 2.79 (td, J=10.3, 7.0 Hz, 1H), 2.25 (s, 3H), 2.07-2.17 (m, 1H), 1.87-1.94 (m, 1H), 1.79-1.87 (m, 1H), 1.70-1.79 (m, 2H), 1.58-1.69 (m, 1H)

LR MS (ES+): 619 (MH+)
LR MS (ES−): 617 (M−H)

Example 221

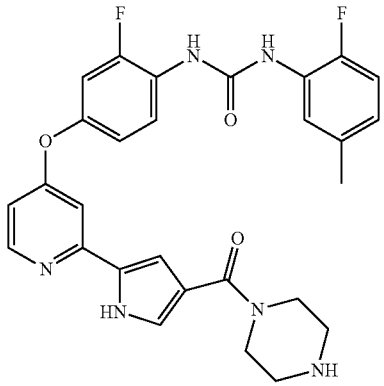 [SMILES: Cc1ccc(F)c(NC(=O)Nc2ccc(Oc3ccnc(-c4cc(C(=O)N5CCNCC5)c[nH]4)c3)cc2F)c1]

1-(2-fluoro-5-methylphenyl)-3-[2-fluoro-4-({2-[4-(piperazin-1-ylcarbonyl)-1H-pyrrol-2-yl]pyridin-4-yl}oxy)phenyl]urea To a stirred solution of tert-butyl 4-[(5-{4-[3-fluoro-4-({[(2-fluoro-5-methylphenyl)amino]carbonyl}amino)phenoxy]pyridin-2-yl}-1H-pyrrol-3-yl)carbonyl]piperazine-1-carboxylate (200 mg, 0.32 mmol) in 10 ml of methylene chloride was added 3 ml of TFA. The mixture was stirred at room temperature for 30 minutes, and evaporated to dryness under reduced pressure. The residue was re-dissolved in 5 ml of methanol and poured into 100 ml of water with vigorous stirring. Saturated NaHCO$_3$ solution was added until pH=9. The precipitates were filtered, washed with water and dried in vacuo to give the crude, which was purified by silica gel chromatography eluting with 12% methanol in chloroform to give 1-(2-fluoro-5-methylphenyl)-3-[2-fluoro-4-({2-[4-(piperazin-1-ylcarbonyl)-1H-pyrrol-2-yl]pyridin-4-yl}oxy)phenyl]urea as white solid. Yield: 145 mg, 86%

¹H NMR (DMSO-d₆): 11.83 (br. s., 1H), 9.05 (s, 1H), 8.94 (s, 1H), 8.37 (d, J=5.9 Hz, 1H), 8.21 (t, J=9.1 Hz, 1H), 7.98 (dd, J=7.9, 2.3 Hz, 1H), 7.36 (d, 1H), 7.23 (dd, J=11.7, 2.9 Hz, 1H), 7.10 (s, 1H), 7.06-7.10 (m, 1H), 6.99 (dd, J=8.7, 1.6 Hz, 1H), 6.90 (t, J=2.2 Hz, 1H), 6.79 (dt, J=5.5, 2.7 Hz, 1H), 6.68 (dd, J=5.7, 2.5 Hz, 1H), 3.42-3.56 (m, 4H), 2.61-2.70 (m, 4H), 2.25 (s, 3H)

Example 222

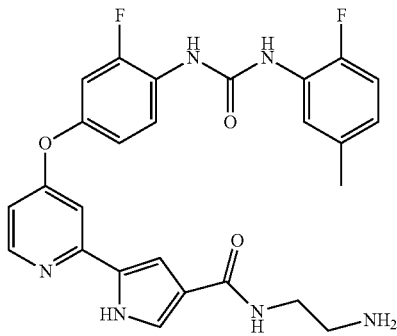 [SMILES: Cc1ccc(F)c(NC(=O)Nc2ccc(Oc3ccnc(-c4cc(C(=O)NCCN)c[nH]4)c3)cc2F)c1]

N-(2-aminoethyl)-5-{4-[3-fluoro-4-({[(2-fluoro-5-methylphenyl)amino]carbonyl}amino)phenoxy]pyridin-2-yl}-1H-pyrrole-3-carboxamide To a stirred suspension of tert-butyl (2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}ethyl) carbamate (300 mg, 0.49 mmol) in 10 ml of methylene chloride was added 3 ml of trifluoroacetic acid. The mixture was stirred at room temperature for 30 minutes and evaporated to dryness under reduced pressure. The residue was re-dissolved in MeOH (5 ml) and poured into 100 ml of water with vigorous stirring. Saturated NaHCO₃ solution was added until pH=8~9. The precipitates were filtered, washed with water and dried in vacuo to give N-(2-aminoethyl)-5-{4-[3-fluoro-4-({[(2-fluoro-5-methylphenyl)amino] carbonyl}amino)phenoxy]pyridin-2-yl}-1H-pyrrole-3-carboxamide as beige solid. Yield: 200 mg, 80%.

LR MS (ES+): 507 (M+Na+)

LR MS (ES−): 505 (M−H)

Example 223

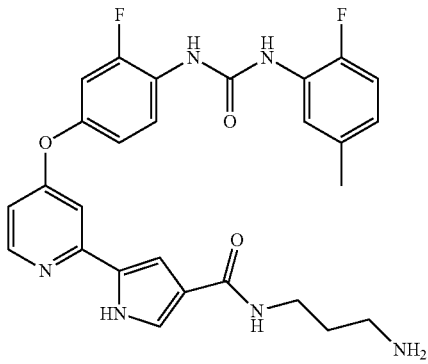 [SMILES: Cc1ccc(F)c(NC(=O)Nc2ccc(Oc3ccnc(-c4cc(C(=O)NCCCN)c[nH]4)c3)cc2F)c1]

N-(3-aminopropyl)-5-{4-[3-fluoro-4-({[(2-fluoro-5-methylphenyl)amino]carbonyl}amino)phenoxy]pyridin-2-yl}-1H-pyrrole-3-carboxamide To a stirred suspension of tert-butyl (3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl) carbamate (450 mg, 0.72 mmol) in 10 ml of methylene chloride was added 5 ml of trifluoroacetic acid. The mixture was stirred at room temperature for 20 minutes and evaporated to dryness under reduced pressure. The residue was re-dissolved in MeOH (5 ml) and poured into 100 ml of water with vigorous stirring. Saturated NaHCO₃ solution was added until pH=8~9. The precipitates were filtered, washed with water and dried in vacuo to give N-(3-aminopropyl)-5-{4-[3-fluoro-4-({[(2-fluoro-5-methylphenyl)amino] carbonyl}amino)phenoxy]pyridin-2-yl}-1H-pyrrole-3-carboxamide as grey solid. Yield: 320 mg, 85%.

LR MS (ES+): 521 (MH+)

Example 224

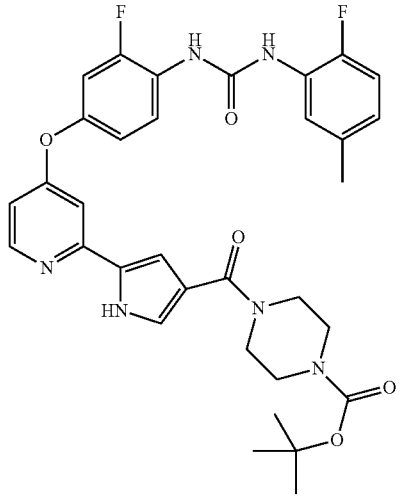 [SMILES: Cc1ccc(F)c(NC(=O)Nc2ccc(Oc3ccnc(-c4cc(C(=O)N5CCN(C(=O)OC(C)(C)C)CC5)c[nH]4)c3)cc2F)c1]

tert-butyl 4-[(5-{4-[3-fluoro-4-({[(2-fluoro-5-methylphenyl)amino]carbonyl}amino)phenoxy]pyridin-2-yl}-1H-pyrrol-3-yl)carbonyl]piperazine-1-carboxylate To a stirred solution of 5-{4-[3-fluoro-4-({[(2-fluoro-5-methylphenyl)amino]carbonyl}amino)phenoxy]pyridin-2-yl}-1H-pyrrole-3-carboxylic acid (300 mg, 0.65 mmol) in 10 ml of anhydrous DMF were added HATU (296 mg, 0.78 mmol) and N,N-diisopropylethylamine (185 mg, 1.43 mmol). The mixture was stirred at room temperature for 10 minutes, followed by addition of tert-butyl 1-piperazinecarboxylate (182 mg, 0.98 mmol). The mixture was stirred for another 10 minutes and poured into 100 ml of water. 1M HCl was added slowly until pH=5. The precipitates were filtered, washed with water and dried in vacuo to give tert-butyl 4-[(5-{4-[3-fluoro-4-({[(2-fluoro-5-methylphenyl)amino] carbonyl}amino)phenoxy]pyridin-2-yl}-1H-pyrrol-3-yl) carbonyl]piperazine-1-carboxylate as white solid. Yield: 290 mg, 84%.

¹H NMR (acetone): 11.10 (br. s., 1H), 8.52 (d, J=3.2 Hz, 1H), 8.38-8.44 (m, 3H), 8.15 (dd, J=7.9, 2.3 Hz, 1H), 7.37 (d, J=2.3 Hz, 1H), 7.31 (dd, J=3.2, 1.8 Hz, 1H), 7.12 (dd, J=11.7, 2.9 Hz, 1H), 6.99-7.06 (m, 3H), 6.81-6.85 (m, 1H), 6.79 (dd, J=5.9, 2.6 Hz, 1H), 3.64-3.71 (m, 4H), 3.41-3.47 (m, 4H), 2.31 (s, 3H), 1.44 (s, 9H)

LR MS (ES+): 655 (M+Na+)
LR MS (ES−): 631 (M−H)

Example 225

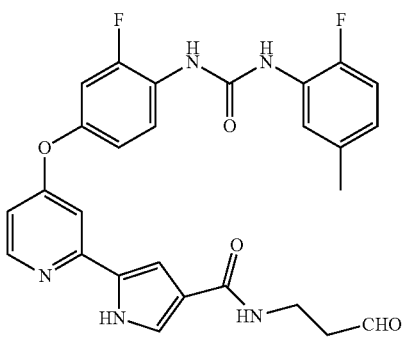 [SMILES: Cc1ccc(F)c(NC(=O)Nc2ccc(Oc3ccnc(-c4cc(C(=O)NCCC=O)c[nH]4)c3)cc2F)c1]

5-{4-[3-fluoro-4-({[(2-fluoro-5-methylphenyl)
amino]carbonyl}amino)phenoxy]pyridin-2-yl}-N-(3-
oxopropyl)-1H-pyrrole-3-carboxamide To a stirred solution of N-(3,3-diethoxypropyl)-5-{4-[3-fluoro-4-({[(2-fluoro-5-methylphenyl)amino]carbonyl}amino)phenoxy]pyridin-2-yl}-1H-pyrrole-3-carboxamide (240 mg, 0.40 mmol) in 10 ml of THF, was added 2M HCl (1 ml, 2 mmol). The mixture was stirred at room temperature for 1 hour, and poured into 100 ml of water with vigorous stirring. The precipitates were filtered, washed with water and dried in vacuo to give 5-{4-[3-fluoro-4-({[(2-fluoro-5-methylphenyl)amino]carbonyl}amino)phenoxy]pyridin-2-yl}-N-(3-oxopropyl)-1H-pyrrole-3-carboxamide as brown solid. Yield: 186 mg, 89%.

LR MS (ES+): 542 (M+Na+)
LR MS (ES−): 518 (M−H)

Example 226

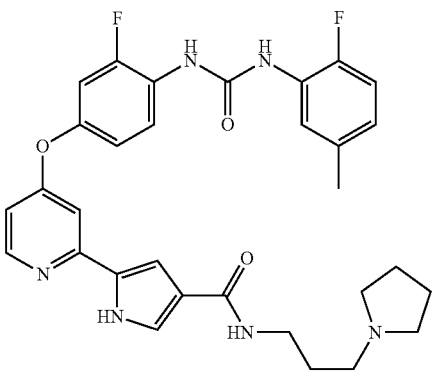 [SMILES: Cc1ccc(F)c(NC(=O)Nc2ccc(Oc3ccnc(-c4cc(C(=O)NCCCN5CCCC5)c[nH]4)c3)cc2F)c1]

5-{4-[3-fluoro-4-({[(2-fluoro-5-methylphenyl)
amino]carbonyl}amino)phenoxy]pyridin-2-yl}-N-(3-
pyrrolidin-1-ylpropyl)-1H-pyrrole-3-carboxamide To a stirred solution of 5-{4-[3-fluoro-4-({[(2-fluoro-5-methylphenyl)amino]carbonyl}amino)phenoxy]pyridin-2-yl}-1H-pyrrole-3-carboxylic acid (200 mg, 0.43 mmol) in 10 ml of anhydrous DMF were added HATU (198 mg, 0.52 mmol) and N,N-diisopropylethylamine (166 mg, 1.3 mmol). The mixture was stirred at room temperature for 10 minutes, followed by addition of N-(3-aminopropyl)pyrrolidine (110 mg, 0.86 mmol). The mixture was stirred for another 5 minutes and poured into 100 ml of water. The precipitates were filtered, washed with water and dried in vacuo to give the crude which was purified by silica gel chromatography eluting with 10-20% of methanol in chloroform to give 5-{4-[3-fluoro-4-({[(2-fluoro-5-methylphenyl)amino]carbonyl}amino)phenoxy]pyridin-2-yl}-N-(3-pyrrolidin-1-ylpropyl)-1H-pyrrole-3-carboxamide as white solid. Yield: 160 mg, 65%.

$^1$H NMR (DMSO-$d_6$): 11.78 (t, J=2.9 Hz, 1H), 9.06 (dd, J=2.1, 0.6 Hz, 1H), 8.94 (d, J=2.6 Hz, 1H), 8.38 (d, J=5.6 Hz, 1H), 8.23 (t, J=9.1 Hz, 1H), 7.98 (dd, J=7.6, 2.1 Hz, 1H), 7.89 (t, J=5.7 Hz, 1H), 7.32 (dd, J=3.2, 1.8 Hz, 1H), 7.26 (dd, J=11.9, 2.8 Hz, 1H), 7.16 (d, J=2.6 Hz, 1H), 7.09 (dd, J=11.4, 8.2 Hz, 1H), 7.03-7.05 (m, 1H), 7.02 (ddd, J=9.0, 2.9, 1.0 Hz, 1H), 6.77-6.81 (m, 1H), 6.74 (dd, J=5.9, 2.3 Hz, 1H), 3.14-3.22 (m, 2H), 2.40 (br. s., 6H), 2.25 (s, 3H), 1.58-1.67 (m, 6H)

LR MS (ES+): 575 (MH+)
LR MS (ES−): 573 (M−H)

The following Example 232 was prepared using the experiment procedure described in Example 234, but with the appropriate reagent, reaction conditions and reactant substitutions that will be readily realized by those of ordinary skill in this art without the exercise of undue experimentation.

Example 227

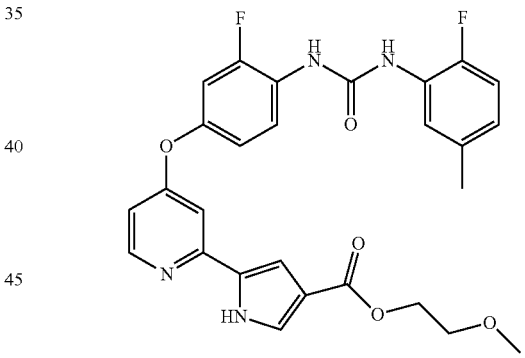

2-methoxyethyl 5-{4-[3-fluoro-4-({[(2-fluoro-5-
methylphenyl)amino]carbonyl}amino)phenoxy]pyri-
din-2-yl}-1H-pyrrole-3-carboxylate $^1$H NMR (DMSO-$d_6$): 12.12 (t, J=3.1 Hz, 1H), 9.05 (d, J=2.1 Hz, 1H), 8.94 (d, J=2.3 Hz, 1H), 8.39 (d, J=5.6 Hz, 1H), 8.22 (t, J=9.1 Hz, 1H), 7.98 (dd, J=8.2, 2.1 Hz, 1H), 7.41 (dd, J=3.4, 1.6 Hz, 1H), 7.39 (d, J=2.3 Hz, 1H), 7.25 (dd, J=11.7, 2.6 Hz, 1H), 7.10 (d, J=2.3 Hz, 1H), 7.09 (dd, J=12.0, 9.1 Hz, 1H), 7.00 (ddd, J=9.2, 2.7, 1.0 Hz, 1H), 6.77-6.81 (m, 1H), 6.73 (dd, J=5.7, 2.5 Hz, 1H), 4.23-4.26 (m, 2H), 3.55-3.59 (m, 2H), 3.27 (s, 3H), 2.25 (s, 3H)

LR MS (ES+): 545 (M+Na+)
LR MS (ES−): 521 (M−H)

The following Example 228 was prepared using the experiment procedure described in Example 207, but with the appropriate reagent, reaction conditions and reactant substi-

Example 228

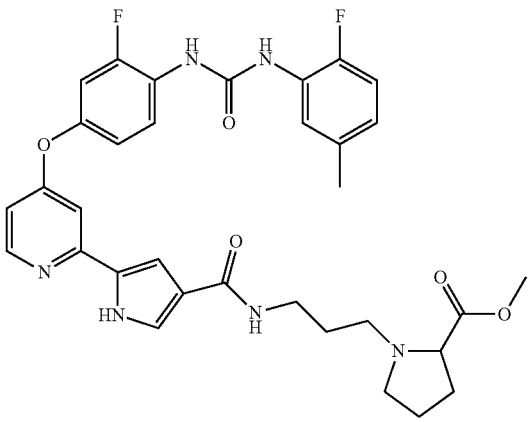 [SMILES: COC(=O)C1CCCN1CCCNC(=O)c1c[nH]c(-c2cc(Oc3ccc(NC(=O)Nc4cc(C)ccc4F)c(F)c3)ccn2)c1]

methyl 1-(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)pyrrolidine-2-carboxylate $^1$H NMR (DMSO-d$_6$): 11.78 (t, J=3.1 Hz, 1H), 9.05 (d, J=2.6 Hz, 1H), 8.94 (d, J=2.6 Hz, 1H), 8.38 (d, J=5.9 Hz, 1H), 8.23 (t, J=9.1 Hz, 1H), 7.98 (dd, J=7.9, 2.6 Hz, 1H), 7.84 (t, J=5.7 Hz, 1H), 7.32 (dd, J=2.9, 1.8 Hz, 1H), 7.26 (dd, J=11.7, 2.9 Hz, 1H), 7.15 (d, J=2.3 Hz, 1H), 7.09 (dd, J=11.3, 8.4 Hz, 1H), 7.04-7.05 (m, 1H), 7.01 (ddd, J=9.0, 2.8, 1.2 Hz, 1H), 6.77-6.81 (m, 1H), 6.74 (dd, J=5.7, 2.5 Hz, 1H), 3.57 (s, 3H), 3.16-3.21 (m, 2H), 3.14 (dd, J=9.0, 5.4 Hz, 1H), 2.94-3.02 (m, 1H), 2.62 (dt, J=11.7, 7.6 Hz, 1H), 2.37 (dt, J=12.3, 6.3 Hz, 1H), 2.26-2.32 (m, 1H), 2.25 (s, 3H), 1.94-2.05 (m, 1H), 1.67-1.78 (m, 3H), 1.57 (quin, J=7.0 Hz, 2H)

LR MS (ES+): 633 (MH+)
LR MS (ES−): 631 (M−H)

Example 229

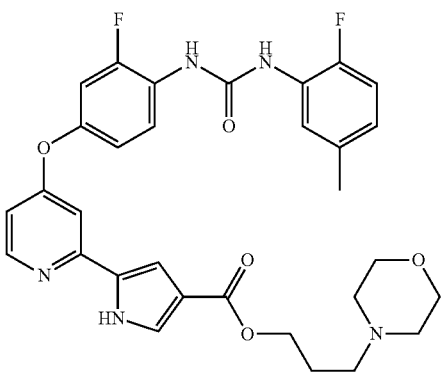 [SMILES: Cc1ccc(F)c(NC(=O)Nc2ccc(Oc3ccnc(-c4cc(C(=O)OCCCN5CCOCC5)c[nH]4)c3)cc2F)c1]

3-morpholin-4-ylpropyl 5-{4-[3-fluoro-4-({[(2-fluoro-5-methylphenyl)amino]carbonyl}amino)phenoxy]pyridin-2-yl}-1H-pyrrole-3-carboxylate To a stirred suspension of 5-{4-[3-fluoro-4-({[(2-fluoro-5-methylphenyl)amino]carbonyl}amino)phenoxy]pyridin-2-yl}-1H-pyrrole-3-carboxylic acid (200 mg, 0.43 mmol) and N-(3-dimethylaminopropyl)-N'-ethylcarbodiimide hydrochloride (EDC, 124 mg, 0.65 mmol) in 10 ml of anhydrous tetrahydrofuran were added N-(3-hydroxypropyl)morpholine (125 mg, 0.86 mmol) and 4-dimethylaminopyridine (10 mg, 0.08 mmol). The mixture was heated at 60° C. for 16 hours, cooled to room temperature and evaporated to dryness. The residue was purified by silica gel chromatography eluting with 3~5% of methanol in chloroform to afford 3-morpholin-4-ylpropyl 5-{4-[3-fluoro-4-({[(2-fluoro-5-methylphenyl)amino]carbonyl}amino)phenoxy]pyridin-2-yl}-1H-pyrrole-3-carboxylate as white solid. Yield: 90 mg, 35%.

$^1$H NMR (DMSO-d$_6$): 12.10 (t, J=3.1 Hz, 1H), 9.05 (d, J=2.6 Hz, 1H), 8.94 (d, J=2.6 Hz, 1H), 8.39 (d, J=5.9 Hz, 1H), 8.22 (t, J=9.1 Hz, 1H), 7.98 (dd, J=7.9, 2.3 Hz, 1H), 7.41 (dd, J=3.2, 1.5 Hz, 1H), 7.39 (d, J=2.3 Hz, 1H), 7.24 (dd, J=11.7, 2.6 Hz, 1H), 7.07-7.11 (m, 2H), 7.00 (dd, J=8.9, 2.8 Hz, 1H), 6.77-6.81 (m, 1H), 6.72 (dd, J=5.7, 2.5 Hz, 1H), 4.15 (t, J=6.6 Hz, 2H), 3.53 (t, J=4.7 Hz, 4H), 2.35 (t, J=7.2 Hz, 2H), 2.32 (br. s., 4H), 2.25 (s, 3H), 1.78 (quin, J=6.9 Hz, 2H)

LR MS (ES+): 592 (MH+)
LR MS (ES−): 590 (M−H)

Example 230

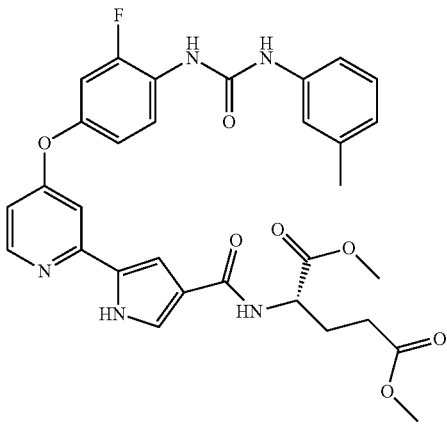 [SMILES: COC(=O)CC[C@H](NC(=O)c1c[nH]c(-c2cc(Oc3ccc(NC(=O)Nc4cccc(C)c4)c(F)c3)ccn2)c1)C(=O)OC]

dimethyl 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioate To a stirred solution of 5-{4-[3-fluoro-4-({[(3-methylphenyl)amino]carbonyl}amino)phenoxy]pyridin-2-yl}-1H-pyrrole-3-carboxylic acid (150 mg, 0.34 mmol) in 10 ml of anhydrous DMF were added HATU (156 mg, 0.41 mmol) and N,N-diisopropylethylamine (175 mg, 1.36 mmol). The mixture was stirred at room temperature for 10 minutes, followed by addition of L-glutamic acid dimethyl ester hydrochloride (108 mg, 0.51 mmol). The mixture was stirred for another 10 minutes and poured into 100 ml of water. The precipitates were filtered, washed with water and dried in vacuo to give the crude, which was purified by silica gel chromatography eluting with 3~5% methanol in chloroform to give dimethyl 2-{[(5-{4-[3-fluoro-4-({[(3-methylphenyl)amino] carbonyl}amino)phenoxy]pyridin-2-yl}-1H-pyrrol-3-yl) carbonyl]amino}pentanedioate as white solid. Yield: 120 mg, 59%.

¹H NMR (DMSO-d₆): 11.87 (t, J=2.9 Hz, 1H), 8.96 (s, 1H), 8.56 (d, J=2.6 Hz, 1H), 8.38 (d, J=5.6 Hz, 1H), 8.20 (t, J=9.1 Hz, 1H), 8.11 (d, J=7.6 Hz, 1H), 7.43 (dd, J=3.1, 1.9 Hz, 1H), 7.27 (s, 1H), 7.25 (dd, J=11.7, 2.9 Hz, 1H), 7.19-7.23 (m, 2H), 7.12-7.17 (m, 2H), 7.01 (dd, J=8.1, 2.5 Hz, 1H), 6.79 (d, J=7.3 Hz, 1H), 6.73 (dd, J=5.7, 2.5 Hz, 1H), 4.37 (ddd, J=9.6, 7.6, 5.1 Hz, 1H), 3.59 (s, 3H), 3.55 (s, 3H), 2.40 (t, J=7.5 Hz, 2H), 2.26 (s, 3H), 1.98-2.10 (m, 1H), 1.86-1.97 (m, 1H)

LR MS (ES+): 626 (M+Na+)
LR MS (ES−): 602 (M−H)

Example 231

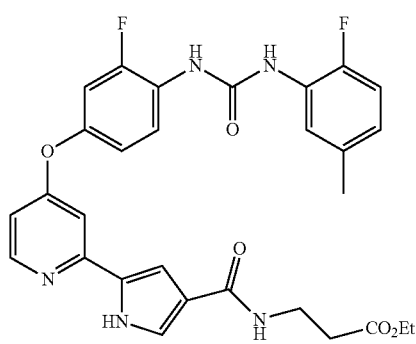 [SMILES: CCOC(=O)CCNC(=O)c1c[nH]c(-c2cc(Oc3ccc(NC(=O)Nc4cc(C)ccc4F)c(F)c3)ccn2)c1]

ethyl 3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propanoate To a stirred solution of 5-{4-[3-fluoro-4-({[(2-fluoro-5-methylphenyl)amino]carbonyl}amino)phenoxy]pyridin-2-yl}-1H-pyrrole-3-carboxylic acid (200 mg, 0.43 mmol) in 10 ml of anhydrous DMF were added HATU (179 mg, 0.47 mmol) and N,N-diisopropylethylamine (166 mg, 1.29 mmol). The mixture was stirred at room temperature for 10 minutes, followed by addition of β-alanine ethyl ester hydrochloride (100 mg, 0.65 mmol). The mixture was stirred for another 10 minutes and poured into 100 ml of water with vigorous stirring. 1M HCl was added slowly until pH=5. The precipitates were filtered, washed with water and dried in vacuo to give ethyl 3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propanoate as white solid. Yield: 200 mg, 82%.

¹H NMR (DMSO-d₆): 11.81 (br. s., 1H), 9.06 (d, J=2.1 Hz, 1H), 8.94 (d, J=2.6 Hz, 1H), 8.38 (d, J=5.6 Hz, 1H), 8.23 (t, J=9.1 Hz, 1H), 7.98 (dd, J=7.9, 2.3 Hz, 1H), 7.93 (t, J=5.7 Hz, 1H), 7.35 (br. s., 1H), 7.26 (dd, J=11.7, 2.9 Hz, 1H), 7.17 (d, J=2.6 Hz, 1H), 7.09 (dd, J=11.3, 8.4 Hz, 1H), 7.06-7.08 (m, 1H), 7.02 (dd, J=8.7, 2.8 Hz, 1H), 6.77-6.81 (m, 1H), 6.74 (dd, J=5.7, 2.5 Hz, 1H), 4.03 (q, 2H), 3.35-3.39 (m, 2H), 2.49 (t, J=7.04 Hz, 2H), 2.25 (s, 3H), 1.14 (t, J=7.0 Hz, 3H)

LR MS (ES+): 564 (MH+)
LR MS (ES−): 562 (M−H)

Example 232

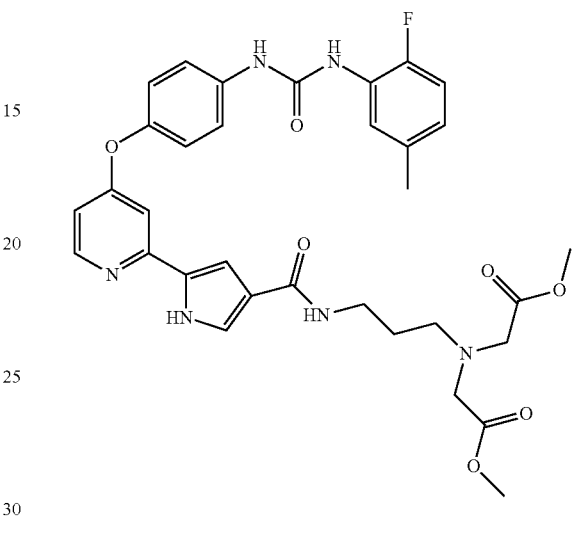

dimethyl 2,2'-[(3-{[(5-{4-[4-({[(2-fluoro-5-methylphenyl)amino]carbonyl}amino)phenoxy]pyridin-2-yl}-1H-pyrrol-3-yl)carbonyl]amino}propyl)imino] diacetate To a stirred suspension of N-(3-aminopropyl)-5-{4-[4-({[(2-fluoro-5-methylphenyl)amino]carbonyl}amino)phenoxy]pyridin-2-yl}-1H-pyrrole-3-carboxamide (200 mg, 0.40 mmol) and N,N-diisopropylethylamine (0.5 ml, 2.8 mmol) in 10 ml of anhydrous THF was added methyl bromoacetate (200 mg, 1.30 mmol). The mixture was heated at 60° C. for 16 hours and poured into 100 ml of water with vigorous stirring. The precipitates were filtered and dried in vacuo to give the crude, which was purified by silica gel chromatography eluting with 5% of MeOH in CHCl₃ to afford dimethyl 2,2'-[(3-{[(5-{4-[4-({[(2-fluoro-5-methylphenyl)amino]carbonyl}amino)phenoxy]pyridin-2-yl}-1H-pyrrol-3-yl)carbonyl]amino}propyl)imino]diacetate as white solid. Yield: 210 mg, 82%.

¹H NMR (DMSO-d₆): 11.77 (t, J=2.9 Hz, 1H), 9.14 (s, 1H), 8.46 (d, J=2.9 Hz, 1H), 8.35 (d, J=5.6 Hz, 1H), 7.96 (dd, J=7.9, 2.3 Hz, 1H), 7.79 (t, J=5.7 Hz, 1H), 7.52-7.56 (m, 2H), 7.32 (dd, J=3.1, 1.6 Hz, 1H), 7.11-7.15 (m, 3H), 7.08 (dd, J=11.4, 8.2 Hz, 1H), 7.02 (dd, J=2.3, 1.8 Hz, 1H), 6.76-6.80 (m, 1H), 6.68 (dd, J=5.6, 2.3 Hz, 1H), 3.56 (s, 6H), 3.48 (s, 4H), 3.12-3.20 (m, 2H), 2.63 (t, J=7.0 Hz, 2H), 2.25 (s, 3H), 1.54 (quin, J=7.0 Hz, 2H)

LR MS (ES+): 669 (M+Na+)
LR MS (ES−): 645 (M−H)

Example 233

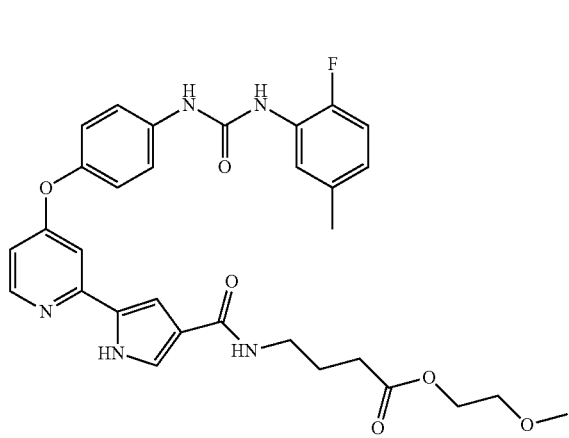 [SMILES: COCCOC(=O)CCCNC(=O)c1c[nH]c(-c2cc(Oc3ccc(NC(=O)Nc4cc(C)ccc4F)cc3)ccn2)c1]

2-methoxyethyl 4-{[(5-{4-[4-({[(2-fluoro-5-methylphenyl)amino]carbonyl}amino)phenoxy]pyridin-2-yl}-1H-pyrrol-3-yl)carbonyl]amino}butanoate To a stirred solution of 4-{[(5-{4-[4-({[(2-fluoro-5-methylphenyl)amino]carbonyl}amino)phenoxy]pyridin-2-yl}-1H-pyrrol-3-yl)carbonyl]amino}butanoic acid (300 mg, 0.56 mmol) in 10 ml of anhydrous DMF were added HATU (255 mg, 0.67 mmol) and N,N-diisopropylethylamine (217 mg, 1.68 mmol). The mixture was stirred at room temperature for 10 minutes, followed by addition of 2-methoxyethanol (0.50 ml, 6.3 mmol). The mixture was heated at 66° C. for 1 hour, and poured into 100 ml of water with vigorous stirring. 1M HCl was added dropwise until pH=4. The precipitates were filtered, washed with water and dried in vacuo to give the crude, which was purified by silica gel chromatography eluting with ethyl acetate to give 2-methoxyethyl 4-{[(5-{4-[4-({[(2-fluoro-5-methylphenyl)amino]carbonyl}amino)phenoxy]pyridin-2-yl}-1H-pyrrol-3-yl)carbonyl]amino}butanoate as white solid. Yield: 215 mg, 65%.

$^1$H NMR (DMSO-$d_6$): 11.78 (t, J=3.1 Hz, 1H), 9.14 (s, 1H), 8.46 (d, J=2.9 Hz, 1H), 8.35 (d, J=5.6 Hz, 1H), 7.96 (dd, J=7.9, 2.3 Hz, 1H), 7.85 (t, J=5.9 Hz, 1H), 7.52-7.56 (m, 2H), 7.33 (dd, J=3.2, 1.8 Hz, 1H), 7.11-7.15 (m, 3H), 7.08 (dd, J=11.3, 8.4 Hz, 1H), 7.03 (dd, J=2.5, 1.9 Hz, 1H), 6.76-6.80 (m, 1H), 6.68 (dd, J=5.6, 2.3 Hz, 1H), 4.07-4.10 (m, 2H), 3.45-3.49 (m, 2H), 3.21 (s, 3H), 3.13-3.19 (m, 2H), 2.32 (t, J=7.5 Hz, 2H), 2.25 (s, 3H), 1.70 (quin, J=7.2 Hz, 2H)

LR MS (ES+): 612 (M+Na+)

LR MS (ES−): 588 (M−H)

The following Example 234 was prepared using the experiment procedure described in Example 233, but with the appropriate reagent, reaction conditions and reactant substitutions that will be readily realized by those of ordinary skill in this art without the exercise of undue experimentation.

Example 234

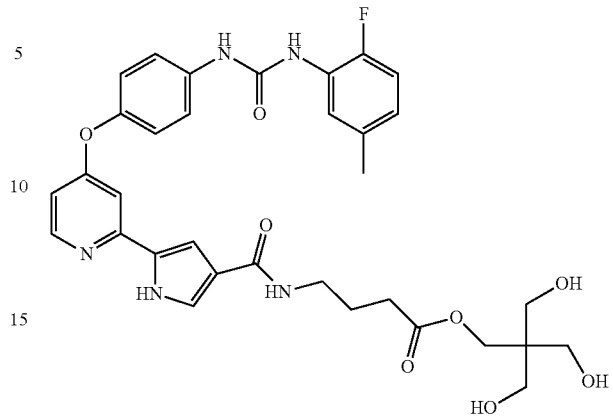

3-hydroxy-2,2-bis(hydroxymethyl)propyl 4-{[(5-{4-[4-({[(2-fluoro-5-methylphenyl)amino]carbonyl}amino)phenoxy]pyridin-2-yl}-1H-pyrrol-3-yl)carbonyl]amino}butanoate $^1$H NMR (DMSO-$d_6$): 11.79 (t, J=2.9 Hz, 1H), 9.14 (s, 1H), 8.46 (d, J=2.6 Hz, 1H), 8.35 (d, J=5.9 Hz, 1H), 7.96 (dd, J=7.6, 2.3 Hz, 1H), 7.88 (t, J=5.7 Hz, 1H), 7.52-7.56 (m, 2H), 7.35 (dd, J=3.2, 1.8 Hz, 1H), 7.12-7.15 (m, 3H), 7.08 (dd, J=11.3, 8.4 Hz, 1H), 7.04 (dd, J=2.5, 1.9 Hz, 1H), 6.76-6.80 (m, 1H), 6.68 (dd, J=5.6, 2.3 Hz, 1H), 4.33 (t, J=5.4 Hz, 3H), 3.89 (s, 2H), 3.33 (d, J=5.3 Hz, 6H), 3.17 (q, J=6.7 Hz, 2H), 2.29 (t, J=7.5 Hz, 2H), 2.25 (s, 3H), 1.70 (quin, J=7.2 Hz, 2H)

LR MS (ES+): 672 (M+Na+)

LR MS (ES−): 648 (M−H)

Example 235

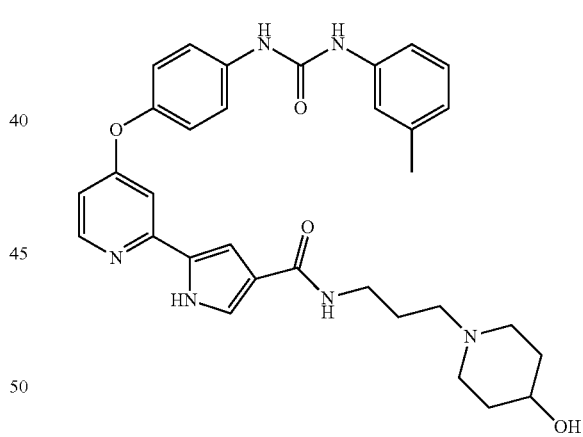

N-[3-(4-hydroxypiperidin-1-yl)propyl]-5-{4-[4-({[(3-methylphenyl)amino]carbonyl}amino)phenoxy]pyridin-2-yl}-1H-pyrrole-3-carboxamide To a stirred solution of 5-{4-[4-({[(3-methylphenyl)amino]carbonyl}amino)phenoxy]pyridin-2-yl}-N-(3-oxopropyl)-1H-pyrrole-3-carboxamide (150 mg, 0.31 mmol) in 10 ml of anhydrous DMF were added 4-hydroxypiperidine (59 mg, 0.58 mmol) and acetic acid (10 mg, 0.17 mmol). The mixture was stirred at room temperature for 60 minutes, followed by addition of 1M sodium cyanoborohydride solution in THF (0.60 ml, 0.60 mmol). Stirring was continued for another 60 minutes and the mixture was poured into 50 ml of water. The precipitates were filtered, washed with water and dried to give the crude, which was purified by silica gel flash chromatography eluting with 20% of MeOH in CHCl₃ to give N-[3-(4-hydroxypiperidin-1-yl)propyl]-5-{4-[4-({[(3-methylphenyl)amino]carbonyl}amino)phenoxy]pyridin-2-yl}-1H-pyrrole-3-carboxamide as off-white solid. Yield: 102 mg, 58%.

LR MS (ES+): 569 (MH+)
LR MS (ES−): 567 (M−H)

Example 236

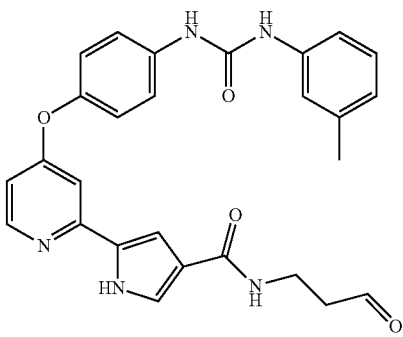 [SMILES: Cc1cccc(NC(=O)Nc2ccc(Oc3ccnc(-c4cc(C(=O)NCCC=O)c[nH]4)c3)cc2)c1]

5-{4-[4-({[(3-methylphenyl)amino]carbonyl}amino)phenoxy]pyridin-2-yl}-N-(3-oxopropyl)-1H-pyrrole-3-carboxamide To a stirred solution of N-(3-hydroxypropyl)-5-{4-[4-({[(3-methylphenyl)amino]carbonyl}amino)phenoxy]pyridin-2-yl}-1H-pyrrole-3-carboxamide (1.0 g, 2.06 mmol) in 20 ml of anhydrous DMF was added Dess-Martin periodinane (1.22 g, 2.88 mmol). The mixture was stirred at room temperature under nitrogen for 80 minutes and poured into 100 ml of water with vigorous stirring. Saturated NaHCO₃ solution was added until pH=9. The precipitates were filtered, washed with water and dried in vacuo to give the crude 5-{4-[4-({[(3-methylphenyl)amino]carbonyl}amino)phenoxy]pyridin-2-yl}-N-(3-oxopropyl)-1H-pyrrole-3-carboxamide as light brown solid, which was used in the next step without further purification. Yield: 1.0 g, 100%.

LR MS (ES+): 484 (MH+)
LR MS (ES−): 482 (M−H)

Example 237

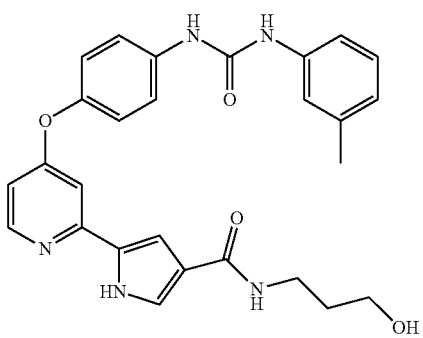 [SMILES: Cc1cccc(NC(=O)Nc2ccc(Oc3ccnc(-c4cc(C(=O)NCCCO)c[nH]4)c3)cc2)c1]

N-(3-hydroxypropyl)-5-{4-[4-({[3-methylphenyl)amino]carbonyl}amino)phenoxy]pyridin-2-yl}-1H-pyrrole-3-carboxamide To a stirred solution of 5-{4-[4-({[(3-methylphenyl)amino]carbonyl}amino)phenoxy]pyridin-2-yl}-1H-pyrrole-3-carboxylic acid (1.00 g, 2.34 mmol) in 20 ml of anhydrous DMF were added HATU (1.07 g, 2.80 mmol) and N,N-diisopropylethylamine (604 mg, 4.68 mmol). The mixture was stirred at room temperature for 10 minutes, followed by addition of 3-amino-1-propanol (263 mg, 3.51 mmol). The mixture was stirred for another 5 minutes and poured into 200 ml of water with vigorous stirring. The precipitates were filtered, washed with water and dried in vacuo to give N-(3-hydroxypropyl)-5-{4-[4-({[(3-methylphenyl)amino]carbonyl}amino)phenoxy]pyridin-2-yl}-1H-pyrrole-3-carboxamide as white solid. Yield: 1.10 g, 97%.

¹H NMR (DMSO-d₆): 12.02 (br. s., 1H), 8.82 (s, 1H), 8.62 (s, 1H), 8.41 (d, J=6.2 Hz, 1H), 7.85-7.95 (m, 1H), 7.53-7.61 (m, 2H), 7.45-7.51 (m, 1H), 7.25-7.31 (m, 2H), 7.19-7.25 (m, 2H), 7.09-7.19 (m, 3H), 6.81-6.88 (m, 1H), 6.78 (d, J=7.3 Hz, 1H), 3.42 (t, J=6.3 Hz, 2H), 3.22 (q, J=6.5 Hz, 2H), 2.26 (s, 3H), 1.61 (quin, J=6.7 Hz, 2H)

LR MS (ES+): 486 (M+Na+)
LR MS (ES−): 484 (M−H)

Example 238

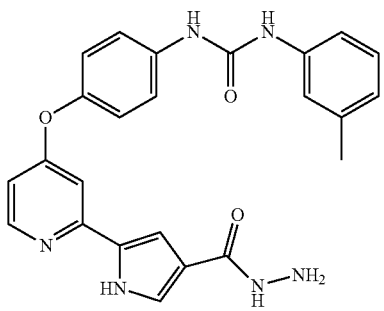 [SMILES: Cc1cccc(NC(=O)Nc2ccc(Oc3ccnc(-c4cc(C(=O)NN)c[nH]4)c3)cc2)c1]

1-[4-({2-[4-(hydrazinocarbonyl)-1H-pyrrol-2-yl]pyridin-4-yl}oxy)phenyl]-3-(3-methylphenyl)urea To a stirred solution of 5-{4-[4-({[(3-methylphenyl)amino]carbonyl}amino)phenoxy]pyridin-2-yl}-1H-pyrrole-3-carboxylic acid (100 mg, 0.23 mmol) in 10 ml of anhydrous DMF were added HATU (105 mg, 0.28 mmol) and N,N-diisopropylethylamine (89 mg, 0.69 mmol). The mixture was stirred at room temperature for 10 minutes, followed by addition of hydrazine monohydrate (0.25 ml, 5.2 mmol). The mixture was stirred for another 5 minutes and poured into 100 ml of water. The precipitates were filtered, washed with water and dried in vacuo to give 1-[4-({2-[4-(hydrazinocarbonyl)-1H-pyrrol-2-yl]pyridin-4-yl}oxy)phenyl]-3-(3-methylphenyl)urea as white solid. Yield: 98 mg, 95%.

¹H NMR (DMSO-d₆): 11.83 (br. s., 1H), 9.22-9.36 (m, 1H), 8.74 (s, 1H), 8.57 (s, 1H), 8.35 (d, J=5.6 Hz, 1H), 7.51-7.56 (m, 2H), 7.36 (br. s., 1H), 7.27 (s, 1H), 7.19-7.23 (m, 1H), 7.09-7.15 (m, 4H), 7.02-7.06 (m, 1H), 6.77 (d, J=7.9 Hz, 1H), 6.67 (dd, J=5.9, 2.3 Hz, 1H), 2.25 (s, 3H)

LR MS (ES+): 465 (M+Na+)
LR MS (ES−): 441 (M−H)

Example 239

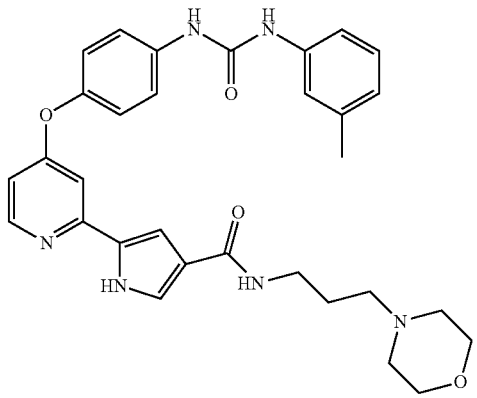 [SMILES: Cc1cccc(NC(=O)Nc2ccc(Oc3ccnc(-c4cc(C(=O)NCCCN5CCOCC5)c[nH]4)c3)cc2)c1]

5-{4-[4-({[(3-methylphenyl)amino]carbonyl}amino)phenoxy]pyridin-2-yl}-N-(3-morpholin-4-ylpropyl)-1H-pyrrole-3-carboxamide To a stirred solution of 5-{4-[4-({[(3-methylphenyl)amino]carbonyl}amino)phenoxy]pyridin-2-yl}-1H-pyrrole-3-carboxylic acid (100 mg, 0.23 mmol) in 10 ml of anhydrous DMF were added HATU (106 mg, 0.28 mmol) and N,N-diisopropylethylamine (90 mg, 0.70 mmol). The mixture was stirred at room temperature for 10 minutes, followed by addition of N-(3-aminopropyl)morpholine (68 mg, 0.47 mmol). The mixture was stirred for another 5 minutes and poured into 100 ml of water. The precipitates were filtered, washed with water and dried in vacuo to give 5-{4-[4-({[(3-methylphenyl)amino]carbonyl}amino)phenoxy]pyridin-2-yl}-N-(3-morpholin-4-ylpropyl)-1H-pyrrole-3-carboxamide as white solid. Yield: 110 mg, 85%.

$^1$H NMR (DMSO-$d_6$): 11.77 (t, J=2.9 Hz, 1H), 8.74 (s, 1H), 8.57 (s, 1H), 8.35 (d, J=5.9 Hz, 1H), 7.83 (t, J=5.7 Hz, 1H), 7.51-7.55 (m, 2H), 7.32 (dd, J=3.1, 1.6 Hz, 1H), 7.27 (s, 1H), 7.21 (d, J=8.5 Hz, 1H), 7.10-7.15 (m, 4H), 7.01 (dd, J=2.5, 1.9 Hz, 1H), 6.77 (d, J=7.3 Hz, 1H), 6.67 (dd, J=5.6, 2.3 Hz, 1H), 3.53 (t, J=4.7 Hz, 4H), 3.14-3.19 (m, 2H), 2.26-2.33 (m, 6H), 2.25 (s, 3H), 1.60 (quin, J=7.1 Hz, 2H)

LR MS (ES+): 555 (MH+)
LR MS (ES−): 553 (M−H)

Example 240

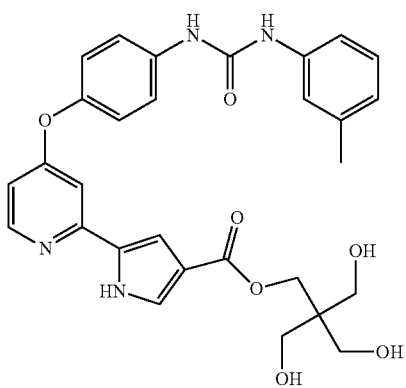 [SMILES: Cc1cccc(NC(=O)Nc2ccc(Oc3ccnc(-c4cc(C(=O)OCC(CO)(CO)CO)c[nH]4)c3)cc2)c1]

3-hydroxy-2,2-bis(hydroxymethyl)propyl 5-{4-[4-({[(3-methylphenyl)amino]carbonyl}amino)phenoxy]pyridin-2-yl}-1H-pyrrole-3-carboxylate To a stirred suspension of 5-{4-[4-({[(3-methylphenyl)amino]carbonyl}amino)phenoxy]pyridin-2-yl}-1H-pyrrole-3-carboxylic acid (150 mg, 0.35 mmol) and N-(3-dimethylaminopropyl)-N'-ethylcarbodiimide hydrochloride (EDC, 102 mg, 0.53 mmol) in 10 ml of anhydrous tetrahydrofuran were added pentaerythritol (143 mg, 1.05 mmol) and 4-dimethylaminopyridine (10 mg, 0.08 mmol). The mixture was heated at 60° C. for 16 hours, cooled to room temperature and evaporated to dryness. The residue was purified by C-18 reverse phase chromatography eluting with a gradient of 10~50% of acetonitrile in water to afford 3-hydroxy-2,2-bis(hydroxymethyl)propyl 5-{4-[4-({[(3-methylphenyl)amino]carbonyl}amino)phenoxy]pyridin-2-yl}-1H-pyrrole-3-carboxylate as white solid. Yield: 46 mg, 24%.

$^1$H NMR (DMSO-$d_6$): 12.08 (t, J=2.9 Hz, 1H), 8.73 (s, 1H), 8.57 (s, 1H), 8.36 (d, J=5.6 Hz, 1H), 7.50-7.56 (m, 2H), 7.40 (dd, J=3.2, 1.8 Hz, 1H), 7.38 (d, J=2.3 Hz, 1H), 7.27 (s, 1H), 7.21 (d, J=8.5 Hz, 1H), 7.13 (t, J=7.6 Hz, 1H), 7.11 (d, J=9.1 Hz, 2H), 7.07-7.09 (m, 1H), 6.77 (d, J=7.6 Hz, 1H), 6.62 (dd, J=5.9, 2.3 Hz, 1H), 4.34 (t, J=5.3 Hz, 3H), 4.03 (s, 2H), 3.42 (d, J=5.3 Hz, 6H), 2.25 (s, 3H)

LR MS (ES+): 547 (MH+)
LR MS (ES−): 545 (M−H)

The following Example 241 was prepared using the experiment procedure described in Example 238, but with the appropriate reagent, reaction conditions and reactant substitutions that will be readily realized by those of ordinary skill in this art without the exercise of undue experimentation.

Example 241

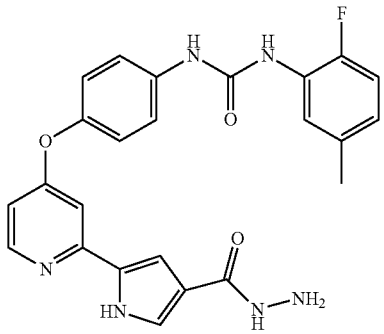 [SMILES: Cc1ccc(F)c(NC(=O)Nc2ccc(Oc3ccnc(-c4cc(C(=O)NN)c[nH]4)c3)cc2)c1]

1-(2-fluoro-5-methylphenyl)-3-[4-({2-[4-(hydrazinocarbonyl)-1H-pyrrol-2-yl]pyridin-4-yl}oxy)phenyl]urea $^1$H NMR (DMSO-$d_6$): 11.79 (t, J=3.1 Hz, 1H), 9.16 (s, 1H), 9.11 (t, J=4.0 Hz, 1H), 8.47 (d, J=2.6 Hz, 1H), 8.35 (d, J=5.9 Hz, 1H), 7.96 (dd, J=7.9, 2.3 Hz, 1H), 7.52-7.56 (m, 2H), 7.34 (dd, J=2.9, 1.8 Hz, 1H), 7.11-7.15 (m, 3H), 7.08 (dd, J=11.4, 8.2 Hz, 1H), 7.03 (dd, J=2.5, 1.9 Hz, 1H), 6.75-6.81 (m, 1H), 6.67 (dd, J=5.6, 2.3 Hz, 1H), 4.21 (d, J=3.8 Hz, 2H), 2.25 (s, 3H)

LR MS (ES+): 483 (M+Na+)
LR MS (ES−): 459 (M−H)

Example 242

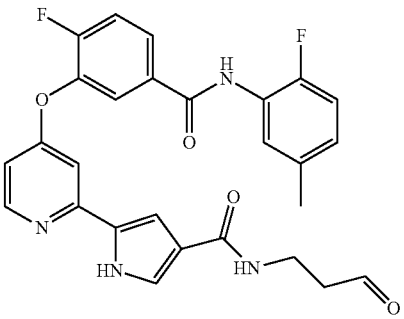 [SMILES: Cc1ccc(F)c(NC(=O)c2ccc(F)c(Oc3ccnc(-c4cc(C(=O)NCCC=O)c[nH]4)c3)c2)c1]

5-[4-(2-fluoro-5-{[(2-fluoro-5-methylphenyl)amino]carbonyl}phenoxy)pyridin-2-yl]-N-(3-oxopropyl)-1H-pyrrole-3-carboxamide To a stirred solution of N-(3,3-diethoxypropyl)-5-[4-(2-fluoro-5-{[(2-fluoro-5-methylphenyl)amino]carbonyl}phenoxy)pyridin-2-yl]-1H-pyrrole-3-carboxamide (250 mg, 0.43 mmol) in 10 ml of tetrahydrofuran was added 1 ml of 1M HCl (1.0 mmol). The mixture was stirred at room temperature for 60 minutes and poured into 100 ml of water. The precipitates were filtered, washed with water and dried in vacuo to give 5-[4-(2-fluoro-5-{[(2-fluoro-5-methylphenyl)amino]carbonyl}phenoxy)pyridin-2-yl]-N-(3-oxopropyl)-1H-pyrrole-3-carboxamide as white solid. Yield: 205 mg, 94%.

$^1$H NMR (DMSO-$d_6$): 11.83 (t, J=3.1 Hz, 1H), 10.12 (s, 1H), 9.65 (t, J=1.9 Hz, 1H), 8.41 (d, J=5.6 Hz, 1H), 7.97-8.01 (m, 2H), 7.95 (t, J=5.7 Hz, 1H), 7.61-7.66 (m, 1H), 7.32-7.37 (m, 2H), 7.25 (d, J=2.3 Hz, 1H), 7.14 (dd, J=10.6, 8.2 Hz, 1H), 7.09-7.10 (m, 1H), 7.02-7.06 (m, 1H), 6.80 (dd, J=5.7, 2.5 Hz, 1H), 3.40-3.48 (m, 2H), 2.59 (td, J=6.6, 2.1 Hz, 2H), 2.27 (s, 3H)

LR MS (ES−): 503 (M−H)

The following Example 248 was prepared using the experiment procedure described in Example 184, but with the appropriate reagent, reaction conditions and reactant substitutions that will be readily realized by those of ordinary skill in this art without the exercise of undue experimentation.

Example 243

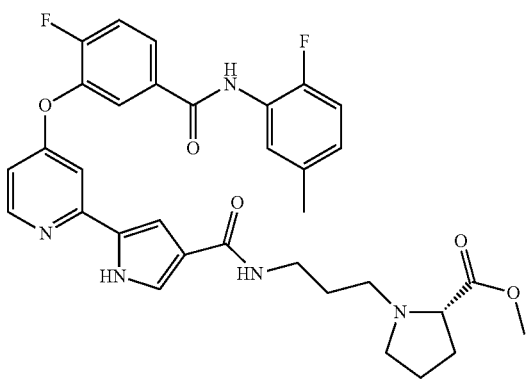 [SMILES: COC(=O)[C@@H]1CCCN1CCCNC(=O)c1c[nH]c(-c2cc(Oc3cc(C(=O)Nc4cc(C)ccc4F)ccc3F)ccn2)c1]

methyl (2S)-1-{3-[({5-[4-(2-fluoro-5-{[(2-fluoro-5-methylphenyl)amino]carbonyl}phenoxy)pyridin-2-yl]-1H-pyrrol-3-yl}carbonyl)amino]propyl}pyrrolidine-2-carboxylate $^1$H NMR (DMSO-$d_6$): 11.82 (br. s., 1H), 10.13 (s, 1H), 8.42 (d, J=5.9 Hz, 1H), 7.94-8.04 (m, 2H), 7.86 (t, J=5.7 Hz, 1H), 7.58-7.69 (m, 1H), 7.32-7.38 (m, 2H), 7.25 (d, J=2.3 Hz, 1H), 7.11-7.19 (m, 1H), 7.08-7.11 (m, 1H), 7.01-7.09 (m, 1H), 6.81 (dd, J=5.7, 2.5 Hz, 1H), 3.58 (s, 3H), 3.11-3.24 (m, 3H), 2.93-3.05 (m, 1H), 2.56-2.70 (m, 1H), 2.37-2.45 (m, 1H), 2.30-2.37 (m, 1H), 2.27 (s, 3H), 1.93-2.09 (m, 1H), 1.65-1.81 (m, 3H), 1.52-1.65 (m, 2H)

LR MS (ES+): 618 (MH+)

LR MS (ES−): 616 (M−H)

The following Example 249 was prepared using the experiment procedure described in Example 264, but with the appropriate reagent, reaction conditions and reactant substitutions that will be readily realized by those of ordinary skill in this art without the exercise of undue experimentation.

Example 244

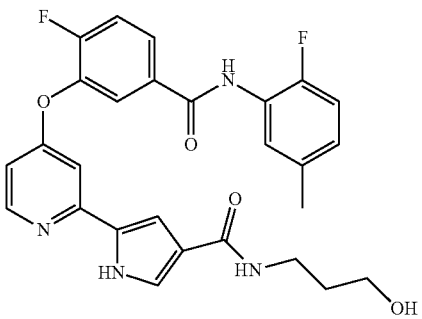 [SMILES: Cc1ccc(F)c(NC(=O)c2ccc(F)c(Oc3ccnc(-c4cc(C(=O)NCCCO)c[nH]4)c3)c2)c1]

5-[4-(2-fluoro-5-{[(2-fluoro-5-methylphenyl)amino]carbonyl}phenoxy)pyridin-2-yl]-N-(3-hydroxypropyl)-1H-pyrrole-3-carboxamide $^1$H NMR (DMSO-$d_6$): 11.82 (br. s., 1H), 10.13 (s, 1H), 8.42 (d, J=5.9 Hz, 1H), 7.95-8.04 (m, 2H), 7.83 (t, J=5.7 Hz, 1H), 7.59-7.70 (m, 1H), 7.32-7.40 (m, 2H), 7.26 (d, J=2.3 Hz, 1H), 7.12-7.13 (m, 1H), 7.11-7.19 (m, 1H), 7.01-7.09 (m, 1H), 6.81 (dd, J=5.6, 2.3 Hz, 1H), 4.43 (t, J=5.3 Hz, 1H), 3.41 (q, J=6.2 Hz, 2H), 3.15-3.26 (m, 2H), 2.27 (s, 3H), 1.60 (quin, J=6.7 Hz, 2H)

LR MS (ES+): 507 (MH+)

LR MS (ES−): 505 (M−H)

Example 245

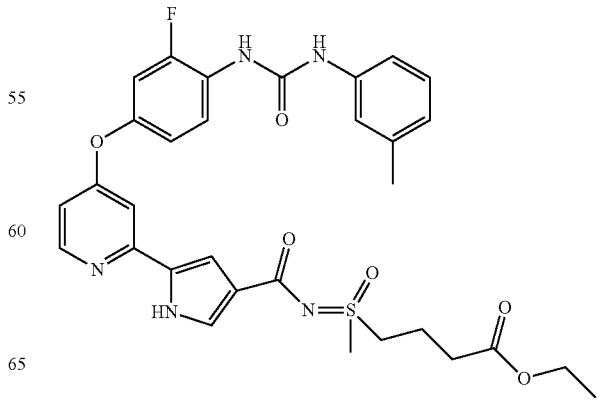

323 ethyl 4-{N-[(5-{4-[3-fluoro-4-({[(3-methylphenyl)amino]carbonyl}amino)phenoxy]pyridin-2-yl}-1H-pyrrol-3-yl)carbonyl]-S-methylsulfonimidoyl}butanoate Example 246

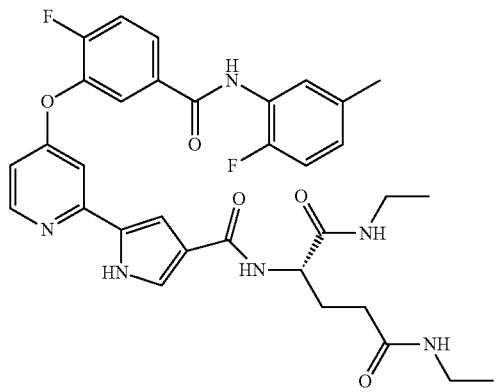 [SMILES: CCNC(=O)CC[C@H](NC(=O)c1c[nH]c(-c2cc(Oc3cc(C(=O)Nc4cc(C)ccc4F)ccc3F)ccn2)c1)C(=O)NCC]

N,N'-diethyl-2-[({5-[4-(2-fluoro-5-{[(2-fluoro-5-methylphenyl)amino]carbonyl}phenoxy)pyridin-2-yl]-1H-pyrrol-3-yl}carbonyl)amino]pentanediamide To a stirred solution of 2-[({5-[4-(2-fluoro-5-{[(2-fluoro-5-methylphenyl)amino]carbonyl}phenoxy)pyridin-2-yl]-1H-pyrrol-3-yl}carbonyl)amino]pentanedioic acid (100 mg, 0.17 mmol) and N-(3-dimethylaminopropyl)-N'-ethylcarbodiimide hydrochloride (EDC, 83 mg, 0.43 mmol) in 10 ml of anhydrous DMF was added 2M ethylamine solution in THF (0.43 ml, 0.86 mmol). The mixture was stirred at room temperature for overnight and poured into 100 ml of water. The precipitates were filtered, washed with water and dried in vacuo to give the crude, which was purified by silica gel chromatography eluting with 5-8% of methanol in chloroform to afford N,N'-diethyl-2-[({5-[4-(2-fluoro-5-{[(2-fluoro-5-methylphenyl)amino]carbonyl}phenoxy)pyridin-2-yl]-1H-pyrrol-3-yl}carbonyl)amino]pentanediamide as white solid. Yield: 76 mg, 69%.

$^1$H NMR (DMSO-d$_6$): 11.86 (t, J=3.1 Hz, 1H), 10.12 (s, 1H), 8.42 (d, J=5.6 Hz, 1H), 7.96-8.01 (m, 2H), 7.79-7.83 (m, 2H), 7.75 (t, J=5.6 Hz, 1H), 7.63 (dd, J=10.4, 9.0 Hz, 1H), 7.46 (dd, J=3.2, 1.8 Hz, 1H), 7.34 (dd, J=7.2, 2.2 Hz, 1H), 7.28 (d, J=2.3 Hz, 1H), 7.19 (dd, J=2.5, 1.9 Hz, 1H), 7.14 (dd, J=10.6, 8.5 Hz, 1H), 7.02-7.07 (m, 1H), 6.80 (dd, J=5.7, 2.5 Hz, 1H), 4.20-4.32 (m, 1H), 3.02-3.08 (m, 2H), 2.97-3.03 (m, 2H), 2.26 (s, 3H), 2.00-2.15 (m, 2H), 1.86-1.97 (m, 1H), 1.73-1.85 (m, 1H), 0.98 (t, J=7.2 Hz, 3H), 0.94 (t, J=7.2 Hz, 3H)

LR MS (ES+): 633 (MH+)
LR MS (ES−): 631 (M−H)

324

Example 247

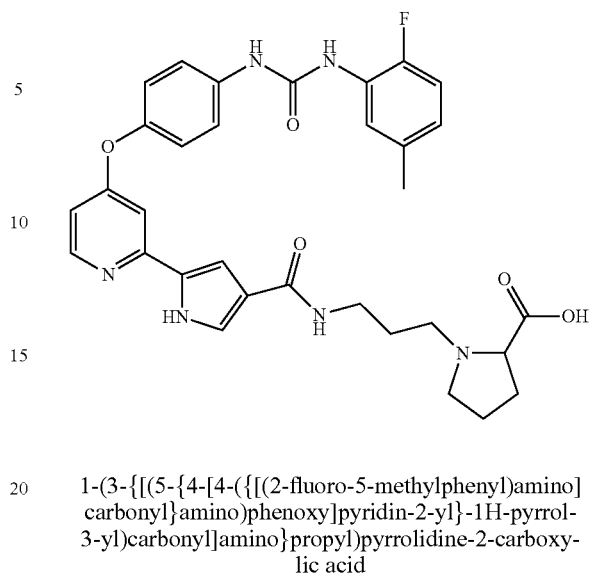

1-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)pyrrolidine-2-carboxylic acid To a stirred solution of methyl 1-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)pyrrolidine-2-carboxylate (Example 50) (68 mg, 0.11 mmol) in a mixture of THF/MeOH (5 ml/5 ml) was added 1M NaOH solution (1 ml, 1 mmol). The mixture was stirred at room temperature for 16 hours and poured into 30 ml of water. 1M HCl was added dropwise with vigorous stirring until pH=7. The precipitates were filtered, washed with water and dried in vacuo to give 1-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)pyrrolidine-2-carboxylic acid as light reddish solid. Yield: 60 mg, 91%.

LR MS (ES+): 601 (MH+)
LR MS (ES−): 599 (M−H)

Example 248

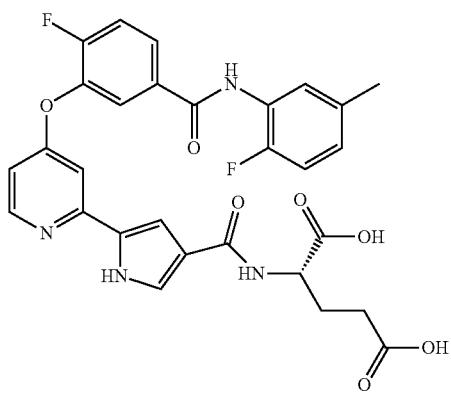 [SMILES: Cc1ccc(F)c(NC(=O)c2ccc(F)c(Oc3ccnc(-c4cc(C(=O)N[C@@H](CCC(=O)O)C(=O)O)c[nH]4)c3)c2)c1]

2-[({5-[4-(2-fluoro-5-{[(2-fluoro-5-methylphenyl)amino]carbonyl}phenoxy)pyridin-2-yl]-1H-pyrrol-3-yl}carbonyl)amino]pentanedioic acid To a stirred solution of dimethyl 2-[({5-[4-(2-fluoro-5-{[(2-fluoro-5-methylphenyl)amino]carbonyl}phenoxy)pyridin-2-yl]-1H-pyrrol-3-yl}carbonyl)amino]pentanedioate (320 mg, 0.53 mmol) in MeOH (20 ml) was added 1M NaOH solution (2 ml, 2 mmol). The mixture was stirred at room temperature for 16 hours and poured into 100 ml of water. 1M HCl was added dropwise until pH=4. The precipitates were filtered, washed with water and dried in vacuo to give 2-[({5-[4-(2-fluoro-5-{[(2-fluoro-5-methylphenyl)amino]carbonyl}phenoxy)pyridin-2-yl]-1H-pyrrol-3-yl}carbonyl)amino]pentanedioic acid as white solid. Yield: 305 mg, 100%.

$^1$H NMR (DMSO-d$_6$): 12.47 (br. s., 1H), 12.09 (br. s., 1H), 11.88 (t, J=2.9 Hz, 1H), 10.12 (s, 1H), 8.42 (d, J=5.9 Hz, 1H), 7.94-8.02 (m, 3H), 7.63 (dd, J=10.4, 8.4 Hz, 1H), 7.46 (dd, J=3.2, 1.8 Hz, 1H), 7.35 (dd, J=7.3, 2.6 Hz, 1H), 7.29 (d, J=2.6 Hz, 1H), 7.18-7.21 (m, 1H), 7.14 (dd, J=10.6, 8.5 Hz, 1H), 7.02-7.07 (m, 1H), 6.80 (dd, J=5.7, 2.5 Hz, 1H), 4.32 (ddd, J=9.8, 7.7, 4.8 Hz, 1H), 2.30 (t, J=7.6 Hz, 2H), 2.27 (s, 3H), 1.97-2.07 (m, 1H), 1.80-1.91 (m, 1H)

LR MS (ES+): 579 (MH+)

LR MS (ES−): 577 (M−H)

The following Example 249 was prepared using the experiment procedure described in Example 259, but with the appropriate reagent, reaction conditions and reactant substitutions that will be readily realized by those of ordinary skill in this art without the exercise of undue experimentation.

Example 249

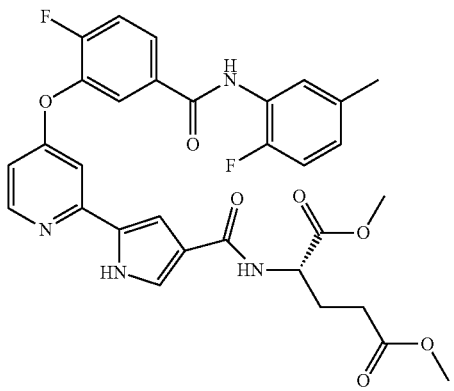 [SMILES: COC(=O)CC[C@H](NC(=O)c1c[nH]c(-c2cc(Oc3cc(C(=O)Nc4cc(C)ccc4F)ccc3F)ccn2)c1)C(=O)OC]

dimethyl 2-[({5-[4-(2-fluoro-5-{[(2-fluoro-5-methylphenyl)amino]carbonyl}phenoxy)pyridin-2-yl]-1H-pyrrol-3-yl}carbonyl)amino]pentanedioate $^1$H NMR (DMSO-d$_6$): 11.94 (br. s., 1H), 10.13 (s, 1H), 8.44 (d, J=5.9 Hz, 1H), 8.13 (d, J=7.3 Hz, 1H), 7.95-8.05 (m, 2H), 7.60-7.69 (m, 1H), 7.49 (dd, J=3.1, 1.6 Hz, 1H), 7.35 (dd, J=7.5, 2.5 Hz, 1H), 7.31 (d, J=2.3 Hz, 1H), 7.21 (t, J=2.2 Hz, 1H), 7.10-7.19 (m, 1H), 7.01-7.09 (m, 1H), 6.84 (dd, J=5.9, 2.3 Hz, 1H), 4.30-4.46 (m, 1H), 3.61 (s, 3H), 3.56 (s, 3H), 2.41 (t, J=7.5 Hz, 2H), 2.27 (s, 3H), 1.99-2.13 (m, 1H), 1.84-1.99 (m, 1H)

LR MS (ES+): 607 (MH+)

LR MS (ES−): 605 (M−H)

Example 250

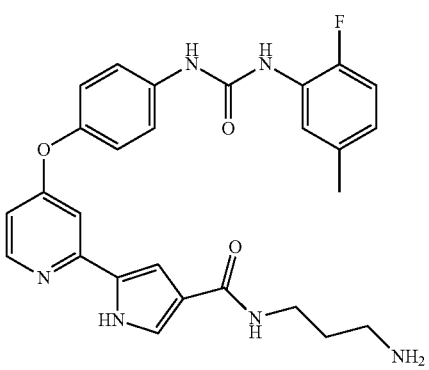 [SMILES: Cc1ccc(F)c(NC(=O)Nc2ccc(Oc3ccnc(-c4cc(C(=O)NCCCN)c[nH]4)c3)cc2)c1]

N-(3-aminopropyl)-5-{4-[4-({[(2-fluoro-5-methylphenyl)amino]carbonyl}amino)phenoxy]pyridin-2-yl}-1H-pyrrole-3-carboxamide To a stirred suspension of tert-butyl (3-{[(5-{4-[4-({[(2-fluoro-5-methylphenyl)amino]carbonyl}amino)phenoxy]pyridin-2-yl}-1H-pyrrol-3-yl)carbonyl]amino}propyl)carbamate (70 mg, 0.12 mmol) in 10 ml of methylene chloride was added 1 ml of trifluoroacetic acid. The mixture was stirred at room temperature for 2 hours and evaporated to dryness under reduced pressure. The residue was re-dissolved in MeOH (5 ml) and poured into 100 ml of water with vigorous stirring. Saturated NaHCO$_3$ solution was added until pH=8-9. The precipitates were filtered, washed with water and dried in vacuo to give N-(3-aminopropyl)-5-{4-[4-({[(2-fluoro-5-methylphenyl)amino]carbonyl}amino)phenoxy]pyridin-2-yl}-1H-pyrrole-3-carboxamide as yellow solid. Yield: 40 mg, 63%.

LR MS (ES+): 503 (MH+)
LR MS (ES−): 501 (M−H)

Example 251

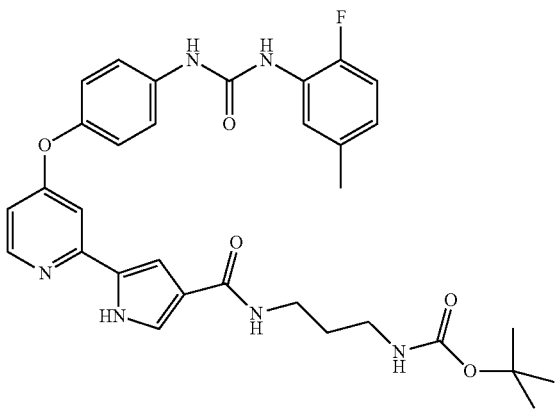 [SMILES: Cc1ccc(F)c(NC(=O)Nc2ccc(Oc3ccnc(-c4cc(C(=O)NCCCNC(=O)OC(C)(C)C)c[nH]4)c3)cc2)c1]

tert-butyl (3-{[(5-{4-[4-({[(2-fluoro-5-methylphenyl)amino]carbonyl}amino)phenoxy]pyridin-2-yl}-1H-pyrrol-3-yl)carbonyl]amino}propyl)carbamate To a stirred solution of 5-{4-[4-({[(2-fluoro-5-methylphenyl)amino]carbonyl}amino)phenoxy]pyridin-2-yl}-1H-pyrrole-3-carboxylic acid (100 mg, 0.22 mmol) in 10 ml of anhydrous DMF were added HATU (100 mg, 0.26 mmol) and N,N-diisopropylethylamine (85 mg, 0.66 mmol). The mixture was stirred at room temperature for 10 minutes, followed by addition of N-Boc-1,3-propanediamine (57 mg, 0.33 mmol). The mixture was stirred for another 5 minutes and poured into 100 ml of water with vigorous stirring. 2M HCl was added dropwise until pH=5. The precipitates were filtered, washed with water and dried in vacuo to give tert-butyl (3-{[(5-{4-[4-({[(2-fluoro-5-methylphenyl)amino]carbonyl}amino)phenoxy]pyridin-2-yl}-1H-pyrrol-3-yl)carbonyl]amino}propyl)carbamate as white solid. Yield: 120 mg, 89%.

$^1$H NMR (DMSO-$d_6$): 11.79 (br. s., 1H), 9.16 (s, 1H), 8.47 (d, J=2.6 Hz, 1H), 8.35 (d, J=5.6 Hz, 1H), 7.96 (dd, J=7.5, 2.2 Hz, 1H), 7.81 (t, J=5.9 Hz, 1H), 7.51-7.56 (m, 2H), 7.32 (dd, J=3.2, 1.8 Hz, 1H), 7.12-7.15 (m, 2H), 7.11-7.13 (m, 1H), 7.08 (dd, J=11.4, 8.2 Hz, 1H), 7.01-7.02 (m, 1H), 6.76-6.80 (m, 1H), 6.75 (t, J=6.3 Hz, 1H), 6.69 (dd, J=5.9, 2.3 Hz, 1H), 3.14 (q, J=6.7 Hz, 2H), 2.91 (q, J=6.7 Hz, 2H), 2.25 (s, 3H), 1.53 (quin, J=7.0 Hz, 2H), 1.33 (s, 9H)

LR MS (ES+): 625 (M+Na+)
LR MS (ES−): 601 (M−H)

Example 252

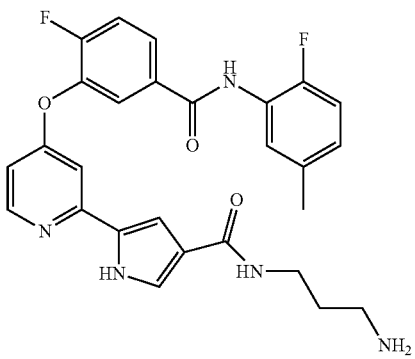 [SMILES: Cc1ccc(F)c(NC(=O)c2ccc(F)c(Oc3ccnc(-c4cc(C(=O)NCCCN)c[nH]4)c3)c2)c1]

N-(3-aminopropyl)-5-[4-(2-fluoro-5-{[(2-fluoro-5-methylphenyl)amino]carbonyl}phenoxy)pyridin-2-yl]-1H-pyrrole-3-carboxamide To a stirred suspension of tert-butyl {3-[({5-[4-(2-fluoro-5-{[(2-fluoro-5-methylphenyl)amino]carbonyl}phenoxy)pyridin-2-yl]-1H-pyrrol-3-yl}carbonyl)amino]propyl}carbamate (100 mg, 0.165 mmol) in 10 ml of methylene chloride was added 1 ml of trifluoroacetic acid. The mixture was stirred at room temperature for 60 minutes and evaporated to dryness under reduced pressure. The residue was re-dissolved in MeOH (5 ml) and poured into 100 ml of water with vigorous stirring. Saturated NaHCO$_3$ solution was added until pH=8-9. The precipitates were filtered, washed with water and dried in vacuo to give N-(3-aminopropyl)-5-[4-(2-fluoro-5-{[(2-fluoro-5-methylphenyl)amino]carbonyl}phenoxy)pyridin-2-yl]-1H-pyrrole-3-carboxamide as grey solid.

Yield: 70 mg, 84%.
LR MS (ES+): 506 (MH+)
LR MS (ES−): 504 (M−H)

The following Example 253 was prepared using the experiment procedure described in Example 254, but with the appropriate reagent, reaction conditions and reactant substitutions that will be readily realized by those of ordinary skill in this art without the exercise of undue experimentation.

Example 253

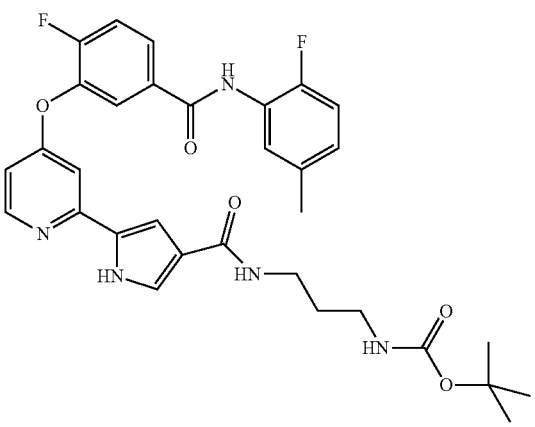 [SMILES: Cc1ccc(F)c(NC(=O)c2ccc(F)c(Oc3ccnc(-c4cc(C(=O)NCCCNC(=O)OC(C)(C)C)c[nH]4)c3)c2)c1]

tert-butyl {3-[({5-[4-(2-fluoro-5-{[(2-fluoro-5-methylphenyl)amino]carbonyl}phenoxy)pyridin-2-yl]-1H-pyrrol-3-yl}carbonyl)amino]propyl}carbamate $^1$H NMR (DMSO-$d_6$): 11.82 (t, J=2.9 Hz, 1H), 10.12 (s, 1H), 8.41 (d, J=5.9 Hz, 1H), 7.96-8.01 (m, 2H), 7.81 (t, J=5.9 Hz, 1H), 7.60-7.66 (m, 1H), 7.36 (dd, J=3.2, 1.8 Hz, 1H), 7.34 (dd, J=7.2, 2.2 Hz, 1H), 7.25 (d, J=2.6 Hz, 1H), 7.14 (dd, J=10.6, 8.5 Hz, 1H), 7.11 (dd, J=2.6, 1.8 Hz, 1H), 7.02-7.07 (m, 1H), 6.80 (dd, J=5.7, 2.5 Hz, 1H), 6.75 (t, J=6.0 Hz, 1H), 3.12-3.18 (m, 2H), 2.87-2.96 (m, 2H), 2.26 (s, 3H), 1.54 (quin, J=7.0 Hz, 2H), 1.34 (s, 9H)

LR MS (ES+): 606 (MH+)
LR MS (ES−): 604 (M−H)

Example 254

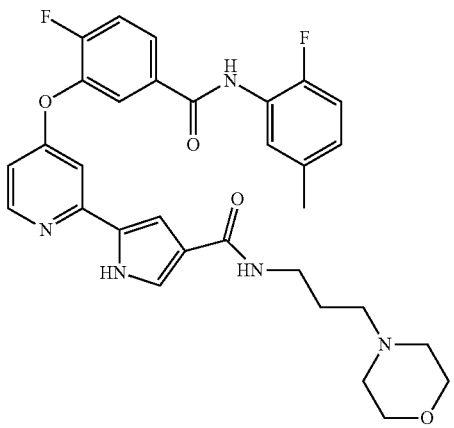 [SMILES: Cc1ccc(F)c(NC(=O)c2ccc(F)c(Oc3ccnc(-c4cc(C(=O)NCCCN5CCOCC5)c[nH]4)c3)c2)c1]

5-[4-(2-fluoro-5-{[(2-fluoro-5-methylphenyl)amino]carbonyl}phenoxy)pyridin-2-yl]-N-(3-morpholin-4-ylpropyl)-1H-pyrrole-3-carboxamide To a stirred solution of 5-[4-(2-fluoro-5-{[(2-fluoro-5-methylphenyl)amino]carbonyl}phenoxy)pyridin-2-yl]-1H-pyrrole-3-carboxylic acid (100 mg, 0.22 mmol) in 10 ml of anhydrous DMF were added HATU (100 mg, 0.26 mmol) and N,N-diisopropylethylamine (85 mg, 0.66 mmol). The mixture was stirred at room temperature for 10 minutes, followed by addition of N-(3-aminopropyl)morpholine (48 mg, 0.33 mmol). The mixture was stirred for another 5 minutes and poured into 100 ml of water. The precipitates were filtered, washed with water and dried in vacuo to give 5-[4-(2-fluoro-5-{[(2-fluoro-5-methylphenyl)amino]carbonyl}phenoxy)pyridin-2-yl]-N-(3-morpholin-4-ylpropyl)-1H-pyrrole-3-carboxamide as white solid. Yield: 122 mg, 95%.

$^1$H NMR (DMSO-$d_6$): 11.81 (br. s., 1H), 10.12 (s, 1H), 8.41 (d, J=5.6 Hz, 1H), 7.96-8.01 (m, 2H), 7.84 (br. s., 1H), 7.61-7.65 (m, 1H), 7.36 (dd, 1H), 7.34 (dd, J=7.3, 2.3 Hz, 1H), 7.25 (d, J=2.3 Hz, 1H), 7.14 (dd, J=10.4, 8.4 Hz, 1H), 7.11 (dd, J=2.3, 1.8 Hz, 1H), 7.02-7.07 (m, 1H), 6.80 (dd, J=5.7, 2.5 Hz, 1H), 3.54 (br. s., 4H), 3.18 (q, J=6.6 Hz, 2H), 2.31 (br. s., 6H), 2.27 (s, 3H), 1.61 (br. s., 2H)

LR MS (ES+): 576 (MH+)
LR MS (ES−): 574 (M−H)

Example 255

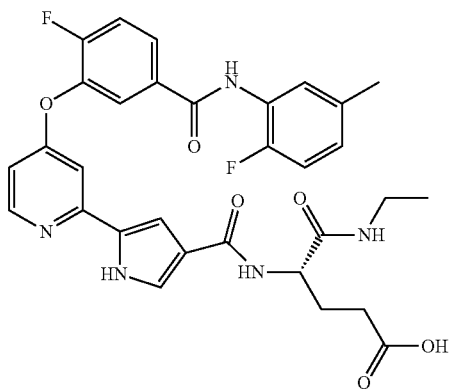 [SMILES: CCNC(=O)[C@H](CCC(=O)O)NC(=O)c1c[nH]c(-c2cc(Oc3cc(C(=O)Nc4cc(C)ccc4F)ccc3F)ccn2)c1]

5-(ethylamino)-4-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoic acid To a stirred solution of tert-butyl 5-(ethylamino)-4-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoate (75 mg, 0.11 mmol) in 5 ml of methylene chloride was added 1 ml of TFA. The mixture was stirred at room temperature for 90 minutes, and evaporated to dryness under reduced pressure. The residue was re-dissolved in 5 ml of methanol and poured into 100 ml of water with vigorous stirring. The precipitates were filtered, washed with water and dried in vacuo to give 5-(ethylamino)-4-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoic acid as white solid. Yield: 60 mg, 87%.

$^1$H NMR (DMSO-$d_6$): 12.05 (br. s., 1H), 11.90 (br. s., 1H), 10.13 (s, 1H), 8.43 (d, J=5.9 Hz, 1H), 7.97-8.02 (m, 2H), 7.83 (t, J=5.6 Hz, 1H), 7.79 (d, J=8.2 Hz, 1H), 7.64 (dd, J=9.7, 8.8 Hz, 1H), 7.50 (br. s., 1H), 7.34 (dd, J=7.5, 1.9 Hz, 1H), 7.31 (d, J=2.1 Hz, 1H), 7.23 (br. s., 1H), 7.14 (dd, J=10.3, 8.5 Hz, 1H), 7.02-7.07 (m, 1H), 6.83 (d, J=5.3 Hz, 1H), 4.32 (td, J=8.7, 5.3 Hz, 1H), 3.00-3.09 (m, 2H), 2.27 (s, 3H), 2.18-2.25 (m, 2H), 1.88-1.99 (m, 1H), 1.74-1.86 (m, 1H), 0.97 (t, J=7.2 Hz, 3H)

LR MS (ES+): 606 (MH+)
LR MS (ES−): 604 (M−H)

Example 256

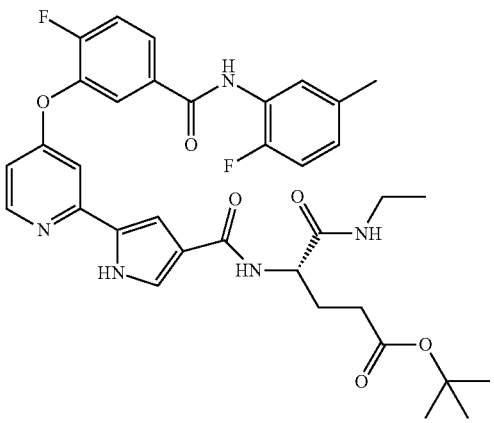 [SMILES: CCNC(=O)[C@H](CCC(=O)OC(C)(C)C)NC(=O)c1c[nH]c(-c2cc(Oc3cc(C(=O)Nc4cc(C)ccc4F)ccc3F)ccn2)c1]

tert-butyl 5-(ethylamino)-4-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoate To a stirred suspension of 5-tert-butoxy-2-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoic acid (150 mg, 0.24 mmol) in 10 ml of anhydrous tetrahydrofuran were added HATU (109 mg, 0.29 mmol) and N,N-diisopropylethylamine (93 mg, 0.72 mmol). The mixture was heated at 60° C. for 15 minutes and cooled to room temperature, followed by addition of 2M ethylamine solution in THF (0.18 ml, 0.36 mmol). The mixture was stirred for another 5 minutes and poured into 100 ml of water with vigorous stirring. 1M HCl was added dropwise until pH=4. The precipitates were filtered, washed with water and dried in vacuo to give the crude, which was purified by silica gel chromatography eluting with 3~5% methanol in chloroform to give tert-butyl 5-(ethylamino)-4-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoate as white solid. Yield: 100 mg, 64%.

$^1$H NMR (DMSO-$d_6$): 11.86 (br. s., 1H), 10.12 (s, 1H), 8.42 (d, J=5.6 Hz, 1H), 7.96-8.01 (m, 2H), 7.82 (t, J=5.7 Hz, 1H), 7.77 (d, J=8.2 Hz, 1H), 7.63 (dd, J=10.1, 8.7 Hz, 1H), 7.48 (dd, J=2.9, 1.8 Hz, 1H), 7.34 (dd, J=7.3, 1.8 Hz, 1H), 7.29 (d, J=2.3 Hz, 1H), 7.19-7.22 (m, 1H), 7.14 (dd, J=10.4, 8.4 Hz, 1H), 7.02-7.06 (m, 1H), 6.80 (dd, J=5.6, 2.3 Hz, 1H), 4.31 (td, J=8.7, 5.3 Hz, 1H), 2.99-3.10 (m, 2H), 2.26 (s, 3H), 2.17-2.24 (m, 2H), 1.86-1.96 (m, 1H), 1.72-1.83 (m, 1H), 1.35 (s, 9H), 0.97 (t, J=7.2 Hz, 3H)

LR MS (ES+): 662 (MH+)
LR MS (ES−): 660 (M−H)

Example 257

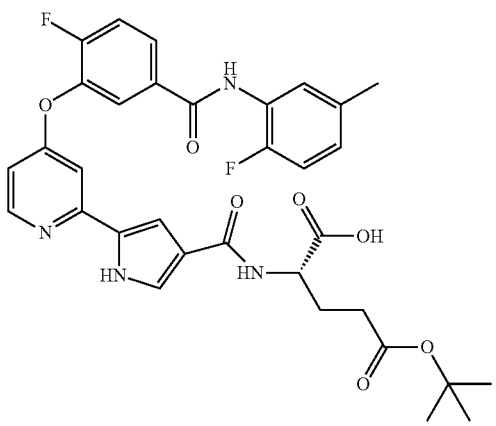 [SMILES: Cc1ccc(F)c(NC(=O)c2ccc(F)c(Oc3ccnc(-c4cc(C(=O)N[C@@H](CCC(=O)OC(C)(C)C)C(=O)O)c[nH]4)c3)c2)c1]

5-tert-butoxy-2-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoic acid To a stirred solution of 5-[4-(2-fluoro-5-{[(2-fluoro-5-methylphenyl)amino]carbonyl}phenoxy)pyridin-2-yl]-1H-pyrrole-3-carboxylic acid (150 mg, 0.33 mmol) in 10 ml of anhydrous DMF were added HATU (150 mg, 0.39 mmol) and N,N-diisopropylethylamine (128 mg, 0.99 mmol). The mixture was stirred at room temperature for 10 minutes, followed by addition of L-Glutamic acid 5-tert-butyl ester (102 mg, 0.50 mmol). The mixture was heated at 60° C. for 30 minutes, cooled to room temperature, and poured into 100 ml of water. 2M HCl was added dropwise with vigorous stirring until pH=4. The precipitates were filtered, washed with water and dried in vacuo to give 5-tert-butoxy-2-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoic acid as white solid. Yield: 185 mg, 87%.

$^1$H NMR (DMSO-d$_6$): 12.49 (br. s., 1H), 11.88 (br. s., 1H), 10.12 (s, 1H), 8.42 (d, J=5.9 Hz, 1H), 7.96-8.02 (m, 2H), 7.95 (d, J=7.9 Hz, 1H), 7.63 (dd, J=10.1, 8.7 Hz, 1H), 7.46 (dd, J=3.1, 1.6 Hz, 1H), 7.34 (dd, J=7.3, 1.8 Hz, 1H), 7.29 (d, J=2.6 Hz, 1H), 7.19 (dd, J=2.6, 1.8 Hz, 1H), 7.14 (dd, J=10.4, 8.4 Hz, 1H), 7.02-7.06 (m, 1H), 6.80 (dd, J=5.6, 2.3 Hz, 1H), 4.32 (ddd, 1H), 2.28 (t, J=7.9 Hz, 2H), 2.26 (s, 3H), 1.94-2.04 (m, 1H), 1.80-1.89 (m, 1H), 1.36 (s, 9H)

LR MS (ES-): 633 (M-H)

Example 258

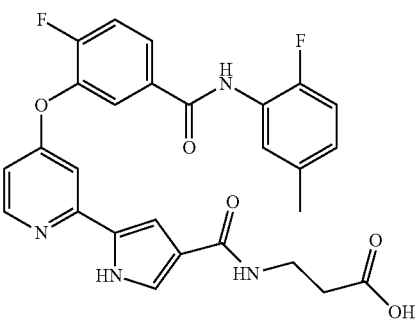 [SMILES: Cc1ccc(F)c(NC(=O)c2ccc(F)c(Oc3ccnc(-c4cc(C(=O)NCCC(=O)O)c[nH]4)c3)c2)c1]

3-[({5-[4-(2-fluoro-5-{[(2-fluoro-5-methylphenyl)amino]carbonyl}phenoxy)pyridin-2-yl]-1H-pyrrol-3-yl}carbonyl)amino]propanoic acid To a stirred solution of methyl 3-[({5-[4-(2-fluoro-5-{[(2-fluoro-5-methylphenyl)amino]carbonyl}phenoxy)pyridin-2-yl]-1H-pyrrol-3-yl}carbonyl)amino]propanoate (82 mg, 0.15 mmol) in a mixture of THF/MeOH (10 ml/10 ml) was added 1M NaOH solution (1 ml, 1 mmol). The mixture was stirred at room temperature for 2 hours and poured into 100 ml of water. 1M HCl was added dropwise until pH=4. The precipitates were filtered, washed with water and dried in vacuo to give 3-[({5-[4-(2-fluoro-5-{[(2-fluoro-5-methylphenyl)amino]carbonyl}phenoxy)pyridin-2-yl]-1H-pyrrol-3-yl}carbonyl)amino]propanoic acid as white solid. Yield: 70 mg, 88%.

$^1$H NMR (DMSO-d$_6$): 12.15 (br. s., 1H), 11.85 (br. s., 1H), 10.13 (s, 1H), 8.42 (d, J=5.6 Hz, 1H), 8.00 (d, J=5.9 Hz, 1H), 7.97-7.99 (m, 1H), 7.91 (t, J=5.6 Hz, 1H), 7.61-7.66 (m, 1H), 7.38 (br. s., 1H), 7.35 (dd, J=7.6, 2.1 Hz, 1H), 7.26 (d, J=2.3 Hz, 1H), 7.11-7.16 (m, 2H), 7.02-7.07 (m, 1H), 6.82 (dd, J=5.6, 2.1 Hz, 1H), 3.32-3.38 (m, 2H), 2.43 (t, J=7.0 Hz, 2H), 2.27 (s, 3H)

LR MS (ES-): 519 (M-H)

Example 259

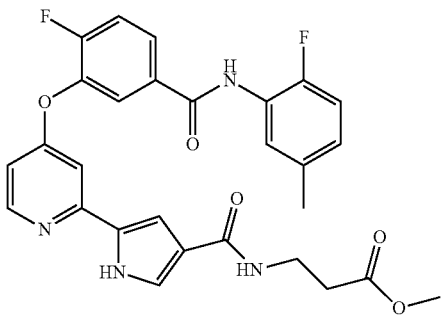

methyl 3-[({5-[4-(2-fluoro-5-{[(2-fluoro-5-methylphenyl)amino]carbonyl}phenoxy)pyridin-2-yl]-1H-pyrrol-3-yl}carbonyl)amino]propanoate To a stirred solution of 5-[4-(2-fluoro-5-{[(2-fluoro-5-methylphenyl)amino]carbonyl}phenoxy)pyridin-2-yl]-1H-pyrrole-3-carboxylic acid (100 mg, 0.22 mmol) in 10 ml of anhydrous DMF were added HATU (100 mg, 0.26 mmol) and N,N-diisopropylethylamine (85 mg, 0.66 mmol). The mixture was stirred at room temperature for 10 minutes, followed by addition of β-alanine methyl ester hydrochloride (46 mg, 0.33 mmol). The mixture was stirred for another 5 minutes and poured into 100 ml of water. 2M HCl was added dropwise with vigorous stirring until pH=4. The precipitates were filtered, washed with water and dried in vacuo to give methyl 3-[({5-[4-(2-fluoro-5-{[(2-fluoro-5-methylphenyl)amino]carbonyl}phenoxy)pyridin-2-yl]-1H-pyrrol-3-yl}carbonyl)amino]propanoate as white solid. Yield: 110 mg, 92%.

$^1$H NMR (DMSO-d$_6$): 11.83 (br. s., 1H), 10.12 (s, 1H), 8.41 (d, J=5.6 Hz, 1H), 7.96-8.02 (m, 2H), 7.94 (t, J=5.7 Hz, 1H), 7.63 (dd, J=10.1, 9.0 Hz, 1H), 7.37 (dd, J=2.9, 1.8 Hz, 1H), 7.34 (dd, J=7.5, 1.9 Hz, 1H), 7.26 (d, J=2.3 Hz, 1H), 7.14 (dd, J=10.4, 8.4 Hz, 1H), 7.10 (dd, J=2.3, 1.8 Hz, 1H), 7.02-7.07 (m, 1H), 6.80 (dd, J=5.7, 2.5 Hz, 1H), 3.57 (s, 3H), 3.36-3.41 (m, 2H), 2.52 (t, J=6.9 Hz, 2H), 2.27 (s, 3H)

LR MS (ES+): 557 (M+Na+)

LR MS (ES-): 533 (M-H)

Example 260

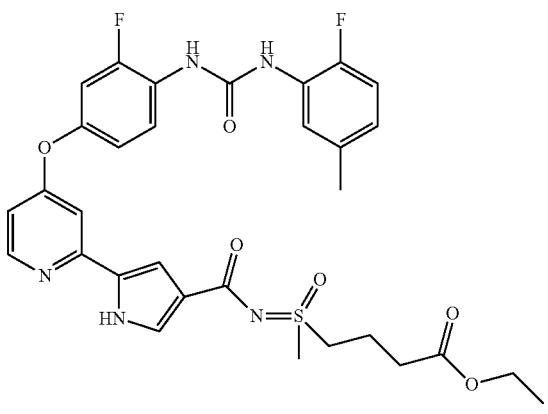 [SMILES: CCOC(=O)CCCS(C)(=O)=NC(=O)c1c[nH]c(-c2cc(Oc3ccc(NC(=O)Nc4cc(C)ccc4F)c(F)c3)ccn2)c1]

ethyl 4-{N-[(5-{4-[3-fluoro-4-({[(2-fluoro-5-methylphenyl)amino]carbonyl}amino)phenoxy]pyridin-2-yl}-1H-pyrrol-3-yl)carbonyl]-S-methylsulfonimidoyl}butanoate

Example 261

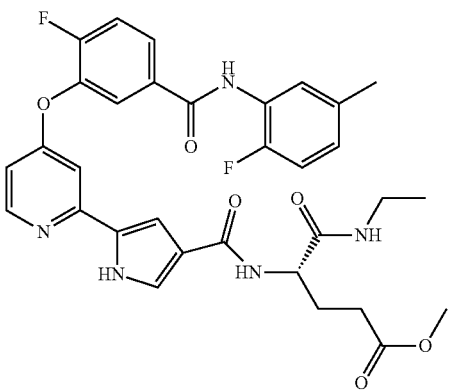 [SMILES: CCNC(=O)[C@H](CCC(=O)OC)NC(=O)c1c[nH]c(-c2cc(Oc3cc(C(=O)Nc4cc(C)ccc4F)ccc3F)ccn2)c1]

methyl 5-(ethylamino)-4-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoate To a stirred suspension of 2-[({5-[4-(2-fluoro-5-{[(2-fluoro-5-methylphenyl)amino]carbonyl}phenoxy)pyridin-2-yl]-1H-pyrrol-3-yl}carbonyl)amino]-5-methoxy-5-oxopentanoic acid (260 mg, 0.44 mmol) in 20 ml of anhydrous tetrahydrofuran were added HATU (200 mg, 0.53 mmol) and N,N-diisopropylethylamine (170 mg, 1.32 mmol). The mixture was heated at 60° C. for 15 minutes and cooled to room temperature, followed by addition of 2-Methylamine solution in THF (0.44 ml, 0.88 mmol). The mixture was stirred for another 5 minutes, and poured into 100 ml of water with vigorous stirring. 1M HCl was added dropwise until pH=4. The precipitates were filtered, washed with water and dried in vacuo to give the crude, which was purified by silica gel chromatography eluting with 2~5% methanol in chloroform to give methyl 5-(ethylamino)-4-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoate as white solid. Yield: 127 mg, 47%.

$^1$H NMR (DMSO-$d_6$): 11.87 (br. s., 1H), 10.12 (s, 1H), 8.42 (d, J=5.6 Hz, 1H), 7.95-8.01 (m, 2H), 7.85 (t, J=5.6 Hz, 1H), 7.79 (d, J=8.2 Hz, 1H), 7.63 (dd, J=10.1, 8.7 Hz, 1H), 7.48 (dd, J=3.1, 1.6 Hz, 1H), 7.34 (dd, J=7.5, 1.9 Hz, 1H), 7.29 (d, J=2.6 Hz, 1H), 7.20 (dd, J=2.5, 1.6 Hz, 1H), 7.14 (dd, J=10.4, 8.4 Hz, 1H), 7.02-7.07 (m, 1H), 6.80 (dd, J=5.9, 2.3 Hz, 1H), 4.32 (td, J=8.7, 5.6 Hz, 1H), 3.54 (s, 3H), 2.97-3.10 (m, 2H), 2.29-2.33 (m, 2H), 2.26 (s, 3H), 1.91-2.01 (m, 1H), 1.78-1.89 (m, 1H), 0.97 (t, J=7.2 Hz, 3H)

LR MS (ES+): 642 (M+Na+)

LR MS (ES−): 618 (M−H)

Example 262

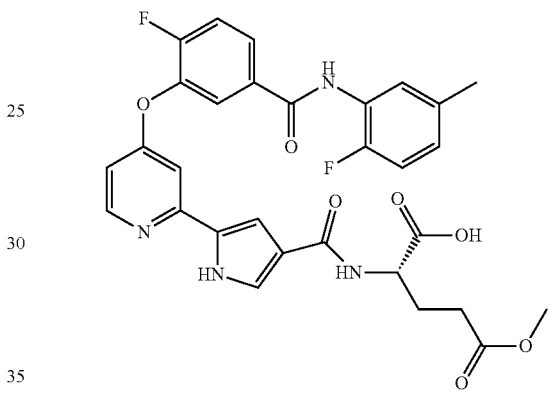

2-[({5-[4-(2-fluoro-5-{[(2-fluoro-5-methylphenyl)amino]carbonyl}phenoxy)pyridin-2-yl]-1H-pyrrol-3-yl}carbonyl)amino]-5-methoxy-5-oxopentanoic acid To a stirred solution of 5-[4-(2-fluoro-5-{[(2-fluoro-5-methylphenyl)amino]carbonyl}phenoxy)pyridin-2-yl]-1H-pyrrole-3-carboxylic acid (60 mg, 0.13 mmol) in 10 ml of anhydrous DMF were added HATU (61 mg, 0.16 mmol) and N,N-diisopropylethylamine (52 mg, 0.40 mmol). The mixture was stirred at room temperature for 10 minutes, followed by addition of 5-methyl L-glutamate (32 mg, 0.20 mmol). The mixture was heated at 60° C. for 1 hour, cooled to room temperature and poured into 100 ml of water with vigorous stirring. 2M HCl was added slowly until pH=4. The precipitates were filtered, washed with water and dried in vacuo to give 2-[({5-[4-(2-fluoro-5-{[(2-fluoro-5-methylphenyl)amino]carbonyl}phenoxy)pyridin-2-yl]-1H-pyrrol-3-yl}carbonyl)amino]-5-methoxy-5-oxopentanoic acid as white solid. Yield: 30 mg, 38%.

$^1$H NMR (DMSO-$d_6$): 12.53 (br. s., 1H), 11.89 (br. s., 1H), 10.12 (s, 1H), 8.43 (d, J=5.9 Hz, 1H), 7.96-8.01 (m, 3H), 7.63 (dd, J=10.3, 8.5 Hz, 1H), 7.47 (dd, J=3.1, 1.6 Hz, 1H), 7.34 (dd, J=7.3, 2.1 Hz, 1H), 7.29 (d, J=2.3 Hz, 1H), 7.18-7.20 (m, 1H), 7.14 (dd, J=10.4, 8.4 Hz, 1H), 7.01-7.07 (m, 1H), 6.81 (dd, J=5.6, 2.3 Hz, 1H), 4.32 (ddd, J=9.5, 8.0, 5.1 Hz, 1H), 3.55 (s, 3H), 2.37-2.41 (m, 2H), 2.26 (s, 3H), 1.99-2.10 (m, 1H), 1.83-1.95 (m, 1H)

LR MS (ES−): 591 (M−H)

Example 263

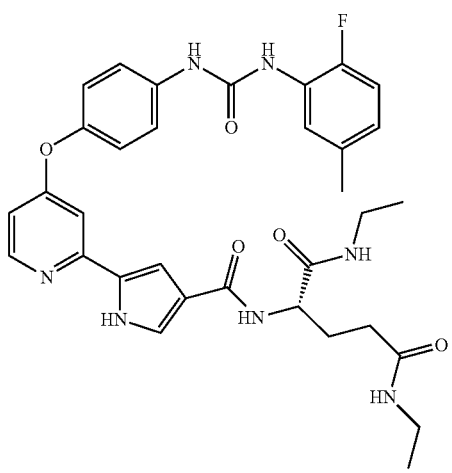 [SMILES: CCNC(=O)CC[C@H](NC(=O)c1c[nH]c(-c2cc(Oc3ccc(NC(=O)Nc4cc(C)ccc4F)cc3)ccn2)c1)C(=O)NCC]

N,N'-diethyl-2-{[(5-{4-[4-({[(2-fluoro-5-methylphenyl)amino]carbonyl}amino)phenoxy]pyridin-2-yl}-1H-pyrrol-3-yl)carbonyl]amino}pentanediamide To a stirred solution of 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioic acid (Example 63) (100 mg, 0.17 mmol) in 10 ml of anhydrous DMF was added N-(3-dimethylaminopropyl)-N'-ethylcarbodiimide hydrochloride (EDC, 84 mg, 0.44 mmol). The mixture was stirred at room temperature for 30 minutes, followed by addition of 2-Methylamine solution in THF (0.45 ml, 0.90 mmol). The mixture was stirred for another 16 hours, and poured into 100 ml of water with vigorous stirring. 2M HCl was added dropwise until pH=4. The precipitates were filtered, washed with water and dried to give the crude, which was purified by silica gel chromatography eluting with 3~5% of methanol in chloroform to afford N,N'-diethyl-2-{[(5-{4-[4-({[(2-fluoro-5-methylphenyl)amino]carbonyl}amino)phenoxy]pyridin-2-yl}-1H-pyrrol-3-yl)carbonyl]amino}pentanediamide as white solid. Yield: 60 mg, 55%.

$^1$H NMR (DMSO-$d_6$): 11.82 (br. s., 1H), 9.14 (s, 1H), 8.46 (d, J=2.6 Hz, 1H), 8.36 (d, J=5.6 Hz, 1H), 7.96 (dd, J=7.9, 2.1 Hz, 1H), 7.82 (d, J=8.2 Hz, 1H), 7.80 (t, J=5.6 Hz, 1H), 7.75 (t, J=5.3 Hz, 1H), 7.51-7.56 (m, 2H), 7.42 (dd, J=3.1, 1.6 Hz, 1H), 7.15 (d, J=2.3 Hz, 1H), 7.12-7.15 (m, 2H), 7.11 (dd, J=2.6, 1.8 Hz, 1H), 7.08 (dd, J=11.3, 8.4 Hz, 1H), 6.75-6.80 (m, 1H), 6.68 (dd, J=5.9, 2.3 Hz, 1H), 4.25 (td, J=8.6, 5.1 Hz, 1H), 3.02-3.07 (m, 2H), 2.97-3.02 (m, 2H), 2.25 (s, 3H), 2.00-2.14 (m, 2H), 1.86-1.95 (m, 1H), 1.74-1.83 (m, 1H), 0.97 (t, J=7.2 Hz, 3H), 0.93 (t, J=7.3 Hz, 3H)

LR MS (ES+): 652 (M+Na+)

LR MS (ES−): 628 (M−H)

Example 264

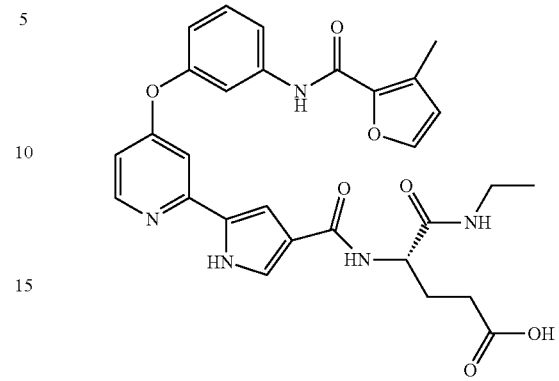

5-(ethylamino)-4-({[5-(4-{3-[(3-methyl-2-furoyl)amino]phenoxyl}pyridin-2-yl)-1H-pyrrol-3-yl]carbonyl}amino)-5-oxopentanoic acid To a stirred solution of tert-butyl 5-(ethylamino)-4-({[5-(4-{3-[(3-methyl-2-furoyl)amino]phenoxy}pyridin-2-yl)-1H-pyrrol-3-yl]carbonyl}amino)-5-oxopentanoate (34 mg, 0.055 mmol) in 5 ml of methylene chloride was added 2 ml of TFA. The mixture was stirred at room temperature for 1 hour, and evaporated to dryness under reduced pressure. The residue was re-dissolved in 5 ml of methanol and poured into 100 ml of water with vigorous stirring. The precipitates were filtered, washed with water and dried in vacuo to give 5-(ethylamino)-4-({[5-(4-{3-[(3-methyl-2-furoyl)amino]phenoxy}pyridin-2-yl)-1H-pyrrol-3-yl]carbonyl}amino)-5-oxopentanoic acid as white solid. Yield: 26 mg, 84%.

$^1$H NMR (DMSO-$d_6$): 12.04 (br. s., 1H), 11.85 (br. s., 1H), 10.19 (s, 1H), 8.39 (d, J=5.6 Hz, 1H), 7.82 (t, J=5.7 Hz, 1H), 7.78 (d, J=8.2 Hz, 1H), 7.76 (d, J=1.5 Hz, 1H), 7.68-7.70 (m, 1H), 7.68 (d, J=1.8 Hz, 1H), 7.45 (dd, J=3.1, 1.6 Hz, 1H), 7.38-7.43 (m, 1H), 7.25 (d, J=2.3 Hz, 1H), 7.16 (dd, J=2.3, 1.8 Hz, 1H), 6.88-6.91 (m, 1H), 6.74 (dd, J=5.6, 2.3 Hz, 1H), 6.56 (d, J=1.5 Hz, 1H), 4.31 (td, J=8.7, 5.3 Hz, 1H), 2.98-3.10 (m, 2H), 2.29 (s, 3H), 2.17-2.26 (m, 2H), 1.89-1.98 (m, 1H), 1.75-1.84 (m, 1H), 0.97 (t, J=7.2 Hz, 3H)

LR MS (ES−): 558 (M−H)

Example 265

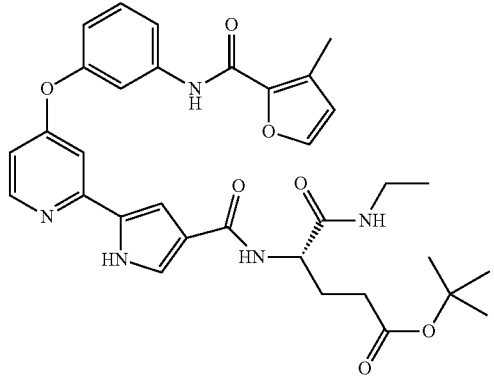 [SMILES: CCNC(=O)[C@H](CCC(=O)OC(C)(C)C)NC(=O)c1c[nH]c(-c2cc(Oc3cccc(NC(=O)c4occc4C)c3)ccn2)c1]

tert-butyl 5-(ethylamino)-4-({[5-(4-{3-[(3-methyl-2-furoyl)amino]phenoxy}pyridin-2-yl)-1H-pyrrol-3-yl]carbonyl}amino)-5-oxopentanoate To a stirred suspension of 5-tert-butoxy-2-({[5-(4-{3-[(3-methyl-2-furoyl)amino]phenoxy}pyridin-2-yl)-1H-pyrrol-3-yl]carbonyl}amino)-5-oxopentanoic acid (100 mg, 0.17 mmol) in 10 ml of anhydrous tetrahydrofuran were added HATU (76 mg, 0.20 mmol) and N,N-diisopropylethylamine (66 mg, 0.51 mmol). The mixture was heated at 60° C. for 15 minutes and cooled to room temperature, followed by addition of 2-Methylamine solution in THF (0.25 ml, 0.50 mmol). The mixture was stirred for another 5 minutes and poured into 100 ml of water with vigorous stirring. 1M HCl was added dropwise until pH=4. The precipitates were filtered, washed with water and dried in vacuo to give the crude, which was purified by silica gel chromatography eluting with 3~5% methanol in chloroform to give tert-butyl 5-(ethylamino)-4-({[5-(4-{3-[(3-methyl-2-furoyl)amino]phenoxy}pyridin-2-yl)-1H-pyrrol-3-yl]carbonyl}amino)-5-oxopentanoate as white solid. Yield: 82 mg, 78%.

$^1$H NMR (DMSO-$d_6$): 11.84 (br. s., 1H), 10.19 (s, 1H), 8.39 (d, J=5.6 Hz, 1H), 7.80 (t, J=5.6 Hz, 1H), 7.75-7.79 (m, 2H), 7.68-7.70 (m, 1H), 7.68 (d, J=1.5 Hz, 1H), 7.45 (dd, J=3.1, 1.6 Hz, 1H), 7.38-7.43 (m, 1H), 7.24 (d, J=2.3 Hz, 1H), 7.16 (dd, J=2.6, 1.8 Hz, 1H), 6.88-6.91 (m, 1H), 6.74 (dd, J=5.9, 2.3 Hz, 1H), 6.56 (d, J=1.8 Hz, 1H), 4.30 (td, J=8.7, 5.4 Hz, 1H), 2.99-3.09 (m, 2H), 2.29 (s, 3H), 2.13-2.25 (m, 2H), 1.86-1.96 (m, 1H), 1.75-1.81 (m, 1H), 1.34 (s, 9H), 0.97 (t, J=7.2 Hz, 3H)

LR MS (ES+): 638 (M+Na+)
LR MS (ES−): 614 (M−H)

Example 266

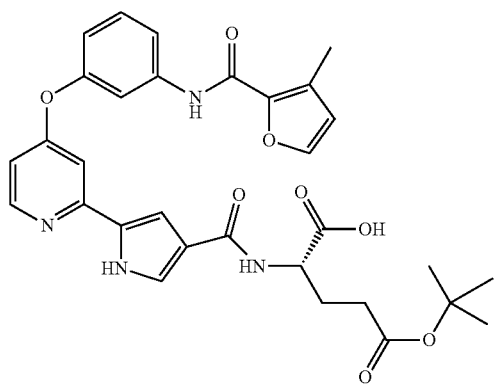 [SMILES: Cc1ccoc1C(=O)Nc1cccc(Oc2ccnc(-c3cc(C(=O)N[C@@H](CCC(=O)OC(C)(C)C)C(=O)O)c[nH]3)c2)c1]

5-tert-butoxy-2-({[5-(4-{3-[(3-methyl-2-furoyl)amino]phenoxy}pyridin-2-yl)-1H-pyrrol-3-yl]carbonyl}amino)-5-oxopentanoic acid To a stirred solution of 5-tert-butyl 1-methyl 2-({[5-(4-{3-[(3-methyl-2-furoyl)amino]phenoxy}pyridin-2-yl)-1H-pyrrol-3-yl]carbonyl}amino)pentanedioate (170 mg, 0.28 mmol) in a mixture of THF/MeOH (10 ml/10 ml) was added 1M NaOH solution (2 ml, 2 mmol). The mixture was stirred at room temperature for 2 hours and poured into 100 ml of water. 1M HCl was added dropwise until pH=4. The precipitates were filtered, washed with water and dried in vacuo to give 5-tert-butoxy-2-({[5-(4-{3-[(3-methyl-2-furoyl)amino]phenoxy}pyridin-2-yl)-1H-pyrrol-3-yl]carbonyl}amino)-5-oxopentanoic acid as white solid. Yield: 145 mg, 87%.

$^1$H NMR (DMSO-$d_6$): 12.48 (br. s., 1H), 11.88 (br. s., 1H), 10.20 (s, 1H), 8.40 (d, J=5.9 Hz, 1H), 7.95 (d, J=7.6 Hz, 1H), 7.76 (d, J=1.8 Hz, 1H), 7.67-7.71 (m, 2H), 7.45 (br. s., 1H), 7.41 (t, J=8.2 Hz, 1H), 7.26 (d, J=1.5 Hz, 1H), 7.16 (br. s., 1H), 6.90 (ddd, J=8.2, 2.2, 1.0 Hz, 1H), 6.76 (d, J=3.8 Hz, 1H), 6.56 (dd, J=1.8, 0.6 Hz, 1H), 4.31 (ddd, J=9.8, 7.9, 4.8 Hz, 1H), 2.29 (s, 3H), 2.25-2.29 (m, 2H), 1.94-2.05 (m, 1H), 1.79-1.89 (m, 1H), 1.35 (s, 9H)

LR MS (ES−): 587 (M−H)

Example 267

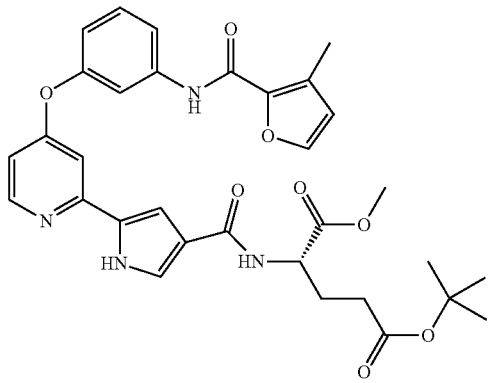 [SMILES: COC(=O)[C@H](CCC(=O)OC(C)(C)C)NC(=O)c1c[nH]c(-c2cc(Oc3cccc(NC(=O)c4occc4C)c3)ccn2)c1]

5-tert-butyl 1-methyl 2-({[5-(4-{3-[(3-methyl-2-furoyl)amino]phenoxy}pyridin-2-yl)-1H-pyrrol-3-yl]carbonyl}amino)pentanedioate To a stirred solution of 5-(4-{3-[(3-methyl-2-furoyl)amino]phenoxy}pyridin-2-yl)-1H-pyrrole-3-carboxylic acid (Example 32)(140 mg, 0.35 mmol) in 10 ml of anhydrous DMF were added HATU (160 mg, 0.42 mmol) and N,N-diisopropylethylamine (135 mg, 1.05 mmol). The mixture was stirred at room temperature for 10 minutes, followed by addition of L-Glutamic acid 5-tert-butyl 1-methyl ester hydrochloride (135 mg, 0.53 mmol). The mixture was stirred for another 5 minutes and poured into 100 ml of water. 2M HCl was added dropwise with vigorous stirring until pH=4. The precipitates were filtered, washed with water and dried in vacuo to give 5-tert-butyl 1-methyl 2-({[5-(4-{3-[(3-methyl-2-furoyl)amino]phenoxy}pyridin-2-yl)-1H-pyrrol-3-yl]carbonyl}amino)pentanedioate as white solid. Yield: 170 mg, 81%.

$^1$H NMR (DMSO-$d_6$): 11.96 (br. s., 1H), 10.21 (s, 1H), 8.42 (d, J=5.9 Hz, 1H), 8.10 (d, J=7.6 Hz, 1H), 7.77 (d, J=1.5 Hz, 1H), 7.68-7.72 (m, 2H), 7.48 (br. s., 1H), 7.42 (t, J=8.4 Hz, 1H), 7.29 (br. s., 1H), 7.19 (br. s., 1H), 6.91 (dd, J=7.6, 1.8 Hz, 1H), 6.80 (br. s., 1H), 6.56 (d, J=1.2 Hz, 1H), 4.37 (ddd, J=9.5, 7.5, 5.3 Hz, 1H), 3.60 (s, 3H), 2.29 (s, 3H), 2.28 (t, J=7.6 Hz, 2H), 1.94-2.02 (m, 1H), 1.82-1.91 (m, 1H), 1.35 (s, 9H)

LR MS (ES+): 625 (M+Na+)
LR MS (ES−): 601 (M−H)

Example 268

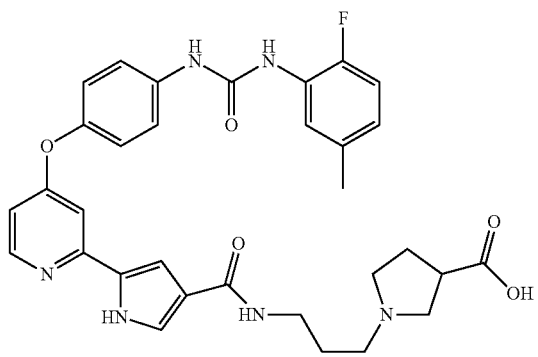 [SMILES: Cc1ccc(F)c(NC(=O)Nc2ccc(Oc3ccnc(-c4cc(C(=O)NCCCN5CCC(C(=O)O)C5)c[nH]4)c3)cc2)c1]

1-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)pyrrolidine-3-carboxylic acid To a stirred solution of tert-butyl 1-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)pyrrolidine-3-carboxylate (22 mg, 0.033 mmol) in 2 ml of methylene chloride was added 1 ml of TFA. The mixture was stirred at room temperature for 16 hours, and evaporated to dryness under reduced pressure. The residue was re-dissolved in 2 ml of methanol and poured into 10 ml of water with vigorous stirring. Saturated $NaHCO_3$ solution was added dropwise until pH=7. The precipitates were filtered, washed with water and dried in vacuo to give 1-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)pyrrolidine-3-carboxylic acid as light reddish solid.

Yield: 18 mg, 90%.

The following Example 269 was prepared using the experiment procedure described in Example 271, but with the appropriate reagent, reaction conditions and reactant substitutions that will be readily realized by those of ordinary skill in this art without the exercise of undue experimentation.

Example 269

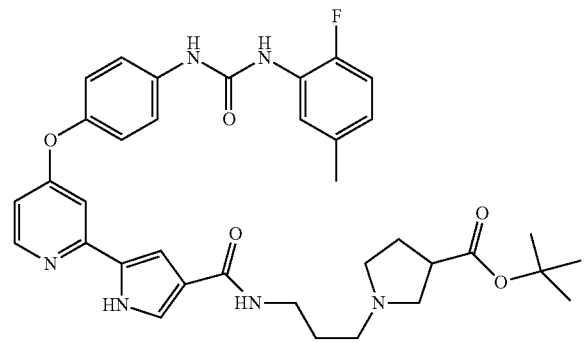 [SMILES: Cc1ccc(F)c(NC(=O)Nc2ccc(Oc3ccnc(-c4cc(C(=O)NCCCN5CCC(C(=O)OC(C)(C)C)C5)c[nH]4)c3)cc2)c1]

tert-butyl 1-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)pyrrolidine-3-carboxylate

LR MS (ES+): 657 (MH+)

LR MS (ES−): 655 (M−H)

Example 270

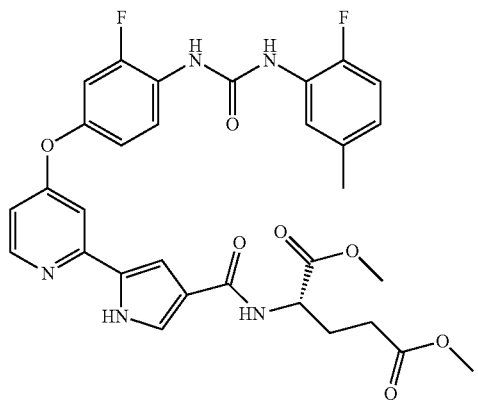 [SMILES: COC(=O)CC[C@H](NC(=O)c1c[nH]c(-c2cc(Oc3ccc(NC(=O)Nc4cc(C)ccc4F)c(F)c3)ccn2)c1)C(=O)OC]

dimethyl 2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}pentanedioate A mixture of 5-{4-[3-fluoro-4-({[(2-fluoro-5-methylphenyl)amino]carbonyl}amino)phenoxy]pyridin-2-yl}-1H-pyrrole-3-carboxylic acid (120 mg, 0.26 mmol), HATU (110 mg, 0.29 mmol) and N,N-diisopropylethylamine (100 mg, 0.78 mmol) in anhydrous DMF (10 ml) was stirred at room temperature for 10 minutes, followed by addition of L-glutamic acid dimethyl ester hydrochloride (66 mg, 0.31 mmol). The mixture was heated at 50° C. for 15 minutes, cooled to room temperature and poured into 100 ml of water with vigorous stirring. 2M HCl was added dropwise until pH=4. The precipitates were filtered, washed with water and dried in vacuo to give dimethyl 2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}pentanedioate as white solid. Yield: 130 mg, 81%.

$^1$H NMR (DMSO-$d_6$): 11.91 (br. s., 1H), 9.08 (d, J=2.3 Hz, 1H), 8.97 (d, J=2.6 Hz, 1H), 8.42 (d, J=5.6 Hz, 1H), 8.25 (t, J=9.1 Hz, 1H), 8.14 (d, J=7.6 Hz, 1H), 8.01 (dd, J=7.9, 2.3 Hz, 1H), 7.47 (dd, J=3.1, 1.6 Hz, 1H), 7.30 (dd, J=11.7, 2.6 Hz, 1H), 7.24 (d, J=2.6 Hz, 1H), 7.17-7.18 (m, 1H), 7.12 (dd, J=11.4, 8.2 Hz, 1H), 7.05 (ddd, J=9.0, 2.8, 1.2 Hz, 1H), 6.81-6.83 (m, 1H), 6.77 (dd, J=5.7, 2.5 Hz, 1H), 4.38-4.42 (m, 1H), 3.62 (s, 3H), 3.58 (s, 3H), 2.42 (t, J=7.5 Hz, 2H), 2.28 (s, 3H), 2.07 (dtd, J=13.6, 7.9, 5.4 Hz, 1H), 1.91-1.98 (m, 1H)

LR MS (ES+): 644 (M+Na$^+$)

LR MS (ES−): 620 (M−H)

Example 271

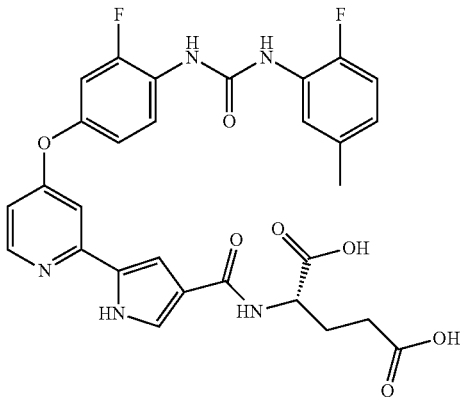 [SMILES: Cc1ccc(F)c(NC(=O)Nc2ccc(Oc3ccnc(-c4cc(C(=O)N[C@@H](CCC(=O)O)C(=O)O)c[nH]4)c3)cc2F)c1]

2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}pentanedioic acid To a stirred solution of dimethyl 2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}pentanedioate (75 mg, 0.12 mmol) in 10 ml of MeOH was added 2 ml of 1M NaOH. The mixture was heated at 60° C. for one hour, cooled to room temperature and poured into 100 ml of water with vigorous stirring. 2M HCl was added dropwise until pH=4. The precipitates were filtered, washed with water and dried in vacuo to give 2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}pentanedioic acid as off-white solid. Yield: 72 mg, 100%.

$^1$H NMR (DMSO-$d_6$): 12.48 (br. s., 1H), 12.10 (br. s., 1H), 11.88 (br. s., 1H), 9.06 (d, J=1.5 Hz, 1H), 8.94 (d, J=2.1 Hz, 1H), 8.39 (d, J=5.6 Hz, 1H), 8.23 (t, J=9.1 Hz, 1H), 7.93-8.02 (m, 2H), 7.45 (br. s., 1H), 7.27 (dd, J=11.7, 2.6 Hz, 1H), 7.23 (s, 1H), 7.17 (br. s., 1H), 7.09 (dd, J=11.3, 8.4 Hz, 1H), 7.02 (dd, J=9.1, 1.5 Hz, 1H), 6.79 (td, J=5.2, 2.5 Hz, 1H), 6.75 (d, J=3.5 Hz, 1H), 4.32 (ddd, J=9.5, 7.8, 5.0 Hz, 1H), 2.30 (t, J=7.6 Hz, 2H), 2.25 (s, 3H), 1.95-2.08 (m, 1H), 1.79-1.92 (m, 1H)

LR MS (ES−): 592 (M−H)

Example 272

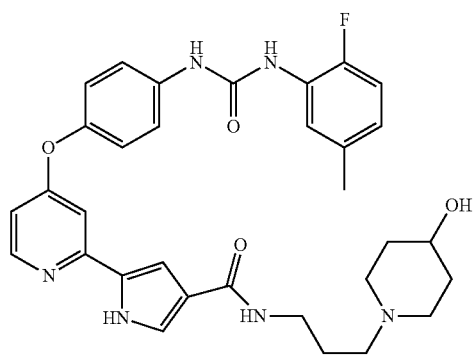 [SMILES: Cc1ccc(F)c(NC(=O)Nc2ccc(Oc3ccnc(-c4cc(C(=O)NCCCN5CCC(O)CC5)c[nH]4)c3)cc2)c1]

5-{4-[4-({[(2-fluoro-5-methylphenyl)amino]carbonyl}amino)phenoxy]pyridin-2-yl}-N-[3-(4-hydroxypiperidin-1-yl)propyl]-1H-pyrrole-3-carboxamide To a stirred solution of 5-{4-[4-({[(2-fluoro-5-methylphenyl)amino]carbonyl}amino)phenoxy]pyridin-2-yl}-N-(3-oxopropyl)-1H-pyrrole-3-carboxamide (100 mg, 0.20 mmol) in 10 ml of anhydrous DMF were added 4-hydroxypiperidine (30 mg, 0.30 mmol) and acetic acid (10 mg, 0.17 mmol). The mixture was stirred at room temperature for 30 minutes, followed by addition of 1M sodium cyanoborohydride solution in THF (0.30 ml, 0.30 mmol) and stirring was continued for one more hour. The mixture was poured into 100 ml of water. The precipitates were filtered, washed with water and dried to give the crude, which was purified by silica gel flash chromatography eluting with 20% of MeOH in CHCl$_3$ to give 5-{4-[4-({[(2-fluoro-5-methylphenyl)amino]carbonyl}amino)phenoxy]pyridin-2-yl}-N-[3-(4-hydroxypiperidin-1-yl)propyl]-1H-pyrrole-3-carboxamide as white solid. Yield: 55 mg, 47%.

LR MS (ES+): 587 (MH+)

LR MS (ES−): 585 (M−H)

Example 273

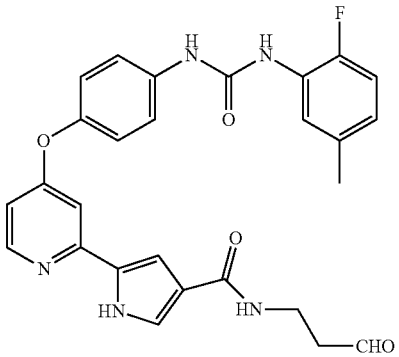 [SMILES: Cc1ccc(F)c(NC(=O)Nc2ccc(Oc3ccnc(-c4cc(C(=O)NCCC=O)c[nH]4)c3)cc2)c1]

5-{4-[4-({[(2-fluoro-5-methylphenyl)amino]carbonyl}amino)phenoxy]pyridin-2-yl}-N-(3-oxopropyl)-1H-pyrrole-3-carboxamide To a stirred solution of N-(3,3-diethoxypropyl)-5-{4-[4-({[(2-fluoro-5-methylphenyl)amino]carbonyl}amino)phenoxy]pyridin-2-yl}-1H-pyrrole-3-carboxamide (800 mg, 1.39 mmol) in 10 ml of THF was added 2M HCl (1 ml, 1 mmol). The mixture was stirred at room temperature under nitrogen for 1.5 hours, and poured into 100 ml of water with vigorous stirring. The precipitates were filtered, washed with water, and dried in vacuo to give 5-{4-[4-({[(2-fluoro-5-methylphenyl)amino]carbonyl}amino)phenoxy]pyridin-2-yl}-N-(3-oxopropyl)-1H-pyrrole-3-carboxamide as off-white solid. Yield: 680 mg, 98%.

LR MS (ES+): 524 (M+Na+)

LR MS (ES−): 500 (M−H)

Example 274

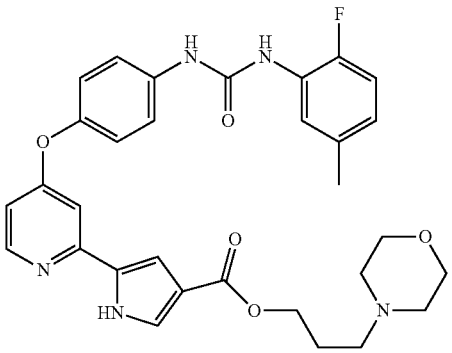 [SMILES: Cc1ccc(F)c(NC(=O)Nc2ccc(Oc3ccnc(-c4cc(C(=O)OCCCN5CCOCC5)c[nH]4)c3)cc2)c1]

3-morpholin-4-ylpropyl 5-{4-[4-({[(2-fluoro-5-methylphenyl)amino]carbonyl}amino)phenoxy]pyridin-2-yl}-1H-pyrrole-3-carboxylate To a stirred suspension of 5-{4-[4-({[(2-fluoro-5-methylphenyl)amino]carbonyl}amino)phenoxy]pyridin-2-yl}-1H-pyrrole-3-carboxylic acid (100 mg, 0.22 mmol) and N-(3-dimethylaminopropyl)-N'-ethylcarbodiimide hydrochloride (EDC, 63 mg, 0.33 mmol) in 10 ml of anhydrous tetrahydrofuran were added N-(3-hydroxypropyl)morpholine (64 mg, 0.44 mmol) and 4-dimethylaminopyridine (10 mg, 0.08 mmol). The mixture was heated at 60° C. for 3 hours, cooled to room temperature and evaporated to dryness. The residue was purified by silica gel chromatography eluting with 3~5% of methanol in chloroform to afford 3-morpholin-4-ylpropyl 5-{4-[4-({[(2-fluoro-5-methylphenyl)amino]carbonyl}amino)phenoxy]pyridin-2-yl}-1H-pyrrole-3-carboxylate as white solid. Yield: 72 mg, 56%.

LR MS (ES+): 574 (MH+)
LR MS (ES−): 572 (M−H)

Example 275

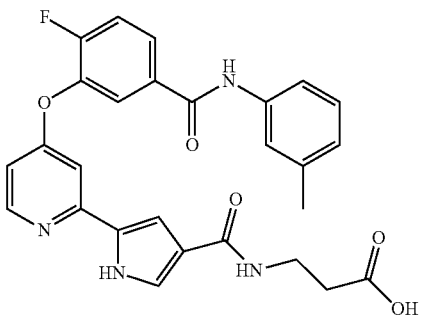 [SMILES: Cc1cccc(NC(=O)c2ccc(F)c(Oc3ccnc(-c4cc(C(=O)NCCC(=O)O)c[nH]4)c3)c2)c1]

3-[({5-[4-(2-fluoro-5-{[(3-methylphenyl)amino]carbonyl}phenoxy)pyridin-2-yl]-1H-pyrrol-3-yl}carbonyl)amino]propanoic acid To a stirred solution of methyl 3-[({5-[4-(2-fluoro-5-{[(3-methylphenyl)amino]carbonyl}phenoxy)pyridin-2-yl]-1H-pyrrol-3-yl}carbonyl)amino]propanoate (80 mg, 0.16 mmol) in a mixture of THF/MeOH (5 ml/5 ml) was added 1M NaOH solution (1 ml, 1 mmol). The mixture was stirred at room temperature for 3 hours and poured into 50 ml of water. 1M HCl was added dropwise until pH=4. The precipitates were filtered, washed with water and dried in vacuo to give 3-[({5-[4-(2-fluoro-5-{[(3-methylphenyl)amino]carbonyl}phenoxy)pyridin-2-yl]-1H-pyrrol-3-yl}carbonyl)amino]propanoic acid as white solid. Yield: 70 mg, 90%.

$^1$H NMR (DMSO-$d_6$): 12.15 (br. s., 1H), 11.85 (br. s., 1H), 10.18 (s, 1H), 8.42 (d, J=5.6 Hz, 1H), 8.02 (dd, J=7.6, 2.3 Hz, 1H), 7.97-8.00 (m, 1H), 7.91 (t, J=5.6 Hz, 1H), 7.63 (dd, J=10.3, 8.8 Hz, 1H), 7.55 (s, 1H), 7.52 (d, J=8.5 Hz, 1H), 7.38 (br. s., 1H), 7.26 (d, J=2.3 Hz, 1H), 7.20 (t, J=7.8 Hz, 1H), 7.12 (br. s., 1H), 6.91 (d, J=7.6 Hz, 1H), 6.81 (dd, J=5.7, 2.5 Hz, 1H), 3.32-3.37 (m, 2H), 2.43 (t, J=7.0 Hz, 2H), 2.27 (s, 3H)

LR MS (ES−): 501 (M−H)

Example 276

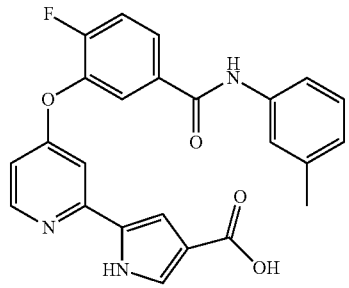

5-[4-(2-fluoro-5-{[(3-methylphenyl)amino]carbonyl}phenoxy)pyridin-2-yl]-1H-pyrrole-3-carboxylic acid

Example 277

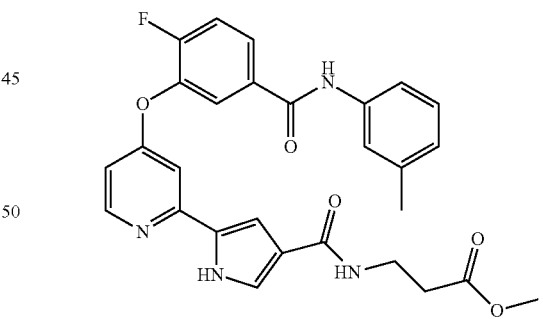

methyl 3-[({5-[4-(2-fluoro-5-{[(3-methylphenyl)amino]carbonyl}phenoxy)pyridin-2-yl]-1H-pyrrol-3-yl}carbonyl)amino]propanoate To a stirred solution of 5-[4-(2-fluoro-5-{[(3-methylphenyl)amino]carbonyl}phenoxy)pyridin-2-yl]-1H-pyrrole-3-carboxylic acid (Example 275) (100 mg, 0.23 mmol) in 10 ml of anhydrous DMF were added HATU (100 mg, 0.26 mmol) and N,N-diisopropylethylamine (85 mg, 0.66 mmol). The mixture was stirred at room temperature for 10 minutes, followed by addition of β-alanine methyl ester hydrochloride (46 mg, 0.33 mmol). The mixture was stirred for another minutes and poured into 100 ml of water. 2M HCl was added dropwise with vigorous stirring until pH=4. The precipitates were filtered, washed with water and dried in vacuo to give methyl 3-[({5-[4-(2-fluoro-5-{[(3-methylphenyl)amino] carbonyl}phenoxy)pyridin-2-yl]-1H-pyrrol-3-yl}carbonyl) amino]propanoate as white solid. Yield: 110 mg, 92%.

$^1$H NMR (DMSO-$d_6$): 11.95 (br. s., 1H), 10.19 (s, 1H), 8.44 (d, J=5.9 Hz, 1H), 8.03 (dd, J=7.6, 2.3 Hz, 1H), 8.00 (ddd, J=8.7, 4.5, 2.3 Hz, 1H), 7.97 (t, J=5.7 Hz, 1H), 7.64 (dd, J=10.3, 8.5 Hz, 1H), 7.55 (s, 1H), 7.52 (d, J=8.5 Hz, 1H), 7.43 (br. s., 1H), 7.31 (br. s., 1H), 7.20 (t, J=7.8 Hz, 1H), 7.18 (br. s., 1H), 6.91 (d, J=7.9 Hz, 1H), 6.88 (br. s., 1H), 3.57 (s, 3H), 3.35-3.42 (m, 2H), 2.52 (t, J=6.9 Hz, 2H), 2.27 (s, 3H)

LR MS (ES+): 539 (M+Na+)

LR MS (ES−): 515 (M−H)

Example 278

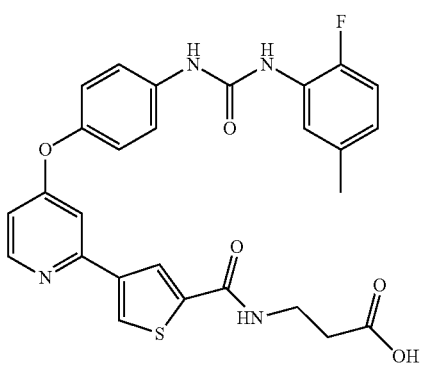 [SMILES: Cc1ccc(F)c(NC(=O)Nc2ccc(Oc3ccnc(-c4csc(C(=O)NCCC(=O)O)c4)c3)cc2)c1]

3-{[(4-{4-[4-({[(2-fluoro-5-methylphenyl)amino] carbonyl}amino)phenoxy]pyridin-2-yl}-2-thienyl) carbonyl]amino}propanoic acid To a stirred solution of methyl 3-{[(4-{4-[4-({[(2-fluoro-5-methylphenyl)amino]carbonyl}amino)phenoxy]pyridin-2-yl}-2-thienyl)carbonyl]amino}propanoate (85 mg, 0.16 mmol) in a mixture of THF/MeOH (5 ml/5 ml) was added 1M NaOH solution (2 ml, 2 mmol). The mixture was heated at 50° C. for one hour and poured into 100 ml of water. 1M HCl was added dropwise with vigorous stirring until pH=4. The precipitates were filtered, washed with water and dried in vacuo to give 3-{[(4-{4-[4-({[(2-fluoro-5-methylphenyl)amino] carbonyl}amino)phenoxy]pyridin-2-yl}-2-thienyl)carbonyl] amino}propanoic acid as white solid. Yield: 80 mg, 96%.

$^1$H NMR (DMSO-$d_6$): 12.17 (br. s., 1H), 9.15 (s, 1H), 8.68 (t, J=5.6 Hz, 1H), 8.46 (d, J=2.6 Hz, 1H), 8.44 (d, J=5.6 Hz, 1H), 8.36 (d, J=1.2 Hz, 1H), 8.33 (d, J=1.2 Hz, 1H), 7.95 (dd, J=7.9, 2.3 Hz, 1H), 7.51-7.56 (m, 2H), 7.41 (d, J=2.3 Hz, 1H), 7.12-7.17 (m, 2H), 7.08 (dd, J=11.4, 8.2 Hz, 1H), 6.77-6.80 (m, 1H), 6.76 (dd, J=5.9, 2.3 Hz, 1H), 3.38-3.44 (m, 2H), 2.49 (t, J=7.0 Hz, 2H), 2.25 (s, 3H)

LR MS (ES−): 533 (M−H)

Example 279

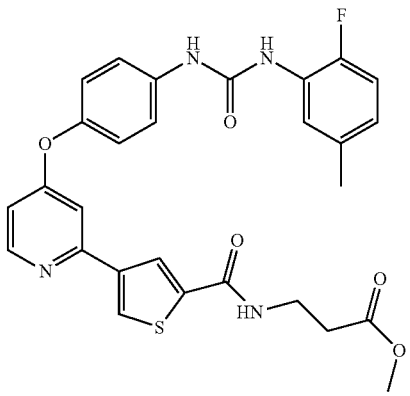 [SMILES: COC(=O)CCNC(=O)c1cc(-c2cc(Oc3ccc(NC(=O)Nc4cc(C)ccc4F)cc3)ccn2)cs1]

methyl 3-{[(4-{4-[4-({[(2-fluoro-5-methylphenyl) amino]carbonyl}amino)phenoxy]pyridin-2-yl}-2-thienyl)carbonyl]amino}propanoate To a stirred solution of 4-{4-[4-({[(2-fluoro-5-methylphenyl)amino]carbonyl}amino)phenoxy]pyridin-2-yl}thiophene-2-carboxylic acid (Example 123) (100 mg, 0.22 mmol) in 10 ml of anhydrous DMF were added HATU (100 mg, 0.26 mmol) and N,N-diisopropylethylamine (85 mg, 0.66 mmol). The mixture was stirred at room temperature for 10 minutes, followed by addition of β-alanine methyl ester hydrochloride (46 mg, 0.33 mmol). The mixture was stirred for another 10 minutes, and poured into 100 ml of water with vigorous stirring. 1M HCl was added dropwise until pH=4. The precipitates were filtered, washed with water and dried in vacuo to give methyl 3-{[(4-{4-[4-({[(2-fluoro-5-methylphenyl)amino]carbonyl}amino)phenoxy]pyridin-2-yl}-2-thienyl)carbonyl]amino}propanoate as off-white solid. Yield: 115 mg, 97%.

$^1$H NMR (DMSO-$d_6$): 9.21 (s, 1H), 8.70 (t, J=5.6 Hz, 1H), 8.45-8.50 (m, 2H), 8.36 (d, J=18.2 Hz, 2H), 7.93-7.97 (m, 1H), 7.55 (d, J=8.8 Hz, 2H), 7.45 (br. s., 1H), 7.16 (d, J=9.1 Hz, 2H), 7.08 (dd, J=11.3, 8.4 Hz, 1H), 6.72-6.88 (m, 2H), 3.58 (s, 3H), 3.39-3.50 (m, 2H), 2.57 (t, J=6.9 Hz, 2H), 2.25 (s, 3H)

LR MS (ES+): 571 (M+Na+)

LR MS (ES−): 547 (M−H)

3.2 Biological Testing

Biological data for the compounds of the present invention was generated by the use of one or more of the following assays.

VEGF Stimulated Ca.sup.++Signal in Vitro

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 96-well fibronectin coated black-walled plates overnight at 37 degree. C./5% CO.sub.2. Cells were loaded with calcium indicator Fluo-4 for 45 minutes at 37 degree. C. Cells were washed 4 times (Original Cell Wash, Labsystems) to remove extracellular dye. Test compounds were reconstituted in 100% DMSO and added to the cells to give a final DMSO concentration of 0.1%. For screening, cells were pre-incubated with test agents for 30 minutes, at a single concentration (10 mu.M) or at concentrations ranging from 0.01 to 10.0 mu.M followed by VEGF stimulation (5 ng/mL). Changes in fluorescence at 516 nm were measured simultaneously in all 96 wells using a cooled CCD camera. Data were generated by determining max-min fluorescence levels for unstimulated, stimulated, and drug treated samples. $IC_{50}$ values for test compounds were calculated from % inhibition of VEGF stimulated responses in the absence of inhibitor.

VEGFR2Kinase Assay

The cytoplasmic domain of the human VEGF receptor (VEGFR-2) was expressed as a Histidine-tagged fusion protein following infection of insect cells using an H is engineered baculovirus. His-VEGFR-2 was purified to homogeneity, as determined by SDS-PAGE, using nickel resin chromatography. Kinase assays were performed in 96 well microtiter plates that were coated overnight with 30 mu.g of poly-Glu-Tyr (4:1) in 10 mM Phosphate Buffered Saline (PBS), pH 7.2-7.4. The plates were incubated with 1% BSA and then washed four times with PBS prior to starting the reaction. Reactions were carried out in 120 mu.L reaction volumes containing 3.6 mu.M ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 0.5 ng of purified protein. Following a ten minute incubation at 25 degree. C., the reactions were washed four times with PBS containing 0.05% Tween-20. 100 .mu.1 of a monoclonal anti-phosphotyrosine antibody-peroxidase conjugate was diluted 1:10000 in PBS-Tween-20 and added to the wells for 30 minutes. Following four washes with PBS-Tween-20, 100 mu.1 of O-phenylenediamine Dihydrochloride in Phosphate-citrate buffer, containing urea hydrogen peroxide, was added to the wells for 7 minutes as a colorimetric substrate for the peroxidase. The reaction was terminated by the addition of 100 mu.1 of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values. Compounds of the current invention have the IC50 value in the range of 0.01 to 500 nM.

VEGF-induced Dermal Extravasation in Guinea Pig (Miles Assay)

Male Hartley guinea pigs (300-600 g) were anesthetized with isofluorane, sheared, and given a single dose of drug or the respective vehicle. The guinea pigs were dosed orally unless indicated otherwise in Table 3. Ten minutes prior to the end of drug treatment, guinea pigs were anesthetized with isofluorane, and 0.5% Evans blue dye (EBD) in PBS (13-15 mg/kg dose of EBD) was injected intravenously. After 5 minutes, triplicate intradermal injections of 100 ng rhVEGF.sub.165 in 100 mu.1 PBS and of 100 mu.1 PBS alone were administered on the flank. After 20 minutes, each animal was cuthanized with Pentosol, and the skin containing the intradermal injection sites was removed for image analysis.

Using an analog video camera coupled to a PC, an image of each trans-illuminated skin sample was captured, and the integrated optical density of each injection site was measured using ImagePro 4. For each skin sample, the difference between the mean optical density of the VEGF sites and mean optical density of the PBS sites is the measure of VEGF-induced EBD extravasation in that animal. These measured values were averaged per study group to determine the mean VEGF-induced EBD extravasation for each experimental condition, and the group means were then compared to assess inhibition of VEGF-induced EBD extravasation in the drug-treated groups relative to the vehicle-treated controls.

To determine the dose required for 50% inhibition (ID.sub.50), the percent inhibition data was plotted as a function of oral dose, using the 'best-fit' analysis within MicroSoft Excel software. The ID.sub.50 value was verified visually by using the plotted data (horizontal line from 50% y value, at intersection with best-fit line drop vertical line to x axis (dose).

Laser-induced Choroidal Neovascularization (CNV) in Rat (CNV Assay).

CNV was induced and quantified in this model as previously described (Edelman and Castro. Exp. Eye Res. 2000; 71:523-533). On day 0, male Brown Norway rats (200-300 g) were anesthetized with 100 mg/kg Ketamine and 10 mg/kg Xylazine, and pupils were dilated with 1% Tropicamide. Using the blue-green setting of a Coherent Novus Argon Laser, 3 laser burns (90 mW for 0.1 s; 100 .mu.m diameter) were given to each eye between the retinal vessels around the optic nerve head. Rats were dosed with test compounds in their indicated vehicles orally once daily.

On day 10, rats were sacrificed with 100% $CO_2$, and blood vessels were labeled by vascular perfusion with 10 mg/ml FITC-dextran (MW 2.times.10.sup.6). Using an epifluorescence microscope (20.times.) coupled to a spot digital camera and a PC, images were obtained from the flat mounts of the RPE-choroid-sclera from each eye, and the area occupied by hyperfluorescent neovessels within each laser lesion was measured using ImagePro 4 software.

To determine the dose required for 50% inhibition (ID.sub.50), the percent inhibition data was plotted as a function of oral dose, using the 'best-fit' analysis within MicroSoft Excel software. The ID.sub.50 value was verified visually by using the plotted data (horizontal line from 50% y value, at intersection with best-fit line drop vertical line to x axis (dose).

The foregoing description can be employed to practice the present invention, and represents the best mode contemplated. It should not be construed as limiting the overall scope hereof Rabbit Eye VEGF Permeability Model Assay used was detailed by Jeffrey Edelman, etc in Exp. Eye. Res. 80 (2005), Pg 249-258.

PDGF Stimulated $Ca^{2+}$ Signal in Vitro

Automated FLIPR (Fluorometric Imaging Plate Reader) technology was used to screen for inhibitors of PDGF induced increases in intracellular calcium levels in fluorescent dye loaded endothelial cells. NHDF-Ad (Normal human dermal fibroblasts) (Lonza) were seeded in 384-well fibronectin coated black-walled plates overnight at 37° C./5% $CO_2$. Cells were loaded with calcium indicator Fluo-4 for 45 minutes at 37° C. Cells were washed 4 times (ELx405-CW, Bio-Tek) to remove extracellular dye. Test compounds were reconstituted in 100% DMSO and added to the cells to give a final DMSO concentration of 0.1%. For screening, cells were pre-incubated with test agents for 30 minutes, at a single concentration (10 μM) or at concentrations ranging from 0.001 nM to 10 μM followed by PDGF stimulation (10 ng/mL). Changes in fluorescence at 515 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of PDGF stimulated responses in the absence of inhibitor.

Table II and III present the biodata of some of the compounds of the present invention.

TABLE II

Biodata of Compounds of the Present Invention with Amide Linker

| Example# | VEGFR2 Cellular IC$_{50}$ (nM) | VEGFR2 Enzyme IC$_{50}$ (nM) | VEGFR1 Enzyme IC$_{50}$ (nM) | PDGFβ Cellular IC$_{50}$ (nM) |
|---|---|---|---|---|
| 1 |  | 28 |  |  |
| 2 | 8 | 28 |  |  |
| 3 |  | 28 |  |  |
| 4 | 6 | 29 |  |  |
| 5 |  | 2956 |  |  |
| 6 |  | 506 |  |  |
| 7 | 12 | 34 |  |  |
| 8 | 8 | 28 |  |  |
| 9 | 30 | 47 |  |  |
| 10 | 46 | 41 |  |  |
| 11 | 28 | 23 | 34 |  |
| 12 |  |  |  |  |
| 13 | 16 | 27 |  |  |
| 14 | 15 | 33 | 15 |  |
| 15 | 51 | 26 |  | 73 |
| 16 | 17 | 21 |  |  |
| 17 | 22 | 20 |  | 61 |
| 18 | 10 | 31 |  |  |
| 19 | 30 | 37 |  | 135 |
| 20 | 83 | 28 |  |  |
| 21 | 12 | 24 |  | 39 |
| 22 | 18 | 29 | 13 | 105 |
| 23 | 13 | 35 |  |  |
| 24 | 55 | 24 |  |  |
| 25 | 30 | 25 |  |  |
| 26 | 39 | 120 |  |  |
| 27 | 45 | 66 |  |  |
| 28 | 38 | 52 |  |  |
| 29 | 18 | 55 |  |  |
| 30 | 29 | 37 |  | 94 |
| 31 | 14 | 29 | 20 |  |
| 32 | 22 | 46 |  |  |
| 33 | 18 | 56 |  |  |
| 34 | 7 | 70 |  |  |
| 35 | 27 | 29 |  |  |
| 36 |  | 10028 |  |  |
| 37 | 1005 | 2610 |  |  |

TABLE III

Biodata of Compounds of the Present Invention with Urea Linker

| Example# | VEGFR2 Cellular IC$_{50}$ (nM) | VEGFR2 Enzyme IC$_{50}$ (nM) | VEGFR1 Enzyme IC$_{50}$ (nM) | PDGFβ Cellular IC$_{50}$ (nM) |
|---|---|---|---|---|
| 38 |  | 10 |  |  |
| 39 |  | 23 |  |  |
| 40 |  | 11 |  |  |
| 41 |  | 11 |  |  |
| 42 |  | 60 |  |  |
| 43 |  | 16 |  |  |
| 44 |  | 24 |  |  |
| 45 |  | 17 |  |  |
| 46 | 2 | 28 |  |  |
| 47 | 107 | 17 |  |  |
| 48 | 16 | 12 |  |  |
| 49 | 145 | 27 |  |  |
| 50 | 5 | 32 |  |  |
| 51 |  | 16 |  |  |
| 52 |  | 25 |  |  |
| 53 | 43 | 28 |  | 44 |
| 54 | 130 | 29 |  | 191 |
| 55 | 32 | 23 |  | 26 |
| 56 | 81 | 20 |  |  |
| 57 | 102 | 45 |  |  |
| 58 | 211 | 36 |  |  |
| 59 | 34 | 29 |  |  |
| 60 | 27 | 23 |  |  |
| 61 | 91 | 39 |  |  |
| 62 | 122 | 43 |  |  |
| 63 | 111 | 30 |  |  |
| 64 | 16 | 39 |  |  |
| 65 |  | 15 | 4 |  |
| 66 |  | 17 | 3 |  |
| 67 | 31 | 31 |  |  |
| 68 |  | 16 |  |  |
| 69 |  | 24 | 5 |  |
| 70 | 2 | 20 |  |  |
| 71 |  | 20 |  |  |
| 72 | 7 | 15 |  |  |
| 73 |  | 11 |  |  |
| 74 | 7 | 12 |  |  |
| 76 | 2 | 14 | 3 |  |
| 76 | 3 | 14 |  |  |
| 77 | 8 | 10 |  |  |
| 78 | 25 | 15 | 4 |  |
| 79 | 13 | 38 |  |  |
| 80 | 176 | 69 |  |  |
| 81 |  | 19 |  |  |
| 82 | 17 | 19 |  |  |
| 83 |  | 22 | 5 |  |
| 84 |  | 13 |  |  |
| 85 | 6 | 30 |  |  |
| 86 |  | 27 |  |  |
| 87 | 5 | 25 |  |  |
| 88 | 374 | 477 |  |  |
| 89 | 5 | 23 |  |  |
| 90 | 8 | 17 | 6 | 21 |
| 91 | 17 | 14 |  | 38 |
| 92 | 37 | 9 |  | 39 |
| 93 | 6 | 5 | 5 | 14 |
| 94 | 10 | 6 |  | 10 |
| 95 | 30 | 32 |  |  |
| 96 | 3 | 17 |  | 69 |
| 97 | 8 | 18 |  |  |
| 98 | 62 | 51 |  |  |
| 99 | 49 | 46 |  |  |
| 100 | 12 | 13 |  |  |
| 101 | 4 | 8 |  | 82 |
| 102 | 10 | 35 |  | 8 |
| 103 | 24 | 20 |  |  |
| 104 | 23 | 27 |  |  |
| 105 | 87 | 15 |  |  |
| 106 | 16 | 21 |  |  |
| 107 | 13 | 21 |  |  |
| 108 | 17 | 14 | 13 | 43 |
| 109 | 16 | 23 |  |  |
| 110 | 8 | 38 | 10 | 32 |
| 111 | 13 | 71 |  |  |
| 112 | 13 | 18 |  |  |
| 113 | 23 | 25 |  |  |
| 114 | 13 | 22 |  |  |
| 115 | 2 | 15 | 2 | 44 |
| 116 | 12 | 17 |  |  |
| 117 | 6 | 18 |  |  |
| 118 | 22 | 85 |  |  |
| 119 | 12 | 54 |  |  |
| 120 | 43 | 98 |  |  |
| 121 | 37 | 14 | 20 | 102 |
| 122 | 142 | 130 |  |  |
| 123 | 13 | 24 |  | 85 |
| 124 | 23 | 36 |  |  |
| 125 | 22 | 31 |  |  |
| 126 | 16 | 116 |  |  |
| 127 | 20 | 21 |  | 91 |
| 128 | 10 | 53 |  |  |
| 129 | 12 | 102 |  |  |
| 130 | 5 | 43 | 16 | 32 |
| 131 | 8 | 31 |  |  |
| 132 | 22 | 15 |  |  |
| 133 | 66 | 15 |  |  |
| 134 | 4 | 31 | 4 |  |
| 135 | 11 | 47 |  |  |
| 136 | 29 | 22 |  |  |

TABLE III-continued

Biodata of Compounds of the Present Invention with Urea Linker

| Example# | VEGFR2 Cellular IC$_{50}$ (nM) | VEGFR2 Enzyme IC$_{50}$ (nM) | VEGFR1 Enzyme IC$_{50}$ (nM) | PDGFβ Cellular IC$_{50}$ (nM) |
|---|---|---|---|---|
| 137 | 14 | 33 | | |
| 138 | | 30 | | |
| 139 | 14 | 30 | | |
| 140 | | 10000 | | |
| 141 | | 2704 | | |
| 142 | 111 | 28 | | |
| 143 | 16 | 12 | | |
| 144 | 28 | 26 | | |
| 145 | 10000 | 10000 | | |
| 146 | 10000 | 7007 | | |
| 147 | 10000 | 3505 | | |
| 148 | 10000 | 1382 | | |

TABLE IV

Biodata of Compounds of the Present Invention with Amide or Urea Linker

| Example# | VEGFR2 Cellular IC$_{50}$ (nM) | VEGFR2 Enzyme IC$_{50}$ (nM) | VEGFR1 Enzyme IC$_{50}$ (nM) | PDGFβ Cellular IC$_{50}$ (nM) | PDGFβ Enzyme IC$_{50}$ (nM) |
|---|---|---|---|---|---|
| 149 | | 4 | 6 | | 13 |
| 150 | | 5 | 7 | | 16 |
| 154 | 14 | 7 | 8 | | 15 |
| 155 | 4 | 8 | 7 | | 20 |
| 156 | 9 | 11 | 8 | | 31 |
| 157 | 3 | 10 | 8 | | 39 |
| 158 | 11 | 11 | 6 | | 29 |
| 159 | 26 | 11 | 9 | | 33 |
| 160 | | 9 | 7 | | 19 |
| 161 | 10 | 9 | 9 | | 20 |
| 164 | 5 | 9 | 10 | | 17 |
| 165 | 12 | 10 | 17 | | 35 |
| 166 | | 5 | 6 | | 11 |
| 167 | 11 | 9 | 21 | | 27 |
| 168 | 11 | 10 | 17 | | 12 |
| 171 | 21 | 23 | 91 | | 33 |
| 172 | 13 | 10 | 11 | | 19 |
| 174 | | 8 | | | 42 |
| 175 | | | | 32 | 34 |
| 176 | | | | 78 | 38 |
| 177 | | 15 | | | |
| 178 | | 24 | 60 | | |
| 179 | | 21 | 50 | | |
| 180 | | 14 | 32 | | 53 |
| 181 | | 22 | 65 | | 132 |
| 182 | | 33 | 86 | | |
| 183 | | 24 | 100 | | |
| 184 | | 19 | 51 | | 49 |
| 185 | 8 | 16 | 40 | | 63 |
| 186 | | | | | |
| 187 | | 15 | 27 | | 98 |
| 188 | 5 | 27 | 32 | | |
| 189 | 15 | 34 | 37 | | |
| 191 | | 25 | 42 | | |
| 192 | | 26 | 34 | | |
| 193 | 11 | 31 | 35 | | |
| 194 | | 23 | 25 | | |
| 195 | | 7 | 9 | | 19 |
| 196 | | 8 | 10 | | 19 |
| 205 | | 8 | 9 | | 15 |
| 206 | | 9 | 12 | | 17 |
| 207 | | 7 | 10 | | 17 |
| 210 | | 12 | 8 | | 13 |
| 211 | 3 | 9 | 8 | | 12 |
| 212 | 6 | 13 | 20 | | 45 |
| 213 | 3 | 9 | 13 | | 38 |
| 214 | | 22 | 8 | | 23 |
| 215 | 4 | 5 | 13 | | 34 |
| 216 | | 17 | 16 | 214 | 59 |
| 217 | 10 | 5 | 10 | | 21 |
| 218 | | 5 | 9 | | 16 |
| 219 | 8 | 9 | 8 | | 29 |
| 220 | | 13 | 11 | | 23 |
| 221 | 15 | 11 | 7 | | 19 |
| 222 | | 9 | 15 | | 29 |
| 223 | | 13 | 12 | | 16 |
| 224 | | 10 | 21 | | |
| 226 | | 6 | 9 | | |
| 227 | | 9 | 11 | | |
| 228 | | 11 | 8 | | 9 |
| 229 | 13 | 11 | 11 | | 9 |
| 230 | 2 | 6 | 9 | 31 | 12 |
| 231 | | | | 32 | 43 |
| 232 | 5 | 9 | 16 | | 20 |
| 233 | 5 | 9 | | | 22 |
| 234 | | 8 | 11 | | 17 |
| 235 | | | 14 | | 15 |
| 237 | 3 | 8 | 8 | | 19 |
| 238 | 4 | 19 | | | 28 |
| 239 | 2 | 7 | | | 16 |
| 240 | | 7 | | | |
| 241 | 4 | 10 | 19 | | 27 |
| 243 | 5 | 16 | 39 | | 80 |
| 244 | | 12 | 31 | | 94 |
| 246 | | 42 | 62 | | 54 |
| 247 | | 15 | 25 | | 21 |
| 248 | | 56 | 28 | | 157 |
| 249 | | 33 | 46 | | 55 |
| 250 | | 24 | 8 | | 54 |
| 251 | | 46 | 18 | | 79 |
| 252 | | 24 | 25 | | 99 |
| 253 | | 64 | 36 | | 200 |
| 254 | | 24 | 35 | | 35 |
| 255 | | 28 | 44 | | 185 |
| 256 | | 55 | 24 | | 167 |
| 257 | | 53 | 18 | | 180 |
| 258 | | 36 | 21 | | 41 |
| 259 | | 35 | 23 | | 47 |
| 261 | | 12 | | 108 | 100 |
| 262 | | 67 | | | 66 |
| 263 | | 14 | | | 46 |
| 265 | | 18 | | | |
| 266 | | 31 | | | |
| 268 | | 15 | | | |
| 270 | 8 | 7 | 8 | | 18 |
| 272 | | 19 | | | |
| 274 | 10 | 11 | 16 | | 27 |
| 275 | | 19 | | | |
| 277 | | 13 | | | |
| 278 | | 14 | 15 | | 16 |
| 279 | 1 | 21 | | | 23 |

What is claimed is:

1. A compound selected from the group consisting of:

5-{4-[4-({[(2-fluoro-5-methylphenyl)amino]carbonyl}amino)phenoxy]pyridin-2-yl}-N-[3-(2H-tetrazol-5-yl)propyl]-1H-pyrrole-3-carboxamide;

5-{4-[4-({[(2-fluoro-5-methylphenyl)amino]carbonyl}amino)phenoxy]pyridin-2-yl}-N-[2-(2H-tetrazol-5-yl)ethyl]-1H-pyrrole-3-carboxamide;

N-(3,3-diethoxypropyl)-5-{4-[4-({[(3-methylphenyl)amino]carbonyl}amino)phenoxy]pyridin-2-yl}-1H-pyrrole-3-carboxamide;

N-(2-aminoethyl)-5-{4-[4-({[(2-fluoro-5-methylphenyl)amino]carbonyl}amino)phenoxy]pyridin-2-yl}-1H-pyrrole-3-carboxamide;

tert-butyl (2-{[(5-{4-[4-({[(2-fluoro-5-methylphenyl)amino]carbonyl}amino)phenoxy]pyridin-2-yl}-1H-pyrrol-3-yl)carbonyl]amino}ethyl)carbamate;

methyl [(3-{[(5-{4-[4-({[(2-fluoro-5-methylphenyl)amino]carbonyl}amino)phenoxy]pyridin-2-yl}-1H-pyrrol-3-yl)carbonyl]amino}propyl)amino]acetate;

methyl [(2-{[(5-{4-[4-({[(2-fluoro-5-methylphenyl)amino]carbonyl}amino)phenoxy]pyridin-2-yl}-1H-pyrrol-3-yl)carbonyl]amino}ethyl)amino]acetate;

dimethyl 2,2'-[(2-{[(5-{4-[4-({[(2-fluoro-5-methylphenyl)amino]carbonyl}amino)phenoxy]pyridin-2-yl}-1H-pyrrol-3-yl)carbonyl]amino}ethyl)imino]diacetate;

ethyl [4-(2-{[(5-{4-[4-({[(2-fluoro-5-methylphenyl)amino]carbonyl}amino)phenoxy]pyridin-2-yl}-1H-pyrrol-3-yl)carbonyl]amino}ethyl)piperazin-1-yl]acetate;

ethyl [4-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)piperazin-1-yl]acetate 5-{4-[4-({[(2-fluoro-5-methylphenyl)amino]carbonyl}amino)phenoxy]pyridin-2-yl}-N-{3-[2-(hydroxymethyl)morpholin-4-yl]propyl}-1H-pyrrole-3-carboxamide;

5-{4-[4-({[(2-fluoro-5-methylphenyl)amino]carbonyl}amino)phenoxy]pyridin-2-yl}-N-{3-[3-(hydroxymethyl)piperidin-1-yl]propyl}-1H-pyrrole-3-carboxamide methyl rel-(2R,4S)-1-(2-{[(5-{4-[4-({[(2-fluoro-5-methylphenyl)amino]carbonyl}amino)phenoxy]pyridin-2-yl}-1H-pyrrol-3-yl)carbonyl]amino}ethyl)-4-hydroxypyrrolidine-2-carboxylate;

5-{4-[4-({[(2-fluoro-5-methylphenyl)amino]carbonyl}amino)phenoxy]pyridin-2-yl}-N-(2-oxoethyl)-1H-pyrrole-3-carboxamide;

N-(2,2-diethoxyethyl)-5-{4-[4-({[(2-fluoro-5-methylphenyl)amino]carbonyl}amino)phenoxy]pyridin-2-yl}-1H-pyrrole-3-carboxamide;

methyl rel-(2R,4S)-1-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)-4-hydroxypyrrolidine-2-carboxylate;

4-methoxy-4-oxobutyl 5-{4-[4-({[(2-fluoro-5-methylphenyl)amino]carbonyl}amino)phenoxy]pyridin-2-yl}-1H-pyrrole-3-carboxylate;

5-{[(5-{4-[4-({[(2-fluoro-5-methylphenyl)amino]carbonyl}amino)phenoxy]pyridin-2-yl}-1H-pyrrol-3-yl)carbonyl]amino}pentanoic acid;

ethyl 5-{[(5-{4-[4-({[(2-fluoro-5-methylphenyl)amino]carbonyl}amino) phenoxy]pyridin-2-yl}-1H-pyrrol-3-yl)carbonyl]amino}pentanoate;

ethyl 4-(2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}ethyl)piperazine-1-carboxylate;

5-{4-[3-fluoro-4-({[(2-fluoro-5-methylphenyl)amino]carbonyl}amino)phenoxy]pyridin-2-yl}-N-(2-oxoethyl)-1H-pyrrole-3-carboxamide;

N-(2,2-diethoxyethyl)-5-{4-[3-fluoro-4-({[(2-fluoro-5-methylphenyl)amino]carbonyl}amino)phenoxy]pyridin-2-yl}-1H-pyrrole-3-carboxamide;

ethyl 4-{3-[({5-[4-(2-fluoro-5-{[(2-fluoro-5-methylphenyl)amino]carbonyl}phenoxy)pyridin-2-yl]-1H-pyrrol-3-yl}carbonyl)amino]propyl}piperazine-1-carboxylate;

ethyl 4-(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)piperazine-1-carboxylate;

ethyl 3-{[(4-{4-[3-fluoro-4-({[(2-fluoro-5-methylphenyl)amino]carbonyl}amino)phenoxy]pyridin-2-yl}-2-thienyl)carbonyl]amino}propanoate;

methyl 3-{[(5-{4-[3-fluoro-4-({[(3-methylphenyl)amino]carbonyl}amino)phenoxy]pyridin-2-yl}-1H-pyrrol-3-yl)carbonyl]amino}propanoate;

methyl 3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propanoate;

methyl 4-{[(5-{4-[4-({[(2-fluoro-5-methylphenyl)amino]carbonyl}amino)phenoxy]pyridin-2-yl}-1H-pyrrol-3-yl)carbonyl]amino}butanoate;

5-{4-[4-({[(2-fluoro-5-methylphenyl)amino]carbonyl}amino)phenoxy]pyridin-2-yl}-N-(4-hydrazino-4-oxobutyl)-1H-pyrrole-3-carboxamide;

dimethyl 2,2'-({3-[({5-[4-(2-fluoro-5-{[(2-fluoro-5-methylphenyl)amino]carbonyl}phenoxy)pyridin-2-yl]-1H-pyrrol-3-yl}carbonyl)amino]propyl}imino)diacetate dimethyl 2,2'-({2-[({5-[4-(2-fluoro-5-{[(2-fluoro-5-methylphenyl)amino]carbonyl}phenoxy)pyridin-2-yl]-1H-pyrrol-3-yl}carbonyl)amino]ethyl}imino)diacetate methyl ({3-[({5-[4-(2-fluoro-5-{[(2-fluoro-5-methylphenyl)amino]carbonyl}phenoxy)pyridin-2-yl]-1H-pyrrol-3-yl}carbonyl)amino]propyl}amino)acetate;

methyl ({2-[({5-[4-(2-fluoro-5-{[(2-fluoro-5-methylphenyl)amino]carbonyl}phenoxy)pyridin-2-yl]-1H-pyrrol-3-yl}carbonyl)amino]ethyl}amino)acetate;

N-(2-aminoethyl)-5-[4-(2-fluoro-5-{[(2-fluoro-5-methylphenyl)amino]carbonyl}phenoxy)pyridin-2-yl]-1H-pyrrole-3-carboxamide tert-butyl {2-[({5-[4-(2-fluoro-5-{[(2-fluoro-5-methylphenyl)amino]carbonyl}phenoxy)pyridin-2-yl]-1H-pyrrol-3-yl}carbonyl)amino]ethyl}carbamate;

5-[4-(2-fluoro-5-{[(2-fluoro-5-methylphenyl)amino]carbonyl}phenoxy)pyridin-2-yl]-N-[3-(4-hydroxypiperidin-1-yl)propyl]-1H-pyrrole-3-carboxamide;

1-[4-({2-[4-(azetidin-1-ylcarbonyl)-1H-pyrrol-2-yl]pyridin-4-yl}oxy)phenyl]-3-(2-fluoro-5-methylphenyl)urea;

5-[4-(2-fluoro-5-{[(2-fluoro-5-methylphenyl)amino]carbonyl}phenoxy)pyridin-2-yl]-N-[3-(4-methylpiperazin-1-yl)propyl]-1H-pyrrole-3-carboxamide;

5-[4-(2-fluoro-5-{[(2-fluoro-5-methylphenyl)amino]carbonyl}phenoxy)pyridin-2-yl]-N-(3-pyrrolidin-1-ylpropyl)-1H-pyrrole-3-carboxamide;

methyl 1-[3-({[5-(4-{4-fluoro-3-[(3-methyl-2-furoyl)amino]phenoxy}pyridin-2-yl)-1H-pyrrol-3-yl]carbonyl}amino)propyl]pyrrolidine-2-carboxylate;

5-(4-{4-fluoro-3-[(3-methyl-2-furoyl)amino]phenoxy}pyridin-2-yl)-N-[3-(4-hydroxypiperidin-1-yl)propyl]-1H-pyrrole-3-carboxamide;

5-(4-{4-fluoro-3-[(3-methyl-2-furoyl)amino]phenoxy}pyridin-2-yl)-N-(3-oxopropyl)-1H-pyrrole-3-carboxamide;

5-(4-{4-fluoro-3-[(3-methyl-2-furoyl)amino]phenoxy}pyridin-2-yl)-N-(3-piperidin-1-ylpropyl)-1H-pyrrole-3-carboxamide;

5-(4-{4-fluoro-3-[(3-methyl-2-furoyl)amino]phenoxy}pyridin-2-yl)-N-(3-pyrrolidin-1-ylpropyl)-1H-pyrrole-3-carboxamide;

5-(4-{4-fluoro-3-[(3-methyl-2-furoyl)amino]phenoxy}pyridin-2-yl)-N-[3-(4-methylpiperazin-1-yl)propyl]-1H-pyrrole-3-carboxamide;

5-(4-{4-fluoro-3-[(3-methyl-2-furoyl)amino]phenoxy}pyridin-2-yl)-N-(3-morpholin-4-ylpropyl)-1H-pyrrole-3-carboxamide;

N-{3-[(2,3-dihydroxypropyl)(methyl)amino]propyl}-5-{4-[3-fluoro-4-({[(2-fluoro-5-methylphenyl)amino]carbonyl}amino)phenoxy]pyridin-2-yl}-1H-pyrrole-3-carboxamide;

methyl [(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)amino]acetate;

3-{[(4-{4-[3-fluoro-4-({[(2-fluoro-5-methylphenyl)amino]carbonyl}amino) phenoxy]pyridin-2-yl}-2-thienyl)carbonyl]amino}propanoic acid;

methyl 3-{[(4-{4-[3-fluoro-4-({[(2-fluoro-5-methylphenyl)amino]carbonyl}amino)phenoxy]pyridin-2-yl}-2-thienyl)carbonyl]amino}propanoate;

3-{[(4-{4-[3-fluoro-4-({[(2-fluoro-5-methylphenyl)amino]carbonyl}amino)phenoxy]pyridin-2-yl}-1H-pyrrol-2-yl)carbonyl]amino}propanoic acid;

methyl 3-{[(4-{4-[3-fluoro-4-({[(2-fluoro-5-methylphenyl)amino]carbonyl}amino)phenoxy]pyridin-2-yl}-1H-pyrrol-2-yl)carbonyl]amino}propanoate;

N-(3,3-diethoxypropyl)-4-{4-[3-fluoro-4-({[(2-fluoro-5-methylphenyl)amino]carbonyl}amino)phenoxy]pyridin-2-yl}thiophene-2-carboxamide;

N-(3,3-diethoxypropyl)-4-{4-[3-fluoro-4-({[(2-fluoro-5-methylphenyl)amino]carbonyl}amino)phenoxy]pyridin-2-yl}-1H-pyrrole-2-carboxamide;

N-(3,3-diethoxypropyl)-5-(4-{4-fluoro-3-[(3-methyl-2-furoyl)amino]phenoxy}pyridin-2-yl)-1H-pyrrole-3-carboxamide;

N-(3,3-diethoxypropyl)-5-[4-(2-fluoro-5-{[(2-fluoro-5-methylphenyl)amino]carbonyl}phenoxy)pyridin-2-yl]-1H-pyrrole-3-carboxamide;

5-{4-[3-fluoro-4-({[(2-fluoro-5-methylphenyl)amino]carbonyl}amino)phenoxy]pyridin-2-yl}-N-{3-[3-(hydroxymethyl)piperidin-1-yl]propyl}-1H-pyrrole-3-carboxamide;

5-{4-[3-fluoro-4-({[(2-fluoro-5-methylphenyl)amino]carbonyl}amino)phenoxy]pyridin-2-yl}-N-{3-[2-(hydroxymethyl)morpholin-4-yl]propyl}-1H-pyrrole-3-carboxamide;

5-{4-[3-fluoro-4-({[(2-fluoro-5-methylphenyl)amino]carbonyl}amino)phenoxy]pyridin-2-yl}-N-[3-(4-hydroxypiperidin-1-yl)propyl]-1H-pyrrole-3-carboxamide;

N-(3,3-diethoxypropyl)-5-{4-[4-({[(2-fluoro-5-methylphenyl)amino]carbonyl}amino)phenoxy]pyridin-2-yl}-1H-pyrrole-3-carboxamide;

N-(3,3-diethoxypropyl)-5-{4-[3-fluoro-4-({[(2-fluoro-5-methylphenyl)amino]carbonyl}amino)phenoxy]pyridin-2-yl}-1H-pyrrole-3-carboxamide;

{[(5-{4-[3-fluoro-4-({[(2-fluoro-5-methylphenyl)amino]carbonyl}amino)phenoxy]pyridin-2-yl}-1H-pyrrol-3-yl)carbonyl]amino}acetic acid;

methyl {[(5-{4-[3-fluoro-4-({[(2-fluoro-5-methylphenyl)amino]carbonyl}amino)phenoxy]pyridin-2-yl}-1H-pyrrol-3-yl)carbonyl]amino}acetate;

tert-butyl (3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)carbamate;

dimethyl 2,2'-[(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)imino]diacetate;

2,2'-[(3-{[(5-{4-[4-({[(2-fluoro-5-methylphenyl)amino]carbonyl}amino)phenoxy]pyridine-2-yl}-1H-pyrrol-3-yl)carbonyl]amino}propyl)imino]diacetic acid;

dimethyl 2,2'-[(2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}ethyl)imino]diacetate;

tert-butyl (2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}ethyl)carbamate;

methyl rel-(2R,4S)-1-(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)-4-hydroxypyrrolidine-2-carboxylate;

{4-[(5-{4-[3-fluoro-4-({[(2-fluoro-5-methylphenyl)amino]carbonyl}amino)phenoxy]pyridin-2-yl}-1H-pyrrol-3-yl)carbonyl]piperazin-1-yl}acetic acid;

ethyl {4-[(5-{4-[3-fluoro-4-({[(2-fluoro-5-methylphenyl)amino]carbonyl}amino)phenoxy]pyridin-2-yl}-1H-pyrrol-3-yl)carbonyl]piperazin-1-yl}acetate;

1-(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)pyrrolidine-2-carboxylic acid;

1-(2-fluoro-5-methylphenyl)-3-[2-fluoro-4-({2-[4-(piperazin-1-ylcarbonyl)-1H-pyrrol-2-yl]pyridin-4-yl}oxy)phenyl]urea;

N-(2-aminoethyl)-5-{4-[3-fluoro-4-({[(2-fluoro-5-methylphenyl)amino]carbonyl}amino)phenoxy]pyridin-2-yl}-1H-pyrrole-3-carboxamide;

N-(3-aminopropyl)-5-{4-[3-fluoro-4-({[(2-fluoro-5-methylphenyl)amino]carbonyl}amino)phenoxy]pyridin-2-yl}-1H-pyrrole-3-carboxamide;

tert-butyl 4-[(5-{4-[3-fluoro-4-({[(2-fluoro-5-methylphenyl)amino]carbonyl}amino)phenoxy]pyridin-2-yl}-1H-pyrrol-3-yl)carbonyl]piperazine-1-carboxylate;

5-{4-[3-fluoro-4-({[(2-fluoro-5-methylphenyl)amino]carbonyl}amino)phenoxy]pyridin-2-yl}-N-(3-oxopropyl)-1H-pyrrole-3-carboxamide;

5-{4-[3-fluoro-4-({[(2-fluoro-5-methylphenyl)amino]carbonyl}amino)phenoxy]pyridin-2-yl}-N-(3-pyrrolidin-1-ylpropyl)-1H-pyrrole-3-carboxamide;

2-methoxyethyl 5-{4-[3-fluoro-4-({[(2-fluoro-5-methylphenyl)amino]carbonyl}amino)phenoxy]pyridin-2-yl}-1H-pyrrole-3-carboxylate;

methyl 1-(3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propyl)pyrrolidine-2-carboxylate;

3-morpholin-4-ylpropyl 5-{4-[3-fluoro-4-({[(2-fluoro-5-methylphenyl)amino]carbonyl}amino)phenoxy]pyridin-2-yl}-1H-pyrrole-3-carboxylate;

dimethyl 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioate;

ethyl 3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propanoate;

dimethyl 2,2'-[(3-{[(5-{4-[4-({[(2-fluoro-5-methylphenyl)amino]carbonyl}amino)phenoxy]pyridin-2-yl}-1H-pyrrol-3-yl)carbonyl]amino}propyl)imino]diacetate;

2-methoxyethyl 4-{[(5-{4-[4-({[(2-fluoro-5-methylphenyl)amino]carbonyl}amino)phenoxy]pyridin-2-yl}-1H-pyrrol-3-yl)carbonyl]amino}butanoate;

3-hydroxy-2,2-bis(hydroxymethyl)propyl 4-{[(5-{4-[4-({[(2-fluoro-5-methylphenyl)amino]carbonyl}amino) phenoxy]pyridin-2-yl}-1H-pyrrol-3-yl)carbonyl] amino}butanoate;

N-[3-(4-hydroxypiperidin-1-yl)propyl]-5-{4-[4-({[(3-methylphenyl)amino]carbonyl}amino)phenoxy]pyridin-2-yl}-1H-pyrrole-3-carboxamide;

5-{4-[4-({[(3-methylphenyl)amino]carbonyl}amino)phenoxy]pyridin-2-yl}-N-(3-oxopropyl)-1H-pyrrole-3-carboxamide;

N-(3-hydroxypropyl)-5-{4-[4-({[(3-methylphenyl) amino]carbonyl}amino)phenoxy]pyridin-2-yl}-1H-pyrrole-3-carboxamide;

1-[4-({2-[4-(hydrazinocarbonyl)-1H-pyrrol-2-yl]pyridin-4-yl}oxy)phenyl]-3-(3-methylphenyl)urea;

5-{4-[4-({[(3-methylphenyl)amino]carbonyl}amino)phenoxy]pyridin-2-yl}-N-(3-morpholin-4-ylpropyl)-1H-pyrrole-3-carboxamide;

3-hydroxy-2,2-bis(hydroxymethyl)propyl 5-{4-[4-({[(3-methylphenyl)amino]carbonyl}amino)phenoxy]pyridin-2-yl}-1H-pyrrole-3-carboxylate;

1-(2-fluoro-5-methylphenyl)-3-[4-({2-[4-(hydrazinocarbonyl)-1H-pyrrol-2-yl]pyridin-4-yl}oxy)phenyl]urea;

5-[4-(2-fluoro-5-{[(2-fluoro-5-methylphenyl)amino] carbonyl}phenoxy)pyridin-2-yl]-N-(3-oxopropyl)-1H-pyrrole-3-carboxamide;

methyl (2S)-1-{3-[({5-[4-(2-fluoro-5-{[(2-fluoro-5-methylphenyl)amino]carbonyl}phenoxy)pyridin-2-yl]-1H-pyrrol-3-yl}carbonyl)amino]propyl}pyrrolidine-2-carboxylate;

5-[4-(2-fluoro-5-{[(2-fluoro-5-methylphenyl)amino] carbonyl}phenoxy)pyridin-2-yl]-N-(3-hydroxypropyl)-1H-pyrrole-3-carboxamide;

ethyl 4-{N-[(5-{4-[3-fluoro-4-({[(3-methylphenyl) amino]carbonyl}amino)phenoxy]pyridin-2-yl}-1H-pyrrol-3-yl)carbonyl]-S-methylsulfonimidoyl}butanoate;

N,N'-diethyl-2-[({5-[4-(2-fluoro-5-{[(2-fluoro-5-methylphenyl)amino]carbonyl}phenoxy)pyridin-2-yl]-1H-pyrrol-3-yl}carbonyl)amino]pentanediamide;

1-(3-{[(5-{4-[4-({[(2-fluoro-5-methylphenyl)amino] carbonyl}amino)phenoxy]pyridin-2-yl}-1H-pyrrol-3-yl)carbonyl]amino}propyl)pyrrolidine-2-carboxylic acid;

(102') 2-[({5-[4-(2-fluoro-5-{[(2-fluoro-5-methylphenyl) amino]carbonyl}phenoxy)pyridin-2-yl]-1H-pyrrol-3-yl}carbonyl)amino]pentanedioic acid;

dimethyl 2-[({5-[4-(2-fluoro-5-{[(2-fluoro-5-methylphenyl)amino]carbonyl}phenoxy)pyridin-2-yl]-1H-pyrrol-3-yl}carbonyl)amino]pentanedioate;

N-(3-aminopropyl)-5-{4-[4-({[(2-fluoro-5-methylphenyl)amino]carbonyl}amino)phenoxy]pyridin-2-yl}-1H-pyrrole-3-carboxamide;

tert-butyl (3-{[(5-{4-[4-({[(2-fluoro-5-methylphenyl) amino]carbonyl}amino)phenoxy]pyridin-2-yl}-1H-pyrrol-3-yl)carbonyl]amino}propyl)carbamate;

N-(3-aminopropyl)-5-[4-(2-fluoro-5-{[(2-fluoro-5-methylphenyl)amino]carbonyl}phenoxy)pyridin-2-yl]-1H-pyrrole-3-carboxamide;

tert-butyl {3-[({5-[4-(2-fluoro-5-{[(2-fluoro-5-methylphenyl)amino]carbonyl}phenoxy)pyridin-2-yl]-1H-pyrrol-3-yl}carbonyl)amino]propyl}carbamate;

5-[4-(2-fluoro-5-{[(2-fluoro-5-methylphenyl)amino] carbonyl}phenoxy)pyridin-2-yl]-N-(3-morpholin-4-ylpropyl)-1H-pyrrole-3-carboxamide;

5-(ethylamino)-4-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoic acid;

tert-butyl 5-(ethylamino)-4-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoate;

5-tert-butoxy-2-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoic acid;

3-[({5-[4-(2-fluoro-5-{[(2-fluoro-5-methylphenyl)amino] carbonyl}phenoxy)pyridin-2-yl]-1H-pyrrol-3-yl}carbonyl)amino]propanoic acid;

methyl 3-[({5-[4-(2-fluoro-5-{[(2-fluoro-5-methylphenyl)amino]carbonyl}phenoxy)pyridin-2-yl]-1H-pyrrol-3-yl}carbonyl)amino]propanoate;

ethyl 4-{N-[5-{4-[3-fluoro-4-({[(2-fluoro-5-methylphenyl)amino]carbonyl}amino)phenoxy]pyridin-2-yl}-1H-pyrrol-3-yl)carbonyl]-S-methylsulfonimidoyl}butanoate;

methyl 5-(ethylamino)-4-[({5-[4-(2-fluoro-5-{[(2-fluoro-5-methylphenyl)amino]carbonyl}phenoxy)pyridin-2-yl]-1H-pyrrol-3-yl}carbonyl)amino]-5-oxopentanoate;

2-[({5-[4-(2-fluoro-5-{[(2-fluoro-5-methylphenyl)amino] carbonyl}phenoxy)pyridin-2-yl]-1H-pyrrol-3-yl}carbonyl)amino]-5-methoxy-5-oxopentanoic acid;

N,N'-diethyl-2-{[(5-{4-[4-({[(2-fluoro-5-methylphenyl) amino]carbonyl}amino)phenoxy]pyridin-2-yl}-1H-pyrrol-3-yl)carbonyl]amino}pentanediamide;

5-(ethylamino)-4-({[5-(4-{3-[(3-methyl-2-furoyl)amino] phenoxy}pyridin-2-yl)-1H-pyrrol-3-yl] carbonyl}amino)-5-oxopentanoic acid;

tert-butyl 5-(ethylamino)-4-({[5-(4-{3-[(3-methyl-2-furoyl)amino]phenoxy}pyridin-2-yl)-1H-pyrrol-3-yl] carbonyl}amino)-5-oxopentanoate;

5-tert-butoxy-2-({[5-(4-{3-[(3-methyl-2-furoyl)amino] phenoxy}pyridin-2-yl)-1H-pyrrol-3-yl] carbonyl}amino)-5-oxopentanoic acid;

5-tert-butyl 1-methyl 2-({[5-(4-{3-[(3-methyl-2-furoyl) amino]phenoxy}pyridin-2-yl)-1H-pyrrol-3-yl] carbonyl}amino)pentanedioate;

1-(3-{[(5-{4-[4-({[(2-fluoro-5-methylphenyl)amino] carbonyl}amino)phenoxy]pyridin-2-yl}-1H-pyrrol-3-yl)carbonyl]amino}propyl)pyrrolidine-3-carboxylic acid;

tert-butyl 1-(3-{[(5-{4-[4-({[(2-fluoro-5-methylphenyl) amino]carbonyl}amino) phenoxy]pyridin-2-yl}-1H-pyrrol-3-yl)carbonyl]amino}propyl)pyrrolidine-3-carboxylate;

dimethyl 2-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}pentanedioate;

2-{[(5-{4-[3-fluoro-4-({[(2-fluoro-5-methylphenyl) amino]carbonyl}amino)phenoxy]pyridin-2-yl}-1H-pyrrol-3-yl)carbonyl]amino}pentanedioic acid;

5-{4-[4-({[(2-fluoro-5-methylphenyl)amino] carbonyl}amino)phenoxy]pyridin-2-yl}-N-[3-(4-hydroxypiperidin-1-yl)propyl]-1H-pyrrole-3-carboxamide;

5-{4-[4-({[(2-fluoro-5-methylphenyl)amino] carbonyl}amino)phenoxy]pyridin-2-yl}-N-(3-oxopropyl)-1H-pyrrole-3-carboxamide;

3 morpholin-4-ylpropyl 5-{4-[4-({[(2-fluoro-5-methylphenyl)amino]carbonyl}amino)phenoxy]pyridin-2-yl}-1H-pyrrole-3-carboxylate;

3-[({5-[4-(2-fluoro-5-{[(3-methylphenyl)amino]carbonyl}phenoxy)pyridin-2-yl]-1H-pyrrol-3-yl}carbonyl)amino]propanoic acid;

5-[4-(2-fluoro-5-{[(3-methylphenyl)amino]carbonyl}phenoxy)pyridin-2-yl]-1H-pyrrole-3-carboxylic acid;

methyl 3-[({5-[4-(2-fluoro-5-{[(3-methylphenyl)amino]carbonyl}phenoxy)pyridin-2-yl]-1H-pyrrol-3-yl}carbonyl)amino]propanoate;

3-{[(4-{4-[4-({[(2-fluoro-5-methylphenyl)amino]carbonyl}amino)phenoxy]pyridin-2-yl}-2-thienyl)carbonyl]amino}propanoic acid; and methyl 3-{[(4-{4-[4-({[(2-fluoro-5-methylphenyl)amino]carbonyl}amino)phenoxy]pyridin-2-yl}-2-thienyl)carbonyl]amino}propanoate, or a pharmaceutically acceptable salt thereof.

2. A pharmaceutical composition comprising a therapeutic effective amount of at least one compound of claim 1 or a pharmaceutically acceptable salt thereof and at least one pharmaceutically acceptable carrier.

3. The pharmaceutical composition of claim 2, wherein the composition comprises tablets, capsules, intravenous injections, intramuscular injections, local injections, topical creams, gels and ointments, eye drops, eye ointments, eye sprays, ophthalmic suspensions, ophthalmic emulsions, intravitreal injections, subtenon injections, ophthalmic bioerodible implant, and non-bioerodible ophthalmic inserts and depots.

4. A method for the treatment of a disease or condition selected from the group consisting of diabetic retinopathy, macular degeneration, age-related macular degeneration, and retinopathy of prematurity, comprising administering to a mammal in need of such treatment at least one compound of claim 1 or a pharmaceutically acceptable salt thereof.

* * * * *